US010087463B2

(12) United States Patent
Fraser et al.

(10) Patent No.: US 10,087,463 B2
(45) Date of Patent: *Oct. 2, 2018

(54) METHODS AND COMPOSITIONS FOR TRANSPOSITION USING MINIMAL SEGMENTS OF THE EUKARYOTIC TRANSFORMATION VECTOR PIGGYBAC

(75) Inventors: Malcolm J. Fraser, Granger, IN (US); Xu Li, Sharon, MA (US)

(73) Assignee: University of Notre Dame Du Lac, Notre Dame, IN (US)

( * ) Notice: Subject to any disclaimer, the term of this patent is extended or adjusted under 35 U.S.C. 154(b) by 373 days.

This patent is subject to a terminal disclaimer.

(21) Appl. No.: 11/454,947

(22) Filed: Jun. 19, 2006

(65) Prior Publication Data
US 2010/0221824 A1     Sep. 2, 2010

Related U.S. Application Data

(63) Continuation-in-part of application No. 10/826,523, filed on Apr. 19, 2004, now Pat. No. 7,105,343, which is a continuation-in-part of application No. 10/001,189, filed on Oct. 30, 2001, now Pat. No. 6,962,810.

(60) Provisional application No. 60/244,984, filed on Nov. 1, 2000, provisional application No. 60/244,667, filed on Oct. 31, 2000.

(51) Int. Cl.
*C12N 15/85* (2006.01)
*C12N 15/90* (2006.01)

(52) U.S. Cl.
CPC ............ *C12N 15/85* (2013.01); *C12N 15/90* (2013.01); *C12N 2800/204* (2013.01); *C12N 2800/90* (2013.01)

(58) Field of Classification Search
None
See application file for complete search history.

(56) References Cited

U.S. PATENT DOCUMENTS

| | | | |
|---|---|---|---|
| 6,218,185 B1 * | 4/2001 | Shirk et al. | 435/455 |
| 6,551,825 B1 | 4/2003 | Shirk et al. | |
| 6,773,914 B1 | 8/2004 | Handler | |
| 6,962,810 B2 | 11/2005 | Fraser et al. | |
| 7,105,343 B1 | 9/2006 | Fraser et al. | |
| 2002/0116723 A1 * | 8/2002 | Grigliatti et al. | 800/8 |
| 2002/0173634 A1 | 11/2002 | Fraser et al. | |
| 2002/0199216 A1 * | 12/2002 | MacRae | 800/279 |

FOREIGN PATENT DOCUMENTS

WO  WO 2005042753 A1 *  5/2005
WO  WO 2006122442 A1 * 11/2006

OTHER PUBLICATIONS

X70275, GI: 406850, publicly available Oct. 1993.*
GenBank Accession No. DQ340395, GI: 84872947, publicly available Dec. 31, 2006.*
Zimowska et al. Highly conserved piggyBac elements in noctuid species of *Lepidoptera*. Insect Biochemistry and Molecular Biology, vol. 36, pp. 421-428, 2006.*
GenBank Accession No. AF402295, GI: 15986716, publicly available Oct. 9, 2001.*
GenBank Accession No. AR307779, publicly available Jun. 2003.*
Xu et al. Identification and characterization of piggyBac-like elements in the genome of domesticated silkworm, *Bombyx mori*. Molecular Genetics and Genomics, vol. 276, No. 1, pp. 31-40, Jul. 2006.*
Paveltiz et al. PGDB5: a neural-specific intron-containing piggyBac transposase domesticated over 500 million years ago and conserved from cephalochordates to humans. Mobile DNA, vol. 4, 23, 2013, printed as pp. 1/17-17/17.*
Ausubel, et al., "Short Protocols in Molecular Biology: A Compendium of Methods from Current Protocols in Molecular Biology," 2002, vol. 1 edition 5, John Wiley & Sons, Inc., cover and bibliographic information only.
Ausubel, et al., "Short Protocols in Molecular Biology: A Compendium of Methods from Current Protocols in Molecular Biology," 2002, vol. 2, edition 5, John Wiley & Sons, Inc., cover and bibliographic information only.
Beeman RW, Stauth DM (1999), Nature, 402: 370-371.
Becker, et al., "Maize Activator transposase has a bipartite DNA binding that recognizes subterminal sequences and the terminal inverted repeats," Mol Gen Genet, 1997, p. 219-230, v. 254, Springer-Verlag.
Beeman, et al., "Rapind cloning of insect transposon insertion junctions using 'universal' PCR," Insect Molecular Biology, 1997, p. 83-88, v. 6 i. 1, Blackwell Science Ltd.
Berghammer, et al., "A universal marker for transgenic insects," Nature, Nov. 25, 1999, p. 370-371, v. 402, Macmillan Magazines Ltd.
Elick, et al., "Analysis of the cis-acting DNA elements required for piggyBac transposable element excision," Mol Gen Genet, 1997, p. 605-610, v. 255, Springer-Verlag.

(Continued)

*Primary Examiner* — Jennifer Ann Dunston
(74) *Attorney, Agent, or Firm* — Workman Nydegger

(57) ABSTRACT

The present invention provides a method for transforming an insect genome that has a much enhanced transformation frequency. The vectors and plasmids employed in the method are further described as transposition vectors that include a minimal amount of nucleotide sequence homologous to a 5' region and a 3' region of a native piggyBac nucleic acid sequence. The transformed cells or embryos may also be developed into transgenic organisms. Disclosed are minimal piggyBac-based plasmid constructs that comprises a minimal nucleic acid sequence homologous to a 5' end of a piggyBac nucleic acid sequence (about 60-80 bp, particularly 66 bp) and a relatively long (300 to about 380 bp, particularly 311 bp or 378 bp) continuous nucleic acid sequence homologous to a 3' end of a piggyBac native nucleic acid sequence. Methods employing these constructs include the use of a helper plasmid. Transformation frequencies employing the constructs are enhanced 100-fold or higher over that transformation frequency obtained using other than the herein described constructs.

4 Claims, 169 Drawing Sheets

Specification includes a Sequence Listing.

(56) References Cited

OTHER PUBLICATIONS

Cary, et al., "Transposon Mutagenesis of Baculoviruses: Analysis of Trichoplusia ni Transposon IFP2 Insertions within the FP-Locus of Nuclear Polyhedrosis Viruses," Virology, 1989, v. 172, Academic Press, Inc., p. 156-169.

Elick, et al., "Excision of the piggyback transposable element in vitro is a precise event that is enhanced by the expression of its encoded transposase," Genetica, 1996, p. 33-41, v. 98, Kluwer Academic Publishers.

Elick, et al., "PCR analysis of insertion site specificity, transcription, and structural uniformity of the Lepidoptera transposable element IFP2 in the TN-368 cell genome," Genetica, 1996, p. 127-139, v. 97, Kluwer Academic Publishers.

Elick, et al., "Analysis of the cis-acting DNA elements required for piggyBack transposable element excision," Mol Gen Genet, 1997, p. 605-610, v. 255, Springer-Verlag.

Fraser, et al., "Acquisition of Host Cell DNA Sequences by Baculoviruses: Relationship Between Host DNA Insertions and FP Mutants of Autographa californica and Galleria mellonella Nuclear Polyhedrosis Viruses," Journal of Virology, 1983, p. 287-300, v. 47 i. 2, american Society for Microbiology.

Fraser, et al., "Transposon-Mediated Mutagenesis of a Baculovirus," Virology, 1985, p. 356-361, v. 145, Academic Press, Inc.

Fraser, et al., "Assay for Movement of Lepidopteran Transposon IFP2 in Insect Cells Using a Baculovirus Genome as a Target DNA," Virology, 1995, p. 397-407, v. 211, Academic Press, Inc.

Fraser, et al., "Precise excision of TTAA-specific lepidopteran transposons piggyBac (IFP2) and tagalong (TFP3) from the baculovirus genome in cell lines from two species of *Lepidoptera*," Insect Molecular Biology, 1996, p. 141-151, v. 5 i. 2, Blackwell Science Ltd.

Geier, et al., "Recognition Sequence of the dam Methylase of *Escherichia coli* K12 and Mode of Cleavage of Dpn I Endonuclease*," The Journal of Biological Chemistry, 1979, p. 1408-1413, v. 254, n. 4, i. Feb. 25.

Gierl, et al., "TnpA product encoded by the transposable element En-1 of *Zea Mays* is a DNA binding protein," IRL Press Limited, Oxford, England, EMBO J. 7(13) : 4045-53.

Goryshin, et al., "DNA length, binding, and twisting constraints on IS50 transposition," Proc. Natl. Acad. Sci. USA., 1994, p. 10834-10838, v. 91.

Grossman, et al., "The piggyBac element is capable of precise excision and transposition in cells and embryos of the mosquito, *Anopheles gamblae*," Insect Biochemistry and Molecular Biology, 2000, p. 909-914, v. 30, Elsevier Science Ltd.

Grossman, et al., "Germline tranformation of the malaria vector, Anopheles gambiae, with the piggyBac transposable element," Insect Molecular Biology, 2001, p. 597-604, v. 10 i. 6, Blackwell Science Ltd.

Grossniklaus, et al., "The *Drosophila* sloppy paired locus encodes two proteins involved in segmentation that show homology to mammalian transcription factors," Genes & Development, 1992, p. 1030-1051, v. 6, Cold Spring Harbor Laboratory.

Handler, et al., "The lepidopteran transposon bector, piggyBac, mediates germ-line transformation in the Mediterranean fruit fly," Proc. Natl. Acad. Sci. USA, 1998, p. 7520-7525, v. 95, The National Academy of Sciences.

Handler, et al., "Germline transformation of *Drosophila melanogaster* with the *piggyBac* transposon vector," Insect Molecular Biology, 1999, p. 449457, v. 8 i. 4, US Government.

Handler, et al., "The *piggyBac* transposon mediates germ-line transformation in the Oriental fruit fly and closely related elements exist in its genome," Insect Molecular Biology, 2000, pp. 605-612, v. 9 i. 6, Blackwell Science Ltd.

Handler, et al., "Polyubiquitin-Regulated DsRed Marker for Transgenic Insects," BioTechniques, 2001, p. 820-828, v. 31.

Handler, et al., "Transformation of the Caribbean fruit fly, *Anastrepha suspense*, with a piggyBac vector marked with polyubiquitin-regulated GFP," Insect Biochemistry and Molecular Biology, 2000, p. 199-205, v. 31, Elsevier Science Ltd.

Handler M. Alfred, "Use of the piggyBac transposon for germ-line transformation of insects," Insect Biochemistry and Molecular Biology, 2002, p. 1211-1220, v. 32, Elsevier Science Ltd.

Hediger, et al., "Genetic transformation of the housefly *Musca domestica* with the lepidopteran derived transposon piggyBac," Insect Molecular Biology, 2001, p. 113-119, v. 10 i. 2, Blackwell Science Ltd.

Heinrich, et al., "Germ-line transformation of the Australian sheep blowfly *Lucilia cuprina*," Insect Molecular Biology, 2002, p. 1-10, v. 11 i. 1, Royal Entomological Society.

Hirt, Bernhard, "Selective Extraction of Polyoma DNA from Infected Mouse Cell Cultures," J. Mol. Bio., 1967, p. 367-369, v. 26.

Horn, et al., "A versatile vector set for animal transgenesis," Dev Genes Evol, 2000, p. 630-637, v. 210, Springer-Verlag.

Ivics, et al., "Molecular Reconstruction of Sleeping Beauty, a Tc1-like Transposon from Fish, and Its Transposon in Human Cells," Cell, 1997, p. 501-510, v. 91, Cell Press.

Jarvis, et al., "Use of early baculovirus promoters for continuous expression and efficient processing of foreign gene products in stably transformed lepidopteran cells," Biotechnology, 1990, p. 950-955, v. 8 i. 10, PubMed.

Jasinskiene, et al., "Structure of Hermes integrations in the germline of the yellow fever mosquito, *Aedes aegypti*," Insect Molecular Biology, 2000, p. 11-18, v. 9 i. 1, Blackwell Science Ltd.

Kaufman, et al., "*Drosophila* P Element Transposase Recognizes Internal P Element DNA Sequences," Cell, 1989, p. 359-371, v. 59, Cell Press.

Kokoza, et al., "Efficient transformation of the yellow fever mosquito *Aedes aegypti* using the piggyBac transposable element vector pBac[3x P3—EGFP AFM]," Insect Biochemistry and Molecular Biology, 2001, p. 1137-1143, v. 31, Elsevier Science Ltd.

Kunze, et al., "The putative trasposase of transposable element Ac from *Zea Mays* L. interacts with subterminal sequences of Ac," p. 3177-3185, IRL Press, 1989 EMBO J 8 (11).

Li, et al., "piggyBac-mediated transposition in *Drosophila melanogaster*: an evaluation of the use of constitutive promoters to control transposase gene expression," Insect Molecular Biology, 2001, p. 447-455, v. 10 i. 5, Blackwell Science Ltd.

Li, et al., "The minimum internal and external sequence requirements for transposition of the eukaryotic transformation vector piggBac," Mol Genet Genomics, 2001, p. 190-198, v. 266, Springer-Verlag.

Liu, et al., "Function Dissection of the cis-Acting Sequences of the *Arabidopsis* Transposable Element Tag1 Reveals Dissimilar Subterminal Sequence and Minimal Spacing Requirements for Transposition," Genetics, 2001, p. 817-830, v. 157, Genetics Society of America.

Lobo, et al., "Transposition of the piggBac element in embryos of *Drosophila melanogaster, Aedes aegypti and Trichoplusia ni*," Mol Gen Genet, 1999, p. 803-810, v. 261, Springer-Verlag.

Lobo, et al., "Mobiolity of piggyBac transposon in embryos of the vectors of Dengue fever (*Aedes albopictus*) and La Crosse encephalitits (*Ae. Triseriatus*)," Mol Genet Genomics, 2001, p. 66-71, v. 265, Springer-Verlag.

Lobo, et al., "Germ line transformation of the yellow fever mosquito, *Aedes aegypti*, mediated by transpositional insertion of a piggyBac vector," Insect Molecular Biology, 2002, p. 133-139, v. 11 i. 2, Royal Entomoligical Society.

Lohe, et al., "Efficient Mobilization of mariner in Vivo Requires Multiple Internal Sequences," Genetics, 2002, p. 519-526, v. 160, Genetics Society of America.

Lozovsky, et al., "Unexpected Stability of mariner Transgenes in *Drosophila*," Genetics, 2002, p. 527-535, v. 160, Genetics Society of America.

Mandrioli, et al. "Stable transformation of a *Mamestra brassicae* (*Lepidoptera*) cell line with *Lepidopteran*-derived transposon *piggyback*" Insect Biochem. Mol. Bio., 2002, p. 1-5, V. 33 I. 1, Elsevier Science Ltd.

Mullins, et al. "cis-acting DNA sequence requirements for P-element transposition" Genes & Development., 1989, p. 729-738, v. 3 i. 5, Cold Spring Harbor Laboratory Press.

Nolan, et al. "*piggyback*-mediated germline transformation of the malaria mosquito *Anopheles stephensi* using the red fluorescent protein dsRED as a selectable marker," The Journal of Biological

(56) References Cited

OTHER PUBLICATIONS

Chemistry, 2002, p. 8759-8762, v 277 n. 11, The American Society for Biochemistry and Molecular Biology Inc.

Ochman, et al. "Genetic application of an inverse polymerase chain reaction," Genetics, 1988, p. 621-623, v. 120 i. 3, Genetics Society of America.

Peloquin, et al. "Germ-line transformation of pink bollworm (*Lepidoptera:gelechiidae*) mediated by the *piggyback* transposable element," Insect Molecular Biology, 2000, p. 323-333, v. 9 i. 3, Blackwell Science Ltd.

Perera, et al. "Germ-line transformation of the South American malaria vector, *Anopheles albimanus*, with a *piggyback*/EGFP transposon vector is routine and highly efficient" Insect Molecular Biology, 2002, p. 291-297, v. 11 i. 4, The Royal Entomological Society.

Pfaffle, et al. "Studies on Rates of Nucleosome Formation with DNA under Stress," The Journal of Biological Chemistry, 1990, p. 16821-16829, v. 265 n. 28 i. of Oct. 5, The American Society for Biochemistry and Molecular Biology, Inc.

Rio, et al. "Identification and purification of a *Drosophila* protein that binds to the terminal 31-base-pair inverted repeats of P transposable element," Proc. Natl. Acad. Sci. USA, 1988, p. 8929-8933, v. 85, Biochemistry.

Rubin, et al. "Genetic transformation of *Drosophila* with transposable element vectors," Science, 1982, p. 348-353, v. 218, AAAS.

Rubin, et al., "Vectors for P element-mediated gene transfer in *Drosophila*," Nucleic Acids Research, 1983, p. 6341-6351, v. 11 n. 18, IRL Press Limited.

Saedler, et al., Transposable Elements. 1996, Soringer-Verlag, cover, title page, and bibliographic info. only.

Sambrook, et al., "Molecular Cloning: A Laboratory Manual,"1989, New York: Cold Spring Harbor Press, cover and bibliographis information only.

Sarkar, et al., "Transposition of the *Hermes* element in embryos of the vector mosquito, *Aedes aegypti*," Insect Biochem. Molec. Biol., 1997, p. 359-363, v. 27 n. 5, Elsevier Science Ltd.

Sarkar, et al. "The Hermes element from Musca domestica can transpose in four families of cyclorrhaphan flies," Genetica, 1997, p. 15-29, v. 99, Kluwer Academic Publishers.

Sarkar, et al., "Molecular evolutionary analysis of the widespread piggyBac transposon family and related "domesticated" sequences," Mol. Gen Genomics, 2003, p/ 173-180, v. 270, Springer-Verlag.

Sekar, Vaithilingam, "A Rapid Screening Procedure for the Identification of Recombinant Bacterial Clones," BioTecniques, 1987, p. 11-13, v. 5 n. 1.

Sumitani, et al., "Germline transformation of the sawfly, *Athalia rosae* (*Hymenoptera: Symphyta*), mediated by a piggyBac-derived vector," Insect Biochemistry and Molecular Biology, 2003, p. 449-458, v. 33, Elsevier Science Ltd.

Tamura, et al., "Germline transformation of the silkworm *Bombyx mori* L. using a piggyBac transposon-derived vector," Nature Biotechnoly, 2000, p. 81-84, v. 18, Nature America Inc.

Thibault, et al., "Precise excision and transposition of piggyBac in pink bollworm embryos," Insect Molecular Biology, 1999, p. 119-123, v. 8 i. 1, Blackwell Science Ltd.

Thomas, et al., "3xP3-EGFP marker facilitates screening for transgenic silkworm *Bombyx mori* L. from the embryonic stage onwards," Insect Biochemistry and Molecular Biology, 2002, p. 247-253, v. 23, Elsevier Science Ltd.

Thummel, et al., "New pCaSpeR P element vectors," Drosophila Information Newsletter Reprints, 1992, p. 150-151, v. 71.

Toshiki, et al., "Germline transformation of the silkworm *Bombyx mori* L. using a piggyBac transposon-derived vector," Nature Biotechnology, 2000, p. 81-84, v.18, Nature America Inc.

Tosi, et al., "cis and trans factors affecting Mos1 mariner evolution and transposition in vitro, and its potential for functional genomics," Nucleic Acids Research, 2000, p. 784-790, v. 28 n. 3, 2000, Oxford University Press.

Trentmann, et al., "The transoposable element En/Spm-encoded TNPA protein contains a DNA binding and dimerization domain," Mol Gen Genet, 1993, p. 201-208, v. 238, Spriner-Verlag.

Wang, et al., "TTAA serves as the target site for TFP3 Lepidopteran insertions in both nuclear polyhedrosis virus and Trichoplusia ni genomes," Insect Molecular Biology, 1993, p. 109-116, v. 1 i. 3.

Zayed, et al., "Teh DNA-bending protein HMGB1 is a cellular cofactor of Sleeping Beauty transposition," Nucleic Acids Research, 2003, p. 2312-2322, v. 31 n. 9, Oxford University Press.

Amsterdam et al., (1999), "Retrovirus-mediated insertional mutagenesis in zebrafish," *Methods in Cell Biol.*, 60:87-98.

Aoki et al., (1987), "Complete nucleotide sequence of pTZ12, a chloramphenicol-resistance plasmid of Bacillus subtillis," *Gene*, 51:107-111.

Bonin et al., (2004), "A piggyBac transposon gene trap for the analysis of gene expression and function in *Drosophila*," *Genetics*, 167:1801-1811.

Bron et al., (1990), "Plasmids used in Bacillus," in *Molecular Biology Methods for Bacillus*, pp. 75-173, Harwood et al., eds., John Wiley & Sons Ltd.

Coates et al., (1995), "The transposable element mariner can excise in non-drosophilid insects," *Mol. Gen. Genet.*, 249:246-252.

Coates et al., (1997), "Interplasmid transposition of the mariner transposable element in no-drosophilid insects," *Mol Gen. Genet.*, 253:728-733.

Ding et al., (2005), "Efficient transposition of the piggyBac (PB) transposon in mammalian cells and mice," *Cell*, 122:473-483.

Fraser et al., (2000), "The TTAA-Specific family of transposable elements: identification, functional characterization, and utility for transformation of insects," in *Insect Transgenesis: Methods and Applications*, pp. 249-268, CRC Press LLC.

Gaiano et al., (1996), "Highly efficient germ-line transmission of proviral insertions in zebrafish," *Proc. Natl. Acad. Sci. USA*, 93:7777-7782.

Gaiano et al., (1996), "Insertional Mutagenesis and rapid cloning of essential genes in zebrafish," *Nature*, 383:829-832.

Gluzman et al., (1981), "SV40-Transformed simian cells support the replication of early SV40 mutants," *Cell*, 23:175-182.

Gonzalez-Estevez et al., (2003), "Transgenic planarian lines obtaines by electroporation using transposon-derived vectors and an eye-specific GFP marker," *Proc. Natl. Acad. Sci. USA*, 100:14046-14051.

Hacker et al., (2003), "piggyBac-based insertional mutagenesis in the presence of stably integrated P elements in *Drosophila*," *Proc. Natl. Acad. Sci. USA*, 100:7720-7725.

Handler et al., (2004), "Post-integration stabilization of a transposon vector by terminal sequence deletion in *Drosophila melanogaster*," *Nature Biotech.*, 22:1150-1154.

Horn et al., (2003), "piggyBac-based insertional mutagenesis and enhancer detections as a tool for functional insect genomics," *Genetics*, 163:647-661.

Izsvak et al., (2002), "Sleeping beauty, a wide host-range transposon vector for genetic transformation in vertebrates," *J. Mol. Biol.*, 302:93-102.

Kawakami et al., (1998), "Excision of the Tol2 transposable element of the medaka fish, *Oryzias latipes*, in zebrafish, *Dani rerio*," *Gene*, 225:17-22.

Kawakami et al., (2000), "Identification of a functional transposase of the Tol2 element, an Ac-like element from the Japanese medaka fish, and its transposition in the zebrafish germ lineage," *Proc. Natl. Acad. Sci. USA*, 97:11403-11408.

Kim et al., (2004), "Ectopic expression of a cecropin transgene in the human malaria vector mosquito *Anopheles gambiae* (*diptera: culcidae*): effects on susceptibility to plasmodium," *J. Med. Entomol.*, 41:447-455.

Korn et al., (1992), Enhancer trap integration in mouse embryonic stem cells gives rise to staining patterns in chimaeric embryos with a high frequency and detects endogenous genes, *Mechanisms of Development*, 39:95-109.

Li et al., (2005), "PiggyBac internal sequences are necessary for efficient transformation of target genomes," *Insect Mol. Biol.*, 14:17-30.

(56) References Cited

OTHER PUBLICATIONS

Lin et al., (1994), "Integration and Germ-Line Transmission of a Pseudotyped Retroviral Vector in Zebrafish," *Science*, 265:666-669.

Linney et al., (1999), "Transgene expression in zebrafish: a comparison of retroviral-vector and DNA-Injection approaches," *Developmental Biol.*, 213: 207-216.

Lobo et al., (2006), "Interplasmid transposition demonstrates piggyBac mobility in vertebrate species," *Genetica*, 12:347-357.

Lorenzen et al., (2003), "piggyBac-mediated germline transformation in the beetle *Tribolium castaneum*," Insect Mol. Biol., 12:433-440.

Luo et al., (1998), "Chromosomal transposition of a Tc 1/mariner-like element in mouse embryonic stem cells," *Proc. Natl. Acad. Sci. USA*, 95:10769-10773.

Parks et al., (2004), "Systematic generation of high-resolution deletion coverage of the *Drosophila melanogaster* genome," *Nature Genetics*, 36:288-292.

Romano et al., (2001), "Efficient in vitro and in vivo gene regulation of a retrovirally delivered pro-apoptotic factor under the control of the *Drosophila* HSP70 promoter," *Gene Therapy*, 8:600-607.

Ryder et al., (2003), "Transposable elements as tools for genomics and genetics in *Drosophila*," *Briefings in Functional Genomics and Proteomics*, 2:57-71.

Sablitzky et al., (1993), "High frequency expression of integrated proviruses derived from Enhancer trap retroviruses," *Cell Growth & Differentiation*, 4:451-459.

Thibault et al., (2004), "A complementary transposon tool kit for *Drosophila melanogaster* using P and piggyBac," *Nature Genetics*, 36:283-287.

Wang et al., (1989), "Transposon mutagenesis of baculoviruses: analysis of TFP3 lepidopteran transposon insertions at the FP locus of nuclear polyhedrosis viruses," *Gene*, 81:97-108.

Xiong et al., (1999), "Retroviral promoter-trap insertion into a novel mammalian septin gene expressed during mouse neuronal development," *Mechanism of Development*, 86:183-191.

\* cited by examiner

| PLASMIDS | INSERTION SEQUENCE | IPTA FREQUENCY |
|---|---|---|
| pIAO-P/L-TTAA | TTAA | 0 |
| pIAO-P/L-TTAA2 | TTAATTAA | 0 |
| pIAO-P/L | TTAATCTAGAGGATCCTCTAGATTAA (XbaI/BamHI/XbaI)--(SEQ ID NO:35)-- | $5.4 \times 10^{-3}$ |
| pIAO-P/L-18 bp | TTAATCTAGACGTACGCGGAGCTTAA--(SEQ ID NO:36)-- | $1.0 \times 10^{-6}$ |
| pIAO-P/L-22 bp | TTAATCTAGCTAGTACTAGAACTAGATTAA--(SEQ ID NO:37)-- | $3.6 \times 10^{-6}$ |
| pIAO-P/L-40 bp | TTAATCTAGTTCTAGACTAGCGGCCGCCACTAGTACTAGCTAGTAA--(SEQ ID NO:38)-- | $2.5 \times 10^{-5}$ |
| pIAO-P/L-55 bp | TTAATCTAGTTCCTAGACTGCCGCGTCCTAGACGTACGCGGCCACTA-GTACTAGCTAGATTAA--(SEQ ID NO:39)-- | $1.2 \times 10^{-4}$ |
| pIAO-P/L-73 bp | 63bp of Lambda PvuII fragment between XbaI sites of pIAO-P/L | $1.3 \times 10^{-4}$ |
| pIAO-P/L-212 bp | 63 bp + 141 bp of Lambda PvuII fragment between XbaI sites of pIAO-P/L | $3.1 \times 10^{-4}$ |
| pIAO-P/L-354 bp | 43 bp of Lambda PvuII fragment between XbaI sites of pIAO-P/L | $2.9 \times 10^{-4}$ |
| pIAO-P/L-589 bp | 579 bp of Lambda PvuII fragment between XbaI sites of pIAO-P/L | $3.2 \times 10^{-4}$ |
| pIAO-P/L-2.2 kb | 2.2 kb of Lambda HindIII fragment between XbaI sites of pIAO-P/L | $3.4 \times 10^{-4}$ |

FIG. 2(A)

Sequence Range: 1 to 7670

```
100  AACGCGCGGGGAGAGGCGGTTGCGTATTGGGCGCTCTTCCGCTTCCTCGCTCACTGACTCGCTGCGCTCGGTCGTTCGGCTGCGGCGAGCGGTATCAGC
200  TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
          >ori
          |——|
300  GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA
400  GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT
500  GGCGCTTTCTCAATGCTCACGCTGTAGGTATCTCAGTTCGGTGTAGTCGTTCGCTCCAAGCTGGGCTGTGTGCACGAACCCCCCGTTCAGCCCGACCGC
600  TGCGCCTTATCCGGTAACTATCGTCTTGAGTCCAACCCGGTCAGCCCACTGGCAGCAGCCACTGGTAACAGGATTAGCAGAGCGAGGT
700  ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT
800  CGGAAAAAGAGTTGGTAGCTCTTGATCTTTTCTACGGGGTCTGACGCTCAGTGGAACGAAAACTCACGTTAAGGGATTTTGGTCATGAGATTATCAAAAAGGATCT
900  TCTCAAGAAGATCCTTTGATCTTTTCTACGGGGTCTGACGCTCAGTGGAACGAAAACTCACGTTAAGGGATTTTGGTCATGAGATTATCAAAAAGGATCT
1000 TCACCTAGATCCTTTTAAATTAAAAATGAAGTTTTAAATCAATCTAAAGTATATATGAGTAAACTTGGTCTGACAGTTACCAATGCTTAATCAGTGAGGC
                                                                                              <W H K I L S A
```

<——— AMP RESIST

FIG. 2(C1)

```
1100
ACCTATCTCAGGCGATCTGTCTATTTCGTTCATCCATAGTTGCCTGTGTAGATAACTACGATACGGGAGGGCTTACCATCTGGCCCAGT
 G  I  E  A  I  Q  R  N  R  E  D  M  T  A  Q  S  G  T  T  Y  I  V  V  I  R  S  P  K  G  D  P  G  L
                                      AMP RESIST

1200
GCTGCAATGATACCGCGAGACCCACGCTCACCGGCTCCCAGATTTATCAGCAGATTGGCAGCCGGAAGGGCCGAGCGCAGAAGTGGTCCTGCAACTT
 A  A  I  I  G  R  S  G  R  E  G  A  G  S  K  D  A  I  F  W  G  A  P  L  A  S  R  L  L  P  G  A  V  K
                                      AMP RESIST

1300
TATCCGCCTCCATCCAGTCTATTAATTGTTGCCGGGAAGCTAGAGTAAGTAGTTCGCCAGTTAATAGTTTGCGCAACGTTGTTGCCATTGCTACAGGCAT
 D  A  E  M  W  D  I  L  Q  Q  R  S  A  L  T  L  L  E  G  T  L  L  K  R  L  T  T  A  M  A  V  P  M
                                      AMP RESIST

1400
CGTGGTGTCAGCGCTCGTCGTTTGGTATGGCTTCATTCAGCTCCGGTTCCCAACGATCAAGGCGAGTTACATGATCCCCATGTTGTGCAAAAAGCGGTT
 T  D  R  E  D  N  P  I  A  E  N  L  E  P  E  W  R  D  L  R  T  V  H  D  G  M  N  H  L  F  A  T
                                      AMP RESIST

1500
AGCTCCTTCGGTCCTCCGATCGTTGTCAGAAGTAAGTTGGCCCAGCAGTGTTATCACTCATGGTTATGCAGCACTGCATAATTCTCTTACTGTCATGCCAT
 L  E  K  P  G  G  I  T  T  L  L  L  N  A  A  T  N  D  S  M  T  I  A  A  S  C  L  E  R  V  T  M  G  D
                                      AMP RESIST

1600
CCGTAAGATGCTTTTCTGTGACTGGTGAGTACTCAACCAAGTCATTCTGAGAATAGTGTATGCGGCGACCGAGTTGCTCTTGCCCGGCGTCAATACGGGA
 T  L  H  K  E  T  V  P  S  Y  E  V  L  D  N  Q  S  Y  H  I  R  R  G  L  Q  E  Q  G  A  D  I  R  S
                                      AMP RESIST

1700
TAATACCGCGCCACATAGCAGAACTTTAAAAGTGCTCATCATTGGAAAACGTTCTTCGGGGCGAAAACTCTCAAGGATCTTACCGCTGTTGAGATCCAGT
 L  V  A  G  C  L  L  V  K  F  T  S  M  M  P  F  R  E  E  P  R  F  S  E  L  I  K  G  S  N  L  D  L
                                      AMP RESIST
```

FIG. 2(C1)a

```
1800
TCGATGTAACCCACTCGTGCACCAACTGATCTTCAGCATCTTTACTTTCACCAGCGTTTCTGGGTGAGCAAAAACAGGAAGCAAAATGCCGCAAAAA
 E  I  Y  G  V  R  A  G  L  Q  D  E  A  D  K  V  L  T  E  P  H  A  F  V  P  L  C  F  A  A  F  F
                                                AMP RESIST
1900
AGGGAATAAGGCGACACGGAAATGTTGAATACTCATACTCTCCTTTTTCAATATATTGAAGCATTTATCAGGTTATTGTCTCATGAGCGGATACAT
 P  I  L  A  V  R  F  H  Q  I  S  M --(SEQ ID NO:58)--
         AMP RESIST
2000
ATTTGAATGTATTTAGAAAAATAAACAAATAGGGGTTCCGCGACATTCCCGAAAAGTGCCACCTGACGTCTAAGAAACCATTATTATCATGACATTA

2100
ACCTATAAAATAGGCGTATCACGGGGCCCTGAGGTGAACCAATTGTCACACGTAATATTACGACAACTACCGTGCACAGGCTTTGATAACTCCTTCACG
 R  Y  F  Y  A  Y  *  P  A  R  L  H  V  L  Q  *  V  Y  *  S  L  *  R  A  C  A  K  I  V  G  E  R
                                                    ORF1 N-TERM [SPLIT]
2200
TAGTATTCACCGAGTGGTACTCCGTTGGTCTGTGTTCCCAAATAAGGCATTCCATTTATCATATACTTCGTACCACTGTCACACATCATGAGGA
 L  I  *  R  T  T  S  R  Q  D  T  N  R  K  G  F  L  A  N  W  K  D  Y  V  E  Y  W  Q  *  V  D  H  P
                                                    ORF1 N-TERM [SPLIT]
2300
TTTTTATTCCATACTTACTGGCTTGTTGGGATATACATCCTAAAACCAAGTAACGGACACCGTCCTCCTAAAACCATCTATGGTCAAATGAGCCCC
 N  K  N  W  V  *  K  A  Q  K  P  Y  V  D  *  V  S  V  R  *  F  W  T  V  T  *  R  H  D  F  S  G  R
                                                    ORF1 N-TERM [SPLIT]
2400
TGGAGTGTAATTTTGTATGCACTGATGGATAAAGAGATCCCATATTTTCTAACAGGAGTAAATACATCGTTTTCTGAAGTGTGGCCGTATACTTTG
 S  H  L  K  T  H  V  S  P  Y  L  S  G  M  N  K  *  C  S  Y  I  C  R  K  R  S  T  H  A  T  Y  K  Q
                                                    ORF1 N-TERM [SPLIT]
```

```
3300
ATGGAAACCGTCGATATTCAGCCATGTGCCTTCTTCCGCGTGCAGCAGATGGCCGATGCTGGTTTCCATCAGTTGCTGTTGTTGACTGTAGCGGCTGATGTTG
<H  F  G  D  I  N  L  W  T  G  E  E  A  H  L  L  H  R  H  S  T  E  M  L  Q  Q  S  Y  R  S  I  N
                                              LACZ

3400
AACTGGAAGTGCCGCCACTGTGTGGGCCATAATTCGGCGGCTCCCAGCGGCAGACCGTTTCGCTCGGGAAGACTACGGGGTATACATGT
<F  Q  F  D  G  R  W  Q  H  P  G  Y  N  L  E  R  T  G  C  R  L  G  N  E  S  P  F  V  Y  P  T  Y  M  D
                                              LACZ

3500
CTGACAATGGCAGATCCCAGCGGTCAAAACAGGCGGTCGGGATAGTTTCTTGCGGCCCTAATCCGAGCCAGTTACCCGCTCTGCTAC
<S  L  P  L  D  W  R  D  F  C  A  A  T  L  R  D  P  Y  N  E  Q  P  G  L  G  L  W  N  V  R  E  A  V
                                              LACZ

3600
CTGCGCCAGCTGGCAGTTCAGGCCAATCCGCGGCCAATGCGGGATGCGTATCGCCCACTTCAACATCAACGGTAATCGCCATTGACCACTACCATCAATC
<Q  A  L  Q  C  N  L  G  I  R  A  P  H  P  T  D  S  A  V  E  V  D  V  T  I  A  M  Q  G  S  G  D  I
                                              LACZ

3700
CGGTAGTTTTCCGGCTGATAAATAAGTTTTCCCCTGATGCTGCCACGCGTGAGCGGTCGTAATCAGCACCGCATCAGCAAGTGTATCGCCGTGCACT
<R  Y  T  K  R  S  I  F  L  T  K  G  Q  H  Q  W  A  H  A  T  T  I  L  V  A  D  A  L  T  D  A  T  C  Q
                                              LACZ

3800
GCAACAACGCTGCTTCCGGCTGTAATGCCCCAGGCGTTAGGTCAATGCGCGTCTTCACTTACGCCAATGTCGTT
<L  L  A  A  E  A  Q  Y  H  G  A  A  K  W  R  E  V  W  A  N  P  D  I  R  T  A  E  S  V  G  I  D  N
                                              LACZ

3900
ATCCAGCGGTGCACGGGTGAACTGATCGCGCAGCAGTTGTTTTTTATCGCCAATCCACATCTGTGAAAGAAAGCCTGACTGGCGGTTAAAT
<D  L  P  A  R  T  F  Q  D  R  L  P  T  L  L  Q  K  K  D  G  I  W  M  Q  S  L  F  G  S  Q  R  N  F
                                              LACZ
```

FIG. 2(C1)d

```
4000
TGCCAACGCTTATTACCAGCTCGATGCAAAAATCCATTTCGCTGGTTGTTCAGATGCGGATGGCGTGGGACGGGGGAGGCGTCACACTGAGGTTTT
<Q V  Q R K N G L E I C F D M E S T  T L  H P I A H S A A P L T V S L N E
                                    LACZ

4100
CCGCCAGACGCCACTGCTGCCAGGCCTTCTGACATGCGGCCTGTTGCCACTACGCGTTGTTCGACTGTGAGCCAGAGTTGCCCGGC
<A L R W Q Q W A S I H G A E S  W A T A N P Q V V R V T L W L Q G A
                                LACZ

4200
GCTCTCCGGCTGCGTAGTTCAGGCAGTTCAATCAACTGTTTACCTTGTGGAGGACATCCAGAGGCACTTCACCGCTTGCCAGCGGCTTACCATCCAGC
<S E P Q P L E P L E I L Q K G  Q P A V D L P V E G S A L P K G D L
                                LACZ

4300
GCCACCATCCAGTGCAGGAGCTCGTTATCGCTATGACGAACAGGTATTCGCTGGTCACTTCGATGGTTGCCCGGATAAACGAACTGAAAAACTGCT
<A V M W H L E N D S H R F L Y E S  T V E I T Q G S L R F Q F F Q Q
                                  LACZ

4400
GCTGGTGTTTGCTCCGTCAGCGCTGATGCGGCGTGCGCAAAGACCAGTCGGCGTTCATACAGAACCGATCGTTCGGCGTATCGCCAAAATC
<Q H K A E T L A P H P T R D A F V L G N M C F Q R D N P T D G F F D
                                    LACZ

4500
ACCGGCCCGTAAGCCGACCACGGTTGCCGTTTTCATCATATATTAATCAGCGACTGATCCACCCAGTCCCAGACGAAGCCCCTGTAAACGGGGATACTGA
<G G Y A S W P N G N E D Y K I L S  Q D V W D W V F G G Q L R P Y Q
                                  LACZ

4600
CGAAAACGCCTGCCAGTATTAGCGAAACCGCCAAGACTGTTACCCATGCGTGGGCGTATTCGCAAAGGATCAGCGGCGCGTCTCCAGTAGCGAAA
<R F A Q W Y K A F G G L S N G M A H A Y E C L I L P R T E G P L S L
                                LACZ
```

FIG. 2(C1)e

```
4700
GCCATTTTTGATGGACCATTTCGGCACAGCCGGAAGGGCTGGTCTTCATCCACGGGCGTACATCGGGCAAATAATATCGGTGTGGCCGTGTGTCGGC
 W  K  K  I  S  W  K  P  V  A  P  F  P  Q  D  E  D  V  R  A  Y  M  P  C  I  I  D  T  A  T  T  D  A
                                                    LACZ

4800
TCCGCCGCCCTTCATACTGCACCGGGGCGGGGAAGGATCGACAGATTTGATCCAGCCGATACAGCCGCGTCGTGATTAGCGCCGTGATTCATTCCCAGC
 G  G  G  E  Y  Q  V  P  R  S  P  D  V  S  K  I  W  R  Y  L  A  D  H  N  A  G  H  S  E  N  G  L
                                                    LACZ

4900
GACCAGATGATCACACTCGGGTGCCGGTGATTACGATCCGCTGCACCATTCGCGTTACGCGTTCGCTCATCGGGTAGCCAGCGGGATCATCGGTCAGACGAT
 S  W  I  I  V  S  P  H  N  R  D  R  Q  V  M  R  T  V  R  E  S  M  A  P  L  W  R  P  D  D  T  L  R  N
                                                    LACZ

5000
TCATTGGCACCATGCCGTGGGTTTCAATATTGCTTCATCCACCACATACAGGCCGTAGCGTCGCACAGCGTGTACCACAGCGGATGGTTCGGATAATG
 M  P  V  M  G  H  T  E  I  N  A  E  D  V  V  Y  L  G  Y  R  D  C  L  T  Y  W  L  P  H  N  P  Y  H
                                                    LACZ

5100
CGAACAGGGCACGGGCGTTAAAGCGGGTTAAGTTGTTCTGCTTCATCAGCAGGATATCCTGCACCATCGTCTGCTCATCCATGCAGAGGATGATGCTCG
 C  R  V  A  N  F  N  N  Q  K  M  L  L  I  D  Q  V  M  T  Q  E  D  M  V  Q  G  H  L  P  H  H  E
                                                    LACZ

5200
TGACGGTTAACGCCTCGAATCAGCAACGGCTTGCCGTTCAGCAGCAGAGACCATTTTCAATCCGGAATCTCGCGGAAACCGACATGCAGGCTTCTGCTT
 H  R  N  V  G  R  I  L  L  P  K  G  N  L  L  L  G  N  E  I  R  V  E  R  F  G  V  D  C  A  E  A  E
                                                    LACZ

5300
CAATCAGCCGTGCCGCTCGGCCGTGTGCAGTTCAACCACCGACGATAGAGATTCGGGATTTCCGACGTTCAGACGTAG
 I  L  T  G  D  A  T  H  L  E  V  V  A  R  Y  L  N  P  I  E  A  S  W  L  K  P  N  E  V  N  L  R  L
                                                    LACZ
```

*FIG. 2(C1)f*

```
5400
TGTGACGCGGATCGGCATAACCACCAGCGCTCATCGATAATTTCACCGCCCGAAAGGCGCGGTTGCCGCTGCGTTCACCCTGCCATAAAGAAACT
<V  T  V  R  D  A  Y  G  G  R  E  D  I  I  E  G  G  E  P  A  T  G  S  A  V  Q  T  E  G  Q  W  L  S  V
                                                LACZ

5500
GTTACCCGTAGGTAGTCACGCAACTCGCCCGCACATCTGAACTTCAGCCTCCAGTACAGCCGGGCTGAAATCATTAAAGCGAGTGGCAACATGGAAAT
<V  T  V  R  L  Y  D  R  L  E  G  C  M  Q  V  E  A  E  L  V  A  R  S  F  D  D  N  F  R  T  A  V  H  F  D
                                                LACZ

5600
CGCTGATTTGTGTAGTCGGTTTATGCAGCAACGAGACGTCACGGAAAATGCCGCTCATCGCCACATATCCTGATCTTCCAGATAACTGCCGTCACTCCA
<V  S  I  Q  T  T  P  K  H  L  L  S  V  D  R  F  I  G  S  M  R  W  M  D  Q  D  E  L  Y  S  G  D  S  W
                                                LACZ

5700
ACGCAGCACCATCACCGGGAGGGCGGTTTCTCCCGGCGCTAAAAATGCGCTCAGTTCAAATTCAGACGGCAAACGACTGTCCTGGCCGTAACCGACCCAG
<V  R  L  V  M  V  A  L  R  N  E  G  A  R  L  F  A  S  L  D  F  E  S  P  L  R  S  D  Q  G  Y  G  V  W
                                                LACZ

5800
CGCCCGTTGCACCACAGATGAAACGCCGAGTTAACGCCATCAAAATAATTCGCGTCCTGTAGCCAGCTTTCATCAACATTAAATGTGAGCG
<V  R  G  N  C  W  L  H  F  A  S  N  V  G  D  F  I  I  R  T  Q  G  E  Q  L  W  S  E  D  V  N  F  T  L  S
                                                LACZ

5900
AGTAACAACCCGTCGGATTCTCCGTGGGAACAAACGGCGGATTGACCGTAATGGGATAGTTACGTTGGTGTAGATGGGCCATCGTAACCGTGCATCTG
<V  Y  C  G  T  P  N  E  T  P  V  F  P  P  P  N  V  T  I  P  Y  T  V  N  T  Y  I  P  A  D  Y  G  H  M  Q
                                                LACZ
```

```
6000 CCAGTTTGAGGGACGACGACGGGATCCGTTTTTTATTACAAACTGTTACGAAAACAGTAAATACTTATTTATTCGGACCAACAATGTTATTCTTA
     <__ ORF1 N-TERM [S                                                 <V  L  L  T  *  E  *
   <W  N  S  P  V  V  P  D  T  K  K  N  C  F  Q  *   S  F  L  L  I  S  I  *   E  S  W  C --(SEQ ID NO:60)--
                                                LACZ
6100 CCTCTAATAGTCCTCTGTGGCAAGGTCAAGATTCTGTTAGAAGCCAATGAAGAACCTGGTTGTTCAATAACATTTGTCGTCTAATATTCCACTACGCT
   <R  *   Y  D  E  T  A  L  D  L  N  Q  *   F  G  I  F  F  R  T  T  *   Y  C  K  T  R  R  I  N  *  *  A
                                              ORF1 N-TERM [SPLIT]
6200 TGACGTTGGCTGACACTTCATGTACCTCATCTATAAACGCTTCTTCTGTATCGCTCTGGACGTCTCACTTACGTGATCTGATATTTCACTGTCAGAATC
   <Q  R  Q  S  V  S  *   T  G  *   R  Y  V  S  R  R  Y  R  E  P  R  R  *   K  R  S  R  R  I  N  *   Q  *  F  G
                                              ORF1 N-TERM [SPLIT]
6300 CTCACCAACAAGCTCGTCATCCGCCTTGCAGAAGAGCAGAGGATATGCCTAAAGAACATCCATTTATTATATATTAGTCACGATATCTAT
   <*  W  C  A  R  *   R  R  A  S  S  C  L  P  Y  A  *   R  R  F  F  M  G  A --(SEQ ID NO:61)--
                                              ORF1 N-TERM [SPLIT]
6400 AACAAGAAAATATATATATAAGTTATCACGTAAGTAGAACATGAAATAACAATATTAATTATCGTATGAGTTAAATCTTAAAAGTCACGTAAAAGAT
6500 AATCATGCCGTCATTTTGACTCACGCGGTCGTTATAGTTCAAAATCAGTGACACTTACCGCCATTGACAAGCACGCCTCAGCCGAGCTCCAAGCGGCGACTG
6800 AGATGTCCTAAATTGCAAACAGGCGACGGATTCGCGCAGGATTCGCGGCTATTGAAAAGAGAGAGAGCAATATTTCAAGAATGCGTCAATTTACGCAGACTATCTTCT
                                                            RIGHT TERMINAL REPEAT _____>
```

FIG. 2(C1)i

```
6700
AGGGTTAATCTAGCTTTCTAATTTAACCTTTGTCAGGTTACCAACTACTAAGGTTGTAGGCTCAAGAGGGTGTGTCCTGCTAGGTAAAATAACTGACC
 <K  R  I  *  G  K  D  P  *  W  S  S  L  N  Y  A  *  S  P  T  D  Q  R  L  Y  I  V  S  R
      EA31 (296); CODON START=1; DB XREF=PID:G215131; TRA [SPLIT]
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]
  ∧
  ∨ ∨∨∨
6800
TGTCGAGCTTAAATATTCTATATGTGTTCTTTCTGCAAAAAACTGGGAAGTGAGTAATGAAATTATTCTAACATTTATCTGCATCATACCTTCCGAG
 <D  L  K  I  N  *  I  T  T  R  E  A  F  F  H  P  L  S  Y  H  F  *  K  *  C  K  D  A  D  Y  R  G  L
      EA31 (296); CODON START=1; DB XREF=PID:G215131; TRA [SPLIT]
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]
  ∧
  ∨∨∨
6900
CATTTATTAAGCATTTCGCTATAAGTTCTCGCTGAAGAGGTAGTTTTTCATTGTACTTACCTTCATCTCTGTTCATTATCATCGCTTTAAAACGGT
 <M  *  *  A  N  R  *  -- (SEQ ID NO:64)--
      EA31 (296); CO
             EA59 (525); CODON START=1; DB XREF=PID:G215132; TRA
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]
  ∧
  ∨∨∨
                        <S  Y  T  R  A  P  L  P  L  K  K  M  T  S  *  R  *  R  Q  E  N  D  D  S  K  F  R  N
```

```
7400
TGCTACTGACATTATGGCTGTATATAATAAAGAATTTATGCAGGCAATGTTTATCATTCCGTACAATAATGCCATAGGCCACCTATTCGTCTTCCTACT
<S  S  V  N  H  S  Y  I  I  F  S  N  I  C  A  I  N  I  M  G  Y  L  L  A  M  P  W  R  N  T  K  R  S
                                         ORF1 C-TERM
<V

7500
GCAGGTCATCACAGAACACATTTGGTCTAGGCGTGTCCACTCCGCCTTTAGTTTGATTATAATACATAACCATTTGCGGTTTACCGGTACTTTCGTTGATA
<C  T  M  V  S  S  C  M  Q  D  L  T  D  V  G  G  K  T  Q  N  Y  Y  M  V  M  Q  P  K  G  T  S  E  N  I
                                         ORF1 C-TERM
<V

7600
GAAGCATCCTCATCACAAGATGATAATAAGTATACCATCTTAGCTGGCTTCCGGTTTATATGAGACGAGAGTAAGGGGTCCGTCAAAACAAAACATCGATG
<S  A  D  E  D  C  S  S  L  L  Y  V  M  K  A  P  K  P  K  Y  S  V  L  T  L  P  G  D  F  C  F  M  S  T
                                         ORF1 C-TERM
<V

TTCCCACTGGCCTGGAGGACTGTTTTCAGTACTTCCGGTATCTCCGCGTTTGTTTGATCGCACGGTACC  --(SEQ ID NO:57)--
<G  V  P  R  S  R  S  N  K  L  V  E  P  I  E  R  K  N  S  R  V  T  G    --(SEQ ID NO:62)--
                ORF1 C-TERM
```

*FIG. 2(C1)j* pIAO-P/L-Lambda-2.2kb

Sequence Range: 1 to 9984

100
AACGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGC

200
TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
>Ori

300
GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA

400
GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT

500
GGCGCTTTCTCAATGCTCACGCTGTAGGTATCTCAGTTCGGTGTAGGTCGTTCGCTCCAAGCTGGGCTGTGTGCACGAACCCCCCGTTCAGCCCGACCGC

600
TGCGCCTTATCCGGTAACTATCGTCTTGAGTCCAACCCGGTAAGACACGACTTATCGCCACTGGCAGCAGCCACTGGTAACAGGATTAGCAGAGCGAGGT

700
ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT

800
CGGAAAAAGAGTTGGTAGCTCTTGATCCGGCAAACAAACCACCGCTGGTAGCGGTGGTTTTTTTGTTTGCAAGCAGCAGATTACGCGCAGAAAAAAGGA

900
TCTCAAGAAGATCCTTTGATCTTTTCTACGGGGTCTGACGCTCAGTGGAACGAAAACTCACGTTAAGGGATTTTGGTCATGAGATTATCAAAAAGGATCT

*FIG. 2(C2)*

```
1000
TCACCTAGATCCTTTAAATTAAAAATGAAGTTTTAAATCAATCTAAAGTATATATGAGTAAACTTGGTCTGACAGTTACCAATGCTTAATCAGTGAGGC
                                                                    <W  H  K  I  L   S  A
                                                                    <      AMP RESIST

1100
ACCTATCTCAGGCGATCTGTCTATTTCGTTCATCCATAGTTGCCTGACTCCCCGTCGTGTAGATAACTACGGGATACGGGAGGGCTTACCATCTGGCCCCAGT
<G  I  E  A  I  Q  R  N  R  E  D  M  T  A  Q  S  G  T  T  Y  I  V  V  I  R  S  P  K  G  D  P  G  L
<                                         AMP RESIST

1200
GCTGCAATGATACCGCGAGACCCACGCTCACCGGCTCCAGATTTATCAGCAATAAACCAGCCAGCCGGAAGGGCCGAGCGCAGAAGTGGTCCTGCAACTT
<A  A  I  G  R  S  G  R  E  G  A  G  S  K  D  A  I  F   W  G  A  P  L  A  S  R  L  L  P  G  A  V  K
<                                         AMP RESIST

1300
TATCCGCCTCCATCCAGTCTATTAATTGTTGCCGGGAAGCTAGAGTAAGTTCGCCAGTTAATAGTTTGCGCAACGTTGTTGCCATTGCTACAGGCAT
<D  A  E  M  W  D  I  L  Q  Q  R  S  A  L  T  L  L  E  G  T  L  L  K  R  L  T  T  A  M  A  V  P  M
<                                         AMP RESIST

1400
CGTGGTGTCACGCTCGTCGTTTGGTATGGCTTCATTCAGCTCCGGTTCCCAACGATCAAGGCGAGTTACATGATCCCCATGTTGTGCAAAAAAGCGGTT
<T  D  R  E  D  N  P  I  A  E  N  L  E  P  E  W  R  D  L  R  T  V  H  D  G  M  N  H  L  F  A  T
<                                         AMP RESIST

1500
AGCTCCTTCGGTCCTCCGATCGTTGTCAGAAGTAAGTTGGCCGCAGTGTTATCACTCATGGTTATGGCAGCACTGCATAATTCTCTTACTGTCATGCCAT
<L  E  K  P  G  G  I  T  T  L  L  L  N  A  A  T  N  D  S  M  T  I  A  A  S  C  L  E  R  V  T  M  G  D
<                                         AMP RESIST

1600
CCGTAAGATGCTTTTCTGTGACTGGTGAGTACTCAACCAAGTCATTCTGAGAATAGTGTATGCGGCGACCGAGTTGCTCTTGCCCGGCGTCAATACGGGA
<T  L  H  K  E  T  V  P  S  Y  E  V  L  D  N  Q  S  Y  H  I  R  R  G  L  Q  E  Q  G  A  D  I  R  S
<                                         AMP RESIST
```

*FIG. 2(C2)a*

```
1700
     TAATACCGCGCCACATAGCAGAACTTTAAAAGTGCTCATCATTGGAAAACGTTCTTCGGGGCCGAAAACTCTCAAGGATCTTACCGCTGTTGAGATCCAGT
    <L  I  T  R  A  H  I  A  E  L  *  S  A  H  H  W  K  T  F  F  G  G  E  N  S  Q  D  L  T  A  V  E  I  Q  <
    <V  Y  R  A  P  T  S  R  T  L  K  V  L  I  I  G  K  R  S  S  G  R  K  T  L  K  D  L  T  L  *  R  S  P  <
    <L  V  A  G  C  L  L  V  K  F  T  S  M  M  P  F  R  E  E  P  R  F  S  E  L  I  K  G  S  N  L  D  L  <
                                      AMP RESIST

1800
     TCGATGTAACCACTCGTGCACCCAACTGATCTTCAGCATCTTTTACTTTCACCAGCGTTTCTGGGTGAGCAAAAACAGGAAGGCAAAATGCCGCAAAAA
    <S  M  *  P  L  V  H  P  T  D  L  Q  H  L  L  L  S  P  A  F  L  G  E  Q  K  Q  E  G  K  C  R  K  <
    <R  C  N  P  L  C  T  Q  L  I  F  S  I  F  Y  F  H  Q  R  F  W  V  S  K  N  R  K  A  N  A  A  K  <
    <E  I  Y  G  V  R  A  G  L  Q  D  E  A  D  K  V  K  V  L  T  E  P  H  A  F  V  P  L  C  F  A  A  F  F  <
                                      AMP RESIST

1900
     AGGGAATAAGGGCGACACGGAAATGTTGAATACTCATATCTCTCCTTTTTCAATATATTATTGAAGCATTTATCAGGGTTATTGTCTCATGAGCGGATACAT
    <R  E  *  G  R  H  G  N  V  E  Y  S  Y  L  S  L  F  Q  Y  I  I  E  A  F  I  R  V  I  V  S  *  R  D  T  <
    <G  K  *  G  D  T  E  M  L  N  T  H  I  S  P  F  F  N  I  L  L  K  H  L  S  G  L  L  S  H  E  R  I  H  <
    <P  I  L  A  V  R  F  H  Q  I  S  M  --(SEQ ID NO:58)--
                                      AMP RESIST

2000
     ATTTGAATGTATTTAGAAAAATAGGGCGTTCCGCGCACATTTCCCGAAAAGTGCCACCTGACGTCTAAGAAACCATTATTATCATGACATTA
    <I  *  N  V  F  R  K  I  G  R  S  A  H  F  P  E  K  C  H  L  T  S  K  K  P  L  L  S  *  H  *  <
    <F  E  C  I  *  E  N  R  A  F  R  A  H  F  P  R  K  V  P  P  D  V  *  E  T  I  I  I  M  T  L  <

2100
     ACCTATAAAATAGGCGTATCACGGGCCCTGAGGTGAACCAATTGTCACACGTAATATTACGACAACTACCGTGCACAGGCTTTGATAACTCCTTCACG
    <T  Y  K  I  G  V  S  R  A  L  R  *  T  N  C  H  T  *  Y  Y  D  N  Y  R  A  Q  A  L  I  T  P  S  R  <
    <P  I  K  *  A  Y  H  G  P  *  G  E  P  I  V  T  R  N  I  T  T  T  T  V  H  R  L  *  *  L  L  H  <
    <R  Y  F  Y  A  Y  *  P  A  R  L  H  V  L  Q  *  V  Y  *  S  L  *  R  A  C  A  K  I  V  G  E  R  <
                                                    ORF1 N-TERM [SPLIT]

2200
     TAGTATTCACCGAGTGTACTCCGTTGTTCTGTGTCCTTCCCAAATAAGGCATTCCATTTATCATATACTTCGTACCACTGTCACACATCATGAGGA
    <*  Y  S  P  S  V  L  R  C  S  V  S  F  P  N  K  A  F  H  L  S  Y  T  S  Y  H  C  H  T  S  *  <
    <S  I  H  R  V  Y  S  V  V  L  C  P  S  Q  I  R  H  S  I  Y  I  L  R  T  T  V  T  H  *  E  <
    <L  I  *  R  T  T  S  R  Q  D  T  N  R  K  G  F  L  A  N  W  K  D  Y  V  E  Y  W  Q  *  V  D  H  P  <
                                      ORF1 N-TERM [SPLIT]

2300
     TTTTTATTCCATACTTACTGGCTTGTTTGGGATATACATCCTAAAACCAAGTAACGTCCTCTAAAACCAAGTAACGACACCGTCTATGTCAAATGAGCCCC
    <F  L  F  H  T  Y  W  L  V  W  D  I  H  P  K  T  K  *  R  P  L  K  P  S  N  D  *  L  F  H  L  *  S  P  <
    <F  Y  S  I  L  T  G  L  F  G  I  Y  I  L  K  P  S  N  V  L  *  N  Q  V  T  T  P  L  C  Q  M  S  P  <
    <N  K  N  W  V  *  K  A  Q  K  P  Y  V  D  *  V  S  V  T  R  *  F  W  T  V  T  *  R  H  D  F  S  G  R  <
                                      ORF1 N-TERM [SPLIT]
```

```
3200
ATTTTTGACACCAGACCAACTGTAGCGACCGGCTCGCCGATACTGACGGGCTCTCCAGGAGTCTGCTCCACCAATCCCCAT
<K  Q  C  W  V  L  Q  Y  H  Y  R  G  A  S  L  Q  F  E  A  S  V  S  P  S  W  S  D  D  G  G  I  G  M
V V                                         LACZ

3300
ATGGAAACCGTCGATATTCAGCCATGTGCCTTCTTCCGGTGCAGCAGATGGCGATGGCTGGTTTCCATCAGTTGCTGTTGACTGTAGCGGCTAGCGATGTTG
<H  F  G  D  I  N  L  W  T  G  E  E  A  H  L  L  H  R  H  S  T  E  M  L  Q  Q  Q  S  Y  R  S  I  N
V V                                         LACZ

3400
AACTGGAAGTCGCCGCGCCACTGGTGTGTGGGCCATAATTCGCGCCGTCCCGCAGCGCAGACCGTTTCGCTCGGGAAGACGTACGGGTATACATGT
<F  Q  F  D  G  R  W  Q  H  P  G  Y  N  L  E  R  T  G  C  R  L  G  N  E  S  P  F  V  Y  P  T  Y  M  D
V V                                         LACZ

3500
CTGACAATGGCAGATCCCAGCGGTCAAAACAGGCGGTCAGTAAGGCGGTCGGGATAGTTTTCTTGCGGCCCTAATCCGAGCCAGTTACCGCTCTGCTAC
<S  L  P  L  D  W  R  D  F  C  A  A  T  L  R  D  P  Y  N  E  Q  P  G  L  G  L  W  N  V  R  E  A  V
V V                                         LACZ

3600
CTGCGCCAGCTGGCAGTTCAGCGCCAATCCGCGCCGGATGCGGTGTATCGCGCCACTTCAACATCAACGTAATCGCCATTGACCACTACCATCAATC
<Q  A  L  Q  C  N  L  G  I  R  A  P  H  P  T  D  S  A  V  E  V  D  V  T  I  A  M  Q  G  S  G  D  I
V V                                         LACZ

3700
CGGTAGGTTTCCGGCTGATAATAAGGTTTCCCTGATGCTGCAACGCGTCGTAATCAGCACCGCCGATCAGCAGTGTATCTGCCGTGCACT
<R  Y  T  K  R  S  I  F  L  T  K  G  Q  H  Q  W  A  H  A  T  T  I  L  V  A  D  A  L  T  D  A  T  C  Q
V V                                         LACZ

3800
GCAACAACGCTGCTTCCGGCTTCCGCCTGGCTAATGGCCCCGCCCTTCCAGCGTTCGACCGTTCAATGGGTTAGGGTCAATGCGCTTCACTTACGCCAATGTCGTT
<L  A  A  E  A  Q  Y  H  G  A  A  K  W  R  E  V  W  A  N  P  D  I  R  T  A  E  S  V  G  I  D  N
V V                                         LACZ
```

FIG. 2(C2)d

```
3900
ATCCAGCGGTGCACGGGTGAACTGATCGCGCAGCGGCGTCAGCAGTTGTTTTTATCGCCAATCCACATCTGTGAAAGAAAGCCTGACTGGCGGTTAAAT
< D  L  P  A  R  T  F  Q  D  R  L  P  T  L  L  Q  K  D  G  I  W  M  Q  S  L  F  G  S  Q  R  N  F
                                                  LACZ
4000
TGCCAACGGCTTATTACCCAGCTCGATGCAAAAATCCATTTCGCTGGTGGTCAGATGCGGGATGCGGGAGCGCGGACGCGTCACACTGAGGTTTT
< Q  W  R  K  N  G  L  E  I  C  F  D  M  E  S  T  L  H  P  I  A  H  S  A  A  P  L  T  V  S  L  N  E
                                                  LACZ
4100
CCGCCAGAGCGCCACTGCTGCCAGGCGCTGATGTGCCCGGCTTCTGACCATGCGGTCGGTTGCACTACGGCGTACTGTGAGCCAGAGTTGCCCGGC
< A  L  R  W  Q  Q  W  A  S  I  H  G  A  E  S  W  A  T  A  N  P  Q  V  V  R  V  T  L  W  L  Q  G  A
                                                  LACZ
4200
GCTCTCCGGCTGCGTGAGTTCAGGCAGTTCAATCAACTGTTTACCTTGCAGGGCTGATCCAGAGGCCACTTCACCGCTTGCCAGCGGCTTACCATCCAGC
< S  E  P  Q  P  L  E  P  L  E  I  L  Q  K  G  Q  P  A  V  D  L  P  V  E  G  S  A  L  P  K  G  D  L
                                                  LACZ
4300
GCCACCATCCAGTGCAGGAGCTCGTTATGACGGAACAGGTATTCGCTGGTCACTTCGATGGTTTGCCCGGATAAACGGAACTGGAAAAACTGCT
< A  V  M  W  H  L  L  E  N  D  S  H  R  F  L  Y  E  S  T  V  E  I  T  Q  G  S  L  R  F  Q  F  F  Q
                                                  LACZ
4400
GCTGGTGTTTGCTTCCGTCAGGATGCTGGATCCGGCAAAGACCAGTCGTTCGGCGATCGTTCGGCGTATCGCCAAAATC
< Q  H  K  A  E  T  L  A  P  H  P  T  R  D  A  F  V  L  G  N  M  C  F  Q  R  D  N  P  T  D  G  F  D
                                                  LACZ
4500
ACCGCCGTAAGCCGACCACGGGTTGCCGTTTTCATCATATTTAATCAGCGACTGATCCACCCAGTCCCAGACGAAGCCCCTGTAAACGGGATACTGA
< G  G  Y  A  S  W  P  N  G  N  E  D  Y  K  I  L  S  Q  D  V  W  D  W  V  F  G  G  Q  L  R  P  Y  Q
                                                  LACZ
```

*FIG. 2(C2)e*

```
4600
CGAAACGCCCTGCCAGTATTTAGCGAAACCGCCAAGACTGTTACCATGCGGTGGGCGTGTATTCGCAAAGGATCAGGCGGCGCGTCTCTCCAGTAGCGAAA
 <R  F  A  Q  W  Y  K  A  F  G  G  L  S  N  G  M  A  H  A  Y  E  C  L  I  L  P  R  T  E  G  P  L  S  L
                                              LACZ

4700
GCCATTTTTTGATGGACCATTTCGGCAGACCGGGAAGGGCTGTCTTTCATCCACGCGGCGGTACATCGGGCAAATAATATCGTGGCCGTGTGTCGGC
 <W  K  K  I  S  W  K  P  V  A  P  P  Q  D  E  D  V  R  A  Y  M  P  C  I  D  T  A  T  T  D  A
                                              LACZ

4800
TCCGCCGCCTTCATACTGCACCGGGGCGGGAAGGATCGACAGATTTGATCCAGCGCGTCGTGATTAGCGCCGTGGCCTGATTCATTCCCAGC
 <G  G  G  E  Y  Q  V  P  R  S  P  D  V  S  K  I  W  R  Y  L  A  D  H  N  A  G  H  G  S  E  N  G  L
                                              LACZ

4900
GACCAGATGATCACACTCGGGTGATTACGACCATTCGCGCTTCGCTCATCGCCGGTAGCCAGCGCGGATCATCGGTCAGACGAT
 <S  W  I  I  V  S  P  H  N  R  D  R  Q  V  M  R  T  V  R  E  S  M  A  P  L  W  R  P  D  D  T  L  R  N
                                              LACZ

5000
TCATTGGCACCATGCCGTTGGGTTTCAATATTGGCTTCATCCACAGCCGGTCGCCGTAGCGGTGCACACAGCCGTGTACCACAGCGGATGGTTCGGATAATG
 <M  P  V  M  G  H  T  E  I  N  A  E  D  V  V  Y  L  G  Y  R  D  C  L  T  Y  W  L  P  H  N  P  Y  H
                                              LACZ

5100
CGAACAGGCGCACGGCGTTAAAGTTGTTCTGCTTCATCAGGATATCCTGCAGCATCGTCTGCTCATCCATGCAGAGGATGATGCTCG
 <S  C  R  V  A  N  F  N  N  Q  K  M  L  L  I  D  Q  V  M  T  Q  E  D  M  V  Q  G  H  L  P  H  H  E
                                              LACZ

5200
TGACGGTTAACGCCTCGAATCAGCAACGGCTTGCCTTCAGCAGCAGCAGACCATTTCAATCCGCACCTCGGGGAAACCGACATCGCAGGCTTCTGCTT
 <H  R  N  V  G  R  I  L  L  P  K  G  N  L  L  L  G  N  E  I  R  V  E  R  F  G  V  D  C  A  E  A  E
                                              LACZ
```

*FIG. 2(C2)f*

```
5300
CAATCAGCGGTGCCCTCGGCGGTGTGCAGTTCAACCACCGCACGATAGAGATTCGGCGGATTTCGGCGCTCCACAGTTTCGGGTTTTCGACGTTCAGACGTAG
<I  L  T  G  D  A  T  H  L  E  V  V  A  R  Y  L  N  P  I  E  A  S  W  L  K  P  N  E  V  N  L  R  L
                                                                    LACZ

5400
TGTGACGGCGATCGGCATAACCACCACGCTCATCGATAATTTCACCGCCGGAAAGGCGGGTCCGCTGGCCGGACCTGCGTTTCACCCTGCCATAAAGAAACT
<T  V  R  D  A  Y  G  G  R  E  D  I  I  E  G  G  F  P  A  T  G  S  A  V  Q  T  E  G  Q  W  L  S  V
                                                                    LACZ

5500
GTTACCCGTAGGTAGTCACGCAACTCGCCCGCACATCTGAACTTCAGCGTACAGAGCCTGAAATCATCATTAAAGCGAGTGCAACATGAAAT
<T  V  R  L  Y  D  R  L  E  G  C  M  Q  V  E  A  E  L  V  A  R  S  F  D  D  N  F  R  T  A  V  H  F  D
                                                                    LACZ

5600
CGCTGATTGTGTAGTCGGTTATGCAGCAACGAGACGTTCACGGAAAATGCCGCTCATCCGCCACATATCCTGATCTTCCAGATAACTGCCGTCACTCCA
<S  I  Q  T  T  T  P  K  H  L  L  S  V  D  R  F  F  I  G  S  M  R  W  M  D  Q  D  E  L  Y  S  G  D  S  W
                                                                    LACZ

5700
ACGCAGCAGCACCATCACGCGGAGGCGGTTTCTCCGGGCGTAAAAAATGCGCTCAGTCAAATTCAGACGGCAAACGACTGTCCTGGCCGTAACGACCCAG
<R  L  V  M  V  A  L  R  N  E  G  A  R  L  F  A  S  L  D  F  E  S  P  L  R  S  D  Q  G  Y  G  V  W
                                                                    LACZ

5800
CGCCCGTTGCACCAGATGAAACGCCAGTTAACGCCATCAAAATAATTCGCTTCCTGAGCCAGCTTTCATCAACATTAAATGTGAGCG
<R  G  N  C  W  L  H  F  A  S  N  V  G  D  F  I  R  T  Q  G  E  Q  L  W  S  E  D  V  N  F  T  L  S
                                                                    LACZ

5900
AGTAACAACCCGCTCGGATTCTCCGTGGGAACAAACGGGCGGATTGACCGTAATGGGCATCGTAACCGTGCATCTG
<Y  C  G  T  P  N  E  T  P  V  F  P  P  N  V  T  I  P  Y  T  V  N  T  Y  I  P  A  D  Y  G  H  M  Q
                                                                    LACZ
```

*FIG. 2(C2)g*

```
6000
CCAGTTTGAGGGGACGACGAGACGGGATCCGTTTTTTTATTACAAAAACTGTTACGAAAACAGTAAAATACTTATTTATTCGGACCAACAATGTTTATTCTTA
<W  N  S  P  V  V  V  P  D  T  K  K  N  C  F  Q  *   S  F  L  L  I  S  I  *  E  S  W  C --(SEQ ID NO:60)--
                                                LACZ                                <V  L  L  T  *  E  *
                                                                                    <___ORF1 N-TERM [S

6100
CCTCTAATAGTCCTCTGTGGCAAGTTCAAGATTCTGTTAGAAGCCAATGAAGAACCTGGTTGTTCAATAACATTTTGTTCGTCTAATATTTCACTACGCT
<R  *  Y  D  E  T  A  L  D  L  N  Q  *  F  G  I  E  F  R  T  *  Y  C  K  T  R  R  I  N  *  *  A
                                    ORF1 N-TERM [SPLIT]

6200
TGACGTTGGCTGACACTTCATGTACCTACTCCATCTATAAACGCTTCTTCTGTATCGCTCTGGACGTCTTCACTTACGTGATCGATATTCACTGTCAGAATC
<Q  R  Q  S  V  S  *  T  G  *  R  Y  V  S  R  R  Y  R  E  P  R  R  *  K  R  S  R  I  N  *  Q  *  F  G
                                                ORF1 N-TERM [SPLIT]

6300
CTCACCACCAACAAGCTCGTCATGCCTTGAGAAGAGAGAGGATATGCTCATCGTCTAAAGAACATCCCATTTTATTATATATTAGTCACGATATCTAT
<*  W  C  A  R  *  R  R  A  S  S  C  L  P  Y  A  *  R  R  F  F  M  G  A --(SEQ ID NO:61)--
<___ORF1 N-TERM [SPLIT]

6400
AACAAGAAAATATATATATAAGTAGAACATGAAATAACATGATTATCGTATGAGTTAAATCTTAAAAGTCACGTAAAAGAT

6500
AATCATGCGTCATTTGACTCACGCGGTCGTTATAGTTCAAAATCAGTGACACTTACCGCATTGACAAGCACGCCTCAGCCGAGCTCCAAGCCGGCGACTG

6600
AGATGTCCTAAATTGCAAACAGCAGCGGATTCGCGCTATTTAGAAAGAGAGCAATATTTCAAGAATGCATGCGTCAATTTTACGCAGACTATCTTTCT
                                                                                RIGHT TERMINAL REPEAT  >
```

*FIG. 2(C2)h*

```
6700
AGGGTTAAATCTAGCTTTTCTAATTTAACCTTTGTCAGGTTACCAACTACTAAGGTTGTAGGCTCAAGAGGGTGTGTCCTGTCGTAGTAAATAACTGACC
 <K R I * G K D P * W S S L N Y A * S P T D Q R L Y I V S R
     EA31 (296); CODON START=1; DB XREF=PID:G215131; TRA [SPLIT]
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

6800
TGTCGAGCTTAATATTCTATATTGTTGTTCTTTCTGCAAAAAAGTGGGGAAGTGAGTAATGAAATTATTTCTAACATTTATCTGCATCATACCTTCCGAG
 <D L K I N * I T T R E A F F H P L S Y H F * K * C K D A D Y R G L
     EA31 (296); CODON START=1; DB XREF=PID:G215131; TRA [SPLIT]
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

6900
CATTTATTAAGCATTCGCTATAAGTTCGCTGGAAGAGGTAGTTTTTCATTGTACTTTACCTTCATCTCTGTTCATTATCATCGCTTTTAAACGGT
 <M * * A N R * --(SEQ ID NO: 64)--
     EA31 (296); CO
 <S Y T R A P L P L K K M T S * R * R Q E N D D S K F R N
     EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
```

*FIG. 2(C2)i*

```
7000 TCGACCTTCTAATCCTATCTGACCATTATAATTTTTAGAATGGTTTCATAAGAAAGCTCTGAATCAACGGACTGCGATAATAAGTGTGGTATCCAGAA
     <S R R I R D S W * L K K S H N * L F A R F * R V A I I L P P I W F
     EA59 (525); CODON START=1; DB XREF=PID:G215132; TRA
     MRNA-PL (ALT.; VIA T'J4 TERMINATOR) [SPLIT]
     MRNA-PL (ALT.; VIA T'J3 TERMINATOR) [SPLIT]
     MRNA-PL (ALT.; VIA T'J2 TERMINATOR) [SPLIT]
     MRNA-PL (ALT.; VIA T'J1 TERMINATOR) [SPLIT]

7100 TTTGTCACTTCAAGTAAAAACACCTAGTTAAAACACCTCACGAGTTCTCACCGAATGTCTCAATATCCGACGGATAATATTTATTGCTTCTCTTGACC
     <K D S * T F V G * S N F C R L E * R I D * Y G S P Y Y K N S R K V
     EA59 (525); CODON START=1; DB XREF=PID:G215132; TRA
     MRNA-PL (ALT.; VIA T'J4 TERMINATOR) [SPLIT]
     MRNA-PL (ALT.; VIA T'J3 TERMINATOR) [SPLIT]
     MRNA-PL (ALT.; VIA T'J2 TERMINATOR) [SPLIT]
     MRNA-PL (ALT.; VIA T'J1 TERMINATOR) [SPLIT]

7200 GTAGGACTTTCCACATGCAGGATTTTGGAACCCTCTTGCAGTACTACTGGGAATGAGTTGCAATTATTGCTACACCATTGCCTGCATCGAGTAAGTCGCT
     <T P S E V H L I K S G R A T S S P F S N C N N S C W Q T C R T L R K
     EA59 (525); CODON START=1; DB XREF=PID:G215132; TRA
     MRNA-PL (ALT.; VIA T'J4 TERMINATOR) [SPLIT]
     MRNA-PL (ALT.; VIA T'J3 TERMINATOR) [SPLIT]
     MRNA-PL (ALT.; VIA T'J2 TERMINATOR) [SPLIT]
     MRNA-PL (ALT.; VIA T'J1 TERMINATOR) [SPLIT]
```

*FIG. 2(C2)j*

```
7300
TAATGTTCGTAAAAAGCAGAGAGCAAGGTGGATGCAGATGAACCTCTGGTTCATCGAATAAAACTAATGACTTTTCGCCAACGACATCTACTAATCTT
 I  N  T  F  F  C  L  A  F  T  S  A  S  S  G  R  T  *  R  I  F  S  I  V  K  R  W  R  C  R  S  I  K
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7400
GTGATAGTAAATAAAACAATTGCATGTCCAGAGCTCATTCGAAGCAGATATTTCTGGATATTGTCATAAAACAATTAGTGAATTTATCATCGTCCACTT
 H  Y  Y  I  F  C  N  C  T  W  L  E  N  S  A  S  I  E  P  Y  Q  *  L  V  I  *  H  I  *  R  G  S
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7500
GAATCTGTGGTTCATTAGTCTCTTAACTCTTCATATTTAGAAATGAGGCTGATGAGTTCCATATTGAAAAGTTTTCATCACTACTTAGTTTTTGATAGC
 S  D  T  T  *  T  K  V  R  *  I  *  F  H  P  Q  H  T  G  Y  K  F  L  K  *  *  K  T  K  Q  Y  S
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
```

*FIG. 2(C2)k*

7600
TTCAAGCCAGAGTTGTCTTTTCTATCTACTCTCATACAACCAATAAATGCTGAAATGAATTCTAAGCGGAGATCGCCTAGTGATTTAAACTATTGCTG
<* A L T T K K * R S E Y L W Y I S F H I R L P S R R T I K F * Q Q
      EA59 (525); CODON START=1; DB XREF=PID:G215132; TRA
      MRNA-PL (ALT.; VIA T'J4 TERMINATOR) [SPLIT]
      MRNA-PL (ALT.; VIA T'J3 TERMINATOR) [SPLIT]
      MRNA-PL (ALT.; VIA T'J2 TERMINATOR) [SPLIT]
      MRNA-PL (ALT.; VIA T'J1 TERMINATOR) [SPLIT]

7700
GCAGCATTCTTGAGTCCAATATAAAAGTATTGTGTACCTTTTGCTGGGTCAGTTGTCTTTAGGAGGAGTAAAAGGATCAAATGCACTAAACGAAACTG
<C C E Q T W Y L L I T Y R K S P * T T R * S S Y F S * I C * V F S
      EA59 (525); CODON START=1; DB XREF=PID:G215132; TRA
      MRNA-PL (ALT.; VIA T'J4 TERMINATOR) [SPLIT]
      MRNA-PL (ALT.; VIA T'J3 TERMINATOR) [SPLIT]
      MRNA-PL (ALT.; VIA T'J2 TERMINATOR) [SPLIT]
      MRNA-PL (ALT.; VIA T'J1 TERMINATOR) [SPLIT]

7800
AAACAAGCGGATCGAAAATATCCCTTTGGGATTCTTGACTCGATAAGTCTATTATTTCAGAGAAAAAATATTCATTGTTTTCTGGGTTGGTGATTGCACC
<F C A I S F I G K P N K V R Y T * * K L F F I * Q K R P Q H N C W
      EA59 (525); CODON START=1; DB XREF=PID:G215132; TRA
      MRNA-PL (ALT.; VIA T'J4 TERMINATOR) [SPLIT]
      MRNA-PL (ALT.; VIA T'J3 TERMINATOR) [SPLIT]
      MRNA-PL (ALT.; VIA T'J2 TERMINATOR) [SPLIT]
      MRNA-PL (ALT.; VIA T'J1 TERMINATOR) [SPLIT]

FIG. 2(C2)I

```
7900
AATCATTCCATTCAAATTGTTTGTTTACCACACCCATTCCGCCCGATAAAGCATGAATGTTCGTGCTGGGCATAGAATTAACCGTCACCTCAAAAGGT
<D N I I Q I V C V L P H P P I R P I K H E C S W L G I E L T V T S K G
 D N W E F N N N * W V W E A R Y F C S H E H Q A Y F * G D G * F T
                EA59 (525); CODON_START=1; DB_XREF=PID:G215132; TRA
                MRNA-PL (ALT.; VIA T'J4 TERMINATOR) [SPLIT]
                MRNA-PL (ALT.; VIA T'J3 TERMINATOR) [SPLIT]
                MRNA-PL (ALT.; VIA T'J2 TERMINATOR) [SPLIT]
                MRNA-PL (ALT.; VIA T'J1 TERMINATOR) [SPLIT]

8000
ATAGTTAAATCACTGAATCCGGGAGCACTTTTTCTATTAAATGAAAAGTGGAAATCTGACAATTCTGGCAAACCATTAACACGTGGAACTGTCCAT
<Y N F Q I R S C K K * I F L P F R V I R A F W K V C T R V T W
                EA59 (525); CODON_START=1; DB_XREF=PID:G215132; TRA
                MRNA-PL (ALT.; VIA T'J4 TERMINATOR) [SPLIT]
                MRNA-PL (ALT.; VIA T'J3 TERMINATOR) [SPLIT]
                MRNA-PL (ALT.; VIA T'J2 TERMINATOR) [SPLIT]
                MRNA-PL (ALT.; VIA T'J1 TERMINATOR) [SPLIT]

8100
GAATTTCTGAAAGAGTTACCCCTCTAAGTAATGAGGTGTTAAGGACGCTTTCATTTTCAATGTCGGCTAATCGATTGGCCATACTACTAAATCCTGAAT
<S N R F S N G R * T I L H * P R K * K * H R S I S K A M S S F G S Y
                EA59 (525); CODON_START=1; DB_XREF=PID:G215132; TRA
                MRNA-PL (ALT.; VIA T'J4 TERMINATOR) [SPLIT]
                MRNA-PL (ALT.; VIA T'J3 TERMINATOR) [SPLIT]
                MRNA-PL (ALT.; VIA T'J2 TERMINATOR) [SPLIT]
                MRNA-PL (ALT.; VIA T'J1 TERMINATOR) [SPLIT]
```

*FIG. 2(C2)m*

```
8200
AGCTTTAAGAAGGTTATGTTTAAAACCATGCGCTTAATTTGCTGAGATTAACATAGTAGTCAATGCTTTCACCTAAGGAAAAAACATTTCAGGGAGTTGA
<S * S P * T * F W R K I Q Q S * C L L * H K * R L F V N * P T S
        EA59 (525); CODON_START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]

8300
CTGAATTTTTTATCTATTAATGAATAAGTGCTTACTTCTTCTTTTTGACCTACAAAAACCAATTTAACATTTCCGATATCGCATTTTTCACCATGCTCAT
<Q I K * R N I F L H K S R R K S R C F W N * C K R Y R M K * W A *
        EA59 (525); CODON_START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]

8400
CAAAGACAGTAAGATAAAACATTGTAACAAAGGAATAGTCATTCCAACCATCTGCTCGTAGGAATGCCTTATTTTTTCTACTGCAGGAATATACCCGCC
<* L C Y S L V N Y C L F L * E L W R S T P I G * K K R S C S Y V --(SEQ ID NO:65)--
        EA59 (525); CODON_START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]
```

FIG. 2(C2)n

8500
TCTTTCAATAACACTAAACTCCAACATATAGTAACCCTTAATTTTATTAAATAACCGCAATTTATTGGCGGCAACACAGGATCTCTCTTTAAGTTAC
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

8600
TCTCTATTACATACGTTTTCCATCTAAAAATTAGTAGTATTGAACTTAACGGGGCATCGTATTGTAGTTTTCCATATTTAGCTTTCTGCTTCCTTTTGGA
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

8700
TAACCCACTGTTATTCATGTTGCATGGTGCACTGTTTATACCAACGATATAGTCTATTAATGCATATATAGTATCGCCGAACGATTAGCTCTTCAGGCTT
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

8800
CTGAAGAAGCGTTTCAAGTACTAATAAGCCGATAGATAGCCACGGACTTCGTAGCCATTTTTCATAAGTGTTAACTTCCGCTCCTCGCTCATAACAGACA
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

FIG. 2(C2)o

```
8900
TTCACTACAGTTATGGCGAAAGGTATGCATGCTGGGGTGTGTGGGGAAGTCGTGAAAGAAAGAAGTCAGCTGCTGCGTTTGACATCACTGCTATCTTCTTA
               MRNA-PL (ALT.; VIA T'J4 TERMINATOR) [SPLIT]
               MRNA-PL (ALT.; VIA T'J3 TERMINATOR) [SPLIT]
               MRNA-PL (ALT.; VIA T'J2 TERMINATOR) [SPLIT]
               MRNA-PL (ALT.; VIA T'J1 TERMINATOR) [SPLIT]

9000
CTGGTTATGCAGGTCCTAGTGGGTGGCACACAAAGCTAGATTAACCCTAGAAAGATAATCATATTGTGACGTACGTTAAAGATAATCATGCGTAAAAATTG
 MRNA-PL (ALT.; VIA T'J4 TERM
 MRNA-PL (ALT.; VIA T'J3 TERM
 MRNA-PL (ALT.; VIA T'J2 TERM
 MRNA-PL (ALT.; VIA T'J1 TERM
                                                                        LEFT TERMINAL REPEAT

9100
ACGCATGTGTTTTTATCGGTCTCGTATATCGAGGTTTATTTATTAATTTGAATAGATATTAAGTTTTTATTTATTACACTTACATACTAATAATAAATTC

9200
AACAAACAATTTATTTATGTTTATTTATTTATTTAAAAAAAAAACAAAAACTCAAAATTTCTTCTAAAGTAACAAAACTTTTAAACATTCTCTCTTTTACAA

9300
AAATAAACTTATTTTGTACTTTAAAAACAGTCATGTTGTATTATAAATAAGTAATTAGCTTAACTTATACATAATAGAAACAAATTATACTTATTAGTC
                                                                                              <D
                                                                                               \/

9400
AGTCCAGAAACAACTTGGCACATATCAATATTATGCTCTCGACAAATAACTTTTTGCATTTTTTGCACGATGCATTGCCTTTGCCCTTATTTTAGAG
<T  W  F  C  S  Q  C  M  D  I  N  H  E  R  C  I  V  K  K  C  K  K  C  S  A  N  A  K  R  R  I  K  S
                    ORF1 C-TERM
```

FIG. 2(C2)p

```
9500
GGGCAGTAAGTACAGTAAGTACGTTTTTTCATTACTGGCTCTTCAGTACTGTCATCTGATGTACCAGGCACTTCATTGGCAAAATATTAGAGATATTAT
 <P  C  Y  T  C  Y  T  R  K  K  M  V  P  E  E  T  S  D  D  S  T  G  P  V  E  N  P  L  I  N  S  I  N  D
                                              ORF1 C-TERM
 v

9600
CGGCGCAAATATCTCTTCAAAGTAGGAGCTTCTAAACGATGACGTCAGGCCTCATGTAAAGGTTTCTCATAAATTTTTGCGACTTTG
 <R  L  Y  R  K  L  T  P  A  E  L  R  N  R  M  F  S  S  T  L  S  M  Y  L  N  R  M  F  K  K  R  S  Q
                                              ORF1 C-TERM
 v

9700
AACCTTTTCTCCCTTGCTACTGACATTATGGCTGTATATAATAAAAGAATTTATGCAGGCAATGTTTATCATTCCGTACAATAATGCCATAGGCCACCTA
 <V  K  E  G  K  S  S  V  N  H  S  Y  I  I  F  S  N  I  C  A  I  N  I  M  G  Y  L  L  A  M  P  W  R
                                              ORF1 C-TERM
 v

9800
TTCGTCTTCCTACTGCAGGTCATCACAGAACACATTTGGTCTAGCGTGTCCACTCCGCCCTTTAGTTTGATTATAATACATAACCATTTGCGGTTTACCGG
 <N  T  K  R  S  C  T  M  V  S  C  M  Q  D  L  T  D  V  G  G  K  T  Q  N  Y  Y  M  V  M  Q  P  P  K  G  T
                                              ORF1 C-TERM
 v

9900
TACTTTCGTTGATAGAAGCCATTCCATCACAAGATGATAATAAGTATACCATCTTAGCTGGCTTCGGTTTATATGAGACGAGAGTAAGGGGTCCGTCAAA
 <S  E  N  I  S  A  D  E  D  C  S  S  L  L  Y  V  M  K  A  P  K  P  K  Y  S  V  L  T  L  P  G  D  F
                                              ORF1 C-TERM
 v

ACAAAACATCGATGTTCCCACTGGCCTGGAGGCACTGTTTTCAGTACTTCCGCGTTGTTTGATCGCACGGTACC  --(SEQ ID NO:63)--
 <C  F  M  S  T  G  V  P  R  S  R  S  N  K  L  V  E  P  I  E  R  K  N  S  R  V  T  G  --(SEQ ID NO:66)--
                                              ORF1 C-TERM
 v
```

*FIG. 2(C2)q*

ITR Cartridge Sequence    Sequence Range: 1 to 707

```
                                                        50
GGATCCCATGCGTCAATTTTACGCAGACTATCTTTCTAGGGTTAATCTAG
        _____RIGHT TERMINAL REPEAT_____>
                                                       100
CTGCATCAGGATCATATCGTCGGGTCTTTTTTCCGGCTCAGTCATCGCCC
                                                       150
AAGCTGGCGCTATCTGGGCATCGGGGAGGAAGAAGCCCGTGCCTTTTCCC
                                                       200
GCGAGGTTGAAGCGGCATGGAAAGAGTTTGCCGAGGATGACTGCTGCTGC
                                                       250
ATTGACGTTGAGCGAAAACGCACGTTTACCATGATGATTCGGGAAGGTGT
                                                       300
GGCCATGCACGCCTTTAACGGTGAACTGTTCGTTCAGGCCACCTGGGATA
                                                       350
CCAGTTCGTCGCGGCTTTTCCGGACACAGTTCCGGATGGTCAGCCCGAAG
                                                       400
CGCATCAGCAACCCGAACAATACCGGCGACAGCCGGAACTGCCGTGCCGG
                                                       450
TGTGCAGATTAATGACAGCGGTGCGGCGCTGGGATATTACGTCAGCGAGG
                                                       500
ACGGGTATCCTGGCTGGATGCCGCAGAAATGGACATGGATACCCCGTGAG
                                                       550
TTACCCGGCGGGCGCGCCTCGTTCATTCACGTTTTTGAACCCGTGGAGGA
                                                       600
CGGGCAGACTCGCGGTGCAAATGTGTTTTACAGCGTGATGGAGCAGATGA
                                                       650
AGATGCTCGACACGCTGCAGAACACGCAGCTAGATTAACCCTAGAAAGAT
                                                          >
                                                   _____
                                                       700
AATCATATTGTGACGTACGTTAAAGATAATCATGCGTAAAATTGACGCAT
           _____LEFT TERMINAL REPEAT_____>

GGGATCC --(SEQ ID NO:40)--
_>
```

FIG. 3(C1)

pXL-Bac
Sequence Range: 1 to 3662

100 CTAAATTGTAAGCGTTAATATTTTGTTAAATTTTCGCGTTAAATTTTTGTTAAATCAGCTCATTTTTTAACCAATAGGCCGAAATCGGCAAAATCCCTTAT
200 AAATCAAAAGAATAGACCGAGATAGGGTTGAGTGTTGTTCCAGTTTGGAACAAGAGTCCACTATTAAAGAACGTGACTCCAACGTCAAAGGGCGAAAAA
300 CCGTCTATCAGGGCGATGCCCACTACGTGAACCATCACCCTAATCAAGTTTTTTGGGGTCGAGGTGCCGAGTGCCCTAAAGCACTAAATCGGAACCCTAAAGGGAG
400 CCCCCGATTTAGAGCTTGACGGGGAAAGCCGGCGAACGTGGCGAGAAAGGAAGAAAGCGAAAGGAGCGGGCGCTAGGGCGCTGGCAAGTGTAGCG
500 GTCACGCTGCGCGTAACCACCACACACCCCGCGCTTAATGCGCCGCTACAGGGCGCGTCCCATTCGCCATTCAGGCTGCGCAACTGTTGGGAAGGGCGAT
600 CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700 TAAAACGACGGCCAGTGAGCGCGCCTCGTTCATTCACGTTTTTGAACCCGTGGAGGACGGCAGACTCGCGGTGCAAATGTGTTTACAGCGTGATGGAG
800 CAGATGAAGATGCTCGACACGCTGCAGAACACGCAGCTAGATTAACCCTAGAAAGATAATCATATTGTGACGTACGTTAAAGATAATCATGCGTAAAATT
                                                                                    LEFT TERMINAL REPEAT
900 GACGCATGGGATCTGTAATACGACTCACTATAGGGCGAATTGGGTACCGGGCCCCCCCTCGAGGTCGACGGTATCGATAAGCTTGATATCGAATTCCTGC

>MCS_of_pBSII

*FIG. 3(C2)*

```
1000
AGCCCGGGGATCCACTAGTTCTAGAGCGGCCGCCACCGCGGTGGAGCTCCAGCTTTTGTTCCCTTTAGTGAGGGTTAATTAGATCCATGCGTCAATTT
1100
TACGCAGACTATCTTTCTAGGGTTAATCTAGCTGCATCAGGATCATATCGTCGGTCTCTTTTTCCGGCTCAGTCATCGCCCAAGCTGGCGTATCTGGGC
    RIGHT TERMINAL
1200
ATCGGGGAGGAAGAGCCCGTGCCTTTTCCCGCGAGGTTGAAGCGGCATGGAAAGAGTTTGCCGAGGATGACTGCTGCATTGACGTTGAGCGAAAAC
1300
GCACGTTTACCATGATGATTCGGGAAGGTGTGGCCATGCACGCCCTTTAACGGTGAACTGTTCGTTCAGGCCACCTGGGATACCAGTTCGTCGGGCTTTT
1400
CCGGACACAGTTCCGGATGGTCAGCCCGAAGCGCATCAGCAACAATACCGGCAACAGCCCGAACTGCCGTGCCGGTGTGCCAGATTAATGACAGC
1500
GGTGCGGCGCGCTGGGATATTACGTCAGCGAGGACGGGTATCCCTGGCTGAGATACCCGTGAGTTACCCGGCGGGGCGCGCTT
1600
GGCGTAATCATGGTCATAGCTGTTTCCTGTGTGAAATTGTTATCCGCTCACTGCCCGCTTTCCAGTCGGGAAACCTGTCGTGCCAGCTGCATTAATGAATCGGCCAAC
1700
GCCTAATGAGTGAGCTAACTCACATTAATTGCGTTGCGCTCACTGCCCGCTTTCCGGCTCGTTTCGGCTGCGGCGAGCGGTATCAGCTCA
1800
GCGCGGGGAGAGGCGGTTTGCGTATTGGGCGCCAGGGTGGTTTTTCTTTTCACCAGTGAGACGGGCAACAGCTGATTGCCCTTCACCGCCTGGCCCTGAGAGAGTTGCAGCAAGCGGT
1900
CTCAAAAGGCGGTAATACGGTTATCCACAGAATCAGGGGATAACGCAGGAAAGAACATGTGAGCAAAAGGCCAGCAAAAGGCCAGGAACCGTAAAAAGGCC
2000
GCGTTGCTGGCGTTTTTCCATAGGCTCCGCCCCCCTGACGAGCATCACAAAAATCGACGCTCAAGTCAGAGGTGGCGAAACCCGACAGGACTATAAAGAT
```

*FIG. 3(C2) CONT.*

```
2100
ACCAGGGCGTTTCCCCCTGGAAGCTCCCTCGTGCGCTCTCCTGTTCCGACCCTGCCGCTTACCGGATACCTGTCCGCCTTTCTCCCCTTCGGGAAGCGTGGC
2200
GCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGC
2300
GCCTTATCCGGTAACTATCGTCTTGAGTCCAACCCGGTAAGACACGACTTATCGCCACTGGCAGCAGCCACTGGTAACAGGATTAGCAGAGCGAGGTATG
2400
TAGGCGGTGCTACAGAGTTCTTGAAGTGGTGGCCTAACTACGGCTACACTAGAAGGACAGTATTTGGTATCTGCGCTCTGCTGAAGCCAGTTACCTTCGG
2500
AAAAAGAGTTGGTAGCTCTTGATCCGGCAAACAAACCACCGCTGGTAGCGGTGGTTTTTTTGTTGCAAGCAGCAGATTACGCGCAGAAAAAAAGGATCT
2600
CAAGAAGATCCTTTGATCTTTTCTACGGGGTCTGACGCTCAGTGGAACGAAAACTCACGTTAAGGGATTTTGGTCATGAGATTATCAAAAAGGATCTTCA
          <ColE1_origin
2700
CCTAGATCCTTTTAAATTAAAAATGAAGTTTTAAATCAATCTAAAGTATATATGAGTAAACTTGGTCTGACAGTTACCAATGCTTAATCAGTGAGGCACC
                                                                                 < AMPCILLIN RESISTAN
2800
TATCTCAGCGATCTGTCTATTTCGTTCATCCATAGTTGCCTGACTCCCCGTCGTGTAGATAACTACGATACGGGAGGGCTTACCATCTGGCCCCAGTGCT
<                         AMPCILLIN RESISTANCE
2900
GCAATGATACCGCGAGACCCACGCTCACCGGCTCCAGATTTATCAGCAATAAACCAGCCAGCCGGAAGGGCCGAGCGCAGAAGTGGTCCTGCAACTTTAT
<                       AMPCILLIN RESISTANCE
```

*FIG. 3(C2) CONT.*

```
3000
CCGCCTCCATCCAGTCTATTAATTGTTGCCGGGAAGCTAGAGTAGTAAGTAGTTCGCCAGTTAATAGTTTGCGCAACGTTGTTGCCATTGCTACAGGCATCGT
     <                                          AMPCILLIN RESISTANCE
3100
GGTGTCACGCTCGTCGTTTGGTATGGCTTCATTCAGCTCCGGTTCCCAACGATCAAGGCGAGTTACATGATCCCCCATGTTGTGCAAAAAAGCGGTTAGC
     <                                          AMPCILLIN RESISTANCE
3200
TCCTTCGGTCCTCCGATCGTTGTCAGAAGTAAGTTGGCCGCAGTGTTATCACTCATGGTTATGGCAGCACTGCATAATTCTCTTACTGTCATGCCATCCG
     <                                          AMPCILLIN RESISTANCE
3300
TAAGATGCTTTTCTGTGACTGGTGAGTACTCAACCAAGTCATTCTGAGAATAGTGTATGCGGCGACCGAGTTGCTCTTGCCCGGCGTCAATACGGGATAA
     <                                          AMPCILLIN RESISTANCE
3400
TACCGCGCCACATAGCAGAACTTTAAAAGTGCTCATCATTGGAAAACGTTCTTCGGGGCGAAAACTCTCAAGGATCTTACCGCTGTTGAGATCCAGTTCG
     <                                          AMPCILLIN RESISTANCE
3500
ATGTAACCCACTCGTGCACCCAACTGATCTTCAGCATCTTTTACTTTCACCAGCGTTTCTGGGTGAGCAAAAACAGGAAGGCAAAATGCCGCAAAAAAGG
     <                                          AMPCILLIN RESISTANCE
3600
GAATAAGGGCGACACGGAAATGTTGAATACTCATACTCTTCCTTTTTCAATATTATTGAAGCATTTATCAGGGTTATTGTCTCATGAGCGGATACATATT
     <                                          AMPCILLIN RESISTANCE

TGAATGTATTTAGAAAAATAAACAAATAGGGGTTCCGCGCACATTTCCCCGAAAAGTGCCAC --(SEQ ID NO:41)--
```

*FIG. 3(C2) CONT.*

Plasmid name: p32
Plasmid size: 10.34 kb pBSII-hs-orf
Sequence Range: 1 to 5533

```
100
CTAAATTGTAAGCGTTAATATTTGTTAAATTTTGTTAAATCAGCTCATTTTTAACCAATAGGCCGAAATCGGCAAAATCCCTTAT
200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA
300
CCGTCTATCAGGGCGATGGCCCACTACGTGAACCATCACCCTAATCAAGTTTTTTGGGGTCGAGGTGCCGTAAAGCACTAAATCGAACCCTAAAGGGAG
400
CCCCCGATTTAGAGCTTGACGGGGAAAGCCGGCAACGTGGCGAGAAAGGAAGGAAGAAAGCGAAAGGAGCGGGGCGCTAGGGCGCTGGCAAGTGTAGCG
500
GTCACGCTGCGCGTAACCACCACACCCGGCGCTTAATGCCGCCTACAGGGCGCGTCCCATTCGCCATTCAGGCTGCCAACTGTTGGGAAGGGCGAT
600
CGGTGCGGGCCCTCTTCGCTATTACGCCAGCTGGCGAAAGGGGGATGTGCTGCAAGGCGATTAAGTGGGTAACGCCAGGGTTTTCCCAGTCACGACGTTG
700
TAAAACGACGGCCAGTGAGCGCGCGTAATACGACTCACTATAGGGCGAATTGGGTACCGGGCCCCCCCCTCGAGGTCGACGGTATCGATAAGCTATCCAGT
800
GCAGTAAAATAAAAATATGTTTTTTAAATCTACATTCTCCAAAAAAAGGTTTATTAACTTACATACATACTAGAATTGATCCCGATCCCC
900
CTAGAATCCCAAAACAAACTGGTTATTGTGGTAGGTCATTTGTTGTTGGCAGAAGAAAACTCGAGAAATTTCTCGGCCGTTATTCGTTATTCTCTCTTTTC
1000
TTTTTGGGTCTCCCCTCTCGCACTAAGTCTCTCCACTCTGTCACACAGTAAACGGCATACTGCTCTCGTTGGTTCGAGAGAGCGCCTCGAATGTTCG
1100
CGAAAAGAGCGCCGGAGTATAAATAGAGCGCTTCGTCTACGGAGCGACAATTCAATTCAAACAAGCAAAGTGAACACGTCGCTAAGCGAAAGCTAAGCAA
```

FIG. 5(B)

```
1200
ATAAACAAGCGCAGCTGAACAAGCTAAACAATCTGCAGTAAAGTGAATCAATTAAAAGTAACCAGCAACCAAGTAAATCAACTGCAAC
                                                  <hsp70_promoter
1300
TACTGAAATCTGCCAAGAAGTAATTATTGAATACAAGAAGAGAACTCTGAATAGGGAATTGGGAATTCCTGCAGCCCGGGGATCCTATATATAATAAAATG
1400
GGTAGTTCTTTAGACGATGAGCATATCCTCTCTGCTCTTCTGCAAAGCGATGACGAGCTTGTGGTGAGGATTCTGACAGTGAAATATCAGATCACGTAA
1500
GTGAAGATGACGTCCAGAGCCGATACAGAAGAAGCGTTTATAGATGAGGTACATGAAGTGCAGCCACAAGCGGTAGTGAAATATTAGACGAACAAAA
1600
TGTTATTGAACAACCAGGTTCTTCATTGGCTTCTAACAGAATCTTGACCTTGCCACAGAGGACTATTAGAGAGTAAGAATAAACATTGTTGGTCAACTTCA
1700
AAGTCCACGAGGGCGTAGCCGAGTCTCTGCACTGAACATTGTCAGATCTCAAAGAGGTCCGACGCGTATGTGCCGCAATATATATGACCCACTTTTATGCT
1800
TCAAACTATTTTTTACTGATGAGATAATTTCGGAAATTGTAAAATGGACAAATGCTGAGATATCATTGAAACGTCGGGAATCTATGACAGGTGCTACATT
1900
TCGTGACACGAATGAAGATGAAATCTATGCTTTCTTTGGTATTCTGGTAATGACACAGTGAGAAAAGATAACCACATGTCCACAGATGACCTCTTTGAT
2000
CGATCTTTGTCAATGGTGTACGTCTCTGTAATGAGTCGTGATCGTTTGATTTTTGATACGATGTCTTAGAATGGATGACAAAGTATACGGCCACAC
2100
TTCCGAGAAAACGATGTATTACTCCCTGTTAGAAAAATATGGGATCTCTTATCCATCAGTGCATACAAAATTACACTCCAGGGGCTCATTGACCATAGA
2200
TGAACAGTTACTTGGTTTTAGAGGACGGTGTCCGTTAGGATGTATATCCCAAACAAGCCAAGTAAGTATGGAATAAAAATCCTCATGATGTGTGACAGT
```

*FIG. 5(B) CONT.*

```
2300
GGTACGAAGTATATGATAAATGCCTTATTTGGGAAGAGGAACACAGACCAACGGAGTACCACTCGGTGAATACTACGTGAAGGAGTTATCAAAGC
2400
CTGTGCACGGTAGTTGTCGTAATATTACGTGTGACAATTGGTTCACCTCAATCCCTTGGCAAAAAAACTTACTACAGAACCGTATAAGTTAACCATTGT
2500
GGGAACCGTGCGATCAAACAAACAAACGCGAGATACCGGAAGTACTGAAAAAACAGTCGCTCCAGGCCAGTGGGAACATCGATGTTTTGTTTTGACGGACCCTT
2600
ACTCTCGTCTCATATAAACCGAAGCCAGCTAAGATGGTATACTTATTATCATCTTGTGATGAGGATGCTTCTATCAACGAAAGTACCGGTAAACCGCAAA
2700
TGGTTATGTATTATAATCAAACTAAAGGCGGAGTGGACACGCTAGACCAAATGTGTTCTCGTGATGACCTGCAGTAGGAAGACGAATAGGTGGCTATGGC
2800
ATTATTGTACGGAATGATAAACATTGCCTGCATAAATTCTTTTATTATATACAGCCATAATGTCAGTAGCAAGGGAGAAAAGGTTCAAAGTCGCAAAAA
2900
TTTATGAGAAACCTTTACATGAGCCTGACGTCGTTTATGCGTAAGCGTTTAGAAGCTCCTACTTTGAAGAGATATTGCGCGATAATATCTCTAATA
3000
TTTTGCCAAATGAAGTGCCTGGTACATCAGATGACAGTAGTGAAGAGCCAGTAATGAAAAACGTACTTACTCTGTACTTACTGCCCCTCTAAAATAAGGCG
3100
AAAGGCAAAATGCATCGTGCAAAAAATGCAAAAAAGTTATTTGTCGAGAGCATAATATTGATATGTGCCAAAGTTGTTTCTGACTGACTAATAAGTATAAT
3200
TTGTTTCTATTATGTATAAGTTAAGCTAATTACTTATTTTATAATACAAACATGACTGTTTTAAAGTACAAAATAAGTTTATTTTTGTAAAAGAGAGAAT
3300
GTTTAAAAGTTTTGTTACTTTAGAAGAAATTTGAGTTTTTGTTTTTTTTAATAAAATAAAACATAAATAAATTGTTTGTTGAATTGGATCCACTA
3400
GTTCTAGAGGGCCCGCCACCGCGGTGGAGCTCCAGCTTTTGTTCCCTTTAGTGAGGGTTAATTGCGCGCTTGGCGTAATCATGGTCATAGCTGTTTCCTG
```

*FIG. 5(B) CONT.*

```
3500
TGTGAAATTGTTATCCGCTCACAATTCCACACAACATACGAGCCGGAAGCATAAAGTGTAAAGCCTGGGGTGCCTAATGAGTGAGCTAACTCACATTAAT
3600
TGCGTTGCGCTCACTGCCCGCTTTCCAGTCGGGAAACCTGTCGTGCCAGCTGCATTAATGAATCGGCCAACGCGCGGGGAGAGCGGTTTGCGTATTGGG
3700
CGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAG
3800
AATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCG
3900
CCCCCCTGACGAGCATCACAAAAATCGACGCTCAAGTCAGAGGTGGCGAAACCCGACAGGACTATAAAGATACCAGGCGTTTCCCCCTGGAAGCTCCCTC
4000
GTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTATC
4100
TCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTC
4200
CAACCCGGTAAGACACGACTTATCGCCACTGGCAGCAGCCACTGGTAACAGGATTAGCAGAGCGAGGTATGTAGGCGGTGCTACAGAGTTCTTGAAGTGG
4300
TGGCCTAACTACGGCTACACTAGAAGGACAGTATTTGGTATCTGCGCTCTGCTGAAGCCAGTTACCTTCGGAAAAAGAGTTGGTAGCTCTTGATCCGGCA
4400
AACAAACCACCGCTGGTAGCGGTGGTTTTTTTGTTTGCAAGCAGCAGATTACGCGCAGAAAAAAAGGATCTCAAGAAGATCCTTTGATCTTTTCTACGGG
4500
GTCTGACGCTCAGTGGAACGAAAACTCACGTTAAGGGATTTTGGTCATGAGATTATCAAAAAGGATCTTCACCTAGATCCTTTTAAATTAAAAATGAAGT
```

```
<ColE1_origin
  |
4600
TTTAAATCAATCTAAAGTATATATGAGTAAACTTGGTCTGACAGTTACCAATGCTTAATCAGTGAGGCACCTATCTCAGCGATCTGTCTATTTCGTTCAT
                                                    AMPCILLIN RESISTANCE                              >
4700
CCATAGTTGCCTGACTCCCCGTCGTGTAGATAACTACGATACGGGAGGGCTTACCATCTGGCCCCAGTGCTGCAATGATACCGCGAGACCCACGCTCACC
                                                    AMPCILLIN RESISTANCE                              >
4800
GGCTCCAGATTTATCAGCAATAAACCAGCCAGCCGGAAGGGCCGAGCGCAGAAGTGGTCCTGCAACTTTATCCGCCTCCATCCAGTCTATTAATTGTTGC
                                                    AMPCILLIN RESISTANCE                              >
4900
CGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTT
                                                    AMPCILLIN RESISTANCE                              >
5000
CATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAG
                                                    AMPCILLIN RESISTANCE                              >
5100
TAAGTTGGCCGCAGTGTTATCACTCATGGTTATGGCAGCACTGCATAATTCTCTTACTGTCATGCCATCCGTAAGATGCTTTTCTGTGACTGGTGAGTAC
                                                    AMPCILLIN RESISTANCE                              >
5200
TCAACCAAGTCATTCTGAGAATAGTGTATGCGGCGACCGAGTTGCTCTTGCCCGGCGTCAATACGGGATAATACCGCGCCACATAGCAGAACTTTAAAAG
                                                    AMPCILLIN RESISTANCE                              >
5300
TGCTCATCATTGGAAAACGTTCTTCGGGGCGAAAACTCTCAAGGATCTTACCGCTGTTGAGATCCAGTTCGATGTAACCCACTCGTGCACCCAACTGATC
                                                    AMPCILLIN RESISTANCE                              >
```

*FIG. 5(B) CONT.*

```
5400
TTCAGCATCTTTTACTTTCACCAGCGTTTCTGGGTGAGCAAAAACAGGAAGGCAAAATGCCGCAAAAAAGGGAATAAGGGCGACACGGAAATGTTGAATA
                                                 AMPCILLIN RESISTANCE
5500
CTCATACTCTTCCTTTTTCAATATATTATTGAAGCATTTATCAGGGTTATTGTCTCATGAGCGGATACATATTTGAATGTATTTAGAAAAATAAACAAATAG

GGGTTCCGCGCACATTTCCCCGAAAAGTGCCAC --(SEQ ID NO:42)--
```

*FIG. 5(B) CONT.*

Sequence Range: 1 to 4971

100
CTAAATTGTAAGCGTTAATATTTGTTAAATTTTTGTTAAATCAGCTCATTTTTAACCAATAGGCCGAAATCGGCAAATCCCTTAT

200
AAATCAAAAGAATAGACCGAGATAGGGTTGAGTGTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAGAAAGCGAAAGGAGCGGGCGCTAGGGCGCTGGCAAGTGTAGCG

500
GTCACGCTGCGCGTAACCACCACACACCCGCGCTTAATGCGCCGCTACAGGGCGCGTCCCATTCAGGCTGCCAACTGTGTGGGAAGGGCGAT

600
CGGTGCGGGCCCTTCGCTATTACGCCAGCGCGCGTAACTGGGCGAAAGGGGGATCGTGCTCGCAAGCGATTAAGTTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCTCGAGGTCGACGTATCGATAAGCTTGATATC

800
GAATTCCTGCAGCCCGGGGATCCTATATAAATAAATGGTAGTTCTTTAGACGATGAGCATATCCTCTCGCTCTTCTGCAAAGCGATGACGAGCTTGT

900
TGGTGAGGATTCTGACAGTGAAATATCACGTAAGTGAAGATGACGTCCAGAGCGATACAGAAGAAGCGTTTATAGATGAGGTACATGAAGTGCAG

1000
CCAACGTCAAGCGGTAGTGAAATATTAGACGAACAAATGTTATTGAACAACCAGGTTCTTCATTGGCTTCTAACAGAATCTTGACCTTGCCACAGAGGA

1100
CTATTAGAGGTAAGAATAAACATTGTTGGTCAACTTCAAAGTCCGAGTCTCTGCACTGAACATTGTCAGATCTCAAAGAGAGTCCGAC

FIG. 6(B)

1200
GCGTATGTGCCGCAATATATGACCCACTTTTATGCTTCAAACTATTTTTACTGATGAGATAATTTCGGAAATTGTAAAATGGACAAATGCTGAGATA

1300
TCATTGAAACGTCGGGAATCTATGACAGGTGCTACATTTCGTGACACGAATGAAGATGAAATCTATGCTTTCTTTGGTATTCTGGTAATGACAGCAGTGA

1400
GAAAAGATAACCACATGTCCACAGATGACCTCTTTGATCGATCTTGTCAATGGTGTACGTCTCTGTAATGAGTCGTGATCGTTTGATTTTTGATACG

1500
ATGTCTTAGAATGGATGACAAAGTATACGGCCCACACTTCGAGAAAACCATGTATTTACTCCCTGTTAGAAAAATATGGGATCTCTTTATCCATCAGTGC

1600
ATACAAAATTACACTCCAGGGCTCATTTGACCATAGATGAACAGTTACTTGGTTTTAGAGGACGGTGTCCGTTTAGGATGTATATCCAAACAAGCCAA

1700
GTAAGTATGGAATAAAAATCCTCATGATGTGTGACAGTGGTACGAAGTATATGATAAATGGAATGCCTTATTGGGAAGAGGAACACAGACCAACGGAGT

1800
ACCACTCGGTGAATACTACGTGAAGGAGTTATCAAAGCCTGTGCACGGTAGTGTCGTAATATTACGTGTGACAATTGGTTCACCTCAATCCCTTTGGCA

1900
AAAAACTTACTACAAGAACCGTATAAGTTAACCATTGTGGAACCGTGCGATCAAACAAACGGAGATACCGAAGTACTGAAAAACAGTCGCTCCAGGC

2000
CAGTGGGAACATCGATGTTTGTTTTGACGGACCCCTTACTCTCGTCTCATATAACCGAAGCCAGCTAAGATGCTATACTTATTATCATCTTGTGATGA

2100
GGATGCTTCTATCAACGAAAGTACCGTAAACCGCAAATGGTTATGTATTATAATCAAACTAAAGGCGGAGTGGACACGCTAGACCAAATGTGTTCTGTG

2200
ATGACCTGCACTAGGAGACGAATAGGTGGCCTATGGCATTATTGTACGAATGATGATAAACATTGCCTGCATAAATCTTTATTATATACAGCCATAATG

2300
TCAGTAGCAAGGGAGAAAAGTTCAAAGTCGCAAAAAATTTATGAGAAACCTTTACATGAGCCTGACGTCATCGTTTATGCGTAAGCGTTTAGAAGCTCC

FIG. 6(B) CONT.

```
2400
TACTTTGAAGAGATATTTGCGCGATAATATCTCTAATATTTGCCAAATGAAGTGCCTGTACATCAGATGACAGTACTGAAGAGCCAGTAATGAAAAAA
2500
CGTACTTACTGTACTTACTGCCCCTCTAAAATAAGGCGAAATGCATCGTGCAAAAAAGTTATTGTCGAGAGCATAATATTGATA
2600
TGTGCCAAAGTTGTTTCTGACTAATAAGTATAATTGTTTCTATTATGTATAAGCTAATTACTTATTTATAATACAACATGACTGTTTTT
2700
AAAGTACAAAATAAGTTTATTTTGTAAAGAGAATGTTTAAAGTTTTGTTACTTTAGAAGAAATTTTGAGTTTTTGTTTTTTTAATAAATAAAT
2800
AAACATAAATAAATTGTTGTTGAATTGGATCCACTAGTTCTAGAGCGGCCGCCACCGCGGTGGAGCTCCAGCTTTTGTTCCCTTTAGTGAGGGTTAAT
2900
TGCGCGCTTGGCGTAATCATGGTCATAGCTGTTTCCTGTGTGAAATTGTTATCCGCTCACAATTCCACACAACATACGAGCCGGAAGCATAAAGTGTAAA
3000
GCCTGGGGTGCCTAATGAGTGAGCTAACTCACATTAATTGCGTTGCGCTCACTGCCCGCTTTCCAGTCGGGAAACCTGTCGTGCCAGCTGCATTAATGAA
                                >ColE1_origin
3100
TCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGT
3200
ATCAGCTCACTCAAAGGCGGTAATACGGTTATCCACAGAATCAGGGGATAACGCAGGAAAGAACATGTGAGCAAAAGGCCAGCAAAAGGCCAGGAACCGT
3300
AAAAAGGCCGCGTTGCTGGCGTTTTTCCATAGGCTCCGCCCCCCTGACGAGCATCACAAAAATCGACGCTCAAGTCAGAGGTGGCGAAACCCGACAGGAC
3400
TATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGG
```

FIG. 6(B) CONT.

3500
AAGCGTGGGCGCTTTCTCATAGCTCACGCTGTAGGTATCTCAGTTCGGTGTAGGTCGTTCGCTCCAAGCTGGGCTGTGTGCACGAACCCCCGTTCAGCCC

3600
GACCGCTGCGCCTTATCCGGTAACTATCGTCTTGAGTGTCCAACCCGGTAAGACACGACTTATCGCCACTGGCAGCAGCCACTGGTAACAGGATTAGCAGAG

3700
CGAGGTATGTAGGCGGTGCTACAGAGTTCTTGAAGTGGTGGCCTAACTACGGCTACACTAGAAGGACAGTATTTGGTATCTGCGCTCTGCTGAAGCCAGT

3800
TACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAA

3900
AAAGGATCTCAAGAAGATCCTTTGATCTTTTCTACGGGGTCTGACGCTCAGTGGAACGAAAACTCACGTTAAGGGATTTTGGTCATGAGATTATCAAAAA

4000
GGATCTTCACCTAGATCCTTTTAAATTAAAAATGAAGTTTTAAATCAATCTAAAGTATATATGAGTAAACTTGGTCTGACAGTTACCAATGCTTAATCAG
                   >

4100
TGAGGCACCTATCTCAGCGATCTGTCTATTTCGTTCATCCATAGTTGCCTGACTCCCCGTCGTGTAGATAACTACGATACGGGAGGGCTTACCATCTGGC
     AMPCILLIN RESISTANCE

4200
CCCAGTGCTGCAATGATACCGCGAGACCCACGCTCACCGGCTCCAGATTTATCAGCAATAAACCAGCCAGCCGGAAGGGCCGAGCGCAGAAGTGGTCCTG
                                                AMPCILLIN RESISTANCE

4300
CAACTTTATCCGCCTCCATCCAGTCTATTAATTGTTGCCGGGAAGCTAGAGTAAGTAGTTCGCCAGTTAATAGTTTGCGCAACGTTGTTGCCATTGCTAC
                                                AMPCILLIN RESISTANCE

4400
AGGCATCGTGGTGTCACGCTCGTCGTTTGGTATGGCTTCATTCAGCTCCGGTTCCCAACGATCAAGGCAGTTACATGATCCCCCATGTTGTGCAAAAAA
                                                AMPCILLIN RESISTANCE

*FIG. 6(B) CONT.*

```
4500
GCGGTTAGCTCCTCCTTCGGTCCTCCGATCGTTGTCAGAAGTAAGTTGGCCGCAGTGTTATCACTCATGGTTATGGCAGCACTGCATAATTCCTTACTGTCA
                                                    AMPCILLIN RESISTANCE

4600
TGCCATCCGTAAGATGCTTTTCTGTGACTGGTGAGTACTCAACCAAGTCATTCTGAGAATAGTGTATGCGGCGACCGAGTTGCTCTTGCCCGGCGTCAAT
                                                    AMPCILLIN RESISTANCE

4700
ACGGGATAATACCGCGCCACATAGCAGAACTTTAAAAGTGCTCATCATTGGAAAACGTTCTTCGGGGCGAAAACTCTCAAGGATCTTACCGCTGTTGAGA
                                                    AMPCILLIN RESISTANCE

4800
TCCAGTTCGATGTAACCCACTCGTGCACCCAACTGATCTTCAGCATCTTTTACTTTCACCAGCGTTTCTGGGTGAGCAAAAACAGGAAGGCAAAATGCCG
                                                    AMPCILLIN RESISTANCE

4900
CAAAAAAGGGAATAAGGGCGACACGGAAATGTTGAATACTCATACTCTTCCTTTTTCAATATTATTGAAGCATTTATCAGGGTTATTGTCTCATGAGCGG
                              AMPCILLIN RESISTANCE

ATACATATTTGAATGTATTTAGAAAAATAAACAAATAGGGGTTCCGCGCACATTTCCCCGAAAAGTGCCAC --(SEQ ID NO:43)--
```

*FIG. 6(B) CONT.*

Sequence Range: 1 to 5523

100
CTAAATTGTAAGCGTTAATATTTTGTTAAATTTCGCGTTAAATTTTGTTAAATCAGCTCATTTTTTAACCAATAGGCCGAAATCGGCAAATCCCTTAT

200
AAATCAAAAGAATAGACCGAGATAGGGTTGAGTGTGTGTTCCAGTTTGGAACAAGAGTCCACTATTAAAGAACGTGACTCCAACGTCAAAGGGCGAAAAA

300
CCGTCTATCAGGGCGATGCCCACTAGTGAACCATCACCCTAATCAAGTTTTTTGGGGTCGAGTGCCGTAAAGCACTAAATCGAACCCTAAAGGGAG

400
CCCCCGATTTAGAGCTTGACGGGAAAGCCGGTGCCGAGAAAGGAAGAAAGCGAAAGGAGCGGGGCGCTAGGGCGCTGGCAAGTGTAGCG

500
GTCACGCTGCGCGTAACCACCACACCCGCCGCGCCTTAATGCCGCCGCTACAGGGCGCGTCCCATTCGCCATTCAGCCTGCGCAACTGTTGGGAAGGCGAT

600
CGGTGCGGGCCTCTTCGCTATTACGGCCAGCTGAGCGCGCGTAATACGACTCACTATAGGGCGAATTGGGTACCGGGCCCCCCCTCGAGGTCGACGGTATCGATAAGCTTCGATGT

700
TAAAACGACGGCCAGTGAGCGCGCGTAATACGACTCACTATAGGGCGAATTGGGTACCGGGCCCCCCCTCGAGGTCGACGGTATCGATAAGCTTCGATGT

800
CTTTGTGATGCGCCAGCATTTTTGTAGGTTATTGATAAAATGAACGGATACAGTTGCCCGACATTATCATTAAATCCTTGGCGTAGAATTGTCGGTCC

900
ATTGTCCCGTGTGCCGCTAGCATGCCCGCTAACGGACCTCGTACTTTTGGCTTCAAAGTTTTGCCGCACAGACAAAATGTGCCACACTTGCAGCTCTGCATG

1000
TGTGCGCGTTACCACAAATCCCAACGGCGCAGTGTACTTGTTGTATGCAAATAAATCTCGATAAAGGCGGCGGCGAATGCAGCTGATCACGTACGCT

1100
CCTCGTGTTCCGTTCAAGGACGGTGTTATCGACCTCAGATTAATGTTTATCGGCCGACTGTTTTCGTATCCGCTCACCAAACGCGTTTTTGCATTAACAT

FIG. 8(B)

```
1200
TGTATGTCGGCGATGTTCTATATCTAATTTGAATAAATAAACGATAACCGCGTTGTTTTAGAGGGCATAATAAAGAAATATTGTTATCGTGTTCGCC
1300
ATTAGGGCAGTATAAATTGACGTTCATGTTGGATATTGTTTCAGTTGCAAGTGAATTCCTGCAGCCCGGGGATCCTATATAATAAAATGGGTAGTTCTT
1400
TAGACGATGAGCATATCCTCTGCTCTTCTGCAAAGCGATGACGAGCTTGTTGGTGAGGATTCTGACAGTGAAATATCAGATCACGTAAGTGAAGATGA
1500
CGTCCAGAGCGATACAGAAGAAGCGTTTATAGATGAGGTACATGAAGTGCAGCCAACGTCAAGCGGTAGTGAAATATTAGACGAACAAATGTTATTGAA
1600
CAACCAGGTTCTTCATTGGCTTCTAACAGAATCTTGACCTTGCCACAGAGGACTATTAGAGGTAAGAATAAACATTGTTGGTCAACTTCAAAGTCCACGA
1700
GGCGTAGCCGAGTCTCTGCACTGAACATTGTCAGATCTCAAAGAGGTCCGACGCGTATGTGCCGCAATATATGACCCACTTTTATGCTTCAAACTATT
1800
TTTTACTGATGAGATAATTCGGAAATTGTAAAATGCTGAGATATCATTGAAACGTCGGGAATCTATGACAGGTGCTACATTTCGTGACACG
1900
AATGAAGATGAAATCTATGCTTTCTTCTTTGGTATTCTGGTAATGACAGTGAGAAAAGATAACCACATGTCCACAGATGACCTCTTTGATCGATCTTTGT
2000
CAATGGTGTACGTCTCTGTAATGAGTCGTGATCGTTTTGATTTTTGATACGATGCTTAGAATGGATGACAAAGTATACGGCCCACACTTCGAGAAAA
2100
CGATGTATTACTCCTGTTAGAAAATATGGGATCTCTTTATCCATCAGTGCATACAAATTACACTCCAGGGGCTCATTTGACCATAGATGAACAGTTA
2200
CTTGGTTTTAGAGGACGGTGTCCGTTTAGGATGTATATCCCAAACAAGCCAAGTATGGAATAAAAATCCTATGATGTGTGACAGTGGTACCGAAGT
2300
ATATGATAAATGGAATGCCTTATTTGGGAAGAGGAACACAGAACAACGGAGTACCACTCGGTGAATACTACGTGAAGGAGTTATCAAAGCCTGTGCACGG
```

*FIG. 8(B) CONT.*

2400
TAGTTGTCGTAATATTACGTGTGACAATTGGTTCACCTCAATCCCTTTGCCAAAAAACTTACTACAAGAACCGTATAAGTTAACCATTGTGGGAACCGTG

2500
CGATCAAACAAACGCGAGATACCGGAAGTACTGAAAAAACAGTCGCTCCAGGCCAGTGGGAACATCGATGTTTTGTTTTTGACGGACCCCTTACTCTCGTCT

2600
CATATAAACCGAAGCCAGCTAAGATGGTATACTTATTATTATCATCTTGTGATGAGGATGCTTCTATCAACGAAAGTACCGGTAAACCGCAAATGGTTATGTA

2700
TTATAATCAAACTAAAGGCGGAGTGGACACGCTAGACCAAATGTGTTCTGTGATGACCTGCAGTAGGAAGACGAATAGGTGGCCTATGGCATTATTGTAC

2800
GGAATGATAAACATTGCCTGCATAAATTCTTTATTATATACAGCCATAATGTCAGTAGCAAGGGAGAAAAGGTTCAAAGTCGCAAAAATTTATGAGAA

2900
ACCTTTACATGAGCCTGACGTCATCGTTTATGCGTAAGCGTTTAGAAGCTCCTACTTTGAAGAGATATTTGCGCGATAATATCTCTAATATTTTGCCAAA

3000
TGAAGTGCCTGGTACATCAGATGACAGTACTGAAGAGCCCAGTAATGAAAAAACGTACTACTGCCCCCTCTAAAATAAGGCGAAAGGCAAAT

3100
GCATCGTGCAAAAATGCAAAAAGTTATTGTCGAGAGCATAATATTGATATGTGCCAAAGTTGTTTCTGACTGACTAATAAGTATAATTGTTTCTAT

3200
TATGTATAAGTTAAGCTAATTACTTATTTTATAATAACACATGACTGTTTTAAAGTACAAAATAAGTTTATTTTGTAAAAGAGAATGTTAAAAGT

3300
TTTGTTACTTTAGAAGAAATTTGAGTTTTTGTTTTTTAATAAATAATAAACATAAATAAATTGTTGTTGAATTGGATCCACTAGTTCTAGAGC

3400
GGCCGCCACCGCGGTGGAGCTCCAGCTTTTGTTCCCTTTAGTGAGGGTTAATTGCGCGCTTGGCGTAATCATGGTCATAGCTGTTTCCTGTGTGAAATTG

*FIG. 8(B) CONT.*

```
3500
TTATCCGCTCACAATTCCACACAACATACGAGCCGAAGCATAAAGTGTAAAGCCTGGGGTGCCTAATGAGTGAGCTAACTCACATTAATTGCGTTGCGC
>ColE1_origin
|
3600
TCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCG
3700
CTTCCTCGCTCACTGACTCGCTGCGCTCGGTCGTTCGGCTGCGGCGAGCGGTATCAGCTCACTCAAAGGCGGTAATACGGTTATCCACAGAATCAGGGGA
3800
TAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGAC
3900
GAGCATCACAAAAATCGACGCTCAAGTCAGAGGTGGCGAAACCCGACAGGACTATAAAGATACCAGGCGTTTCCCCCTGGAAGCTCCCTCGTGCGCTCTC
4000
CTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGT
4100
GTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTA
4200
AGACACGACTTATCGCCACTGGCAGCAGCCACTGGTAACAGGATTAGCAGAGCGAGGTATGTAGGCGGTGCTACAGAGTTCTTGAAGTGGTGGCCTAACT
4300
ACGGCTACACTAGAAGGACAGTATTTGGTATCTGCGCTCTGCTGAAGCCAGTTACCTTCGGAAAAAGAGTTGGTAGCTCTTGATCCGGCAAACAAACCAC
4400
CGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCT
4500
CAGTGGAACGAAAACTCACGTTAAGGGATTTTGGTCATGAGATTATCAAAAAGGATCTTCACCTAGATCCTTTTAAATTAAAAATGAAGTTTTAAATCAA
4600
TCTAAAGTATATATGAGTAAACTTGGTCTGACAGTTACCAATGCTTAATCAGTGAGGCACCTATCTCAGCGATCTGTCTATTTCGTTCATCCATAGTTGC
              AMPCILLIN RESISTANCE
```

*FIG. 8(B) CONT.*

4700
CTGACTCCCCGTCGTGTAGATAACTACGATACGGGAGGGCTTACCATCTGGCCCCAGTGCTGTGCAATGATACGGGAGACCCACGCTCACCGGCTCCAGAT
          AMPCILLIN RESISTANCE                                                                    >

4800
TTATCAGCAATAAACCAGCAGCCGGAAGGGCCGAGCCGCAGAAGTGGTCCTGCAACTTTATCGCCTCCATCCAGTCTATTAATTGTTGCCGGAAGCTA
          AMPCILLIN RESISTANCE                                                                  >

4900
GAGTAAGTAGTTCGCCAGTTAATAGTTTGCGCAACGTTGTTGCCATTGCTACAGGCATCGTGGTGTCACGCTCGTCGTTTGGTATGGCTTCATTCAGCTC
          AMPCILLIN RESISTANCE                                                                   >

5000
CGGTTCCCAACGATCAAGGCGAGTTACATGATCCCCCATGTTGTGCAAAAAAGCGGTTAGCTCCTTCGGTCCTCCGATCGTTGTCAGAAGTAAGTTGGCC
          AMPCILLIN RESISTANCE                                                                   >

5100
GCAGTGTTATCACTCATGGTTATGGCAGCACTGCATAATTCTTACTGTCTAAGATGCTTTTCTGTGACTGGTGAGTACTCAACCAAGT
          AMPCILLIN RESISTANCE                                                            >

5200
CATTCTGAGAATAGTGTATGCGGCGACCGAGTTGCTCTTGCCCGGCGTCAATACGGGATAATACCGCGCCACATAGCAGAACTTTAAAGTGCTCATCAT
          AMPCILLIN RESISTANCE                                                                  >

5300
TGGAAAACGTTCTTCGGGGCGAAAACTCTCAAGGATCTTACCGCTGTTGAGATCCAGTTCGATGTAACCCACTCGTGCACCCAACTGATCTTCAGCATCT
          AMPCILLIN RESISTANCE                                                                   >

5400
TTTACTTTCACCAGCGTTTCTGGGTGAGCAAAAACAGGAAGGCAAAATGCCGCAAAAAAGGGAATAAGGGCGACACGGAAATGTTGAATACTCATACTCT
          AMPCILLIN RESISTANCE                                                                   >

5500
TCCTTTTTTCAATATTATTGAAGCATTTATCAGGGTTATTGTCTCATGAGCGGATACATATTTGAATGTATTTAGAAAAATAAACAAATAGGGGTTCCGCG
CACATTTCCCCGAAAAGTGCCAC --(SEQ ID NO:44)--

*FIG. 8(B) CONT.* p3XP3-DsRed-orf
Sequence Range: 1 to 6984

100
TAGTTATTAATAGTAATCAATTACGGGGTCATTAGTTCATAGCCCATATATGGAGTTCCGCGTTACATAACTTACGGTAAATGGCCCGCCTGGCTGACCG
                                                        CMV PROMOTER

200
CCCAACGACCCCCGCCCATTGACGTCAATAATGACGTATGTTCCCATAGTAACGCCAATAGGGACTTTCCATTGACGTCAATGGGTGGAGTATTTACGGT
                                                        CMV PROMOTER

300
AAACTGCCCACTTGGCAGTACATCAAGTGTATCATATGCCAAGTACGCCCCCTATTGACGTCAATGACGGTAAATGGCCCGCCTGGCATTATGCCCAGTA
                                                        CMV PROMOTER

400
CATGACCTTATGGGACTTTCCTACTTGGCAGTACATCTACGTATTAGTCATCGCTATTACCATGGTGATGCGGTTTTGGCAGTACATCAATGGGCGTGGA
                                                        CMV PROMOTER

500
TAGCGGTTTGACTCACGGGGATTTCCAAGTCTCCACCCCATTGACGTCAATGGGAGTTTGTTTTGGCACCAAAATCAACGGGACTTTCCAAAATGTCGTA
                                                        CMV PROMOTER

600
ACAACTCCGCCCCATTGACGCAAATGGGCGGTAGGCGTGTACGGTGGGAGGTCTATATAAGCAGAGCTGGTTTAGTGAACCGTCAGATCCGCTAGCGCTA
                                                        CMV PROMOTER

700
CCGGACTCAGATCCTATATAATAAAATGGGTAGTTCTTTAGACGATGAGCATATCCTCTCTGCCTCTTCTGCAAAGCCGATGACGAGCTTGTTGGTGAGGAT
                                                         PIGGYBAC ORF

800
TCTGACAGTGAAATATCAGATCACGTAAGTGAAGATGACGCTCCAGAGCGATACAGAGAAGACGCGTTTATAGATGAGGTACATGAAGTGCAGCCAACGTCAA
                                 PIGGYBAC ORF

*FIG. 9(B)*

```
900
GCGGGTAGTGAAATATTAGACGAACAAAATGTTATTGAACAACCAGTTCTTCATTGGCTTCTTAACAGAATCTTGACCTTGCCACAGAGAGACTATTAGAGG
     PIGGYBAC ORF

1000
TAAGAATAAACATTGTTGGTCAACTTCAAAGTCCACAGAGAGCGTAGCCCGAGTCTCTGCACTGAACATTGTCAGATCTCAAAGAGTCCGACGCGTATGTGC
     PIGGYBAC ORF

1100
CGAATATATATGACCCACTTTTATGCTTCAAACTATTTTTTACTGATGAGATAATTTCGGAAATTGTAAAATGGACAAATGCTGAGATATCATTGAAAC
     PIGGYBAC ORF

1200
GTCGGGAATCTATGACAGGTGCTACATTTCGTGACACGAATGAAGATGAAATCTATGCTTTCTTTGGTATTCTGGTAATGACAGCAGTGAGAAAGATAA
     PIGGYBAC ORF

1300
CCACATGTCCACAGATGACCTCTTTGATCGATCTTTGTCAATGGTGTACGTCTCTGTAATGAGTCGTGATCGTTTGATTTTTGATACGATGTCTTAGA
     PIGGYBAC ORF

1400
ATGGATGACAAAGTATACGGCCCACACTTCGAGAAAAATGGGATCTCTTATCCATCAGTGCATACAAAATT
     PIGGYBAC ORF

1500
ACACTCCAGGGCTCATTGACCATAGATGAACAGTTACTTGGTTGTTTAGAGGACGGTGTCCGTTTAGGATGTATATCCCAAACAAGCCAAGTAAGTATGG
     PIGGYBAC ORF

1600
AATAAAAATCCTCATGATGTGTGACAGTGGTACGAAGTATATGATAAATGGAATGCCTTATTTGGGAAGAGGAACACAGACCAACGGAGTACCACTCGGT
     PIGGYBAC ORF

1700
GAATACTACGTGAAGGAGTTATCAAGCCTGTGCACGGTAGTTGTCGTAATATTACGTGTGACAATTGGTTCACCTCAATCCCTTTGGCAAAAAACTTAC
     PIGGYBAC ORF
```

*FIG. 9(B) CONT.*

```
1800
TACAAGAACCGTATAAGTTAACCATTGTGGGAACCGTGCCGATCAAACAAACGCGAGATACCGGAAGTACTGAAAAACAGTCGCTCCAGGCCAGTGGGAAC
     PIGGYBAC ORF

1900
ATCGATGTTTTGTTTGACGGACCCCTTACTCTCGTCTCATATAAACCGAAGCCAGCTAAGATGGTATACTTATTATCATCTTGTGATGAGGATGCTTCT
     PIGGYBAC ORF

2000
ATCAACGAAAGTACCGGTAAACCGCAAATGGTTATGTATTATAATCAAACTAAAGGGCGGAGTGGACACGCTAGACCAAATGTGTTCTGTGATGACCTGCA
     PIGGYBAC ORF

2100
GTAGGAAGACGAATAGGTGGCCTATGGCATTATTGTACGGAATGATAAACATTGCCTGCATAAATTCTTTTATTATATACAGCCATAATGTCAGTAGCAA
     PIGGYBAC ORF

2200
GGGAGAAAAGGTTCAAAGTCGCAAAAATTTATGAGAAACCTTTACATGAGCCTCATCGTTTATGCGTAAGCGTTTAGAAGCTCCTACTTTGAAG
     PIGGYBAC ORF

2300
AGATATTTGCGCGATAATATCTCTAATATTTTGCCAAATGAAGTGCCTGGTACATCAGATGACAGTACTGAAGAGCCAGTAATGAAAAAACGTACTTACT
     PIGGYBAC ORF

2400
GTACTTACTGCCCCTCTAAAATAAGGCGAAAGGCAAATGCATCGTGCAAAAAATGCAAAAAAGTTATTGTCGAGAGCATAATATTGATATGTGCCAAAG
     PIGGYBAC ORF

2500
TTGTTTCTGACTAATAAGTATAATTGTTTCTATTATGTATAAGTTAAGCTAATTACTTATTTTATAATACAACATGACTGTTTTAAAGTACAAA
     PIGGYBAC ORF

2600
ATAAGTTTATTTTGTAAAGAGAGAATGTTTAAAAGTTTTGTTACTTTAGAAGAAATTTGAGTTTTGTTTTTTTAATAAATAAACATAAAT
     PIGGYBAC ORF
```

*FIG. 9(B) CONT.*

2700
AAATTGTTTGTTGAATTGGATCTCGAGGTTCCCACAATGGTTAATTCGAGCTCGCCCGGGATCTAATTCAATTAGAGCTAATTCAATTAGAGCTAAT
  PIGGYBAC ORF       >                                          3XP3 PROMOTER

2800
TCAATTAGGATCCAAGCTTATCGATTTCGAACCCTCGACCGCCGGAGTATAAATAGAGGCGCTTCGTCTACGGAGCGACAATTCAATTCAAACAAGCAAA
                                               3XP3 PROMOTER

2900
GTGAACACGTCGCTAAGCGAAAGCTAAGCAAATAAACAAGCCAGCTGAACAAGCTAAACAATCGGGGTACCGCTAGAGTCGACGGTACCGCGGGCCCGG
                                               3XP3 PROMOTER

3000
GATCCACCGGTCGCCACCATGAATTCTGCAGTCGACGGTACCGCGGGCCCGGGATCCACCGGTCGCCACCATGGTCGCTCCTCCAAGAACGTCATCAAG
      3XP3 PROMOTER                >                                           DSRED GENE

3100
GAGTTCATGCGCTTCAAGGTGCGCATGGAGGGCACCGTGAACGGCCACGAGTTCGAGATCGAGGGCGAGGGCGAGGGCCGCCCCTACGAGGGCCACAACA
                                                                                 DSRED GENE

3200
CCGTGAAGCTGAAGGTGACCAAGGGCGGCCCCCTGCCCTTCGCCTGGGACATCCTGTCCCCCCAGTTCCAGTACGGCTCCAAGGTGTACGTGAAGCACCC
                                                    DSRED GENE

3300
CGCCGACATCCCCGACTACAAGAAGCTGTCCTTCCCCGAGGGCTTCAAGTGGGAGCGCGTGATGAACTTCGAGGACGGCGGCGTGGTGACCGTGACCCAG
                                                    DSRED GENE

3400
GACTCCTCCCTGCAGGACGGCTGCTTCATCTACAAGGTGAAGTTCATCGGCGTGAACTTCCCCTCCGACGGCCCCGTAATGCAGAAGAAGACCATGGGCT
                                                    DSRED GENE

*FIG. 9(B) CONT.*

```
3500
GGGAGGCCTCCACCGAGCGCCTGTACCCCGACGGCGTGCTGAAGGGCGAGATCCACAAGGCCCTGAAGCTGAAGGACGGCGGCCACTACCTGGTGGA
             DSRED GENE
3600
GTTCAAGTCCATCTACATGGCCAAGAAGCCCGTGCAGCTGCCCGGCTACTACTACGTGGACTCCAAGCTGGACATCACCTCCCACAACGAGACTACACC
             DSRED GENE
3700
ATCGTGGAGCAGTACGAGCGCACCGAGGGCCGCCACCACCTGTTCCTGTAGCGGCCGCGACTCTAGATCATAATCAGCCATACCACATTTGTAGAGGTTT
             DSRED GENE
3800
TACTTGCTTTAAAAAACCTCCCACACCTCCCCCTGAACCTGAAACATAAAATGAATGCAATTGTTGTTGTTAACTTGTTTATTGCAGCTTATAATGGTTA
3900
CAAATAAAGCAATAGCATCACAAATTTCACAAATAAAGCATTTTTTCACTGCATTCTAGTTGTGGTTTGTCCAAACTCATCAATGTATCTTAAGGCGTA
>f1_single-strand_DNA_origin
4000
AATTGTAAGCGTTAATATTTTGTTAAAATTCGCGTTAAATTTTTGTTAAATCAGCTCATTTTTTAACCAATAGGCCGAAATCGGCAAAATCCCTTATAAA
4100
TCAAAAGAATAGACCGAGATAGGGTTGAGTGTTGTTCCAGTTTGGAACAAGAGTCCACTATTAAAGAACGTGGACTCCAACGTCAAAGGGCGAAAAACCG
4200
TCTATCAGGGCGATGGCCCACTACGTGAACCATCACCCTAATCAAGTTTTTTGGGGTCGAGGTGCCGTAAAGCACTAAATCGGAACCCTAAAGGGAGCCC
4300
CCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCGGTC
```

*FIG. 9(B) CONT.*

4400
ACGCTGCGCGTAACCACCACACCCGCCGCGCTTAATGCGCCGCTACAGGGGCGTCAGTGGCACTTTTCGGGGAAATGTGCGCGAACCCCTATTGTT
>Bacerial_promoter_for_expressioin_of_Kan_resistance_gene 4500
TATTTTTCTAAATACATTCAAATATGTATCCGCTCATGAGACAATAACCCTGATAAATGCTTCAATAATATTGAAAAAGGAAGAGTCCTGAGGCGGAAAG
>SV40_early_promoter_and_origin_of_replication 4600
AACCAGCTGTGGAATGTGTGTCAGTTAGGGTGTGGAAAGTCCCCAGGCTCCCCAGCAGGCAGAAGTATGCAAAGCATGCATCTCAATTAGTCAGCAACCA 4700
GGTGTGGAAAGTCCCCAGGCTCCCCAGCAGGCAGAAGCATGCAAAGCATGCATCTCAATTAGTCAGCAACCATATAGTCCCGCCCCTAACTCCGCCCATCCC 4800
GCCCCCTAACTCCGCCCAGTTCCGCCCATTCTCCGCCCCATGGCTGACTAATTTTTTTTATTTATGCAGAGGCCGAGGCCGCCTCTGAGCTATTC 4900
CAGAAGTAGTGAGGAGGCTTTTTTGGAGGCCTAGGCTTTTGCAAAGATCGATCAAGAGACAGGATGAGGATCGTTTCGCATGATTGAACAAGATGGATTG 5000
CACGCAGGTTCTCCGGCCGCTTGGGTGGAGAGGCTATTCGGCTATGACTGGGCACAACAGACAATCGGCTGCTCTGATGCCGCCGTGTTCCGGCTGTCAG
KANAMYCIN RESISTANCE GENE 5100
CGCAGGGGCGCCCGGTTCTTTTTGTCAAGACCGACCTGTCCGGTGCCCTGAATGAACTGCAAGACGAGGCAGCGCGGCTATCGTGGCTGGCCACGACGGG
KANAMYCIN RESISTANCE GENE 5200
CGTTCCTTGCGCAGCTGTGCTCGACGTTGTCACTGAAGCGGGAAGGGACTGGCTGCTATTGGGCGAAGTGCCGGGGCAGGATCTCCTGTCATCTCACCTT
KANAMYCIN RESISTANCE GENE

*FIG. 9(B) CONT.*

```
5300
GCTCCTGCCGAGAAAGTATCCATCATGGCTGATGCAATGCGGCGGCTGCATACGCTTGATCCGGCTACCTGCCCATTCGACCACCAAGCGAAACATCGCA
                                                KANAMYCIN RESISTANCE GENE
5400
TCGAGCGAGCACGTACTCGGATGAAGCCGGTCTTGTCGATCAGGATGATCTGGACGAAGAGCATCAGGGGCTCGCGCCAGCGAACTGTTCGCCAGGCT
                                                KANAMYCIN RESISTANCE GENE
5500
CAAGGCGAGCATGCCCGACGGCGAGGATCTCGTCGTGACCCATGGCGATGCCTGCTTGCCGAATATCATGGTGGAAAATGGCCGCTTTTCTGGATTCATC
                                                KANAMYCIN RESISTANCE GENE
5600
GACTGTGGCCGGCTGGGTGTGGCGGACCGCTATCAGGACATAGCGTTGGCTACCCGTGATATTGCTGAAGAGCTTGGCGGCGAATGGGCTGACCGCTTCC
                                                KANAMYCIN RESISTANCE GENE
5700
TCGTGCTTTACGGTATCGCCGCTCCCGATTCGCAGCGCATCGCCTTCTATCGCCTTCTTGACGAGTTCTTCTGAGCGGGACTCTGGGGTTCGAAATGACC
                                                KANAMYCIN RESISTANCE GENE
5800
GACCAAGCGACGCCCAACCTGCCATCACGAGATTTCGATTCCACCGCCGCCTTCTATGAAAGGTTGGGCTTCGGAATCGTTTTCCGGACGCCGGCTGGA
5900
TGATCCTCCAGCGCGGGGATCTCATGCTGGAGTTCTTCGCCCACCCTAGGGGGAGGCTAACTGAAACACGGAAGGAGACAATACCGGAAGGAACCCGCGC
>Herpes_simplex_virus_(HSV)_thymidine_kinase_(TK)_polyA_signals
6000
TATGACGGCAATAAAAAGACAGAATAAAACGCACGGTGTTGGGTCGTTTGTTCATAAACGCGGGGTTCGGTCCCAGGGCTGGCACTCTGTCGATACCCCA
6100
CCGAGACCCCATTGGGGCCAATACGCCCGCGTTTCTTCCTTTTCCCCACCCCACCCCCCAAGTTCGGGTGAAGGCCCAGGGCTCGCAGCCAACGTCGGGG
```

*FIG. 9(B) CONT.*

```
6200
CGGCAGGCCCTGCCATAGCCTCAGGTTACTCATATATACTTTAGATTGATTTAAAACTTCATTTTTAATTTAAAAGGATCTAGGTGAAGATCCTTTTTGA

>pUC_plasmid_replication_origin

6300
TAATCTCATGACCAAAATCCCTTAACGTGAGTTTTCGTTCCACTGAGCGTCAGACCCCGTAGAAAAGATCAAAGGATCTTCTTGAGATCCTTTTTTCTG
6400
CGCGTAATCTGCTGCTTGCAAACAAAAAAACCACCGCTACCAGCGGTGGTTTGTTTGCCGGATCAAGAGCTACCAACTCTTTTTCCGAAGGTAACTGGCT
6500
TCAGCAGAGCGCAGATACCAAATACTGTCCTTCTAGTGTAGCCGTAGTTAGGCCACCACTTCAAGAACTCTGTAGCACCGCCTACATACCTCGCTCTGCT
6600
AATCCTGTTACCAGTGGCTGCTGCCAGTGGCGATAAGTCGTGTCTTACCGGGTTGGACTCAAGACGATAGTTACCGGATAAGGCGCAGCGGTCGGGCTGA
6700
ACGGGGGGTTCGTGCACACAGCCCAGCTTGGAGCGAACGACCTACACCGAACTGAGATACCTACAGCGTGAGCTATGAGAAAGCGCCACGCTTCCCGAAG
6800
GGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGT
6900
CGGGTTTCGCCACCTCTGACTTGAGCGTCGATTTTTGTGATGCTCGTCAGGGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCCTGATTCTGTGGATAACCGTATTACCGCCATGCAT --(SEQ ID NO:45)--
```

```
Sequence Range: 1 to 4613

100
AGCGCCCAATACGCAAACCGCCTCTCCCGCGCGTTGGCCGATTCATTAATGCAGCTGGCACGACAGGTTCCCGACTGGAAAGCGGGCAGTGAGCGCAA
     200
CGCAATTAATGTGAGTTAGCTCACTCATTAGGCACCCCCAGGCTTTACACTTTATGCTTCCGGCTCGTATGTTGTGTGGAATTGTGAGCGGATAACAATTT
     300
CACACAGGAAACAGCTATGACCATGATTACGCCAAGCTTGGTACCGAGCTCGGATCCACTAGTAACGGCCGCCAGTGTGCTGGAATTCGGCTTGGATCCC
    >
     400
ATGCGTCAATTTACGCGAGACTATCTTTCTAGGGTTAATCTAGCTGCATCAGGATCATATCGTCGGGTCTTTTTTCCGGCTCAGTCATCGCCAAGCTGG
                                                        L H Q D H I V G S F F R L S H R P S W>
                                        B (CAPSID COMPONENT;533); CODON_START=1; DB_XREF=P >
                                                        L H Q D H I V G S F F R L S H R P S W>
                                        PROCESSED B; CODON_START=1 [SPLIT] >
         RIGHT TERMINAL REPEAT            >
     500
CGCTATCTGGGCATCGGGGAGGAAGAAGCCCGTGCCTTTTCCCGCGAGGTTGAAGCGGCATGAAAGAGTTTGCCGAGGATGACTGCTGCATTGACG
 R Y L G I G E E E A R A F S R E V E A A W K E F A E D D C C I D>
       B (CAPSID COMPONENT;533); CODON_START=1; DB_XREF=PID:G215108; TRA [SPLIT]
 R Y L G I G E E E A R A F S R E V E A A W K E F A E D D C C I D>
                                        PROCESSED B; CODON_START=1 [SPLIT]
```

*FIG. 10(B)*

```
600
TTGAGCCGAAAACGCACGTTTACCATGATGATTCGGGAAGTGTGTGGCCATGCACGCCTTTAACGGTGAACTGTTCGTTCAGGCCACCTGGGATACCAGTTC
  V  E  R  K  R  T  F  T  M  M  I  R  E  G  V  A  M  H  A  F  N  G  E  L  F  V  Q  A  T  W  D  T  S  S>
       B (CAPSID COMPONENT;533); CODON_START=1; DB_XREF=PID:G215108; TRA [SPLIT]           ^
  V  E  R  K  R  T  F  T  M  M  I  R  E  G  V  A  M  H  A  F  N  G  E  L  F  V  Q  A  T  W  D  T  S  S>
                           PROCESSED B; CODON_START=1 [SPLIT]                              ^

700
GTCGCGGCTTTTCCGGACACAGTTCAGTGTGTCCGATGGTCAGCCCCGAAGCGCATCAGCAACCCGAACAATACCGGCGACAGCCGAACTGCCGTGCCGGTGTGCAG
  S  R  L  F  R  T  Q  F  R  M  V  S  P  K  R  I  S  N  P  N  N  T  G  D  S  R  N  C  R  A  G  V  Q>
       B (CAPSID COMPONENT;533); CODON_START=1; DB_XREF=PID:G215108; TRA [SPLIT]           ^
  S  R  L  F  R  T  Q  F  R  M  V  S  P  K  R  I  S  N  P  N  N  T  G  D  S  R  N  C  R  A  G  V  Q>
                           PROCESSED B; CODON_START=1 [SPLIT]                              ^

800
ATTAATGACAGCGGTGCGGCGCTGGGCTATTACGTCAGCGAGGACGGGTATCCTGGCTGGATGCCGCAGAAATGACATGGATACCCGTGAGTTACCCG
  I  N  D  S  G  A  A  L  G  Y  Y  V  S  E  D  G  Y  P  G  W  M  P  Q  K  W  T  W  I  P  R  E  L  P>
       B (CAPSID COMPONENT;533); CODON_START=1; DB_XREF=PID:G215108; TRA [SPLIT]           ^
  I  N  D  S  G  A  A  L  G  Y  Y  V  S  E  D  G  Y  P  G  W  M  P  Q  K  W  T  W  I  P  R  E  L  P>
                           PROCESSED B; CODON_START=1 [SPLIT]                              ^

900
GCGGGGCGCGCCCTCGTTCATTCACGTTTTTGAACCCGTGGAGGACGGGCAGACTCGCGGTGCAAATGTGTTTTACAGCGTGATGGAGCAGATGAAGATGCT
  G  G  R  A  S  F  I  H  V  F  E  P  V  E  D  G  Q  T  R  G  A  N  V  F  Y  S  V  M  E  Q  M  K  M  L>
       B (CAPSID COMPONENT;533); CODON_START=1; DB_XREF=PID:G215108; TRA [SPLIT]           ^
  G  G  R  A  S  F  I  H  V  F  E  P  V  E  D  G  Q  T  R  G  A  N  V  F  Y  S  V  M  E  Q  M  K  M  L>
                           PROCESSED B; CODON_START=1 [SPLIT]                              ^
```

FIG. 10(B)a

```
1000
CGACACGCTGCAGAGAACACGCAGCTAGATTAACCCTAGAAAGATAATCATATTGTGACGTACGTTAAAGATAATCATGCGTAAAATTGACGCATGGGATCC
 D  T  L  Q  N  T  Q>  --(SEQ ID NO:47)--
 B (CAPSID COMPO      >
 D  T  L  Q  N  T  Q>  --(SEQ ID NO:47)--
    PROCESSED B; CO   >
                        LEFT TERMINAL REPEAT                 >

1100
AAGCCGAATTCTGCAGATATCCATCACACTGGCGGCCGCTCGAGCATGCATCTAGAGGGCCCAATTCGCCCTATAGTGAGTCGTATTACAATTCACTGGC

1200
CGTCGTTTTACAACGTCGTGACTGGGAAAACCCTGGCGTTACCCAACTTAATCGCCTTGCAGCACATCCCCCTTTCGCCAGCTGGCGTAATAGCGAAGAG

1300
GCCCGCACCGATCGCCCTTCCCAACAGTTGCGCAGCCTGAATGGCGAATGGGACGCGCCCTGTAGCGGCGCATTAAGCGCGGCGGGTGTGGTGGTTACGC

1400
GCAGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCT

1500
AAATCGGGGCTCCCTTTAGGGTTCCGATTTAGAGCTTTACGGCACCTCGACCCCAAAAAACTTGATTTGGGTGATGGTTCACGTAGTGGGCCATCGCCC

1600
TGATAGACGGTTTTTCGCCCTTTGACGTTGGAGTCCACGTTCTTTAATAGTGGACTCTTGTTCCAAACTGGAACAACACTCAACCCTATCGCGGTCTATT

1700
CTTTTGATTTATAAGGGATTTTGCCGATTTCGGCCTATTGGTTAAAAAATGAGCTGATTTAACAAATTCAGGGCGCAAGGGCTGCTAAAGGAACCGGAAC

1800
ACGTAGAAAGCCAGTCCGCAGAAACGGTGCTGACCCCGGATGAATGTCAGCTACTGGGCTATCTGGACAAGGGAAAACGCAAGCGCAAAGAGAAAGCAGG
```

*FIG. 10(B)b*

1900 TAGCTTGCAGTGGGCTTACATGGCGATAGCTAGACTGGGCGGTTTATGGACACAGCAAGCGAACCGGAATTGCCAGCTGGGGCGCCCTCTGGTAAGGTTGG
2000 GAAGCCCTGCAAAGTAAACTGGATGGCTTTCTTGCCGCCAAGGATCTGATGGCGCAGGGGATCAAGATCTGATCAAGAGACAGGATGAGGATCGTTTCGC
2100 ATGGATTGAACAAGATGGATTGCACGCAGGTTCTCCGGCCAGGTTCTCCGGCCGCTTGGGTGTGGAGAGGCTATTCGGCTATGACTGGGCACAACAGACAATCGGCTGCTCTGATG
2200 CCGCCCGTGTTCCGGCTGTCAGCGCAGGGGCGCCCGGTTCCTTGCGCAGCTGTCACTGAAGCGGGAAGGACTGGCTGCTATTGGGCGAAGTGCCGGGGCAG
2300 ATCGTGGCTGGCCACGACGGGGCGTTCCTTGCGCAGCTGTCACTGAAGCGGGAAGGACTGGCTGCTATTGGGCGAAGTGCCGGGGCAG
2400 GATCTCCTGCTCATCTCGCCCTTGCCTCCTGCCGAGAAAGTATCCATCATGGCTGATGCAATGCGGCGGCTGCATACGCTTGATCCGGCTACCTGCCATTCG
2500 ACCACCAAGCGAAACATCGCATCGAGCGAGCACGTCTTGTCGATCAGGATGATCTGGACGAAGAGCATCAGGGGCTCGCGCC
2600 AGCCGAACTGTTCGCAGGCTCAAGGCGCGCATGCCCGACGGCGAGGATCTCGTCGTGACCCATGGCGATGCCTGCTTGCCGAATATCATGGTGAAAAT
2700 GGCCGCTTTTCTGGATTCAACGACTGTGGCCGGCTGGGTGGCCGACCGCTATCAGGACATAGCGTTGGATACCCGTGATATTGCTGAAGAGCTTGGCG
2800 GCGAATGGGCTGACCGCTTCCCGATTCCCGATTCGCAGCGCATCGCCTTCTATCGCCTTCTTGACGAGTTCTTCTGAATTGA
2900 AAAAGGAAGAGTATGAGTATTCAACATTTCCGTGTCGCCCTTATTCCCTTTTTGCGGCATTTGCCTTCCTGTTTTTGCTCACCCAGAAACGCTGGTGA

*FIG. 10(B)c*

3000
AAGTAAAAGATGCTGAAGATCAGTTGGGTGCACGAGTGGGTTACATCGAACTGATCTCAACAGCGGTAAGATCCTTGAGAGTTTTCGCCCCGAAGAACG

3100
TTTTCCAATGATGAGCACTTTTAAAGTTCTGCTATGTCATACACTATTATCCCGTATTGACGCCGGCAAGAGCAACTCGGTCGCCGGGCGCCGGTATTCT

3200
CAGAATGACTTGGTTGAGTACTCCACCAGTCACAGAAAAGCATCTTACGGATGGCATGACAGTAAGAGAATTATGCAGTGCTGCCATAACCATGAGTGATA

3300
ACACTGCGGCCAACTTACTTCTGACAACGATCGGAGGACCGAAGGAGCTAACCGCTTTTTTGCACAACATGGGGATCATGTAACTCGCCTTGATCGTTG

3400
GGAACCGGAGCTGAATGAAGCCATACCAAACGACGAGAGTGACACCACGATGCCTGTAGCAATGCCAACAACGTTGCGCAAACTATTAACTGGCGAACTA

3500
CTTACTCTAGCTTCCCGGCAACAATTAATAGACTGGATGGAGGCGGATAAAGTTGCAGGACCACTTCTGCGCTCGGCCCTTCCGGCTGGCTGGTTTATTG

3600
CTGATAAATCTGGAGCCGGTGAGCGTGGGTCTCGCGGTATCATTGCAGCAGTGGGCCAGATGGTAAGCCCTCCCGTATCGTAGTTATCTACACGACGGG

3700
GAGTCAGGCAACTATGGATGAACGAAATAGACAGATCGCTGAGATAGGTGCCTCACTGATTAAGCATTGGTAACTGTCAGACCAAGTTTACTCATATATA

3800
CTTTAGATTGATTAAAACTTCATTTTTAATTTAAAAGGATCTAGGTGAAGATCCTTTTTGATAATCTCATGACCAAATCCCTTAACGTGAGTTTTCGT

3900
TCCACTGAGCGTCAGACCCCGTAGAAAAGATCAAAGGATCTTCTTGAGATCCTTTTTTTCTGCGCGTAATCTGCTGCTTGCAAACAAAAAACCACCGCT

4000
ACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTG

*FIG. 10(B)d*

```
4100
TAGCCGTAGTTAGGCCACCACTTCAAGAACTCTGTAGCACCGCCTACATACCTCGCTCTGCTAATCCTGTTACCAGTGGCTGCTGCCAGTGGCGATAAGT
4200
CGTGTCTTACCGGGTTGGACTCAAGACGATAGTTACCGGATAAGGCGCAGCGGTCGGGCTGAACGGGGGGTTCGTGCACACAGCCCAGCTTGGAGCGAAC
4300
GACCTACACCGAACTGAGATACCTACAGCGTGAGCATTGAGAAAGCGCCACGCTTCCCGAAGGGAGAAAGGCGGACAGGTATCCGGTAAGCGGCAGGTC
4400
GGAACAGGAGAGCGCACGAGGGAGCTTCCAGGGGGAAACGCCTGGTATCTTTATAGTCCTGTCGGGTTTCGCCACCTCTGACTTGAGCCTCGATTTTTGT
4500
GATGCTCGTCAGGGGGCGGAGCCTATGAGAAAAACGCCTGGAGCCTTTTTACGGTTCCTGGCCTTTTGCTCGGCCTTTTGCTCACATGTTCTTTCC
4600
TGCCGTTATCCCCTGATTCTGTGATAACCGTATTACCGCCTTTGAGTGAGCTGATACCGCTCGCCGCAGCCGAACGACCGAGCGCAGCGAGTCAGTGAGC
GAGGAAGCGGAAG --(SEQ ID NO:46)--
```

*FIG. 10(B)e* p(PZ)-Bac-EYFP
Sequence Range: 1 to 8999

100
ACCGAAGTATACACTTAAATTCAGTGCACGTTTGCTTGTTGTTGAGAGGAAAGTTGTGTGCGGACGAATTTTTTTTGAAAACATTAACCCTTACGTGGAAT

200
AAAAAAAATGAAATATTGCAAATTTTGCTGCAAAGCTGTGACTGGAGTAAATTAATTCACGTGCCGAAGTGTGCTATTAAGAGAGAAAATTGTGGAGCA

300
GAGCCTTGGGTGCAGCCTTTGGTGAAAACTCCCAAATTTGTGATACCCACTTTAATGATTCGCAGTGGAAGGCTGCACCTGCAAAAGGTCAGACATTTAAA

400
AGGAGGCGACTCAACGCAGAGATGCCGTACCTAGTAAAGTGATAGAGCCTGAACCAGAAAAGATAAAGAAGGCTATACCAGTGGGAGTACACAAACAGAGT

500
AAGTTTGAATAGTAAAAAAAATCATTTATGTAAACAATAACGTGACTGTGCGTTAGGTCCTGTTCATTGTTTAATGAAAATAAGAGCTTGAGGGAAAAAA

600
TTCGTACTTTGGAGTACGAAATGCGTCGTTTAGAGCAGAGCCGAATTCACTGGCCCGTCGTTTTACAACGTCGTGACTGGGAAAACCCTGGCGTTACCCA

700
ACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGC

800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT

900
GGCAGATGCACGGTTACGATGCGCCCATCTACACCAACGTAACCTATCCCATTACGGTCAATCCGCCGTTTGTTCCCACGGAGAATCCGACGGGTTGTTA

1000
CTCGCTCACATTTAATGTTGATGAAAGCTGGCTACAGGAAGGCCAGACGCGAATTATTTTGATGGCGTTAACTCGGCGTTTCATCTGTGGTGCAACGGG

1100
CGCTGGGTCGGTTACGGCCAGGACAGTCGTTTGCCGTCTGAATTTGACCTGAGCGCATTTTTACGCGCCGGAGAAAACCGCCTCGCGGTGATGGTGCTGC

*FIG. 12(B)*

1200 GTTGGAGTGACGGCAGTTATCTGGAAGATCAGGATATGTGGGCGATGAGCGGGCATTTCCGTGACGTCTCGTTGCTGCATAAACCGACTACACAAATCAG
1300 CGATTTCCATGTTGCCACTCGCTTTAATGATGATTTCAGCCGCGTGTACTGGAGGCTGAAGTTCAGATGTGCGGCGAGTTGCTGACTACCTACGGGTA
1400 ACAGTTTCTTTATGGCAGGGTGAAACGCAGGTCGCCAGCGGCACCGCGCCTTTCGGCGGTGAAATTATCGATGAGCGTGGTGTTATGCCGATCGCGTCA
1500 CACTACGGTCTGAACGTCGAAAAACCCGAATCTGTGGAGCGCGCCGAAAATCCCGAATCTCTATCGTGCGGTGGTTGAACTGCACACCGCCGACGGCACGCTGAT
1600 TGAAGCAGAAGCCTGCGATGTCGGTTTCCGCGAGGTGCGCGGATTGAAAATGTCTGCTGCTGAACGGCAAGCCGTTGCTGATTCGAGGCGTTAACCGT
1700 CACGAGCAGCATCATCCTCTGCATGGTCAGGTCATGATGAGCCGCTGTGCGACCGCTGTATGTGGTGATGAAGCCAATATTGAAACCCACGGCATGGTGCCAAT
1800 CGCATTATCGAACCATCCGCTGTGGTACACGCTGGCCGATGAGCGTAACGCGAATGGTGCAGCCGCGATCGTAATCACCCGAGTGTGATCATCTGG
1900 GAATCGTCTGACCGATGATCCCGCTGGCTACCGGCGATGAGCGAACGCGTAACGCGCTGTATCGCTGGATCAAATCTGTCGATCCTTCCCGCCGGTGCAGTATGAAGGCGGGCCG
2000 TCGCTGGGGAATGAATCAGGCCACGGCCACCGATATATTTGCCCGATGTACGCGGCGTGATGAAGACCAGCCCTTCCCGGCCTTGCCGAAATGGTCCATCAAAAATG
2100 GAGCCCGACACCACGGGCCACCGATATTATTTGCCCGATGTACGCGGCGTGATGAAGACCAGCCCTTCCCGGCCTTGCCGAAATGGTCCATCAAAAATG
2200 GCTTTTCGCTACCTGGAGACGCCCCGCTGATCCTTTGCGAATACGCCACGCGATGGGTAACAGTCTTGGCGGTTTCGCTAAATACTGCAGGCGTTT
2300 CGTCAGTATCCCCGTTTACAGGGCGGCTTCGTCTGGGACTGGTGGATCAGTCGCTGATTAAATATGATGAAAACGGCAACCCGTGGTCGGCTTACGGCG

*FIG. 12(B) CONT.*

2400
GTGATTTTGGCGATACGCCGAACGATGCCAGTTCTCTGTATGAACGTCTCGTCTTTGCCGACCGCACGCCGCATCCAGCGCTGACGGAAGCAAAACACCA

2500
GCAGCAGTTTTTCCAGTTCCGTTATCGGGCAAACCATCGAAGTGACCAGCGAATAACCTGTTCCGTCATAGCGATAACGAGCTCCTGCACTGACTGATGGTG

2600
GCGCTGGATGTGTAAGCCGCTGGCAAGCGGTGAAGTGCCTCGGATGTCGCTCCACAAGTAAACAGTGATTGAACTGCCTGAACTACCGCAGCCGGAGA

2700
GCGCCGGGCAACTCTGGCTCACAGTACCGTAGTGCAACCGAACGCGACCGCATGTCAGAAGCGGGCACATCAGCGCCTGGCAGCAGTGGCGTCTGGC

2800
GGAAAACCTCAGTGTGACGCTCCCCGCCGCTCCCACGCCATCCCGCGATAAAAACAGCCGAAATGGATTTTTGCATCGAGCTGGTAATAAGCGTTGG

2900
CAATTTAACCGCCAGTCAGGCTTTCTCTTTCACAGATGTGGATTGGCGATAAAAACAACTGCTGACGCCTGGGTCGAACGCTGGAAGCGCAGCGTTGTT

3000
ATAACGACATTGGCGTAAGTGAAGCGACCCGCATTGACCCTAACGCCTGGGTGCTGATTACGACCGCTGCGCAGCATCAGGGCGAAAACCTTATTATCAGCCGGAAAACCTAC

3100
GCAGTGCACGGCAGATACACTTGCTGATGCGGTGCTGATTACCGACGCGCTGCGCAGCATCAGGGCGAAAACCTTATTATCAGCCGGAAAACCTAC

3200
CGGATTGATGGTAGTGGTCAAATGGCGATTACCGTTGATGTTGAAGTGGGCGAGCGATACACCCGATCCCGGCGGATTGGCCTGAACTGCCAGCTGGCGC

3300
AGTTAGCAGAGCGGGTAAACTGGCTCGGATTAGGGCCGCCCTTACTGCCGCCTGTTTTGACCGCTGGGATCTGCCATTGTC

3400
AGACATGTATACCCCGTACGTCTTCCCGAGCGAAAACGGTCTGCGCCTGCGGGACGCGGCGAATTGAATTATGGCCCACACCAGTGGCGGCGACTTCCAG

3500
TTCAACATCAGCCGCTACAGTCAACAGCAACTGATGAAACCAGCCATCGCCGCCGGAAGAAGGCACATGCTGAATATCGACGGTTTCC

*FIG. 12(B) CONT.*

3600
ATATGGGGATTGGTGGCGACGACTCCTGGAGCCCGTCAGTATCGGGCGGAATTCCAGCTGAGCGCCGTGCTACCATTACCAGTTGGTCTGGTGTCGGGG

3700
ATCCGTCGACTAAGGCCAAAGAGTCTAATTTTGTTCATCAATGGGTTATAACATATGGGTTATATTATAAGTTGTTTAAGTTTTTGAGACTGATAAG

3800
AATGTTTCGATCGAATATTCCATAGAACAACAATAGTATTACCTAATTACCAAGTCTTAATTTAGCAAAAATGTTATTGCTTATAGAAAAATAAATTAT

3900
TTATTTGAAATTTAAAGTCAACTTGTCATTTAATGTCTTGTAGACTTTTGAAAGTCTTACGATACAATTAGTATCTAATATACATGGGTTCATTCTACAT

4000
TCTATATTAGTGATGATTTCTTTAGCTAGTAATACATTTTAATTATATTCGGCTTTGATGATTTTCTGATTTTTTCCGAACGGATTTTCGTAGACCCTTT

4100
CGATCTCATAATGGCTCATTTTATTGCGATGGACCGGTCAGGAGAGCTCCACTTTTGAATTTCTGTTCCGCAGACACCGCATTTGTAGCACATAGCCGGGAC

4200
ATCCGGTTTGGGGAGATTTTCCAGTCTCTGTTGCAATGGTTTTCGAGGCGCATACGCTCTATATCCTCCGAACGGCGCTGGTTGACC

4300
CTAGCATTTACATAAGGATCAGCAGCAAAATTGCCCTCGCTTCATTGCCCGGAATCACAGCAATCAGAGTGTCCCTTCGTTACGATGGATATTCAGGT

4400
GCGAACCGCACACAAAGCTCTCGCCGCACACTCCACACTGATATGGTCGCTCGCCCTGTGGCCGCATATGGATCTTAAGGTCGTTGGACTGCACAAAG

4500
CTCTTGCTGCACATTTGCAGGAGTACGGCCTTTGACCCGTGTGCAATCGCATGTCGCGCCAGCTTGTTCTGCGAAATAAACTTCTTGGAGCAGATGC

4600
GGCCGCCCGGGGTGGGCGAAGAACTCCAGCATGAGATCCCCGCCGGCGTCCCGGAGGATCATCCAGCCGGCGATTCCGAAAACGATTCCGAAGCCCAACCTTTCAT

4700
AGAAGGCGGCGGTGGAATCGAAATCTCGTGATGGCAGGTTGGGCGTCGCTTGGTCGTCGTCATTTCGAACCCAGAGTCCCGCTCAGAAGAACTCGTCAAGA

*FIG. 12(B) CONT.*

4800
AGGCGATAGAAGGCGATGCGCTGCGAATCGGGAGCGGGCGATACCGTAAAGCACGAGGAAGCGTCAGCCCATTCGCCGCCAAGCTCTTCAGCAATATCAC

4900
GGGTAGCCAACGCTATGTCCTGATAGCGGTCCGCCCACACCCAGCCCGGCCACAGTCGATGAATCCAGAAAAGCGGCCATTTTCCACCATGATATTCGGCAA

5000
GCAGGCATCGCCATGGGTCACGACGAGATCCTCGCCCGTCGGGCATGCGCCCTTGAGCCTGGGCGAACAGTTCGGCTGCGGCGAGCCCCTGATGCTCTTCG

5100
TCCAGATCATCCTGATCGACAAGACCGGCTTCCATCCGAGTACGTGCTCGCTCGATGCGATGTTTCGCTTGGTGGTCGAATGGGCAGTAGCCGGATCAA

5200
GCGTATGCAGCCGCCCGCATTGCATCAGCCATGATGATACTTTCTCGGCAGAGCAAGGTGAGATGACAGGAGATCCTGCCCCGGCACTTCGCCCAATAG

5300
CAGCCAGTCCCTTCCCGCTTCAGTGACAACGTCGAGCACGTGCGCAAGGAACGCCCGTCGTGGCCAGCCACGATAGCCGCTGCCTCGTCCTGCAGT

5400
TCATTCAGGGCACCGACAGGTCGGTCTTGACAAAAGAACGGGCGCCCTGCGCTGACAGCCGGAACACGGGCCATCAGAGCCGATTGTCTGTT

5500
GTGCCCAGTCATAGCCGGAATAGCCTCTCCACCCAAGGCGGCCGAGAACCTGCGTGCAATCCATCTTGTTCAATCATGCGAAACGATCCTCATCCTGTCTC

5600
TTGATCAGATCTTGATCCCCTGCGCCATCAGATCCTTGGCGCAAGAAAGCCATCCAGTTTACTTTGCAGGGCTTCCCAACCTTACCAGAGGGCGCCCCA

5700
GCTGGCAATTCCGGTTCGCTTGCTTGCTGTCCATAAAACCGCCCAGTCTATCGCCATGTAAGCCCACTGCAAGCTACCTGCTTTCTCTTTGGCTTGCGT

5800
TTTCCCTTGTCCAGATAGCCCAGTAGCTGACATTCATCCGGGGTCAGCACCGTTTCGCGGACTGGCTTTCTACGTGTTCCGCTTCCCTTTAGCAGCCCTT

5900
GCGCCCTGAGTGCTGCTTGCGGCAGCGTGAAGCTAATTCATGGTTATAAATTTTGTTAAATCAGCTCATTTTTAACCAATAGGGCGAAATCGGCAAAATCC

*FIG. 12(B) CONT.*

6000 CTTATAAATCAAAGAATAGCCCGAGATAGGGTTGAGTGTGTTGTTCCAGTTTGGAACAAGAGTCCACTATTAAAGAACGTGGACTCCAACGTCAAAGGGCG
6100 AAAAACCGTCTATCAGGGCGATGCGCGGATCAGCTTATGCGGTGTGAAATACCGCACAGATGCGTAAGGAGAAAATACCGCATCAGGCGCTCTTCCGCTT
6200 CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300 CGCAGGAAAGAACATGTGAGCAAAAGGCCAGCAACCGTAAAAAGGCCGCGTTGCTGGCGTTTTTCCATAGGCTCCGCCCCCCTGACGAG
6400 CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500 TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600 GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700 CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800 GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900 TGGTAGCGGCGGTTTTTTGTTTGCAAGCAGCAGATTACGCGCAGAAAAAAAGGATCTCAAGAAGATCCTTTGATCTTTTCTACTGAACGGTGATCCCCA
7000 CCGGAATTGCGGGCGGGAATTCTCATGTTTGACAGCTTATCATGATAAGCTGGCCCGCTCTAGAACTAGTGTTCCCACAATGTTAATTCGAGCTCGCC
 3XP3-EYFP MARKER ⟩
7100 CGGGGATCTAATTCAATTAGAGACTAATTCAATTAGGATCCAAGCTTATCGATTCGAACCCTCGACCGCCGAGTATAAATAGA ⟩
 3XP3-EYFP MARKER

*FIG. 12(B) CONT.*

```
7200 GGCGCTTCGTCTACGGAGCGACAATTCAATTCAAACAAGCAAAGTGAACACGTCGCTAAGCGAAAGCTAAGCAAATAAACAAGCGCAGCTGAACAAGCTA
                                                                                                    3XP3-EYFP MARKER

7300 AACAATCGGGGTACCGCTAGAGTCGACGGTACGATCCACCGGTCGCCACCATGGTGAGCAAGGGCGAGGAGCTGTTCACCGGGGTGGTGCCCATCCTGGT
                                                                                                    3XP3-EYFP MARKER

7400 CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC
                                                                                                    3XP3-EYFP MARKER

7500 ACCGGCAAGCTGCCCGTGCCCTGGCCCACCCTCGTGACCACCTTCGGCTACGGCCTGCAGTGCTTCGCCCGCTACCCCGACCACATGAAGCAGCACGACT
                                                                                                    3XP3-EYFP MARKER

7600 TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGG
                                                                                                    3XP3-EYFP MARKER

7700 CGACACCCTGGTGAACCGCATCGAGCTGAAGGGCATCGACTTCAAGGAGGACGGCAACATCCTGGGGCACAAGCTGGAGTACAACTACAACAGCCACAAC
                                                                                                    3XP3-EYFP MARKER

7800 GTCTATATCATGGCCGACAAGCAGAAGAACGGCATCAAGGTGAACTTCAAGATCCGCCACAACATCGAGGACGGCAGCGTGCAGCTCGCCGACCACTACC
                                                                                                    3XP3-EYFP MARKER

7900 AGCAGAACACCCCCATCGGCGACGGCCCCGTGCTGCTGCCCGACAACCACTACCTGAGCTACCAGTCCGCCCTGAGCAAAGACCCCAACGAGAAGCGCGA
                                                                                                    3XP3-EYFP MARKER

8000 TCACATGGTCCTGCTGGAGTTCGTGACCGCCGCGGGGATCACTCTCGGCATGGACGAGCTGTACAAGTAAAGCGGCCGCGACTCTAGATCATAATCAGCC
                                                                                                    3XP3-EYFP MARKER
```

*FIG. 12(B) CONT.*

```
8100
ATACCACATTTGTAGAGGTTTACTTGCTTTAAAAAACCTCCCACACCTCCCCCTGAACCTGAAACATAAAATGAATGCAATTGTTGTTGTTAACTTGTT
                                                     3XP3-EYFP MARKER                                >
8200
TATTGCAGCTTATAATGTTACAAATAAAGCAATAGCATCACAAATTTCACAAATAAAGCATTTTTTCACTGCATTCTAGTGTGTGGTTGTCAAACTC
                                                     3XP3-EYFP MARKER                                >
8300
ATCAATGTATCTTAAAGCTTATCGATACGCCTACGGCACTAGTGGATCCATGCGTCAATTTTACGCATGATTATCTTAACGTACGTCACAATATGATT
   3XP3-EYFP MARKER                              <         LEFT TERMINAL REPEAT
8400
ATCTTTCTAGGGTTAATCTAGCTGCGTGTTCTGCAGCCGTGTGTCGAGCATCTTCATCGCTCCATCACGCTGTAAAACACATTTGCACCGGAGTCTGCCCG
<
8500
TCCTCCACGGGTTCAAAAACGTGAATGAACGAGGCGCCCCGGGTAACTCACGGGGTATCCATGTCCATTTCTGCGCATCCAGCCAGGATACCCGT
8600
CCTCGCTGACGTAATATCCCAGCGCCGCCACCGCTGTCATTAATCTGCACACCGGCACGGCAGTTCCGGCGTGTGCCGGTATTGTTCCGGTTGCTGATGCG
8700
CTTCGGGCTGACCATCCGAACTGTGTCCGAAAAGCCGGCGACGAACTGGTATCCCAGGTGGCCTGAACGAACAGTTCACCGTTAAAGGCGTGCATGGCC
8800
ACACCCTTCCCGAATCATCATGGTAAACGTGCGTTTTCGCTCAACGTCAATGCAGCAGCAGTCATCCTCGGCAAACTCTTTCCATGCCGCTTCAACCTCGC
8900
GGGAAAAGGCACGGGCTTCTTCCTCCCCGATGCCCAGATAGCGCCAGCTTGGGCGATGACTGAGCCGGAAAAAAGACCCGACGATATGATCCTGATGCAG
CTAGATTAACCCTAGAAAGATAGTCTGCGTAAAATTGACGCATGGGATCCCCCCGGGCTGCAGGAATTCGATATCAAGCTTATCGATACCGTCGAAGCTT
      RIGHT TERMINAL REPEAT                                                  --(SEQ ID NO:48)--
<
```

*FIG. 12(B) CONT.* p(PZ)-Bac-ECFP
Sequence Range: 1 to 9012

```
100
ACCGAAGTATACACTTAAATTCAGTGCACGTTTGCTTGTTGAGAGAGAAAGGTTGTGTGCGACGAATTTTTTTTGAAACATTAACCCTTACGTGAAT
200
AAAAAAAATGAAATATTGCAAATTTGCTGCAAAGCTGTGACTGAGTAAAATTAATTCACGTGCCAAGTGTGCTATTAAGAGAAAATGTGGAGCA
300
GAGCCCTTGGGTGCAGCCCTTGGTGAAAACTCCCAAATTTGTGATACCCACTTTAATGATTCGCAGTGGAAGGCTGCACCTGCAAAAGTCAGACATTTAAA
400
AGGAGGCGACTCAACGCAGATGCCGTACCTAGTAAAGTGATAGAGCCTGAACCAGAAAAGATAAAGAAGGCTATACCAGTGGGAGTACACAAACAGAGT
500
AAGTTTGAATAGTAAAAAAATCATTTATGTAAACAATAACGTGACTGTGCGTTAGGTCCTGTTCATTGTTAATGAAATAAGAGCTTGAGGGAAAAAA
600
TTCGTACTTTGGAGTACGAAATGCGTCGTTTAGAGCAGCCGAATTCACTGGCCGTCGTGACTGGGAAAACCCTGGCGTTACCCA
700
ACTTAATCGCCTTGCAGCACATCCCCCCTTTCGCCAGCTGGCGTAATAGCGAAGAGGCCCGCACCGATCGCCCTTCCCAACAGTTGCCGACAGCCTGAATGGC
800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT
900
GGCCAGATGCACGGTTACGATGCGCCCATCTACACCAACGTAACCTATCCCATTACGGTCAATCCCCGTTTGTTCCCACGGAGAATCCGACGGGTTGTTA
1000
CTCGCTCACATTTAATGTTGATGAAAGCTGGCTACAGGAAGGCCAGACGCGAATTATTTTTGATGGCGTTAACTCGGCGTTTCATCTGTGGTGCAACGGG
1100
CGCTGGGTCGGTTACGGCCAGGACAGTCGTTTGCCGTCTGAATTGACCTGAGCGCATTTTTACGCGCCGGAGAAAACCGCCTCGCGGTGATGGTGCTGC
```

FIG. 13(B)

1200 GTTGGAGTGACGGCAGTTATCTGGAAGATCAGGATATGTGGCGGATGAGCGGCCATTTTCCGTGACGTCTCGTTGCTGCATAAACGACTACACAAATCAG
1300 CGATTTCCATGTTGCCACTCGCTTAATGATGATTTCAGCCGCGCTGTACTGTGGAGGCTGAAGTTCAGATGTGCGGCGAGTTGCTGTGACTACCTACGGTA
1400 ACAGTTTCTTTATGCAGGGTGAAACGCAGGTCGCCAGCGGCACCGGCCCTTTCGGCGGTGAAATTATCGATGAGCGTGGTGTTATGCCGATCGCGTCA
1500 CACTACGTCTGAACGTCGAAAACCCGAAACTGTGGAGCGCCGAAATCTCTATCGTGCCGTGGTTGAACTGCACACCCGCCGACGGCACGCTGAT
1600 TGAAGCAGAAGCCTGCGATGTCGGTTTCCGCGAGGTGCGATTGAAAATGGTCTGCTGCTGAACGGCAAGCCGTTGCTGTGATTCGAGGCGTTAACCGT
1700 CACGAGCAGCATCATCCTCTGCATGTCAGGTCATGATGAGCAGATGGTGCAGGATATCCTGCTGATGAAGCAGAACAACTTTAACGCCCGTGCCGCTGTT
1800 CGCATTATCCGAACCATCCGCTGTGGTACACGCTGTGCCGACCGCCTACGGCCTGTATGTGGTGATGAAGCCAATATTGAAACCACGCATGGTGCCAAT
1900 GAATCGTCTGACCGATGATCCGGCGCTACCGGGCGATGAGCGAACGCGTAACGCCGAATGGTGCAGCCGCCATCGTAATCACCCGAGTGTGATCATCTGG
2000 TCGCTGGGGAATGAATCAGGCCACGCGGATATTATTTGCCCGATGAAGACCAGCCCTTCCCGCCGGTGTGCCGAAATGGTCCATCAAAAAATG
2100 GAGCCGACACCACCGGCCACCGATATTATTTGCCCGATGAAGACCAGCCCTTCCCGCCGGTGTGCCGAAATGGTCCATCAAAAAATG
2200 GCTTTCGCTACCTGGAGAGACGCGCCCCGCTGATCCTTTGCGAATACGCCCACGCGATGGTAACAGTCTTGGCGGTTTCGCTAAATACTGGCAGGCGTTT
2300 CGTCAGTATCCCGTTTACAGGGCGGCCTTCGTCTGGAACTGGTGGATCGGTGGATCAGTCGCTGATTAAATATGATGAAAACGGCAACCCGTGGTCGGCCTTACGGCG

*FIG. 13(B) CONT.*

2400
GTGATTTGGGCGATACGCCGAACGATCGCCAGTTCTGTATGAACGGTCTCGGTCTTTGCCGACCGCACGCCGCATCCAGCGCCTGACGGAAGCAAAACACCA
2500
GCAGCAGTTTTCCAGTTCCGTTTATCCGGCAAAACCATCGAAGTGACCAGCGAATACTGTTCCGTCATAGCGATAACGAGCTCCTGCACTGGATGGTG
2600
GCGCTGGATGGCTAAGCCGCTGGCAAGCGGTGAAGTGCCCTCGGATGTCGCTCCACAAGGTAAACAGTTGATTGAACTGCCTGAACTACCGCAGCCGGAGA
2700
GCGCCCGGGCAACTCTGGCTCACAGTACGCGTAGTGCAACCGAACGCGACCGCATGGTCAGAAGCCGGGCACATCAGCGCCTGGCACAGTGGCGTCTGGC
2800
GGAAAACCTCAGTGTGACGCTCCCCCGCGTCCCACGCCATCCCGCATCTGACCACCAGCGGAAATGGATTTTTGCATCGAGCTGGGTAATAAGCGTTGG
2900
CAATTTAACCGCCAGTCAGGCTTTCTTTCACAGATGTGGATTGGCGATAAAACAACTGCTGACGCCGCTGCGCGATCAGTCACCCGTGCACCGCTGG
3000
ATAACGACATTGGCGTAAGTGAAGCGACCCGCATTGACCCTAACGCCTGGGTCGAACGCTGGAAGCGCGGGCCATTACCAGGCCGAAGCAGCGTTGTT
3100
GCAGTGCACGGCAGATACACTTGCTGATGCGGTGCTGATTACGACCGCTCACGCGTGGCAGCATCAGGGAAAACCTTATTTATCAGCCGGAAAACCTAC
3200
CGGATTGATGGTAGTGGTCAAATGGCGATTACCGTTGATGTTGAAGTGGCGAGCGATACACCGATCCGGCGCATCCGGCGATTGGCCTGAACTGCCAGCTGGCGC
3300
AGGTAGCAGAGCGGGTAAACTGGCTCGGATTAGGGCGCAAGAAAACTATCCCGACCGCCCTTACTGCCGCCTGTTTTGACCGCTGGGATCTGCCATTGTC
3400
AGACACATGTATACCCCGTACGTCTTCCCGAGCGAAAACGGTCTGCGCTGCGGACGCGCGAATTGAATTATGCCCACACCAGTGGCGGCGACTTCCAG
3500
TTCAACATCAGCCGCTACAGTCAACAGCAACTGATGGAAACCAGCCATCGCCATCTGCCACGGGAAGAAGGCACATGGCTGAATATCGACGGTTTCC

FIG. 13(B) CONT.

3600 ATATGGGGATTGGTGTGGCGACGACTCCTGGAGCCCGTCAGTATCGGGCGAATTCCAGCTGAGCCGGTCGCTGCTACCATTACCAGTTGGTCTCGGTGTCGGGG

3700 ATCCGTCGACTAAGGCCAAAGAGTCTAATTTTTGTTCATCAATGGGTTATATCATATGGTTATATATAAGTTGTTTAAGTTTTGAGACTGATAAG

3800 AATGTTTCGATCGAATATTCCATAGAACAACAATAGTATTACCTAATTACCAAGTCTTAATTTAGCAAAAATGTTATTGCTTATAGAAAAATAAATTAT

3900 TTATTTGAAAATTTAAAGTCAACTTGTCATTTAAGTCTTGTAGACTTTTGAAAGTCTTACGATACAATTAGTATCTAATATACATGGTTCATTCTACAT

4000 TCTATATTAGTGATGATTTCTTTAGCTAGTAATACATTTTAATTATATTCGGCTTTGATGATTTTCTGATTTTTCCGAACGGATTTTCGTAGACCCTTT

4100 CGATCTCATAATGGCTCATTTTATTGCGATGACGGTCAGGAGAGCTCCACTTTTGAATTTCTGTTCGCAGACACCGCATTGTAGCACATAGCCGGGAC

4200 ATCCGGTTTGGGAGATTTTCCAGTCTCTGTTGCAATTGGTTTTCGGGAATGCGTTCAGGCGCATACGCTCTATATCCTCCGAACGGCGCTGTTGACC

4300 CTAGCATTACATAAGGATCAGCAGCAAAATTGCCTCTGCTTCATTGCCCGGAATCACAGCCAATCAGATGTCCCTTTCGGTTACGATGGATATTCAGGT

4400 GCGAACCGCGCACACAAAGCTCTCGCCGCACACTCCACACTGATATGGTCGCTCGCCCTGTGGCGCCCAGCTTGTTCTCGCAATAAACTTCTTGGACTGCACAAAG

4500 CTCTTGCTGCACATTTGCAGGAGTACGGCCTTTGACCCGTGTGCAATCGATGTCGCGCAATCGATATCCAGCGCCGGGCGTCCCGGAAAACGATTCCGAAGCCCAACCTTTCAT

4600 GGCCCGCCCGGGGTGGGCGAAGAACTCCAGCATGAGATCATCCCGCGCTGGAGGATCATCCAGCGCCGGGCGTCCCGGAAAACGATTCCGAAGCCCAACCTTTCAT

4700 AGAAGGCGGGCGGTGGAATCGAATCTCGTGATGGCAGGTTGGGCGTGCGTTGGTCGTCATTCGAACCCCAGAGTCCCGCTCAGAAGAACTCGTCAAGA

*FIG. 13(B) CONT.*

4800
AGGCGATAGAAGGCGATGCGCTGCGAATCGGGAGCGGCGATACCGTAAAGCACGAGGAAGCGGTCAGCCTTCATTCGCCGCCAAGCTCTTCAGCAATATCAC
4900
GGGTAGCCAACGCTATGTCCTGATAGCGTCCGCCACACCCAGCCGGCCACAGTCGATGAATCCAGAAAAGCGGCCATTTTCCACCATGATATTCGGCAA
5000
GCAGGCATCGCCATGGTTCACGACGAGATCCTGCGCGTCGGGCATGCGCGCCTTGAGCCTGGGCGAACAGTTCGGCTGCTGGCGAGCCCCTGATGCTCTTCG
5100
TCCAGATCATCCTGATCGACAAGACCGGCTTCCATCCGAGTACGTGTCGCTCGATGCGATGTTTCGCTTGGTGGTGTCGAATGGGCAGGTAGCCGGATCAA
5200
GCGTATGCAGCCGCCCGCATTGCATCAGCCATGATGGATACTTTCTCGGAGCAAGGTGAGATGACAGGAGATCCTGCCCCCGGCACTTCGCCCAATAG
5300
CAGCCAGTCCCTTCCCGCTTCAGTGACAACGTCGGTCTTGACAAAAGAACCGGGCCCCTGCGCTGACAGCCGGCATCAGAGCAGCCGATTGTCTGTT
5400
TCATTCAGGGCACCGGACAGGTCGGTCTTGACAAAAGAACCGGGCCCCTGCGCTGACAGCCGGCATCAGAGCAGCCGATTGTCTGTT
5500
GTGCCCAGTCATAGCCGAATAGCCTCTCCACCCAGCGGCCGGAGAACCTGCGTGCAATCCATCTTGTTCAATCATGCGAAACGATCCTCATCCTGTCTC
5600
TTGATCAGATCTTGATCCCCCTGCGCCATCAGATCCTTGGCGGCAAGAAAGCCATCCAGTTTACTTTGCAGGGCTTCCCAACCTTACCAGAGGGCGCCCCA
5700
GCTGGCAATTCCGGTTCGCTTGCTGCTGTCCATAAAACGCCCAGTCTAGCTATCGCCATGTAAGCCCACTGCAAGCTACCTGCTTTCTCTTTGCGCTTGCGT
5800
TTTCCCTTGTCCAGATAGCTGACATTCATCCGGGTCAGCACCGTTTCTGCGGACTGGCTTCTACGTGTTCCGCTTCCTTAGCAGCCCTT
5900
GCGCCCTGAGTGCTTGCGGCAGCCGGTGAAGCTAATTCATGGTTATAAATTTTTGTTAAATCAGCTCATTTTTAACCAATAGGCCGAAATCGGCAAAATCC

*FIG. 13(B) CONT.*

6000 CTTATAAATCAAAAGAATAGCCCGAGATAGGGTTGAGTGTTGTTCCAGTTTGGAACAAGAGTCCACTATTAAAGAACGTGGACTCCAACGTCAAAGGGCG
6100 AAAAACCGTCTATCAGGGCGATGCCGGATCAGCTTATGCCGGTGTGAAATACCGCACAGATGCGTAAGGAGAAAATACCGCATCAGGGCGCTCTTCCGCTT
6200 CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300 CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400 CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500 TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600 GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700 CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800 GCTACACTAGAAGGACAGTATTTGTATCTGCGCTCTGCTGAAGCCAGTTACCTTCGGAAAAAGAGTTGGTAGCTCTTGATCCGGCAAACAAACCACCGC
6900 TGGTAGCGGCGGTTTTTTGTTTGCAAGCAGCAGATTACGCGCAGAAAAAAAGGATCTCAAGAAGATCCTTTGATCTTTTCTACGAACGGTGATCCCCA
7000 CCGGAATTGCGCGCGGGCGAATTCTCATGTTTGACAGCTTATCATGTTTGACAGCTTATCATCGATAAGCTGTTGCCGCTCTAGAACTAGTGTCCCACAATGGTTGTTCCCACAATGGTTAATTCGAGCTCGCC
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯
3XP3-EYFP MARKER
7100 CGGGGATCTAATTCAATTAGAACTAATTCAATTAGAGCTAATTCAATTAGAGATCCAAGCTTATCGATTTCGAACCCTCGACCGCCGGAGTATAAATAGA
⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯
3XP3-EYFP MARKER

*FIG. 13(B) CONT.*

```
7200
GGCGGCTTCGTCTACGAGGCGACAATTCAATTCAAACAAGCAAAGTGAACACGTCGCTAAGCGAAAGCTAAGCAAATAAACAAGCGCAGCTGAACAAGCTA
                                      3XP3-EYFP MARKER
7300
AACAATCGGGTACCGCTAGAGTCGACGGTACGATCCACCGGTCGCCACCATGGTGAGCAAGGGCGAGGAGCTGTTCACCGGGGTGGTGCCCATCCTGGT
                                      3XP3-EYFP MARKER
7400
CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC
                                      3XP3-EYFP MARKER
7500
ACCGGCAAGCTGCCCGTGCCCTGGCCCACCCTCGTGACCACCCTGACCTGGGGCGTGCAGTGCTTCAGCCGCTACCCCGACCACATGAAGCAGCACGACT
                                      3XP3-EYFP MARKER
7600
TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGG
                                      3XP3-EYFP MARKER
7700
CGACACCCTGGTGAACCGCATCGAGCTGAAGGGCATCGACTTCAAGGAGGACGGCAACATCCTGGGGCACAAGCTGGAGTACAACTACATCAGCCACAAC
                                      3XP3-EYFP MARKER
7800
GTCTATATCACCGCCGACAAGCAGAAGAACGGCATCAAGGCCAACTTCAAGATCCGCCACAACATCGAGGACGGCAGCGTGCAGCTCGCCGACCACTACC
                                      3XP3-EYFP MARKER
7900
AGCAGAACACCCCCATCGGCGACGGCCCCGTGCTGCCCGACAACCACTACCTGAGCACCCAGTCCGCCCTGAGCAAAGACCCCAACGAGAAGCGCGA
                                      3XP3-EYFP MARKER
8000
TCACATGGTCCTGCTGGAGTTCGTGACCGCCGCCGGGATCACTCTCGGCATGGACGAGCTGTACAAGTAAAGCGGCCGCGACTCTAGATCATAATCAGCC
                                      3XP3-EYFP MARKER
```

FIG. 13(B) CONT.

8100
ATACCACATTTGTAGAGGTTTTACTTGCTTTAAAAAAACCTCCCCCCTGAACCTGAAACATAAAATGAATGTGTTGTTAACTTGTT
                                                        3XP3-EYFP MARKER

8200
TATTGCAGCTTATAATGGTTACAAATAAAGCATCACAAATTTCACAAATAAAGCATTTTTTCACTGCATTCTAGTTGTGGTTTGTCCAAACTC
                                                        3XP3-EYFP MARKER

8300
ATCAATGTATCTTAAAGCTTATCGATACGCGTACGGCGCCTAGGGCCGGCCCGATTGGATCCCATGCTCAATTTTACGCATGATTATCTTAACGTACG
                3XP3-EYFP MARKER                                                    LEFT TERMINAL REPEAT

8400
TCACAATATGATTATCTTTCTAGGGTTAATCTAGCTGCGTGTTCTGCAGCGTCGAGCATCTTCATCTGCTCCATCACGCTGTAAACACATTTGCACC
        LEFT TERMINAL REPE

8500
GCGAGTCTGCCCGTCCTCCACGGGTCAAAAAACGTGAATGAACGAGGCGCGCCCGGGTAACTCACGGGTATCCATGTCCATTTCTCGCCGCATCCAG

8600
CCAGGATACCCGTCCTCGCTGACGTAATATCCAGCGCCGCACCGCTGTCATTAATCTGCACACCGGCAGTTCCGGCTGCGTGCCGTATTGTTCG

8700
GGTTGCTGATGCGCTTCGGGCTGACCATCCGGAAAAGCCGGACGAACTGGTATCCCAGGTGGCCTGAACGAACAGTTCACCGTTAAA

8800
GGCGTGCATGGCCACACCTTCCCGGAAAAGGCACGGGCTTCTTCCCTCCCCGATGCCCAGATAGCGCCAGCTTGGGCGATGACTGAGCCCAGTCAATGCAGCCGGAAAAAAGACCCGACGATAT

8900
GCTTCAACCTCGCGGGAAAAGGCACGGGCTTCTTCCTCCCCGATGCCCAGATAGCGCCAGCTTGGGCGATGACTGAGCCCAGTCAATGCAGCCGGAAAAAAGACCCGACGATAT

9000
GATCCTGATGCAGCTAGATTAACCCTAGAAAGATAGTCTGCGTAAATTGACGCATGGATCCCCCGGGCTGCAGGAATTCGATATCAAGCTTATCGATA
                                RIGHT TERMINAL REPEAT

CCGTCGAAGCTT -- (SEQ ID NO:49) --

FIG. 13(B) CONT.

```
P(PZ)-Bac-EGFP
Sequence Range: 1 to 9013
100
ACCGAAGTATACACTTAAATTCAGTGCACGTTTGCTTGTTGAGAGAAAGGTTGTGTGCGGACGAATTTTTTTGAAAACATTAACCCTTACGTGGAAT
200
AAAAAAAATGAAATATTGCAAATTTTGCTGCAAAGCTGTGACTGGGTAAAATTAATTCACGTGCCGAAGTGTGCTATTAAGAGAAAATTGTGGAGCA
300
GAGCCTTGGGTGCAGCCTTGGTGCTGAAAACTCCCAAATTTGTGATACCCACTTTAATGATTCGCAGTGGAAGGCTGCACCTGCAAAAGGTCAGACATTTAAA
400
AGGAGGGCGACTCAACGCAGATGCCGTACCTAGTAAAGTGATAGAGCCTGAACCAGAAAAGATAAAGAAGGCTATACCAGTGGGAGTACACAAACAGAGT
500
AAGTTTGAATAGTAAAAAAAAATCATTTATGTAAACAATAACGTGACTGTGCGTTAGTCCTGTTCATTGTTTAATGAAAATAAGAGCTTGAGGAAAAAA
600
TTCGTACTTTGGAGTACGAAATGCGTCGTTTAGAGACAGCAGCCGAATTCACTGGCCGTCGTTTTACAACGTCGTGACTGGGAAAACCCTGGCGTTACCCA
700
ACTTAATCGCCTTGCAGCACATCCCCCTTTCGCCAGCTGGCGTAATAGCGAAGAGGCCCACCGATCGCCCTTCCCAACAGTTGCGCAGCCTGAATGGC
800
GAATGGCGCTTTGCCTGGTTTCCGGCACCAGAAGCGGTGCCGGAAAGCTGGCTGGAGTGCGATCTTCCTGAGGCCGATACTGTCGTCCCCTCAAACT
900
GGCAGATGCACGGTTACGATGCGCCCATCTACACCAACGTAACCTATCCCATTACGGTCAATCCGCCGTTTGTTCCCACGGAGAATCCGACGGGTTGTTA
1000
CTCGCTCACATTTAATGTTGATGAAAGCTGGCTACAGGAAGGCCAGACGCGAATTATTTTTGATGGCGTTAACTCGGCGTTTCATCTGTGGTGCAACGGG
1100
CGCTGGGTCGGTTACGGCCAGGACAGTCGTTTGCCGTCTGAATTTGACCTGAGCGCATTTTTACGCGCCGGAGAAAACCGCCTCGCGGTGATGGTGCTGC
```

*FIG. 14(B)*

```
1200
GTTGGAGTGACGGCAGTTATCTGAAGATCAGGATATGTGGCGATGAGCGGCATTTCCGTGACGTCTCGTTGCTGCATAAACCGACTACACAAATCAG
1300
CGATTTCCATGTTGCCACTCGCTTTAATGATGATTTCAGCCGCTGTACTGGAGGCTGAAGTTCAGATGTGCGGCGAGTTGCTGCTGACTACCTACGGGTA
1400
ACAGTTTCTTTATGGCAGGGTGAAACGCAGTCGCCAGCGGCCCTTTCGGCGGTGAAATTATCGATGAGCGTGGTGGTTATGCCGATCGCGTCA
1500
CACTACGTCTGAACGTCGAAACCCGAAATCTGGAGCGCCGAAATCTCTATCGTGCGGTGGTTGAACTGCACACCGCCGACGGCACGCTGAT
1600
TGAAGCAGAAGCCTGCGATGTCGGTTTCCGCGAGTGCCGATTGAAAATGGTCTGCTGCTGAACGGCAAGCCGTTGCTGATTCGAGGCGTTAACCGT
1700
CACGAGCATCATCCTCTGCATGGTCAGGTTCATGGATGAGCAGACAGATGGTGCAGGATATCCTGCTGATGAAGCAATATTGAAACCCACGGCATGGTGCCAAT
1800
CGCATTATCCGAACCATCCGCTGTGCTACACGCTGTGCGACCGCTGTATGGTGGATGAAGCGAATGCGCGATCGTAATCACCCGAGTGTGATCATCTGG
1900
GAATCGTCTGACCGATGATCCGCGCTGGCTACCGGCGATGAGCGAACGCGTAACGCGAATGGTGCAGCGCGATCGTAATCAAATCTGTCGATCTTCCCGCCGGTGCAGTATGAAGGCGGCG
2000
TCGCTGGGAATGAATCAGGCCACGGCGCTAATCACGACGGCGCTGTATCGCTGATCAAATCGACGGCGTGATGAAGACCAGCCCTTCCCGCCTGTGCCGAAATGGTCCATCAAAAATG
2100
GAGCCGACACCGGCCACCGATATTATTGCCCGATCGTACGGCGGTGATGAAGACCAGCCCTTCCCGCCTGTGCCGAAATGGTCCATCAAAAATG
2200
GCTTTCGCTACCTGGAGAGACGCGCCCGCTGATCCTTTCGGAATACGCCACGCGATGGGTAACAGTCTTGGCGGTTTCGCTAAATACTGGCAGGCGTTT
2300
CGTCAGTATCCCCGTTTACAGGGCGGCTTCGTCTGGACTGGGTCGATCAGTCGCTGATTAAATATGATGAAAACGGCAACCCGTGCTGGCTTACGGCG
```

*FIG. 14(B) CONT.*

```
2400
GTGATTTTGGCGATACGCCGAACGATCGCCAGTTCTGTATGAACGGTCTGGTCTTTGCCGACCGCATCCAGCGCTGACGGAAGCAAAACACCA
2500
GCAGCAGTTTTTCCAGTTCCGTTTATCCGGCAAACCATCGAAGTGACCAGCGAATACCTGTTCCGTCATAGCGATAACGAGCTCCTGCACTGGATGGTG
2600
GCGCCTGGATGGTAAGCCGCTGGACAAGCGGTGAAGTGCCTGAAGTGCCTCTGGATGTCGCTCACAAGGTAAACAGTTGATTGAACTGCCTGAACTACCGCAGCCGGAGA
2700
GCGCCCGGGCAACTCTGGCTCACAGTACGCGTAGTGCAACCGAACGACCGCATGGTCAGAAGCCGGGCACATCAGCGCCTGGCAGCAGTGGGCTCTGGC
2800
GGAAAACCTCAGTGTGACGCTCCCCGCCGTCCCACGCCATCCCGCCGCGAAATGGATTTTTGCATCGAGCTGGGTAATAAGCGTTGG
2900
CAATTTAAACCGCCAGTCAGGCTTTCTTTCACAGATGTGGATTGGCGATAAAAACAACTGCTGACGCCGCTGCGCGATCAGTTCACCGTGCACCGCTGG
3000
ATAACGACATTGGCGTAAGTGAAGCGACCCGCATTGACCCTAACGCCTGGGTCGAACGCTGGAAGGCGGGGCCATTACCAGGCCGAAGCAGCGTTGTT
3100
GCAGTGCACGGGCAGATACACTTGCTGATGCGGTGCTGATTACGACCGCTCACGCGTGGCAGCATCAGGGGGCGAAAAACCTTATTTATCAGCCGGAAAAACCTAC
3200
CGGATTGATGTGAGTGGTCAAATGGCGATTACCGTTGATGTTGAAGTGGCCGAGCGATACACCCGCATCCGGCGCGGATTGGCCTGAACTGCCAGCTGGCGC
3300
AGGTAGCAGAGCGGGTAAACTGGCTCGGATTAGGGCCCGCAAGAGAAAACTATCCCGACCGCCCTTACTGCCGCCTGTTTTGACCGCTGGGATCTGCCATTGTC
3400
AGACATGTATACCCGCTACGTCTTCCCGAGCGAAAACGGTCTGCGCGGAGCGGCGAATTGAATTATGCCCACACCAGTGGCGGGCGACTTCCAG
3500
TTCAACATCAGCCGCTACAGTCAACAGCAACTGATGGAAACCAGCCATCGCCATCTGCTGCACCGGAAGAAGGCACATGGCTGAATATCGACGGTTTCC
```

*FIG. 14(B) CONT.*

```
3600
ATATGGGGATTGGTGGCGACGACTCCTGGAGCCCGTCAGTATCGGGCGAATTCCAGCTGAGCGCCGGTCGCTGCCGGTCGCTGCCGTACCATTGGTCGGG
3700
ATCCGTCGACTAAGGCCAAAGAGTCTAATTTTTGTTCATCAATGGGTTATAACATATGGGTTATATTATAAGTTGTTTTAAGTTTTTGAGACTGATAAG
3800
AATGTTTCGATCGAATATTCCATAGAACAACAATAGTATTACCTAATTACCAAGTCTTAATTTAGCAAAAATGTTATTGCTTATAGAAAAATAAATTAT
3900
TTATTTGAAATTTAAAGTCACAACTTGTCATTTAAGTCTTGAAAGTCTTACGATACAATTAGTATCTAATATACATGGTTCATTCTACAT
4000
TCTATATTAGTGATGATTCTTTAGCTAATACATTTAATTATATTCGGCTTTGATGATTTTCTGAATTTTCTGTTCCGACACCGCATTGTAGCACATAGCCGGAC
4100
CGATCTCATAATGCTCATTTATTGCGATGCGGTCAGGAGAGCTCCACTTTTGAATTTCTGTTCCGGAATGCGTTGCAGGCGCATACGCTCTATATCCTCGAACGGCGCTGGTTGACC
4200
ATCCGGTTTGGGGAGATTTCCAGTCTCTGTTGCAATTGGTTTCGGCAAATTTGCCTCTCATTGCCCGGAATCACAGCAATCAGATGTCCCTTTCGGTTACGATGGATATTCAGGT
4300
CTAGCATTTACATAAGGATCAGCACAAAGCTCGCCGCACACTCCACACTGATATGGTCGCTCGCCCGTGTGCCGCCATATGTGTCGCTTGGAGCTGCAATCTTAAGGTCGTTGGACTGCACAAAG
4400
GCGAACCGCACACAAAGCTCTCGCCGCACATTTGCAGGAGTACGGCCTTGACCCGTGTGCAATCGCATGGCCCTTGTTCTGCGAAATAAACTTCTTGGAGCAGATGC
4500
CTCTTGCTGCACATTTGCAGGAGTACGGCCTTGACCCGTGTGCAATCGCATGAGATCATCCAGCCGCGGCGTCCCGGAAAACGATTCCGAAGCCCAACCTTTCAT
4600
GGCCGCCCGGGTGGGCGAAGAACTCCAGCATGAGATCCCCGCGCTGGAGGATCATCCAGCCGCGGCGTCCCGGAAAACGATTCCGAAGCCCAACCTTTCAT
4700
AGAAGGCGGCCGTTGGGCGTCGCTTGGTCGGTCATTTCGAACCCCAGAGTCCCGCTCAGAAGAACTCGTCAAGA
4800
AGGCGATAGAAGGCGATGCGCTGCGAATCGGGAGCGGCGATACCGTAAAGCACGAGGAAGCGGTCAGCCCATTCGCCGCCAAGCTCTTCAGCAATATCAC
```

FIG. 14(B) CONT.

```
4900 GGGTAGCCAACGCTATGTCCTGATAGCGGTCCGCCCACACCCAGCCGGGCCACAGTCGATGAATCCAGAAAAGCGGCCATTTCCACCATGATATTCGGCAA
5000 GCAGGCATCGCCATGGTCACGACGAGATCCTCGCCGTCGGGCATGCGCGCCTTGAGCCTGGCGAACAGTTCGGCTGGCGAGCCCCTGATGCTCTTCG
5100 TCCAGATCATCCTGATCGACAAGACCGGCTTCCATCCGAGTACGTGCTGCTCGATGCGATGTTTCGCTTGGTGGTCGAATGGGCAGTAGCCGGATCAA
5200 GCGTATGCAGCCGCCGCATTGCATCAGCCATGATGGATACTTTCTCGGCAGGAGCAAGGTGAGATGACAGGAGATCCTGCCCCGGCACTTCGCCCAATAG
5300 CAGCCAGTCCCTTCCGCTTCAGTGACAACGTCGAGCACAGCTGCGCAAGGAACGCCCGTCGTGCCAGCCACGATAGCGCGCTGCCTCGTCCTGCAGT
5400 TCATTCAGGGCACCGACAGGTCGGTCTTGACAAAAGAACCGGGCCCCTGCGCTGACAGCCGGAACATCAGAGCAGCCGATTGTCTGTT
5500 GTGCCCAGTCATAGCCGAATAGCCCTCTCCACCCAAGCGGCCGGAGAACCTGCGTGCAATCATCTTGTTCAATCATGCGAAACGATCCTCATCCTGTCTC
5600 TTGATCAGATCTTGATCCCCTGCGCCATCAGATCCTTGCGGCAAGAAAGCCATCCAGTTTACTTTGCAGGGCCTTCCCAACCTTACCAGAGGGCGCCCCA
5700 GCTGGCAATTCCGGTTCGCTTGCTGTCCATAAAACCGCCAGTCTAGCTATCGCCACTGCAAGCTACCTGCTTTCTCTTTGCGCTTGCGT
5800 TTTCCCTTGTCCAGATAGCCCAGTAGCTGACATTCATCCGGGTCAGCACCGTTTCTGCGGACTGGCTTTCTACGTGTTCCGCTTCCTTTAGCAGCCCTT
5900 GCGCCCTGAGTGCTTGCGGCAGCCGTGAAGCTAATTCATGGTTATAAATTTTTGTAAATCAGCTCATTTTTAACCAATAGCCGAAATCGGCAAAATCC
6000 CTTATAAATCAAAAGAATAGCCCGAGATAGGGTTGAGTGTGTTCCAGTTTGGAACAAGAGTCCACTATTAAAGAACGTGACTCCAACGTCAAAGGGCG
6100 AAAAACCGTCTATCAGGGCGATGGCCGGATCAGCTTATGCGGTGTGAAATACCGCACAGATGCGTAAGGAGAAAATACCGCATCAGGCGCTCTTCCGCTT
```

*FIG. 14(B) CONT.*

6200 CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300 CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400 CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500 TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600 GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700 CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800 GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900 TGGTAGCGGTGGTTTTTTGTTTGCAAGCAGCAGATTACGCGCAGAAAAAAAGGATCTCAAGAAGATCCTTTGATCTTTTCTTACGAACGGTGATCCCCA
7000 CCGGAATTGCCGCGGAATTCTCATGTTTGACAGCTTATCATCGATAAGCTGGCCGCTCTAGAACTAGTGTTCCCACAATGGTTAATTCGAGCTCGCC
     3XP3-EYFP MARKER
7100 CGGGGATCTAATTCAATTAGAGACTAATTCAATTAGATCCAAGCTTATCGATTTCGAACCCTCGACCGCCGGAGTATAAATAGA
     3XP3-EYFP MARKER
7200 GGCGCTTCGTCTACGGAGCGACAATTCAAACAAGCAAAGTGAACACGTCGCTAAGCGAAAGCTAAGCAAATAAACAAGCCAGCTGAACAAGCTA
     3XP3-EYFP MARKER

*FIG. 14(B) CONT.*

7300
AACAATCGGGTACCGCTAGAGTCGACGGTACCGCGGGCCCGGGATCCACCGGTCGCCACCATGGTGAGCAAGGGCGAGGAGCTGTTCACCGGGGTGGTG
                                                    3XP3-EYFP MARKER

7400
CCCATCCTGGTCGAGCTGGACGGCGACGTAAACGGCCACAAGTTCAGCGTGTCCGGCGAGGGCGAGGGCGATGCCACCTACGGCAAGCTGACCCTGAAGT
                                                    3XP3-EYFP MARKER

7500
TCATCTGCACCACCGGCAAGCTGCCCGTGCCCTGGCCCACCCTCGTGACCACCCTGACCTACGGCGTGCAGTGCTTCAGCCGCTACCCCGACCACATGAA
                                                    3XP3-EYFP MARKER

7600
GCAGCACGACTTCTTCAAGTCCGCCATGCCCGAAGGCTACGTCCAGGAGCGCACCATCTTCTTCAAGGACGACGGCAACTACAAGACCCGCGCCGAGGTG
                                                    3XP3-EYFP MARKER

7700
AAGTTCGAGGGCGACACCCTGGTGAACCGCATCGAGCTGAAGGGCATCGACTTCAAGGAGGACGGCAACATCCTGGGGCACAAGCTGGAGTACAACTACA
                                                    3XP3-EYFP MARKER

7800
ACAGCCACAACGTCTATATCATGCCCGACAAGCAGAAGAACGGCATCAAGGTGAACTTCAAGATCCGCCACAACATCGAGGACGGCAGCGTGCAGCTCGC
                                                    3XP3-EYFP MARKER

7900
CGACCACTACCAGCAGAACACCCCCATCGGCGACGGCCCCGTGCTGCTGCCCGACAACCACTACCTGAGCACCCAGTCCGCCCTGAGCAAAGACCCCAAC
                                                    3XP3-EYFP MARKER

8000
GAGAAGCGCGATCACATGGTCCTGCTGGAGTTCGTGACCGCCGCCGGGATCACTCTCGGCATGGACGAGCTGTACAAGTAAAGCGGCGACTCTAGAT
                                                    3XP3-EYFP MARKER

8100
CATAATCAGCCATACCACATTTGTAGAGGTTTTACTTGCTTTAAAAAACCTCCCACACCTCCCCCTGAACCTGAAACATAAAATGAATGCAATTGTTGTT
                                                    3XP3-EYFP MARKER

*FIG. 14(B) CONT.*

```
8200
GTTAACTTGTTTATTGCAGCTTATAATGGTTACAAATAAGCAATAGCATCACAAATTTCACAAATAAAGCATTTTTTCACTGCATTCAGTGTGGTT
                                                        3XP3-EYFP MARKER                          >

8300
TGTCCAAACTCATCAATGTATCTTAAAGCTTATCGATACGGCGTTACGGGCGCCTAGTGATCCCATGCGTCAATTTACGCATGATTATCTTAACGTAC
                      3XP3-EYFP MARKER                    >                        LEFT TERMINAL REPEAT

8400
GTCACAATATGATTATCTTCTAGGGTTAATCTAGCTGCGTGTTCTGCAGCGTGTCGAGCATCTTCATCTGCTCCATCACGCTGTAAACACATTTGCAC
<       LEFT TERMINAL REPEA

8500
CGCGAGTCTGCCCGTCCTCCACGGGTTCAAAAACGTGAATGAACGAGGCGGCCGCCCGGGTATCCATGTCCATTTCTGCGGCATCCA

8600
GCCAGGAGATACCCGTCCTCTGCGCTGACGTAATATCCCAGCGCCGCTGTCATTAATCTGCACACCGGCACGGCAGTTCCGGCTGTGCGCGGTATTGTTC

8700
GGGTTGCTGATGCGCGTTCGGGGCTGTCCGGAACATCGTCGGTATCCCAGGTGCCTGAACGAACAGTTCACCGTAA

8800
AGGCGTGCATGCCACACCTTCCCGGGAAAAGGCACGGGCTTCTTCCCTGCCGGATGACTGAGCCGGAAAAAAGACCCGACGATA

8900
CGCTTCAACCTCGCGGGAAAAGGCACGGGCTTCTTCCCTGATGCGTTTTCGCTCAATGCAGCAGCTTGGGCGATGACTGAGCCGGAAAAAAGACCCGACGATA

9000
TGATCCCTGATGCAGCTAGATTAACCCTAGAAAGATAGTCTGCGTAAAATTGACGCATGGATCCCCCGGGCTGCAGGAATTCGATATCAAGCTTATCGAT
                                                    <         RIGHT TERMINAL REPEAT

ACCGTCGAAGCTT --(SEQ ID NO:50)--
```

*FIG. 14(B) CONT.* pXL-Bac-EYFP
Sequence Range: 1 to 4951

100 CTAAATTGTAAGCGTTAATATTTTGTTAAATTTTGCGTTAAATTTGCGTTAAATTCAGCTCATTTTTTAACCAATAGGCCGAAATCGGCAAAATCCCTTAT
200 AAATCAAAAGAATAGACCGAGATAGGGTTGAGTGTTGTTCCAGTTTGGAACAAGAGTCCACTATTAAAGAACGTGACTCCAACGTCAAAGGGCGAAAAA
300 CCGTCTATCAGGGCGATGGCCCACTACGTGAACCATCAAGTTTTTGGGGTCGAGGTGCCGAGTGCCGTAAAGCACTAAATCGAACCCTAAAGGGAG
400 CCCCCGATTTAGAGCTTGACGGGGAAAGCCGGCGAACGTGGCGAGAAAGGAAGAAAGCGAAAGGAGCGGGCGCTAGGGCGCTGGCAAGTGTAGCG
500 GTCACGCTGCGCGTAACCACCACACCCGCCGCTTAATGCGCCGCTACAGGGCGCGTCCCATTCGCCATTCAGGCTGCGCAACTGTTGGGAAGGGCGAT
600 CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700 TAAAACGACGGCCAGTGAGCGCGCGTAACTCACACGGGTATCCATGTCCATTTCTGCGCGTGTCGCCGGCAGTTCCGGCTGTGCTGATGCCTTCGGGCTGACCAT
800 ATCCCAGCGCCCGCTGTCATTAATCTGCACACGGACGAACTGTGGTATCCCAGGTGCCCTGAACGAACAGTTCACCGTTAAAGGCGTGCATGGCCACACCTTCCCGAATC
900 CCGGAACTGTGTCCGGAAAAGCCGGACTTGCGCTCAATGCAGCAGCTGGGCGATGACTGAGCCGATATGATCCTGATGCAGCTAGATTAACCCTAG
1000 ATCATGTAAACGTGCGTTTCGCTCAACGTCAATGCAGCAGCTTGGGCGATGACTGAGCCGATGACTGAGCCGAAAAAAGACCCGACGATATGATCCTGATGCAGCTAGATTAACCCTAG
1100 CTTCTTCCCTCCCCGATGCCGCTAAAATTGACGCATGATCTAATTAACCCTCACTAAAGGGAACAAAAGCTGGAGCTCCACCGCGGTGGCGGCCGCTCTAGAACTAGT
1200 AAAGATAGTCTGCGTAAAATTGACGCATGATCTAATTAACCCTCACTAAAGGGAACAAAAGCTGGAGCTCCACCGCGGTGGCGGCCGCTCTAGAACTAGT
< RIGHT TERMINAL REPEAT

*FIG. 15(B)*

```
1300 GTTCCCACAATGGTTAATTCGAGCTCGCCCCGGGGATCTAATTCAATTGAGAGACTAATTCAATTAGAGATCCAAGCTTATCGATTTC
                                    3XP3-EYFP MARKER

1400 GAACCCTCGACCGCCGGAGTATAAATAGAGGCGCTTCGTCTACGGAGCCGACAATTCAATTCAAACAAGCAAAGTGAACACGTCGCTAAGCGAAAGCTAAG
                                    3XP3-EYFP MARKER

1500 CAAATAAACAAGCGCAGCTGAACAAGCTAAACAATCGGGGTACCGCTAGAGTCGACGGTACCGATCCACCGGTCGCCACCATGTGAGCAAGGGCGAGGAG
                                    3XP3-EYFP MARKER

1600 CTGTTCACCGGGGTGGTGCCCATCCTGGTCGAGCTGGACGGCGACGTAAACGGCCACAAGTTCAGCGTGTCCGGCGAGGGCGATGCCACCTACG
                                    3XP3-EYFP MARKER

1700 GCAAGCTGACCCTGAAGTTCATCTGCACCACCGGCAAGCTGCCCGTGCCCTGGCCCACCCTCGTGACCACCTTCGGCTACGGCCTGCAGTGCTTCGCCCG
                                    3XP3-EYFP MARKER

1800 CTACCCCGACCACATGAAGCAGCACGACTTCTTCAAGTCCGCCATGCCCGAAGGCTACGTCCAGGAGCGCACCATCTTCTTCAAGGACGACGGCAACTAC
                                    3XP3-EYFP MARKER

1900 AAGACCCGCGCCGAGGTGAAGTTCGAGGGCGACACCCTGGTGAACCGCATCGAGCTGAAGGGCATCGACTTCAAGGAGGACGGCAACATCCTGGGGCACA
                                    3XP3-EYFP MARKER

2000 AGCTGGAGTACAACTACAACAGCCACAACGTCTATATCATGGCCGACAAGCAGAAGAACGGCATCAAGGTGAACTTCAAGATCCGCCACAACATCGAGGA
                                    3XP3-EYFP MARKER
```

*FIG. 15(B) CONT.*

```
2100
CGGCAGCGTGCAGCTCGCCGACCACTACCAGCAGAGAACACCCCCATCGGCGACGGCCCCGTGCTGCTGCCCGACAACCACTACCTGAGCTACCAGTCCGCC
                                                         3XP3-EYFP MARKER                                  >
2200
CTGAGCAAAGACCCCAACGAGAAGCGCGATCACATGTCCTGCTGAGTTCGTGACCGCCGGGATCACTCTCGGCATGGACGAGCTGTACAAGTAAA
                                                         3XP3-EYFP MARKER                        >
2300
GCGGGCCGCGGACTCTAGATCATAATCAGCCATACCACATTGTAGAGGTTTTACTTGCTTTAAAAAACCTCCCACACCTCCCCCCTGAACCTGAAACATAAA
                                                         3XP3-EYFP MARKER                                  >
2400
ATGAATGCAATTGTTGTTGTTAACTTGTTTATTGCAGCTTATATAATGGTTACAAATAAAGCAATAGCATCACAAATTTCACAAATAAAGCATTTTTTTCAC
                                                         3XP3-EYFP MARKER                                  >
2500
TGCATTCTAGTTGTTGGTTTGTCCAAACTCATCAATGTATCTTAAAGCTTATCGATACGCGTACGGCGCGCCTAGGCACTAGTGGATCCCCCGGGCTGCAG
                                                                             >
2600
GAATTCGATATCAAGCTTATCGATACCGTCGACCTCGAGGGGGGCCCGGTACCCAATTCGCCCTATAGTGAGTCGTATTAAGATCACGCGTAGATCCAT
                                                                                                        <
2700
GCGTCAATTTTACGCATGATTATCTTTAACGTACTTCACAATATGATTATCTTTCTAGGGTTAATCTAGCTGCGTTCTCGCAGCGTGTCGAGCATCTTC
<
2800
ATCTGCTCCATCACGCTGTAAACACATTTGCACCGGAGTCTGCCCGTCTCCACGGGTTCAAAAACGTGAATGAACGAGGCGGCCTTGGCGTAATCAT
          LEFT TERMINAL REPEAT
2900
GGTCATAGCTGTTTCCTGTGTGAAATTGTTATCCGCTCACAATTCCACACAACATACGAGCCGGAAGCATAAAGTGTAAAGCCTGGGGTGCCTAATGAGT
```

*FIG. 15(B) CONT.*

```
3000
GAGCTAACTCACATTAATTGCGTTGCGCTCACTGCCCGCTTTCCAGTCGGGAAACCTGTCGTGCCAGCTGCATTAATGAATCGGCCAACGCGCGGGGAGA
                                                  >ColE1_origin
                                                  |――|
3100
GGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGG 3200
TAATACGGTTATCCACAGAATCAGGGGATAACGCAGGAAAGAACATGTGAGCAAAAGGCCAGCAAAAGGCCAGGAACCGTAAAAAGGCCGCGTTGCTGGC 3300
GTTTTTCCATAGGCTCCGCCCCCCTGACGAGCATCACAAAAATCGACGCTCAAGTCAGAGGTGGCGAAACCCGACAGGACTATAAAGATACCAGGCGTTT 3400
CCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATA 3500
GCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGG 3600
TAACTATCGTCTTGAGTCCAACCCGGTAAGACACGACTTATCGCCACTGGCAGCAGCCACTGGTAACAGGATTAGCAGAGCGAGGTATGTAGGCGGTGCT 3700
ACAGAGTTCTTGAAGTGGTGGCCTAACTACGGCTACACTAGAAGGACAGTATTTGGTATCTGCGCTCTGCTGAAGCCAGTTACCTTCGGAAAAAGAGTTG 3800
GTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCC 3900
TTTGATCTTTTCTACGGGGTCTGACGCTCAGTGGAACGAAAACTCACGTTAAGGGATTTTGGTCATGAGATTATCAAAAAGGATCTTCACCTAGATCCTT 4000
TTAAATTAAAAATGAAGTTTTAAATCAATCTAAAGTATATATGAGTAAACTTGGTCTGACAGTTACCAATGCTTAATCAGTGAGGCACCTATCTCAGCGA
                                                                        ――――――――――
                                                                        AMPICILLIN RESISTANCE  >
```

*FIG. 15(B) CONT.*

```
4100
TCTGTCTATTTCGTTCATCCATAGTTGCCTGACTCCCCGTCGTGTAGATAACTACGATACGGGAGGGCTTACCATCTGGCCCCAGTGCTGCAATGATACC
                                              AMPCILLIN RESISTANCE
4200
GCGAGAGACCCACGCTCACCGGCTCCAGATTTATCAGCAATAAACCAGCCAGCCGAAGGGCCGAGCGCAGAAGTGTCCTGCAACTTTATCCGCCTCCATC
                                              AMPCILLIN RESISTANCE
4300
CAGTCTATTAATTGTTGCGGGAAGCTAGAGTAAGTAGTTCGCCAGTTAATAGTTTGCGCAACGTTGTTGCCATTGCTACAGGCATCGTGGTGTCACGCT
                                              AMPCILLIN RESISTANCE
4400
CGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCC
                                              AMPCILLIN RESISTANCE
4500
TCCGATCGTTGTCAGAAGTAAGTTGGCCGCAGTGTTATCACTCATGGTTATGGCAGCACTGCATAATTCTCTTACTGTCATGCCATCCGTAAGATGCTTT
                                              AMPCILLIN RESISTANCE
4600
TCTGTGACTGGTGAGTACTCAACCAAGTCATTCTGAGAATAGTGTATGCGGCGACCGAGTTGCTCTTGCCCGGCGTCAATACGGGATAATACCGCGCCAC
                                              AMPCILLIN RESISTANCE
4700
ATAGCAGAACTTTAAAAGTGCTCATCATTGGAAAACGTTCTTCGGGGCGAAAACTCTCAAGGATCTTACCGCTGTTGAGATCCAGTTCGATGTAACCCAC
                                              AMPCILLIN RESISTANCE
4800
TCGTGCACCCAACTGATCTTCAGCATCTTTTACTTTCACCAGCGTTTCTGGGTGAGCAAAAACAGGAAGGCAAAATGCCGCAAAAAGGGAATAAGGGCG
                                              AMPCILLIN RESISTANCE
4900
ACACGGAAATGTTGAATACTCATACTCTTCCTTTTTCAATATTATTGAAGCATTTATCAGGGTTATTGTCTCATGAGCGGATACATATTTGAATGTATTT
 AMPCILLIN RESISTANCE

AGAAAAATAAACAAATAGGGGTTCCGCGCACATTTCCCGAAAAGTGCCAC  --(SEQ ID NO:51)--
```

FIG. 15(B) CONT.

pXL-Bac-EGFP
Sequence Range: 1 to 4952

100
CTAAATTGTAAGCGTTAATATTTGTTAAATTCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGAACCCTAAAGGGAG

400
CCCCCGATTTAGAGCTTGACGGGGAAAGCCGGCTGGCCGAGAAAGGAAGAAAGCGAAAGGAGCGGGGCGCTAGGGCGCTGGCAAGTGTAGCG

500
GTCACGCTGCGCGTAACCACCACACCCGCCGCGCTTAATGCCGCTACAGGGCGCGTCCCATTCAGGCTGCGCAACTGTTGGGAAGGGCGAT

600
CGGTGCGGGCCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCCCGCCGGGTAACTCACGGGTATCCATGTCCATTTCTGCGGCATCCAGCCAGGATACCCGTCCTCGCTGACGTAAT

800
ATCCCAGCGCCGACGCGCTGTCATTAATCTGCACACACCGGGCAGTTCCGGCCTGTGCGCCTGAACGAACAGTTCACCGTTAAAGCGTGCATGGCCACACCTTCCCGAATC

900
CCGGAACTGTGTCCGGAAAGCCGCGACGAACTGGTATCCCAGGTGGCCTGAACGCAGTCAATGCAGCAGTCATCCTCGGCAAACTCTTTCCATGCCGCTTCAACCTCGCGGGAAAGGCACGGG

1000
ATCATGTGTAAACGTGCGTTTCGCTCAACGTCAATGCAGCTAGATAGCCCAGCTTGGGCGATGACTGAGCCGGAAAAAGACCCGACGATATGATCCTGATGCAGCTAGATTAACCCTAG

1100
CTTCTTCCTCCCCGATGCCCAGATAGCCCAGCTTGGGCGATGACTGAGCCGGAAAAAGACCCGACGATATGATCCTGATGCAGCTAGATTAACCCTAG

FIG. 16(B)

1200 AAAGATAGTCTGCGTAAAATTGACGCATGATTCTAATTAACCCTCACTAAAGGGAACAAAAGCTGGAGCTCCACCGCGGTGGCGGCCGCTCTAGAACTAGT
     RIGHT TERMINAL REPEAT

1300 GCCGTACGCGTATCGATAAGCTTTAAGATACATTGATGAGTTTGGACAAACCACAACTAGAATGCAGTGAAAAAAATGCTTTATTTGTGAAATTTGTGAT
                                                          3XP3-EGFP MARKER

1400 GCTATTGCTTTATTTGTAACCATTATAAGCTGCAATAAACAAGTTAACAACAACAATTGCATTCATTTTATGTTTCAGGTTCAGGGGGAGGTGTGGGAGG
                                                          3XP3-EGFP MARKER

1500 TTTTTTAAAGCAAGTAAAACCTCTACAAATGTGGTATGGCTGATTATGATCTAGAGTCGCGGCCGCTTTACTTGTACAGCTCGTCCATGCCGAGAGTGAT
                                                          3XP3-EGFP MARKER

1600 CCCGGCGGCGGTCACGAACTCCAGCAGGACCATGTGATCGCGCTTCTCGTTGGGGTCTTTGCTCAGGGCGGACTGGGTGCTCAGGTAGTGGTTGTCGGGC
                                                          3XP3-EGFP MARKER

1700 AGCAGCACGGGGCCGTCGCCGATGGGGGTGTTCTGCTGGTAGTGGTCGGCGAGCTGCACGCTGCCGTCCTCGATGTTGTGGCGGATCTTGAAGTTCACCT
                                                          3XP3-EGFP MARKER

1800 TGATGCCGTTCTTCTGCTTGTCGGCCATGATATAGACGTTGTGGCTGTTGTAGTTGTACTCCAGCTTGTGCCCCAGGATGTTGCCGTCCTCCTTGAAGTC
                                                          3XP3-EGFP MARKER

1900 GATGCCCTTCAGCTCGATGCGGTTCACCAGGGTGTCGCCCTCGAACTTCACCTCGGCGCGGGTCTTGTAGTTGCCGTCGTCCTTGAAGAAGATGGTGCGC
                                                          3XP3-EGFP MARKER

2000 TCCTGGACGTAGCCTTCGGGCATGGCGGACTTGAAGAAGTCGTGCTGCTTCATGTGGTCGGGGTAGCGGCTGAAGCACTGCACGCCGTAGGTCAGGGTGG
                                                          3XP3-EGFP MARKER

2100 TCACGAGGGTGGGCCAGGGCACGGGCAGCTTGCCGGTGGTGCAGATGAACTTCAGGGTCAGCTTGCCGTAGGTGGCATGCCCTGCCCTCGCCGGACAC
                                                          3XP3-EGFP MARKER

*FIG. 16(B) CONT.*

2200 GCTGAACTTGTGGCCGTTTACGTCGCCGTCCAGCTCGACCAGGATGGGCACCACCCCGGTGAACAGCTCCTGCCCTTGCTCACCATGTGGCGACCGGT
     3XP3-EGFP MARKER

2300 GGATCCCGGGCCCGGTACCGTCGACTCTAGAGGATCCCCGATTGTTAGCTTGTTCAGCTGCGCTTGTTTATTTGCTTAGCTTTCGCTTAGCGACGTG
     3XP3-EGFP MARKER

2400 TTCACTTTGCTTGTTGAATTGAATTGTCGCTCCGTAGACGAAGCGCCTCTATTATACTCCCGGCCGTCGAGGGTTCGAAATCGATAAGCTTGGATCCTA
     3XP3-EGFP MARKER

2500 ATTGAATTAGCTCTAATTAGTTGAATTGAATTAGATCCCCGGGCGAGCTCGAATTAACCATTGTGGAACACTAGTGGATCCCCCGGGCTGCA
     3XP3-EGFP MARKER

2600 GGAATTCGATATCAAGCTTATCGATACCGTCGACCTCGAGGGGGGGCCCGGTACCCAATTCGCCCTATAGTGAGTCGTATTAAGATCACGCGTAGATCCA
     LEFT TERMINAL REPEAT

2700 TGCGTCAATTTTACGCATGATTATCTTTAAGTACGTCACAATATGATTATCTTTCTAGGGTTAATCTAGCTGCCTGTCTCGCAGCGTGTCGAGCATCTT

2800 CATCTGCTCCATCACGCTGTAAAACACATTTGCACCGCGAGTCTGCCCGTCCTCCACGGGTTCAAAACGTGAATGAACGAGGGCGCTTGGCGTAATCA

2900 TGGTCATAGCTGTTTCCTGTGTGAAATTGTTATCCGCTCACAATTCCACACAACATACGAGCCGGAAGCATAAAGTGTAAAGCCTGGGGTGCCTAATGAG

3000 TGAGCTAACTCACATTAATTGCGTTGCGCTCACTGCCCGCTTTCCAGTCGGGAAACCTGTCGTGCCAGCTGCATTAATGAATCGGCCAACGCGCGGGGAG
3100 AGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCG

3200 GTAATACGGTTATCCACAGAATCAGGGGATAACGCAGGAAAGAACATGTGAGCAAAAGGCCAGCAAAAGGCCAGGAACCGTAAAAAGGCCGCGTTGCTGG
     COLE1 ORIGIN

*FIG. 16(B) CONT.*

```
3300
CGTTTTTCCATAGGCTCCGCCCCCTGACGAGCATCACAAAAATCGACGCTCAAGTCAGAGGTGGCGAAACCCGACAGGACTATAAAGATACCAGGCGTT
                                                COLE1 ORIGIN

3400
TCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCAT
                                                COLE1 ORIGIN

3500
AGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCG
                                                COLE1 ORIGIN

3600
GTAACTATCGTCTTGAGTCCAACCCGGTAAGACACGACTTATCGCCACTGGCAGCAGCCACTGGTAACAGGATTAGCAGAGCGAGGTATGTAGGCGGTGC
                                                COLE1 ORIGIN

3700
TACAGAGTTCTTGAAGTGGTGGCCTAACTACGGCTACACTAGAAGGACAGTATTTGGTATCTGCGCTCTGCTGAAGCCAGTTACCTTCGGAAAAAGAGTT
                                                COLE1 ORIGIN

3800
GGTAGCTCTTGATCCGGCAAACAAACCACCGCTGGTAGCGGTGGTTTTTTTGTTTGCAAGCAGCAGATTACGCGCAGAAAAAAGGATCTCAAGAAGATC
                                                COLE1 ORIGIN

3900
CTTTGATCTTTTCTACGGGGTCTGACGCTCAGTGGAACGAAAACTCACGTTAAGGGATTTTGGTCATGAGATTATCAAAAAGGATCTTCACCTAGATCCT
                                                COLE1 ORIGIN

4000
TTTAAATTAAAAATGAAGTTTTAAATCAATCTAAAGTATATATGAGTAAACTTGGTCTGACAGTTACCAATGCTTAATCAGTGAGGCACCTATCTCAGCG
                                                                    ^
                                                       COLE1 ORIGIN

4100
ATCTGTCTATTTCGTTCATCCATAGTTGCCTGACTCCCCGTCGTGTAGATAACTACGATACGGGAGGGCTTACCATCTGGCCCCAGTGCTGCAATGATAC
                                                                    AMPCILLIN RESISTANCE                  ^
                                                AMPCILLIN RESISTANCE
```

*FIG. 16(B) CONT.*

```
4200 CGGCGAGACCCACGCTCACCGGCTCCAGATTTATCAGCAATAAACCAGCCAGCCCGGAAGGGCCGAGCGCAGAAGTGGTCCTGCAACTTTATCCGCCTCCAT
     AMPCILLIN RESISTANCE                                                                                >

4300 CCAGTCTATTAATTGTTGCGGGAAGCTAGAGTAAGTAGTTCGCCAGTTAATAGTTTGCGCAACGTTGTTGCCATTGCTACAGGCATCGTGGTGTCACGC
     AMPCILLIN RESISTANCE                                                                              >

4400 TCGTCGTTTGGTATGGCTTCATTCAGCTCCGGTTCCCAACGATCAAGGCGAGTTACATGATCCCCCATGTTGTGCAAAAAAGCGGTTAGCTCCTTCGGTC
     AMPCILLIN RESISTANCE                                                                               >

4500

CTCCGATCGTTGTCAGAAGTAAGTTGGCCGCAGTGTTATCACTCATGGTTATGGCAGCACTGCATAATTCTCTTACTGTCATGCCATCCGTAAGATGCTT
     AMPCILLIN RESISTANCE                                                                               >

4600 TTCTGTGACTGGTGAGTACTCAACCAAGTCATTCTGAGAATAGTGTATGCGGCGACCGAGTTGCTCTTGCCCGGCGTCAATACGGGATAATACCGCGCCA
     AMPCILLIN RESISTANCE                                                                              >

4700 CATAGCAGAACTTTAAAAGTGCTCATCATTGGAAAACGTTCTTCGGGGCGAAAACTCTCAAGGATCTTACCGCTGTTGAGATCCAGTTCGATGTAACCCA
     AMPCILLIN RESISTANCE                                                                              >

4800 CTCGTGCACCCAACTGATCTTCAGCATCTTTTACTTTCACCAGCGTTTCTGGGTGAGCAAAAACAGGAAGGCAAAATGCCGCAAAAAAGGGAATAAGGGC
     AMPCILLIN RESISTANCE                                                                              >

4900 GACACGGAAATGTTGAATACTCATACTCTTCCTTTTTCAATATTATTGAAGCATTTATCAGGGTTATTGTCTCATGAGCGGATACATATTTGAATGTATT
     AMPCILLIN RESISTANCE      >

TAGAAAAATAAACAAATAGGGGTTCCGCGCACATTTCCCCGAAAAGTGCCAC --(SEQ ID NO:52)--
```

*FIG. 16(B) CONT.* pXL-Bac-ECFP
Sequence Range: 1 to 4941

100
CTAAATTGTAAGCGTTAATATTTTGTTAAAATTCGCGTTAAATTTTTGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAAGGGAAGCGAAAGGAGCGGGCGCTAGGGCGCTGGCAAGTGTAGCG

500
GTCACGCTGCGCGTAACCACCACACCCGCCGCGCTTAATGCGCCGCTACAGGGCGCGTCCCATTCGCCATTCAGGCTGCGCAACTGTTGGGAAGGGCGAT

600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCCCGCTGTCATTAATCTGCACACCGGCAGTTCCGGCATCCAGCCAGGATACCCTCCTCGCTGACGTAAT

800
ATCCCAGCGCCCGACGCTGTCATTAATCTGCACACCGGCAGTTCCGGCCGTGTATTGTTGCGCCAGTTCCGGCCGTATTGTTCGGGTTGCGATGCGCTTCGGGCTGACCAT

900
CCGGAACTGTGTCCGGAAAGCCGCGACGAACTGTATCCAGGTGGCCTGAACGACAGTTCACCGTTAAAGGCGTGCATGGCCACACCTTCCCGAATC

1000
ATCATGGTAAACGTGCGTTTCGCTCAACGTCAATGCAGCAGTCATCCTCGGCAAACTCTTTCCATGCCGCTTCAACCTCGCGGGAAAAGGCACGGG

1100
CTTCTTCCCTCCCCGATGCCCAGATAGCCCAGCTTGGGCGATGACTGAGCCGGAAAAAGACCCGACGATATGATCCTGATGCAGCTAGATTAACCCTAG

FIG. 17(B)

```
1200
AAGATAGTCTGCGTAAAATTGACGCATGATCTAATTAACCCTCACTAAAGGGAACAAAAGCTGGAGCTCCACCGCGGTGGCGGCCGCTCTAGAACTAGT
    <  RIGHT TERMINAL REPEAT
1300
GTTCCCACAATGTGTTAATTCGAGCTCGCCCCGGGGATCTAATTCAATTAGAGACTAATTCAATTAGAGCTAATTCAATTAGAGCTAATTAGAGATCAAGCTTATCGATTTC
                                                                    3XP3-ECFP MARKER                                    >
1400
GAACCCTCGACCGCCGGAGTATAAATAGAGGCGCTTCGTCTACGGAGCGACAATTCAATTCAAACAAGCAAAGTGAACACGTCGCTAAGCGAAAGCTAAG
                                                                    3XP3-ECFP MARKER                                    >
1500
CAAATAAACAAGGCCAGCTGAACAAGCTAAACAATCGGGGTACCGCTAGAGTCGACGGTACGATCCACCGGTCGCCACCATGGTGAGCAAGGGCGAGGAG
                                                                    3XP3-ECFP MARKER                                    >
1600
CTGTTCACCGGGGTGGTGCCCATCCTGGTCGAGCTGGACGGCGACGTAAACGGCCACAAGTTCAGCGTGTCCGGCGAGGGCGATGCCACCTACG
                                                                    3XP3-ECFP MARKER                                    >
1700
GCAAGCTGACCCTGAAGTTCATCTGCACCACCGGCAAGCTGCCCGTGCCCTGGCCCACCCTCGTGACCACCCTGACCTGGGGGTGCAGTGCTGCTTCAGCCG
                                                                    3XP3-ECFP MARKER                                    >
1800
CTACCCCGACCACATGAAGCAGCACGACTTCTTCAAGTCCGCCATGCCCGAAGGCTACGTCCAGGAGCGCACCATCTTCTTCAAGGACGACGGCAACTAC
                                                                    3XP3-ECFP MARKER                                    >
1900
AAGACCCGGCGCGAGTGAAGTTCGAGGGCGACACCCTGGTGAACCGCATCGAGCTGAAGGGCATCGACTTCAAGGAGGACGGCAACATCCTGGGGCACA
                                                                    3XP3-ECFP MARKER                                    >
2000
AGCTGGAGTACAACTACATCAGCCACAACGTCTATATCACCGCCGACAAGCAGAAGAACGGCATCAAGGCCAACTTCAAGATCCGCCACAACATCGAGGA
                                                                    3XP3-ECFP MARKER                                    >
```

*FIG. 17(B) CONT.*

```
2100
CGGCAGCGTGCAGCTCGCCGACCACTACCAGCAGAGAACACCCCGACGGCGGCCCCGTGCTGCTGCCGACAACCACTACCTGAGCACCCAGTCCGCC
                                              3XP3-ECFP MARKER
2200
CTGAGCAAAGACCCCAACGAGAAGCGCGATCACATGGTCCTGCTGGAGTTCGTGACCGCCGGGATCACTCTCGGCATGGACGAGCTGTACAAGTAAA
                                              3XP3-ECFP MARKER
2300
GCGGCCGGACTCTAGATCATAATCAGCCATACCACATTTGTAGAGGTTTTACTTGCTTTAAAAAACCTCCCACACCTCCCCCTGAACCTGAAACATAAA
                                              3XP3-ECFP MARKER
2400
ATGAATGCAATTGTTGTTGTTAACTTGTTTATTGCAGCTTATAAATGGTTACAAATAAAGCAATAGCATCACAAATTCACAAATAAAGCATTTTTTCAC
                                              3XP3-ECFP MARKER
2500
TGCATTCTAGTTGTGGTTTGTCCAAACTCATCAATGTATCTTAAAGCTTATCGATACGCGTACGGCACTAGTGGATCCCCGGGCTGCAGGAATTCGATA
2600
TCAAGCTTATCGATACCGTCGACCTCGAGGGGGGCCCGGTACCCAATTCGCCCTATAGTGAGTCGTATTAAGATCACGCGTAGATCCATGCGTCAATTT
2700
TACGCATGATTATCTTAACGTACGTCACAATATGATTATCTTTCTAGGGTTAATCTAGCTGCGTTCTCGAGCATCTTCATCTGCTCCA
  LEFT TERMINAL REPEAT
2800
TCACGCTGTAAACACATTTGCACGCGAGTCTGCCCGTCCCCACGGGTTCAAAAACGTGAATGAACGAGGCGCGCTTGGCGTAATCATGGTCATAGCT
2900
GTTTCCTGTGTGAAATTGTTATCCGCTCACAATTCCACACAACATACGAGCCGGAAGCATAAAGTGTAAAGCCTGGGGTGCCTAATGAGTGAGCTAACTC
3000
ACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGC
```

*FIG. 17(B) CONT.*

```
>ColE1_origin
3100 GTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTT
3200 ATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCAT
3300 AGGCTCCGCCCCCCTGACGAGCATCACAAAAATCGACGCTCAAGTCAGAGGTGGCGAAACCCGACAGGACTATAAAGATACCAGGCGTTTCCCCCTGGAA
3400 GCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTG
3500 TAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGT
3600 CTTGAGTCCAACCCGGTAAGACACGACTTATCGCCACTGGCAGCAGCCACTGGTAACAGGATTAGCAGAGCGAGGTATGTAGGCGGTGCTACAGAGTTCT
3700 TGAAGTGGTGGCCTAACTACGGCTACACTAGAAGGACAGTATTTGGTATCTGCGCTCTGCTGAAGCCAGTTACCTTCGGAAAAAGAGTTGGTAGCTCTTG
3800 ATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTT
3900 TCTACGGGGTCTGACGCTCAGTGGAACGAAAACTCACGTTAAGGGATTTTGGTCATGAGATTATCAAAAAGGATCTTCACCTAGATCCTTTTAAATTAAA
4000 AATGAAGTTTTAAATCAATCTAAAGTATATATGAGTAAACTTGGTCTGACAGTTACCAATGCTTAATCAGTGAGGCACCTATCTCAGCGATCTGTCTATT
                                    AMPCILLIN RESISTANCE
```

*FIG. 17(B) CONT.*

```
4100
TCGTTCATCCATATAGTTGCCTGACTCCCCGTCGTGTAGATAACTACGATACGGGAGGGCTTACCATCTGGCCCCAGTGCTGCAATGATACCGCGAGACCCA
                                                          AMPCILLIN RESISTANCE

4200
CGCTCACCGGCTCCAGATTTATCAGCAATAAACCAGCCAGCCGGAAGGGCCGAGCGCAGAAGTGGTCCTGCAACTTTATCCGCCTCCATCCAGTCTATTA
                                                          AMPCILLIN RESISTANCE

4300
ATTGTTGCCGGGAAGCTAGAGTAAGTAGTTCGCCAGTTAATAGTTTGCGCAACGTTGTTGCCATTGCTACAGGCATCGTGGTGTCACGCTCGTCGTTTGG
                                                          AMPCILLIN RESISTANCE

4400
TATGGCTTCATTCAGCTCCGGTTCCCAACGATCAAGGCGAGTTACATGATCCCCATGTTGTGCAAAAAAGCGGTTAGCTCCTTCGGTCCTCCGATCGTT
                                                          AMPCILLIN RESISTANCE

4500
GTCAGAAGTAAGTTGGCCGCAGTGTTATCACTCATGGTTATGGCAGCACTGCATAATTCTCTTACTGTCATGCCATCCGTAAGATGCTTTTCTGTGACTG
                                                          AMPCILLIN RESISTANCE

4600
GTGAGTACTCAACCAAGTCATTCTGAGAATAGTGTATGCGGCGACCGAGTTGCTCTTGCCCGGCGTCAATACGGGATAATACCGCGCCACATAGCAGAAC
                                                          AMPCILLIN RESISTANCE

4700
TTTAAAAGTGCTCATCATTGGAAAACGTTCTTCGGGGCGAAAACTCTCAAGGATCTTACCGCTGTTGAGATCCAGTTCGATGTAACCCACTCGTGCACCC
                                                          AMPCILLIN RESISTANCE

4800
AACTGATCTTCAGCATCTTTTACTTTCACCAGCGTTTCTGGGTGAGCAAAAACAGGAAGGCAAAATGCCGCAAAAAAGGGAATAAGGCGACACGGAAAT
                                                          AMPCILLIN RESISTANCE

4900
GTTGAATACTCATACTCTTCCTTTTTCAATATTATTGAAGCATTTATCAGGGTTATTGTCTCATGAGCGGATACATATTTGAATGTATTTAGAAAAATAA
        AMPCILLIN R    >

ACAAATAGGGGTTCCGCGCACATTTCCCGAAAAGTGCCAC  --(SEQ ID NO:53)--
```

FIG. 17(B) CONT.

PBS-ITR-ECFP
Sequence Range: 1 to 4943

100
CACCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT

200
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC

300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA

400
ATAGTGGACTCTTGTTCCAAACTGGAACAACACTCAACCCTATCTCGGTCTATTCTTTTGATTTATAAGGGATTTTGCCGATTTCGCCTATTGGTTAAA

500
AAATGAGCTGATTTAACAAAAATTTAACGCGAATTTTAACAAATATTAACGCGAATTCCATTCGCCATTCAGGCTGCGCAACTGTTGGGAAGGGC

600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG

700
TTGTAAAACGACGGCCAGTGAATTGTAATACGACTCACTATAGGGCGAATTGGGTACCGGGCCCCCCCTCGAGGTCGACGGTATCGATAAGCTTGATATC

800
GAATTCCTGCAGCCCGGGGGATCCCATGCGTCAATTTTACGCAGACTATCTTTCTAGGGTTAATCTAGCTGCATCAGATCATATCGTCGGTCTTTTTT
RIGHT TERMINAL REPEAT >

900
CCGGCTCAGTGCATCGCCAAGCTGGCCTATCTGGGCATCGGGAGGAAGAAGCCCGTGCCTTTTCCCGCGAGTTGAAGCGGCATGAAAGAGTTTGCC

1000
GAGGATGACTGCTGCTGCATTGACGTTGAGCGAAAACGCACGTTTACCATGATGATTCGGGAAGGTGTGGCCATGCACGCCTTTAACGGTGAACTGTTCG

1100
TTCAGGCCACCTGGGATACCAGTTCGTCGCGGCTTTTCCGGACACAGTTCCGGATGTCAGCCGCATTCAGCAATGCCGAACCCGAACAATACCGGCGACAG

FIG. 18(B)

```
1200
CCGGAACTGCCGTGCCGGTGTGCAGATTAATGACAGCGGTGCGGCGCTGGATATTACGTCAGCGAGGACGGGTATCCTGGCTGGATGCCGCAGAAATGG
1300
ACATGGATACCCCGTGAGTTACCCGGCTTCGTTCATTCACGTTTTTGAACCCGTGGAGGACGGGCAGACTCGCGGTGCAAATGTGTTTACAGCGTGA
1400
TGGAGCAGATGAAGATGCTCGACACGCTGCAGAACACGGCTAGATTAACCTAGAAAGATAATCATATTGTGACGTACGTTAAAGATAATCATGCGTA
                                                                            LEFT TERMINAL REPEAT
1500
AAATTGACGCATGGGATCCACTAGTGTTCCCACAATGGTTAATTCGAGCTCGCCCGGGATCTAATTCAATTAGAGACTAATTCAATTAGAGCTAATTCA
                                           3XP3-ECFP MARKER
1600
ATTAGGATCCAAGCTTATCGATTTCGAACCCTCGACCCGCCCGGAGTATAAATAGAGGCGCTTCGTCTACGGAGCGACAATTCAATTCAAACAAGCAAAGTG
                                                        3XP3-ECFP MARKER
1700
AACACGTCGCTAAGCGAAAGCTAAGCAAATAAACAAGCCAGCTGAACAAGCTAAACAATCGGGTACCGCTAGAGTCGACGGTACGATCCACCGGTCGC
                                                                                 3XP3-ECFP MARKER
1800
CACCATGGTGAGCAAGGGCGATGCCACCTACGGCAAGCTGACCCTGAAGTTCATCTGCACCACCGGCAAGCTGCCCGTGCCCTGGCCCACCCTCGTGACCACCCTGA
                                                                                  3XP3-ECFP MARKER
1900
GAGGGCGAGGGCGATGCCACCTACGGCAAGCTGACCCTGAAGTTCATCTGCACCACCGGCAAGCTGCCCGTGCCCTGGCCCACCCTCGTGACCACCCTGA
                                                                                  3XP3-ECFP MARKER
2000
CCTGGGGCGTGCAGTGCTTCAGCCGCTACCCCGACCACATGAAGCAGCACGACTTCTTCAAGTCCGCCATGCCCGAAGGCTACGTCCAGGAGCGCACCAT
                                                                                  3XP3-ECFP MARKER
2100
CTTCTTCAAGGACGACGGCAACTACAAGACCCGCGCCGAGGTGAAGTTCGAGGGCGACACCCTGGTGAACCGCATCGAGCTGAAGGGCATCGACTTCAAG
                                                                                  3XP3-ECFP MARKER
```

*FIG. 18(B) CONT.*

2200
GAGGACGGGCAACATCCTGGGGCACAAGCTGGAGTACAACTACATCAGCCACACAAGTCTATATCACCGCCGACAAGCAGAAGAACGGCATCAAGGCCAACT
_____
3XP3-ECFP MARKER

2300
TCAAGATCCGCCACAACATCGAGGACGGCAGCGTGCAGCTCGCCGACCACTACCAGCAGAACACCCCCATCGGCGACGGCCCCGTGCTGCTGCCGACAA
_____
3XP3-ECFP MARKER

2400
CCACTACCTGAGCACCCAGTCCGCCCTGAGCAAAGACCCCAACGAGAAGCGCGATCACGTGGTCCTGCTGGAGTTCGTGACCGCCGCCGGGATCACTCTC
_____
3XP3-ECFP MARKER

2500
GGCATGGACGAGCTGTACAAGTAAAGCGGCCGCGACTCTAGATCATAATCAGCCATACCACATTTGTAGAGGTTTTACTTGCTTTAAAAAACCTCCCACA
_____
3XP3-ECFP MARKER

2600
CCTCCCCCCTGAACCTGAAACATAAAATGAATGCAATTGTTGTTGTTAACTTGTTTATTGCAGCTTATAATGGTTACAAATAAAGCAATAGCATCACAAAT
_____
3XP3-ECFP MARKER

2700
TTCACAAATAAAGCATTTTTTTCACTGCATTCTAGTTGTGGTTTGTCCAAACTCATCAATGTATCTTAAAGCTTATCGATACCGTCCGCGGCCGCCTAGG
_____
3XP3-ECFP MARKER

2800
CCGGCCGATACTAGTTCTAGAGCGGCCGCCACCGCGGTGGAGCTCCAGCTTTTGTTCCCTTTAGTGAGGGTTAATTCGAGCTTGGCGTAATCATGGTCA
_____

2900
TAGCTGTTTCCTGTGTGAAATTGTTATCCGCTCACAATTCCACACAACATACGAGCCGGAAGCATAAAGTGTAAAGCCTGGGGTGCCTAATGAGTGAGCT

3000
AACTCACATTAATTGCGTTGCGCTCACTGCCCGCTTTCCAGTCGGGAAACCTGTCGTGCCAGCTGCATTAATGAATCGGCCAACGCGCGGGGAGAGGCGG

*FIG. 18(B) CONT.*

>ColE1_origin

3100 TTTGCGGTATTGGGCGCTCTTCCGCTTCCTCGCTCACTGACTCGCTGCGCTCGGTCGTTCGGCTGCGGCGAGCGGTATCAGCTCACTCAAAGGCGGTAATA
3200 CGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTT
3300 TCCATAGGCTCCGCCCCCCTGACGAGCATCACAAAAATCGACGCTCAAGTCAGAGGTGGCGAAACCCGACAGGACTATAAAGATACCAGGCGTTTCCCCC
3400 TGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCA
3500 CGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACT
3600 ATCGTCTTGAGTCCAACCCGGTAAGACACGACTTATCGCCACTGGCAGCAGCCACTGGTAACAGGATTAGCAGAGCGAGGTATGTAGGCGGTGCTACAGA
3700 GTTCTTGAAGTGGTGGCCTAACTACGGCTACACTAGAAGGACAGTATTTGGTATCTGCGCTCTGCTGAAGCCAGTTACCTTCGGAAAAAGAGTTGGTAGC
3800 TCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGA
3900 TCTTTTCTACGGGGTCTGACGCTCAGTGGAACGAAAACTCACGTTAAGGGATTTTGGTCATGAGATTATCAAAAAGGATCTTCACCTAGATCCTTTTAAA
4000 TTAAAAATGAAGTTTTAAATCAATCTAAAGTATATATGAGTAAACTTGGTCTGACAGTTACCAATGCTTAATCAGTGAGGCACCTATCTCAGCGATCTGT
                                                                                                 AMPCILLIN RESISTANCE
4100 CTATTTCGTTCATCCATAGTTGCCTGACTCCCCGTCGTGTAGATAACTACGATACGGGAGGGCTTACCATCTGGCCCCAGTGCTGCAATGATACCGCGAG
     AMPCILLIN RESISTANCE

*FIG. 18(B) CONT.*

```
4200
ACCCACGCTCACCGGCTCCAGATTTATCAGCAATAAACCAGCCAGCCGGAAGGGCCGAGCCGAGAAGTGGTCCTGCAACTTTATCCGCCTCCATCCAGTC
                                         AMPCILLIN RESISTANCE
4300
TATTAATTGTGCCGGGAAGCTAGAGTAAGTAGTTCGCCAGTTAATAGTTTGCGCAACGTTGTTGCCATTGCTACAGGCATCGTGGTGTCACGCTCGTCG
                                         AMPCILLIN RESISTANCE
4400
TTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGA
                                         AMPCILLIN RESISTANCE
4500
TCGTTGTCAGAAGTAAGTTGGCCGCAGTGTTATCACTCATGGTTATGGCAGCACTGCATAATTCTCTTACTGTCATGCCATCCGTAAGATGCTTTTCTGT
                                         AMPCILLIN RESISTANCE
4600
GACTGGTGAGTACTCAACCAAGTCATTCTGAGAATAGTGTATGCGGGCGACCGAGTTGCTCTTGCCCGGCGTCAATACGGGATAATACCGCGCCACATAGC
                                         AMPCILLIN RESISTANCE
4700
AGAACTTTAAAAGTGCTCATCATTGGAAAACGTTCTTCGGGGCGAAAACTCTCAAGGATCTTACCGCTGTTGAGATCCAGTTCGATGTAACCCACTCGTG
                                         AMPCILLIN RESISTANCE
4800
CACCCAACTGATCTTCAGCATCTTTTACTTTCACCAGCGTTTCTGGGTGAGCAAAAACAGGAAGGCAAAATGCCGCAAAAAAGGGAATAAGGGCGACACG
                                         AMPCILLIN RESISTANCE
4900
GAAATGTTGAATACTCATACTCTTCCTTTTTCAATATATTATTGAAGCATTTATCAGGGTTATTGTCTCATGAGCGGATACATATTTGAATGTATTAGAAA
     AMPCILLIN RESISTANCE

AATAAACAAATAGGGGTTCCGCGCACATTTCCCCGAAAAGTGC --(SEQ ID NO:54)--
```

*FIG. 18(B) CONT.*

PBS-ITR-EGFP
Sequence Range: 1 to 4944

100
CACCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT
200
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC
300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA
400
ATAGTGGACTCTTGTTCCAAACTGGAACAACACTCAACCCTATCTCGGTCTATTCTTTTGATTTATAAGGGATTTTGCCGATTTCGGCCTATTGGTTAAA
500
AAATGAGCTGATTTAACAAAAATTTAACGCGAATTTTAACAAATATTAACGCTTACAATTTCCATTCGCCATTCAGGCTGCGCAACTGTTGGGAAGGGC
600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG
700
TTGTAAAACGACGGCCAGTGAATTGTAATACGACTCACTATAGGGCGAATTGGGTACCCGGGGATCCCCCCTCGAGGTCGACGGTATCGATAAGCTTGATATC
800
GAATTCCTGCAGCCCGGGGGATCCACTAGTTCTAGAGCGGCCGCCACCGCGGTGGAGCTCCAGCTTTTGTTCCCTTTAGTGAGGGTTAATTCTGAGCTTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGCTAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACAGGATTAGCAGAGCGAGGTATGTAGGCGGTGCTACAGAGTTCTTGAAGTGGTGGCCTAACTACGGCTACACTAGAAGAACAGTATTTGGTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATATGAGTAAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATAGTGTATGCGGCGACCGAGTTGCTCTTGCCCGGCGTCAATACGGGATAATACCGCGCCACATAGCAGAACTTTAAAAGTGCTCATCATTGGAAAACGTTCTTCGGGGCGAAAACTCTCAAGGATCTTACCGCTGTTGAGATCCAGTTCGATGTAACCCACTCGTGCACCCAACTGATCTTCAGCATCTTTTACTTTCACCAGCGTTTCTGGGTGAGCAAAAACAGGAAGGCAAAATGCCGCAAAAAAGGGAATAAGGGCGACACGGAAATGTTGAATACTCATACTCTTCCTTTTTCAATATTATTGAAGCATTTATCAGGGTTATTGTCTCATGAGCGGATACATATTTGAATGTATTTAGAAAAATAAACAAATAGGGGTTCCGCGCACATTTCCCCGAAAAGTGCCACCTGACGTCTAAGAAACCATTATTATCATGACATTAACCTATAAAAATAGGCGTATCACGAGGCCCTTTCGTCTCGCGCGTTTCGGTGATGACGGTGAAAACCTCTGACACATGCAGCTCCCGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTAACTATGCGGCATCAGAGCAGATTGTACTGAGAGTGCACCATATGCGGTGTGAAATACCGCACAGATGCGTAAGGAGAAAATACCGCATCAGGCGCCATTCGCCATTCAGGCTGCGCAACTGTTGGGAAGGGCGATCGGTGCGGGCCTCTTCGCTATTACGCCAGCTGGCGAAAGGGGGATGTGCTGCAAGGCGATTAAGTTGGGTAACGCCAGGGTTTTCCCAGTCACGAC
900
CCGGCCTCAGTCATCGCCCAAGCTGGCGCTATCTGGGCCATCGGGGAAAGCCCGGCCCTGCCTTTTCCCCGAGGTTGAAGCGGCATGAAAGAGTTTGCC
1000
GAGGATGACTGCTGCTGCATTGACGTTGAGCGAAAACGCACGTTTACCATGATGATTCGGAAGGTGTGGCCATGCACGCCTTTAACGTGAACTGTTCG
1100
TTCAGGCCACCTGGGATACCAGTTCGTCGCGGCTTTTCCGACACAGTTCCGTGGAGCAAAGGGCATCAGCAACCCGAACAATACCGGGACAG

FIG. 19(B)

```
1200
CCGGAACTGCCGTGCCGGTGTGCAGATTAATGACAGCGGTGCGGCGCTGGAGATATTACGTCAGCGAGGACGGGTATCCTGGCTGCTGGATGCCGCAGAAATGG
1300
ACAATGGATACCCCGTGAGTTACCCGGGCGCTCGTTCATTCACGTTTTTGAACCCGTGAGGACGGGCAGACTCCGCGGTGTGCAAATGTGTTTACAGCGTGA
1400
TGGAGCAGATGAAGATGCTCGACACGCTAGATTAACCCTAGAAAGATAATCATATTGTGACGTACGTTAAAGATAATCATGCCTA
                                                                LEFT TERMINAL REPEAT
1500
AAAATTGACGCATGGGATCCACTAGTGTTCCCACAATGTTAATTCGAGCTCGCCCGGGGATCTAATTAGAGACTAATTCAATTAGAGCTAATTCA
                                                          ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                                                                        3XP3-EGFP MARKER
1600
ATTAGGATCCAAGCTTATCGATTTCGAACCCTCGACCGCCGGAGTATAAATAGAGGGCGCTTCGTCTACGGAGCGACAATTCAATTCAAACAAGCAAAGTG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
1700
AACACGTCGCTAAGCGAAAGCTAAGCAAATAAACAAGCCAGCTGAACAAGCTAAACATCGGGTACCGCTAGAGTCGACGGTACCGCGGGCCCGGGAT
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
1800
CCACCGGTCGCCACCATGGTGAGCAAGGGCGAGGAGCTGTTCACCGGGGTGGTGCCCATCCTGGTCGAGCTGGACGGCGACGTAAACGGCCACAAGTTCA
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
1900
GCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGT
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
2000
GACCACCCTGACCTACGGCGTGCAGTGCTTCAGCCGCTACCCCGACCACATGAAGCAGCACGACTTCTTCAAGTCCGCCATGCCCGAAGGCTACGTCCAG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
2100
GAGCGCACCATCTTCTTCAAGGACGACGGCAACTACAAGACCCGCGCCGAGGTGAAGTTCGAGGGCGACACCCTGGTGAACCGCATCGAGCTGAAGGGCA
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
3XP3-EGFP MARKER
```

*FIG. 19(B) CONT.*

```
2200
TCGACTTCAAGGAGGACGGCAACATCCTGGGCACAAGCTGGAGTACAACTACAACAGCCACAAGTCTATATCATGGCCGACAAGCAGAAGAACGGCAT
                                                             3XP3-EGFP MARKER
2300
CAAGGTGAACTTCAAGATCCGCCACAACATCGAGGACGGCAGCGTGCAGCTCGCCGACCACTACCAGCAGAACACCCCCATCGGCGACGGCCCCGTGCTG
                                                             3XP3-EGFP MARKER
2400
CTGCCCGACAACCACTACCTGAGCACCCAGTCCGCCCTGAGCAAAGACCCCAACGAGAAGCGCGATCACATGGTCCTGCTGGAGTTCGTGACCGCCGCCG
                                                             3XP3-EGFP MARKER
2500
GGATCACTCTCGGCATGGACGAGCTGTACAAGTAAAGCGGCGACTCTAGATCATAATCAGCCATACCACATTTGTAGAGGTTTTACTTGCTTTAAAA
                                                             3XP3-EGFP MARKER
2600
AACCTCCCACACCTCCCCCTGAACCTGAAACATAAAATGAATGCAATTGTTGTTGTTAACTTGTTTATTGCAGCTTATAATGTTACAAATAAAGCAATA
                                                             3XP3-EGFP MARKER
2700
GCATCACAAATTTCACAAATAAAGCATTTTTTTCACTGCATTCTAGTTGTGGTTTGTGTCCAAACTCATCAAGTATCTTAAAGCTTATCGATACGGCTACG
                                                             3XP3-EGFP MARKER
2800
GCGCGCCTAGACTAGTTCTAGAGCGGCCGCCACCGCGTGGAGCTCCAGCTTTTGTTCCCTTTAGTGAGGGTTAATTTCGAGCTTGGCGTAATCATGGTC
      >                                                      ─────────
2900
ATAGCTGTTTCCTGTGTGAAATTGTTATCCGCTCACAATTCCACACAACATACGAGCCGGAAGCATAAAGTGTAAAGCCTGGGGTGCCTAATGAGTGAGC
3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG
```

*FIG. 19(B) CONT.*

>ColE1_origin

```
3100 GTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAAT
3200 ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT
3300 TTCCATAGGCTCCGCCCCCCTGACGAGCATCACAAAAATCGACGCTCAAGTCAGAGGTGGCGAAACCCGACAGGACTATAAAGATACCAGGCGTTTCCCC
3400 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC
3500 ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC
3600 TATCGTCTTGAGTCCAACCCGGTAAGACACGACTTATCGCCACTGGCAGCAGCCACTGGTAACAGGATTAGCAGAGCGAGGTATGTAGGCGGTGCTACAG
3700 AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG
3800 CTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTG
3900 ATCTTTTCTACGGGGTCTGACGCTCAGTGGAACGAAAACTCACGTTAAGGGATTTTGGTCATGAGATTATCAAAAAGGATCTTCACCTAGATCCTTTTAA
4000 ATTAAAAATGAAGTTTTAAATCAATCTAAAGTATATATGAGTAAACTTGGTCTGACAGTTACCAATGCTTAATCAGTGAGGCACCTATCTCAGCGATCTG
                                                                                    AMPCILLIN RESISTANCE
4100 TCTATTTCGTTCATCCATAGTTGCCTGACTCCCCGTCGTGTAGATAACTACGATACGGGAGGGCTTACCATCTGGCCCCAGTGCTGCAATGATACCGCGA
                                                                           AMPCILLIN RESISTANCE
```

FIG. 19(B) CONT.

4200
GACCCAGCGCTCACCGGCTCCAGATTTATCAGCAATAAACCAGCCAGCCGGAAGGGCCGAGCGCAGAAGTGTCCTGCAACTTTATCCGCCTCCATCCAGT
          AMPCILLIN RESISTANCE

4300
CTATTAATTGTTGCCGGGAAGCTAGAGTAAGTAGTTCGCCAGTTAATAGTTGCGCAACGTTGTTGCCATTGCTACAGGCATCGTGGTGTCACGCTCGTC
          AMPCILLIN RESISTANCE

4400
GTTTGGTATGGCTTCATTCAGCTCCGGTTCCCAACGATCAAGGCGAGTTACATGATCCCCATGTTGTGCAAAAAAGCGGTTAGCTCCTTCGGTCCTCCG
          AMPCILLIN RESISTANCE

4500
ATCGTTGTCAGAAGTAAGTTGGCCGCAGTGTTATCACTCATGGTTATGGCAGCACTGCATAATTCTCTTACTGTCATGCCATCCGTAAGATGCTTTTCTG
          AMPCILLIN RESISTANCE

4600
TGACTGGTGAGTACTCAACCAAGTCATTCTGAGAATAGTGTATGCGGCGACCGAGTTGCTCTTGCCCGGCGTCAATACGGGATAATACCGCGCCACATAG
          AMPCILLIN RESISTANCE

4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
          AMPCILLIN RESISTANCE

4800
GCACCCAACTGATCTTCAGCATCTTTTACTTTCACCAGCGTTTCTGGGTGAGCAAAAACAGGAAGGCAAAATGCCGCAAAAAAGGGAATAAGGGCGACAC
          AMPCILLIN RESISTANCE

4900
GGAAATGTTGAATACTCATACTCTTCCTTTTTCAATATTATTGAAGCATTTATCAGGGTTATTGTCTCATGAGCGGATACATATTTGAATGTATTTAGAA
          AMPCILLIN RESISTANCE

AAATAAACAAATAGGGGTTCCGCGCACATTTCCCCGAAAAGTGC -- (SEQ ID NO:55) --

pBS-ITR-EYFP
Sequence Range: 1 to 4944

```
   1 CACCCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT
 101 CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC
 201 CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA
 301 ATAGTGGACTCTTGTTCCAAACTGGAACAACACTCAACCCTATCTCGGTCTATTCTTTTGATTTATAAGGGATTTTGCCGATTTCGGCCTATTGGTTAAA
 401 AAATGAGCTGATTTAACAAAAATTTAACGCGAATTTTAACAAATATTAACGCGAATTAGAGTCGAAGGCGATTGCTGCAAGGCGATTAAGTTGGGTAACGCCAGGGTTTCCCAGTCACGACG
 501 GATCGGTGCGGGCCTCTTCGCTATTACGCCAGCTGGCGAAAGGGGGATGTGCTGCAAGGCGATTAAGTTGGGTAACGCCAGGGTTTCCCAGTCACGACG
 601 TTGTAAAACGACGGCCAGTGAATTGTAATACGACTCACTATAGGGCGAATTGGGTACCGGGCCCCCCCTCGAGGTCGACGGTATCGATAAGCTTGATATC
 701 GAATTCCTGCAGCCCGGGGGATCCACTAGTTCTAGAGCGGCCGCCACCGCGGTGGAGCTCCAGCTTTTGTTCCCTTTAGTGAGGGTTAATCTAGCTGCATCAGGATCATATCGTCGGTCTTTTT
 801 CCGGCTCAGTCATCGCCCAAGCTGGCGCTATCGGGGCATCGGGGAGGAAGAAGCCCGTGCCTTTCCCGAGGTTGAAGCGGCATGGAAAGAGTTTGCC
 901 GAGGATGACTGCTGCTGCATTGACGTTGAGCGGAAAACGCGTTACCATGATGATTCGGGAAGGTGTGGCCATGCACGCCTTTAACGTGAACTGTTCG
1001 TTCAGGGCACCTGGATACCAGTTCGTCGCGGCTTTTCCGGACACAGTTCCGACATGGTCAGCCCGAAGCGCATCAGCAACCCGAACAATACCGGCGACAG
```

RIGHT TERMINAL REPEAT
                                                    ─────────────────────>

```
1200
CCGGAACTGCCGTGCCGGTGTGCAGATTAATGACAGCGGTGCGGGCCGCTGGGATATTACGTCAGCGAGGACGGGTATCCTGGCTGATGCCGCAGAAATGG
1300
ACATGGATACCCCGTGAGTTACCCGGCGGCTTCGTTCATTCACGTTTTTGAACCCGTGGAGGACGGGCAGACTCGCGGTGCAAATGTGTTTTACAGCGTGA
1400
TGGAGCAGATGAAGATGCTCGACACGCTAGACAACACGCTAGATTAACCCTAGAAAGATAATCATATTGTGACGTACGTTAAAGATAATCATGCGTA
                                                                    LEFT TERMINAL REPEAT          ^
1500
AAATTGACGCATGGGATCCACTAGTGTTCCCACAATGTGTTAATTCGAGCTCGCCGGGATCTAATTCAATTAGAGACTAATTCAATTAGAGCTAATTCA
      ^
1600                                                                                           ^
ATTAGGATCCAAGCTTATCGATTTCGAACCCTCGACCGCCCGGAGTATAAATAGAGGCGCTTCGTCTACGGAGCGACAATTCAATTCAAACAAGCAAAGTG
                                                  3XP3-EYFP MARKER
1700                                                                                                ^
AACACGTCGCTAAGCGAAAGCTAAGCAAATAAACAAGCGCAGCTGAACAAGCTAAACAATCGGGTGTACCGCTAGAGTCGACGGTACGATCCACCGGTCGC
                                              3XP3-EYFP MARKER
1800                                                                                                ^
CACCATGGTGAGCAAGGGCGAGGAGCTGTTCACCGGGGTGGTGCCCATCCTGGTCGAGCTGGACGGCGACGTAAACGGCCACAAGTTCAGCGTGTCCGGC
                                      3XP3-EYFP MARKER
1900                                                                                              ^
GAGGGCGAGGGCGATGCCACCTACGGCAAGCTGACCCTGAAGTTCATCTGCACCACCGGCAAGCTGCCCGTGCCCTGGCCCACCCTCGTGACCACCTTCG
                                      3XP3-EYFP MARKER
2000                                                                                              ^
GCTACGGCCTGCAGTGCTTCGCCCGCTACCCCGACCACATGAAGCAGCACGACTTCTTCAAGTCCGCCATGCCCGAAGGCTACGTCCAGGAGCGCACCAT
                                      3XP3-EYFP MARKER
2100                                                                                                ^
CTTCTTCAAGGACGACGGCAACTACAAGACCCGCGCCGAGGTGAAGTTCGAGGGCGACACCCTGGTGAACCGCATCGAGCTGAAGGGCATCGACTTCAAG
                                      3XP3-EYFP MARKER
```

*FIG. 20(B) CONT.*

```
2200
GAGGACGGCAACATCCTGGGCACAAGCTGGAGTACAACTACAACAGCCACAAGTCTATATCATGCCGACAAGCAGAAGAACGGCATCAAGGTGAACT
                                                    3XP3-EYFP MARKER                                >

2300
TCAAGATCCGCCACACATCGAGGACGGCAGCGTGCAGCTCGCCGACCACTACCAGCAGAACACCCCCATCGGCGACGGCCCCGTGCTGCTGCCCGACAA
                                                    3XP3-EYFP MARKER                                >

2400
CCACTACCTGAGCTACCAGTCCGCCCTGAGCAAAGACCCCAACGAGAAGCGCGATCACATGGTCCTGCTGGAGTTCGTGACCGCCGCCGGGATCACTCTC
                                                    3XP3-EYFP MARKER                                >

2500
GGCATGGACGAGCTGTACAAGTAAAGCGGCCGACTCTAGATCATAATCAGCCATACCACATTTGTAGAGGTTTTACTTGCTTTAAAAAACCTCCCACA
                                                    3XP3-EYFP MARKER                                >

2600
CCTCCCCCTGAACCTGAAACATAAAATGAATGCAATTGTTGTTGTTAACTTGTTTATTGCAGCTTATAATGTTACAAATAAAGCAATAGCATCACAAAT
                                                    3XP3-EYFP MARKER                                >

2700
TTCACAAATAAAGCATTTTTTCACTGCATTCTAGTTGTGGTTTGTCCAAACTCATCAATGTATCTTAAAGCTTATCGATACGGCTACGGCGCGCCTAGG
                                                    3XP3-EYFP MARKER                                >

2800
CCGGCCGATCACTAGTTCTAGAGCGGCCGCCACCGCGTGGAGCTCCAGCTTTTGTTCCCTTTAGTGAGGGTAATTTCGAGCTTGGCGTAATCATGGTC
          >

2900
ATAGCTGTTTCCTGTGTGAAATTGTTATCCGCTCACAATTCCACACAACATACGAGCCGGAAGCATAAAGTGTAAAGCCTGGGGTGCCTAATGAGTGAGC

3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG
```

*FIG. 20(B) CONT.*

>ColE1_origin

```
3100 GTTTGCGGTATTGGGCGCTCTTCCGCTTCCTCGCTCACTGACTCGCTGCGCTCGGTCGTTCGGCTGCGGCGAGCGGTATCAGCTCACTCAAAGGCGGTAAT
3200 ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT
3300 TTCCATAGGCTCCGCCCCCCTGACGAGCATCACAAAAATCGACGCTCAAGTCAGAGGTGGCGAAACCCGACAGGACTATAAAGATACCAGGCGTTTCCCC
3400 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC
3500 ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC
3600 TATCGTCTTGAGTCCAACCCGGTAAGACACGACTTATCGCCACTGGCAGCAGCCACTGGTAACAGGATTAGCAGAGCGAGGTATGTAGGCGGTGCTACAG
3700 AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG
3800 CTCTTGATCCGGCAAACAAACCACCGCTGGTAGCGGTGGTTTTTTTGTTTGCAAGCAGCAGATTACGCGCAGAAAAAAGGATCTCAAGAAGATCCTTTG
3900 ATCTTTTCTACGGGGTCTGACGCTCAGTGGAACGAAAACTCACGTTAAGGGATTTTGGTCATGAGATTATCAAAAAGGATCTTCACCTAGATCCTTTTAA
4000 ATTAAAAATGAAGTTTTAAATCAATCTAAAGTATATATGAGTAAACTTGGTCTGACAGTTACCAATGCTTAATCAGTGAGGCACCTATCTCAGCGATCTG
                                                                              AMPCILLIN RESISTANCE
4100 TCTATTTCGTTCATCCATAGTTGCCTGACTCCCCGTCGTGTAGATAACTACGATACGGGAGGGCTTACCATCTGGCCCCAGTGCTGCAATGATACCGCGA
     AMPCILLIN RESISTANCE
```

*FIG. 20(B) CONT.*

```
4200
GACCCACGCTCACCGGCTCCAGATTTATCAGCAATAAACCAGCCAGCCGGAAGGGCCGAGCGCAGAAGTGGTCCTGCAACTTTATCCGCCTCCATCCAGT
                                         AMPCILLIN RESISTANCE                                      >

4300
CTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
                                         AMPCILLIN RESISTANCE                                      >

4400
GTTTGGTATGGCTTCATTCAGCTCCGGTTCCCAACGATCAAGGCGAGTTACATGATCCCCCATGTTGTGCAAAAAGCGGTTAGCTCCTTCGGTCCTCCG
                                         AMPCILLIN RESISTANCE                                      >

4500
ATCGTTGTCAGAAGTAAGTTGGCCGCAGTGTTATCACTCATGTTATGGCAGCACTGCATAATTCTCTTACTGTCATGCCATCCGTAAGATGCTTTTCTG
                                         AMPCILLIN RESISTANCE                                      >

4600
TGACTGGTGAGTACTCAACCAAGTCATTCTGAGAATAGTGTATGCGGCGACCGAGTTGCTCTTGCCCGGCGTCAATACGGGATAATACCGCGCCACATAG
                                         AMPCILLIN RESISTANCE                                      >

4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
                                         AMPCILLIN RESISTANCE                                      >

4800
GCACCCAACTGATCTTCAGCATCTTTTACTTTCACCAGCGTTTCTGGGTGAGCAAAAACAGGAAGGCAAAATGCCGCAAAAAGGGAATAAGGGCGACAC
                                         AMPCILLIN RESISTANCE                                      >

4900
GGAAATGTTGAATACTCATACTCTTCCTTTTTCAATATATTATTGAAGCATTTATCAGGGTTATTGTCTCATGAGCGGATACATATTTGAATGTATTTAGAA
      AMPCILLIN RESISTANCE          >

AAATAAACAAATAGGGGTTCCGCGCACATTTCCCCGAAAAGTGC--(SEQ ID NO:56)--
```

*FIG. 20(B) CONT.* pBSII-Act5c-orf
Sequence Range: 1 to 7411

100
CTAAATTGTAAGCCGTTAATATTTTGTTAAATTCGCGTTAAATTTTTGTTAAATCAGCTCATTTTTAACCAATAGGCCGAAATCGGCAAAATCCCTTAT

200
AAATCAAAAGAATAGACCGAGATAGGTTGAGTGTTGTTCCAGTTTGGAACAAGAGTCCACTATTAAAGAACGTGACTCCAACGTCAAAGGGCGAAAAA

300
CCGTCTATCAGGGCGATGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCCGAGAAAGGAAGAAAGAGCGGGCGCTAGGGCGCTGGCAAGTGTAGCG

500
GTCACGCTGCGCGTAACCACCACACCCCGCGCGCTTAATGCCGCGCGCTACAGGGCGCGTCCCATTCGCCATTCAGGCTGCGCAACTGTTGGGAAGGGCGAT

600
CGGTGCGGGCCCTCTTCGCTATTACGCCAGCTGGCGAAAGGGGGATGTGCTGCAAGGCGATTAAGTGTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCTCGAGGTCGACGGTATCGATAAGCTTGATATC

800
GAATTCTAAAAAAAAAATCATGAATGCATCAACTCTGAATCAAATCTTTGCAGATGCACCTACTTCTCATTTCCACTGTCACATCATTTTCCAGATCTCG
                                                                ACTIN 5C PROMOTER

900
CTGCCCTGTTATGTGGCCCACAAACCAAGACACGTTTTATGGCCATTAAAGCTGGCTGATCGTGCCAAACACCAAATACATATCAATATGTACATTCGAG
                                                                ACTIN 5C PROMOTER

1000
AAAGAAGCGATCAAAGAAGCGTCTTCGGGCGAGTAGGAGAATGCGGAGGAGAAGGAGAACGAGCTGATCTAGTATCTCTCCACAATCCAATGCCAACTGA
                                                                ACTIN 5C PROMOTER

FIG. 21(B)

1100
CCAACTGGCCATATTCGGAGCAATTTGAAGCCAATTTCCATGCCTGGCGATCGCTCCATTCTTGGCTATATGTTTTCACCGTTCCCGGGGCCATTTC
                                          ACTIN 5C PROMOTER

1200
AAAGACTCGTCGGTAAGATAAGATTGTGTCACTCGCTGTCTGCTTCATTTGTCGAAGAATGCTGAGGAATTCGCGATGACGTCGGCGAGTATTTGAA
                                          ACTIN 5C PROMOTER

1300
GAATGAGAATAATTTGTATTTATACGAAAATCAGTTAGTGGAATTTCTACAAAAACATGTTATCTATAGATAATTTGTTGCAAAATATGTTGACTATG
                                          ACTIN 5C PROMOTER

1400
ACAAAGATTGTATGTATATACCTTTAATGTATTCTCATTTTCTTATGTATTATAATGGCAATGATGATACTGATGATATTTAAGATGATGCCAGACCA
                                          ACTIN 5C PROMOTER

1500
CAGGCTGATTTCTGCGTCTCTTTTGCCGAACGCAGTGCATGTGCGGTTGTGTTTTTGGAATAGTTTCAATTTTCGGACTGTCCGCTTTGATTTCAGTTTC
                                          ACTIN 5C PROMOTER

1600
TTGGCTTATTCAAAAGCAAAGTAAAGCCAAAAAAGGAGATGGCAATACCAAATGCGGCAAAAACGTAGTGGAAGGAAAAGGGGTGCGGGGCAGCGGAAG
                                          ACTIN 5C PROMOTER

1700
GAAGGGTGGGGCGGTGGCGGGGTCTGTGGGCGCGACGTTGGAGCCACTCCTTTGACCATGTGCCGTGTGTGTATTATTCGTG
                                          ACTIN 5C PROMOTER

1800
TCTCGCCACTCGCCGGTTGTGTTTTTCTTTTTTATCTCGCTCTCTCTAGCGCCATCTCGTACGCATGCTCAACGCACCGCATGTTGCCGTGTCCTTATGC
                                          ACTIN 5C PROMOTER

1900
GTCATTTTGGCTCGAAATAGGCCAATTATTTAAACAAAGATTAGTCAACGAAAACGCTAAAATAAGTCTACAATATGGTTACTTATTGCCATGTGTG
                                          ACTIN 5C PROMOTER

*FIG. 21(B) CONT.*

```
2000
TGCAGCCAACGATAGCAACAAAGCAACAACACAGTGGCTTTCCCTCTTTCACTTTTTGTTTGCAAGCGCTGCGAGCAAGACGGCACGACCGGCAAACG
              ACTIN 5C PROMOTER

2100
CAATTACGCTGACAAAGAGCAGACGAAGTTTTGGCCGAAAAACATCAAGGCGCCCTGATACGAATGCATTTGCAATAACAATTGCGATATTTAATATGTT
              ACTIN 5C PROMOTER

2200
TATGAAGCTGTTTGACTTCAAAACACACAAAAAAAAATAAAACAATTATTTGAAAGAGAATTAGGAATCGGACAGCTTATCGTTACGGGCTAACAGC
              ACTIN 5C PROMOTER

2300
ACACCGAGACGAGAAATAGCTTACCTGACGTCACAGCCTCTGGAAGAACTGCCGCCAAGCAGACGATGCAGAGAGACGACACATAGAGTAGCGGAGTAGGCCA
              ACTIN 5C PROMOTER

2400
GCGTAGTAGTACGCATGTGCTTGTGTGTGAGGGTCTCTCTCTCGTCCTCTTGGCCAAACGCATAGACTGCACTGAGAAAATCGATTACCTATTTTTTA
              ACTIN 5C PROMOTER

2500
TGAATGAATATTTGCACTATTACTATTCAAAACTATTAAGATAGCAATCACATTCAATAGCCAAATACTATACCACCTGAGCGATGCAACGAAATGATCA
              ACTIN 5C PROMOTER

2600
ATTTGAGCAAAAATGCTGCATATTTAGGACGGCATCATTATAGAAATGCTTCTTGCTGTGTACTTTTCTCTCGTCTGGCAGCTGTTTCGCCGTTATTGTT
              ACTIN 5C PROMOTER

2700
AAAACCGGCTTAAGTTAGGTGTGTTTTCTACGACTAGTGATGCCCCTACTAGAAGATGTGTTGCACAAATGTCCCTGAATAACCAATTGAAGTGCAG
              ACTIN 5C PROMOTER

2800
ATAGCAGTAAACGTAAGCTAATATGAATATTTAACTGTAATGTTTAATATCGCTGGACATTACTAATAAACCCACTATAAACACATGTACATATGT
              ACTIN 5C PROMOTER
```

```
2900
ATGTTTTGGCATACAATGAGTAGTTGGGGAAAAAAATGTGTAAAAGCACCGTGACCATCACAGCATAAAGATAACCAGCTGAAGTATCGAATATGAGTAAC
                                    ACTIN 5C PROMOTER                                              >
3000
CCCCAAAATTGAATCACATGCCGCAACTGATAGAGACCCATGGAAGTACACTCTTCATGGCGATATACAAGACACACACAAGCACGAACACCCAGTTGCGGA
                                    ACTIN 5C PROMOTER                                              >
                  >CCATATATGG element
                                ⌐⌐
3100
GGAAATTCTCCGTAAATGAAAACCCAATCGGGCGAACAATTCATACCCATATATGGTAAAAGTTTTGAACGCGACTTGAGAGCGGAGAGCATTGCGGCTGA
                                                                    ACTIN 5C PROMOTER              >
        >TATA-box
           ⌐⌐
3200
TAAGGTTTTAGCGCTAAGCGGGGCTTTATAAAACGGGCTGCGGGACCAGTTTTCATATCGGATCCTATATAATAAAATGGGTAGTTCTTTAGACGATGAGC
              ACTIN 5C PROMOTER                       >                  IFP2 ORF BAMHI CARTRIDGE
3300
ATATCCCTCCTCTGCTCTTCTGCAAAGCGATGACGAGCTTGTTGGTGAGGATTCTGACAGTGAAATATCAGATCACGTAAGTGAAGATGACGTCCAGAGCGA
                                   IFP2 ORF BAMHI CARTRIDGE                                        >
3400
TACAGAAGAAGCGTTTATAGATGAGGTACATGAAGTGCAGCCAACGTCAAGCGGTAGTGAAATATTAGACGAACAAATGTTATTGAACAACCAGGTTCT
                                   IFP2 ORF BAMHI CARTRIDGE                                        >
3500
TCATTGGCTTCTAACAGAATCTTGACCTTGCCCACAGAGGACTATTAGAGGAGTAAGAATAAACATTGTTGGTCAACTTCAAAGTCCACGAGGCGTAGCCGAG
                                   IFP2 ORF BAMHI CARTRIDGE                                        >
```

*FIG. 21(B) CONT.*

```
3600
TCTCTGCACTGAACATTGTCAGATCTCAAAGAGTCCGACGCGTATGTGCCGCAATATATGACCCACTTTTATGCTTCAAACTATTTTTACTGATGA
     IFP2 ORF BAMHI CARTRIDGE
3700
GATAATTTCGGAAATTGTAAAATGGACAAATGCTGAGATATCATTGAAACGTCGGAATCTATGACAGGTGTACATTTCGTGACACGAATGAAGATGAA
     IFP2 ORF BAMHI CARTRIDGE
3800
ATCTATGCTTTCTTTGGTATTCTGGTAATGACAGCAGTGAGAAAAGATAACCACATGTCCACAGATGACCTCTTTGATCGATCTTTGTCAATGGTGTACG
     IFP2 ORF BAMHI CARTRIDGE
3900
TCTCTGTAATGAGTCGTGATCGTTTTGATTTTTTTGATACGATGTCTTAGAATGGATGACAAAAGTATACGGCCCACACTTCGAGAAAACGATGTATTTAC
     IFP2 ORF BAMHI CARTRIDGE
4000
TCCTGTTAGAAAAATATGGGATCTCTCTTTATCCATCAGTGCATACAAAATTACACTCCAGGGGCTCATTTGACCATAGATGAACAGTTACTTGGTTTTAGA
     IFP2 ORF BAMHI CARTRIDGE
4100
GGACGGTGTCCGTTTAGGATGTATATCCCAAACAAGCCAAGTAGTAATGGAATAAAAATCCTCATGATGTGTGACAGTGGTACGAAGTATATGATAAATG
     IFP2 ORF BAMHI CARTRIDGE
4200
GAATGCCTTATTTGGGAGAGGAACACAGACCAACGGAGTACCACTCGGTGTGAATACTACGTGAAGGAGTTATCAAAGCCTGTGCCACGGTAGTTGTCGTAA
     IFP2 ORF BAMHI CARTRIDGE
4300
TATTACGTGTGACAATTGTTCACCTCAATCCCTTTGCAAAAAACTTACTACAAGAACCGTATAAGTTAACCATTGTGGGAACCGTGCGATCAAACAAA
     IFP2 ORF BAMHI CARTRIDGE
4400
CGCGAGATACCGGAAGTACTGAAAAACAGTCGCTCCAGGCCAGTGGGAACATCGATGTTTGTTTGACGACCCCTTACTCTCGTCTCATATAAACCGA
     IFP2 ORF BAMHI CARTRIDGE
```

*FIG. 21(B) CONT.*

4500 AGCCAGCTAAGATGGTATACTTATTATCATCTCTGTGATGAGGATGCTTCTATCAACGAAAGTACCGGTAAACCGCAAATGGTTATGTATTATAATCAAAC
     IFP2 ORF BAMHI CARTRIDGE

4600 TAAAGGCGGAGTGGACACGCTAGACCAAATGTGTTCTCGTGATGACCTGCAGTAGGAAGACGAATAGGTGGCCTATGGCATTATTGTACGGAATGATAAAC
     IFP2 ORF BAMHI CARTRIDGE

4700 ATTGCCTTGCATAAATTCTTTTATTATATACAGCCATAATGTCAGTAGCAAGGGAGAAAAGTTCAAAGTCGCAAAAAATTTATGAGAAACCTTTACATGA
     IFP2 ORF BAMHI CARTRIDGE

4800 GCCTGACGTCATCGTCGTTTATGCGTAAGCGTTTAGAAGCTCCTACTTTGAAGAGATATTGCGCGATAATATCTCTAATATTTGCCAAATGAAGTGCCTGG
     IFP2 ORF BAMHI CARTRIDGE

4900 TACATCAGATGACAGTACTGAAGAGCCAGTAATGAAAAAACTACTTACTGTACTGCCCCTCTAAAATAAGGCGAAAGGCAAATGCATCGTGCAAA
     IFP2 ORF BAMHI CARTRIDGE

5000 AAATGCAAAAAAGTTATTTGTCGAGAGCATAATATTGATATGTGCCAAAGTGTTCTCGACTGACTAATAAGTATAATTTGTTTCTATTATGTATAAGTT
     IFP2 ORF BAMHI CARTRIDGE

5100 AAGCTAATTACTTATTTTATAATACAACATGACTGTTTTAAAGTACAAAATAAATAATTTATTTTTGTAAAAGAGAGAATGTTTAAAAGTTTTGTTACTTTA
     IFP2 ORF BAMHI CARTRIDGE

5200 GAAGAAATTTTGAGTTTTTGTTTTTTAATAAATAAAAATAAAACATAAATAAATTGTTTGTTGAATTGGATCCACTAGTTCTAGAGCGGCCGCCACCGC
     IFP2 ORF BAMHI CARTRIDGE

5300 GGTGGAGCTCCAGCTTTTGTTCCCTTTAGTGAGGGTTAATTGCGCGCTTGGCGTAATCATGGTCATAGCTGTTTCCTGTGTGAAATTGTTATCCGCTCAC

*FIG. 21(B) CONT.*

```
5400
AATTCCACACAACATACGAGCCGAAGCATAAAGTGTAAAGCCTGGGGTGCCTAATGAGTGAGCTAACTCACATTAATTGCGTTGCGCTCACTGCCCGCT
5500
TTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCA
5600
CTGACTCGCTGCGCTCGGTCGTTCGGCTGCGGCGAGCGGTATCAGCTCACTCAAAGGCGGTAATACGGTTATCCACAGAATCAGGGGATAACGCAGGAAA
5700
GAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAA
5800
AATCGACGCTCAAGTCAGAGGTGGCGAAACCCGACAGGACTATAAAGATACCAGGCGTTTCCCCCTGGAAGCTCCCTCGTGCGCTCTCCTGTTCCGACCC
5900
TGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCG
6000
CTCCAAGCTGGGCTGTGTGCACGAACCCCCCGTTCAGCCCGACCGCTGCGCCTTATCCGGTAACTATCGTCTTGAGTCCAACCCGGTAAGACACGACTTA
6100
TCGCCACTGGCAGCAGCCACTGGTAACAGGATTAGCAGAGCGAGGTATGTAGGCGGTGCTACAGAGTTCTTGAAGTGGTGGCCTAACTACGGCTACACTA
6200
GAAGGACAGTATTTGGTATCTGCGCTCTGCTGAAGCCAGTTACCTTCGGAAAAAGAGTTGGTAGCTCTTGATCCGGCAAACAAACCACCGCTGGTAGCGG
6300
TGGTTTTTTTGTTTGCAAGCAGCAGATTACGCGCAGAAAAAAGGATCTCAAGAAGATCCTTTGATCTTTTCTACGGGGTCTGACGCTCAGTGGAACGAA
6400
AACTCACGTTAAGGGATTTTGGTCATGAGATTATCAAAAAGGATCTTCACCTAGATCCTTTTAAATTAAAAATGAAGTTTTAAATCAATCTAAAGTATAT
6500
ATGAGTAAACTTGGTCTGACAGTTACCAATGCTTAATCAGTGAGGCACCTATCTCAGCGATCTGTCTATTTCGTTCATCCATAGTTGCCTGACTCCCCGT
```

*FIG. 21(B) CONT.*

```
6600
CGTGTAGATAACTACGATACGGGAGGGCTTACCATCTGGCCCCAGTGCTGCAATGATACGGCGAGACCCACGCTCACCGGCTCCAGATTTATCAGCAATA
6700
AACCAGCCAGCCGGAAGGGCCGAGCGCAGAAGTGGTCCTGCAACTTTATCCGCTCCATCCAGTCTATTAATTGTTGCCGGAAGCTAGAGTAAGTAGTT
6800
CGCCAGTTAATAGTTTGCGCAACGTTGTTGCCATTGCTACAGGCATCGTGGTGTCACGCTCGTCGTTTGGTATGGCTTCATTCAGCTCCGGTTCCCAACG
6900
ATCAAGGCGAGTTACATGATCCCCATGTTGTGCAAAAAAGCGGTTAGCTCCTTCGGTCCTCCGATCGTTGTCAGAAGTAAGTTGGGCCAGTGTTATCA
7000
CTCATGGTTATGGCAGCACTGCATAATTCTCTTACTGTCATGCCATCCGTAAGATGCTTTTCTGTGACTGGTGAGTACTCAACCAAGTCATTCTGAGAAT
7100
AGTGTATGCGGCGACCGAGTTGCTCTTGCCCGGCGTCAATACGGGATAATACCGCGCCACATAGCAGAACTTTAAAAGTGCTCATCATTGGAAAACGTTC
7200
TTCGGGGCGAAAACTCTCAAGGATCTTACCGCTGTTGAGATCCAGTTCGATGTAACCCACTCGTGCACCCAACTGATCTTCAGCATCTTTTACTTTCACC
7300
AGCGTTTCTGGGTGAGCAAAAACAGGAAGGCAAAATGCCGCAAAAAAGGGAATAAGGGCGACACGGAAATGTTGAATACTCATACTCTTCCTTTTTCAAT
7400
ATTATTGAAGCATTTATCAGGGTTATTGTCTCATGAGCGGATACATATTTGAATGTATTAGAAAAATAAACAAATAGGGGTTCCGCGCACATTTCCCCG

AAAAGTGCCAC --(SEQ ID NO:67)--
```

*FIG. 21(B) CONT.*

Sequence Range: 1 to 10333

100
AAGCTTGGGCTGCAGTCGACGGATCCAAATTCAACAAACAATTTATTTATGTTTATTTATTTATTTAAAAAAAAAAAACAAATTCTTCTAAAG

200
TAACAAAACTTTAAACATTCTCTCTTTACAAAAATAAACTTATTTGTACTTTAAAAACAGTCATGTTGTATTATAAAATAAGTAATTAGCTTAACTT

300
ATACATAATGAAACAAATTATACTTATTAGTCAGTCAGAAACAACTTTGGCACATATCAATATTATGCTCTGACAAATAACTTTTTGCATTTTTGC
                                                              ‾‾‾‾‾‾‾‾‾‾‾‾‾‾‾‾‾‾‾‾‾‾‾‾‾‾‾‾‾‾‾‾‾‾‾
                                                              PIGGYBAC ORF

400
ACGATGCATTGCCTTTCGCCTTATTTTAGAGGGCAGTAAGTACAGTAAGTACGTTTTTTCATTACTGCTCTTCAGTCTGTCATCTGATGTACCAGG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

500
CACTTCATTTGGCAAATATTAGAGATATTATCGCGCAAATATCTCTTCAAAGTAGGAGCTTCTAAACGCTTACGCATAAACGATGACGTCAGGCTCATG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

600
TAAAGGTTTCTCATAAATTTTTTGCGACTTTGAACCTTTTCTCCCTTGCTACTGACATTATGGCTGTATATAATAAAAGAATTTATGCAGGCAATGTTTA
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

700
TCATTCCGTACAATAATGCCATAGGCCACCTATTCGTCTTCCTACTGCAGGTCATCGCAGAAACACATTGGTCTAGCGTGTCCACTCCGCCTTTAGTTTG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

800
ATTATAATACATAACCATTTGCGGTTTACCGGTACTTTCGTTGATAGAAGCATCCTCATCACAGATGATAATAAGTATACCATCTTAGCTGGCTTCGGT
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

900
TTATATGAGACGAGAGTAAGGGTCCGTCAAAACAAAACATGATGTTCCCACTGGCCTGGAGCGACTGTTTTTCAGTACTTCCGGTATCTCGCGTTTGT
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
PIGGYBAC ORF

*FIG. 22*

```
1000 TTGATCGCACGGTTCCCACAATGTGTTAACTTATACGGTTCTTGTAGTAAGTTTTTGCCAAAGGGATTGAGTGAACCAATTGTCACACGTAATATTACG
     ――――――――――――――――――――――――――――――――――――――――――――――――――――――――――――――――――――――――――――――――――――――――――――
                                            PIGGYBAC ORF
1100 ACAACTACCGTGCACAGGCTTTGATAACTCCTTCACGTAGTATTCACCGAGTGGTACTCCGTTGGTCTGTGTTCCTCCTTCCCAAATAAGGCATTCCATTT
     ――――――――――――――――――――――――――――――――――――――――――――――――――――――――――――――――――――――――――――――――――――――――――――
                                            PIGGYBAC ORF
1200 ATCATATACTTCGTACCACTGTCACACATCATGAGGATTTTTATTCCATACTTACTTGGCTTGTTGTTTGGGATATACATCCTAAACGGACACCGTCCTCTAA
     ――――――――――――――――――――――――――――――――――――――――――――――――――――――――――――――――――――――――――――――――――――――――――――
                                            PIGGYBAC ORF
1300 AACCAAGTAACTGTTCATCTATGGTCAAATGAGCCCCTGGAGTGTAATTTTGTATGCACTGATGGATAAAGAGATCCCATATTTTCTAACAGGAGTAAA
     ――――――――――――――――――――――――――――――――――――――――――――――――――――――――――――――――――――――――――――――――――――――――――――
                                            PIGGYBAC ORF
1400 TACATCGTTTTCTCGAAGTGTGGGCCGTATACTTTTGTCATCCATTCTAAGACATCGTATCAAAAATCAAAACGATCACGACTCATTACAGAGACGTAC
     ――――――――――――――――――――――――――――――――――――――――――――――――――――――――――――――――――――――――――――――――――――――――――――
                                            PIGGYBAC ORF
1500 ACCATTGACAAAGATCGATCAAAGAGTCATCGTGGACATGTGTTATCTTTTCCACTGCTGTCATTACCAGAATACCAAAGAAAGCATAGATTTCAT
     ――――――――――――――――――――――――――――――――――――――――――――――――――――――――――――――――――――――――――――――――――――――――――――
                                            PIGGYBAC ORF
1600 CTTCATTCGTGTCACGAAATGTAGCACCTGTCATAGATTCCCAGCGTTTCAATGATATCTCAGCATTGTCCATTTACAATTCCGAAATTATCCATC
     ――――――――――――――――――――――――――――――――――――――――――――――――――――――――――――――――――――――――――――――――――――――――――――
                                            PIGGYBAC ORF
1700 AGTAAAAAATAGTTTGAAGCATAAAAGTGGGTCATATATATATTGCGGCACATACGCGTCCGACCCTCTTTGAGATCTGACAATGTTCAGTGCAGAGACTCGG
     ――――――――――――――――――――――――――――――――――――――――――――――――――――――――――――――――――――――――――――――――――――――――――――
                                            PIGGYBAC ORF
1800 CTACGCCCTCGTGACTTTGAAGTTGACCAACAATGTTTATTCTTACCTCTAATAGTCCTCTGTGGCAAGGTCAAGATTCGTTAGAAGCCAATGAAGAAC
     ――――――――――――――――――――――――――――――――――――――――――――――――――――――――――――――――――――――――――――――――――――――――――――
                                            PIGGYBAC ORF
```

*FIG. 22 CONT.*

```
1900
CTGGTTGTTCAATAACATTTGTTCGTCTAATATTTCACTACCGCTTGACGTTGGCTGCACTTCATGTACCTCATCTATAAACGCTTCTTCTGTATCGCT
     <                                            PIGGYBAC ORF
2000
CTGGACGTCATCTTCACTTACGTGATCTGATATTTCACTGTCAGAATCCTCAGAATCCTCCACCAACAGCTCGTCATCGCTTTGCAGAGAGCAGAGAGGATATGCTCA
     <                                            PIGGYBAC ORF
2100
TCGTCTAAAGAACTACCCATTTATTATATAGGATCCCCGACACCAGACCAACTGGTAATGTAGCGACCGGCGCTCAGCTGAATTAGGCCTTCTAGAC
     <   PIGGYBAC ORF
2200
CGCGGCCCGCAGATCTGTTAACGAATTCCCAATTCCCTATTCAGAGTTCTCTTCTTGTATTCAATAATTACTTCTTGGCAGATTTCAGTAGTTGCAGTTGA
     <                                            HSP 70 PROMOTER
2300
TTTACTTGGTTGCTGCGTTACTTTTAATTGATTCACTTTAACTTGCACTTTACTGCAGATTGTTGTTTAGCTTGTCGCTTGTTTATTTGCTTAGCTT
     <                                            HSP 70 PROMOTER
2400
TCGCTTAGCGACGTGTTCACTTGCTTGTTTGAATTGAATTGTCGCTCCGTAGACCGAAGCGCTCTATTTATACTCCGGCGCTCTTTTCGGCAACATTCGA
     <                                            HSP 70 PROMOTER
2500
GGCGCGCTCTCTCGAACCAACAGAGACCAGTATGCCGTTTACTGTGTGACAGAGTGAGAGAGCATTAGTGCAGAGAGGGAGACCCAAAAGAAAGAGAGA
     <                                            HSP 70 PROMOTER
2600
ATAACGAATAACGGCCAGAGAAATTTCTCGAGTTTTCTTCTGCCAAACAATGACCTACCACAATAACCAGTTTGTTTTGGGATTCTAGGGGATCGGGG
     <                                            HSP 70 PROMOTER
2700
ATCAATTCTAGTGTATGTAAGTTAATAAAACCCTTTTTTGGAGAATGTAGATTTAAAAAAACATATTTTTTTTTATTTTTTACTGCACTGGATATCA
     <
```

*FIG. 22 CONT.*

2800 TTGAACTTATCTGATCAGTTTTAAATTTACTTCGATCCAAGGGTATTGAAGTACCAGTTCTTTCGATTACCTCTCACTCAAAATGACATTCCACTCAA
2900 AGTCAGCGCTGTTTGCCTCCTTCTCTGTCCACAGAAATATCGCCGTCTCTTTCGCCGCTGGTCCGCTATCTCTTTCGCCACCGTTTGTAGCGTTACCTA
3000 GCGTCAATGTCCGCCTTCAGTTGCACTTTGTCAGCGGTTTCGTGACGAAGCTCCAAGCGGTTTACGCCATCAATTAAACACAAAGTGCTGTGCCAAAACT
3100 CCTCTCGCCTTCTTATTTTGTTTGTTTTTGAGTGATTGGGGTGCTGATTGGTTTTGGGTGTAAGCAGGGGAAAGTGTGAAAAATCCCGGCAATGGGC
3200 CAAGAGGATCAGGAGCTATTAATTCGCGAGGCAACACCCATCTGCCGAGCAAAATGTCTCTGCGGCGTGAGAACTGCGACCCACAAAATCCCAAACCGCAATCGCACAAACAAATAGTGAC
3300 TTGATCTATAGGAACTGCGATTGCAACATCAAATTGTCTCGCGCGTATATAAGACAATTTTTAAGATCATATCATGATCAAGACATCTAAAGGCATTCATTTTCGACTACATT
3400 ACGAAACAGATTATTCGGTAGCTGTCGCTATATAAGACAATTTTTAAGATCATATCATGATCAAGACATCTAAAGGCATTCATTTTCGACTACATT
3500 CTTTTTTACAAAAAATATAACAACCAGATATTTTAAGCTGATCCTAGATGCACAAAAAATAAAAGTATAAACCTACTTCGTAGATACTTCGTTTT
3600 GTTCGGGGTTAGATGAGCATAACGCTTGTAGTTGATATTTGAGATCCCCTATCATTGCAGGGTGACAGCGGCTTCCGCAGAGCTGCATTAACCAGG
3700 GCTTCGGGCAGGCCAAAAACTACGGCACGCTCCCTGCCACCCAGTCCGCCGGAGACTCCGGTTCAGGGAGCGGCCAACTAGCCGAGAACCTCACCTATGC
3800 CTGGCACAATATGGACATCTTTGGGCGGTCAATCAGCCGGGCTCCGATGGCGGCAGCTGGTCAACCGGACAACCGGACTATTCTGCAACGAGCGACAC
3900 ATACCGGCGCCCAGGAAACATTTGCTCAAGAACGGTGAGTTTCTATTCGCAGTCGGCTGATCTGTGTGAAATCTTAATAAAGGGTCCAATTACCAATTTG

*FIG. 22 CONT.*

```
4000
AAACTCAGTTTGCGGCTGGCCTATCCGGGGAACTTTTGGCCGTGATGGGCAGTTCCGGTGCCGGAAAGACGACCCTGCTGAATGCCCTTGCCTTTCGA
4100
TCGCCCGCAGGGCATCCAAGTATCGCCATCCGGGATGCCGACTGCTCAATGGCCAACCTGTGGACGCCAGTGGAGATGCAGGCCAGTGCGCCTATGTCCAGC
4200
AGGATGACCTCTTTATCGGCTCCCTAACGGCCAGGGAACACCTGATTTCCAGGCCATGGTGCGGATGCCACGACATCTGACCTATCGGCAGCGAGTGGC
4300
CCGCCGTGGATCAGGTGATCGAGATCCAGGAGCTTTCGCTCAGCAAATGTCAGCACACGATCATCGGTGTGCCCGGCAGGGTGAAAGGTCTGTCCGGGGAGAAAGG
4400
AAGCGTCTGGCATTCGCCTCCGAGGCACTAACCGATCCGCCGCTTCTGATCTGCGATGAGCCCACCTCCGACTGACTCATTACCGCCACAGCGTCG
4500
TCCAGGTGCTGAAGAAGCTGTCGCAGAAGGGCAAGACCGTCATCCCCAGCGAAGCCGTCGACTTCTCTTTCCTAGTGAGTTCGATGTGTTATTAAGGGTATCTAGCATTA
4600
GATGGCCGAGGCAGGGTAGCTTTCTTGGGCACTCCCAGCTGCCCAGTGTCCTACCAACTACAATCCGGCGGACTTTTACGTACAGGTGTTGGCCGTTGTGCCCGGACGG
4700
CATTACATCTCAACTCCTATCCAGCGCTGGGTCGCCAAGATATGCGACAATTTTGCTATTAGCAAAGTAGCCCGGGATATGGAGCAGTTGTTGGCCACCAAAAATTGG
4800
GAGATCGAGTCCCGTGATCGGCAGCCGGAGAATGGGTACACCTACACAAGGCCACCTGGTTCATGCAGTTCCGGGCGTCCTGTGGCGATCCTGGCTGTCGGTGCTCAA
4900
AGAAGCCACTGGAGCCGGAGAATGGGTACACCTACACAAGGCCACCTGGTTCATGCAGTTCCGGGCGTCCTGTGGCGATCCTGGCTGTCGGTGCTCAA
5000
GGAACCACTCCTCGTAAAGTGCGACTTATTCAGACAACGGTGAGTGTTCCAGTGGAAACAAATGATATAACGCTTACAATTCTTGGAAACAAATTCGC
5100
TAGATTTTAGTTAGAATTGCCTGATTCCACACCCTTCTTAGTTTTTTCAATGAGAGATGTATAGTTTATAGTTTGCAGAAAATAAATAAATTCATTTAA
```

*FIG. 22 CONT.*

```
5200
CTCGCGAACATGTTGAAGATATGAATATTAATGAGATGCGAGTAACATTTTAATTGCAGATGGTTGCCATCTTGATTGGCCTCATCTTTTGGGCCAAC
5300
AACTTCACGCAAGTGGGCGTGATGAATATCAACGGAGCCATCTTCCTCTTCCTGACCAACATGACCTTTCAAAACGTCTTTGCCACGATAAATGTAAGTCT
5400
TGTTTAGAATACATTTGCATATTAATAATTACTAACTTTCTAATGAATCGATTCGATTAGTGTTCACCTCAGAGCTGCCAGTTTTTATGAGGGAGGC
5500
CCGAAGTCGACTTTATCGCTGTGACACATACTTTCTGGGCAAAACGATTGCCGAATTACCGCTTTTTCTCACAGTGCCACTGGTCTTCACGGCGATTGCC
5600
TATCCGATGATCGGACTGCGGGCCGGAGTGCTGCACTCTTCTTCAACTGCCTGGTCACTCTCTGGTGGCCAATGTGTCAACGTCCTTCGGATATCTAA
5700
TATCCTGCGCCAGCTCCTCGACCTCGATGGTTGTCGTACCTCTCATGGTTCCGTTACGCCAACGAGGGTCTGCTGATTAACCAATGGGCGACGTGAGCGGGCGAA
5800
GGTGCCAGTATACCTTCAAATGGTTGTCGTACCTCTCATGTTCCGTTACGCCAAGGTCATCCTGGAGACGCTTAACTTCTCCGCCGATCGCCGCTGGACTACGTGG
5900
ATTAGCTGCACATCGTCGAACACCACGTGCCCCAGTTCGGGCAAGGTCATCCTGGAGACGCTTAACTTCTCCGCCGATCGCCGCTGGACTACGTGG
6000
GTCTGGCCATTCTCATCGTGAGCTTCCGGGTGCTCGACATATCTGGCTCTAAGACTTCGGGCCGACGCAAGGAGTAGCCGACATATATCCGAAATAACTG
6100
CTTGTTTTTTTTTTTTACCATTATTACCATCGTGTTTACTGTTATTGCCCCTCAAAAAGCTAATGTAATTATATATTTGTGCCAATAAAACAAGATATGA
6200
CCTATAGAATACAAGTATTTCCCCTTCGAACATCCCCACAAGTAGACTTTGGATTTGTCTTCTAACCAAAAGACTTACACACCTGCATACCTTACATCAA
6300
AAACTCGTTTATCGCTACATAAAACCGGATATATTTTTATATACATTTTCAAATCGCGGCCCTCTTCATAATTCACCTCCACCACCACCACGT
```

*FIG. 22 CONT.*

```
6400
TTCGTAGTTGCTCTTTCGCTGTCTCCCACCCGCTCTCCGCAACACATTCACCTTTTGTTCGACGACCTTGGAGCGACTGTCGTTAGTTCCGGCGATTCG
6500
GTTCGGCTCAAATGGTTCCGAGTGGTTCATTTCGTCTCAATAGAAATAGTAATAAATATTGTATGTACAATTTATTTGCTCCAATATATTGTATATAT
6600
TTCCCTCACAGCTATATTTATTCTAATTAATTATGACTTTTTAAGGTAATTTTTTGTGACCTGTTCGGAGTGATTAGCGTTACAATTTGAACTGAAA
6700
GTGACATCCAGTGTTTGTTCCTGTGTAGATGCATCTCAAAAAAATGGTGGGCATAATAGTGTGTTTATATATATCAAAAATAACAACTATAATAATAA
6800
GAATACATTTAATTAGAAAATGCTTGGATTTCACTGGAACTAGAATTAATTCGGCTGCTCTAAACGACGCATTCGTACTCCAAAGTACGAATTTT
6900
TTCCCTCAAGCTCTTATTTCATTAAACAATGAACAGGACCTAAGCGCACAGTCACGTTATTGTTACATAAATGATTTTTTTACTATTCAAACTTACTC
7000
TGTTTGTGTACTCCCACTGGTATAGCCTTCTTTTATCTTTTCTGGTTCAGGCTCTATCACTTTACTAGTACGGCATCTCGTTGAGTCGCCTCCTTTTA
7100
AATGTCTGACCTTTTGCAGTGCAGCCTTCCACTGCGAATCTTTAAAGTGGGTATCACAAATTGGGAGTTTTCACCAAGGCTGCACCCAAGGCTCTGCT
7200
CCCACAATTTCTCTTAATAGCACACTTCGGCACGTGAATTAATTTTACTCCAGTCACAGCTTTGCAGCAAAATTTGCAATATTTCATTTTTTTTTATTC
7300
CACGTAAGGGTTAATGTTTTCAAAAAAAAAATTCGTCCGACCACTGAATTAAGTGTATACTTCGGTAAGC
7400
TTCGGCTATCGACGGGACCACCTTATGTTATTTCATCATGGGCCAGATCCAGGCCAGTCCAGGCGGAGATCGGGCGGCGGAGAAGTAAGCGTCTCCAGGAT
7500
GACCTTGCCCGAACTGGGGCACGTGGTGTTCGACGATGTGCAGCTAATTCGCCGGCTCCACGTCCGCCCATTGGTTAATCAGCAGACCCTCGTTGGCG
```

*FIG. 22 CONT.*

```
7600
TAACGGAACCATGAGAGGTACGACAACCATTTGAGGTATACTGGCACCGAGCCCGAGTTCAAGAAGAAGGCCGTTTTCCATAGGCTCCGCCCCCTGACG
7700
AGCATCACAAAAATCGACGCTCAAGTCAGAGGTGGCGAAACCCGACAGGACTATAAAGATACCAGGCGTTTCCCCTGAAGCTCCCTGCCGCTCTCC
7800
TGTTCCGACCCTGCCGCTTACCGGATACCTGTCCGCCTTTCTCCCTTCGGGAAGCGTGGCGCTTTCTCAATGCTCACGCTGTAGTATCTCAGTTCGGTG
7900
TAGGTCGTTCGCTCCAAGCTGGGCTGTGTGCACGAACCCCCCGTTCAGCCGACCCGCTGCGCCTTATCCGGTAACTATCGTCTTGAGTCCAACCCGGTAA
8000
GACACGACTTATCGCCACTGGCAGCAGCCACTGGTAACAGGATTAGCAGAGCGAGGTATGTAGGCGGTGCTACAGAGTTCTTGAAGTGGTGGCCTAACTA
8100
CGGCTACACTAGAAGGACAGTATTTGGTATCTGCGCTCTGCTGAAGCCAGTTACCTTCGGAAAAAAGAGTTGGTAGCTCTTGATCCGGCAAACAAACCACC
8200
GCTGGTAGCGGTGGTTTTTTTGTTGCAAGCAGCAGATTACGCGCAGAAAAAAGGATCTCAAGAAGATCCTTTGATCTTTTCTACGGGGTCTGACGCTC
8300
AGTGGAACGAAAACTCACGTTAAGGGATTTTGGTCATGAGATTATCAAAAGGATCTTCACCTAGATCCTTTAAATTAAAAATGAAGTTTTAAATCAAT
8400
CTAAAGTATATATGAGTAAACTTGGTCTGACAGTTACCAATGCTTAATCAGTGAGGCACCTATCTCAGCGATCTGTCTATTTCGTTCATCCATAGTTGCC
8500
TGACTCCCCGTCGTGTAGATAACTACGATACGGGAGGGCTTACCATCTGGCCCCAGTGCTGCAATGATACCGCGAGACCCACGCTCACCGGCTCCAGATT
8600
TATCAGCAATAAACCAGCCAGCCGGAAGGGCCGAGCGCAGAAGTGGTCCTGCAACTTTATCCGCCTCCATCCAGTCTATTAATTGTTGCCGGGAAGCTAG
8700
AGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCC
```

*FIG. 22 CONT.*

```
8800
GGTTCCCAACGATCAAGGCGAGTTACATGATCCCCATGTTGTGCAAAAAGCGGTTAGCTCCTCCTTCGTCCTCCGATCGTTGTCAGAAGTAAGTTGCCG
8900
CAGTGTTATCACTGGTTATGCAGCACTGCATAATTCTCTTACTGTCATGCCATCCGTAAGATGCTTTTCTGTGACTGGTGAGTACTCAACCAAGTC
9000
ATTCTGAGAATAGTGTATGCGGCGACCGAGTTGCTCTTGCCCGGGTCAATACGGGATAATACCGGCCACATAGCAGAACTTTAAAAGTGCTCATCATT
9100
GGAAAAACGTTCTTCGGGGCGAAAACTCTCAAGGATCTTACCGCTGTTGAGATCCAGTTCGATGTAACCCACTCGTGCACCCAACTGATCTTCAGCATCTT
9200
TTACTTTCACCAGCGTTTCTGGGTGAGCAAAAACAGGAAGGCAAATGCCGCAAAAAAGGGAATAAGGGCGACACGGAAATGTTGAATACTCATACTCTT
9300
CCTTTTTCAATATTATTGAAGCATTTATCAGGGTTATTGTCTCATGAGCGGATACATATTTGAATGTATTTAGAAAAATAGGCGTATCACGAGGCCCTTTCGTCTCGCGC
9400
ACATTTCCCCGAAAGTGCCACCTGACGTCTAAGAAACCATTATTATCATGACATTAACCTATAAAATAGGCGTATCACGAGGCCCTTTCGTCTCGCGC
9500
GTTTCGGTGATGACGGTGAAAACCTCTGACACATGCAGCTCCCGAGACGGTCACAGCTTGTCTCGTAAGCGGATGCCCGGAGCAGACAAGCCCGTCAGG
9600
CGCGTCAGCGGGTGTTGGCGGGTGTCGGGGCTGCTTAACTATGCGGCATCAGAGCAGATTGTACTGAGAGTGCACCATATGCGGTGTGAAATACCGCAC
9700
CGAATCGCGCGGAACTAACGACAGTCGCCTCCAAGGTCGTCGAACAAAAGGTGAATGTGTTGCCGGAGAGCGGTGGGAGACAGGAAAGAGCAACTACGAA
9800
ACGTGGTGTGGTGGAGTGAATTATGAAGAGGGGCGCGATTTGAAAAGTATGTATATAAAAAATATCCGGTGTTTATGTAGCGATAAACGAGTTT
9900
TTGATGTAAGGTATGCAGGTGTGTAAGTCTTTTGGTTAGAAGACAAATCCAAAGTCTACTTGTGGGATGTTCGAAGGGGAAATACTTGTATTCTATAGG
```

*FIG. 22 CONT.*

```
10000
TCATATCTTGTTTTTATTGGCACAAATATAATTACATTAGCTTTTTGAGGGGCAATAAACAGTAAACACGATGGTAATAATGGTAAAAAAAAACAAG
10100
CAGTTATTTCGGATATATGTCGGCTACTCCTTGCCTCGGGCCCGAAGTCTTAGAGCCAGATATGCGAGCACCCGGAAGCTCACGATGAGAATGGCCAGAC
10200
CATGATGAAATAACATAAGGTGGTCCCGTCGGCAAGAGACATCCACTTAACGTATGCTTGCAATAAGTGCGAGTGAAAGGAATAGTATTCTGAGTGTCGT
10300
ATTGAGTCTGAGTGAGACAGCGATATGATTGTTGATTAACCCTTAGCATGTCCGTGGGGTTTGAATTAACTCATATATTAATTAGACGAAATTATTTT
AAAGTTTTATTTTTAATAATTGCGAGTACGCA --(SEQ ID NO:68)--
```

*FIG. 22 CONT.*

```
Natural piggyBac orf      1  ATGGGTAGTT CTTTAGACGA TGAGCATATC CTCTCTGCTC TTCTGCAAAG
Optimized piggyBac orf    1  ATGGGTAGca gccTgGAtGA TGAaCATATC CTgagcGCgC TgCTGCAgAG Natural piggyBac orf     51  CGATGACGAG CTTGTTGGTG AGGATTCTGA CAGTGAAATA TCAGATCACG
Optimized piggyBac orf   51  CGAcGAcGAa CTgGTTGGTG AaGATagcGA CAGCGAAATc agCGATCACG Natural piggyBac orf    101  TAAGTGAAGA TGACGTCCAG AGCCGATACAG AAGAAGCGTT TATAGATGAG
Optimized piggyBac orf  101  TgAGcGAAGA cGAcGTtCAG AGCCGATACCG AAGAAGCGTT cATcGACGAa Natural piggyBac orf    151  GTACATGAAG TGCAGCCAAC GTCAAGCGGT AGTGAAATAT TAGACGAACA
Optimized piggyBac orf  151  GTtCACGAAG TGCAGCCgAC cagcAGCGGT AGcGAAATcc TgGAtGAACA Natural piggyBac orf    201  AAATGTTATT GAACAACCAG GTTCTTCATT GGCTTCTAAC AGAATCTTGA
Optimized piggyBac orf  201  gAAcGTTAtc GAACAgCCGg GTagcagccT GGCgagcAAC cGtATCcTGA Natural piggyBac orf    251  CCTTGCCACA GAGGACTATT AGAGGTAAGA ATAAACATTG TTGGTCAACT
Optimized piggyBac orf  251  CCCcTGCCgCA GcGCACCATc cGtGGTAAaA ACAAACACTG TTGGagcACC Natural piggyBac orf    301  TCAAAGTCCA CGAGGCGTAG CCGAGTCTCT GCACTGAACA TTGTCAGATC
Optimized piggyBac orf  301  agcAAaagCA CCCGCCGTAG CCGtGTtagc GCgCTGAACA TTGTtcGtag Natural piggyBac orf    351  TCAAAGAGGT CCGACGCGTA TGTGCCGCAA TATATATGAC CCACTTTTAT
Optimized piggyBac orf  351  cCAgcGtGGT CCGACCCGTA TGTGCCCGCAA cATcTAcGAt CCgCTgCTgT Natural piggyBac orf    401  GCTTCAAACT ATTTTTTACT GATGAGATAA TTTCGGAAAT TGTAAAATGG
Optimized piggyBac orf  401  GCTTCAAACT gTTcTTcACc GATGAaATcA TcagcGAAAT cGTgAAATGG
```

FIG. 23

```
Natural piggyBac orf     451 ACAAATGCTG AGATATCATT GAAACGTCGG GAATCTATGA CAGGTGCTAC
Optimized piggyBac orf   451 ACCAAcGCCG AaATcagccT GAAACGTCGc GAAagcAATGA CCGGCGCGAC Natural piggyBac orf     501 ATTTCGTGAC ACGAATGAAG ATGAAATCTA TGCTTTCTTT GGTATTCTGG
Optimized piggyBac orf   501 cTTcCCGcGAt ACCAACGaaG ATGAaATCTA cGCCTTCTTc GGTATcCTGG Natural piggyBac orf     551 TAATGACAGC AGTGAGAAAA GATAACCACA TGTCCACAGA TGACCTCTTT
Optimized piggyBac orf   551 TgATGACcGC gGTGcGTaAA GATAACCACA TGagCACcGA TGAtCTgTTT Natural piggyBac orf     601 GATCGATCTT TGTCAATGGT GTACGTCTCT GTAATGAGTC GTGATCGTTT
Optimized piggyBac orf   601 GATCGtagcc TGagcATGGT tTACGTtagc GTtATGAGcC GtGAcCGTTT Natural piggyBac orf     651 TGATTTTTTG ATACGATGTC TTAGAATGGA TGACAAAAGT ATACGGCCCA
Optimized piggyBac orf   651 cGATTTtcTG ATcCGTtGTC TgcGtATGGA TGAtAAAAGc ATCCGCCCgA Natural piggyBac orf     701 CACTTCGAGA AAACGATGTA TTTACTCCTG AAATTACACT ATGGGATCTC
Optimized piggyBac orf   701 CcCTgCGCGA AAACGATGTg TTcCACCCCgG TTcGcAAAAT cTGGGATCTg Natural piggyBac orf     751 TTTATCCATC AGTGCATACA AAATTACACC ATTTGACCAT CCAGGGGCTC
Optimized piggyBac orf   751 TTcATCCAcC AGTGCATcCA gAACTACACc CCgGGCGCgC AccTGACCAT Natural piggyBac orf     801 AGATGAACAG TTACTTGGTT TTAGAGGACG GTGTCCGTTT AGGATGTATA
Optimized piggyBac orf   801 cGATGAACAG cTgCTgGGTT TTcGtGtCG cTGTCCGTTT cGtATGTAcA Natural piggyBac orf     851 TCCCAAACAA GCCAAGTAAG TATGGAATAA AAATCCTCAT GATGTGTGAC
Optimized piggyBac orf   851 TCCCgAACAA aCCgAGcAAa TAcGGtATcA AAATCCTgAT GATGTGTGAC
```

*FIG. 23 CONT.*

```
Natural piggyBac orf    901  AGTGGTACGA AGTATATGAT AAATGGAATG CCTTATTTGG GAAGAGGAAC
Optimized piggyBac orf  901  AGcGGTACcA AgTAcATGAT cAAcGgtATG CCgTATcTGG GtcGtGGtAC Natural piggyBac orf    951  ACAGACCAAC GGAGTACCAC TCGGTGAATA CTACGTGAAG GAGTTATCAA
Optimized piggyBac orf  951  cCAGACCAAC GGtGTgCCgC TgGGTGAATA CTACGTGAAa GAacTgagcA Natural piggyBac orf   1001  AGCCTGTGCA CGGTAGTTGT CGTAATATTA CGTGTGACAA TTGGTTCACC
Optimized piggyBac orf 1001  AaCCgGTGCA CGGTAGcTGT CGTAAcATcA CCTGTGACAA cTGGTTCACC Natural piggyBac orf   1051  TCAATCCCTT TGGCAAAAAA CTTACTACAA GAACCGTATA AGTTAACCAT
Optimized piggyBac orf 1051  agcATCCCgc TGGCgAAAAA CCTgCTgCAg GAACCGTATA AacTgACCAT Natural piggyBac orf   1101  TGTGGGAACC GTGCGATCAA ACAAACGCGA GATACCGGAA GTACTGAAAA
Optimized piggyBac orf 1101  cGTGGGtACC GTtCGtagcA ACAAACGtGA aATcCCCGAA GTgCTGAAAA Natural piggyBac orf   1151  ACAGTCGCTC CAGGCCAGTG GGAACATCGA TGTTTTGTTT TGACGGACCC
Optimized piggyBac orf 1151  ACAGcCGtag CCgTcCCgGTG GGCACcagcA TGTTcTGTTTcGAtGGtCCg Natural piggyBac orf   1201  CTTACTCTCG TCTCATATAA ACCGAAGCCA GCTAAGATGG TATACTTATT
Optimized piggyBac orf 1201  CTgACcCTgG TtagcTAcAA ACCGAAaCCG GCgAAaATGGTgTACcTgcT Natural piggyBac orf   1251  ATCATCTTGT GATGAGGATG CTTCTATCAA CGAAAGTACC GGTAAACCGC
Optimized piggyBac orf 1251  gagcagcTGc GACGAaGACG CgagcATCAA CGAAAGcACC GGTAAACCGC Natural piggyBac orf   1301  AAATGGTTAT GTATTATAAT CAAACTAAAG GCGGAGTGGA CACGCTAGAC
Optimized piggyBac orf 1301  AgATGGTTAT GTAcTAcAAC CAgACcAAAG GCGgtGTGGA CACcCTgGAt
```

FIG. 23 CONT.

```
Natural piggyBac orf      1351 CAAATGTGTT CTGTGATGAC CTGCAGTAGG AAGACGAATA GGTGGCCTAT
Optimized piggyBac orf    1351 CAgATGTGCa gcGTtATGAC CTGCAGcCGC AAaACcAAcc GCTGGCCgAT Natural piggyBac orf      1401 GGCATTATTG TACGGAATGA TAAACATTGC CTGCATAAAT TCTTTTATTA
Optimized piggyBac orf    1401 GGCgCTgCTG TACGGtATGA TCAACATCGC CTGCATCAAC agcTTTATcA Natural piggyBac orf      1451 TATACAGCCA TAATGTCAGT AGCAAGGGAG AAAAGGTTCA AAGTCGCAAA
Optimized piggyBac orf    1451 TcTACAGCCA TAACGTtAGC AGCAAaGGtG AAAAaGTTCA gAGCCGCAAA Natural piggyBac orf      1501 AAATTTATGA GAAACCTTTA CATGAGCCTG ACGTCATCGT TTATGCGTAA
Optimized piggyBac orf    1501 AAATTTATGc GtAACCTgTA CATGAGCCTG ACcagcagcT TcATGCGTAA Natural piggyBac orf      1551 GCGTTTAGAA GCTCCTACTT TGAAGAGATA TTTGCGCGAT AATATCTCTA
Optimized piggyBac orf    1551 aCGTcTgGAA GCcCCgACcc TGAAacGtTA TcTGCGCGAT AACATCagcA Natural piggyBac orf      1601 ATATTTTGCC AAATGAAGTG CCTGGTACAT CAGATGACAG TACTGAAGAG
Optimized piggyBac orf    1601 ACATccTGCC gAACgAAGTG CCgGGTACCa gcGATGATAG cACCGAAGAa Natural piggyBac orf      1651 CCAGTAATGA AAAAACGTAC TTACTGTACT TACTGCCCCT CTAAAATAAG
Optimized piggyBac orf    1651 CCgGTgATGA AAAAACGTAC cTACTGTACC TACTGCCCga gcAAAATccG Natural piggyBac orf      1701 GCGAAAGGCA AATGCATCGT GCAAAAAATG CAAAAAAGTT ATTTGTCGAG
Optimized piggyBac orf    1701 cCGtAAaGCg AAcGCgagcT GCAAAAAATG CAAAAAAGTT ATcTGTCGtG Natural piggyBac orf      1751 AGCATAATAT TGATATGTGC CAAAGTTGTT TCTGA--(SEQ ID NO:69)--
Optimized piggyBac orf    1751 AaCATAACAT cGATATGTGC CAgAGCTGTT TCTGA--(SEQ ID NO:70)--
```

*FIG. 23 CONT.*

FIG. 24
A. pCaSpeR-hs-orf
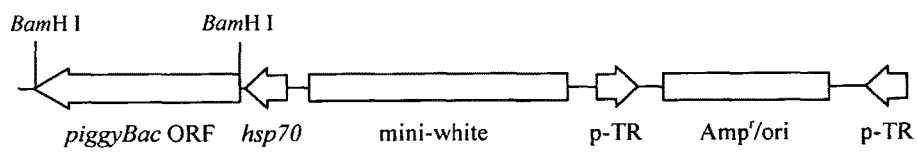
B. p(PZ)-Bac-EYFP
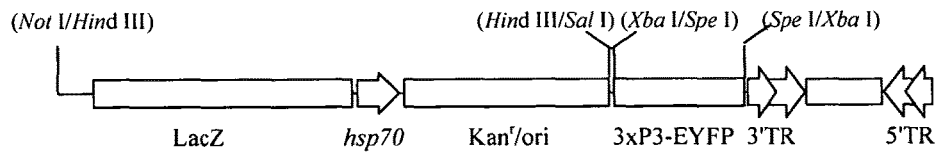
C. pBSII-ITR1.1k-ECFP
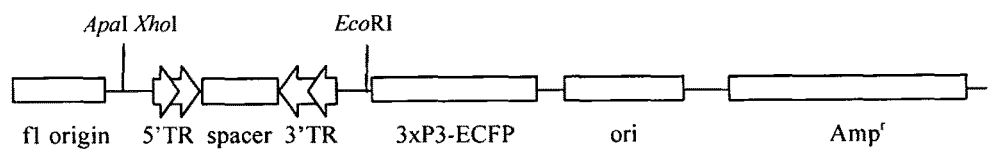
D. pXL-BacII-ECFP
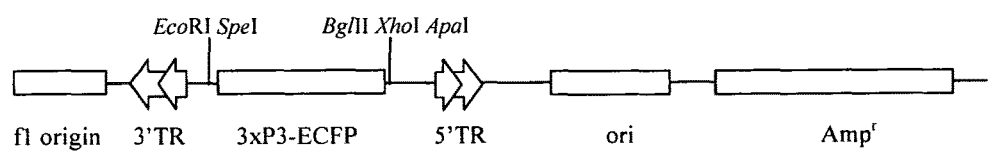

FIG. 26
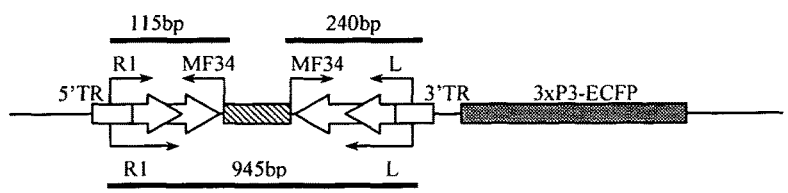
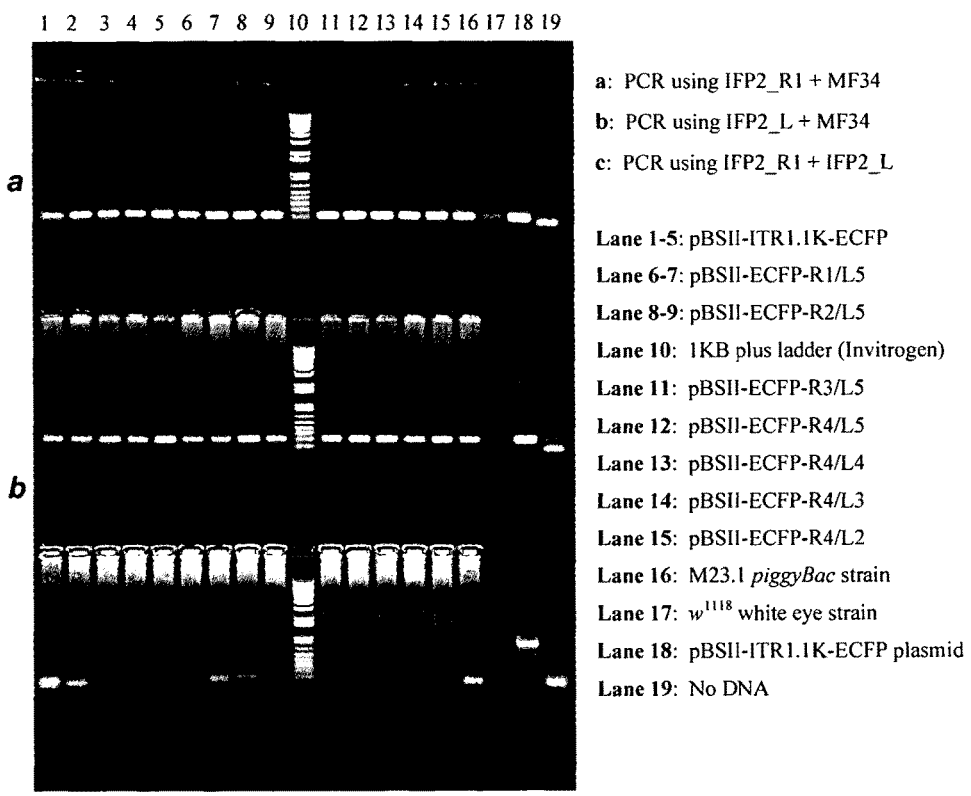
a: PCR using IFP2_R1 + MF34
b: PCR using IFP2_L + MF34
c: PCR using IFP2_R1 + IFP2_L
Lane 1-5: pBSII-ITR1.1K-ECFP
Lane 6-7: pBSII-ECFP-R1/L5
Lane 8-9: pBSII-ECFP-R2/L5
Lane 10: 1KB plus ladder (Invitrogen)
Lane 11: pBSII-ECFP-R3/L5
Lane 12: pBSII-ECFP-R4/L5
Lane 13: pBSII-ECFP-R4/L4
Lane 14: pBSII-ECFP-R4/L3
Lane 15: pBSII-ECFP-R4/L2
Lane 16: M23.1 *piggyBac* strain
Lane 17: $w^{1118}$ white eye strain
Lane 18: pBSII-ITR1.1K-ECFP plasmid
Lane 19: No DNA

FIG. 27
Southern Hybridization of the transformed strains
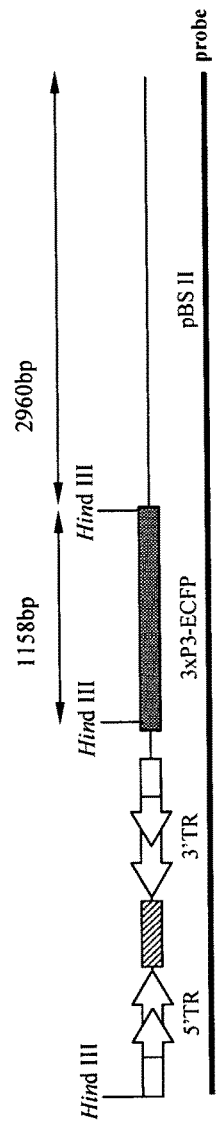
A.
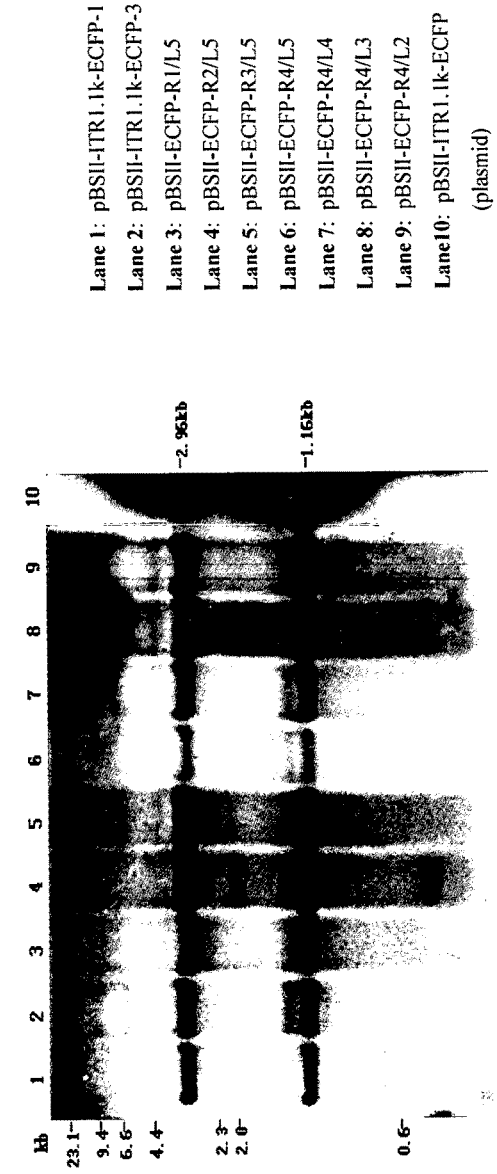
B.

FIG. 30

|  | 13bp TR | 31bp spacer | 19bp IR |
|---|---|---|---|
| Wide-type | CCCTAGAAAGATA | ATCATATTGTGACGTACGTTAAAGATAATCA | TGCGTAAAATTGACGCATG |
| Mutation | CCCTAGAAAGATA | ATCATATTGTGACGTACGTTAAAGATAATCA | TGAGTAAAATTGACGCATG | ated on May 7, 2018 and
METHODS AND COMPOSITIONS FOR TRANSPOSITION USING MINIMAL SEGMENTS OF THE EUKARYOTIC TRANSFORMATION VECTOR PIGGYBAC

CROSS-REFERENCE TO RELATED APPLICATIONS

This application is a Continuation-In-Part of U.S. patent application Ser. No. 10/826,523, filed Apr. 19, 2004 entitled "Methods and Compositions for Transposition Using Minimal Segments of the Eukaryotic Transformation Vector PiggyBac,", now which is a Continuation-In-Part of U.S. patent application Ser. No. 10/001,189, filed Oct. 30, 2001, now issued as U.S. Pat. No. 6,962,810 on Nov. 8, 2005, entitled "Methods and Compositions for Transposition Using Minimal Segments of the Eukaryotic Transformation Vector PiggyBac," filed Oct. 30, 2001, which claims priority to U.S. Provisional Patent Application No. 60/244,984, filed Nov. 1, 2000, and U.S. Provisional Patent Application No. 60/244,667, filed on Oct. 31, 2000. The entire disclosure and contents of the above-identified applications are hereby incorporated by reference.

INCORPORATION BY REFERENCE OF A SEQUENCE LISTING

The sequence listing contained in the file "21395-6_2018-05-07_sequence-listing.txt" created on May 7, 2018 and having a file size of 230,681 bytes and which contains SEQ ID NOs. 1-190 for the current application U.S. Ser. No. 11/454,947 filed on Jun. 19, 2006 is incorporated herein by reference in its entirety.

GOVERNMENT INTEREST STATEMENT

The United States Government has rights in this invention pursuant to USDA/NRI Grant 96-35302-3796, NIH-NIAID 1RO1AI40960, NIH/NIAID 1RO1AI48561, and NIH AI48561.

BACKGROUND

Field of the Invention

The present invention relates generally to transposable elements, and more particularly to the transposon piggybac.

Related Art

Transposable elements (transposons) can move around a genome of a cell and are useful for inserting genes for the production of transgenic organisms. The *Lepidopteran* transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The *Lepidopteran* transposable element piggyBac was originally isolated from the TN-368 *Trichoplusia ni* cell culture as a gene disrupting insertion within spontaneous baculovirus plaque morphology mutants. PiggyBac is a 2475 bp short inverted repeat element that has an asymmetric terminal repeat structure with a 3-bp spacer between the 5' 13-bp TR (terminal repeat) and the 19-bp IR (internal repeat), and a 31-bp spacer between the 3' TR and IR. The single 2.1 kb open reading frame encodes a functional transposase (Cary et al., 1989; Fraser et al., 1983, 1995; Elick et al., 1996a; Lobo et al., 1999; Handler et al., 1998).

PiggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

Transient excision and interplasmid transposition assays have verified movement of this element in the SF21AE *Spodoptera frugiperda* cell line, and embryos of the *Lepidopteran Pectinophora glossypiella*, *Bombyx mori*, and *T. ni*, as well as the *Dipteran* species *Drosophila melanogaster*, *Aedes aegypti*, *Aedes triseriatus*, *Aedes albopictus*. *Anopheles stephensi* and *Anopheles gambiae*. There is also evidence of transposition in the Cos-7 primate cell line, and embryos of the zebra fish, *Danio rerio* (Fraser et al., 1995; Buck et al., 1996b; Fraser et ai, 1996; Elick et al, 1997; Thibault et al, 1999; Tamura et al, 2000; Lobo et al, 1999).

The piggyBac element has been used successfully as a helper-dependent gene transfer vector in a wide variety of insect species, including the Mediterranean fruit fly, *C. capitata, D. melanogaster, Bombyx mori, P. glossypiella, Tribollium casteneum,* and *Ae. aegypti* (Handler et al, 1998, 1999; Tamura et al, 2000; Berghammer et al, 1999).

Excision assays using both wildtype and mutagenized piggyBac terminal sequences demonstrated that the element does not discriminate between proximal or distal duplicated ends, and suggest that the transposase does not first recognize an internal binding site and then scan towards the ends. In addition, mutagenesis of the terminal trinucleotides or the terminal-proximate three bases of the TTAA target sequence eliminates excision at the altered terminus (Elick et al., 1996b).

Although the reported piggyBac vector is useful, length of genes that could be transferred is limited by the size of the other components of the vector. Minimizing the length of the vector to allow more room for the genetic material to be transferred would improve the versatility of the system and reduce costs of preparing synthetic vectors. Previously, the gene to be expressed or transduced was inserted into the middle of the piggyBac transposon in the plasmid p3E1.2. The final construct included the entire length of the piggyBac transposon (2475 bases) and flanking sequences derived from the baculovirus 25K gene region of approximately 813 bases, as well as the plasmid pUC backbone of 2686 bp, and an overall size of approximately 5962 bp. In cloning sequences into the pUC vector, 12 bp of multiple cloning sites DNA was lost. This size limited the effective size of genes that may be inserted, because plasmids larger than 10 KB are generally more difficult to construct, maintain, and transduce into host genomes.

Another problem was that previous cloning regimens involved the excision of a gene, the promoter controlling the gene, and polyadenylation signals, from one plasmid followed by insertion into the piggyBac transfer vector. This procedure was often complicated by the lack of suitable restriction enzyme sites for these manipulations.

SUMMARY

The present invention identifies the specific sequences in a mobile genetic element, the transposon piggyBac, and sequence configurations outside of piggyBac, that are minimally required for full functionality of the sequence as a transposon. Inserting DNA molecules into cells is enhanced using the methods and compositions of the present invention.

The present invention solves problems in use of the piggyBac vector for gene transfer caused by lack of suitable restriction sites to cut the components needed for gene transfer, and limitations on the sizes (lengths) of genes transferred by use of this vector. Methods and compositions of the present invention enlarge the size of the gene that may be transferred in two ways. First, a minimal sequence cartridge may be easily amplified using primers containing desired restriction endonuclease sites, and the cartridge may then be inserted into any plasmid containing the gene with its attendant promoter and polyadenylation signals intact, converting that plasmid into a piggyBac transposon. Second, a multiple cloning site may be inserted into a minimal plasmid vector, facilitating the insertion of genes in this more traditional plasmid vector. The vectors may both be used for applications including producing transgenic organisms, both plants and animals. The present invention has been successful in exemplary transpositions using the primate Cos-7 vertebrate cell line and embryos of the zebra fish, *Danio rerio*, among others.

Methods and compositions are disclosed herein for transferring genes using the minimum internal and external sequences of the transformation vector piggyBac In an embodiment of the invention, all non-essential sequences are removed, including the bulk of the piggyBac internal domain and the flanking baculovirus sequences. By means of the minimal piggyBac cartridge, a DNA molecule may be transferred from a plasmid into a host cell.

In one aspect, the invention provides a DNA molecule that in some embodiments comprises at least 163 consecutive nucleotide base pairs of the 3' terminal region beginning at the 3' terminal base pair, and at least 125 consecutive nucleotide base pairs of the 5' terminal region beginning at the 5' terminal base pair of the piggyBac molecule, the region extending from the restriction site SacI to the end of the piggyBac molecule.

In another aspect, the invention comprises a genetic cartridge designated ITR.

In some embodiments, the invention provides a genetic cartridge designated ITR1.1k.

According to another aspect, the invention provides a vector. In some embodiments, the vector is designated pXL-Bac as shown in FIG. 3. In other embodiments, the vector is designated pXL-BacII-ECFP as shown in FIG. 24 D. In yet additional embodiments, the vector is designated pBSII-ITR1.1k-ECFP as shown in FIG. 24 C.

In other aspects, the invention provides a nucleic acid molecule comprising a nucleic acid sequence. In some embodiments, the nucleic acid sequence comprises a minimal sequence of consecutive nucleotide base pairs (a minimal sequence component) having a sequence that is homologous to a nucleic acid sequence of a 5' terminal region of a piggyBac native nucleic acid sequence, and a longer sequence of consecutive nucleotide base pairs (a longer sequence component) that is homologous to a nucleic acid sequence of a 3' terminal region of a piggyBac native nucleic acid sequence.

In some embodiments, the minimal sequence of consecutive nucleotide base pairs that is homologous to a nucleic acid sequence of a 5' terminal region of the piggyBac native nucleic acid sequence is a sequence of nucleotide base pairs that is about 50 to about 80 base pairs in length, or is about 60 to about 70 base pairs in length, or is 66 base pairs in length. In other embodiments, the minimal sequence of consecutive nucleotide base pairs is defined as comprising a nucleic acid sequence that is homologous to a nucleic acid sequence that is the sequence at nucleotide positions 36 to 100 of the native piggyBac nucleic acid sequence.

In some embodiments, the longer sequence of consecutive nucleotide base pairs from the 3' terminal region of the piggyBac nucleic acid sequence is about 125 to about 450 base pairs in length, or about 200 to about 400 base pairs in length, or about 300 to about 380 base pairs in length, or about 311, 350, or 378 base pairs in length. In some embodiments, the longer sequence of consecutive nucleotide base pairs is defined as comprising a nucleic acid sequence that is homologous to a nucleic acid sequence that is the sequence at nucleotide positions 2031 to 2409 of the native piggyBac sequence.

The homology that the minimal sequence component and the longer sequence component have with the referenced native piggyBac nucleic acid sequence as defined herein is a degree of homology that is sufficient to produce a functionally equivalent activity that is equal or substantially equal to the native piggyBac nucleic acid sequence. Homology may also be described relative to the percent (%) similarity that the minimal sequence component or the longer sequence component has to the referenced native piggyBac nucleic acid sequence. In some embodiments, the homology may be 40% or more, 45% or more, 50% or more, 60% or more, 70% or more, 80% or more, 90% or more, or even up to 100% homology with the nucleic acid sequence of the corresponding native piggyBac sequence.

In some embodiments, the DNA molecule comprises a nucleic acid sequence encoding a phenotypic marker.

In some embodiments, the DNA molecule comprises a nucleic acid sequence encoding a spacer sequence of interest. The spacer sequence may comprise a sequence of any desired length, and in some embodiments, may be described by the term, "stuffer". This "stuffer" may comprise a nucleic acid sequence of about 10 to about 1000 base pairs, or about 20, 30, 40, 50, 60, 100, 200, 300, 400, 500, 700, 800, or even 1000 base pairs or more. In yet other embodiments, the DNA molecule comprises a nucleic acid sequence encoding a molecule of interest, such as a protein, peptide, or a synthetic or non-synthetic, organic, inorganic, or other type of molecule.

In another aspect, the invention provides a plasmid comprising a nucleic acid sequence of a DNA molecule having the minimal nucleotide sequence of consecutive nucleotide base pairs from the 5' terminal region of the piggyBac nucleic acid sequence and the longer nucleotide sequence of consecutive nucleotide base pairs from the 3' terminal region of the piggyBac nucleic acid sequence.

In some embodiments the nucleic acid molecule may comprise a nucleic acid sequence comprising one or more than one minimal sequence of consecutive nucleotide base pairs substantially homologous to a 5' terminal region of a piggyBac nucleic acid sequence, one or more than one longer nucleotide sequence of consecutive nucleotide base pairs substantially homologous to a 3' terminal region of a piggyBac nucleic acid sequence, or any combination thereof and in any desired construct arrangement. By way of example and not limitation, one embodiment of such a nucleic acid molecule may comprise a first minimal sequence of consecutive nucleotide base pairs substantially homologous to a 5' terminal region of a piggyBac nucleic acid sequence, adjacent to a longer nucleotide sequence of consecutive nucleotide base pairs substantially similar to a 3' terminal region of a piggyBac nucleic acid sequence, and a second minimal sequence of consecutive nucleotide base pairs substantially homologous to a 5' terminal region of a piggyBac nucleic acid sequence. In some embodiments, this and any other of the constructs of the present invention may include 1 or more of the small repeat sequences, such as the -CAAAAT- or ACTTATT- small repeat sequences.

In some embodiments, the invention provides a plasmid designated pBSII-ITR1.1k-ECFP.

In other embodiments, the invention provides a plasmid designated pCaSpeR-hs-orf.

In still other embodiments, the invention provides a plasmid p(PZ)-Bac-EYFP (FIG. 29A).

In other embodiments, the invention provides a plasmid pBSII-3xP3-ECFP.

In yet other embodiments, the invention provides a plasmid designated pBSII-ECFP-R4/L. In particular of these embodiments, the plasmid is pBSII-ECFP-R4/$L_2$, pBSII-ECFP-R4/$L_3$, pBSII-ECFP-R4/$L_4$, or pBSII-ECFP-R4/$L_5$ (FIG. 27).

Another broad aspect of the invention provides a method for providing high frequency transformation of an insect genome using a vector comprising the minimal 5' terminal region and longer 3' terminal region sequence of a piggyBac sequence, in the presence of a helper plasmid. In some embodiments, the vector further comprises a small terminal repeat sequence, CAAAAT. In particular embodiments, the helper plasmid is a plasmid pCaSpeR-hs-orf.

In some embodiments, the insect genome is further described as that of an insect. In some embodiments, the insect is a mosquito.

In some embodiments, the method of high frequency transformation may be described as providing a frequency of transformation that is enhanced 100-fold or higher, than transformation frequency employing a vector other that the minimal 5', longer 3' terminal end piggyBac constructs described herein.

In another aspect, the invention provides a transformed cell transformed with a transformation vector comprising a nucleic acid sequence that includes a minimal sequence component homologous to a 5'terminal region of a piggyBac native nucleic acid sequence and a longer sequence component homologous to a 3' terminal region of a piggyBac native nucleic acid sequence. In some embodiments, the transformed cell is an insect cell, such as *Drosophila melanogaster*.

BRIEF DESCRIPTION OF THE DRAWINGS

The invention will be described in conjunction with the accompanying drawings, in which:

FIG. 2A-2C(2). 2A shows the pIAO-P/L insertion series of plasmids and presents interplasmid transposition assay results: (A) lists the pIAO-P/L series of plasmids' insertion sequences (SEQ ID NOS: 35-39) and their interplasmid transposition assay (IPTA) frequencies are shown; all the pIAO-P/L insertion plasmids were co-injected with the piggyBac helper plasmid, phspBac, and the target plasmid, pGDV1, into *T. ni* embryos to perform an interplasmid transposition assay; the results show that when the insertion sequence is less than 40 bp, the transposition frequency drops dramatically; 2B is a schematic representation of the pIAO-P/L series plasmids; the piggyBac sequence was PCR amplified from a p3E1.2B/X plasmid, polhlacZ is from a pD2/-gal DraI/NruI fragment and AMP/ori was PCR amplified from a pUC18 plasmid; and (C1), including 2(C1) and 2(C1)a to 2(C1)j, is the nucleotide sequence of pIAO-P/L (SEQ ID NO: 57) and the amino acid sequences (SEQ ID NOS 58, 142-126, 59, 144-143, 60, 153-145, 61 & 62) (C2), including 2(C2) and 2(C2)a to 2(C2)q, is the nucleotide sequence of pIAO-P/L-Lambda (2.2 kb) (SEQ ID NO: 63) and the amino acid sequences (SEQ ID NOS 58, 142-126, 59, 144-143, 60, 153-145, 61, 157-154, 64, 190-158, 65 & 66);

FIG. 3A-3C(2) represent a schematic representation of an ITR cartridge and pXL-Bac minimum piggyBac vectors; 3A the ITR cartridge may be amplified from the pIAO-P/L-589 bp plasmid using an IR-specific primer; the amplified ITR may convert any existing plasmid into a piggyBac transposon, which may be mobilized if provided with the piggyBac transposase; 3B is a map of the pXL-Bac plasmid (MCS=multiple cloning site, BamHI or BssHII are restriction sites; 3C1 the ITR cartridge nucleotide sequence (SEQ ID NO: 40); and 3C2 is the nucleotide sequence (SEQ ID NO: 41) of pXL-Bac;

FIG. 5A-5B. 5A is a plasmid map showing the piggyBac ORF was amplified as a BamHI cartridge from the p3E1.2 plasmid and cloned into pCaSpeR-hs plasmid, positioning it for transcriptional control by the hsp70 promoter; 5B is the nucleotide sequence (SEQ ID NO: 42) of pCaSpeR-hs-orf;

FIG. 6A-6B. 6A is a plasmid map showing that the piggyBac ORF BamHI cartridge from pCaSpeR-hs-orf was cloned into the pBSII (Stratagene) positioning it for transcription under control of the T7 promoter to form pBSII-IFP2orf; 6B is the nucleotide sequence (SEQ ID NO: 43) of pBSII-IFP2-orf;

FIG. 8A-8B. 8A is a plasmid map showing that the IE1 promoter was PCR amplified from the pIE1FB plasmid (Jarvis et al., 1990) and cloned into the pBSII-IFP2orf plasmid to form pBSII-IE1-orf; 8B is the nucleotide sequence (SEQ ID NO: 44) of pBSII-IE1-orf;

FIG. 9A-9B. 9A is a plasmid map showing that the base plasmid is pDsRed1-N1 (Clontech). The 3xP3 promoter was PCR amplified from pBac [3xP3-EYFPafm] (Horn and Wimmer, 2000) and cloned into the Xho I and EcoR I sites of pDsRed1-N1 to form the p3xP3-DsRed plasmid. The piggyBac ORF BamHI cartridge from pCaSpeR-hs-orf was then cloned into the BglII site of p3xP3 DsRed positioning it under control of the CMV (cytomegalovirus) promoter to form p3xP3-DsRed-orf; 9B is the nucleotide sequence (SEQ ID NO: 45) of p3xP3-DsRed-orf. DsRed is a marker from Invitrogen and 3xP3 is a promoter specific for eyes of insects;

FIG. 10A-10B. 10A is a plasmid map showing that the ITR cartridge was PCR amplified as a BamHI fragment using a piggyBac internal repeat specific primer (5'-GGATCCCATGCGTCAATTTTACGCA-3') (SEQ ID NO:

Figure 11:
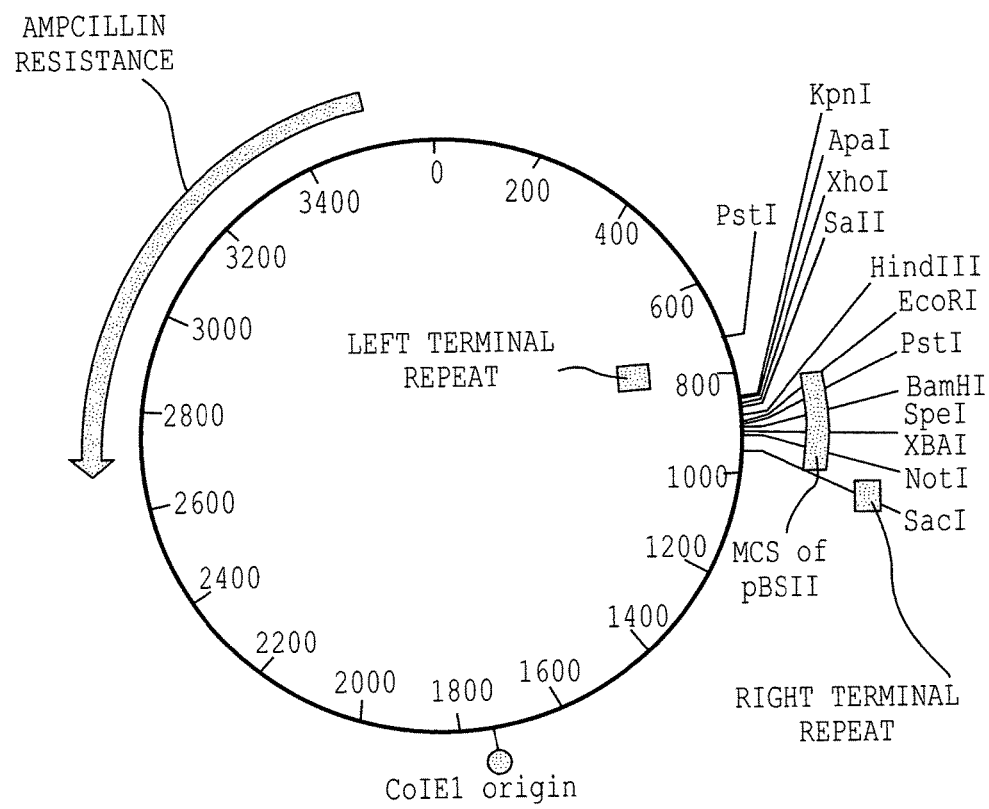
Figure 12:
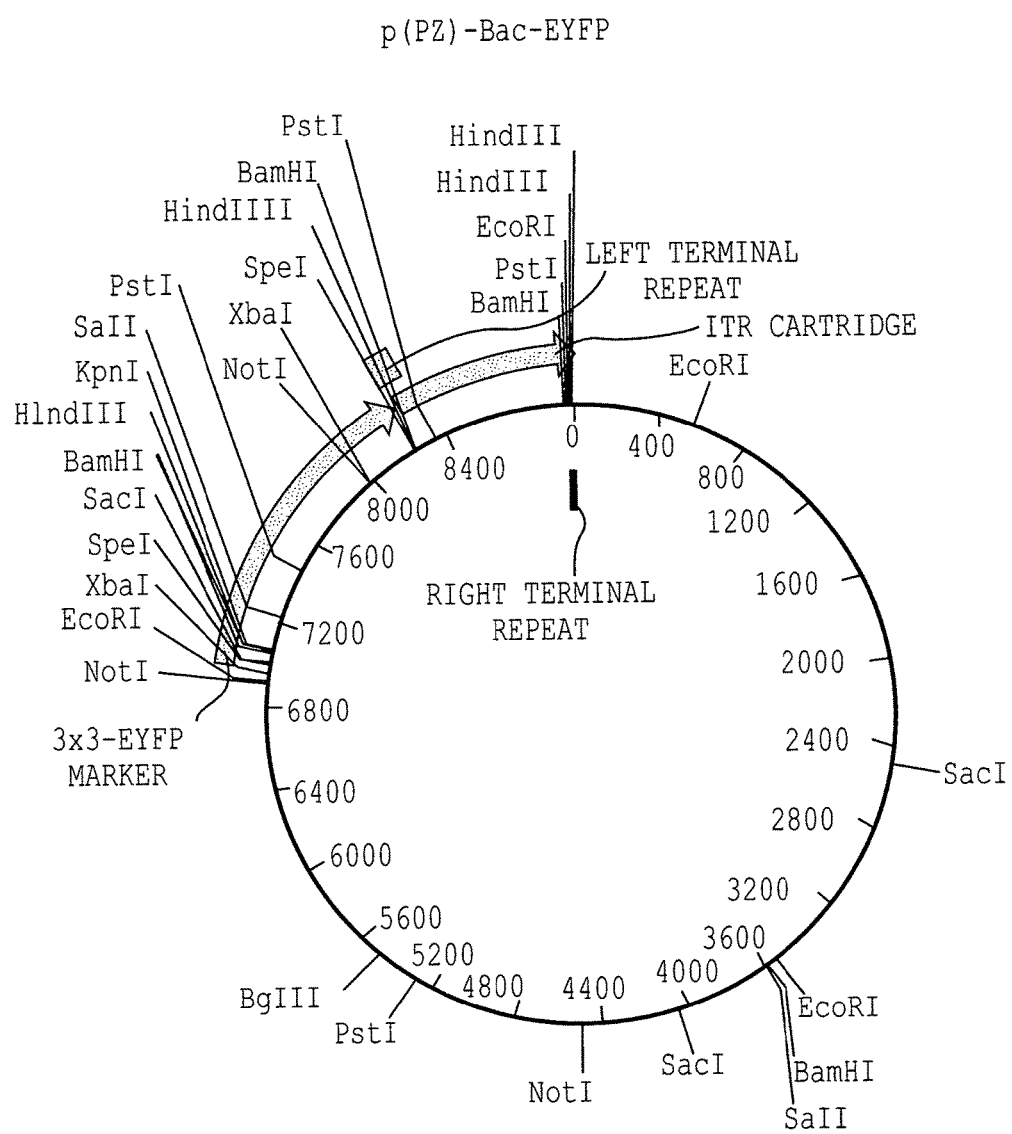
Figure 13A:
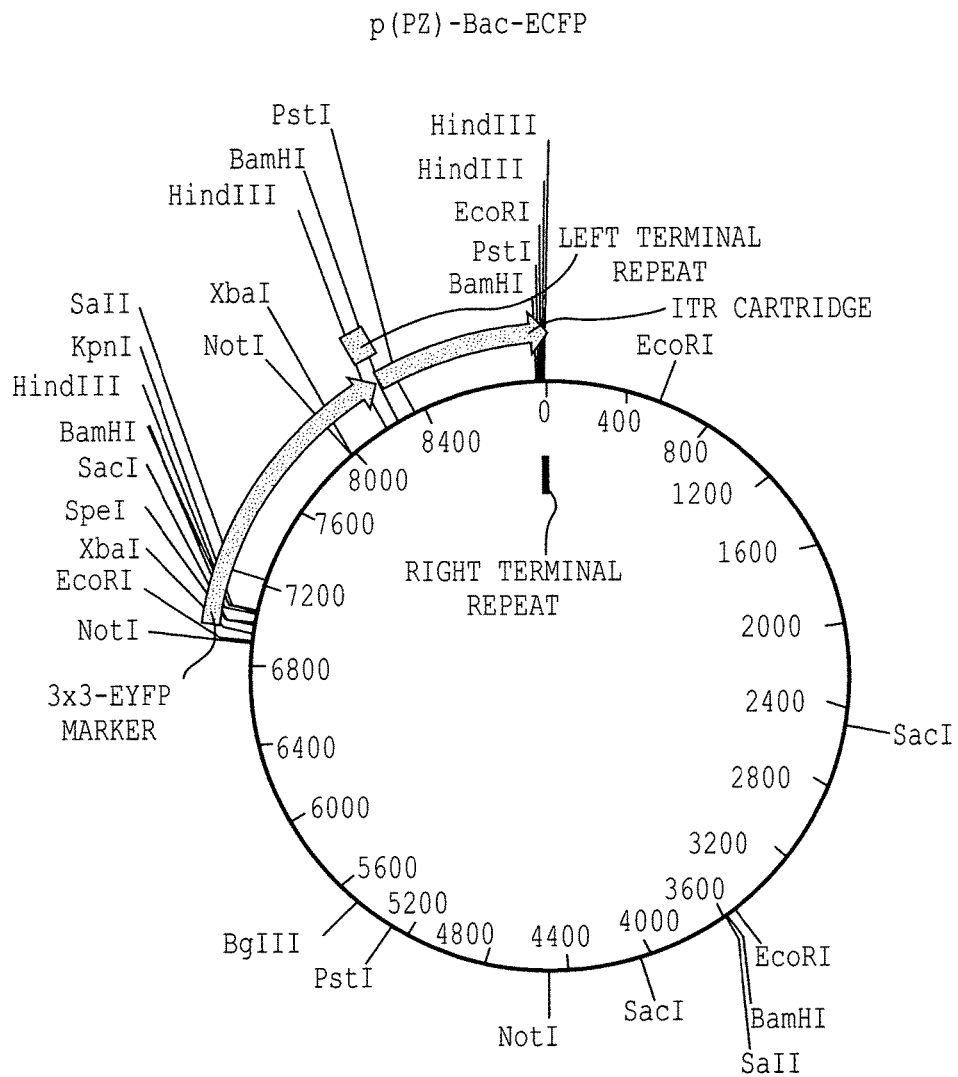
Figure 14A:
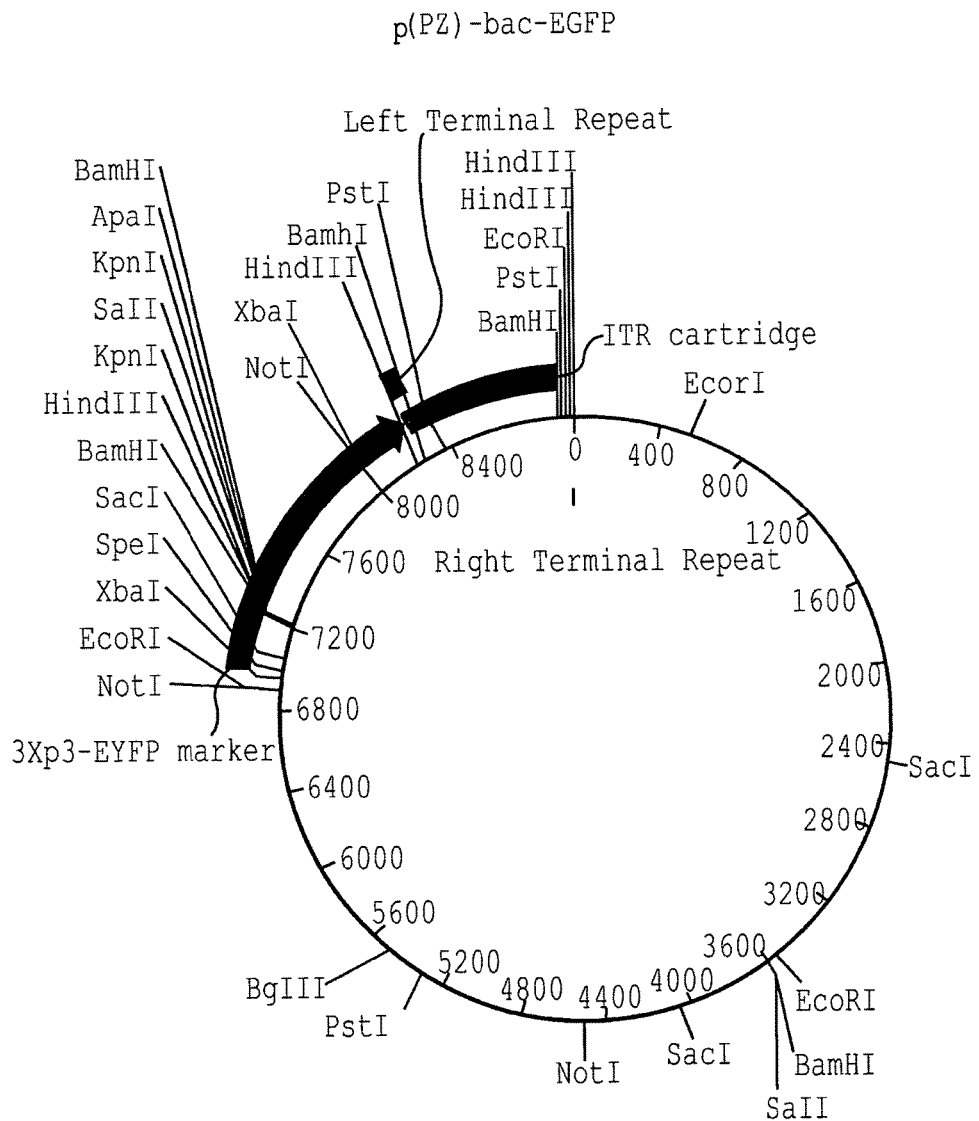
Figure 15A:
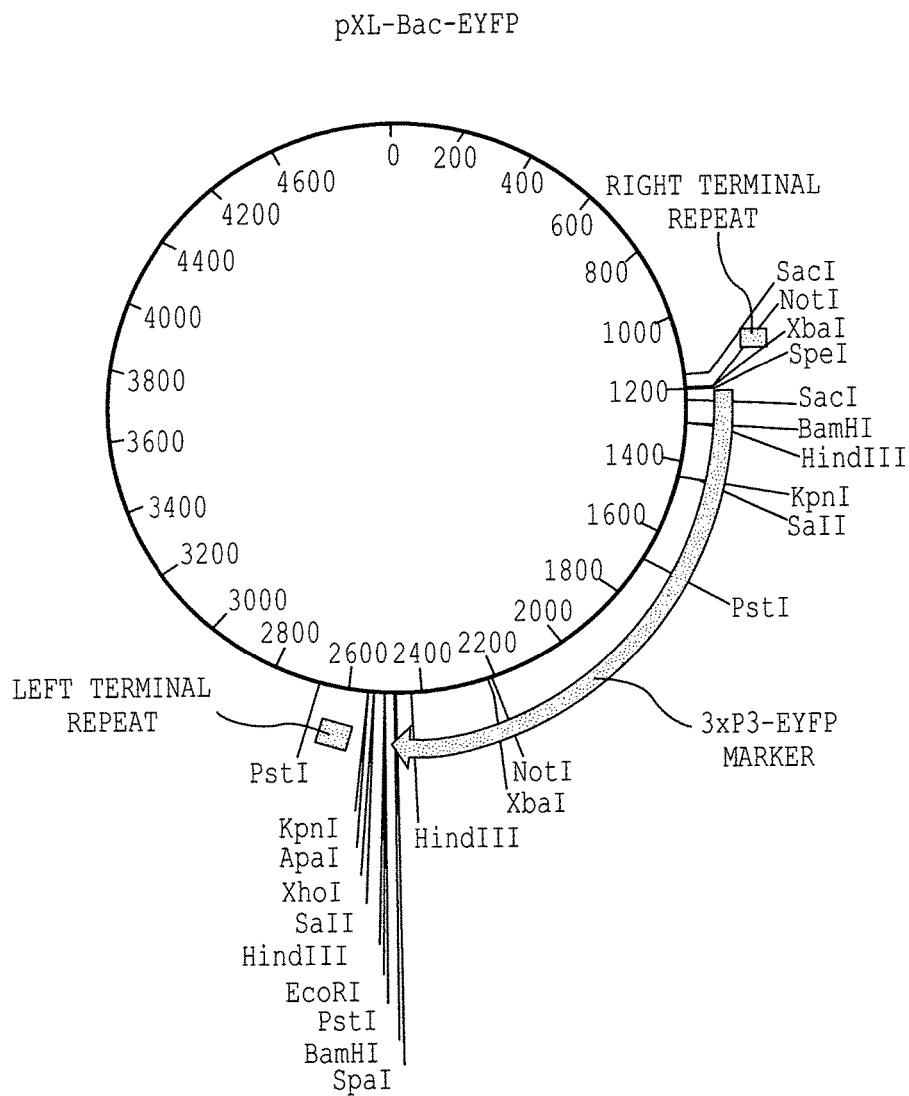
Figure 16A:
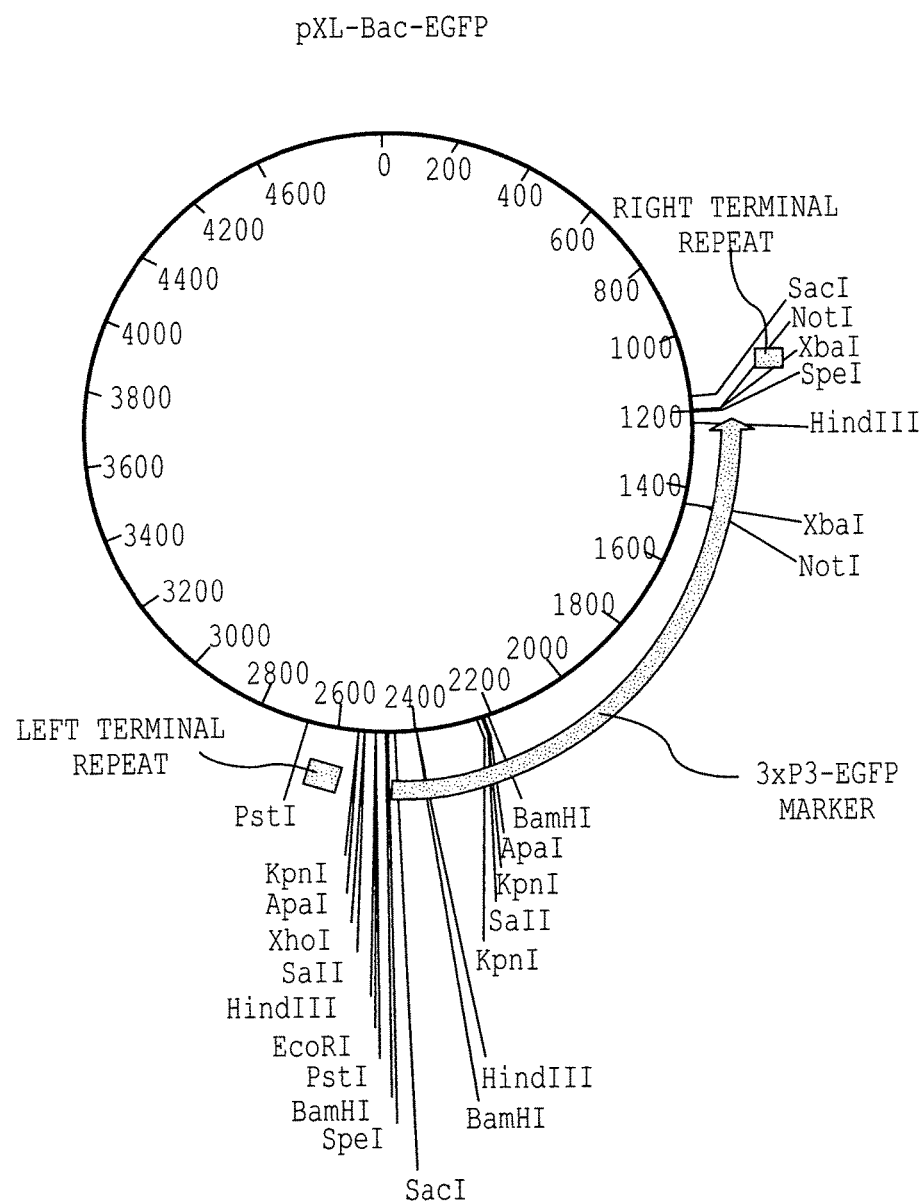
Figure 17A:
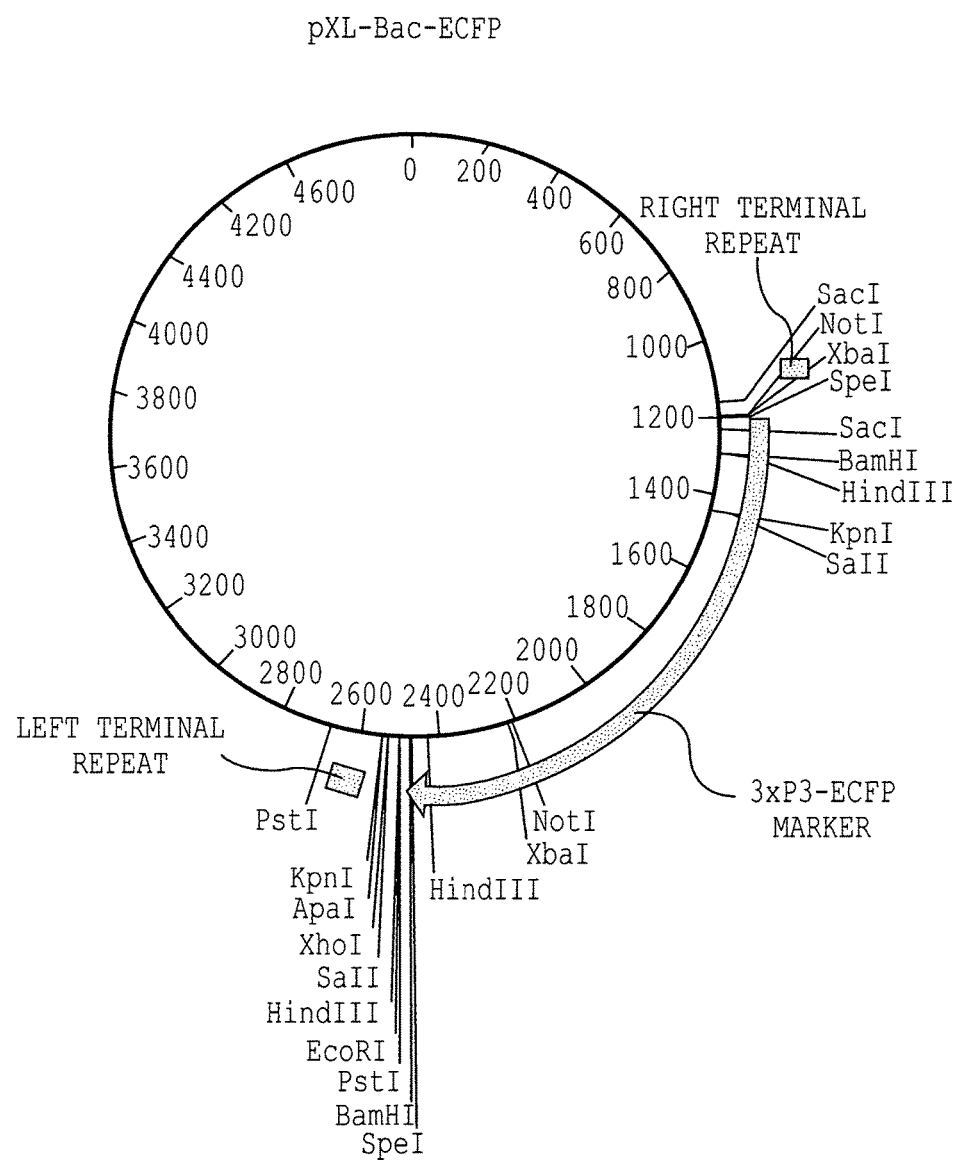
Figure 18A:
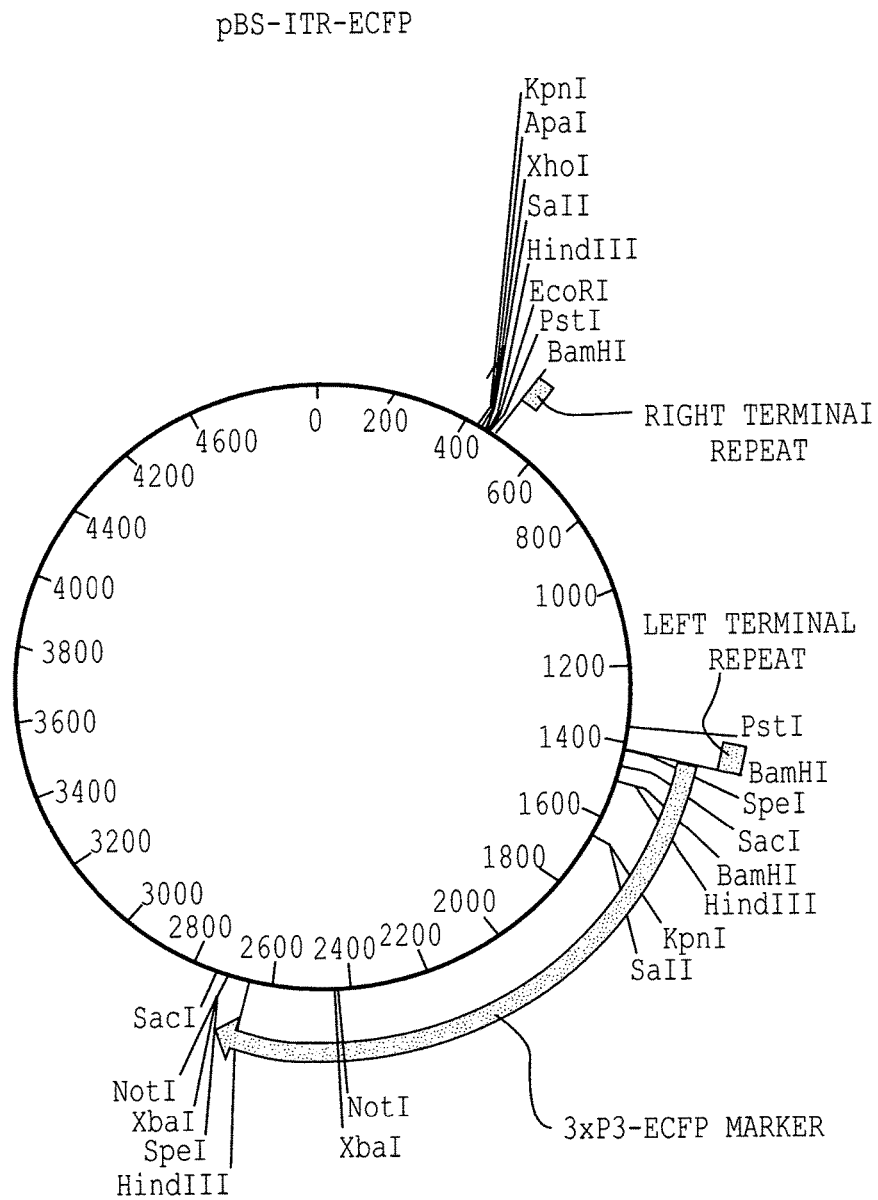
Figure 19A:
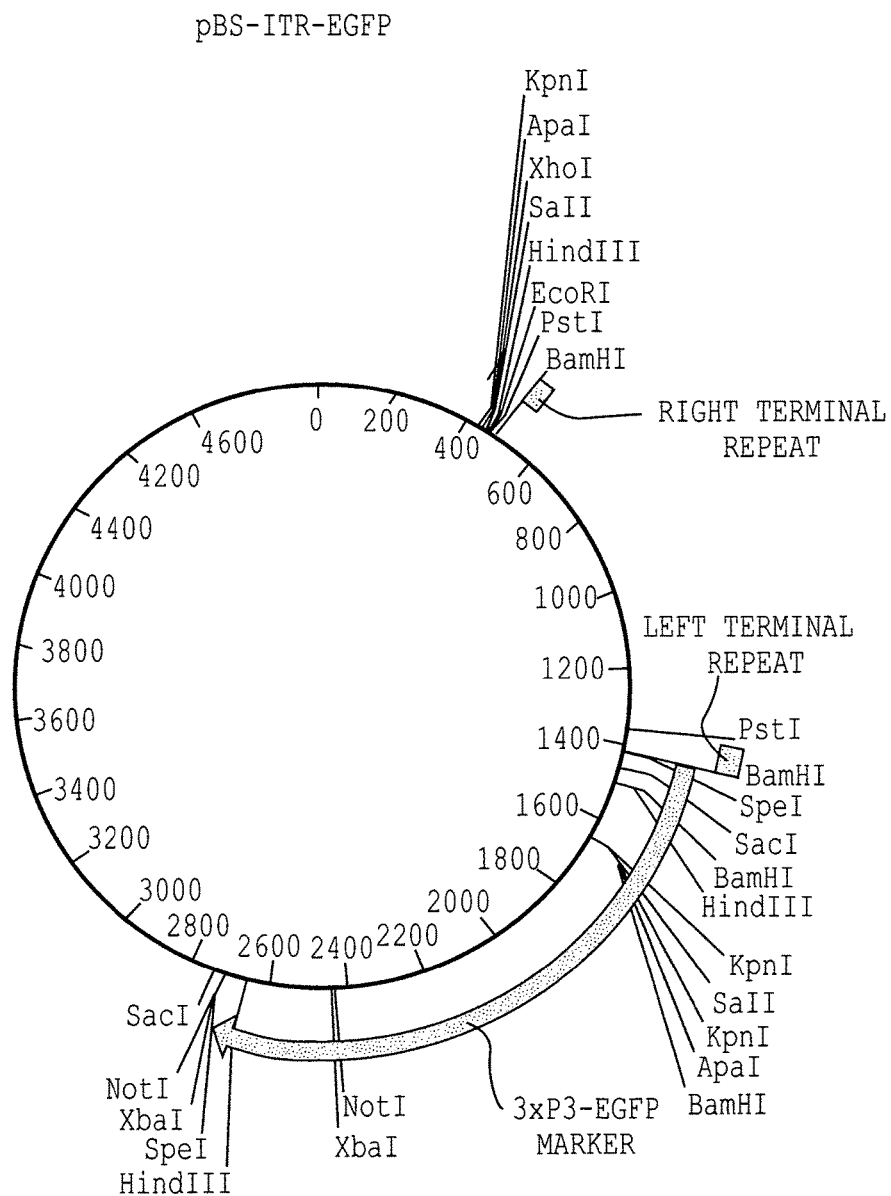
Figure 20A:
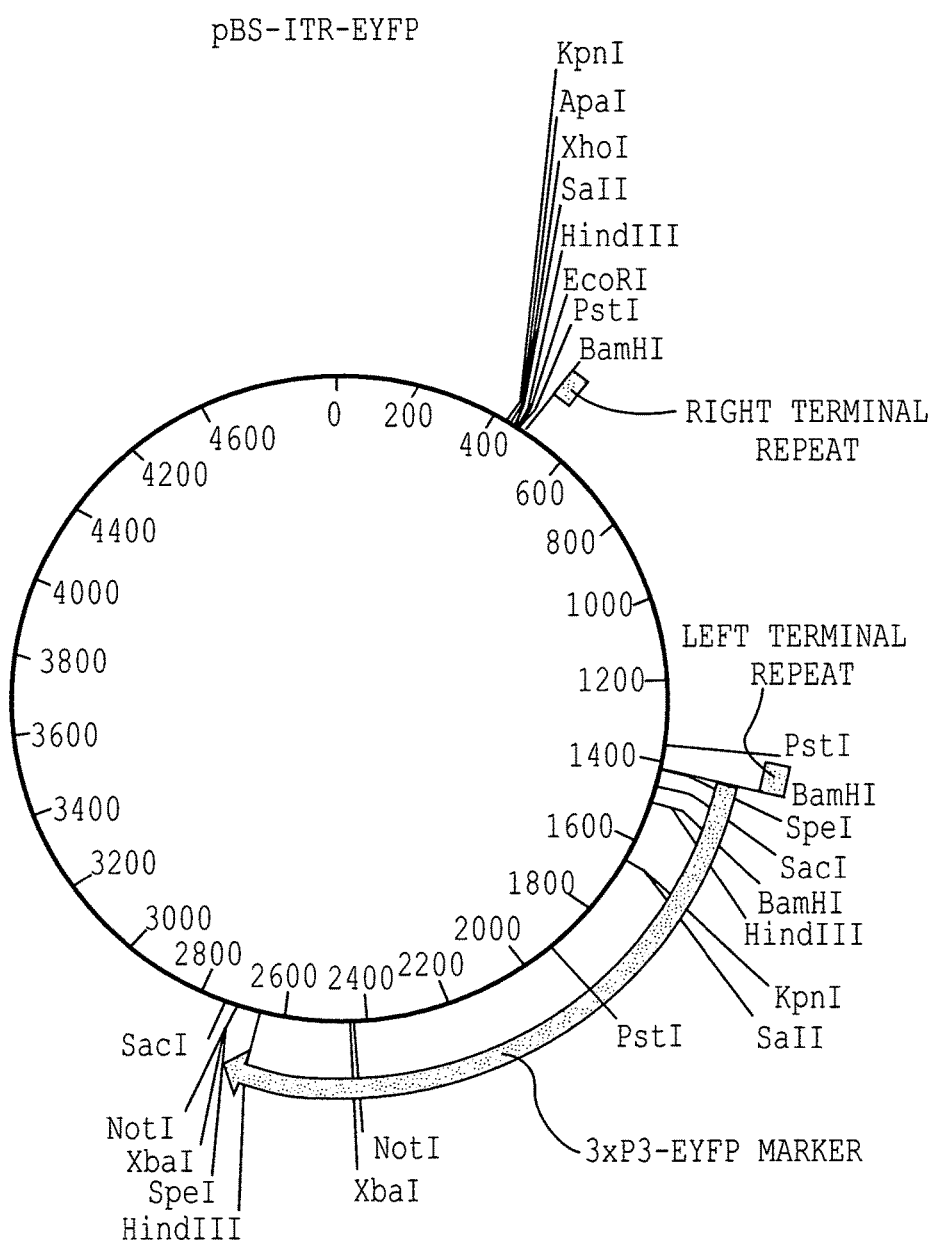
Figure 21A:
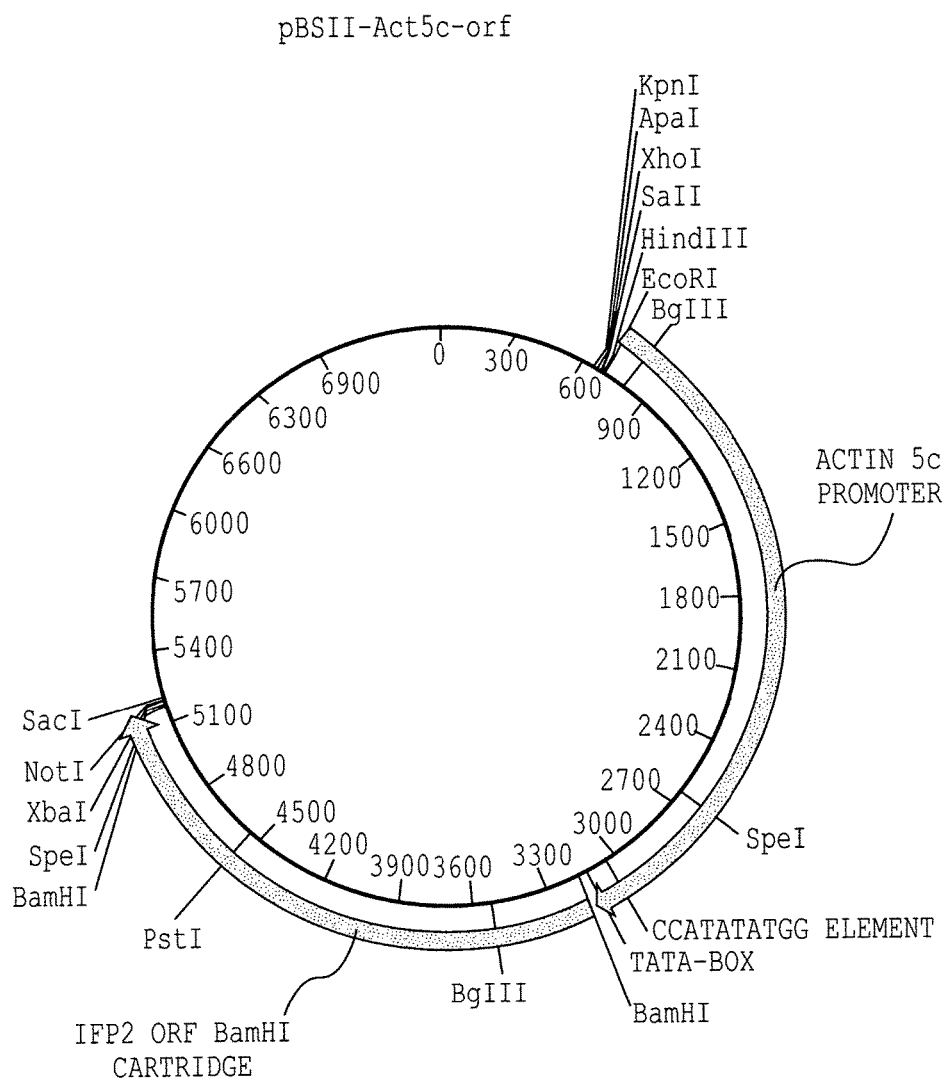

1) and pIAO-P/L-589 bp plasmid as a template, and cloned into the pCRII plasmid (Invitrogen) to form the pCRII-ITR plasmid; 10B is the nucleotide sequence of pCRII-ITR (SEQ ID NO: 46) and the amino acid sequence (SEQ ID NO: 47);

FIG. 11 is a plasmid map showing that the ITR BamHI cartridge was recovered from the pCRII-ITR plasmid and religated, then cut with BssHII and cloned into the BssHII sites of the pBSII plasmid (Stratagene) to form pBS-ITR (rev) plasmid. The Multiple Cloning Sites were PCR amplified as a BglII fragment from the pBSII plasmid and were cloned into the BamHI site to the pXL-Bac plasmid;

FIGS. 12 and 12B. 12 is a plasmid map showing that the P element enhancer trap plasmid pP {PZ} (from Dr. O'Tousa, Univ. of Notre Dame) was digested with Hind III then self-ligated to produce the p(PZ)-HindIII plasmid. The ITR cartridge was excised using Sal I and Not I (blunt-ended) from pCRII-ITR and then cloned into the blunt ended Hind III site to form p(PZ)-Bac. The 3xP3-EYFP was PCR amplified as an Spe I fragment from pBac[3xP3-EYFPafm] (Horn and Wimmer, 2000) and cloned into the Spe I site of p(PZ)-Bac plasmid to form the p(PZ)-Bac-EYFP plasmid; 12B is the nucleotide sequence (SEQ ID NO: 48) of p(PZ)-Bac-EYFP;

FIG. 13A-13B. 13A is a plasmid map showing that the P element enhancer trap plasmid pP{PZ} (from Dr. O'Tousa Univ. of Notre Dame) was digested with HindIII then self-ligated to produce the p(PZ−)-HindIII plasmid. The ITR cartridge was excised using Sal I and Not I (blunt ended) from pCRII-ITR and then cloned into the blunt ended Hind III site to form p(PZ)-Bac. The 3xP3-ECFP was PCR amplified as an Spe I fragment from pBac[3xP3-ECFPafm] (Horn and Wimmer, 2000) and cloned into the Spe I site of the p(PZ)-Bac plasmid to form the p(PZ)-Bac-ECFP plasmid; 13B is the nucleotide sequence (SEQ ID NO: 49) of p(PZ)-Bac-ECFP;

FIG. 14A-14B. 14A is a plasmid map showing that the P element enhancer trap plasmid pP{PZ} (from Dr. O'Tousa, Univ. of Notre Dame) was digested with Hind III then self-ligated to produce the p(PZ)-HindIII plasmid. The ITR cartridge was excised using Sal I and Not I (blunt ended) from pCRII-ITR and then cloned into the blunt ended HindIII site to form p(PZ)-Bac. The 3xP3-EGFP was PCR amplified as an Spe I fragment from pBac[3xP3-EGFPafm] (Horn and Wimmer, 2000) and cloned into the Spe I site of the p(PZ)-Bac plasmid to form the p(PZ)-Bac-EGFP plasmid; 14B is the nucleotide sequence (SEQ ID NO: 50) of p(PZ)-Bac-EGFP;

FIG. 15A-15B. 15A is a plasmid map showing that the 3xP3-EYFP gene was PCR amplified as an Spe I fragment from pBac [3xP3-EYFPafm] (Horn and Wimmer, 2000) and cloned into the Spe I site of the pXL-Bac plasmid to form the pXL-Bac-EYFP plasmid; 15B is the nucleotide sequence (SEQ ID NO: 51) of pXL-Bac-EYFP;

FIG. 16A 16B. 16A is a plasmid map showing that the 3xP3-EGFP gene was PGR amplified as an Spe I fragment from pBac [3xP3-EGFPafm] (Horn and Wimmer, 2000) and cloned into the Spe I site of the pXL-Bac plasmid to form the pXL-Bac-EGFP plasmid; 16B is the nucleotide sequence (SEQ ID NO: 52) of pXL-Bac-EGFP;

FIG. 17A-17B. 17A is a plasmid map showing that the 3xP3-ECFP gene was PCR amplified as an Spe I fragment from pBac [3xP3-ECFPafm] (Horn and Wimmer, 2000) and cloned into the Spe I site of the pXL-Bac plasmid to form the pXL-Bac-ECFP plasmid; 17B is the nucleotide sequence (SEQ ID NO: 53) of pXL-Bac-ECFP;

FIG. 18A-18B. 18A is a plasmid map showing that the 3xP3-ECFP was PCR amplified as an Spe I fragment from pBac[3xP3-ECFPafm] (Horn and Wimmer, 2000) and cloned into the Spe I site of the pBS-ITR plasmid to form the pBS-ITR-ECFP plasmid; 18B is the nucleotide sequence (SEQ ID NO: 54) of pBS-ITR-ECFP;

FIG. 19A-19B. 19A is a plasmid map showing that the 3xP3-EGFP was PCR amplified as an Spe I fragment from pBac[3xP3-EGFPafm] (Horn and Wimmer, 2000) and cloned into the Spe I site of the pBS-ITR plasmid to form the pBS-ITR-EGFP plasmid; 19B is the nucleotide sequence (SEQ ID NO: 55) of pBS-ITR-EGFP;

FIG. 20A-20B. 20A is a plasmid map showing that the 3xP3-EYFP was PCR amplified as an Spe I fragment from pBac[3xP3-EYFPafm] (Horn and Wimmer, 2000) and cloned into the Spe I site of the pBS-ITR plasmid to form the pBS-ITR-EYFP plasmid; 20B is the nucleotide sequence (SEQ ID NO: 56) of pBS-ITR-EYFP;

FIG. 21A-21B. 21A is a plasmid map showing that the Actin 5c promoter was cloned as a BamHI and Eco I fragment (bases 3046 to 3055 of SEQ ID NO: 67) from the pHAct5cEFGP plasmid (from Dr. Atkinson, UC Riverside) into the BamHI and EcoRI sites of the pBSII plasmid (Stratagene) to form the pBSII-Act5c-orf plasmid. The piggyBac ORF BamHI cartridge from pCaSpeR-hs-orf was then cloned into pBSII-Act5c plasmid under control of the Act5c promoter; 21B is the nucleotide sequence (SEQ ID NO: 67) of pBSII-Act5c-orf;

FIG. 22 is the nucleotide sequence (SEQ ID NO: 68) of pCaSpeR-hs-pBac;

FIG. 23 is a comparison of natural and optimized piggyBac nucleotide sequences (SEQ ID NOS: 69 and 70) wherein "optimizing" means using codons specific for insects;

FIG. 24A-24D. 24A shows the construction of plasmids developed in the present work. 24A shows a diagram of the pCaSpeR-hs-orf helper used for the transformation assays. The piggyBac cassette was cloned as a PCR product into the BamH I site of the pCaSpeR-hs adjacent to the hsp70 promoter. 24B shows a diagram of the p(PZ)-Bac-EYFP construct demonstrating the inefficiency of the ITR cartridge. (Li et al., 2001b) for transformation. A 7 kb Hind III fragment containing LacZ, hsp70 and Kan/ori sequences was excised from plasmid p(pz0 (Rubin and Spradling, 1983), and ligated to form a p(PZ)-7 kb intermediate plasmid. The ITR cartridge was excised from pBSII-ITR (Li et al., 2001b) using Not I and Sal I, blunt ended, and inserted into the blunt end Hind III site of the p(PZ)-7 kb plasmid. A 3xP3-EYFP Spe I fragment excised from pBac {3xP3-EYFPafm}(Hormn and Wimmer, 2000) was then inserted into the Xba I site to form p(PZ)-Bac-EYFP. 24C shows a diagram of the pBSII-ITR1.1k-ECFP minimal piggyBac vector constructed by PCR amplification from the pIAO-P/L 589 plasmid (Li et al., 2001b), which contains a minimum piggyBac cartridge with inverted 5' and 3' TRDs separated by a 589 bp λ DNA spacer sequence, and incorporate additional subterminal ID sequences necessary for efficient transformation. This construct is tagged by the addition of the 3xP3-ECFP marker gene excised as a SpeI fragment from the plasmid pBac {3xP3-ECFPafm} (Horn and Wimmer, 2000). 24D shows a diagram of the piggyBac minimal vector pXL-BacII-ECFP, constructed from the pBSII-ITR1.1k plasmid essentially as previously described (Li et al., 2001b), with the addition of the 3xP3-ECFP SpeI fragment from pBac {3xP3-ECFPafm}.

Figure 25:
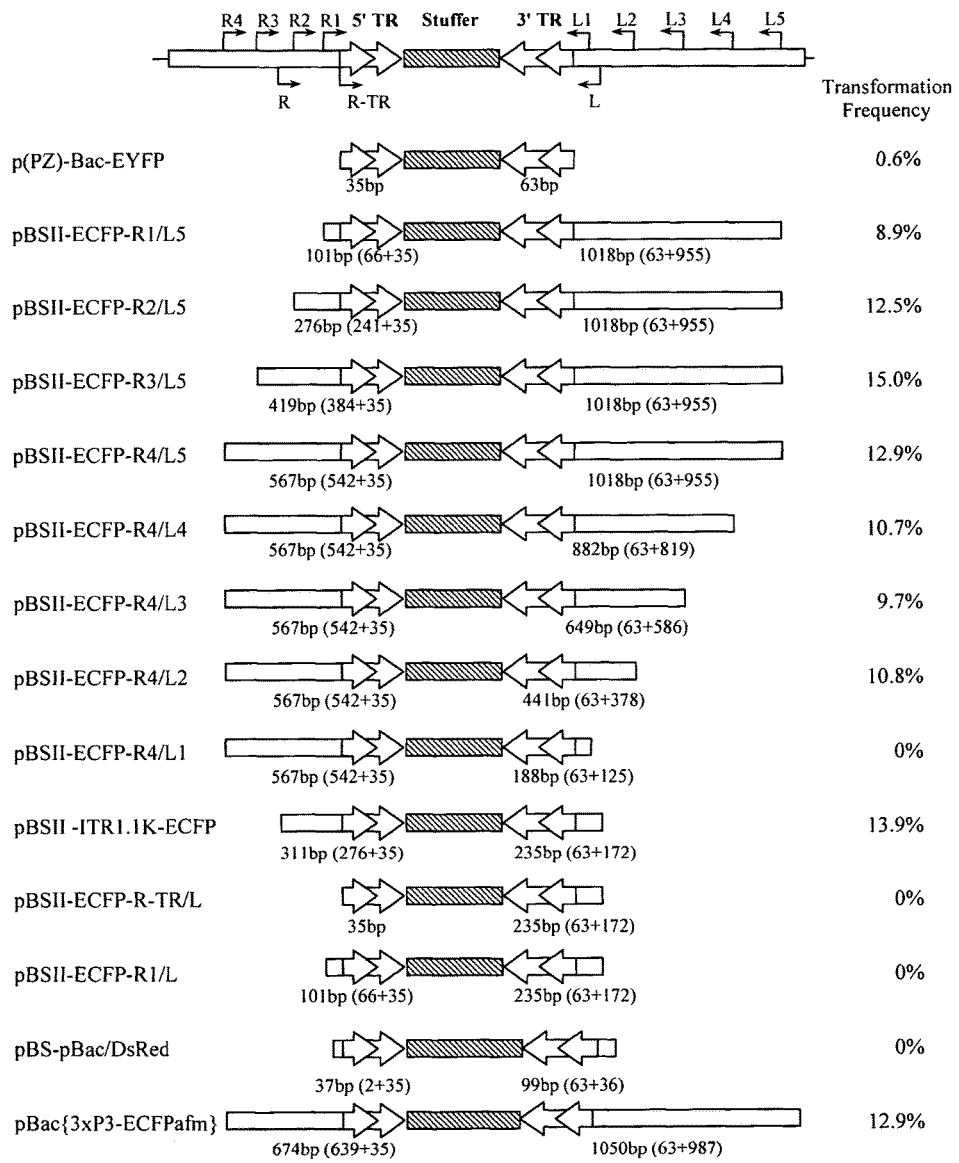

FIG. 25 shows a schematic illustration f TRD and adjacent ID regions present in plasmids and synthetic piggyBac internal deletion series constructs tested for transformation efficiency. The plasmids p(PZ)-Bac-EYFP and all pBSII- ECFP synthetic deletions are based on sequences amplified from the pIAO-P/L-589 construct of Li et al. (2001b). All plasmids have the 35 bp 5' TRD and 63 bp 3' TRD, and include variable lengths of 5' and 3' adjacent ID sequence. The relative transformation frequency for each plasmid is listed to the right for convenience.

FIG. 26A-26B shows a direct PGR analysis of transformed flies. 26A shows a diagram of a generalized synthetic deletion construct indication the position of primers and expected fragment. Three sets of PGR primers were used to verify to piggyBac insertion. The first primer set (IFP2_R1+ MF34) detects the 3' terminal region (115 bp), the second primer set (IFP2_L+MF34) detects the 3' terminal region (240 bp), and the third primer set (IFP2_R1+IFP2_L) detects the presence of the external spacer sequence (945 bp). 26B shows the direct PGR results, a.) the first primer set yields a 115 bp fragment in all transformed strains confirming the 5" terminal region. A less effectively amplified 115 bp fragment is also evident in the vv1118 strain, reflecting the probable presence of piggyBac-like sequences in the *D. melanogaster* genome, b.) The second primer set yields the expected 240 bp fragment in all transformed strains confirming the 3' terminal region, while this fragment is absent in the w'118 strain, c.) The external spacer primer set failed to amplify a sequence in any of the transformed strains or the control w1118.

FIG. 27A-27B shows Southern hybridization analysis of synthetic deletion plasmid transformed strains. Genomic DNAs from selected strain and the pBSII-ITR1.1k-ECFP plasmid control were digested with Hind III and hybridized to the pBSII-ITR1.1k-ECFP plasmid probe. 27A provides a map of the pBSII-ITR1.1k-ECFP plasmid showing the size of expected diagnostic fragments. 27B shows all transformed strains exhibit the two diagnostic bands (2.9 kb and 1.16 kb) and at least two additional bands reflecting the piggyBac terminal adjacent sequences at the site of integration. A weak 1.3 kb band was also observed in all strains that probably represent a piggyBac-like sequence in the w1118 genome. The reduced intensity of the two additional bands representing joining sequences between the piggyBac termini and adjacent genomic DNA in each of the transformed strains is likely due to weaker hybridization of the 200 to 300 bp of AT rich sequences of this region of the probe.

Figure 28:
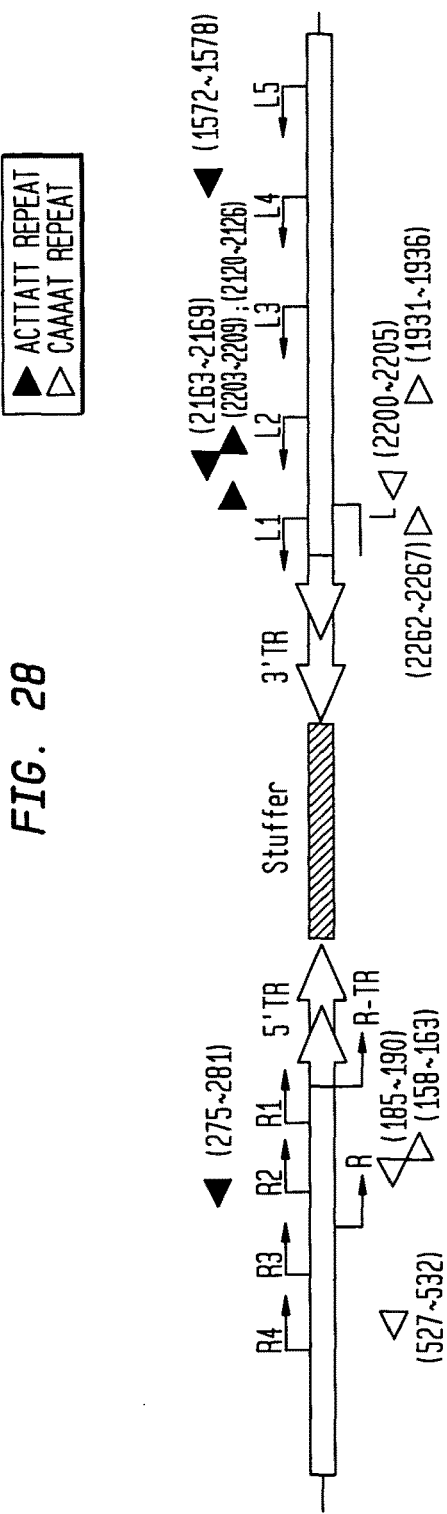

FIG. 28 shows a schematic illustration of the locations of the two short repeat sequence motifs identified in the TRD adjacent ID sequences of piggyBac Several of these repeat motifs are within regions between R and R1, or L and L2, which appear to be the critical regions based on the present transformation results. These repeats are also found in other positions of the piggyBac ID sequence.

FIG. 29A-29B show a Southern hybridization analysis of the single p(PZ)-Bac-EYFP transformant. Genomic DNA from the p(PZ)-Bac-EYFP strain and the $w^{1118}$ white-eye strain were digested with Sal I, with a SalI digest of the p(PZ) plasmid serving as control. The probe was PCR amplified from p(PZ)-Bac-EYFP using the primers 3xP3_for and M13_For. 29A shows a map of the p(PZ)-Bac-EYFP plasmid illustrating the position of Sal I sites, the region used as the probe, and expected size (3.6 kb) for the diagnostic hybridization fragment. 29B shows the two p(PZ)-Bac-EYFP transgenic sublines (lane 2 and 3) exhibit the diagnostic 3.6 kb band and two additional bands representing junction fragments containing genomic sequences and piggyBac ends at the single insertion site.

FIG. 30 shows an identified point mutation in the 3' internal repeat sequence. A point mutation was discovered in the 19 bp internal repeat sequence (IR) of the 3' TRD in all of the constructs derived from the pIAO-P/L 589 plasmid (Li et al., 2001b). This nucleotide substitution from C to A (bold and underlined) had no apparent effect on the transposition frequency of any of these constructs relative to the pBac{3xP3-EYFP} control plasmid (SEQ ID NOS 71 & 72 are disclosed respectively in order of appearance).

DETAILED DESCRIPTION

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "genetic construct" refers to any artificially assembled combination of DNA sequences.

For the purposes of the present invention, the term "helper construct" refers to any plasmid construction that generates the piggyBac transposase gene product upon transfection of cells or injection of embryos.

For the purposes of the present invention, the term "ID region" or "ID regions" relates to a nucleic acid sequence that is derived from the native piggyBac sequence.

For purposes of the present invention, the term, "long" or "longer" as it refers to the length of a 3' terminal region of a piggyBac nucleic acid sequence is defined as a sequence that includes 250 base pairs (bp) or more, 300 bp or more, 350 bp or more, 375 or more, or 400 bp or more.

For purposes of the present invention, term "native" refers to any sequence defined as or recognized to be functionally or otherwise homologous to a piggyBac nucleic acid sequence or amino acid sequence in any species, including but not limited to humans, zebra fish, mosquitoes, *Drosophila melanogaster*, invertebrate.

For the purposes of the present invention, the term "plasmid" refers to any self-replicating extrachromosomal circular DNA molecule capable of maintaining itself in bacteria.

For the purposes of the present invention, the term "spacer" refers to sequences, for example from about 3 bp to about 31 bp or more in length, separating the 5' and 3' (respectively) terminal repeat and internal repeat sequences of the piggyBac transposon.

For purposes of the present invention, the term "substantially homologous" is defined as a nucleic acid sequence that has or is able to elicit the same or substantially similar function activity of a native piggyBac sequence.

For the purposes of the present invention, the term "transgenic organism" refers to an organism that has been altered by the addition of foreign DNA sequences to its genome.

For the purposes of the present invention, the term "vector" refers to any plasmid containing piggyBac ends that is capable of moving foreign sequences into the genomes of a target organism or cell.

Description

The minimal sequence cartridges of the present invention facilitate transposition of DNA molecules of interest into cells, and production of transgenic organisms that include the transferred DNA molecule in some or all of their cells. A DNA molecule(s) is excised from a genetic (transformation) construct, and is transferred to a cell where it is inserted into the cell's genome. The DNA molecule is accompanied by regulatory elements sufficient to allow its expression in the host cell. "Cell" as used herein includes eukaryotic and prokaryotic cells. The genetic transposition construct includes a DNA molecule to be transferred flanked by a pair of transposon terminal inverted repeat nucleotide sequences from the piggyBac transposon. The DNA molecule to be transferred may be any molecule capable of being expressed in a host cell and/or transgenic organism. The method would also transfer cells not able to be expressed.

In the present invention, excision (Elick et al., 1996b) and interplasmid transposition assays (Lobo et al., 1999) were used to determine the relative importance of sequences internal to, or external to, the terminal repeat (TR) and internal repeat (IR) sequence configurations for movement of the piggyBac element.

It was found that progressive deletions within the internal sequence of the element have no noticeable effect on either excision or transposition capabilities. In contrast, deletion of the 3' IR eliminated excision of the element. Construction of vectors having only intact 5' and 3' repeat domains regenerates mobility of the plasmids when supplied with a helper vector expressing a transposase. These features permitted construction of a set of minimal vectors for use in transformation experiments.

The length of the intervening sequence between piggyBac termini in the donor plasmid also affects the piggyBac transposition frequency. In an embodiment of the present invention, a minimal distance of 55 nucleotide base pairs (bp) may be used between target sites and termini to provide for movement of the element. This suggests that the piggyBac transposase binds the termini simultaneously before any cleavage may occur, and/or that the formation of the transposition complex requires DNA bending between the two termini.

An aspect of this invention is that it allows the design of minimally sized genetic vectors that are functional for efficient insertion of genes into host genomes, in particular animal, plant, and insect genomes.

Useful Plasmids Created are:

A) A Transposition PiggyBac ITR Cartridge Plasmid: PCR amplifications and restriction endonuclease cleavage and ligation allowed insertion of a 702 bp fragment containing sequences for piggyBac mobility into any given plasmid of choice, converting the recipient plasmid into an operational transposable sequence capable of being mobilized into an animal genome using the piggyBac transposase gene or purified protein. The pCRII (Invitrogen) plasmid re-amplification using specified primers allows this ITR cartridge to be inserted into any plasmid.

B) Operational Transposable Vectors (pXO and pXL-Bac): Standard restriction endonuclease cleavage and ligation allows insertion of any gene of choice between the minimal sequences of the piggyBac transposon necessary for transposition into the genome of an animal. The total size of the resulting plasmid is preferably not larger than 10 kb.

According to an embodiment of the present invention, the inverted repeat configuration indicated as [TTAA/TR/IR . . . IR/31bp/TR/TTAA] may be utilized to obtain a piggyBac transposon. This observation was arrived at through structured deletion mutagenesis within the piggyBac transposon sequence and examining the properties of both excision and interplasmid transposition of the deleted product.

Additionally, according to an embodiment of the present invention, an insertion sequence between the target site on a plasmid having the terminal repeat configuration [IR/31bp/TR/TTAA . . . insertion sequence . . . TTAA/TR/IR] may be approximately 55 bp to achieve mobility.

For ease of manipulation, a cartridge having the configuration [IR/31bp/TR/TTAA . . . 589 . . . TTAA/TR/IR] which may be inserted within a plasmid, converting that plasmid into a functional piggyBac transposon, was constructed. The cartridge was cloned into the plasmid pCRII (Invitrogen). A cartridge is defined herein as a nucleic acid molecule of a specified construction (plasmid) that may be inserted into a vector.

A cartridge was derived from circularization of the construct A and cutting the construct A with BssHII to cleave at a unique BssHII site within the 589 bp spacer. This yielded a fragment BssHII . . . TTAA/TR/31b/IR/BamHI/IR/TR/TTAA . . . . BssHII. Construct B was derived from a pBSII (Stratagene) plasmid by BssHII deletion of the multiple cloning site (MCS). The linearized fragment was then inserted into the pBSII$^a$BssHII backbone. An MCS primer was synthesized and inserted in the BamHI site.

Construct A allows ease of construction of genetic vectors through use of a simple 702 bp cartridge that may be inserted into any existing plasmid to convert it immediately into a functional transposon.

Construct B allows ease of insertion of any genetic sequence into a plasmid having the minimal terminal sequence requirement for piggyBac mobility. The advantage of this construct is it provides a minimal backbone cloning vector for piggyBac transposon construction.

A kit is contemplated that would contain the two vector constructs along with the original p3E1.2, and/or a helper construct allowing constitutive production of piggyBac transposase in virtually any animal system. Promoter driven expression of the piggyBac transposase using either RSV LTR sequences CMV early promoter, AcMNPV/IE-1 promoter of poly-ubiquitin promoter, among others, is also contemplated.

Excision assays of plasmids containing progressive deletions of the piggyBac internal sequence revealed that the 5', and 3' IR, spacer, and TR configurations are sufficient for piggyBac movement when provided with a transposase in the trans position. Interplasmid transposition assays of plasmids having different sequence lengths between the target sites demonstrated a minimal 55 bp intervening sequence provides for satisfactory piggyBac transposition, whereas lengths less than 40 bp result in dramatic decreases in frequency of transpositions. These results suggest that the piggyBac transposase binds the termini simultaneously before cleavage, and/or that the formation of the transposition complex requires DNA bending between the two termini. Based on these results, a 702 bp cartridge having a minimum piggyBac 5' and 3' terminal region configuration and intervening sequence was constructed. The ability of this region to convert any existing plasmid into a non-autonomous piggyBac transposon was verified. A minimal piggyBac vector, pXL-Bac, that contains an internal multiple cloning site sequence between the terminal regions, was also constructed. These vectors facilitate manipulations of the piggyBac transposon for use in a wide variety of hosts.

The excision assay provides a rapid way to characterize essential sequences involved in piggyBac transposition. The p3E1.2-d-7 and p3E1.2-d-8 plasmids, which retain the entire 3' and 5' IR, spacer and TR sequences, exhibit precise excision. In contrast, the p3E1.2-d-9 plasmid that retains the entire 5' terminal region and only 36 bp of the 3' terminal domain, including the TR and a portion of the 31 bp spacer, does not excise at a detectable frequency. The requirement for an internal 3' IR sequence in the excision process suggests that the IR region might play an essential role in transposase recognition or cleavage of the target site.

An alternative explanation is that simply shortening the internal sequence may hinder the formation of a transposition complex, or the binding of transposase to two termini simultaneously. A similar result is observed with the IS5O elements for which the lengthening of Tn5 internal sequences increases the transposition frequency (Goryshin et al., 1994). However, insertion of a KOα fragment into the p3E1.2-d-9 at the SphI site did not improve the frequency of precise excision events recovered in the excision assay, suggesting that the length of the internal domain is less important than the presence of an intact IR sequence in excision of the piggyBac element.

The interplasmid transposition assays of pIAO-P/L series plasmids demonstrate that when the external sequence separating the terminal repeats is at least 55 bp, the transposition frequency is over $10^{-4}$, while reducing the length to less than 40 bp depresses the frequency of transposition. The inhibition of piggyBac transposition as terminal sequences are brought closer together, suggests that formation of a transposition complex likely precedes DNA cleavage or nicking, and the shorter distances between these termini do not allow proper bending of the sequences to permit formation of the complex, or result in steric hindrance of transposase binding at the termini.

These results also imply a necessity for transposase binding of both termini simultaneously before any cleavage (or nicking) may occur. If the simultaneous binding were not necessary, then the transposase could bind one terminal repeat, cleave it, and then bind the second to cleave, and transposition should occur with equivalent frequencies even with smaller intervening sequences.

Figure 10A:
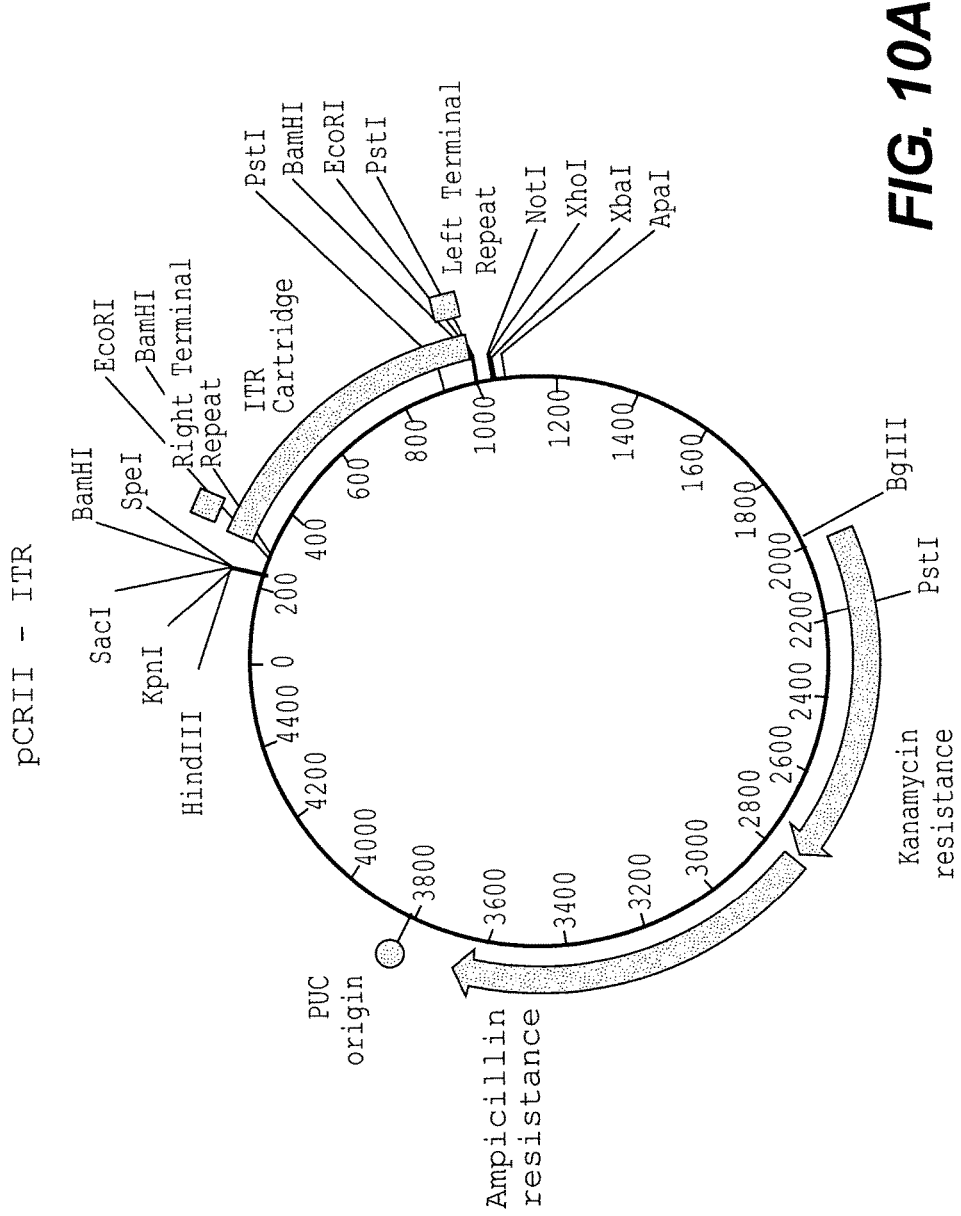

Interplasmid transposition assays using pCRII-ITR (FIG. 10) verify that the terminal configuration IR, spacer, TR are the minimum sequence requirements for efficient piggyBac transposition. The rest of the piggyBac internal sequence is not required if transposase is provided in trans configuration. With the ITR fragment, a minimum piggyBac vector may easily be constructed from any plasmid which reduces vector size and leaves maximum space for desired foreign genes.

Inserting the ITR fragment into pBlueScript II (Stratagene), converts the plasmid into a transposable element that moves with a frequency similar to the intact piggyBac element. This ITR cartridge facilitates the construction of piggyBac transformation vectors from existing plasmids. In addition, the co-integration of the Amp/ori sequences from the donor plasmid into the genome provides an easy way to locate the insertion site because these insertions may be recovered by restriction enzyme digestion, relegation, and transformation. The pXL-Bac (FIG. 11) minimum piggyBac vector replaces the internal sequence of the piggyBac transposon with a multiple cloning site. This plasmid allows any desired foreign genes or sequences to be easily inserted between piggyBac termini for movement in the presence of a helper plasmid. These constructs provide useful tools for the examination and use of piggyBac as a gene transfer vector in a wide variety of organisms.

The following Biological Deposits have been made on the following dates with a recognized International Depository Authority (IDA), the American Tissue Culture Collection (ATCC), at 10801 University Boulevard, Manassas, Va., 20110-2209, U.S.A., in compliance with the guidelines set forth in the Budapest Treaty on the International Recognition of the Deposit of Microorganisms for the Purposes of Patent Procedure. All restrictions on the availability to the public of the materials deposited will be irrevocably removed upon granting of a patent. The deposits will be maintained for a period of 30 years from the date of deposit or for a period of five years after the date of the most recent request of a sample or the enforceable life of the patent, whichever is the longest. If a culture becomes non-viable, it will be replaced with a viable culture of the same kind.

| Deposit Type | Deposit Name | Accession Number | Deposit Date |
|---|---|---|---|
| Plasmid | pXL-BACII-ECFP | ATCC Accession # PTA-7310 | Jan. 12, 2006 |
| Plasmid | pBSII-ITR1.1k-ECFP | ATCC Accession # PTA-7311 | Jan. 12, 2006 |
| Plasmid | pBSII-EXFP-$R_4/L_2$ | ATCC Accession # PTA-122185 | May 14, 2015 |
| Plasmid | pBSII-ECFP-$R_4/L_3$ | ATCC Accession # PTA-122183 | May 14, 2015 |
| Plasmid | pBSII-ECFP-$R_4/L_4$ | ATCC Accession # PTA-122184 | May 14, 2015 |

The invention may now be advantageously described by reference to the following representative examples. These examples are in no way to be interpreted to limit the scope and/or description of any embodiment or method of making or using the invention, and are provided solely for illustrative purposes and for satisfaction of providing the best mode of practicing the invention.

EXAMPLES

Example 1—Excision Assay of p3E1.2 Internal Deletion Series in *T. ni*

The analysis was begun using three plasmids having the most extensive internal deletions, p3E1.2-d-9, p3E1.2-d-8 and p3E1.2-d-7. Sequencing of these three plasmids revealed that p3E1.2-d-8 and p3E1.2-d-7 retained 163 bp and 303 bp of the 3' terminal region, respectively, including the IR, 31 bp spacer, and TR sequence. The p3E1.2-d-9 deletion plasmid retained only 36 bp of the 3' terminal domain, including the 3' TTAA target site, 3' TR and a portion of the 31 bp spacer, but lacked the 3' IR sequence.

Embryos of *T. ni* were injected with combinations of each of the p3E1.2 deletion plasmids and the phspBac helper plasmid. Loss of piggyBac sequences from the deletion series plasmids renders the plasmids resistant to BsiWI and SphI digestion. Transformation of Hirt extract DNAs digested with BsiWI and SphI were compared with transformations employing equal amounts of uncut DNA as a control to determine the frequency of excision. Precise excision events were initially identified by a quick size screen for the characteristic 3.5 kb plasmid in recovered colonies, and these plasmids were then sequenced to confirm the precise excision events.

Figure 1:
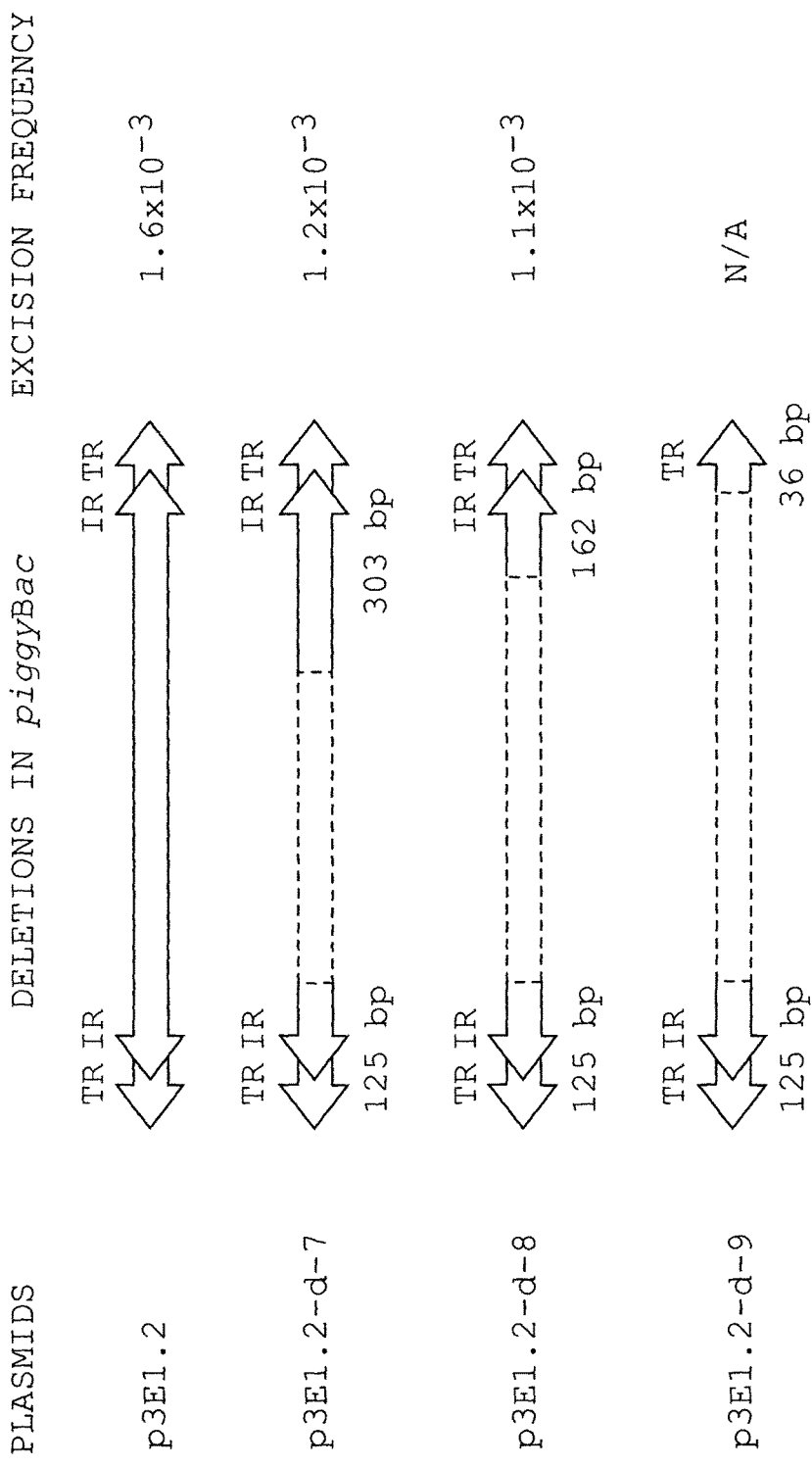
FIG. 1 shows a p3E1.2 deletion series of plasmids and excision assay results; the p3E1.2 plasmid was used to make progressive deletions using the restriction endonuclease ExoIII; three of the maximum deletion plasmids, p3E1.2-d-7, p3E1.2-d-8 and p3E1.2-d-9, were used to perform excision assays in *T. ni* embryos; p3E1.2d-7 and p3E1.2-d-8 plasmids retained the complete 3' terminal repeat configurations and were characterized by a similar excision frequency as the intact p3E1.2 plasmid; however, p3E1.2-d-9 did not yield any excision events, and sequencing results show that its 3' IR and part of the 31 bp spacer sequence are deleted.

A quick size screen method is used to quickly identify the plasmids with changed size directly from colonies (Sekar, 1987). Colonies at least 1 mm in diameter are picked up with pipette tips and resuspended in 10 ml protoplasting buffer (30 mM Tris-HCl pH 8.0, 50 mM NaCl, 20% Sucrose 5 mM EDTA, 100 mg/ml RNase, 100 mg/ml Lysozyme) in the Lux 60 well mini culture plate. A 0.9% agarose gel containing ethidium bromide is preloaded with 4.5 ml lysis solution (80 mM Tris, 0.5% Sucrose, 0.04% Bromophenol Blue, 2% SDS, 2.5 mM EDTA) per well. The bacterial suspension is then loaded into the wells and the gel electrophoresed. Two kinds of markers are needed to distinguish the plasmids with changed size. One is the colony from the control plate or the original plasmid, another is a molecular weight marker. The plasmids with a difference of 500 bp or greater in size are easily distinguished. Both the p3E1.2-d-8 and p3E1.2-d-7 yielded precise excision events at about the same relative frequency, while no excision events were recovered with the maximum deletion plasmid p3E1.2-d-9 (FIG. 1).

Figure 4:
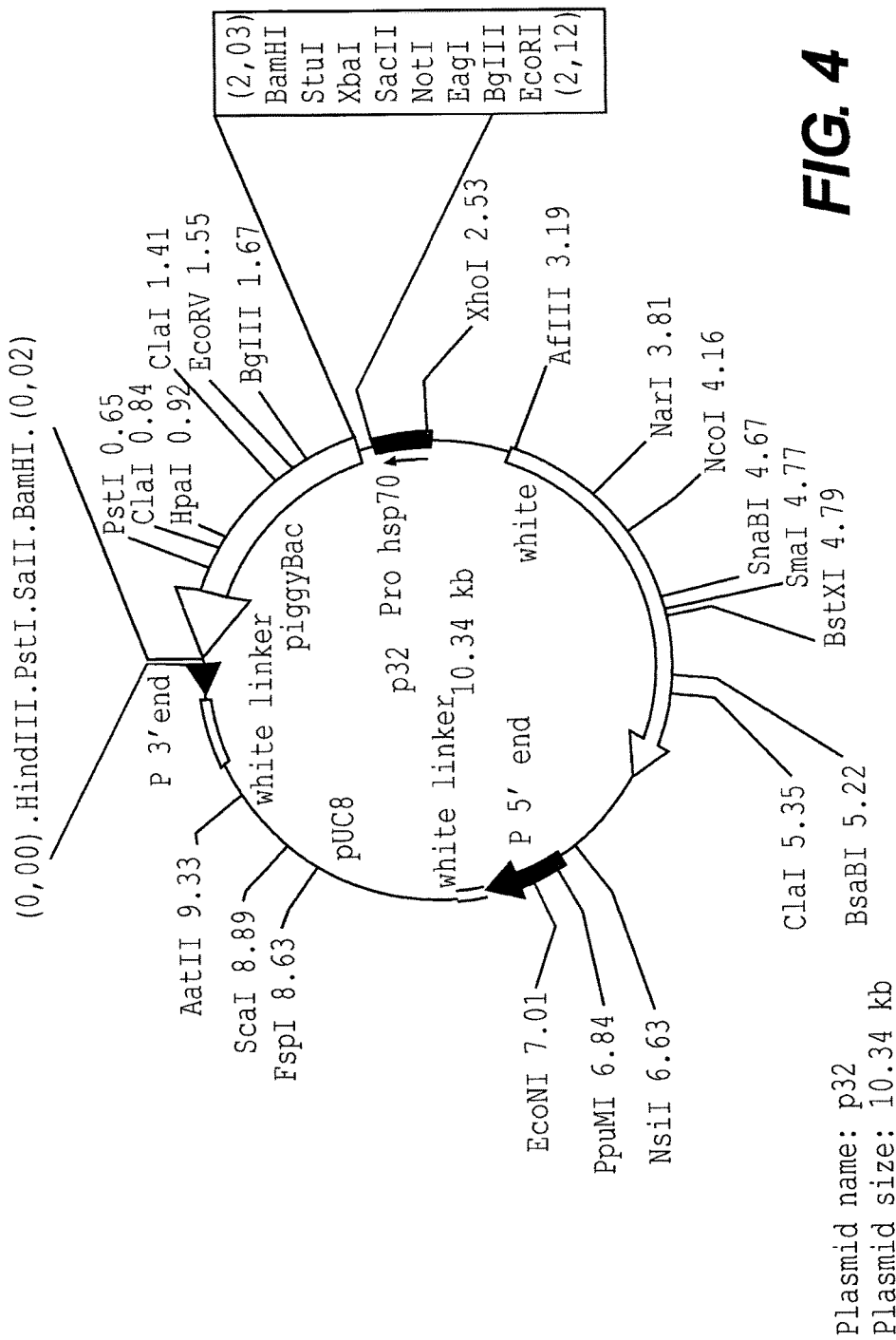
FIG. 4 is a restriction map of plasmid pCaSpeR-hs-orf (p32), containing a 2016 bp PCR BamHI fragment containing piggyBac transposase and its terminator, cloned into BamHI sites of pCaSpeR-hs.
Figure 5A:
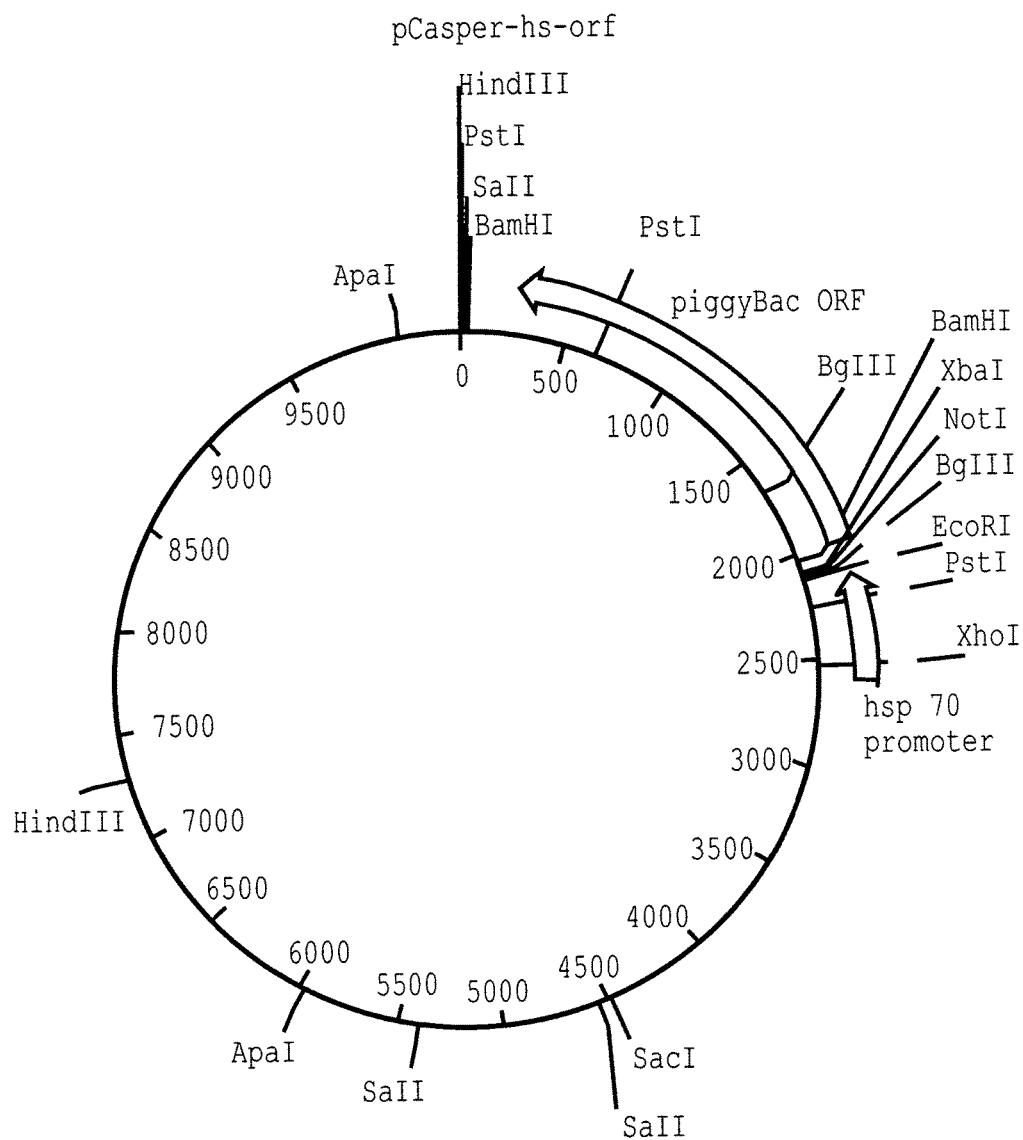

Example 2—Minimal Distance Required Between Termini for Movement of a PiggyBac Transposon Construct The interplasmid transposition assay was carried out essentially as previously described by Lobo et al. (1999), Thibault et al. (1999) and Sarkar et al. (1997a). Embryos were injected with a combination of 3 plasmids. The donor plasmid, pB(KOa), carried a piggyBac element marked with the kanamycin resistance gene, ColE1 origin of replication, and the lacZ gene. The transposase providing helper plasmid, pCaSpeR-pB-orf, expressed the full length of the piggyBac ORF under the control of the D. melanogaster hsp70 promoter. The target B. subtilis plasmid, pGDV1, is incapable of replication in E. coli, and contains the chloramphenicol resistance gene. Upon transposition of the genetically tagged piggyBac element from pB(KOa) into the target plasmid pGDV1 with the help of the transposase provided by the helper pCaSpeR-pB-orf that expresses the piggyBac transposase protein from a minimal hsp70 promoter (see FIG. 4), only the interplasmid transposition product would be able to replicate in E. coli and produce blue colonies on LB/kan/cam/X-gal plates. Embryos were injected with a mixture of the transposase-providing helper plasmid, phsp-Bac, one of the pIAO-P/L series plasmids as the donor, and the pGDV1 target plasmid. Transposition of the tagged piggyBac element from any of the pIAO-P/L plasmids into the target plasmid pGDV1 allows the recipient pGDV1 to replicate in E. coli and produces blue colonies on LB/Amp/Cam/X-gal plates.

A total of 10 blue colonies were randomly picked from each transformation and prepared for sequencing analysis. Initial sequence analysis of the terminal repeat junction showed that all of the sequenced clones had the distinctive duplication of a TTAA tetranucleotide target site, a characteristic feature of piggyBac transposition. A random set of those clones for which the 5' terminus had been sequenced were also examined at their 3' terminus to confirm the duplication of the TTAA site at both ends. The accumulated results confirmed transposon insertion at 12 of the 21 possible TTAA target sites in the pGDV1 plasmid, all of which were previously identified as insertion sites in Lepidopteran assays by Lobo et al. (1999) and Thibault et al. (1999).

Figure 2B:
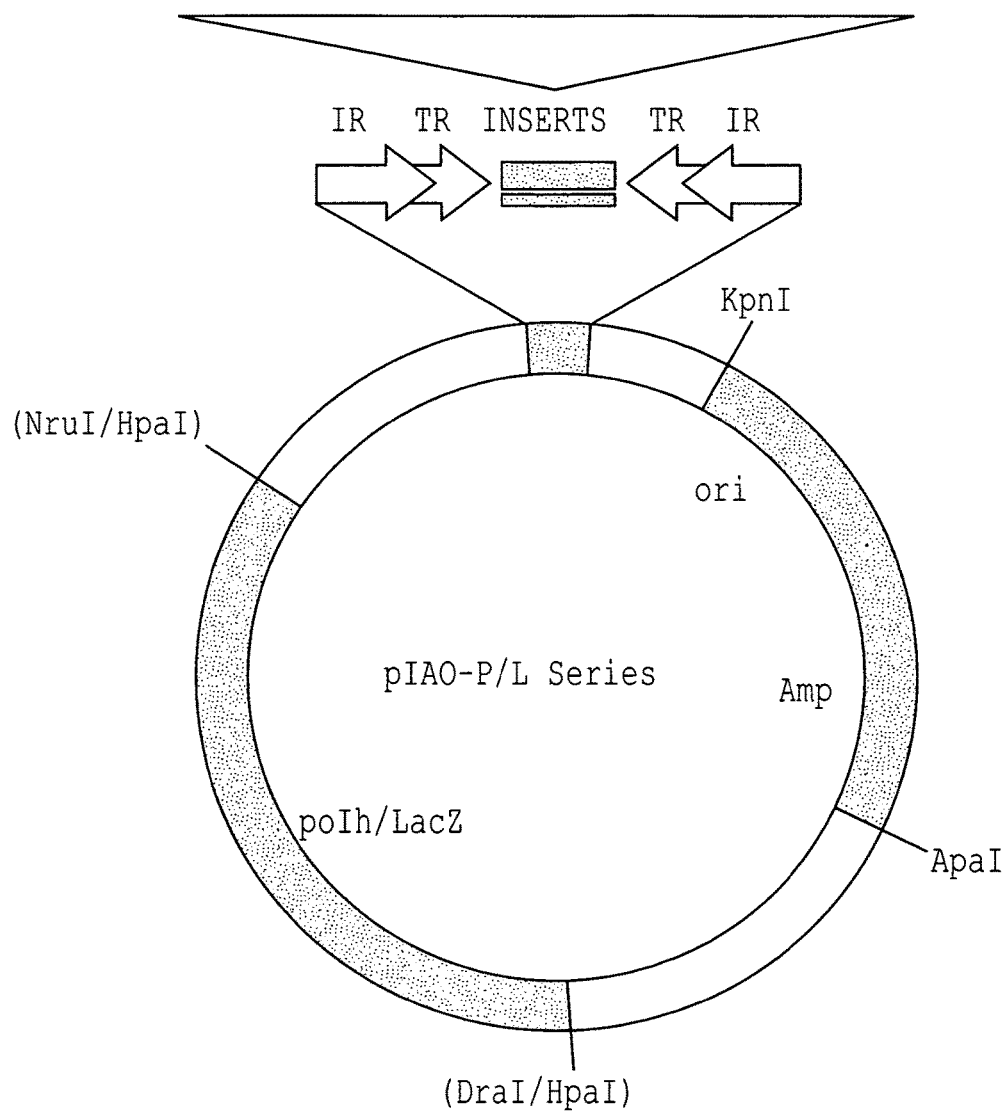
Figure 2(C1):
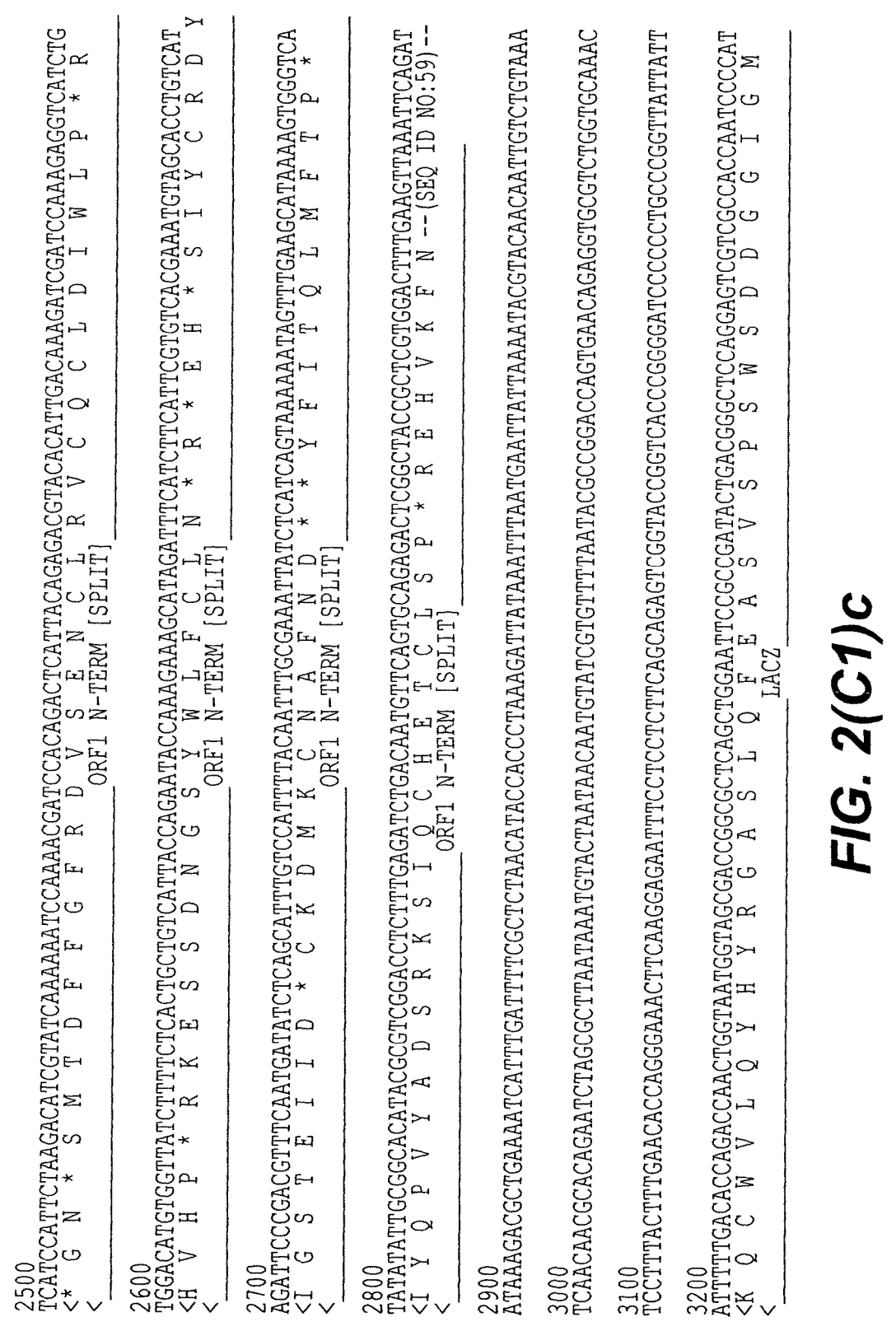
Figure 2(C2):
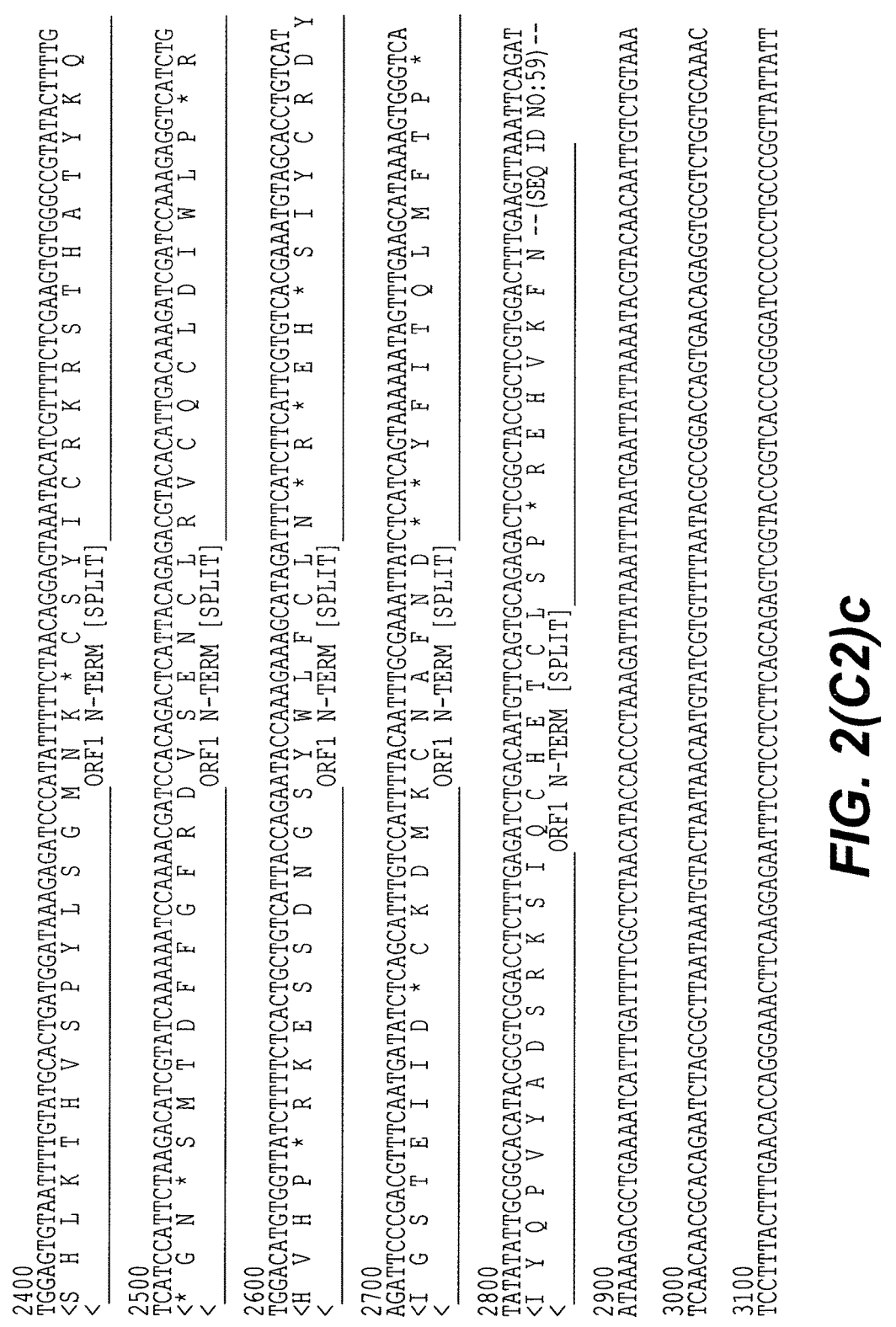

The relative frequency at which a given pIAO-P/L series plasmid was able to undergo transposition into the target plasmid correlated with the sizes of the intervening sequence between the termini. With intervening sequences greater than 55 bp, the transposition frequency was over $1.2 \times 10^{-4}$, which is consistent with the frequency obtained in previous assays with the p3E1.2 derived vectors by Lobo et al. (1999). If the length of the intervening sequence was reduced to 40 bp or less, the frequency of transposition began to decrease dramatically (FIG. 2).

Example 3—Interplasmid Transposition Assay of pCRII-ITR and pBSII-ITR Plasmids

According to an embodiment of the present invention, the excision assay described herein shows that a minimum of 163 bp of the 3' terminal region and 125 bp of the 5' terminal region (from the restriction site SacI to the end of the element) may be used for excision, while the pIAO-P/L constructs showed that a minimal distance of 55 bp between termini may be utilized to effect movement. These data suggested that the inclusion of intact left and right terminal and internal repeats and spacer domains would be sufficient for transposition.

The pCRII-ITR plasmid was constructed following PCR of the terminal domains from pIAO-P/L-589 using a single IR specific primer. A second construct pCRII-JFO3/04 was also prepared using two primers that annealed to the piggyBac 5' and 3' internal domains respectively, in case repeat proximate sequences were required.

The interplasmid transposition assay was performed in T. ni embryos and the plasmids were recovered using LB/Kan/Cam plates (Sambrook et al., 1989) with the controls plated on LB/Amp plates. A total of 10 randomly picked colonies were sequenced, and all were confirmed as resulting from transposition events, having the characteristic tetranucleotide TTAA duplication at the insertion sites. These insertion sites in pGDV1 were among the same previously described (Lobo et al., 1999 and Thibault et al., 1999). The sequencing results also confirmed that all 10 transposition events retained the expected terminal domain configurations. The frequency of transposition events was estimated at $2 \times 10^{-4}$, a similar frequency to that obtained with non-mutagenized constructs for this species (Lobo et al., 1999).

Figure 3A:
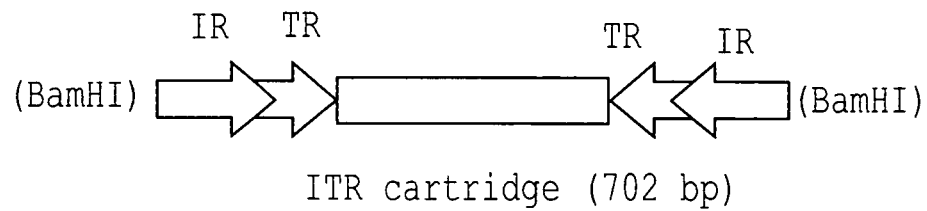
Figure 3B:
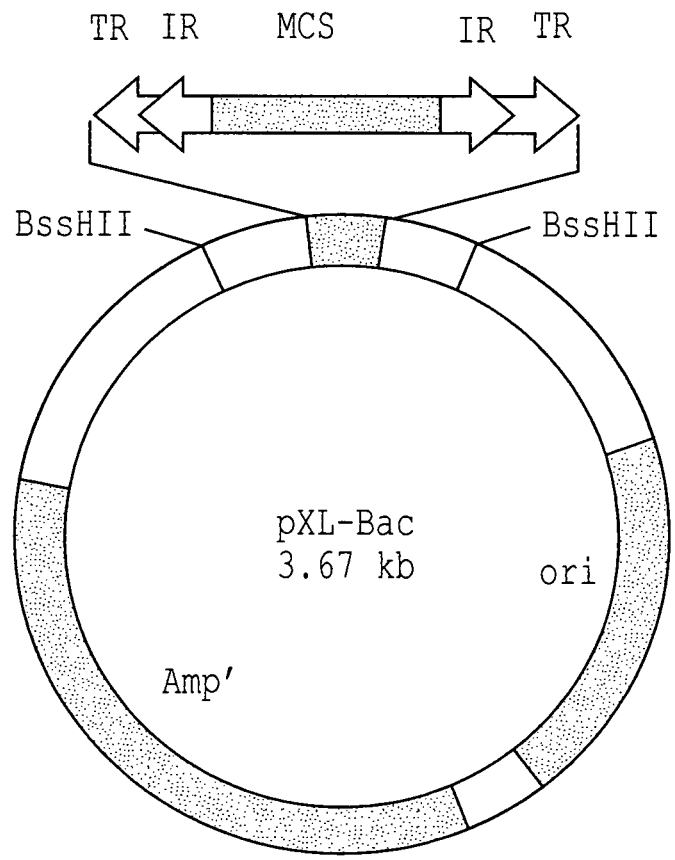

Independent verification that the 702 bp PCR cloned fragment (ITR cartridge, FIG. 3(C1)) may be used as a cartridge to generate transpositionally competent plasmids was obtained by excising the BamHI fragment from pCRII-ITR, and ligating it into the pBlueScript II (Stratagene) plasmid to construct pBSII-ITR. Frequencies similar to those for the pCRII-ITR construct in the interplasmid transposition assay, were obtained.

Example 4—Construction of Minimum PiggyBac Vector pXL-Bac

A new piggyBac minimum vector pXL-Bac (FIG. 3(C2)) was also constructed by combining the 702 bp BamHI ITR fragment with the pBlueScript II BamHI fragment and inserting a PCR amplified pBSII multiple cloning site (MCS) between the terminal repeats. The pXL-Bac vector was tested by inserting an XbaI fragment from πKOα (obtained from A, Sarkar, University of Notre Dame), containing the Kanamycin resistance gene, E. coli replication origin, and Lac a-peptide, into the MCS of pXL-Bac to form pXL-Bac-KOa. Interplasmid transposition assays yielded a frequency of over $10^{-4}$ for transposition of the modified ITR sequence, a similar level as observed for the intact piggyBac element.

Example 5—Derivative Vectors of pXL-Bac

Using the pXL-Bac minimal vector, several derivative vectors may be constructed containing marker genes for detection of successful transformations. In one example, the vectors pXL-Bac-EYFP, pXL-Bac-EGFP, and pXL-Bac-ECFP (FIGS. 15-17) were assembled to contain the 3XP3 promoter driven fluorescent protein genes of Horn and Wimmer (2000) by PCR amplifying these sequences from their respective piggyBac vectors using the primers E*FP-for (5' ACGACTAGTGTTCCCACAATGGTTAATTCG 3') (SEQ ID NO: 2) and E*FP-rev (5' ACGACTAGTGCCGTACGCGTATCGATAAGC 3') (SEQ ID NO: 3) each terminating in an SpeI restriction endonuclease site, and inserting these fragments into the SpeI digested pXL-Bac vector at the unique SpeI site of the multiple cloning site. Vectors constructed in this fashion allow detection of successful transformation by the pXL-Bac vector and may be further modified to include a separate gene of choice and suitable promoter adjacent to the marker gene in the multiple cloning site.

Example 6—Derivative Vectors of pCRII-ITR or pBSII-ITR

Similar modifications may be made to either the pCRII-ITR or the companion vector, pBSII-ITR, by inserting a marker gene into the plasmid adjacent to the ITR cartridge of these plasmids. In one example, the plasmids pBSII-ITR-ECFP, pBSII-ITR-EGFP, and pBSII-ITR-EYFP (FIGS. 18-20) were constructed using the strategy described in Example 5 to PRC amplify an SpeI fragment containing the marker genes from the Horn and Wimmer (2000) piggyBac vectors and insert them into the unique SpeI site of the pBSII-ITR plasmid.

Example 7—Facilitating Expression of the Transposase

Expression of the transposase is important in gaining movement of any of the vectors described herein. To facilitate expression of the transposase, a BamHI cartridge containing only the piggyBac open reading frame sequences was PCR amplified from the piggyBac transposon clone p3E1.2 using the primers BamH1E-for 1 (5' GCTTGA-TAAGAAGAG 3') (SEQ ID NO: 4) and BamH1E-rev 1 (5' GCATGTTGCTTGCTATT 3') (SEQ ID NO: 5). This cartridge was then cloned into the pCaSpeR-hs vector at a unique BamHI site downstream of the *Drosophila* heat shock promoter (pCaSpeR-hs-orf) to effect heat shock induced expression of the piggyBac transposase following co-injection with any piggyBac vector.

Example 8—In Vitro Expression of mRNA of PiggyBac Transposase

Figure 6A:
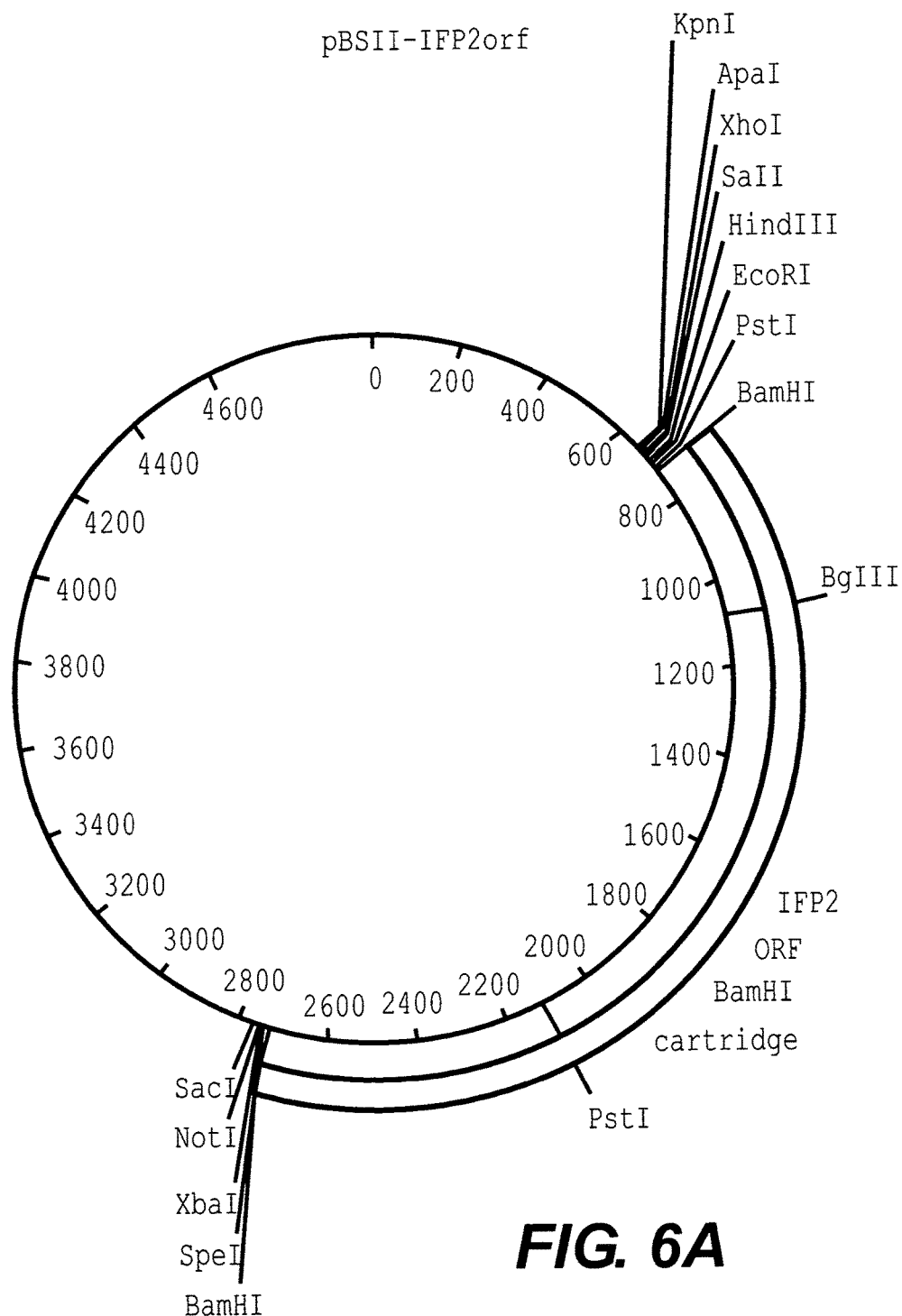

In some eukaryotic systems, the heat shock promoter may not function to express the transposase protein. An additional plasmid was constructed to allow in vitro expression of the messenger RNA sequence of the piggyBac transposase. Co-injection of this mRNA into embryos along with the piggyBac vectors would allow translation of the piggyBac transposase without having to rely on the expression of the mRNA from a promoter which may or may not be active in the desired system. In addition, this strategy provides much more transposase protein in the embryos, leading to a greater mobility of the piggyBac vectors. The BamHI cartridge was excised from the plasmid pCaSpeR-hs-orf by restriction digestion with BamHI and ligated into a BamHI digested commercially available vector; pBSII (Stratagene) to make pBSII-IFP2orf (FIG. 6), allowing in vitro transcription of the piggyBac transposase mRNA under control of the bacteriophage T7 promoter.

Example 9—Alternative Promoters for the PiggyBac Transposase Gene

Figure 7:
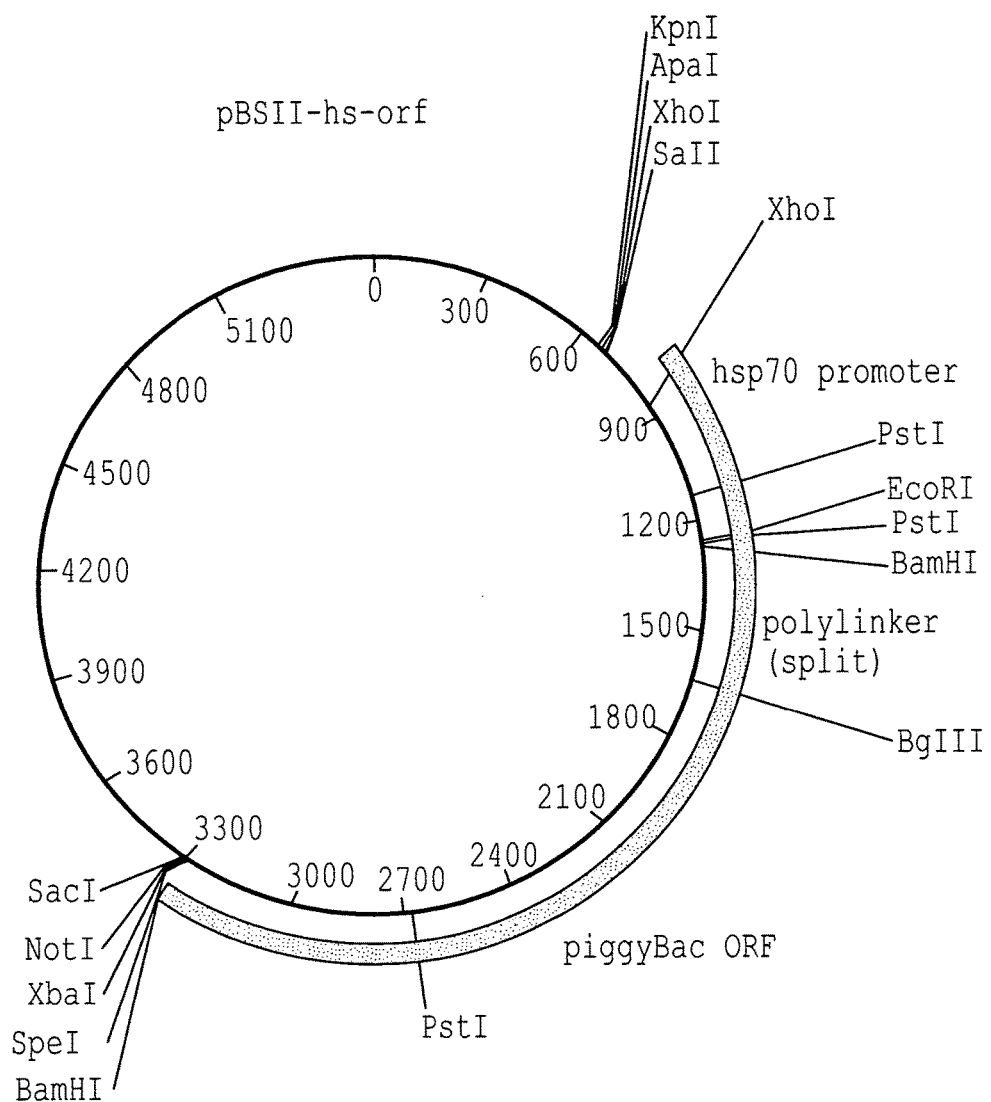
FIG. 7 is a plasmid map showing that the hsp70 promoter was excised from the pCaSpeR-hs plasmid by EcoR I and EcoR V digestion, followed by blunt ending, and cloned into pBSII-IFP2orf at the EcoR I and Hind III (blunt ended) sites to form pBSII-hs-orf (SEQ ID NO: 42)
Figure 8A:
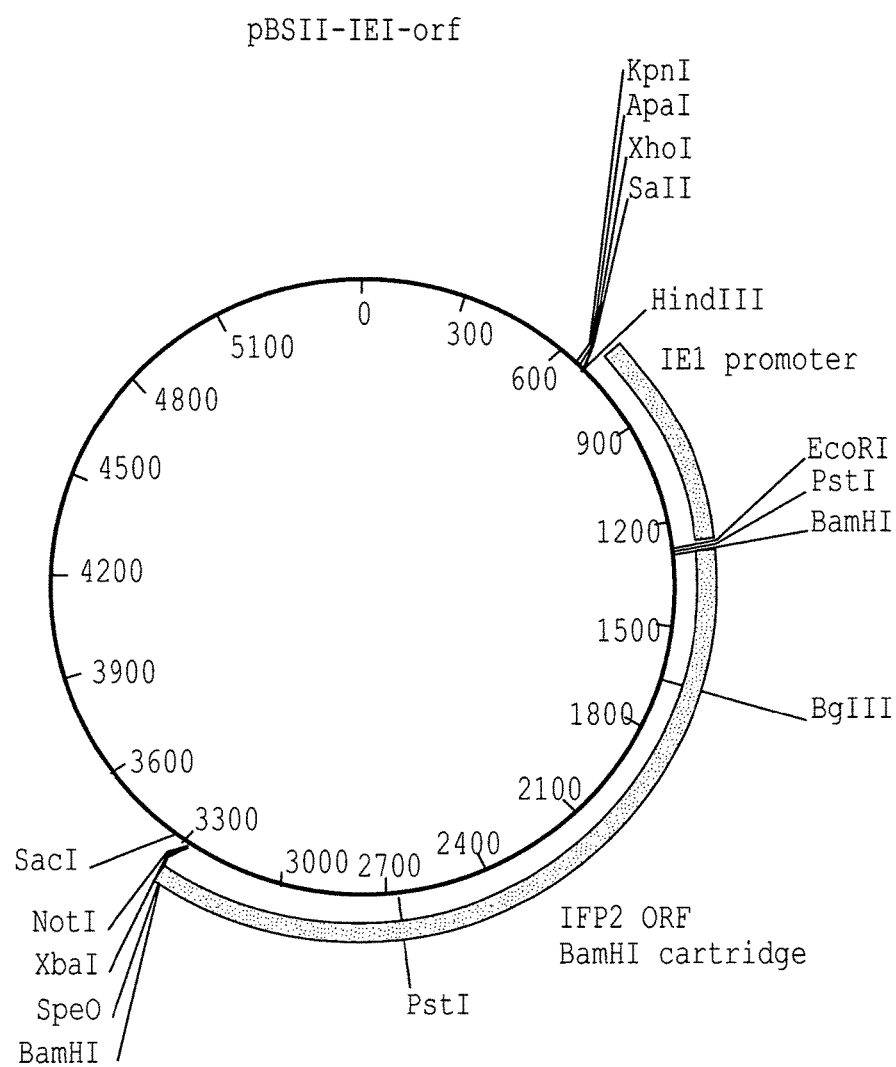

Further modification of pBSII-IFP2orf may be effected to introduce alternative promoters that would drive expression of the piggyBac transposase gene. Three examples are provided. pBSII-hs-orf (FIG. 7) was constructed by excising the heat shock promoter region from pCaSpeR-hs using EcoR I and EcoR V digestion followed by blunt end polishing of the EcoRI terminus, and ligating the fragment to the blunt end polished EcoRI/HindIII digested pBSII-IFP2orf plasmid. The plasmid pBSII-IE1-orf was prepared by PCR amplification of the IE1 promoter from the plasmid pIE1 FB using the primers IE1-Ac-for (5' ACGTAAGCT-TCGATGTCTTTGTGATGCGCC 3') (SEQ ID NO: 6) and IE1-Ac-rev (5' ACGGAATTCACTTGCAACT-GAAACAATATCC 3') (SEQ ID NO: 7) to generate an EcoRI/HindIII tailed fragment that was then inserted into EcoRI and HindIII digested pBSII-IFP2orf. This plasmid allows constitutive expression of the piggyBac transposase in a diversity of eukaryotic systems. A final demonstration was prepared by digesting the plasmid pHAct5cEGFP (Pinkerton et al., 2000) with BamHI and EcoRI to recover the *Drosophila* Actin 5c promoter which was then inserted into pBSII digested with EcoRI and BamHI. The BamHI cartridge from pCaSpeR-hs-orf was excised by digestion with BamHI and cloned downstream of the Actin 5c promoter at the unique BamHI to form the plasmid pBSII-Act5c-orf (FIG. 21). This allows high level expression of the piggyBac transposase in embryos of insects.

Example 10—Transposase Expression in Vertebrate Systems

Figure 9A:
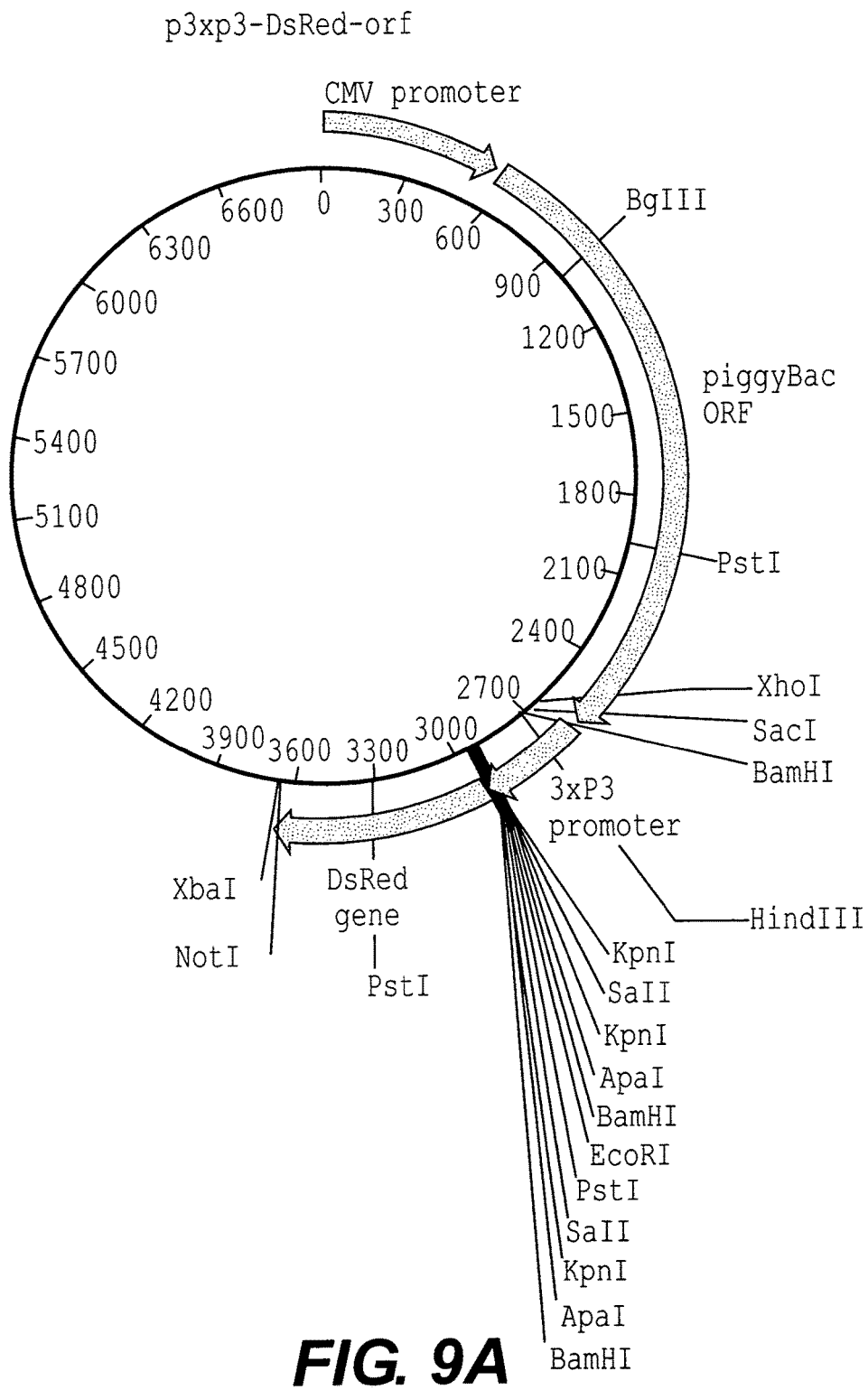

While all of the constructs in Example 9 permit expression of the transposase in insect systems, they may not permit optimal expression of the transposase in vertebrate systems. Using the commercially available pDsRed1-N1 plasmid (Clonetech) the BamHI cartridge was cloned from pBSII-IFP2orf into the BamHI site adjacent to the CMV promoter to effect efficient expression of the piggyBac transposase in vertebrate systems. This plasmid was further modified by adding the 3xP3 promoter through PCR amplification of this promoter from the plasmid pBacI[3XP3-EYFPafm] (Horn and Wimmer, 2000) using the primers 3XP3-for (5' ACTCTCGAGGTTCCCACAATGGTTAAT-TCG 3') (SEQ ID NO: 8) and 3XP3-rev (5' ACTGAAT-TCATGGTGGCGACCGGTGGATCG 3') (SEQ ID NO: 9) to generate a XhoI/EcoRI tailed cartridge that was then cloned into the XhoI and EcoRI digested pDsRed1-N1 backbone to generate the plasmid p3XP3-DsRed-orf (FIG. 9).

Example 11—Optimizing PiggyBac

In some cases it may be preferable to inject transposase protein to permit movement of the piggyBac transposon. The natural piggyBac transposase sequence is not efficiently expressed in prokaryotic systems due to a preponderance of eukaryotic codons. To achieve better expression of the piggyBac transposase in bacterial systems for purification and functional utility a sequence called optimized piggyBac orf (FIG. 23) was created, substituting prokaryotic codon biases wherever possible. This sequence generated the same protein sequence, but represents an artificial gene expressing the piggyBac transposase.

Example 12—Materials and Methods for Examples 1-11

Plasmids
p3E1.2 Deletion Series:
The p3E1.2 plasmid (Fraser et al., 1995) was first linearized using the restriction sites BamHI and EcoRI, blunt ended with the klenow fragment, then religated to construct the p3E1.2(DMCS) eliminating the MCS of the pUC18 sequence. Internal deletions were made using the Erase-A-Base System (Promega). p3E1.2(DMCS) was cut at the unique SacI site within the piggyBac element, generating an ExoIII resistant end, and then cut at the BglII site to generate an ExoIII sensitive end. Fractions of the ExoIII deletion reaction from the BglII site toward the 3' terminus were stopped every 30 seconds, and were blunt ended by S1 nuclease, recircularized, and transformed into DH5a cells. Recovered plasmids were size analyzed using a quick screen method (Sekar, 1987). The presence of intact 3' termini was confirmed using a BsiWI digestion, and then sequenced. Nine consecutive plasmids in the size range of approximately 100~200 bp deletions were recovered and named p3E1.2-d-1 to p3E1.2-d-9, with p3E1.2-d-9 having the maximum deletion (FIG. 1).

pIAO-P/L Series:

The p3E1.2 B/X plasmid was constructed as a pCRII TA clone (Invitrogen) of the entire piggyBac transposon and flanking TTAA targets sites following PCR from the plasmid p3E1.2 using the BamHI/XbaI-tailed primer M1F34 (5'-GGATCCTCTAGATTAACCCTAGAAAGATA-3') (SEQ ID NO: 10). The element and flanking TTAA sites were then excised using the enzyme BamHI and ligated to form a circular molecule. Two outward facing internal piggyBac primers, one with a terminal ApaI site (5'-GAAA GGGCCCGTGATACGCCTATTTTTATAGGTT-3') (SEQ ID NO: 11) and the other with a terminal KpnI site (5'-AATC GGTACCAACGCGCGGGGAGAGGCGGTTTGCG-3') (SEQ ID NO: 12), were used to generate a linear ApaI/KpnI-tailed fragment. This fragment was ligated to a PCR fragment containing the beta-1 actamase gene and E. coli replication origin amplified from pUC18 using an ApaI-tailed primer (5'-CCAA GGGCCCTGACGTGAACCATTGTCACACGT-3') (SEQ ID NO: 13) and a KpnI tailed (5'-TGT GGGTACCGTCGATCAAACAAACGCGAGATACCG-3) (SEQ ID NO: 14) primer pair. The resulting pIAO plasmid contains the circularized piggyBac transposon with ends separated by an 18 bp fragment of DNA having the restriction sites configuration xbaI/BamHI/xbaI, with a beta-lactamase gene and the E. coli origin of replication. The lacZ gene under the control of the polyhedron promoter was excised from pD-2/B-gal (Fraser et al., 1996) using restriction enzymes NruI and DraI, and cloned into the unique HpaI site within the piggyBac element of pIAO to form pIAO-polh/lacZ (pIAO-P/L) plasmid.

The pIAO-P/L-TTAA1 plasmid was constructed by digesting pIAO-polh/lacZ with SphI and BsiWI, and the fragment containing the internal-piggyBac sequence was isolated. Two complementing oligonucleotides, SphI (5'-CGTCAATTTTACGCAGACTATCTTTCTAGGG-3') (SEQ ID NO: 15) and TTAA-SphI (5'-TTAACCCTA-GAAAGATAGTCTGCGTAAAATTGACGCATG-3') (SEQ ID NO: 16), were annealed to form a SphI site on one end and a TTAA overhang on the other end. A second pair of oligonucleotides, BsiWI (5'-GTACGTCACAATATGAT-TATCYTTCTAGGG-3') (SEQ ID NO: 17) and TTAA-BsiWI (5'-TTAACCCTAGAAAGATAATCATATTGT-GAC-3') (SEQ ID NO: 18) were annealed to form a BsiWI site on one end and a TTAA overhang on the other. These two primer pairs were joined using the TTAA overlaps and inserted into the SphI and BsiWI sites of the digested pIAO-polh/lacZ plasmid to form the circular pIAO-P/L-TTAA1 plasmid.

The pIAO-P/L-TTAA2 plasmid was constructed in a similar manner by combining the SphI-terminal primer with TTAATTAA-SphI (5'-TTAATTAACCCTAGAAAGA-TAGTCTGCGTAAAATTGACGCATG-3') (SEQ ID NO: 19), and the BsiWI primer with TTAATTAA-BsiWI (5'-TTAATTAACCCTAGAAAGATAATCATATTGTGAC-3') (SEQ ID NO: 20).

The plasmids pIAO-P/L-2.2 kb, pIAO-P/L-589 bp, pIAO-P/L-354 bp, pIAO-P/L-212 bp and pIAO-P/L-73 bp were constructed by insertion of HindIII or PvuII fragments from the bacteriophage lambda into the blunt ended XbaI site between the adjacent TTAA target sites of pIAO-polh/lacZ.

Plasmids pIAO-P/L-55 bp, pIAO-P/L-40 bp and pIAO-P/L-22 bp were constructed by annealing oligonucleotide pIAO-4501 (5'-CTAGTACTAGTGCGCCGCGTACG TCTAGAGACGCGCAGTCTAGAAD-3') (SEQ ID NO: 21) and pIAO-4502 (5'-TTCTAGACTGCGCGTC TCTAGACGTACGCGGCGCACTAGTACTAGD-3') (SEQ ID NO: 22), forming two XbaI sites and one SpeI site, and ligating them into the blunt ended pIAO-P/L XbaI fragment to generate pIAO-P/L-55 bp. The pIAO-P/L-40 bp plasmid was constructed by cutting pIAO-P/L-55 bp plasmid at the XbaI sites of the inserted fragment and then religating. Cutting pIAO-P/L-40 bp at the XbaI and SpeI sites, and religating formed the pIAO-P/L-22 bp plasmid.

The pIAO-P/L-18 bp plasmid was constructed by PCR amplification of the pIAO-P/L plasmid using the pIAO-18 bp primer (5'-GATGACCTGCAGTAGGAAGACGD3') (SEQ ID NO: 23) and the TR-18 bp primer (5'-GAC TCTAGACGTACGCGGAGCTTAACCCTAGAAAGAT AD3') (SEQ ID NO: 24). The amplified fragment was cut with XbaI and PstI, and ligated to the pIAO-P/L XbaI and PstI cut fragment.

pCRII-ITR, pCRII-JF03/04 and pBS-ITR Plasmids:

The oligonucleotide ITR (5'-GGATTCCATGCGTCAATTTTACGCAD-3') (SEQ ID NO: 25), having the piggyBac IR and a terminal BamHI site, was used to PCR amplify the piggyBac 3' and 5' IRs and TRs along with their spacer regions from the pIAO-P/L-589 bp plasmid. The PCR fragment was TA cloned into pCRII (Invitrogen). The resulting plasmid, pCRII-ITR, replaces the entire internal sequence of piggyBac with the pCRII plasmid sequences. A second plasmid, pCRII-JF03/04, was constructed using the same strategy with the primers JFO3 (5'-GGATCCTCGATATACAGACCGATAAAAACACAT GD-3') (SEQ ID NO: 26) and JF04 (5'-GGTACCATTGCAAACAGCGACGGATTCGCGCTA TD-3') (SEQ ID NO: 27). JFO3 is 83 bp internal to the 5' terminus, JF04 is 90 bp internal to the 3' terminus. To construct the pBS-ITR plasmid, the 702 bp BamHI fragment was excised from the pCRII-ITR plasmid and inserted into the BamHI site of the pBlueScript (Stratagene) plasmid.

pXL-Bac Plasmid:

The 702 bp fragment containing the piggyBac terminal repeats isolated from pCRII-ITR plasmid BamHI digestion was religated to form a circular molecule, followed by BssHII digestion. The pBlueScript II plasmid was also digested by BssHII and the large fragment was band isolated. These two fragments were ligated together to form the pBSII-ITR(Rev) plasmid. The Multiple Cloning Site (MCS) was PCR amplified from the pBSII plasmid using the MCS for (5'-ACGCGT AGATCTTAATACGACTCACTATAGGG-3') (SEQ ID NO: 28) and MCS-rev (5'-ACGCGT AGATCTAATTAACCCTCACTAAAGGG-3') (SEQ ID NO: 29) primers, and cloned into BamHI site of pBSII-ITR (Rev) to construct the pXL-Bac plasmid.

The pXL-Bac minimum piggyBac vector was constructed by circularizing an ITR BamHI fragment, followed by BssHII digestion. The resulting BssHII fragment was then ligated to the pBlueScript II BssHII AMP/ori containing fragment. The multiple cloning site was PCR amplified from pBSII plasmid and inserted into BamHI site to form the pXL-Bac vector. Any desired gene may be inserted into the MCS [the BssHII fragment taken from pBSII (Stratagene)] to construct a piggyBac transposon.

Helper Plasmid:

phspBac (formerly pBhsDSac, Handler et al, 1998) is a transposase-providing helper plasmid that expresses the piggyBac ORF under the control of the *D. melanogaster* hsp70 promoter.

Target Plasmid:

pGDV1 is a *Bacillus subtilis* plasmid (Sarkar et al., 1997a) containing a chloramphenicol resistance gene, and is incapable of replication in *E. coli* unless provided with an *E. coli* origin of replication.

Microinjection:

*T. ni* embryos were collected approximately 2 hours post oviposition and microinjected as described by Lobo et al., (1999). After injection, the embryos were allowed to develop for one hour at room temperature, heat shocked at 37° C. for one hour, and allowed to recover at room temperature overnight. Plasmids were recovered using a modified Hirt (1967) extraction procedure.

Excision Assay:

The excision assay was performed as described by Thibault et al., (1999). Precise excision events were confirmed by sequencing using a fluorescent labeled M13 reverse primer (Integrated DNA Technologies, Inc.).

Interplasmid Transposition Assay:

The interplasmid transposition assay was performed as described by Lobo et al. (1999) and Sarkar et al. (1997a). Plasmids isolated from the injected and heat-shocked embryos, as well as those passaged through *E. coli* only, were resuspended in 20 µl of sterile distilled water and 3 µl of the DNAs were then electroporated into 10 µl of competent *E. coli* DH 10B cells (Gibco-BRL) (Elick et al., 1996a). A 1.0-ml aliquot of SOC (2% w/v Bactotryptone, 0.5% w/v Bacto yeast extract, 8.5 mM NaCl, 2.5 mM Kcl, 10 mM $MgC_2$ 20 mM glucose) was added to the electroporated cells, and the cells were allowed to recover at 37° C. for 15 minutes. An aliquot (1%) of the transformed bacteria was plated on LB plates containing amphicilin (100 µg/ml) and X-Gal (5-bromo-4-chloro-3-indolyl-β3-D-galactosidase; 0.025 µg/ml), and the rest were plated on LB plates containing kanamycin (10 µg/ml), chloramphenicol (10 µg/ml) and X-Gal (0.025 µg/ml). Restriction analysis using HindIII and EcoRV and PCR using outward facing primers specific to piggyBac (JF01: 5'-CCTCGATATACAGAC-CGATAAAACACATG-3' (SEQ ID NO: 30) and JF02: 5'-GCACGCCTCAGCCGAGCTCCAAGGGCGAC-3' (SEQ ID NO: 31)) enabled the preliminary identification of clones with putative interplasmid transposition events. The right insertion site of the clones was sequenced, with the Thermo Sequenase fluorescence-labeled primer sequencing kit (Amersham) and an ALF Express Automated Sequencer (Pharmacia Biotech), using the fluorescence-labeled JF02 primer, while the left insertion site was sequenced with the MF 11 reverse primer (5'-GGATCCCT-CAAAATTTCTTTCTAAAGTA-3') (SEQ ID NO: 32).

To check for plasmid replication in the embryos, Hirt-extracted plasmid DNAs recovered from injected *D. melanogaster* embryos were digested with the restriction enzyme DpnI (Geier and Modrich, 1979). *E. coli* cells were transformed with equal volumes of the digested and undigested plasmid DNAs and plated on LB plates containing kanamycin, chloramphenicol and X-Gal as above.

The pIAO-P/L series transposition events were sequenced using the fluorescent labeled MF 11-reverse primer (5'-GGATCCCTCAAAATTTCTTTCTAAAGTA-3') (SEQ ID NO: 33) and JF02 primer (5'-GCACGCCTCAGC-CGAGCTCCAAGCGGCGAC-3') (SEQ ID NO: 34), and the pCRII-ITR and pBSII-ITR transposition events were sequenced using fluorescent labeled M13 reverse primer.

Automatic Thermocycle Sequencing:

Sequencing was performed using the Thermo Sequenase Fluorescent Labeled Primer Sequencing Kit (Amersham) and the ALF Express Automated Sequencer (Pharmacia Biotech), following standard protocols provided by the manufacturers.

Other Plasmids:

FIGS. 12, 13 and 14 present alternative plasmids that may be useful for gene transfer.

Example 14—Identification of TRD Adjacent Regions

The present invention also provides ID sequences adjacent to the TRD of the piggyBac transposon that contribute to a high frequency of germline transformation in *D. melanogaster*. The present invention provides an analysis of a series of PGR synthesized deletion vectors constructed with the 3xP3-ECFP gene as a transformation marker (Horn and Wimmer, 2000). These vectors define ID sequences immediately adjacent to the 5' TRD and 3' TRD adjacent ID sequences that effect efficient germline transformation of *D. melanogaster*. Using this information, the present invention provides a new ITR cartridge, called ITR1.1K, and verifies its utility in converting an existing plasmid into a mobilizable piggyBac vector that enables efficient germline transformation. The present invention also provides a transposon-based cloning vector, pXL-BacII, for insertion of sequences within a minimal piggyBac transposon and verifies its capabilities in germline transformations.

Example 15—Materials and Methods for Example 12

Plasmids

The pCaSpeR-hs-orf helper plasmid was constructed by PCR amplifying the piggyBac open reading frame using IFP2orf_For and IFP2orf_Rev primers, cloning into the pCRII vector (Invitrogen), excising using BamH I, and inserting into the BamH I site of the P element vector, pCaSpeR-hs (Thummel, et al., 1992). A single clone with the correct orientation and sequence was identified and named pCaSpeR-hs-orf (FIG. 24).

The p(PZ)-Bac-EYFP plasmid was constructed from the p(PZ) plasmid (Rubin and Spradling, 1983) by digesting with Hind III and recircularizing the 7 kb fragment containing LacZ, hsp70 and Kan/ori sequences to form the p(PZ)-7 kb plasmid. The ITR cartridge was excised from pBSII-ITR (Li et al., 2001b) using Not I and Sal I and blunt end cloned into the Hind III site of the p(PZ)-7 kb plasmid. A 3xP3-EYFP marker gene was PCR amplified from pBac{3xP3-EYFPafm} (Horn and Wimmer, 2000), digested with Spe I, and inserted into the Xba I site to form p(PZ)-Bac-EYFP. It contains the LacZ gene, *Drosophila* hsp70 promoter, Kanamycin resistance gene, ColE1 replication origin, 3xP3-EYFP marker and the piggyBac terminal repeats-only ITR cartridge (FIG. 24).

The pBSII-3xP3-ECFP plasmid was constructed by PCR amplifying the 3xP3-ECFP marker gene from pBac{3xP3-ECFPafm} (Horn and Wimmer, 2000) using the primer pair ExFP_For and ExFP_Rev, then digesting the amplified fragment with Spe I, and cloning it into the Xba I site of pBlueScript II plasmid (Stratagene).

The piggyBac synthetic internal deletion plasmids were constructed by PCR amplification from the pIAO-P/L-589 bp plasmid (Li et al., 2001b) using a series of primers. A total of 9 PCR products were generated using the combination of IFP2_R4 against all five IFP2_L primers and IFP2_L5 against all four IFP2_R primers. Two additional PCR products were also obtained using the IPF2_R-TR+IFP2_L and IFP2_R1+IFP2_L primer pairs. These PCR products were then cloned into the pCR II vector using the TOPO TA cloning kit (Invitrogen), excised using Spe I digestion, and cloned into the Spe I site of the pBSII-3xP3-ECFP plasmid to form the piggyBac internal deletion series (FIG. 25). The pBSII-ITR1.1K-ECFP plasmid (FIG. 24) was constructed by cloning the EcoR V/Dra I fragment from pIAO-P/L-589 bp, which contained both piggyBac terminal repeats, into the EcoR V site of pBSII-3xP3-ECFP. The pXL-BacII-ECFP plasmid (FIG. 24) was constructed by PCR amplifying the ITR1.1k cartridge from pBSII-ITR1.1k-ECFP plasmid using MCS_For and MCS_Rev primers flanking by Bgl II site, cutting with Bgl II, religating and cutting again with BssH II, then inserting into the BssH II sites of the pBSII plasmid.

A separate cloning strategy was used to construct pBS-pBac/DsRed. The 731 bp Ase I-blunted fragment from p3E1.2, including 99 bp of 3' piggyBac terminal sequence and adjacent NPV insertion site sequence, was ligated into a unique Kpn I-blunted site in pBS-KS (Stratagene). The resulting plasmid was digested with Sac I and blunted, then digested with Pst I, and ligated to a 173 bp Hinc II-Nsi I fragment from p3E1.2, including 38 bp of 5' piggyBac terminal sequence. The pBS-pBac minimal vector was marked with polyubiquitin-regulated DsRed1 digested from pB[PubDsRed1] (Handler and Harrell, 2001a) and inserted into an EcoR I-Hind III deletion in the internal cloning site within the terminal sequences.

Example 16 Transformation of *Drosophila melanogaster*

The *D. melanogaster* $w^{1118}$ white eye strain was used for all microinjections employing a modification of the standard procedure described by Rubin and Spradling (1982), in which the dechorionation step was eliminated. Equal concentrations (0.5 µg/µl) of each of the internal deletion plasmids, or the control plasmid pBac{3xP3-ECFPafm}, were injected along with an equal amount of the pCaSpeR-hs-orf helper plasmid into fresh fly embryos followed by a one hour heat shock at 37° C. and recovery overnight at room temperature. Emerging adults were individually mated with $w^{1118}$ flies, and progeny larvae were screened using an Olympus SZX12 fluorescent dissecting microscope equipped with GFP (480 nm excitation/510 nm barrier), CFP (436 nm excitation/480 nm barrier), and YFP (500 nm excitation/530 barrier) filter sets. Two positive adults from each of the vials were crossed with $w^{1118}$ to establish germline transformed strains. The pBS-pBac/DsRed1 minimal vector was also injected and screened under HQ Texas Red® set no. 41004 (Handler and Harrell, 2001a).

Direct PCR Analysis

Genomic DNAs from each of the transformed stains, the $w^{1118}$ wild type strain, and a piggyBac positive strain M23.1 (Handler and Harrell, 1999) were prepared using a modified DNAzol procedure. About 60 flies from each strain were combined with 150 µl of DNAzol (Molecular Research Center, Inc.) in a 1.5 ml eppendorf tube. The flies were homogenized, an additional 450 µl of DNAzol was added, and the homogenates were incubated at room temperature for one hour. The DNAs were extracted twice with phenol:chloroform (1:1 ratio), and the aqueous fractions were transferred to new tubes for precipitation of the DNA with an equal volume of 2-propanol. The DNA pellets were washed with 70% ethanol, air dried, and 150 µl of $dH_2O$ containing 10 µg of RNase A was added and resuspended.

Two sets of direct PCRs were performed to identify the presence of piggyBac sequences in transformed fly genomes. Primers MF34 and IFP2_L were used to identify the presence of the piggyBac 3' terminal repeat, while MF34 and IFP2_R1 were used for identifying the piggyBac 5' terminal repeat. To exclude the possibility of recombination, a second PCR was also performed using the IFP2_R1 and IFP2_L primers to amplify the external stuffer fragment (Li et al., 2001) between the terminal repeat regions.

Southern Hybridization Analysis

Southern hybridization analysis was performed using a standard procedure with minor modifications (Ausubel et al. 1994). Approximately 8 µg of genomic DNA (isolated as above) from each of the transformed fly strains was digested with 40 units of Hind III for four hours, followed by agarose gel electrophoresis at 60 Volts for 4 to 5 hours. The gel was then denatured, neutralized and transferred to nylon membranes, and baked at 80° C. for four hours. The membranes were pre-hybridized in the hybridization buffer overnight. A synthetic probe was prepared by nick translation (Invitrogen kit) using $^{32}P$ labeled dGTP against the pBSII-ITR1.1K-ECFP plasmid template. The purified probe was hybridized at 65° C. overnight followed by several washes, and the membranes were first exposed on phosphor screens (Kodak) overnight for scanning with a Storm phosphor Scanner (Molecular Dynamics System), and then exposed on X-ray film (Kodak).

Universal PCR and Inverse PCR Analysis

The piggyBac insertion sites in the transformed fly strains were identified using either universal PCR (Beeman et al., 1997) or inverse PCR techniques (Ochman et al., 1988). For the universal PCR, the IFP2_L (3' TR) or IPR2_R1 (5' TR) primer was combined with one of 7 universal primers during the first round of PCR (94° C. 1 minute, 40° C. 1 minute, 72° C. 2 minutes, 35 cycles). 2 µl of the reaction mixture from the first round of PCR was then used for a second round of PCR (94° C. 1 minute, 50° C. 1 minute, 72° C. 2 minutes, 35 cycles) using IFP2_L1 (3' TR) or iPCR_R1 (5' TR) together with a T7 primer (nested on the universal primer).

Inverse PCRs were performed by digesting 5 ug of the genomic DNAs from each of the transformed strains completely with HinP1 I for the 3' end or Taq I for the 5' end, followed by purification using the Geneclean kit (Q-Biogene) and self-ligation in a 100 ul volume overnight. The self-ligated DNAs were precipitated and resuspended in 30 ul $ddH_2O$. A portion of them were then used for first round PCR (94° C. 1 minute, 40° C. 1 minute, 72° C. 2 minutes, 35 cycles) with primer pairs IFP2_R1+MF14 for the 5' end and JF3+IFP2_Lb for the 3' end. 2 ul of the first round PCR products were used as templates for the second round PCR (94° C. 1 minute, 50° C. 1 minute, 72° C. 2 minutes, 35 cycles) using primer pairs iPCR_R1+iPCR_6 for the 5' end and iPCR_L1+MF04 for the 3' end. The pBSII-ITR1.1k-ECFP strains were slightly different, the primer pair iPCR_L1+IFP2_L-R were used for the 3' end in the second round PCR. All the PCR products were cloned into the pCRII vector (Invitrogen) and sequenced. The sequences were used to BLAST search the NCBI database to identify the locations of the insertions. MacVector 6.5.3 (Oxford Molecular Group) and ClustalX (Jeanmougin et al., 1998) were used for sequence alignments.

Example 17—Transformation Experiments with Synthetic Deletion Constructs

Each of the piggyBac synthetic internal deletion plasmids was formed by PCR amplifying from the pIAO-P/L-589 plasmid (Li et al., 2001) by PCR amplifying across the facing terminal repeats and spacer with primers that recognize 5' or 3' sequences adjacent to the respective TRDs (FIG. 24). The fragments generated were cloned into a pBSII-3xP3-ECFP plasmid and sequenced.

Each of the synthetic deletion series plasmids and the control plasmid, pBac{3xP3-ECFPafm}, were co-injected with the hsp70-regulated transposase helper into $w^{1118}$ embryos, with surviving adults backcrossed, and G1 adult progeny screened for fluorescence. Positive transformants exhibited fluorescent eyes with CFP and GFP filter sets but not with the YFP filter set. Transformation frequencies from all injections are listed in Table 1, below.

these four constructs, only pBSII-ECFP-R4/L1, which represented the greatest deletion of 3' ID sequence (2284~2409 of the piggyBac sequence), failed to yield transformants. Once again, frequencies for the positive transformant constructs were similar to the control (Table 1). It was therefore deduced that the minimal 3' ID sequence requirement for efficient germline transformation was between 125 bp (L1) and 378 bp (L2) of the 3' TRD adjacent ID sequence.

Example 18—Construction of the ITR1.1k Minimal Sequence piggyBacCartridge

To construct a minimal sequence cartridge using the information gained from the synthetic deletion analysis, combinations of 5' and 3' minimal sequences were assembled and their transformation capabilities were tested. The pBSII-ECFP-R-TR/L construct is composed of a 35 bp 5' TRD lacking any 5' ID sequence, coupled to a fragment containing the 65 bp 3' TRD and 172 bp of the adjacent 3' ID sequence. This combination did not yield any transformants, confirming the necessity for having 5' ID sequences in combination with 3' ID sequences for efficient transformation. Unexpectedly, addition of 101 bp of the 5' ID sequences to the 5' TRD sequences in the construct pBSII-

TABLE 1

Transformation of Drosophila melanogaster

| Plasmid | Embryos Injected | Embryos Hatched | Adults Mated | Adults Survied | Transformants Lines ($G_0$) | Transformation Frequency |
|---|---|---|---|---|---|---|
| p(PZ)-Bac-EYFP | 2730 | 376 | 217 | 83 | 1 | 0.6% |
| pBSII-ECFP-R1/L5 | 990 | 240 | 83 | 70 | 6 | 8.9% |
| pBSII-ECFP-R2/L5 | 620 | 75 | 21 | 16 | 2 | 12.5% |
| pBSII-ECFP-R3/L5 | 650 | 127 | 29 | 20 | 3 | 15.0% |
| pBSII-ECFP-R4/L5 | 730 | 182 | 39 | 31 | 4 | 12.9% |
| pBSII-ECFP-R4/L4 | 670 | 169 | 44 | 28 | 3 | 10.7% |
| pBSII-ECFP-R4/L3 | 710 | 147 | 44 | 31 | 3 | 9.7% |
| pBSII-ECFP-R4/L2 | 850 | 191 | 55 | 46 | 5 | 10.8% |
| pBSII-ECFP-R4/L1 | 990 | 231 | 75 | 86 | 0 | 0% |
| pBSII-ITR1.1K-ECFP | 530 | 128 | 43 | 84 | 5 | 13.9% |
| pBSII-ECFP-R-TR/L | 610 | 169 | 62 | 71 | 0 | 0% |
| pBSII-ECFP-R1/L | 840 | 247 | 81 | 69 | 0 | 0% |
| pBac{3xP3-ECFPafm} | 650 | 104 | 45 | 69 | 4 | 12.9% |
| pXL-BacII-ECFP | 1020 | 181 | 42 | 36 | 8 | 22.2% |
| pBSII-ITR1.1k-ECFP* | 515 | 120 | 48 | 22 | 8 | 36.4% |
| pXL-BacII-ECFP* | 533 | 199 | 115 | 88 | 22 | 25.0% |

*The injections were done independently (Handler lab) using a 0.4:0.2 ug/ul vector/helper concentration ratio of DNA. The p(PZ)-Bac-EYFP plasmid yielded a low transformation frequency of 0.6% compared to the control plasmid, pBac{3xP3-ECFPafm}frequency of 12.9% (Table 1).

Eight of the eleven synthetic ID deletion plasmids yielded positive transformants at an acceptable (not significantly different from control, P<0.05) frequency. The 5' ID deletion constructs pBSII-ECFP-R1/L5, pBSII-ECFP-R2/L5, pBSII-ECFP-R3/L5 and pBSII-ECFP-R4/L5 had variable deletions of the piggyBac 5' ID, retaining sequences from 66 bp (nucleotides 36~101 of the piggyBac sequence, GenBank Accession Number: AR307779) to 542 bp (36~567 of the piggyBac sequence). Each of these 5' ID deletions yielded ECFP positive germ line transformants at frequencies from 8.9% to 15.0% (Table 1) when paired with 1 kb of the 3' ID sequence (nucleotides 1454~2409 of the piggyBac sequence). These results suggested that a minimal sequence of no more than 66 bp of the 5' ID may be necessary for efficient germline transposition.

The R4 minimum 5' ID sequence primer was then used in combination with a series of 3' ID deletion primers to generate the constructs pBSII-ECFP-R4/L4, pBSII-ECFP-R4/L3, pBSII-ECFP-R4/L2 and pBSII-ECFP-R4/L1. Of ECFP-R1/L was not sufficient to recover transformation capacity when paired with the 172 bp 3' ID sequences, even though the lower limit of essential 5' ID sequences had been suggested to be 66 bp using pBSII-ECFP-R1/L5 (Table 1). Increasing the 5' ID sequences to 276 bp in the pBSII-ITR1.1k-ECFP plasmid recovered the full transformation capability when paired with the 172 bp 3' ID sequence (Table 2). The minimal operational requirement for 5' ID sequences is therefore between 276 and 101 bp when coupled to a minimal 3' ID sequence of 172 bp.

Two independent verifications of the pBSII-ITR1.1k-ECFP plasmid transforming capabilities were conducted for transformation of D. melanogaster. These transformation experiments resulted in calculated frequencies of 13.9% (FIG. 25) and 36% (Table 1). The discrepancy in frequencies may be attributed to differences in injection protocols between labs. Unless otherwise indicated, the transformation frequencies presented in Table 1 and FIG. 25 were obtained with injections of 0.6:0.6 ug/ul vector:helper concentration ratios. The increased efficiency of transformation for pBSII-ITR1.1k-ECFP observed in the second independent trial seems to be related to a decreased vector:helper concentration in *D. melanogaster*.

Five recovered pBSII-ITR1.1k-ECFP transformed strains were used to perform genetic mapping to identify their chromosome locations. Several of the strains had insertions on the second and third chromosomes (including strain 1), while strain 3 had an insertion on the X chromosome. Strain 1 and strain 3 were chosen for further analyses.

Direct PCR Analysis of Integrations:

Genomic DNAs from each of the transformed strains obtained with the synthetic deletion constructs in FIG. 24, as well as the piggyBac positive strain M23.1 and the negative white eye strain $w^{1118}$, were used to perform two sets of PCRs to verify the presence of the piggyBac 5' and 3' terminal repeat regions. An additional negative control PCR was performed on all transformants to show the absence of the external lambda phage DNA stuffer sequence (FIG. 26).

The first set of PCRs utilized the IFP2_R1 and MF34 primers to amplify the 5' terminal repeat regions, and the second set of PCRs used the IFP2_L and MF34 primers to amplify the 3' terminal repeat regions. All of the synthetic deletion transformed strains, the M23.1 control strain, and the plasmid control yielded a strong PCR product of the correct size for each of the primer sets, confirming the presence of both of the piggyBac terminal repeat regions in all of the transformed strains. Interestingly, the white eye strain $w^{1118}$ yielded a very weak product of the correct size with the 5' terminal repeat PCR amplification, but failed to generate a product with the 3' terminal specific primer set.

A third set of PCRs was performed using the IFP2_R1 and IFP2_L primers in an attempt to amplify the external lambda phage DNA stuffer sequence which would be present if an insertion resulted from recombination of the entire plasmid sequence rather than transposition. The control product from this PCR reaction is a 925 bp fragment, and no such corresponding fragments were generated with any of the transformed strain genomic DNAs.

Figure 29:
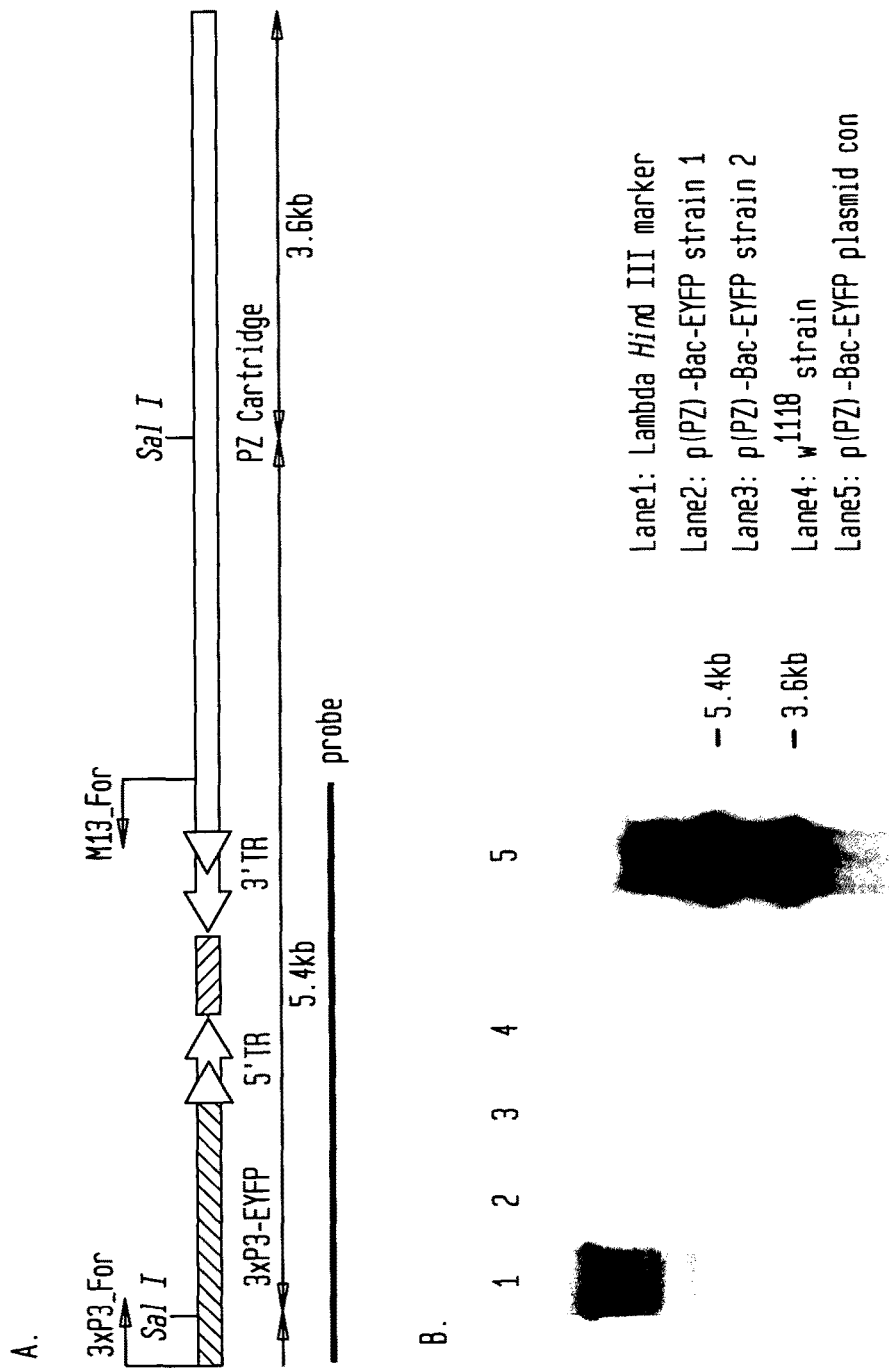

Southern Hybridization Analysis:

Southern hybridization analysis was performed to verify the copy number and further confirm transposition of the piggyBac deletion plasmids into the *Drosophila* genome (FIG. 27 and FIG. 29). Genomic DNAs from two of the pBSII-ITR1.1k-ECFP strains (strain 1 and strain 3) and one of each of the other strains were digested with Hind III, with the pBSII-ITR1.1k-ECFP plasmid Hind III digest as a plasmid control. The Hind III digestion of all transformed strains will generate four fragments if transpositional insertion has occurred: the pBSII plasmid backbone fragment (2960 bp), the 3xP3-ECFP marker fragment (1158 bp), the piggyBac 5' terminus fragment and the piggyBac 3' terminus fragment. Using the pBSII-ITR1.1k-ECFP plasmid as probe, all four fragments generated by the Hind III digestion may be detected.

The diagnostic 2960 bp pBSII backbone and 1158 bp ECFP marker fragments were present in all of the transformed strains examined. All of these strains also exhibited at least two additional bands corresponding to the piggyBac termini and adjacent sequences at the integration site (FIG. 27). These results confirmed that the observed frequencies were the result of transpositional integrations.

Example 19—Analysis of Insertion Site Sequences

To further verify that piggyBac-mediated transposition of the synthetic deletion constructs occurred in these transformants, individual insertion sites were examined by isolating joining regions between the transposon and genomic sequences using either universal PCR or inverse PCR. Subsequent sequencing analysis of these joining regions demonstrated that all of the insertions occurred exclusively at single TTAA target sites that were duplicated upon insertion, and all insertion sites had adjacent sequences that were unrelated to the vector. The two pBSII-ITR1.1k-ECFP strains 1 and 3 have a single insertion on the third and X chromosome respectively.

Example 20—Pairings of 5' PiggyBac Minimum Sequence with Long 3' End Transposon Sequences In these studies, transformation results from synthetic unidirectional deletion plasmids demonstrate that no more than 66 bp (nt 36~101 of the piggyBac sequence) of the piggyBac 5' ID sequence and 378 bp (nt 2031~2409 of the native (wild-type) piggyBac sequence) of the piggyBac 3' ID sequence are necessary for efficient transformation when these deletions are paired with long (378 or 311 bp, respectively, or longer) ID sequences from the opposite end of the transposon. The transformation data from the pBSII-ITR1.1k-ECFP plasmid further defines the 3' ID essential sequence as 172 bp (nt 2237~2409 of the native (wild-type) piggyBac sequence). Combining this same 172 bp 3' ID sequence with only the 5' TRD in the pBSII-ECFP-R-TR/L plasmid yielded no transformants, demonstrating that the 3' ID sequence alone was insufficient for full mobility. Unexpectedly, adding the 66 bp 5' ID sequence in pBSII-ECFP-R1/L also does not allow recovery of full transformation capability in spite of the fact that the same 66 bp does allow full transformation capability when coupled to the larger (378 bp) 3' ID sequence in the pBSII-ECFP-R1/L2. This result cannot be explained by size alone, since the ITR cartridge strategy used to test this deletion sequence construct effectively replaces the rest of the piggyBac ID with the 2961 bp pBSII plasmid sequence.

There appears to be an important sequence within the additional 206 bp of the L2 3' ID sequence that compensates for the smaller 5' ID sequence of R1. The data infer that an analogous sequence at the 5' end should be located within the 210 bp added to the 5' ID sequence in construction of the pBSII-ITR1.1k-ECFP, since this construct exhibits full transforming capability using the L 3' ID sequence. Aligning these two sequences using MacVector 6.5.3 identified two small segments of repeat sequences common between these approximately 200 bp sequences. These repeats, ACTTATT (nt 275~281, 2120~2126 and 2163~2169 of the piggyBac sequence) and CAAAAT (nt 185~190, 158~163 and 2200~2205 of the piggyBac sequence), occur in direct and opposite orientations, and are also found in several other locations of the piggyBac ID (FIG. 28). It seems that a minimum of one set of these repeats on either side of the internal domains are required for the transposon to permit full transforming capability.

Example 21—Materials Used in Transformation Studies with Synthetic Deletion Constructs The present example describes the piggyBac construct materials (e.g. synthetic deletion constructs) used in the transformation of *Drosophila melanogaster*.

Materials and Methods

Plasmids

The pCaSpeR-hs-orf helper plasmid was constructed by PCR amplifying the piggyBac open reading frame using IFP2orf_For and IFP2orf_Rev primers, cloning into the pCRII vector (Invitrogen), excising with BamH I and inserting into the BamH I site of the P element vector, pCaSpeR-hs (Thummel, et al., 1992). A single clone with the correct orientation and sequence was identified and named pCaSpeR-hs-orf (FIG. 24A).

The p(PZ)-Bac-EYFP plasmid (FIG. 24B) was constructed from the p(PZ) plasmid (Rubin and Spradling, 1983) by digesting with Hind III and recircularizing the 7 kb fragment containing LacZ, hsp70 and Kan/ori sequences to form the p(PZ)-7 kb plasmid. The ITR cartridge was excised from pBSII-ITR (Li et al., 2001b) using Not I and Sal I and blunt-end cloned into the Hind III site of the p(PZ)-7 kb plasmid. A 3xP3-EYFP marker gene was PCR amplified from pBac{3xP3-EYFPafm} (Horn and Wimmer, 2000), digested with Spe I, and inserted into the Xba I site to form p(PZ)-Bac-EYFP.

The pBSII-3xP3-ECFP plasmid was constructed by PCR amplifying the 3xP3-ECFP marker gene from pBac{3xP3-ECFPafm} (Horn and Wimmer, 2000) using the primer pair ExFP_For and ExFP_Rev (Table 2), digesting the amplified fragment with Spe I, and cloning it into the Xba I site of pBlueScript II plasmid (Stratagene).

The piggyBac synthetic internal deletion plasmids were constructed by PCR amplification from the pIAO-P/L-589 bp plasmid (Li et al., 2001b) using a series of primers (Table 2). A total of 9 PCR products were generated using the combination of IFP2_R4 against all five IFP2_L primers and IFP2_L5 against all four IFP2_R primers. Two additional PCR products were also obtained using the IPF2_R-TR+ IFP2_L and IFP2_R1+IFP2_L primer pairs. These PCR products were then cloned into the pCR II vector (Invitrogen), excised by Spe I digestion, and cloned into the Spe I site of the pBSII-3xP3-ECFP plasmid to form the piggyBac internal deletion series (FIG. 25). The pBSII-ITR1.1K-ECFP plasmid (FIG. 24C) was constructed by cloning the EcoR V/Dra I fragment from pIAO-P/L-589 bp, which contained both piggyBac terminal repeats, into the EcoR V site of pBSII-3xP3-ECFP. The pXL-BacII-ECFP plasmid (FIG. 24D) was constructed essentially as described previously (Li et al., 2001b) by PCR amplifying the ITR1.1k cartridge from pBSII-ITR1.1k-ECFP plasmid using MCS_For and MCS_Rev primers, each containing flanking Bgl II sites, cutting with Bgl II, religating and cutting again with BssH II, then inserting into the BssH II sites of the pBSII plasmid.

The pBS-pBac/DsRed1 plasmid was constructed by excising the 731 bp Ase I-fragment from p3E1.2, including 99 bp of 3' piggyBac terminal sequence and adjacent NPV insertion site sequence, and ligating it as a blunt fragment into a unique Kpn I-blunted site in pBS-KS (Stratagene). The resulting plasmid was digested with Sac I and blunted, digested with Pst I, and ligated to a 173 bp Hinc II-Nsi I fragment from p3E1.2, including 38 bp of 5' piggyBac terminal sequence. The pBS-pBac minimal vector was marked with the polyubiquitin-regulated DsRed1 digested from pB[PUbDsRed1] (Handler and Harrell, 2001a) and inserted into an EcoR I-Hind III deletion in the internal cloning site within the terminal sequences.

Transformation of Drosophila melanogaster

The D. melanogaster $w^{1118}$ white eye strain was used for all microinjections employing a modification of the standard procedure described by Rubin and Spradling (1982) in which the dechorionation step was eliminated. Equal concentrations (0.5 ug/ul) of each of the internal deletion plasmids or the control plasmid pBac{3xP3-ECFPafm}, were injected along with an equal amount of the pCaSpeR-hs-orf helper plasmid into embryos followed by a one hour heat shock at 37° C. and recovery overnight at room temperature. Emerging adults were individually mated with $w^{1118}$ flies, and progeny were screened as larvae using an Olympus SZX12 fluorescent dissecting microscope equipped with GFP (480 nm excitation/510 nm barrier), CFP (436 nm excitation/480 nm barrier), and YFP (500 nm excitation/530 barrier) filter sets. Two positive adults from each of the vials were crossed with $w^{1118}$ to establish germ-line transformed strains. The pBS-pBac/DsRed1 minimal vector was also injected and screened using a HQ Texas Red® filter no. 41004 (Handler and Harrell, 2001a).

Direct PCR Analysis

Genomic DNAs from each of the transformed stains, the $w^{1118}$ wild type strain, and a piggyBac positive strain M23.1 (Handler and Harrell, 1999) were prepared using a modified DNAzol procedure. About 60 flies from each strain were combined with 150 ul of DNAzol (Molecular Research Center, Inc.) in a 1.5 ml eppendorf tube. The flies were homogenized, an additional 450 ul of DNAzol was added, and the homogenates were incubated at room temperature for one hour. The DNAs were extracted twice with phenol:chloroform (1:1 ratio), and the aqueous fractions were transferred to new tubes for precipitation of the DNA with an equal volume of 2-propanol. The DNA pellets were washed with 70% ethanol, air dried, and resuspended in 150 ul of dH$_2$O containing 10 ug of RNase A.

Two sets of direct PCRs were performed to identify the presence of piggyBac sequences in transformed fly genomes. Primers MF34 and IFP2_L were used to identify the presence of the piggyBac 3' terminal repeat, while MF34 and IFP2_R1 were used for identifying the piggyBac 5' terminal repeat. To exclude the possibility of recombination, a second PCR was also performed using the IFP2_R1 and IFP2_L primers to amplify the external stuffer fragment (Li et al., 2001b) between the terminal repeat regions.

Southern Hybridization Analysis

Southern hybridization analysis was performed using a standard procedure with minor modifications (Ausubel et al. 1994). Approximately 8 ug of genomic DNA (isolated as above) from each of the transformed fly strains was digested with 40 units of Hind III for four hours, followed by agarose gel electrophoresis. The gel was then denatured, neutralized and transferred to nylon membranes, and baked at 80° C. for four hours, and the membranes were pre-hybridized overnight. A synthetic probe was prepared by nick translation (Invitrogen kit) using $^{32}$P labeled dGTP against the pBSII-ITR1.1K-ECFP plasmid template. Purified probe was hybridized at 65° C. overnight followed by several washes, and the membranes were first exposed on phosphor screens (Kodak) overnight for scanning with a Storm phosphor Scanner (Molecular Dynamics System), and then exposed on X-ray film (Kodak).

Universal PCR and Inverse PCR Analysis

The piggyBac insertion sites in the transformed fly strains were identified using either universal PCR (Beeman et al., 1997) or inverse PCR techniques (Ochman et al., 1988). For the universal PCR, the IFP2_L (3' TR) or IPR2_R1 (5' TR) primer was combined with one of 7 universal primers (Table 2) during the first round of PCR (94° C. 1 min, 40° C. 1 min, 72° C. 2 min, 35 cycles). 2 ul of the reaction mix from the first round PCR was then used for a second round of PCR (94° C. 1 min, 50° C. 1 min, 72° C. 2 min, 35 cycles) using IFP2_L1 (3' TR) or iPCR_R1 (5' TR) together with a T7 primer (nested on the universal primer).

Inverse PCRs were performed by digesting 5 ug of the genomic DNAs from each of the transformed strains completely with HinP1 I for the 3' end or Taq I for the 5' end, followed by purification using the Geneclean kit (Q-Biogene) and self-ligation in a 100 ul volume overnight. The self-ligated DNAs were precipitated and resuspended in 30 ul ddH$_2$O. A 5 μl portion of each ligation was used for first round PCR (94° C. 1 min, 40° C. 1 min, 72° C. 2 min, 35 cycles) with primer pairs IFP2_R1+MF14 for the 5' end, and JF3+IFP2_Lb for the 3' end (Table 2). 2 μl of the first round PCR products were used as templates for the second round PCR (94° C. 1 min, 50° C. 1 min, 72° C. 2 min, 35 cycles) using primer pairs iPCR_R1+iPCR_6 for the 5' end and iPCR_L1+MF04 for the 3' end. The primer pair iPCR_L1+ IFP2_L-R was used for the second round PCR of the 3' end of pBSII-ITR1.1k-ECFP strains. All the PCR products were cloned into the pCRII vector (Invitrogen) and sequenced. Sequences were subjected to a BLAST search of the NCBI database to identify the locations of the insertions. MacVector 6.5.3 (Oxford Molecular Group) and ClustalX (Jeanmougin et al., 1998) were used for sequence alignments.

Example 22—Transformation Studies with Synthetic Deletion Constructs

Initial attempts to transform *D. melanogaster* with plasmids having only TRD sequences as specified in previous reports (Li et al., 2001b) yielded transformation frequencies far less than full length piggyBac constructs. The p(PZ)-Bac-EYFP construct contains the ITR cartridge of Li et al. (2001b) composed of the 5' and 3' TRD and the spacer sequence, while the pBS-pBac/DsRed retains only 2 bp of 5' ID and 36 bp of 3' ID sequences in addition to the 5' and 3' TRD. Neither of these constructs were able to generate germ-line transformants at the frequencies previously reported for full length vectors (Handler and Harrell, 1999) or the less extensive internal deletion construct pBac{3xP3-ECFPafm} (Horn and Wimmer, 2000). The potential involvement of piggyBac ID sequences in generating germ line transformations were therefore reexamined.

The requirements for TRD was examined adjacent ID sequences of the piggyBac transposon using a synthesized cartridge strategy based upon construction of the previously reported ITR cartridge (Li et al., 2001b), rather than digesting with an endonuclease and selecting clones representing an internal deletion series. Each of the piggyBac synthetic internal deletion plasmids was formed from the pIAO-P/L-589 plasmid (Li et al., 2001b) by PCR amplification across the facing TRDs and spacer sequences with primers that recognize 5' or 3' ID sequences adjacent to the respective TRDs (FIG. 24). The fragments generated were cloned into a pBSII-3xP3-ECFP plasmid and sequenced (Materials and Methods).

Each of the synthetic deletion series plasmids and the control plasmid, pBac{3xP3-ECFPafm}, were co-injected with the hsp70-regulated transposase helper into w[1118] embryos, with surviving adults backcrossed, and G1 adult progeny screened for fluorescence. Positive transformants exhibited fluorescent eyes with CFP and GFP filter sets but not with the YFP filter set. Transformation frequencies from all injections are listed in Table 3. The p(PZ)-Bac-EYFP plasmid, which was constructed using the ITR cartridge previously described (Li et al., 2001b), yielded a relatively low transformation frequency of 0.6% compared to the control plasmid, pBac{3xP3-ECFPafm} frequency of 12.9% (Table 3).

Eight of the eleven synthetic ID deletion plasmids yielded positive transformants at an acceptable frequency compared to the control. The 5' ID deletion constructs pBSII-ECFP-R1/L5, pBSII-ECFP-R2/L5, pBSII-ECFP-R3/L5 and pBSII-ECFP-R4/L5 had variable deletions of the piggyBac 5' ID, retaining sequences from 66 bp (nucleotides 36~101; GenBank Accession Number: AR307779) to 542 bp (nucleotides 36~567) of the piggyBac sequence. Each of these 5' ID deletions yielded ECFP positive germ-line transformants at frequencies from 8.9% (+/−1.0%) to 15.0% (+/−0.6%) (Table 3) when paired with 1 kb of the 3' ID sequence (nucleotides 1454-2409). These results demonstrated a minimal sequence of no more than 66 bp of the 5' ID is appropriate for effective germ-line transposition.

The R4 minimum 5' ID sequence primer was then used in combination with a series of 3' ID deletion primers to generate the constructs pBSII-ECFP-R4/L4, pBSII-ECFP-R4/L3, pBSII-ECFP-R4/L2 and pBSII-ECFP-R4/L1. Of these four constructs, only pBSII-ECFP-R4/L1, which represented the greatest deletion of 3' ID sequence (2284~2409 of the piggyBac sequence), failed to yield transformants. Once again, frequencies for the constructs that yielded positive transformants compared favorably with the control (Table 3). It was therefore deduced that the minimal 3' ID sequence requirement for efficient germline transformation was between 125 bp (L1) and 378 bp (L2) of the 3' TRD adjacent ID sequence.

Construction of the ITR1.1k Minimal Sequence PiggyBac Cartridge

To construct a minimal sequence cartridge using the information gained from the synthetic deletion analysis combinations of 5' and 3' minimal sequences were constructed and tested for their transformation capabilities. The pBSII-ECFP-R-TR/L construct is composed of a 35 bp 5' TRD lacking any 5' ID sequence, coupled to a fragment containing the 63 bp 3' TRD and 172 bp of the adjacent 3' ID sequence. This combination did not yield any transformants, confirming the necessity for having 5' ID sequences in combination with 3' ID sequences for efficient transformation.

Unexpectedly, addition of 66 bp of the 5' ID sequences to the 5' TRD sequences in the construct pBSII-ECFP-R1/L was not sufficient to recover transformation capacity when paired with the 172 bp 3' ID sequences, even though the lower limit of essential 5' ID sequences as 66 bp using pBSII-ECFP-R1/L5 had been previously defined (Table 4). Increasing the 5' ID sequences to 276 bp in the pBSII-ITR1.1k-ECFP plasmid recovered the full transformation capability when paired with the 172 bp 3' ID sequence (Table 4). The minimal operational sequence requirement for 5' ID sequences is therefore between 276 and 66 bp when coupled to a minimal 3' ID sequence of 172 bp.

Two independent verifications of the pBSII-ITR1.1k-ECFP plasmid transforming capabilities were conducted for transformation of *D. melanogaster*. These transformation studies resulted in calculated frequencies of 13.9% (FIG. 24) and 36% (Table 3). The discrepancy in frequencies may be attributed at least in some part to differences in injection protocols between labs. Unless otherwise indicated, the transformation frequencies presented in Table 3 were obtained with injections of 0.6:0.6 μg/μl vector:helper concentration ratios. The increased efficiency of transformation for pBSII-ITR 1.1k-ECFP observed in the second independent trial seems to be related to a decreased vector:helper concentration in *D. melanogaster*.

Five recovered pBSII-ITR1.1k-ECFP transformed strains were used to perform genetic mapping to identify their chromosome locations. Several of the strains had insertions on the second and third chromosomes (including strain 1), while strain 3 had an insertion on the X chromosome. Strain 1 and strain 3 were chosen for further analyses.

Direct PCR Analysis of Integrations:

Genomic DNAs from each of the transformed strains obtained with the synthetic deletion constructs in FIG. 1, as well as the piggyBac positive strain M23.1 and the negative white eye strain w[1118], were used to perform two sets of PCRs to verify the presence of the piggyBac 5' and 3' terminal repeat regions. An additional negative control PCR was performed on all transformants to show the absence of the external lambda phage DNA stuffer sequence (FIG. 25).

The first set of PCRs utilized the IFP2_R1 and MF34 primers to amplify the 5' terminal repeat regions, and the second set of PCRs used the IFP2_L and MF34 primers to amplify the 3' terminal repeat regions. All of the synthetic deletion transformed strains, the M23.1 control strain, and the plasmid control yielded a strong PCR product of the correct size for each of the primer sets, confirming the presence of both of the piggyBac terminal repeat regions in all of the transformed strains. The white eye strain w[1118] yielded a very weak product of the correct size with the 5' terminal repeat PCR amplification, but failed to generate a product with the 3' terminal specific primer set.

A third set of PCRs was performed using the IFP2_R1 and IFP2_L primers in an attempt to amplify the external lambda phage DNA stuffer sequence which would be present if an insertion resulted from recombination of the entire plasmid sequence rather than transposition. The control product from this PCR reaction is a 925 bp fragment, and no such corresponding fragments were generated with any of the transformed strain genomic DNAs.

Example 23—Southern Hybridization Analysis

Southern hybridization analysis was performed to verify the copy number and further confirm transposition of the piggyBac deletion plasmids into the *Drosophila* genome (FIG. 27, FIG. 29). Genomic DNAs from two of the pBSII-ITR1.1k-ECFP strains (strain 1 and strain 3) and one of each of the other strains were digested with Hind III, with the pBSII-ITR1.1k-ECFP plasmid Hind III digest as a plasmid control. The Hind III digestion of all transformed strains is expected to generate four fragments after transpositional insertion: the pBSII plasmid backbone fragment (2960 bp), the 3xP3-ECFP marker fragment (1158 bp), the piggyBac 5' terminus fragment and the piggyBac 3' terminus fragment. Using the pBSII-ITR1.1k-ECFP plasmid as probe, all four fragments generated by the Hind III digestion may be detected.

The diagnostic 2960 bp pBSII backbone and 1158 bp ECFP marker fragments were present in all of the transformed strains examined. All of these strains also exhibited at least two additional bands corresponding to the piggyBac termini and adjacent sequences at the integration site (FIG. 27). These results confirmed that the observed frequencies were the result of transpositional integrations.

Example 24—Analysis of Insertion Site Sequences

To further verify that piggyBac-mediated transposition of the synthetic deletion constructs occurred in these transformants, individual insertion sites were examined by isolating joining regions between the transposon and genomic sequences using either universal PCR or inverse PCR. Subsequent sequencing analysis of these joining regions demonstrated that all of the insertions occurred exclusively at single TTAA target sites that were duplicated upon insertion, and all insertion sites had adjacent sequences that were unrelated to the vector (Table 4). The two pBSII-ITR1.1k-ECFP strains 1 and 3 have a single insertion on the third and X chromosome respectively. This data is consistent with the information obtained from genetic crosses with balancer strains.

During sequence analysis of the integration sites a reported point mutation in the present constructs was confirmed that occurs at position 2426 in the piggyBac sequence, within the 3' TRD at the boundary of the 31 bp spacer and the internal repeat sequence. This point mutation was apparently generated in constructing the pIAO-P/L plasmid (Li et al., 2001b) and was therefore present in all of the constructs generated by the PCR syntheses employed in these studies. This point mutation had no apparent effect on the transformation frequencies as evidenced by the efficiency of transformation obtained with pBSII-ITR1.1k-ECFP.

The available piggyBac insertion site data from previous reports and these studies were compiled and aligned using ClustalX to identify a potential common insertion site motif (Table 5). No apparent consensus motif arose from the comparison of these sequences outside of the required TTAA target site.

TABLE 2

A listing of the synthetic oligonucleotide primers used (SEQ ID NOS 73-106 respectively in order of appearance:

| Internal Deletion Primers | |
|---|---|
| IFP2_R1 | ACTTCTAGAGTCCTAAATTGCAAACAGCGAC |
| IFP2_R2 | ACTTCTAGACACGTAAGTAGAACATGAAATAAC |
| IFP2_R3 | ACTTCTAGATCACTGTCAGAATCCTCACCAAC |
| IFP2_R4 | ACTTCTAGAAGAAGCCAATGAAGAACCTGG |
| IFP2_L1 | ACTTCTAGAAATAAATAAATAAACATAAATAAATTG |
| IFP2_L2 | ACTTCTAGAGAAAGGCAAATGCATCGTGC |
| IFP2_L3 | ACTTCTAGACGCAAAAAATTTATGAGAAACC |
| IFP2_L4 | ACTTCTAGAGATGAGGATGCTTCTATCAACG |
| IFP2_L5 | ACTTCTAGACGCGAGATACCGGAAGTACTG |
| IFP2_L | ACTTCTAGACTCGAGAGAGAATGTTTAAAAGTTTTGTT |
| IFP2_R-TR | ACTTCTAGACATGCGTCAATTTTACGCAGACTATCTTTC TAGGGTTAATCTAGCTGCATCAGG |

| Other Primers | |
|---|---|
| ExFP_For | ACGACTAGTGTTCCCACAATGGTTAATTCG |
| ExFP_Rev | ACGACTAGTGCCGTACGCGTATCGATAAGC |
| IFP2orf_For | GGATCCTATATAATAAAATGGGTAGTTCTT |
| IFP2orf_Rev | GGATCCAAATTCAACAAACAATTTATTTATG |
| MF34 | GGATCCTCTAGATTAACCCTAGAAAGATA |
| Univ-1 | TAATACGACTCACTATAGGGNNNNNNNNNNCTAT |
| Univ-2 | TAATACGACTCACTATAGGGNNNNNNNNNNAGTGC |
| Univ-3 | TAATACGACTCACTATAGGGNNNNNNNNNNGAATTC |
| Univ-4 | TAATACGACTCACTATAGGGNNNNNNNNNNAGTACT |

TABLE 2-continued

A listing of the synthetic oligonucleotide primers used (SEQ ID NOS 73-106 respectively in order of appearance:

| | |
|---|---|
| Univ-5 | TAATACGACTCACTATAGGGNNNNNNNNNNNAAGCTT |
| Univ-6 | TAATACGACTCACTATAGGGNNNNNNNNNNGGATCC |
| Univ-7 | TAATACGACTCACTATAGGGNNNNNNNNNNNCTAG |
| iPCR_R1 | ATTTTACGCAGACTATCTTTCTA |
| T7 | TTAATACGACTCACTAT |
| MF14 | GGATCCGCGGTAAGTGTCACTGA |
| JF3 | GGATCCTCGATATACAGACCGATAAAAACACATG |
| IFP2_Lb | ACTGGGCCCATACTAATAATAAATTCAACAAAC |
| iPCR_6 | TTATTTCATGTTCTACTTACGTG |
| iPCR_L1 | TGATTATCTTTAACGTACGTCAC |
| MF04 | GTCAGTCCAGAAACAACTTTGGC |
| IFP2_L-R+ | CTAGAAATTTATTTATGTTTATTTATTTATTA |
| MCS_For | ACGCGTAGATCTTAATACGACTCACTATAGGG |
| MCS_Rev | ACGCGTAGATCTAATTAACCCTCACTAAAGGG |

TABLE 3

Transformation of *Drosophila melanogaster*

| Plasmid | Experiment | Embryos Injected | Embryos Hatched | Adults mated | Transformed Lines | Frequency | Overall Frequency | STD DEV | STD ERR |
|---|---|---|---|---|---|---|---|---|---|
| p(PZ)-Bac-EYFP | 1 | 920 | 136 | 55 | 1 | 1.8% | 0.6% | 1.0% | ±0.6% |
| | 2 | 910 | 120 | 56 | 0 | 0.0% | | | |
| | 3 | 900 | 120 | 55 | 0 | 0.0% | | | |
| pBSII-ECFP-R1/L5 | 1 | 350 | 86 | 21 | 2 | 9.5% | 8.9% | 1.8% | ±1.0% |
| | 2 | 280 | 70 | 16 | 1 | 6.3% | | | |
| | 3 | 360 | 84 | 33 | 3 | 9.1% | | | |
| pBSII-ECFP-R2/L5 | 1 | 320 | 37 | 11 | 1 | 9.1% | 12.5% | 7.7% | ±5.4% |
| | 2 | 300 | 38 | 5 | 1 | 20.0% | | | |
| pBSII-ECFP-R3/L5 | 1 | 220 | 39 | 7 | 1 | 14.3% | 15.0% | 0.8% | ±0.6% |
| | 2 | 430 | 88 | 13 | 2 | 15.4% | | | |
| pBSII-ECFP-R4/L5 | 1 | 220 | 59 | 12 | 1 | 8.3% | 12.9% | 5.3% | ±3.7% |
| | 2 | 510 | 123 | 19 | 3 | 15.8% | | | |
| pBSII-ECFP-R4/L4 | 1 | 340 | 108 | 21 | 1 | 4.8% | 10.7% | 16.8% | ±11.9% |
| | 2 | 330 | 61 | 7 | 2 | 28.6% | | | |
| pBSII-ECFP-R4/L3 | 1 | 220 | 39 | 9 | 0 | 0.0% | 9.7% | 12.9% | ±7.4% |
| | 2 | 240 | 53 | 14 | 1 | 7.1% | | | |
| | 3 | 250 | 55 | 8 | 2 | 25.0% | | | |
| pBSII-ECFP-R4/L2 | 1 | 320 | 43 | 11 | 1 | 9.1% | 10.8% | 4.9% | ±3.5% |
| | 2 | 530 | 148 | 25 | 4 | 16.0% | | | |
| pBSII-ECFP-R4/L1 | 1 | 350 | 89 | 30 | 0 | 0.0% | 0.0% | N/A | N/A |
| | 2 | 160 | 33 | 16 | 0 | 0.0% | | | |
| | 3 | 330 | 78 | 25 | 0 | 0.0% | | | |
| | 4 | 150 | 31 | 15 | 0 | 0.0% | | | |
| pBSII-ECFP-R-TR/L | 1 | 280 | 73 | 31 | 0 | 0.0% | 0.0% | N/A | N/A |
| | 2 | 330 | 96 | 40 | 0 | 0.0% | | | |
| pBSII-ECFP-R1/L | 1 | 220 | 63 | 19 | 0 | 0.0% | 0.0% | N/A | N/A |
| | 2 | 290 | 80 | 23 | 0 | 0.0% | | | |
| | 3 | 330 | 104 | 27 | 0 | 0.0% | | | |
| pBac{3xP3-ECFPafm} | 1 | 300 | 45 | 14 | 2 | 14.3% | 12.9% | 1.8% | ±1.3% |
| | 2 | 350 | 59 | 17 | 2 | 11.8% | | | |
| pBSII-ITR1.1K-ECFP | 1 | 530 | 128 | 36 | 5 | 13.9% | 13.9% | N/A | N/A |
| pXL-BacII-ECFP | 1 | 500 | 80 | 14 | 3 | 21.4% | 22.2% | 0.9% | ±0.6% |
| | 2 | 520 | 101 | 22 | 5 | 22.7% | | | |
| pBSII-ITR1.1k-ECFP* | 1 | 515 | 120 | 22 | 8 | 36.4% | 36.4% | N/A | N/A |
| pXL-BacII-ECFP* | 1 | 533 | 199 | 88 | 22 | 25.0% | 25.0% | N/A | N/A |

Table 3 These injections were done independently (Handler lab) using a 0.4:0.2 ug/ul vector/helper concentration ratio of DNA. Statistical analysis of the data show no significant difference between frequencies obtained with any of the synthetic deletion mutants that yielded detectable numbers of transformants and the control plasmid pBac{3xP3-ECFPafm}. The assay cannot be interpreted to represent relative efficiencies of transformation among these constructs, but only whether a particular construct was able to generate transformants at a detectable frequency with the number of surviving injected flies analyzed.

TABLE 4

Transformed *Drosophila* Insertion Sites:

| | Chromosome | Insertion Site Sequence | |
|---|---|---|---|
| Strain Name | Location | 3' junction | 5' junction |
| p(PZ)-Bac-EYFP | 3R | CCAAACTTCGGCGATGTTTTCTTAA--piggyBac-- | |
| pBSII-ITR1.1k-ECFP-1 | 3R | TAGAATTCATGTTTCCAATTTTTTAA--piggyBac-- | |

TABLE 4-continued

Transformed *Drosophila* Insertion Sites:

| Strain Name | Chromosome Location | Insertion Site Sequence 3' junction | 5' junction |
|---|---|---|---|
| pBSII-ITR1.1k-ECFP-3 | X | | --piggyBac--TTAAATTCGCATATGTGCAAATGTT |
| pBSII-ECFP-R1/L5 | 3I | TCGGGTGGCACGTTGTGGATTTTAA--piggyBac-- | TTAAGCATGTCCTTAAGCATAAAT |
| pBSII-ECFP-R2/L5 | 2I | AAATACGTCACTCCCCTTCCCTTAA--piggyBac-- | TTAATGCTAGCTGCATGCAGGATGC |
| pBSII-ECFP-R3/L5 | 2R | AGCTGCACTCACCGGATGTCCTTAA--piggyBac-- | TTAAACAAAAAATGAAACATAAGG |
| pBSII-ECFP-R4/L5 | 2R | CCCAAAGTATAGTTAAATAGCTTAA--piggyBac-- | TTAAAGGAATTAATAAAAATACAA |
| pBSII-ECFP-R4/L4 | 2R | GTTTATTTATGATTAGAGCCTTTAA--piggyBac-- | TTAATCTCCTCCGCCCTTCTTCAATT |
| pBSII-ECFP-R4/L3 | 2R | TGTTGTTTTTTTGTCCCCACGTTTAA--piggyBac-- | TTAAACAAACACCTTTGACAAATTT |
| pBSII-ECFP-R4/L2 | 2I | CTGCCTCTAGCCGCCTGCTTTATTAA--piggyBac-- | TTAATATTAATTGAAAATAAATGCA |

The 5' (SEQ ID NOS 116-123) and 3' (SEQ ID NOS 107-115) flanking sequences for the inserted piggyBac sequences in each strain were obtained using end-specific inverse PCR (Materials and Methods) followed by cloning and sequencing of the recovered fragments. The chromosomal locations were determined from the sequences using the BLAST search program against the available *Drosophila* sequence in the GenBank library.

TABLE 5

Percentage of each nucleotide at piggyBac insertion sites flanking sequences from position −10 to +10.

% of each nucleotide at piggyBac insertion sites flanking sequences

| Nucleotide | −10 | −9 | −8 | −7 | −6 | −5 | −4 | −3 | −2 | −1 | TTAA | +1 | +2 | +3 | +4 | +5 | +6 | +7 | +8 | +9 | +10 |
|---|---|---|---|---|---|---|---|---|---|---|---|---|---|---|---|---|---|---|---|---|---|
| A | 22 | 31 | 38 | 33 | 26 | 27 | 16 | 18 | 18 | 29 | | 41 | 28 | 43 | 41 | 42 | 43 | 28 | 34 | 33 | 40 |
| C | 20 | 19 | 22 | 17 | 17 | 23 | 15 | 20 | 26 | 15 | | 11 | 20 | 18 | 20 | 15 | 17 | 21 | 23 | 16 | 11 |
| G | 28 | 19 | 17 | 16 | 24 | 8 | 24 | 16 | 19 | 12 | | 18 | 29 | 22 | 13 | 20 | 12 | 23 | 6 | 15 | 11 |
| T | 30 | 31 | 23 | 34 | 33 | 42 | 45 | 46 | 37 | 44 | | 30 | 23 | 17 | 26 | 23 | 28 | 28 | 37 | 36 | 38 |

Note:
Percentage of each nucleotide at piggyBac insertion site flanking sequences from position −10 to +10. The available piggyBac insertion sites include insertion sites in transformed insect genomes (Handler et al., 1998; Toshiki et al., 1999; Handler et al., 1999; Peloquin et al., 2000; Thomas et al., 2001; Handler and Harrell, 2000; Hediger et al., 2001; Kokoza et al., 2001; Nolan et al., 2002; Heinrich et al., 2002; Grossman et al., 2001; Lobo et al., 2002; Perera et al., 2002; Mandrioli and Wimmer, 2003; Sumitani et al., 2003; Elick et al., 1996; Li et al., 2001a; data from this report), insertion sites in baculoviruses (Lynne et al., 1989; Fraser et al., 1995) and insertion sites in transposition assay target plasmid pGDV1(Thibault et al., 1999; Grossman et al., 2000; Lobo, Li and Fraser, unpublished and Li et al., 2001a). No consensus aside from the TTAA target site is apparent among these insertion sites. However, the piggyBac transposable element does have a preference of inserting in the TA rich region with 4~5 Ts before and 5~6 As after the TTAA target site.

Attempts to transform insects using plasmids containing a previously reported piggyBac ITR minimal sequence cartridge (Li et al., 2001b), that has facing 5' and 3' TRDs with their respective TTAA target sites and is completely devoid of ID sequences, failed to produce a transformation frequency that was comparable to frequencies obtained with full length or conservative ID deletion constructs (Handler and Harrell, 1999; Horn and Wimmer, 2000).

Frequencies of transposition obtained for the ITR-based p(PZ)-Bac-EYFP and the similarly constructed pBS-pBac/DsRed were far less than expected. While Southern hybridization and inverse PCR analyses did confirm that the single transformant recovered with p(PZ)-Bac-EYFP had resulted from transpositional insertion, the efficient transposition of piggyBac minimal vectors evidenced in interplasmid transposition assays (Li et al., 2001b) did not necessarily predict the properties of piggyBac transposon movement in germline transformations.

The fact that germline transposition involves distinctly different cell populations than interplasmid transposition in injected embryos may explain these discrepancies. Similar discrepancies between transformation results and artificial transposition assays have been reported with other Class II transposons (Tosi and Beverley, 2000; Lohe and Hartl, 2001; Lozovsky et al., 2002). In addition, the Hermes transposable element undergoes normal cut-and-paste transposition in plasmid-based transposition assays (Sarkar et al., 1997a), but germline integrations in *Ae. aegypti* seem to occur either through general recombination or through a partial replicative transposition mechanism (Jasinskiene et al., 2000).

The synthetic cartridge approach used to examine the role of ID sequences in effecting efficient germline transposition has the advantage of examining the involvement of sequences through reconstruction rather than by analysis of successive internal deletions. The main disadvantage of this approach in analyzing piggyBac is the high AT content of the transposon, which limits the position of useful primers. As a result, the present analyses does not define the exact limits of the requisite sequences. However, some of the most effective nucleic acid sequences are delimited to a relatively narrow 250 bp of TRD adjacent nucleic acid sequences.

Transformation results from synthetic unidirectional deletion plasmids shown here demonstrates that no more than about 66 bp (nt 36~101) of the piggyBac 5' nucleic acid sequence and about 378 bp (nt 2031~2409) of the piggyBac 3' nucleic acid sequence are necessary for efficient transformation when these deletions are paired with long (378 or 311 bp, respectively, or longer) nucleic acid sequences from the opposite end of the transposon. The transformation data from the pBSII-ITR1.1k-ECFP plasmid further defines the 3' nucleic acid sequence as 172 bp (nt 2237~2409). Combining this same 172 bp 3' nucleic acid sequence with only the 5' TRD in the pBSII-ECFP-R-TR/L plasmid yielded no transformants, demonstrating that the 3' nucleic acid sequence alone was insufficient for full mobility. Unexpectedly, adding the 66 bp 5' nucleic acid sequence in pBSII-ECFP-R1/L also does not allow recovery of full transformation capability while the same 66 bp does allow full transformation capability when coupled to the larger (955 bp) 3' nucleic acid sequence in pBSII-ECFP-R1/L5. This result cannot be explained by size alone, since the ITR cartridge strategy used to test these deletion sequence constructs effectively replaces the rest of the piggyBac nucleic acid sequence with the 2961 bp pBSII plasmid sequence.

The frequencies obtained for a given construct may be higher or lower relative to the control. The present studies detect the limits of nucleic acid sequences that yield acceptable transformation frequencies, and do not evaluate the effectiveness of the deleted regions relative to one another.

The present results indicate the presence of important nucleic acid sequences between nucleotides 66 and 311 of the 5' nucleic acid sequence used for construction of the pBSII-ITR1.1k-ECFP, since this construct exhibits full transforming capability when matched with the L 3' ID sequence. Compensating sequences must be present in 3' nucleic acid sequences longer than 172 bp, since the 955 bp 3' nucleic acid sequence included with primer L5 is able to compensate for the 66 bp 5' nucleic acid sequence (construct pBSII-ECFP-R1/L5). There was noted a presence of small repeats in the 5' nucleic acid sequence of pBSII-ITR1.1K-ECFP that are matched by similar sequences in the 3' nucleic acid sequences included in construct pBSII-ECFP-R1/L5. These relatively small repeats (FIG. 28) occur in direct or opposite orientations and are also found in several other locations within the piggyBac nucleic acid sequence. There does seem to be a correlation between efficient transgenesis and the presence of at least one CAAAAT repeat in the 3' nucleic acid sequence combined with at least one in the 5' nucleic acid sequence, or the compensating presence of two or three sequence repeats in the 3' nucleic acid sequence. In some embodiments of the present inventive methods of transformation, the presence of this small repeat CAAAAT may be described as facilitating transpositional activity of piggyBac constructs.

Previous observations of efficient interplasmid transposition for the piggyBac ITR construct, completely devoid of piggyBac internal domain nucleic acid sequences (ID), support a mechanism for movement in which the piggyBac transposase binds at the terminal repeat regions (IR, spacer and TR) to effect transposition (Li et al., 2001b). Since the cut-and-paste reactions of excision and transposition do not appear to require ID sequences, the relatively unsuccessful application of the previously constructed ITR cartridge for germ-line transformation suggests the required ID sequences may be involved in other aspects of the transformation process than the mechanics of cut-and-paste. These other aspects seem to be linked to differential movement in germ line cells.

The presence of sequences important for full transforming capability within internal domains of transposons is not without precedent. Transposase binding to target sequences at or near the ends of the element is necessary to generate a synaptic complex that brings the ends of the element together for subsequent DNA cleavage (reviewed by Saedler and Gierl, 1996), but the efficiency of this interaction can be influenced by other sequences in the transposon. Multiple transposase binding sites or accessory factor binding sites are identified in other Class II transposon systems. Efficient transposition of mariner requires the continuity of several internal regions of this element and their proper spacing with respect to the terminal repeats (Lohe and Hartl, 2001; Lozovsky et al., 2002), although they are not essential for in vitro transposition (Tosi and Beverley, 2000). The P element transposase binding occurs at 10 bp subterminal sequences present at both 5' and 3' ends, while the 31 bp terminal inverted repeat is recognized by a *Drosophila* host protein, IRBP (inverted repeat binding protein), and an internally located 11 bp inverted repeat is shown to act as a transpositional enhancer in vivo (Rio and Rubin, 1988; Kaufman et al., 1989; Mullins et al., 1989). The maize Ac transposase binds specifically and cooperatively to repetitive ACG and TCG trinucleotides, which are found in more than 20 copies in both 5' and 3' subterminal regions, although the Ac transposase also weakly interacts with the terminal repeats (Kunze and Starlinger 1989; Becker and Kunze 1997). The TNPA transposase of the En/Spm element binds a 12 bp sequence found in multiple copies within the 5' and 3' 300 bp subterminal repeat regions (Gierl et al., 1988; Trentmann et al., 1993). The *Arabidopsis* transposon Tag1 also requires minimal subterminal sequences and a minimal internal spacer between 238 bp and 325 bp for efficient transposition (Liu et al., 2000). The Sleeping Beauty (SB) transposable element contains two transposase binding sites (DRs) at the end of the ~230 bp terminal inverted repeats (Ivics et al., 1997). The DNA-bending protein HMGB1, a cellular cofactor, was found to interact with the SB transposase in vivo to stimulate preferential binding of the transposase to the DR further from the cleavage site, and promoted bending of DNA fragments containing the transposon IR (Zayed et al., 2003).

These examples demonstrate that the piggyBac transposase or some host accessory factors could be binding to the identified critical TRD adjacent ID regions to promote efficient transposition in germ-line cells. While not intending to be limited to any particular theory or mechanism of action, these subterminal ID sequences may serve as additional piggyBac transposase binding sites, thus increasing the efficiency of movement by cooperative binding of the transposase. Alternatively, these sequences may serve as some accessory factor binding site(s) responsible for efficient alignment of the termini or facilitating association of the transposon with chromatin-complexed genomic sequences.

The present results force a reassessment of the reliability of plasmid-based transposition assays in predicting piggyBac movement for transgenesis. Plasmid-based transposition assays, while facilitating mutational analyses of the transposon, are likely to be reliable predictors of in vivo movement only when alterations lead to a loss of movement. This difference is likely due to the fact that plasmid-based assays indicate the activity of the transposon in somatic cells while transformation assays assess movement in germ-line cells. Chromatin in the primordial germ cells is structured and regulated differently than that of blastoderm cells (reviewed by Wolffe, 1996). This difference could contribute to different results in the two types of assays. Interplamsid transposition assays utilize purified supercoiled DNA as the target, while transformation assays target chromatin. Nucleosome formation on negatively supercoiled DNA occurs virtually instantaneously in vitro (Pfaffle and Jackson, 1990), and target plasmid DNA introduced into the embryo cells would most likely form nucleosome structures, but there will be a significant difference in complexity compared to chromatin. This difference in complexity could be the cause of different transposition results. Alternatively, the absence of additional transposase or accessory factor binding sites on the transposon could result in less efficient translocation of the DNA to the nucleus, or lessened affinity of the transposon/transposase complex for the genomic DNA.

Example 25—TRD Point Mutation Analysis

Sequence analysis of integrated constructs and subsequent detailed analysis of all the constructs confirms a point mutation in the TRD of all constructs examined in this study. This mutation is a C-A transversion in the 19 bp internal repeat sequence of the 3' TRD (FIG. 30). This point mutation originated during construction of the pIAO plasmid (Li et al., 2001b), and is most likely the result of mis-incorporation during PCR amplification. However, our results confirm that this mutation has no significant effect on the transformation efficiency.

Under the conditions of the present direct PGR amplification using piggyBac 5' terminus-specific primers, a weak band of the same size as the expected piggyBac band was generated from control $w^{1118}$ flies. The Southern hybridizations detected a 1.3 kb band in all of the transformants that was distinct from the pBSII backbone fragment (2.96 kb) and 3xP3-ECFP (1.16 kb) marker bands. piggyBac-like. sequences have been detected in many species by PGR and Southern hybridization analysis using probes derived from the piggyBac 5' terminal region, including moths, flies, beetles, etc. (reviewed by Handler, 2002). A homology search against the available sequence database has identified the existence of the piggyBac-like sequences in the *D. melanogaster* genome (Sarkar et ai, 2003). These results reflect the presence of one of these degenerate piggyBac-Wke sequences in the *Drosophila* genome.

The insertion sites in the transformed fly strains were identified by either universal PCR or inverse PCR techniques. All insertions occurred exclusively at TTAA sites verifying that these insertions were due to a specific piggy-Bac transposase-mediated mechanism (Fraser et al., 1995). A ClustalX alignment of all piggyBac insertion sites identified here, including insertion sites in the transposition assay target plasmid pGDV1 (Sarkar et al., 1997b), baculovirus, and transformed insect genomes, does not reveal any further significant similarities (Table 5). The proposed existence of a larger piggyBac insertion consensus sequence YYTTTTTT/AARTAAYAG (SEQ ID NO: 124) (Y=pyrimidine, R=purine, /=insertion point) by Cary et al. (1989) and Grossman et al. (2000), and a short 8 bp consensus sequence A/TNA/TTTAAA/T (SEQ ID NO: 125) proposed by Li et al. (2001a) seem to be contradicted by the accumulated insertion site data. A decided preference was noted for piggyBac insertion within TTAA target sites flanked by 4-5 Ts on the 5' side and 5-6 As on the 3' side (Table 5).

Based on the minimal piggyBac vector pBSII-ITR1.1k-ECFP, a plasmid minimal vector, pXL-BacII-ECFP, was constructed which also yields a high frequency of transformation in *D. melanogaster* (Table 3). The present results confirm that both the pBSIIITR1.1k-ECFP and the pXL-BacII-ECFP minimal vectors can serve as highly efficient piggyBac transformation vectors.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The following materials are hereby specifically incorporated herein by reference in their entirety.
1. Ausubel F M, et al. (1994), Current Protocols in Molecular Biology, John Wiley & Sons, Inc.
2. Becker H A, Kunze R (1997), Mol. Gen. Genet., 254(3): 219-30.
3. Beeman R W, Stauth D M (1997), Insect Mol. Biol., 6(1): 83-8.
4. Berghammer A J, et al. (1999), Nature, 402: 370-371.
5. Buck T A, et al. (1997), Mol. Gen. Genet., 255: 605-610.
6. Cary L C, et al. (1989), Virology, 172: 156-169.
7. Elick T A, et al. (1996a), Genetica, 97(2): 127-139.
8. Elick T A, Bauser C A, Fraser M J Jr (1996b), Genetica., 98(1): 33-41.
9. Elick T A, et al. (1997), Mol. Gen. Genet., 255(6): 605-610.
10. Fraser M J Jr, et al. (1983), J. Virol., 47: 287-300.
11. Fraser M J Jr, et al. (1985), Virology, 145(2): 356-61.
12. Fraser M J Jr, et al. (1995), Virology, 211(2): 397-407.
13. Fraser M J Jr, Ciszczon T, Elick T, Bauser C (1996), Insect Mol. Biol., 5(2): 141-51.
14. Geier, G. and Modrich, P. (1979) J. Biol. Chem., 254 (4):1408-1413.
15. Gierl A, Lutticke S, Saedler H (1988), EMBO J., 7(13): 4045-53.
16. Goryshin I Y, et al. (1994), Proc. Natl. Acad. USA, 91: 10834-10838.
17. Grossman G L, et al. (2000), Insect Biochem. Mol. Biol., 30(10): 909-14.
18. Grossman G L, et al. (2001), Insect Mol. Biol., 10(6): 597-604.
19. Grossniklaus U, et al. (1992), Genes Dev., 6(6): 1030-51.
20. Handler A M, et al. (1998) Proc. Natl. Acad. Sci. USA, 95(13): 7520-5.
21. Handler A M, Harrell R A $2^{nd}$ (1999), Insect Mol. Biol., 8(4): 449-57.
22. Handler A M, McCombs S D (2000), Insect Mol. Biol., 9(6): 605-12.
23. Handler A M, Harrell R A $2^{nd}$ (2001a), Biotechniques, 31(4): pp. 824-8.
24. Handler A M, Harrell R A $2^{nd}$ (2001b), Insect Biochem. Mol. Biol., 31(2): 199-205.
25. Handler A M (2002), Insect Biochem. Mol. Biol., 32(10): 1211-20.
26. Hediger M, et al. (2001), Insect Mol. Biol., 10(2): 113-9.
27. Heinrich J C, et al. (2002), Insect Mol. Biol., 11(1): 1-10.
28. Hirt B (1967), J. Mol. Bio., 26: 367-369.
29. Horn C, Wimmer E A (2000), Dev. Genes Evol., 210 (12): 630-7.
30. Ivics Z, Hackett P B, Plasterk R H, Izsvak Z (1997), Cell, 91(4): 501-10.
31. Jarvis et al. (1990), Biotechnology, 8 (10): 950-955.
32. Jasinskiene N, et al. (2000), Insect Mol. Biol., 9(1): 11-8.
33. Kaufman P D, et al. (1989), Cell, 59(2): 359-71.
34. Kokoza V, et al. (2001), Insect Biochem. Mol. Biol., 31(12): 1137-43.
35. Kunze R, Starlinger P (1989), EMBO J., 8(11): 3177-85.

36. Li X, Heinrich J C, Scott M J (2001a), Insect Mol. Biol., 10(5): 447-55.
37. Li X, Lobo N, Bauser C A, Fraser M J Jr (2001b), Mol. Genet. Gen., 266(2): 190-8.
38. Liu D, et al. (2000), Genetics, 157(2): 817-30.
39. Lobo N, Li X, Fraser M J Jr (1999), Mol. Gen. Genet., 261(4-5): 803-10.
40. Lobo N, et al. (2001), Mol. Genet. Gen., 265(1): 66-71.
41. Lobo N F, et al. (2002), Insect Mol. Biol., 11(2): 133-9.
42. Lohe A R, Hartl D L (2001), Genetics, 160(2): 519-26.
43. Lozovsky E R, et al. (2002), Genetics, 160(2): 527-35.
44. Mandrioli M, Wimmer E A (2002), Insect Biochem. Mol. Biol., 33(1): 1-5.
45. Mullins M C, Rio D C, Rubin G M (1989), Genes Dev., 3(5): 729-38.
46. Nolan T, et al. (2002), J. Biol. Chem., 277(11): 8759-62.
47. Ochman H, et al. (1988), Genetics, 120(3): 621-3.
48. Peloquin J J, et al. (2000), Insect Mol. Biol., 9(3): 323-33.
49. Perera O P, et al. (2002), Insect Mol. Biol., 11(4): 291-7.
50. Pfaffle P, Jackson V (1990), J. Biol. Chem., 265(28): 6821-9.
51. Rio, D C, Rubin G M (1988), Proc. Natl. Acad. Sci. USA, 85: 8929-8933.
52. Rubin G M, Spradling A C (1982), Science, 218(4570): 348-53.
53. Rubin G M, Spradling A C (1983), Nucleic Acids Res., 11(18): 6341-51.
54. Saedler H, Gierl A (Editors) (1996) Transposable Elements, Soringer-Verlag, Berlin.
55. Sambrook J, Fritsch E F, and Maniatis T (1989) Molecular Cloning: A Laboratory Manual (New York: Cold Spring Harbor Press).
56. Sarkar A, Yardley K, Atkinson P W, James A A, O'Brochta D A (1997a), Insect Biochem. Mol. Biol., 27(5): 359-63.
57. Sarkar A, et al. (1997b), Genetica., 99(1): 15-29.
58. Sarkar A, et al. (2003), Mol. Genet. Genomics, 270(2): 173-80.
59. Sekar V (1987), BioTechniques, 5: 11-13.
60. Sumitani M, et al. (2003), Insect Biochem. Mol. Biol., 33(4): 449-458.
61. Tamura T, et al. (2000), Nat. Biotechnol. 18(1): 81-4.
62. Thibault S T, et al. (1999), Insect Mol. Biol., 8(1): 119-23.
63. Thomas J L, et al. (2002), Insect Biochem. Mol. Biol., 32(3): 247-53.
64. Thummel, C S and Pirrotta, V (1992), Dros. Info. Service, 71: 150-150.
65. Tosi L R, Beverley S M (2000), Nucleic Acids Res., 28(3): 784-90.
66. Trentmann S M, Saedler H, Gierl A (1993), Mol. Gen. Genet., 238(1-2): 201-208.
67. Wang H H, Fraser M J Jr (1993), Insect Mol. Biol., 1: 109-116.
68. Zayed H, et al. (2003), Nucleic Acids Res., 31(9): 2313-2322.

What is claimed is:

1. A plasmid selected from the group consisting of pBSII-ECFP-R$_4$/L$_2$ deposited as ATCC Accession # PTA-122185, pBSII-ECFP-R$_4$/L$_3$ deposited as ATCC Accession # PTA-122183, and pBSII-ECFP-R$_4$/L$_4$ deposited as ATCC Accession # PTA-122184.

2. The plasmid of claim 1, wherein the plasmid is ECFP-R$_4$/L$_2$ deposited as ATCC Accession # PTA-122185.

3. The plasmid of claim 1, wherein the plasmid is pBSII-ECFP-R$_4$/L$_3$ deposited as ATCC Accession # PTA-122183.

4. The plasmid of claim 1 wherein the plasmid is pBSII-ECFP-R$_4$/L$_4$ deposited as ATCC Accession # PTA-122184.

* * * * *

SEQUENCE LISTING

```
<160> NUMBER OF SEQ ID NOS: 190

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggatcccatg cgtcaattttt acgca                                              25

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgactagtg ttcccacaat ggttaattcg                                          30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgactagtg ccgtacgcgt atcgataagc                                          30
```

```
<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcttgataag aagag                                                      15

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcatgttgct tgctatt                                                    17

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgtaagctt cgatgtcttt gtgatgcgcc                                      30

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acggaattca cttgcaactg aaacaatatc c                                    31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actctcgagg ttcccacaat ggttaattcg                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
actgaattca tggtggcgac cggtggatcg                                      30

<210> SEQ ID NO 10
```

-continued

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatcctcta gattaaccct agaaagata                                         29

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaagggccc gtgatacgcc tatttttata ggtt                                   34

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatcggtacc aacgcgcggg gagaggcggt ttgcg                                  35

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccaagggccc tgacgtgaac cattgtcaca cgt                                    33

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtgggtacc gtcgatcaaa caaacgcgag ataccg                                 36

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtcaatttt acgcagacta tctttctagg g                                      31

<210> SEQ ID NO 16
<211> LENGTH: 39
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttaaccctag aaagatagtc tgcgtaaaat tgacgcatg                              39

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtacgtcaca atatgattat ctttctaggg                                       30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttaaccctag aaagataatc atattgtgac                                       30

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttaattaacc ctagaaagat agtctgcgta aaattgacgc atg                        43

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttaattaacc ctagaaagat aatcatattg tgac                                  34

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctagtactag tgcgccgcgt acgtctagag acgcgcagtc tagaad                     46

<210> SEQ ID NO 22
<211> LENGTH: 46
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 22
ttctagactg cgcgtctcta gacgtacgcg gcgcactagt actagd                    46

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatgacctgc agtaggaaga cgd                                             23

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gactctagac gtacgcggag cttaaccctga gaaagatad                           39

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggattccatg cgtcaatttt acgcad                                          26

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggatcctcga tatacagacc gataaaaaca catgd                                35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtaccattg caaacagcga cggattcgcg ctatd                                35

<210> SEQ ID NO 28
<211> LENGTH: 32
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 28
acgcgtagat cttaatacga ctcactatag gg                                      32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgcgtagat ctaattaacc ctcactaaag gg                                      32

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctcgatata cagaccgata aaacacatg                                          29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcacgcctca gccgagctcc aagggcgac                                          29

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggatccctca aaatttcttc taaagta                                            27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggatccctca aaatttcttc taaagta                                            27

<210> SEQ ID NO 34
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
gcacgcctca gccgagctcc aagcggcgac                                          30

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttaatctaga ggatcctcta gattaa                                              26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttaatctaga cgtacgcgga gcttaa                                              26

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttaatctagc tagtactaga actagattaa                                          30

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttaatctagt tctagacgta cgcggcgcac tagtactagc tagattaa                      48

<210> SEQ ID NO 39
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttaatctagt tctagactgc gcgtctctag acgtacgcgg cgcactagta ctagctagat         60
taa                                                                       63

<210> SEQ ID NO 40
<211> LENGTH: 707
<212> TYPE: DNA
<213> ORGANISM: Artificial Sequence
```

<220> FEATURE:
<223> OTHER INFORMATION: Description of Artificial Sequence: Synthetic
      ITR cartridge sequence

<400> SEQUENCE: 40

| | | | | | |
|---|---|---|---|---|---|
| ggatcccatg | cgtcaatttt | acgcagacta | tctttctagg | gttaatctag | ctgcatcagg | 60 |
| atcatatcgt | cgggtctttt | ttccggctca | gtcatcgccc | aagctggcgc | tatctgggca | 120 |
| tcggggagga | agaagcccgt | gccttttccc | gcgaggttga | agcggcatgg | aaagagtttg | 180 |
| ccgaggatga | ctgctgctgc | attgacgttg | agcgaaaacg | cacgtttacc | atgatgattc | 240 |
| gggaaggtgt | ggccatgcac | gcctttaacg | gtgaactgtt | cgttcaggcc | acctgggata | 300 |
| ccagttcgtc | gcggcttttc | cggacacagt | tccggatggt | cagcccgaag | cgcatcagca | 360 |
| acccgaacaa | taccggcgac | agccggaact | gccgtgccgg | tgtgcagatt | aatgacagcg | 420 |
| gtgcggcgct | gggatattac | gtcagcgagg | acgggtatcc | tggctggatg | ccgcagaaat | 480 |
| ggacatggat | accccgtgag | ttacccggcg | ggcgcgcctc | gttcattcac | gtttttgaac | 540 |
| ccgtggagga | cgggcagact | cgcggtgcaa | atgtgtttta | cagcgtgatg | gagcagatga | 600 |
| agatgctcga | cacgctgcag | aacacgcagc | tagattaacc | ctagaaagat | aatcatattg | 660 |
| tgacgtacgt | taaagataat | catgcgtaaa | attgacgcat | gggatcc | | 707 |

<210> SEQ ID NO 41
<211> LENGTH: 3662
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 41

| | | | | | |
|---|---|---|---|---|---|
| ctaaattgta | agcgttaata | ttttgttaaa | attcgcgtta | aattttttgtt | aaatcagctc | 60 |
| attttttaac | caataggccg | aaatcggcaa | aatcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcctcgtt | cattcacgtt | tttgaacccg | tggaggacgg | 660 |
| gcagactcgc | ggtgcaaatg | tgttttacag | cgtgatggag | cagatgaaga | tgctcgacac | 720 |
| gctgcagaac | acgcagctag | attaacccta | gaaagataat | catattgtga | cgtacgttaa | 780 |
| agataatcat | gcgtaaaatt | gacgcatggg | atctgtaata | cgactcacta | tagggcgaat | 840 |
| tgggtaccgg | gccccccctc | gaggtcgacg | gtatcgataa | gcttgatatc | gaattcctgc | 900 |
| agcccggggg | atccactagt | tctagagcgg | ccgccaccgc | ggtggagctc | cagcttttgt | 960 |
| tccctttagt | gagggttaat | tagatcccat | gcgtcaattt | tacgcagact | atctttctag | 1020 |
| ggttaatcta | gctgcatcag | gatcatatcg | tcgggtcttt | tttccggctc | agtcatcgcc | 1080 |
| caagctggcg | ctatctgggc | atcggggagg | aagaagcccg | tgccttttcc | cgcgaggttg | 1140 |

```
aagcggcatg gaaagagttt gccgaggatg actgctgctg cattgacgtt gagcgaaaac    1200
gcacgtttac catgatgatt cgggaaggtg tggccatgca cgcctttaac ggtgaactgt    1260
tcgttcaggc cacctgggat accagttcgt cgcggctttt ccggacacag ttccggatgg    1320
tcagcccgaa gcgcatcagc aacccgaaca ataccggcga cagccggaac tgccgtgccg    1380
gtgtgcagat taatgacagc ggtgcggcgc tgggatatta cgtcagcgag acgggtatc    1440 ctggctggat gccgcagaaa tggacatgga taccccgtga gttacccggc gggcgcgctt    1500
ggcgtaatca tggtcatagc tgtttcctgt gtgaaattgt tatccgctca caattccaca    1560
caacatacga gccggaagca taaagtgtaa agcctgggt gcctaatgag tgagctaact    1620
cacattaatt gcgttgcgct cactgcccgc tttccagtcg ggaaacctgt cgtgccagct    1680
gcattaatga atcggccaac gcgcggggag aggcggtttg cgtattgggc gctcttccgc    1740
ttcctcgctc actgactcgc tgcgctcggt cgttcggctg cggcgagcgg tatcagctca    1800
ctcaaaggcg gtaatacggt tatccacaga atcaggggat aacgcaggaa agaacatgtg    1860
agcaaaaggc cagcaaaagg ccaggaaccg taaaaaggcc gcgttgctgg cgttttccca    1920
taggctccgc cccctgacg agcatcacaa aaatcgacgc tcaagtcaga ggtggcgaaa    1980
cccgacagga ctataaagat accaggcgtt tcccctgga agctcctcg tgcgctctcc    2040 tgttccgacc ctgccgctta ccggatacct gtccgccttt ctcccttcgg aagcgtggc    2100 gctttctcat agctcacgct gtaggtatct cagttcggtg taggtcgttc gctccaagct    2160
gggctgtgtg cacgaacccc ccgttcagcc cgaccgctgc gccttatccg gtaactatcg    2220
tcttgagtcc aacccggtaa gacacgactt atcgccactg gcagcagcca ctggtaacag    2280
gattagcaga gcgaggtatg taggcggtgc tacagagttc ttgaagtggt ggcctaacta    2340
cggctacact agaaggacag tatttggtat ctgcgctctg ctgaagccag ttaccttcgg    2400
aaaaagagtt ggtagctctt gatccggcaa acaaaccacc gctggtagcg gtggtttttt    2460
tgtttgcaag cagcagatta cgcgcagaaa aaaaggatct caagaagatc ctttgatctt    2520
ttctacgggg tctgacgctc agtggaacga aaactcacgt taagggattt tggtcatgag    2580
attatcaaaa aggatcttca cctagatcct tttaaattaa aaatgaagtt ttaaatcaat    2640
ctaaagtata tatgagtaaa cttggtctga cagttaccaa tgcttaatca gtgaggcacc    2700
tatctcagcg atctgtctat ttcgttcatc catagttgcc tgactccccg tcgtgtagat    2760
aactacgata cgggagggct taccatctgg ccccagtgct gcaatgatac cgcgagaccc    2820
acgctcaccg gctccagatt tatcagcaat aaaccagcca gccggaaggg ccgagcgcag    2880
aagtggtcct gcaactttat ccgcctccat ccagtctatt aattgttgcc gggaagctag    2940
agtaagtagt tcgccagtta atagtttgcg caacgttgtt gccattgcta caggcatcgt    3000
ggtgtcacgc tcgtcgtttg gtatggcttc attcagctcc ggttcccaac gatcaaggcg    3060
agttacatga tcccccatgt tgtgcaaaaa agcggttagc tccttcggtc ctccgatcgt    3120
tgtcagaagt aagttggccg cagtgttatc actcatggtt atggcagcac tgcataattc    3180
tcttactgtc atgccatccg taagatgctt ttctgtgact ggtgagtact caaccaagtc    3240
attctgagaa tagtgtatgc ggcgaccgag ttgctcttgc ccggcgtcaa tacgggataa    3300
taccgcgcca catagcagaa ctttaaaagt gctcatcatt ggaaaacgtt cttcggggcg    3360
aaaactctca aggatcttac cgctgttgag atccagttcg atgtaaccca ctcgtgcacc    3420
caactgatct tcagcatctt ttactttcac cagcgtttct gggtgagcaa aaacaggaag    3480
gcaaaatgcc gcaaaaaagg gaataagggc gacacggaaa tgttgaatac tcatactctt    3540
```

```
ccttttttcaa tattattgaa gcatttatca gggttattgt ctcatgagcg gatacatatt    3600
tgaatgtatt tagaaaaata aacaaatagg ggttccgcgc acatttcccc gaaaagtgcc    3660
ac                                                                   3662
```

<210> SEQ ID NO 42
<211> LENGTH: 5533
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 42

```
ctaaattgta agcgttaata ttttgttaaa attcgcgtta aattttttgtt aaatcagctc      60 atttttttaac caataggccg aaatcggcaa atcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttgggggt cgaggtgccg taaagcacta atcggaacc ctaaagggag      300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta gggcgaat ttgggtaccgg      660 gccccccctc gaggtcgacg gtatcgataa gctatccagt gcagtaaaaa ataaaaaaaa     720
aatatgtttt tttaaatcta cattctccaa aaaagggttt tattaactta catacatact     780
agaattgatc cccgatcccc ctagaatccc aaaacaaact ggttattgtg gtaggtcatt     840
tgtttggcag aagaaaactc gagaaatttc tctggccgtt attcgttatt ctctcttttc     900
ttttggggtc tcctctctg cactaatgct ctctcactct gtcacacagt aaacggcata     960
ctgctctcgt tggttcgaga gagcgcgcct cgaatgttcg cgaaagagc gccggagtat    1020 aaatagagcg cttcgtctac ggagcgacaa ttcaattcaa acaagcaaag tgaacacgtc    1080
gctaagcgaa agctaagcaa ataaacaagc gcagctgaac aagctaaaca atctgcagta    1140
aagtgcaagt taaagtgaat caattaaaag taaccagcaa ccaagtaaat caactgcaac    1200
tactgaaatc tgccaagaag taattattga atacaagaag agaactctga ataggggaatt    1260 gggaattcct gcagcccggg ggatcctata taataaaatg ggtagttctt tagacgatga    1320
gcatatcctc tctgctcttc tgcaaagcga tgacgagctt gttggtgagg attctgacag    1380
tgaaatatca gatcacgtaa gtgaagatga cgtccagagc gatacagaag aagcgtttat    1440
agatgaggta catgaagtgc agccaacgtc aagcggtagt gaaatattag acgaacaaaa    1500
tgttattgaa caaccaggtt cttcattggc ttctaacaga atcttgacct tgccacagag    1560
gactattaga ggtaagaata acattgttg gtcaacttca aagtccacga ggcgtagccg    1620
agtctctgca ctgaacattg tcagatctca aagaggtccg acgcgtatgt gccgcaatat    1680
atatgaccca cttttatgct tcaaactatt ttttactgat gagataattt cggaaattgt    1740
aaaatggaca aatgctgaga tatcattgaa acgtcgggaa tctatgacag gtgctacatt    1800
tcgtgacacg aatgaagatg aaatctatgc tttctttggt attctggtaa tgacagcagt    1860
```

```
gagaaaagat aaccacatgt ccacagatga cctctttgat cgatctttgt caatggtgta    1920
cgtctctgta atgagtcgtg atcgttttga tttttttgata cgatgtctta gaatggatga    1980
caaaagtata cggcccacac ttcgagaaaa cgatgtattt actcctgtta gaaaaatatg    2040
ggatctcttt atccatcagt gcatacaaaa ttacactcca ggggctcatt tgaccataga    2100
tgaacagtta cttggttttta gaggacggtg tccgtttagg atgtatatcc caaacaagcc    2160
aagtaagtat ggaataaaaa tcctcatgat gtgtgacagt ggtacgaagt atatgataaa    2220
tggaatgcct tatttgggaa gaggaacaca gaccaacgga gtaccactcg gtgaatacta    2280
cgtgaaggag ttatcaaagc ctgtgcacgg tagttgtcgt aatattacgt gtgacaattg    2340
gttcacctca atccctttgg caaaaaactt actacaagaa ccgtataagt taaccattgt    2400
gggaaccgtg cgatcaaaca aacgcgagat accggaagta ctgaaaaaca gtcgctccag    2460
gccagtggga acatcgatgt tttgttttga cggaccccctt actctcgtct catataaacc    2520
gaagccagct aagatggtat acttattatc atcttgtgat gaggatgctt ctatcaacga    2580
aagtaccggt aaaccgcaaa tggttatgta ttataatcaa actaaaggcg agtggacac    2640 gctagaccaa atgtgttctg tgatgacctg cagtaggaag acgaataggt ggcctatggc    2700
attattgtac ggaatgataa acattgcctg cataaattct tttattatat acagccataa    2760
tgtcagtagc aagggagaaa aggttcaaag tcgcaaaaaa tttatgagaa acctttacat    2820
gagcctgacg tcatcgttta tgcgtaagcg tttagaagct cctactttga agagatattt    2880
gcgcgataat atctctaata ttttgccaaa tgaagtgcct ggtacatcag atgacagtac    2940
tgaagagcca gtaatgaaaa aacgtactta ctgtacttac tgcccctcta aaataaggcg    3000
aaaggcaaat gcatcgtgca aaaaatgcaa aaaagttatt tgtcgagagc ataatattga    3060
tatgtgccaa agttgtttct gactgactaa taagtataat ttgtttctat tatgtataag    3120
ttaagctaat tacttatttt ataatacaac atgactgttt ttaaagtaca aaataagttt    3180 attttgtaa aagagagaat gtttaaaagt tttgttactt tagaagaaat tttgagtttt    3240 tgttttttt taataaataa ataaacataa ataaattgtt tgttgaattt ggatccacta    3300
gttctagagc ggccgccacc gcggtggagc tccagctttt gttcccttta gtgagggtta    3360
attgcgcgct tggcgtaatc atggtcatag ctgtttcctg tgtgaaattg ttatccgctc    3420
acaattccac acaacatacg agccggaagc ataaagtgta aagcctgggg tgcctaatga    3480
gtgagctaac tcacattaat tgcgttgcgc tcactgcccg ctttccagtc gggaaacctg    3540
tcgtgccagc tgcattaatg aatcggccaa cgcgcgggga gaggcggttt gcgtattggg    3600
cgctcttccg cttcctcgct cactgactcg ctgcgctcgg tcgttcggct gcggcgagcg    3660
gtatcagctc actcaaaggc ggtaatacgg ttatccacag aatcagggga taacgcagga    3720
aagaacatgt gagcaaaagg ccagcaaaag gccaggaacc gtaaaaaggc cgcgttgctg    3780
gcgtttttcc ataggctccg ccccctgac gagcatcaca aaaatcgacg ctcaagtcag    3840
aggtggcgaa acccgacagg actataaaga taccaggcgt ttccccctgg aagctccctc    3900
gtgcgctctc ctgttccgac cctgccgctt accggatacc tgtccgcctt tctcccttcg    3960
ggaagcgtgg cgctttctca tagctcacgc tgtaggtatc tcagttcggt gtaggtcgtt    4020
cgctccaagc tgggctgtgt gcacgaaccc cccgttcagc ccgaccgctg cgccttatcc    4080
ggtaactatc gtcttgagtc caacccggta agacacgact tatcgccact ggcagcagcc    4140
actggtaaca ggattagcag agcgaggtat gtaggcggtg ctacagagtt cttgaagtgg    4200
```

| | |
|---|---|
| tggcctaact acggctacac tagaaggaca gtatttggta tctgcgctct gctgaagcca | 4260 |
| gttaccttcg gaaaaagagt tggtagctct tgatccggca aacaaaccac cgctggtagc | 4320 |
| ggtggttttt ttgtttgcaa gcagcagatt acgcgcagaa aaaaaggatc tcaagaagat | 4380 |
| cctttgatct tttctacggg gtctgacgct cagtggaacg aaaactcacg ttaagggatt | 4440 |
| ttggtcatga gattatcaaa aaggatcttc acctagatcc ttttaaatta aaaatgaagt | 4500 |
| tttaaatcaa tctaaagtat atatgagtaa acttggtctg acagttacca atgcttaatc | 4560 |
| agtgaggcac ctatctcagc gatctgtcta tttcgttcat ccatagttgc ctgactcccc | 4620 |
| gtcgtgtaga taactacgat acgggagggc ttaccatctg gccccagtgc tgcaatgata | 4680 |
| ccgcgagacc cacgctcacc ggctccagat ttatcagcaa taaaccagcc agccggaagg | 4740 |
| gccgagcgca gaagtggtcc tgcaacttta tccgcctcca tccagtctat taattgttgc | 4800 |
| cgggaagcta gagtaagtag ttcgccagtt aatagtttgc gcaacgttgt tgccattgct | 4860 |
| acaggcatcg tggtgtcacg ctcgtcgttt ggtatggctt cattcagctc cggttcccaa | 4920 |
| cgatcaaggc gagttacatg atcccccatg ttgtgcaaaa aagcggttag ctccttcggt | 4980 |
| cctccgatcg ttgtcagaag taagttggcc gcagtgttat cactcatggt tatggcagca | 5040 |
| ctgcataatt ctcttactgt catgccatcc gtaagatgct tttctgtgac tggtgagtac | 5100 |
| tcaaccaagt cattctgaga atagtgtatg cggcgaccga gttgctcttg cccggcgtca | 5160 |
| atacgggata ataccgcgcc acatagcaga actttaaaag tgctcatcat tggaaaacgt | 5220 |
| tcttcgggge gaaaactctc aaggatctta ccgctgttga gatccagttc gatgtaaccc | 5280 |
| actcgtgcac ccaactgatc ttcagcatct tttactttca ccagcgtttc tgggtgagca | 5340 |
| aaaacaggaa ggcaaaatgc cgcaaaaaag ggaataaggg cgacacggaa atgttgaata | 5400 |
| ctcatactct tcctttttca atattattga agcatttatc agggttattg tctcatgagc | 5460 |
| ggatacatat ttgaatgtat ttagaaaaat aaacaaatag gggttccgcg cacatttccc | 5520 |
| cgaaaagtgc cac | 5533 |

<210> SEQ ID NO 43
<211> LENGTH: 4971
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 43

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt ttttttgggt cgaggtgccg taaagcacta aatcggaacc ctaaagggag | 300 |
| ccccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat tgggtaccgg | 660 |

```
gcccccccctc gaggtcgacg gtatcgataa gcttgatatc gaattcctgc agcccggggg    720
atcctatata ataaaatggg tagttcttta gacgatgagc atatcctctc tgctcttctg    780
caaagcgatg acgagcttgt tggtgaggat tctgacagtg aaatatcaga tcacgtaagt    840
gaagatgacg tccagagcga tacagaagaa gcgtttatag atgaggtaca tgaagtgcag    900
ccaacgtcaa gcggtagtga aatattagac gaacaaaatg ttattgaaca accaggttct    960
tcattggctt ctaacagaat cttgaccttg ccacagagga ctattagagg taagaataaa   1020
cattgttggt caacttcaaa gtccacgagg cgtagccgag tctctgcact gaacattgtc   1080
agatctcaaa gaggtccgac gcgtatgtgc cgcaatatat atgacccact tttatgcttc   1140
aaactatttt ttactgatga gataatttcg gaaattgtaa aatggacaaa tgctgagata   1200
tcattgaaac gtcgggaatc tatgacaggt gctacatttc gtgacacgaa tgaagatgaa   1260
atctatgctt tctttggtat tctggtaatg acagcagtga gaaaagataa ccacatgtcc   1320
acagatgacc tctttgatcg atctttgtca atggtgtacg tctctgtaat gagtcgtgat   1380
cgttttgatt ttttgatacg atgtcttaga atggatgaca aaagtatacg gcccacactt   1440
cgagaaaacg atgtatttac tcctgttaga aaaatatggg atctctttat ccatcagtgc   1500
atacaaaatt acactccagg ggctcatttg accatagatg aacagttact tggttttaga   1560
ggacggtgtc cgtttaggat gtatatccca aacaagccaa gtaagtatgg aataaaaatc   1620
ctcatgatgt gtgacagtgg tacgaagtat atgataaatg gaatgcctta tttgggaaga   1680
ggaacacaga ccaacggagt accactcggt gaatactacg tgaaggagtt atcaaagcct   1740
gtgcacggta gttgtcgtaa tattacgtgt gacaattggt tcacctcaat ccctttggca   1800
aaaaacttac tacaagaacc gtataagtta accattgtgg gaaccgtgcg atcaaacaaa   1860
cgcgagatac cggaagtact gaaaaacagt cgctccaggc cagtgggaac atcgatgttt   1920
tgttttgacg gaccccttac tctcgtctca tataaaccga agccagctaa gatggtatac   1980
ttattatcat cttgtgatga ggatgcttct atcaacgaaa gtaccggtaa accgcaaatg   2040
gttatgtatt ataatcaaac taaaggcgga gtggacacgc tagaccaaat gtgttctgtg   2100
atgacctgca gtaggaagac gaataggtgg cctatggcat tattgtacgg aatgataaac   2160
attgcctgca taaattcttt tattatatac agccataatg tcagtagcaa gggagaaaag   2220
gttcaaagtc gcaaaaaatt tatgagaaac ctttacatga gcctgacgtc atcgtttatg   2280
cgtaagcgtt tagaagctcc tactttgaag agatatttgc gcgataatat ctctaatatt   2340
ttgccaaatg aagtgcctgg tacatcagat gacagtactg aagagccagt aatgaaaaaa   2400
cgtacttact gtacttactg cccctctaaa ataaggcgaa aggcaaatgc atcgtgcaaa   2460
aaatgcaaaa aagttatttg tcgagagcat aatattgata tgtgccaaag ttgtttctga   2520
ctgactaata agtataattt gtttctatta tgtataagtt aagctaatta cttattttat   2580
aatacaacat gactgttttt aaagtacaaa ataagtttat ttttgtaaaa gagagaatgt   2640
ttaaaagttt tgttacttta gaagaaattt tgagtttttg ttttttttta ataaataaat   2700
aaacataaat aaattgtttg ttgaatttgg atccactagt tctagagcgg ccgccaccgc   2760
ggtggagctc cagcttttgt tccctttagt gagggttaat tgcgcgcttg gcgtaatcat   2820
ggtcatagct gtttcctgtg tgaaattgtt atccgctcac aattccacac aacatacgag   2880
ccggaagcat aaagtgtaaa gcctggggtg cctaatgagt gagctaactc acattaattg   2940
cgttgcgctc actgcccgct ttccagtcgg gaaacctgtc gtgccagctg cattaatgaa   3000
tcggccaacg cgcggggaga ggcggtttgc gtattgggcg ctcttccgct tcctcgctca   3060
```

```
ctgactcgct gcgctcggtc gttcggctgc ggcgagcggt atcagctcac tcaaaggcgg    3120
taatacggtt atccacagaa tcagggata acgcaggaaa gaacatgtga gcaaaaggcc    3180
agcaaaaggc caggaaccgt aaaaaggccg cgttgctggc gttttccat aggctccgcc    3240 cccctgacga gcatcacaaa aatcgacgct caagtcagag gtggcgaaac ccgacaggac    3300
tataaagata ccaggcgttt ccccctggaa gctccctcgt gcgctctcct gttccgaccc    3360
tgccgcttac cggatacctg tccgcctttc tcccttcggg aagcgtggcg ctttctcata    3420
gctcacgctg taggtatctc agttcggtgt aggtcgttcg ctccaagctg gctgtgtgc    3480 acgaaccccc cgttcagccc gaccgctgcg ccttatccgg taactatcgt cttgagtcca    3540
acccggtaag acacgactta tcgccactgg cagcagccac tggtaacagg attagcagag    3600
cgaggtatgt aggcggtgct acagagttct tgaagtggtg gcctaactac ggctacacta    3660
gaaggacagt atttggtatc tgcgctctgc tgaagccagt taccttcgga aaagagttg    3720 gtagctcttg atccggcaaa caaccaccg ctggtagcgg tggttttttt gtttgcaagc    3780
agcagattac gcgcagaaaa aaggatctca agaagatcc tttgatcttt tctacggggt    3840
ctgacgctca gtggaacgaa aactcacgtt aagggatttt ggtcatgaga ttatcaaaaa    3900
ggatcttcac ctagatcctt ttaaattaaa aatgaagttt taaatcaatc taaagtatat    3960
atgagtaaac ttggtctgac agttaccaat gcttaatcag tgaggcacct atctcagcga    4020
tctgtctatt tcgttcatcc atagttgcct gactccccgt cgtgtagata actacgatac    4080
gggagggctt accatctggc cccagtgctg caatgatacc gcgagaccca cgctcaccgg    4140
ctccagattt atcagcaata aaccagccag ccggaagggc cgagcgcaga agtggtcctg    4200
caactttatc cgcctccatc cagtctatta attgttgccg ggaagctaga gtaagtagtt    4260
cgccagttaa tagtttgcgc aacgttgttg ccattgctac aggcatcgtg gtgtcacgct    4320
cgtcgtttgg tatggcttca ttcagctccg gttcccaacg atcaaggcga gttacatgat    4380
cccccatgtt gtgcaaaaaa gcggttagct ccttcggtcc tccgatcgtt gtcagaagta    4440
agttggccgc agtgttatca ctcatggtta tggcagcact gcataattct cttactgtca    4500
tgccatccgt aagatgcttt tctgtgactg gtgagtactc aaccaagtca ttctgagaat    4560
agtgtatgcg gcgaccgagt tgctcttgcc cggcgtcaat acgggataat accgcgccac    4620
atagcagaac tttaaaagtg ctcatcattg gaaaacgttc ttcggggcga aaactctcaa    4680
ggatcttacc gctgttgaga tccagttcga tgtaacccac tcgtgcaccc aactgatctt    4740
cagcatcttt tactttcacc agcgtttctg ggtgagcaaa aacaggaagg caaaatgccg    4800
caaaaaaggg aataagggcg acacggaaat gttgaatact catactcttc ctttttcaat    4860
attattgaag catttatcag ggttattgtc tcatgagcgg atacatattt gaatgtattt    4920
agaaaaataa acaaataggg gttccgcgca catttccccg aaaagtgcca c             4971
```

<210> SEQ ID NO 44
<211> LENGTH: 5523
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 44

```
ctaaattgta agcgttaata ttttgttaaa attcgcgtta aatttttgtt aaatcagctc      60
attttttaac caataggccg aaatcggcaa aatcccttat aaatcaaaag aatagaccga     120
```

```
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat gggtaccgg     660 gcccccctc gaggtcgacg gtatcgataa gcttcgatgt ctttgtgatg cgccgacatt     720
tttgtaggtt attgataaaa tgaacggata cagttgcccg acattatcat taaatccttg    780
gcgtagaatt tgtcgggtcc attgtccgtg tgcgctagca tgcccgctaa cggacctcgt    840
acttttggct tcaaaggttt tgcgcacaga caaaatgtgc cacacttgca gctctgcatg    900
tgtgcgcgta accacaaatc ccaacggcgc agtgtacttg ttgtatgcaa ataaatctcg    960
ataaaggcgc ggcgcgcgaa tgcagctgat cacgtacgct cctcgtgttc cgttcaagga   1020
cggtgttatc gacctcagat taatgtttat cggccgactg ttttcgtatc cgctcaccaa   1080
acgcgttttt gcattaacat tgtatgtcgg cggatgttct atatctaatt tgaataaata   1140
aacgataacc gcgttggttt tagagggcat aataaaagaa atattgttat cgtgttcgcc   1200
attagggcag tataaattga cgttcatgtt ggatattgtt tcagttgcaa gtgaattcct   1260
gcagcccggg ggatcctata taataaaatg ggtagttctt tagacgatga gcatatcctc   1320
tctgctcttc tgcaaagcga tgacgagctt gttggtgagg attctgacag tgaaatatca   1380
gatcacgtaa gtgaagatga cgtccagagc gatacagaag aagcgtttat agatgaggta   1440
catgaagtgc agccaacgtc aagcggtagt gaaatattag acgaacaaaa tgttattgaa   1500
caaccaggtt cttcattggc ttctaacaga atcttgacct tgccacagag gactattaga   1560
ggtaagaata acattgttg gtcaacttca aagtccacga ggcgtagccg agtctctgca    1620
ctgaacattg tcagatctca aagaggtccg acgcgtatgt gccgcaatat atatgaccca   1680
cttttatgct tcaaactatt ttttactgat gagataattt cggaaattgt aaaatggaca   1740
aatgctgaga tatcattgaa acgtcgggaa tctatgacag gtgctacatt tcgtgacacg   1800
aatgaagatg aaatctatgc tttctttggt attctggtaa tgacagcagt gagaaaagat   1860
aaccacatgt ccacagatga cctctttgat cgatctttgt caatggtgta cgtctctgta   1920
atgagtcgta tcgttttga ttttttgata cgatgtctta aatggatga caaaagtata     1980 cggcccacac ttcgagaaaa cgatgtattt actcctgtta gaaaaatatg ggatctcttt   2040
atccatcagt gcatacaaaa ttacactcca ggggctcatt tgaccataga tgaacagtta   2100 cttggttta gaggacggtg tccgtttagg atgtatatcc caaacaagcc aagtaagtat    2160
ggaataaaaa tcctcatgat gtgtgacagt ggtacgaagt atatgataaa tggaatgcct   2220
tatttgggaa gaggaacaca gaccaacgga gtaccactcg tgaatactac cgtgaaggag   2280
ttatcaaagc ctgtgcacgg tagttgtcgt aatattacgt gtgacaattg gttcacctca   2340
atccctttgg caaaaaactt actacaagaa ccgtataagt taaccattgt gggaaccgtg   2400
cgatcaaaca aacgcgagat accggaagta ctgaaaaaca gtcgctccag gccagtggga   2460
```

```
acatcgatgt tttgttttga cggacccctt actctcgtct catataaacc gaagccagct   2520
aagatggtat acttattatc atcttgtgat gaggatgctt ctatcaacga aagtaccggt   2580
aaaccgcaaa tggttatgta ttataatcaa actaaaggcg gagtggacac gctagaccaa   2640
atgtgttctg tgatgacctg cagtaggaag acgaataggt ggcctatggc attattgtac   2700
ggaatgataa acattgcctg cataaattct tttattatat acagccataa tgtcagtagc   2760
aagggagaaa aggttcaaag tcgcaaaaaa tttatgagaa acctttacat gagcctgacg   2820
tcatcgttta tgcgtaagcg tttagaagct cctactttga agagatattt gcgcgataat   2880
atctctaata ttttgccaaa tgaagtgcct ggtacatcag atgacagtac tgaagagcca   2940
gtaatgaaaa aacgtactta ctgtacttac tgcccctcta aaataaggcg aaaggcaaat   3000
gcatcgtgca aaaatgcaa aaaagttatt tgtcgagagc ataatattga tatgtgccaa   3060
agttgtttct gactgactaa taagtataat ttgtttctat tatgtataag ttaagctaat   3120
tacttatttt ataatacaac atgactgttt ttaaagtaca aaataagttt atttttgtaa   3180
aagagagaat gtttaaaagt tttgttactt tagaagaaat tttgagtttt tgttttttt   3240
taataaataa ataaacataa ataaattgtt tgttgaattt ggatccacta gttctagagc   3300
ggccgccacc gcggtggagc tccagctttt gttccctta tgagggtta attgcgcgct   3360
tggcgtaatc atggtcatag ctgtttcctg tgtgaaattg ttatccgctc acaattccac   3420
acaacatacg agccggaagc ataaagtgta agcctggggg tgcctaatga gtgagctaac   3480
tcacattaat tgcgttgcgc tcactgcccg ctttccagtc gggaaacctg tcgtgccagc   3540
tgcattaatg aatcggccaa cgcgcgggga gaggcggttt gcgtattggg cgctcttccg   3600
cttcctcgct cactgactcg ctgcgctcgg tcgttcggct gcggcgagcg gtatcagctc   3660
actcaaaggc ggtaatacgg ttatccacag aatcagggga taacgcagga agaacatgt   3720
gagcaaaagg ccagcaaaag gccaggaacc gtaaaaaggc cgcgttgctg gcgtttttcc   3780
ataggctccg cccccctgac gagcatcaca aaaatcgacg ctcaagtcag aggtggcgaa   3840
acccgacagg actataaaga taccaggcgt ttccccctgg aagctccctc gtgcgctctc   3900
ctgttccgac cctgccgctt accggatacc tgtccgcctt tctcccttcg ggaagcgtgg   3960
cgctttctca tagctcacgc tgtaggtatc tcagttcggt gtaggtcgtt cgctccaagc   4020
tgggctgtgt gcacgaaccc cccgttcagc ccgaccgctg cgccttatcc ggtaactatc   4080
gtcttgagtc aacccggta agacacgact tatcgccact ggcagcagcc actggtaaca   4140
ggattagcag agcgaggtat gtaggcggtg ctacagagtt cttgaagtgg tggcctaact   4200
acggctacac tagaaggaca gtatttggta tctgcgctct gctgaagcca gttaccttcg   4260
gaaaaagagt tggtagctct tgatccggca acaaaccac cgctggtagc ggtggttttt   4320
ttgtttgcaa gcagcagatt acgcgcagaa aaaaggatc tcaagaagat cctttgatct   4380
tttctacggg gtctgacgct cagtggaacg aaaactcacg ttaagggatt ttggtcatga   4440
gattatcaaa aaggatcttc acctagatcc ttttaaatta aaaatgaagt tttaaatcaa   4500
tctaaagtat atatgagtaa acttggtctg acagttacca atgcttaatc agtgaggcac   4560
ctatctcagc gatctgtcta tttcgttcat ccatagttgc ctgactcccc gtcgtgtaga   4620
taactacgat acgggagggc ttaccatctg gccccagtgc tgcaatgata ccgcgagacc   4680
cacgctcacc ggctccagat ttatcagcaa taaaccagcc agccggaagg gccgagcgca   4740
gaagtggtcc tgcaacttta tccgcctcca tccagtctat taattgttgc cgggaagcta   4800
gagtaagtag ttcgccagtt aatagtttgc gcaacgttgt tgccattgct acaggcatcg   4860
```

```
tggtgtcacg ctcgtcgttt ggtatggctt cattcagctc cggttcccaa cgatcaaggc     4920
gagttacatg atcccccatg ttgtgcaaaa aagcggttag ctccttcggt cctccgatcg     4980
ttgtcagaag taagttggcc gcagtgttat cactcatggt tatggcagca ctgcataatt     5040
ctcttactgt catgccatcc gtaagatgct tttctgtgac tggtgagtac tcaaccaagt     5100
cattctgaga atagtgtatg cggcgaccga gttgctcttg cccggcgtca atacgggata     5160
ataccgcgcc acatagcaga actttaaaag tgctcatcat tggaaaacgt tcttcggggc     5220
gaaaactctc aaggatctta ccgctgttga tccagttcg atgtaaccc actcgtgcac      5280 ccaactgatc ttcagcatct tttactttca ccagcgtttc tgggtgagca aaaacaggaa     5340
ggcaaaatgc cgcaaaaaag gaataaggg cgacacggaa atgttgaata ctcatactct     5400
tcctttttca atattattga agcatttatc agggttattg tctcatgagc ggatacatat     5460
ttgaatgtat ttagaaaaat aaacaaatag gggttccgcg cacatttccc cgaaaagtgc     5520
cac                                                                   5523

<210> SEQ ID NO 45
<211> LENGTH: 6984
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 45
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta caactccgcc ccattgacg caaatgggcg gtaggcgtgt      540
acggtgggag gtctatataa gcagagctgg tttagtgaac cgtcagatcc gctagcgcta      600
ccggactcag atcctatata ataaaatggg tagttcttta gacgatgagc atatcctctc      660
tgctcttctg caaagcgatg acgagcttgt tggtgaggat tctgacagtg aaatatcaga      720
tcacgtaagt gaagatgacg tccagagcga tacagaagaa gcgtttatag atgaggtaca      780
tgaagtgcag ccaacgtcaa gcggtagtga atattagac gaacaaaatg ttattgaaca      840
accaggttct tcattggctt ctaacagaat cttgaccttg ccacagagga ctattagagg      900
taagaataaa cattgttggt caacttcaaa gtccacgagg cgtagccgag tctctgcact      960
gaacattgtc agatctcaaa gaggtccgac gcgtatgtgc cgcaatatat atgacccact     1020
tttatgcttc aaactatttt ttactgatga gataatttcg gaaattgtaa aatggacaaa     1080
tgctgagata tcattgaaac gtcgggaatc tatgacaggt gctacatttc gtgacacgaa     1140
tgaagatgaa atctatgctt ctttggtat tctggtaatg acagcagtga gaaaagataa     1200
ccacatgtcc acagatgacc tctttgatcg atctttgtca atggtgtacg tctctgtaat     1260
gagtcgtgat cgttttgatt ttttgatacg atgtcttaga atggatgaca aaagtatacg     1320
```

```
gcccacactt cgagaaaacg atgtatttac tcctgttaga aaaatatggg atctctttat    1380
ccatcagtgc atacaaaatt acactccagg ggctcatttg accatagatg aacagttact    1440
tggttttaga ggacggtgtc cgtttaggat gtatatccca aacaagccaa gtaagtatgg    1500
aataaaaatc ctcatgatgt gtgacagtgg tacgaagtat atgataaatg gaatgcctta    1560
tttgggaaga ggaacacaga ccaacggagt accactcggt gaatactacg tgaaggagtt    1620
atcaaagcct gtgcacggta gttgtcgtaa tattacgtgt gacaattggt tcacctcaat    1680 cccttttggca aaaaacttac tacaagaacc gtataagtta accattgtgg gaaccgtgcg    1740
atcaaacaaa cgcgagatac cggaagtact gaaaaacagt cgctccaggc cagtgggaac    1800
atcgatgttt tgttttgacg gaccccttac tctcgtctca tataaaccga agccagctaa    1860
gatggtatac ttattatcat cttgtgatga ggatgcttct atcaacgaaa gtaccggtaa    1920
accgcaaatg gttatgtatt ataatcaaac taaaggcgga gtggacacgc tagaccaaat    1980
gtgttctgtg atgacctgca gtaggaagac gaataggtgg cctatggcat tattgtacgg    2040
aatgataaac attgcctgca taaattcttt tattatatac agccataatg tcagtagcaa    2100
gggagaaaag gttcaaagtc gcaaaaaatt tatgagaaac ctttacatga gcctgacgtc    2160
atcgtttatg cgtaagcgtt tagaagctcc tactttgaag agatatttgc gcgataatat    2220
ctctaatatt ttgccaaatg aagtgcctgg tacatcagat gacagtactg aagagccagt    2280
aatgaaaaaa cgtacttact gtacttactg cccctctaaa ataaggcgaa aggcaaatgc    2340
atcgtgcaaa aaatgcaaaa aagttatttg tcgagagcat aatattgata tgtgccaaag    2400
ttgtttctga ctgactaata agtataattt gtttctatta tgtataagtt aagctaatta    2460 cttatttat aatacaacat gactgttttt aaagtacaaa ataagtttat ttttgtaaaa    2520
gagagaatgt ttaaaagttt tgttacttta gaagaaattt tgagttttg ttttttttta    2580 ataaataaat aaacataaat aaattgtttg ttgaatttgg atctcgaggt tcccacaatg    2640
gttaattcga gctcgcccgg ggatctaatt caattagaga ctaattcaat tagagctaat    2700
tcaattagga tccaagctta tcgatttcga accctcgacc gccggagtat aaatagaggc    2760
gcttcgtcta cggagcgaca attcaattca aacaagcaaa gtgaacacgt cgctaagcga    2820
aagctaagca aataaacaag cgcagctgaa caagctaaac aatcggggta ccgctagagt    2880
cgacggtacc gcgggcccgg gatccaccgg tcgccaccat gaattctgca gtcgacggta    2940
ccgcgggccc gggatccacc ggtcgccacc atggtgcgct cctccaagaa cgtcatcaag    3000
gagttcatgc gcttcaaggt gcgcatggag ggaccgtga acggccacga gttcgagatc    3060
gagggcgagg gcgagggccg cccctacgag ggccacaaca ccgtgaagct gaaggtgacc    3120
aagggcggcc ccctgccctt cgcctgggac atcctgtccc ccagttcca gtacggctcc    3180 aaggtgtacg tgaagcaccc cgccgacatc cccgactaca agaagctgtc cttccccgag    3240
ggcttcaagt gggagcgcgt gatgaacttc gaggacggcg gcgtggtgac cgtgacccag    3300
gactcctccc tgcaggacgg ctgcttcatc tacaaggtga agttcatcgg cgtgaacttc    3360
ccctccgacg gccccgtaat gcagaagaag accatgggct gggaggcctc caccgagcgc    3420
ctgtaccccc gcgacggcgt gctgaagggc gagatccaca aggccctgaa gctgaaggac    3480
ggcggccact acctggtgga gttcaagtcc atctacatgg ccaagaagcc cgtgcagctg    3540
cccggctact actacgtgga ctccaagctg gacatcacct cccacaacga ggactacacc    3600
atcgtggagc agtacgagcg caccgagggc cgccaccacc tgttcctgta gcggccgcga    3660
```

```
ctctagatca taatcagcca taccacattt gtagaggttt tacttgcttt aaaaaacctc    3720
ccacacctcc ccctgaacct gaaacataaa atgaatgcaa ttgttgttgt taacttgttt    3780
attgcagctt ataatggtta caaataaagc aatagcatca caaatttcac aaataaagca    3840 ttttttcac tgcattctag ttgtggtttg tccaaactca tcaatgtatc ttaaggcgta     3900
aattgtaagc gttaatattt tgttaaaatt cgcgttaaat ttttgttaaa tcagctcatt    3960
ttttaaccaa taggccgaaa tcggcaaaat cccttataaa tcaaaagaat agaccgagat    4020
agggttgagt gttgttccag tttggaacaa gagtccacta ttaaagaacg tggactccaa    4080
cgtcaaaggg cgaaaaaccg tctatcaggg cgatggccca ctacgtgaac catcacccta    4140
atcaagtttt tgggggtcga ggtgccgtaa agcactaaat cggaaccctaaagggagccc    4200 ccgatttaga gcttgacggg gaaagccggc gaacgtggcg agaaaggaag ggaagaaagc    4260
gaaaggagcg ggcgctaggg cgctggcaag tgtagcggtc acgctgcgcg taaccaccac    4320
acccgccgcg cttaatgcgc cgctacaggg cgcgtcaggt ggcacttttc ggggaaatgt    4380
gcgcggaacc cctatttgtt tattttttcta aatacattca aatatgtatc cgctcatgag    4440
acaataaccc tgataaatgc ttcaataata ttgaaaaagg aagagtcctg aggcggaaag    4500
aaccagctgt ggaatgtgtg tcagttaggg tgtggaaagt ccccaggctc ccagcaggc    4560 agaagtatgc aaagcatgca tctcaattag tcagcaacca ggtgtggaaa gtccccaggc    4620
tccccagcag gcagaagtat gcaaagcatg catctcaatt agtcagcaac catagtcccg    4680
cccctaactc cgcccatccc gcccctaact ccgcccagtt ccgcccattc tccgccccat    4740
ggctgactaa ttttttttat ttatgcagag gccgaggccg cctcggcctc tgagctattc    4800
cagaagtagt gaggaggctt ttttggaggc ctaggctttt gcaaagatcg atcaagagac    4860
aggatgagga tcgtttcgca tgattgaaca agatggattg cacgcaggtt ctccggccgc    4920
ttgggtggag aggctattcg gctatgactg gcacaacag acaatcggct gctctgatgc     4980
cgccgtgttc cggctgtcag cgcaggggcg cccggttctt tttgtcaaga ccgacctgtc    5040
cggtgccctg aatgaactgc aagacgaggc agcgcggcta tcgtggctgg ccacgacggg    5100
cgttccttgc gcagctgtgc tcgacgttgt cactgaagcg ggaagggact ggctgctatt    5160
gggcgaagtg ccggggcagg atctcctgtc atctcacctt gctcctgccg agaaagtatc    5220
catcatggct gatgcaatgc ggcggctgca tacgcttgat ccggctacct gcccattcga    5280
ccaccaagcg aaacatcgca tcgagcgagc acgtactcgg atggaagccg gtcttgtcga    5340
tcaggatgat ctggacgaag agcatcaggg gctcgcgcca gccgaactgt tcgccaggct    5400
caaggcgagc atgcccgacg gcgaggatct cgtcgtgacc catggcgatg cctgcttgcc    5460
gaatatcatg gtggaaaatg gccgcttttc tggattcatc gactgtggcc ggctgggtgt    5520
ggcggaccgc tatcaggaca tagcgttggc tacccgtgat attgctgaag agcttggcgg    5580
cgaatgggct gaccgcttcc tcgtgcttta cggtatcgcc gctcccgatt cgcagcgcat    5640
cgccttctat cgccttcttg acgagttctt ctgagcggga ctctggggtt cgaaatgacc    5700
gaccaagcga cgcccaacct gccatcacga gatttcgatt ccaccgccgc cttctatgaa    5760
aggttgggct tcggaatcgt tttccgggac gccggctgga tgatcctcca gcgcggggat    5820
ctcatgctgg agttcttcgc ccaccctagg gggaggctaa ctgaaacacg gaaggagaca    5880
ataccggaag gaacccgcgc tatgacggca ataaaaagac agaataaaac gcacggtgtt    5940
gggtcgtttg ttcataaacg cggggttcgg tcccagggct ggcactctgt cgataccccca   6000 ccgagacccc attggggcca atacgcccgc gtttcttcct tttccccacc caccccca     6060
```

```
agttcgggtg aaggcccagg gctcgcagcc aacgtcgggg cggcaggccc tgccatagcc    6120
tcaggttact catatatact ttagattgat ttaaaacttc atttttaatt taaaaggatc    6180
taggtgaaga tccttttttga taatctcatg accaaaatcc cttaacgtga gttttcgttc    6240
cactgagcgt cagaccccgt agaaaagatc aaaggatctt cttgagatcc ttttttttctg    6300 cgcgtaatct gctgcttgca acaaaaaaaa ccaccgctac cagcggtggt ttgtttgccg    6360
gatcaagagc taccaactct ttttccgaag gtaactggct tcagcagagc gcagatacca    6420
aatactgtcc ttctagtgta gccgtagtta ggccaccact tcaagaactc tgtagcaccg    6480
cctacatacc tcgctctgct aatcctgtta ccagtggctg ctgccagtgg cgataagtcg    6540
tgtcttaccg ggttggactc aagacgatag ttaccggata aggcgcagcg gtcgggctga    6600
acggggggtt cctgcacaca gcccagcttg gagcgaacga cctacaccga actgagatac    6660
ctacagcgtg agctatgaga aagcgccacg cttcccgaag ggagaaaggc ggacaggtat    6720
ccggtaagcg gcagggtcgg aacaggagag cgcacgaggg agcttccagg gggaaacgcc    6780
tggtatcttt atagtcctgt cgggtttcgc cacctctgac ttgagcgtcg attttttgtga    6840 tgctcgtcag gggggcggag cctatggaaa aacgccagca acgcggcctt tttacggttc    6900
ctggcctttt gctggccttt tgctcacatg ttctttcctg cgttatcccc tgattctgtg    6960
gataaccgta ttaccgccat gcat                                            6984

<210> SEQ ID NO 46
<211> LENGTH: 4613
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (344)..(922)

<400> SEQUENCE: 46
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
gtaccgagct cggatccact agtaacggcc gccagtgtgc tggaattcgg cttggatccc    300
atgcgtcaat tttacgcaga ctatctttct agggttaatc tag ctg cat cag gat       355
                                                Leu His Gln Asp
                                                 1 cat atc gtc ggg tct ttt ttc cgg ctc agt cat cgc cca agc tgg cgc       403
His Ile Val Gly Ser Phe Phe Arg Leu Ser His Arg Pro Ser Trp Arg
 5              10                  15                  20 tat ctg ggc atc ggg gag gaa gaa gcc cgt gcc ttt tcc cgc gag gtt       451
Tyr Leu Gly Ile Gly Glu Glu Glu Ala Arg Ala Phe Ser Arg Glu Val
            25                  30                  35 gaa gcg gca tgg aaa gag ttt gcc gag gat gac tgc tgc tgc att gac       499
Glu Ala Ala Trp Lys Glu Phe Ala Glu Asp Asp Cys Cys Cys Ile Asp
        40                  45                  50 gtt gag cga aaa cgc acg ttt acc atg atg att cgg gaa ggt gtg gcc       547
Val Glu Arg Lys Arg Thr Phe Thr Met Met Ile Arg Glu Gly Val Ala
    55                  60                  65 atg cac gcc ttt aac ggt gaa ctg ttc gtt cag gcc acc tgg gat acc       595
Met His Ala Phe Asn Gly Glu Leu Phe Val Gln Ala Thr Trp Asp Thr
```

```
              70                  75                  80
agt tcg tcg cgg ctt ttc cgg aca cag ttc cgg atg gtc agc ccg aag    643
Ser Ser Ser Arg Leu Phe Arg Thr Gln Phe Arg Met Val Ser Pro Lys
 85                  90                  95                 100 cgc atc agc aac ccg aac aat acc ggc gac agc cgg aac tgc cgt gcc    691
Arg Ile Ser Asn Pro Asn Asn Thr Gly Asp Ser Arg Asn Cys Arg Ala
                105                 110                 115 ggt gtg cag att aat gac agc ggt gcg gcg ctg gga tat tac gtc agc    739
Gly Val Gln Ile Asn Asp Ser Gly Ala Ala Leu Gly Tyr Tyr Val Ser
            120                 125                 130 gag gac ggg tat cct ggc tgg atg ccg cag aaa tgg aca tgg ata ccc    787
Glu Asp Gly Tyr Pro Gly Trp Met Pro Gln Lys Trp Thr Trp Ile Pro
        135                 140                 145 cgt gag tta ccc ggc ggg cgc gcc tcg ttc att cac gtt ttt gaa ccc    835
Arg Glu Leu Pro Gly Gly Arg Ala Ser Phe Ile His Val Phe Glu Pro
    150                 155                 160 gtg gag gac ggg cag act cgc ggt gca aat gtg ttt tac agc gtg atg    883
Val Glu Asp Gly Gln Thr Arg Gly Ala Asn Val Phe Tyr Ser Val Met
165                 170                 175                 180 gag cag atg aag atg ctc gac acg ctg cag aac acg cag ctagattaac     932
Glu Gln Met Lys Met Leu Asp Thr Leu Gln Asn Thr Gln
                185                 190 cctagaaaga taatcatatt gtgacgtacg ttaaagataa tcatgcgtaa aattgacgca    992
tgggatccaa gccgaattct gcagatatcc atcacactgg cggccgctcg agcatgcatc   1052
tagagggccc aattcgccct atagtgagtc gtattacaat tcactggccg tcgttttaca   1112
acgtcgtgac tgggaaaacc ctggcgttac ccaacttaat cgccttgcag cacatccccc   1172
tttcgccagc tggcgtaata gcgaagaggc ccgcaccgat cgcccttccc aacagttgcg   1232
cagcctgaat ggcgaatggg acgcgccctg tagcggcgca ttaagcgcgg cgggtgtggt   1292
ggttacgcgc agcgtgaccg ctacacttgc cagcgcccta gcgcccgctc ctttcgcttt   1352
cttcccttcc tttctcgcca cgttcgccgg ctttccccgt caagctctaa atcgggggct   1412
ccctttaggg ttccgattta gagctttacg gcacctcgac cgcaaaaaac ttgatttggg   1472
tgatggttca cgtagtgggc catcgccctg atagacggtt tttcgccctt gacgttgga    1532 gtccacgttc tttaatagtg gactcttgtt ccaaactgga acaacactca accctatcgc   1592
ggtctattct tttgatttat aagggatttt gccgatttcg gcctattggt taaaaaatga   1652
gctgatttaa caaattcagg gcgcaagggc tgctaaagga accggaacac gtagaaagcc   1712
agtccgcaga aacggtgctg accccggatg aatgtcagct actgggctat ctggacaagg   1772
gaaaacgcaa gcgcaaagag aaagcaggta gcttgcagtg gcttacatg gcgatagcta    1832 gactgggcgg ttttatggac agcaagcgaa ccggaattgc cagctgggc gccctctggt    1892 aaggttggga agccctgcaa agtaaactgg atggctttct gccgccaag gatctgatgg    1952 cgcaggggat caagatctga tcaagagaca ggatgaggat cgtttcgcat gattgaacaa   2012
gatggattgc acgcaggttc tccggccgct tgggtggaga ggctattcgg ctatgactgg   2072
gcacaacaga caatcggctg ctctgatgcc gccgtgttcc ggctgtcagc gcaggggcgc   2132
ccggttcttt ttgtcaagac cgacctgtcc ggtgccctga tgaactgca ggacgaggca    2192 gcgcggctat cgtggctggc cacgacgggc gttccttgcg cagctgtgct cgacgttgtc   2252
actgaagcgg gaagggactg gctgctattg ggcgaagtgc cggggcagga tctcctgtca   2312
tctcgccttg ctcctgccga gaaagtatcc atcatggctg atgcaatgcg gcggctgcat   2372
acgcttgatc cggctaccctg cccattcgac caccaagcga acatcgcat cgagcgagca   2432
```

```
cgtactcgga tggaagccgg tcttgtcgat caggatgatc tggacgaaga gcatcagggg    2492
ctcgcgccag ccgaactgtt cgccaggctc aaggcgcgca tgcccgacgg cgaggatctc    2552
gtcgtgatcc atggcgatgc ctgcttgccg aatatcatgg tggaaaatgg ccgcttttct    2612
ggattcaacg actgtggccg gctggtgtgt gcggaccgct atcaggacat agcgttggat    2672
acccgtgata ttgctgaaga gcttggcggc gaatgggctg accgcttcct cgtgctttac    2732
ggtatcgccg ctcccgattc gcagcgcatc gccttctatc gccttcttga cgagttcttc    2792
tgaattgaaa aaggaagagt atgagtattc aacatttccg tgtcgccctt attccctttt    2852
ttgcggcatt ttgccttcct gttttgctc acccagaaac gctggtgaaa gtaaaagatg    2912
ctgaagatca gttgggtgca cgagtgggtt acatcgaact ggatctcaac agcggtaaga    2972
tccttgagag ttttcgcccc gaagaacgtt ttccaatgat gagcactttt aaagttctgc    3032
tatgtcatac actattatcc gtattgacg ccgggcaaga gcaactcggt cgccgggcgc    3092
ggtattctca gaatgacttg gttgagtact caccagtcac agaaaagcat cttacggatg    3152
gcatgacagt aagagaatta tgcagtgctg ccataaccat gagtgataac actgcggcca    3212
acttacttct gacaacgatc ggaggaccga aggagctaac cgcttttttg cacaacatgg    3272
gggatcatgt aactcgcctt gatcgttggg aaccggagct gaatgaagcc ataccaaacg    3332
acgagagtga caccacgatg cctgtagcaa tgccaacaac gttgcgcaaa ctattaactg    3392
gcgaactact tactctagct tcccggcaac aattaataga ctggatggag gcggataaag    3452
ttgcaggacc acttctgcgc tcggcccttc cggctggctg gtttattgct gataaatctg    3512
gagccggtga gcgtgggtct cgcggtatca ttgcagcact ggggccagat ggtaagccct    3572
cccgtatcgt agttatctac acgacgggga gtcaggcaac tatggatgaa cgaaatagac    3632
agatcgctga gataggtgcc tcactgatta agcattggta actgtcagac caagtttact    3692
catatatact ttagattgat ttaaaacttc atttttaatt taaaaggatc taggtgaaga    3752
tcctttttga taatctcatg accaaaatcc cttaacgtga gttttcgttc cactgagcgt    3812
cagaccccgt agaaaagatc aaaggatctt cttgagatcc ttttttctg cgcgtaatct    3872 gctgcttgca acaaaaaaa ccaccgctac cagcggtggt ttgtttgccg gatcaagagc    3932
taccaactct ttttccgaag gtaactggct tcagcagagc gcagatacca aatactgtcc    3992
ttctagtgta gccgtagtta ggccaccact tcaagaactc tgtagcaccg cctacatacc    4052
tcgctctgct aatcctgtta ccagtggctg ctgccagtgg cgataagtcg tgtcttaccg    4112
ggttggactc aagacgatag ttaccggata aggcgcagcg tcgggctga acgggggggtt    4172 cgtgcacaca gcccagcttg gagcgaacga cctacaccga actgagatac ctacagcgtg    4232
agcattgaga aagcgccacg cttcccgaag ggagaaaggc ggacaggtat ccggtaagcg    4292
gcagggtcgg aacaggagag cgcacgaggg agcttccagg gggaaacgcc tggtatcttt    4352
atagtcctgt cgggtttcgc cacctctgac ttgagcgtcg attttttgtga tgctcgtcag    4412 gggggcggag cctatggaaa aacgccagca acgcggcctt tttacggttc ctggccttt    4472 gctggccttt tgctcacatg ttctttcctg cgttatcccc tgattctgtg ataaccgta    4532 ttaccgcctt tgagtgagct gataccgctc gccgcagccg aacgaccgag cgcagcgagt    4592
cagtgagcga ggaagcggaa g                                               4613
```

<210> SEQ ID NO 47
<211> LENGTH: 193
<212> TYPE: PRT

<213> ORGANISM: Artificial Sequence
<220> FEATURE:
<223> OTHER INFORMATION: Synthetic Construct

<400> SEQUENCE: 47

```
Leu His Gln Asp His Ile Val Gly Ser Phe Phe Arg Leu Ser His Arg
1               5                   10                  15

Pro Ser Trp Arg Tyr Leu Gly Ile Gly Glu Glu Ala Arg Ala Phe
            20                  25                  30

Ser Arg Glu Val Glu Ala Ala Trp Lys Glu Phe Ala Glu Asp Cys
        35                  40                  45

Cys Cys Ile Asp Val Glu Arg Lys Arg Thr Phe Thr Met Met Ile Arg
    50                  55                  60

Glu Gly Val Ala Met His Ala Phe Asn Gly Glu Leu Phe Val Gln Ala
65                  70                  75                  80

Thr Trp Asp Thr Ser Ser Arg Leu Phe Arg Thr Gln Phe Arg Met
                85                  90                  95

Val Ser Pro Lys Arg Ile Ser Asn Pro Asn Thr Gly Asp Ser Arg
            100                 105                 110

Asn Cys Arg Ala Gly Val Gln Ile Asn Asp Ser Gly Ala Ala Leu Gly
        115                 120                 125

Tyr Tyr Val Ser Glu Asp Gly Tyr Pro Gly Trp Met Pro Gln Lys Trp
130                 135                 140

Thr Trp Ile Pro Arg Glu Leu Pro Gly Gly Arg Ala Ser Phe Ile His
145                 150                 155                 160

Val Phe Glu Pro Val Glu Asp Gly Gln Thr Arg Gly Ala Asn Val Phe
                165                 170                 175

Tyr Ser Val Met Glu Gln Met Lys Met Leu Asp Thr Leu Gln Asn Thr
            180                 185                 190

Gln
```

<210> SEQ ID NO 48
<211> LENGTH: 8999
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 48

```
accgaagtat acacttaaat tcagtgcacg tttgcttgtt gagaggaaag gttgtgtgcg      60
gacgaatttt tttttgaaaa cattaaccct tacgtggaat aaaaaaaaat gaaatattgc     120
aaattttgct gcaaagctgt gactggagta aaattaattc acgtgccgaa gtgtgctatt     180
aagagaaaat tgtgggagca gagccttggg tgcagccttg tgaaaactc ccaaatttgt     240 gatacccact ttaatgattc gcagtggaag gctgcacctg caaaggtca gacatttaaa     300 aggaggcgac tcaacgcaga tgccgtacct agtaaagtga tagagcctga accagaaaag     360 ataaagaag gctataccag tgggagtaca caaacagagt aagtttgaat agtaaaaaaa     420
atcatttatg taacaataa cgtgactgtg cgttaggtcc tgttcattgt ttaatgaaaa     480
taagagcttg agggaaaaaa ttcgtacttt ggagtacgaa atgcgtcgtt tagagcagca     540
gccgaattca ctggccgtcg ttttacaacg tcgtgactgg gaaaaccctg gcgttaccca     600
acttaatcgc cttgcagcac atccccttt cgccagctgg cgtaatagcg aagaggcccg     660
caccgatcgc ccttcccaac agttgcgcag cctgaatggc gaatggcgct ttgcctggtt     720
```

```
tccggcacca gaagcggtgc cggaaagctg gctggagtgc gatcttcctg aggccgatac      780
tgtcgtcgtc ccctcaaact ggcagatgca cggttacgat gcgcccatct acaccaacgt      840
aacctatccc attacggtca atccgccgtt tgttcccacg gagaatccga cgggttgtta      900
ctcgctcaca tttaatgttg atgaaagctg gctacaggaa ggccagacgc gaattatttt      960
tgatggcgtt aactcggcgt ttcatctgtg gtgcaacggg cgctgggtcg gttacggcca     1020
ggacagtcgt ttgccgtctg aatttgacct gagcgcattt ttacgcgccg gagaaaaccg     1080
cctcgcggtg atggtgctgc gttggagtga cggcagttat ctggaagatc aggatatgtg     1140
gcggatgagc ggcattttcc gtgacgtctc gttgctgcat aaaccgacta cacaaatcag     1200
cgatttccat gttgccactc gctttaatga tgatttcagc cgcgctgtac tggaggctga     1260
agttcagatg tgcggcgagt tgcgtgacta cctacgggta acagtttctt tatggcaggg     1320
tgaaacgcag gtcgccagcg gcaccgcgcc tttcggcggt gaaattatcg atgagcgtgg     1380
tggttatgcc gatcgcgtca cactacgtct gaacgtcgaa aacccgaaac tgtggagcgc     1440
cgaaatcccg aatctctatc gtgcggtggt tgaactgcac accgccgacg gcacgctgat     1500
tgaagcagaa gcctgcgatg tcggtttccg cgaggtgcgg attgaaaatg gtctgctgct     1560
gctgaacggc aagccgttgc tgattcgagg cgttaaccgt cacagcatc  atcctctgca     1620 tggtcaggtc atggatgagc agacgatggt gcaggatatc ctgctgatga agcagaacaa     1680 cttaacgcc gtgcgctgtt cgcattatcc gaaccatccg ctgtggtaca cgctgtgcga      1740
ccgctacggc ctgtatgtgg tggatgaagc caatattgaa acccacggca tggtgccaat     1800
gaatcgtctg accgatgatc cgcgctggct accggcgatg agcgaacgcg taacgcgaat     1860
ggtgcagcgc gatcgtaatc acccgagtgt gatcatctgg tcgctgggga atgaatcagg     1920
ccacggcgct aatcacgacg cgctgtatcg ctggatcaaa tctgtcgatc cttcccgccc     1980
ggtgcagtat gaaggcggcg gagccgacac cacggccacc gatattattt gcccgatgta     2040
cgcgcgcgtg gatgaagacc agcccttccc ggctgtgccg aaatggtcca tcaaaaaatg     2100
gctttcgcta cctggagaga cgcgcccgct gatcctttgc gaatacgccc acgcgatggg     2160
taacagtctt ggcggtttcg ctaaatactg gcaggcgttt cgtcagtatc ccgtttaca     2220 gggcggcttc gtctgggact gggtggatca gtcgctgatt aaatatgatg aaaacggcaa     2280
cccgtggtcg gcttacggcg gtgattttgg cgatacgccg aacgatcgcc agttctgtat     2340
gaacggtctg gtcttgccg accgcacgcc gcatccagcg ctgacggaag caaaacacca      2400
gcagcagttt ttccagttcc gtttatccgg gcaaaccatc gaagtgacca gcgaatacct     2460
gttccgtcat agcgataacg agctcctgca ctggatggtg gcgctggatg gtaagccgct     2520
ggcaagcggt gaagtgcctc tggatgtcgc tccacaaggt aaacagttga ttgaactgcc     2580
tgaactaccg cagccggaga gcgccgggca actctggctc acagtacgcg tagtgcaacc     2640
gaacgcgacc gcatggtcag aagccgggca catcagcgcc tggcagcagt ggcgtctggc     2700
ggaaaacctc agtgtgacgc tccccgccgc gtcccacgcc atcccgcatc tgaccaccag     2760
cgaaatggat ttttgcatcg agctgggtaa taagcgttgg caatttaacc gccagtcagg     2820
ctttctttca cagatgtgga ttggcgataa aaaacaactg ctgacgccgc tgcgcgatca     2880
gttcacccgt gcaccgctgg ataacgacat tggcgtaagt gaagcgaccc gcattgaccc     2940
taacgcctgg gtcgaacgct ggaaggcggc gggccattac caggccgaag cagcgttgtt     3000
gcagtgcacg gcagatacac ttgctgatgc ggtgctgatt acgaccgctc acgcgtggca     3060
gcatcagggg aaaaccttat ttatcagccg gaaaacctac cggattgatg gtagtggtca     3120
```

```
aatggcgatt accgttgatg ttgaagtggc gagcgataca ccgcatccgg cgcggattgg    3180
cctgaactgc cagctggcgc aggtagcaga gcgggtaaac tggctcggat tagggccgca    3240
agaaaactat cccgaccgcc ttactgccgc ctgttttgac cgctgggatc tgccattgtc    3300
agacatgtat accccgtacg tcttcccgag cgaaaacggt ctgcgctgcg ggacgcgcga    3360
attgaattat ggcccacacc agtggcgcgg cgacttccag ttcaacatca gccgctacag    3420
tcaacagcaa ctgatggaaa ccagccatcg ccatctgctg cacgcggaag aaggcacatg    3480
gctgaatatc gacggtttcc atatggggat tggtggcgac gactcctgga gcccgtcagt    3540
atcggcggaa ttccagctga gcgccggtcg ctaccattac cagttggtct ggtgtcgggg    3600
atccgtcgac taaggccaaa gagtctaatt tttgttcatc aatgggttat aacatatggg    3660
ttatattata agtttgtttt aagtttttga gactgataag aatgtttcga tcgaatattc    3720
catagaacaa caatagtatt acctaattac caagtcttaa tttagcaaaa atgttattgc    3780
ttatagaaaa ataaaattat ttatttgaaa tttaaagtca acttgtcatt taatgtcttg    3840
tagacttttg aaagtcttac gatacaatta gtatctaata tacatgggtt cattctacat    3900
tctatattag tgatgatttc tttagctagt aatacatttt aattatattc ggctttgatg    3960 atttttctgat ttttttccgaa cggattttcg tagacccttt cgatctcata atggctcatt    4020
ttattgcgat ggacggtcag gagagctcca cttttgaatt tctgttcgca gacaccgcat    4080
ttgtagcaca tagccgggac atccggtttg gggagatttt ccagtctctg ttgcaattgg    4140
ttttcgggaa tgcgttgcag gcgcatacgc tctatatcct ccgaacggcg ctggttgacc    4200
ctagcattta cataaggatc agcagcaaaa tttgcctctg cttcattgcc cggaatcaca    4260
gcaatcagat gtcccttcg gttacgatgg atattcaggt gcgaaccgca cacaaagctc    4320
tcgccgcaca ctccacactg atatggtcgc tcgccctgtg gcgccgcata tggatcttaa    4380
ggtcgttgga ctgcacaaag ctcttgctgc acatttgca ggagtacggc ctttgacccg    4440
tgtgcaatcg catgtgtcgc gccagcttgt tctgcgaaat aaacttcttg gagcagatgc    4500
ggccgcccgg ggtgggcgaa gaactccagc atgagatccc cgcgctggag gatcatccag    4560
ccggcgtccc ggaaaacgat tccgaagccc aacctttcat agaaggcggc ggtggaatcg    4620
aaatctcgtg atggcaggtt gggcgtcgct tggtcggtca tttcgaaccc cagagtcccg    4680
ctcagaagaa ctcgtcaaga aggcgataga aggcgatgcg ctgcgaatcg ggagcggcga    4740
taccgtaaag cacgaggaag cggtcagccc attcgccgcc aagctcttca gcaatatcac    4800
gggtagccaa cgctatgtcc tgatagcggt ccgccacacc cagccggcca cagtcgatga    4860
atccagaaaa gcggccattt tccaccatga tattcggcaa gcaggcatcg ccatgggtca    4920
cgacgagatc ctcgccgtcg ggcatgcgcg ccttgagcct ggcgaacagt tcggctggcg    4980
cgagcccctg atgctcttcg tccagatcat cctgatcgac aagaccggct tccatccgag    5040
tacgtgctcg ctcgatgcga tgtttcgctt ggtggtcgaa tgggcaggta ccggatcaa    5100 gcgtatgcag ccgccgcatt gcatcagcca tgatggatac tttctcggca ggagcaaggt    5160
gagatgacag gagatcctgc cccggcactt cgcccaatag cagccagtcc cttcccgctt    5220
cagtgacaac gtcgagcaca gctgcgcaag gaacgcccgt cgtggccagc cacgatagcc    5280
gcgctgcctc gtcctgcagt tcattcaggg caccggacag gtcggtcttg acaaaaagaa    5340
ccgggcgccc ctgcgctgac agccggaaca cggcggcatc agagcagccg attgtctgtt    5400
gtgcccagtc atagccgaat agcctctcca cccaagcggc cggagaacct gcgtgcaatc    5460
```

```
catcttgttc aatcatgcga aacgatcctc atcctgtctc ttgatcagat cttgatcccc    5520
tgcgccatca gatccttggc ggcaagaaag ccatccagtt tactttgcag ggcttcccaa    5580
ccttaccaga gggcgcccca gctggcaatt ccggttcgct tgctgtccat aaaaccgccc    5640
agtctagcta tcgccatgta agcccactgc aagctacctg ctttctcttt gcgcttgcgt    5700
tttcccttgt ccagatagcc cagtagctga cattcatccg gggtcagcac cgtttctgcg    5760
gactggcttt ctacgtgttc cgcttccttt agcagccctt cgccctgagt gcttgcggc    5820 agcgtgaagc taattcatgg ttataaattt ttgttaaatc agctcatttt ttaaccaata    5880
ggccgaaatc ggcaaaatcc cttataaatc aaaagaatag cccgagatag ggttgagtgt    5940
tgttccagtt tggaacaaga gtccactatt aaagaacgtg gactccaacg tcaaagggcg    6000 aaaaccgtc tatcagggcg atggccggat cagcttatgc ggtgtgaaat accgcacaga    6060
tgcgtaagga gaaaataccg catcaggcgc tcttccgctt cctcgctcac tgactcgctg    6120
cgctcggtcg ttcggctgcg gcgagcggta tcagctcact caaaggcggt aatacggtta    6180
tccacagaat caggggataa cgcaggaaag aacatgtgag caaaaggcca gcaaaaggcc    6240
aggaaccgta aaaaggccgc gttgctggcg ttttttccata ggctccgccc ccctgacgag    6300
catcacaaaa atcgacgctc aagtcagagg tggcgaaacc cgacaggact ataaagatac    6360
caggcgtttc cccctggaag ctccctcgtg cgctctcctg ttccgaccct gccgcttacc    6420
ggatacctgt ccgcctttct cccttcggga agcgtggcgc tttctcatag ctcacgctgt    6480
aggtatctca gttcggtgta ggtcgttcgc tccaagctgg gctgtgtgca cgaaccccc    6540 gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggg gtttttttgt ttgcaagcag cagattacgc    6840
gcagaaaaaa aggatctcaa gaagatcctt tgatctttc ttactgaacg gtgatcccca    6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt acgatccacc ggtcgccacc atggtgagca    7260
agggcgagga gctgttcacc ggggtggtgc ccatcctggt cgagctggac ggcgacgtaa    7320
acggccacaa gttcagcgtg tccggcgagg gcgagggcga tgccacctac ggcaagctga    7380
ccctgaagtt catctgcacc accggcaagc tgcccgtgcc ctggcccacc ctcgtgacca    7440
ccttcggcta cggcctgcag tgcttcgccc gctaccccga ccacatgaag cagcacgact    7500
tcttcaagtc cgccatgccc gaaggctacg tccaggagcg caccatcttc ttcaaggacg    7560
acggcaacta caagacccgc gccgaggtga agttcgaggg cgacaccctg gtgaaccgca    7620
tcgagctgaa gggcatcgac ttcaaggagg acggcaacat cctggggcac aagctggagt    7680
acaactacaa cagccacaac gtctatatca tggccgacaa gcagaagaac ggcatcaagg    7740
tgaacttcaa gatccgccac aacatcgagg acggcagcgt gcagctcgcc gaccactacc    7800
agcagaacac ccccatcggc gacggccccg tgctgctgcc cgacaaccac tacctgagct    7860
```

```
accagtccgc cctgagcaaa gaccccaacg agaagcgcga tcacatggtc ctgctggagt   7920
tcgtgaccgc cgccgggatc actctcggca tggacgagct gtacaagtaa agcggccgcg   7980
actctagatc ataatcagcc ataccacatt tgtagaggtt ttacttgctt taaaaaacct   8040
cccacacctc cccctgaacc tgaaacataa aatgaatgca attgttgttg ttaacttgtt   8100
tattgcagct tataatggtt acaaataaag caatagcatc acaaatttca caaataaagc   8160 attttttca ctgcattcta gttgtggttt gtccaaactc atcaatgtat cttaaagctt   8220
atcgatacgc gtacggcact agtggatccc atgcgtcaat tttacgcatg attatcttta   8280
acgtacgtca caatatgatt atctttctag ggttaatcta gctgcgtgtt ctgcagcgtg   8340
tcgagcatct tcatctgctc catcacgctg taaaacacat ttgcaccgcg agtctgcccg   8400
tcctccacgg gttcaaaaac gtgaatgaac gaggcgcgcc cgccgggtaa ctcacggggt   8460
atccatgtcc atttctgcgg catccagcca ggatacccgt cctcgctgac gtaatatccc   8520
agcgccgcac cgctgtcatt aatctgcaca ccggcacggc agttccggct gtcgccggta   8580
ttgttcgggt tgctgatgcg cttcgggctg accatccgga actgtgtccg gaaaagccgc   8640
gacgaactgg tatcccaggt ggcctgaacg aacagttcac cgttaaaggc gtgcatggcc   8700
acaccttccc gaatcatcat ggtaaacgtg cgttttcgct caacgtcaat gcagcagcag   8760
tcatcctcgg caaactcttt ccatgccgct caacctcgc gggaaaaggc acgggcttct   8820
tcctccccga tgcccagata cgccagcttg ggcgatgac tgagccggaa aaagacccg   8880 acgatatgat cctgatgcag ctagattaac cctagaaaga tagtctgcgt aaaattgacg   8940
catgggatcc cccgggctgc aggaattcga tatcaagctt atcgataccg tcgaagctt   8999
```

<210> SEQ ID NO 49
<211> LENGTH: 9012
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 49

```
accgaagtat acacttaaat tcagtgcacg tttgcttgtt gagaggaaag gttgtgtgcg     60
gacgaatttt ttttgaaaa cattaaccct tacgtggaat aaaaaaaaat gaatattgc    120 aaatttgct gcaaagctgt gactggagta aaattaattc acgtgccgaa gtgtgctatt    180
aagagaaaat tgtgggagca gagccttggg tgcagccttg gtgaaaactc ccaaatttgt    240 gataccact ttaatgattc gcagtggaag gctgcacctg caaaaggtca gacatttaaa    300
aggaggcgac tcaacgcaga tgccgtacct agtaaagtga tagagcctga accagaaaag    360 ataaagaag gctataccag tgggagtaca caaacagagt aagtttgaat agtaaaaaaa    420
atcatttatg taaacaataa cgtgactgtg cgttaggtcc tgttcattgt ttaatgaaaa    480
taagagcttg agggaaaaaa ttcgtacttt ggagtacgaa atgcgtcgtt tagagcagca    540
gccgaattca ctggccgtcg ttttacaacg tcgtgactgg gaaaaccctg gcgttaccca    600
acttaatcgc cttgcagcac atccccctt cgccagctgg cgtaatagcg aagaggcccg    660
caccgatcgc ccttcccaac agttgcgcag cctgaatggc gaatggcgct ttgcctggtt    720
tccggcacca gaagcggtgc cggaaagctg gctggagtgc gatcttcctg aggccgatac    780
tgtcgtcgtc ccctcaaact ggcagatgca cggttacgat gcgcccatct acaccaacgt    840
aacctatccc attacggtca atccgccgtt tgttcccacg gagaatccga cgggttgtta    900
```

```
ctcgctcaca tttaatgttg atgaaagctg gctacaggaa ggccagacgc gaattatttt    960
tgatggcgtt aactcggcgt ttcatctgtg gtgcaacggg cgctgggtcg gttacggcca   1020
ggacagtcgt ttgccgtctg aatttgacct gagcgcattt ttacgcgccg gagaaaaccg   1080
cctcgcggtg atggtgctgc gttggagtga cggcagttat ctggaagatc aggatatgtg   1140
gcggatgagc ggcatttttcc gtgacgtctc gttgctgcat aaaccgacta cacaaatcag   1200
cgatttccat gttgccactc gctttaatga tgatttcagc cgcgctgtac tggaggctga   1260
agttcagatg tgcggcgagt tgcgtgacta cctacgggta acagtttctt tatggcaggg   1320
tgaaacgcag gtcgccagcg gcaccgcgcc tttcggcggt gaaattatcg atgagcgtgg   1380
tggttatgcc gatcgcgtca cactacgtct gaacgtcgaa acccgaaac tgtggagcgc    1440
cgaaatcccg aatctctatc gtgcggtggt tgaactgcac accgccgacg gcacgctgat   1500
tgaagcagaa gcctgcgatg tcggtttccg cgaggtgcgg attgaaaatg gtctgctgct   1560
gctgaacggc aagccgttgc tgattcgagg cgttaaccgt cacgagcatc atcctctgca   1620
tggtcaggtc atggatgagc agacgatggt gcaggatatc ctgctgatga agcagaacaa   1680
ctttaacgcc gtgcgctgtt cgcattatcc gaaccatccg ctgtggtaca cgctgtgcga   1740
ccgctacggc ctgtatgtgg tggatgaagc caatattgaa acccacggca tggtgccaat   1800
gaatcgtctg accgatgatc cgcgctggct accggcgatg agcgaacgcg taacgcgaat   1860
ggtgcagcgc gatcgtaatc acccgagtgt gatcatctgg tcgctgggga tgaatcagg   1920
ccacggcgct aatcacgacg cgctgtatcg ctggatcaaa tctgtcgatc cttcccgccc   1980
ggtgcagtat gaaggcggcg gagccgacac cacggccacc gatattattt gcccgatgta   2040
cgcgcgcgtg gatgaagacc agcccttccc ggctgtgccg aaatggtcca tcaaaaaatg   2100
gctttcgcta cctggagaga cgcgcccgct gatcctttgc gaatacgccc acgcgatggg   2160
taacagtctt ggcggtttcg ctaaatactg gcaggcgttt cgtcagtatc cccgtttaca   2220
gggcggcttc gtctgggact gggtggatca gtcgctgatt aaatatgatg aaaacggcaa   2280
cccgtggtcg gcttacggcg gtgatttttgg cgatacgccg aacgatcgcc agttctgtat   2340
gaacggtctg gtctttgccg accgcacgcc gcatccagcg ctgacggaag caaaacacca   2400
gcagcagttt ttccagttcc gtttatccgg gcaaaccatc gaagtgacca gcgaatacct   2460
gttccgtcat agcgataacg agctcctgca ctggatggtg cgctggatg gtaagccgct   2520
ggcaagcggt gaagtgcctc tggatgtcgc tccacaaggt aaacagttga ttgaactgcc   2580
tgaactaccg cagccggaga gcgccgggca actctggctc acagtacgcg tagtgcaacc   2640
gaacgcgacc gcatggtcag aagccgggca catcagcgcc tggcagcagt ggcgtctggc   2700
ggaaaacctc agtgtgacgc tccccgccgc gtcccacgcc atcccgcatc tgaccaccag   2760
cgaaatggat ttttgcatcg agctgggtaa taagcgttgg caatttaacc gccagtcagg   2820
ctttctttca cagatgtgga ttggcgataa aaaacaactg ctgacgccgc tgcgcgatca   2880
gttcacccgt gcaccgctgg ataacgacat ggcgtaagt gaagcgaccc gcattgaccc    2940
taacgcctgg gtcgaacgct ggaaggcggc gggccattac caggccgaag cagcgttgtt   3000
gcagtgcacg gcagatacac ttgctgatgc ggtgctgatt acgaccgctc acgcgtggca   3060
gcatcagggg aaaaccttat ttatcagccg gaaaacctac cggattgatg gtagtggtca   3120
aatggcgatt accgttgatg ttgaagtggc gagcgataca ccgcatccgg cgcggattgg   3180
cctgaactgc cagctggcgc aggtagcaga gcgggtaaac tggctcggat tagggccgca   3240
```

```
agaaaactat cccgaccgcc ttactgccgc ctgttttgac cgctgggatc tgccattgtc   3300
agacatgtat accccgtacg tcttcccgag cgaaaacggt ctgcgctgcg ggacgcgcga   3360
attgaattat ggcccacacc agtggcgcgg cgacttccag ttcaacatca gccgctacag   3420
tcaacagcaa ctgatggaaa ccagccatcg ccatctgctg cacgcggaag aaggcacatg   3480
gctgaatatc gacggtttcc atatgggggat tggtggcgac gactcctgga gcccgtcagt   3540
atcggcggaa ttccagctga gcgccggtcg ctaccattac cagttggtct ggtgtcgggg   3600
atccgtcgac taaggccaaa gagtctaatt tttgttcatc aatgggttat aacatatggg   3660
ttatattata agtttgtttt aagtttttga gactgataag aatgtttcga tcgaatattc   3720
catagaacaa caatagtatt acctaattac caagtcttaa tttagcaaaa atgttattgc   3780
ttatagaaaa aataaattat ttatttgaaa tttaaagtca acttgtcatt taatgtcttg   3840
tagacttttg aaagtcttac gatacaatta gtatctaata tacatgggtt cattctacat   3900
tctatattag tgatgatttc tttagctagt aatacatttt aattatattc ggctttgatg   3960
attttctgat tttttccgaa cggattttcg tagacccttt cgatctcata atggctcatt   4020
ttattgcgat ggacggtcag gagagctcca cttttgaatt tctgttcgca gacaccgcat   4080
ttgtagcaca tagccgggac atccggtttg gggagatttt ccagtctctg ttgcaattgg   4140
ttttcgggaa tgcgttgcag gcgcatacgc tctatatcct ccgaacggcg ctggttgacc   4200
ctagcattta cataaggatc agcagcaaaa tttgcctctg cttcattgcc cggaatcaca   4260
gcaatcagat gtccctttcg gttacgatgg atattcaggt gcgaaccgca cacaaagctc   4320
tcgccgcaca ctccacactg atatggtcgc tcgccctgtg gcgccgcata tggatcttaa   4380
ggtcgttgga ctgcacaaag ctcttgctgc acattttgca ggagtacggc ctttgacccg   4440
tgtgcaatcg catgtgtcgc gccagcttgt tctgcgaaat aaacttcttg gagcagatgc   4500
ggccgcccgg ggtgggcgaa gaactccagc atgagatccc cgcgctggag gatcatccag   4560
ccggcgtccc ggaaaacgat tccgaagccc aacctttcat agaaggcggc ggtggaatcg   4620
aaatctcgtg atggcaggtt gggcgtcgct tggtcggtca tttcgaaccc cagagtcccg   4680
ctcagaagaa ctcgtcaaga aggcgataga aggcgatgcg ctgcgaatcg ggagcggcga   4740
taccgtaaag cacgaggaag cggtcagccc attcgccgcc aagctcttca gcaatatcac   4800
gggtagccaa cgctatgtcc tgatagcggt ccgccacacc cagccggcca cagtcgatga   4860
atcgagaaaa gcggccattt tccaccatga tattcggcaa gcaggcatcg ccatgggtca   4920
cgacgagatc ctcgccgtcg gcatgcgcgc cttgagcct ggcgaacagt tcggctggcg   4980
cgagcccctg atgctcttcg tccagatcat cctgatcgac aagaccggct tccatccgag   5040
tacgtgctcg ctcgatgcga tgtttcgctt ggtggtcgaa tgggcaggta gccggatcaa   5100
gcgtatgcag ccgccgcatt gcatcagcca tgatggatac tttctcggca ggagcaaggt   5160
gagatgacag gagatcctgc cccggcactt cgcccaatag cagccagtcc cttcccgctt   5220
cagtgacaac gtcgagcaca gctgcgcaag gaacgcccgt cgtggccagc cacgatagcc   5280
gcgctgcctc gtcctgcagt tcattcaggg caccggacag gtcggtcttg acaaaaagaa   5340
ccgggcgccc ctgcgctgac agccggaaca cggcggcatc agagcagccg attgtctgtt   5400
gtgcccagtc atagccgaat agcctctcca cccaagcggc cggagaacct gcgtgcaatc   5460
catcttgttc aatcatgcga aacgatcctc atcctgtctc ttgatcagat cttgatcccc   5520
tgcgccatca gatccttggc ggcaagaaag ccatccagtt tactttgcag gcttcccaa   5580 ccttaccaga gggcgcccca gctggcaatt ccggttcgct tgctgtccat aaaaccgccc   5640
```

```
agtctagcta tcgccatgta agcccactgc aagctacctg ctttctcttt gcgcttgcgt    5700
tttcccttgt ccagatagcc cagtagctga cattcatccg gggtcagcac cgtttctgcg    5760
gactggcttt ctacgtgttc cgcttccttt agcagccctt gcgccctgag tgcttgcggc    5820
agcgtgaagc taattcatgg ttataaattt ttgttaaatc agctcatttt ttaaccaata    5880
ggccgaaatc ggcaaaatcc cttataaatc aaaagaatag cccgagatag ggttgagtgt    5940
tgttccagtt tggaacaaga gtccactatt aagaacgtg gactccaacg tcaaagggcg    6000
aaaaaccgtc tatcagggcg atggccggat cagcttatgc ggtgtgaaat accgcacaga    6060
tgcgtaagga gaaaataccg catcaggcgc tcttccgctt cctcgctcac tgactcgctg    6120
cgctcggtcg ttcggctgcg gcgagcggta tcagctcact caaaggcggt aatacggtta    6180
tccacagaat caggggataa cgcaggaaag aacatgtgag caaaaggcca gcaaaaggcc    6240
aggaaccgta aaaaggccgc gttgctggcg tttttccata ggctccgccc ccctgacgag    6300
catcacaaaa atcgacgctc aagtcagagg tggcgaaacc cgacaggact ataaagatac    6360
caggcgtttc cccctggaag ctccctcgtg cgctctcctg ttccgaccct gccgcttacc    6420
ggatacctgt ccgcctttct cccttcggga agcgtggcgc tttctcatag ctcacgctgt    6480
aggtatctca gttcggtgta ggtcgttcgc tccaagctgg gctgtgtgca cgaaccccc     6540
gttcagcccg accgctgcgc cttatccggt aactatcgtc ttgagtccaa cccgtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggc ggttttttgt ttgcaagcag cagattacgc    6840
gcagaaaaaa aggatctcaa gaagatcctt tgatcttttc ttactgaacg gtgatcccca    6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt acgatccacc ggtcgccacc atggtgagca    7260
agggcgagga gctgttcacc ggggtggtgc ccatcctggt cgagctggac ggcgacgtaa    7320
acggccacaa gttcagcgtg tccggcgagg gcgagggcga tgccacctac ggcaagctga    7380
ccctgaagtt catctgcacc accggcaagc tgcccgtgcc ctggcccacc ctcgtgacca    7440
ccctgacctg gggcgtgcag tgcttcagcc gctaccccga ccacatgaag cagcacgact    7500
tcttcaagtc cgccatgccc gaaggctacg tccaggagcg caccatcttc ttcaaggacg    7560
acggcaacta caagacccgc gccgaggtga agttcgaggg cgacaccctg gtgaaccgca    7620
tcgagctgaa gggcatcgac ttcaaggagg acggcaacat cctggggcac aagctggagt    7680
acaactagat cagccacaac gtctatatca ccgccgacaa gcagaagaac ggcatcaagg    7740
ccaacttcaa gatccgccac aacatcgagg acggcagcgt gcagctcgcc gaccactacc    7800
agcagaacac ccccatcggc gacggccccg tgctgctgcc cgacaaccac tacctgagca    7860
cccagtccgc cctgagcaaa gaccccaacg agaagcgcga tcacatggtc ctgctggagt    7920
tcgtgaccgc cgccgggatc actctcggca tggacgagct gtacaagtaa agcggccgcg    7980
```

```
actctagatc ataatcagcc ataccacatt tgtagaggtt ttacttgctt taaaaaacct    8040
cccacacctc cccctgaacc tgaaacataa aatgaatgca attgttgttg ttaacttgtt    8100
tattgcagct tataatggtt acaaataaag caatagcatc acaaatttca caaataaagc    8160
atttttttca ctgcattcta gttgtggttt gtccaaactc atcaatgtat cttaaagctt    8220
atcgatacgc gtacggcgcg cctaggccgg ccgattggat cccatgcgtc aattttacgc    8280
atgattatct ttaacgtacg tcacaatatg attatctttc tagggttaat ctagctgcgt    8340
gttctgcagc gtgtcgagca tcttcatctg ctccatcacg ctgtaaaaca catttgcacc    8400
gcgagtctgc ccgtcctcca cgggttcaaa acgtgaatg aacgaggcgc gcccgccggg     8460
taactcacgg ggtatccatg tccatttctg cggcatccag ccaggatacc cgtcctcgct    8520
gacgtaatat cccagcgccg caccgctgtc attaatctgc acaccggcac ggcagttccg    8580
gctgtcgccg gtattgttcg ggttgctgat gcgcttcggg ctgaccatcc ggaactgtgt    8640
ccggaaaagc cgcgacgaac tggtatccca ggtggcctga cgaacagtt caccgttaaa     8700 ggcgtgcatg gccacacctt cccgaatcat catggtaaac gtgcgttttc gctcaacgtc    8760
aatgcagcag cagtcatcct cggcaaactc tttccatgcc gcttcaacct cgcgggaaaa    8820
ggcacgggct tcttcctccc cgatgcccag atagcgccag cttgggcgat gactgagccg    8880
gaaaaaagac ccgacgatat gatcctgatg cagctagatt aaccctagaa agatagtctg    8940
cgtaaaattg acgcatggga tcccccgggc tgcaggaatt cgatatcaag cttatcgata    9000
ccgtcgaagc tt                                                        9012

<210> SEQ ID NO 50
<211> LENGTH: 9013
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 50
accgaagtat acacttaaat tcagtgcacg tttgcttgtt gagaggaaag gttgtgtgcg      60
gacgaatttt tttttgaaaa cattaaccct tacgtggaat aaaaaaaaat gaaatattgc     120
aaattttgct gcaaagctgt gactggagta aaattaattc acgtgccgaa gtgtgctatt    180
aagagaaaat tgtgggagca gagccttggg tgcagccttg gtgaaaactc ccaaatttgt    240
gatacccact ttaatgattc gcagtggaag gctgcacctg caaaaggtca gacatttaaa    300
aggaggcgac tcaacgcaga tgccgtacct agtaaagtga tagagcctga accagaaaag    360
ataaaagaag gctataccag tgggagtaca caaacagagt aagtttgaat agtaaaaaaa    420
atcatttatg taaacaataa cgtgactgtg cgttaggtcc tgttcattgt ttaatgaaaa    480
taagagcttg agggaaaaaa ttcgtacttt ggagtacgaa atgcgtcgtt tagagcagca    540
gccgaattca ctgccgtcg ttttacaacg tcgtgactgg gaaaaccctg gcgttaccca     600
acttaatcgc cttgcagcac atccccctttt cgccagctgg cgtaatagcg aagaggcccg    660
caccgatcgc ccttcccaac agttgcgcag cctgaatggc gaatggcgct ttgcctggtt    720
tccggcacca gaagcggtgc cggaaagctg gctgagtgc gatcttcctg aggccgatac      780
tgtcgtcgtc ccctcaaaact ggcagatgca cggttacgat gcgcccatct acaccaacgt    840
aacctatccc attacggtca atccgccgtt tgttcccacg gagaatccga cgggttgtta    900
ctcgctcaca tttaatgttg atgaaagctg gctacaggaa ggccagacgc gaattatttt    960
```

-continued

```
tgatggcgtt aactcggcgt ttcatctgtg gtgcaacggg cgctgggtcg gttacggcca      1020
ggacagtcgt ttgccgtctg aatttgacct gagcgcattt ttacgcgccg gagaaaaccg      1080
cctcgcggtg atggtgctgc gttggagtga cggcagttat ctggaagatc aggatatgtg      1140
gcggatgagc ggcattttcc gtgacgtctc gttgctgcat aaaccgacta cacaaatcag      1200
cgatttccat gttgccactc gctttaatga tgatttcagc cgcgctgtac tggaggctga      1260
agttcagatg tgcggcgagt tgcgtgacta cctacgggta acagtttctt tatggcaggg      1320
tgaaacgcag gtcgccagcg gcaccgcgcc tttcggcggt gaaattatcg atgagcgtgg      1380
tggttatgcc gatcgcgtca cactacgtct gaacgtcgaa aacccgaaac tgtggagcgc      1440
cgaaatcccg aatctctatc gtgcggtggt tgaactgcac accgccgacg gcacgctgat      1500
tgaagcagaa gcctgcgatg tcggtttccg cgaggtgcgg attgaaaatg gtctgctgct      1560
gctgaacggc aagccgttgc tgattcgagg cgttaaccgt cacgagcatc atcctctgca      1620
tggtcaggtc atggatgagc agacgatggt gcaggatatc ctgctgatga agcagaacaa      1680
ctttaacgcc gtgcgctgtt cgcattatcc gaaccatccg ctgtggtaca cgctgtgcga      1740
ccgctacggc ctgtatgtgg tggatgaagc caatattgaa acccacggca tggtgccaat      1800
gaatcgtctg accgatgatc cgcgctggct accggcgatg agcgaacgcg taacgcgaat      1860
ggtgcagcgc gatcgtaatc acccgagtgt gatcatctgg tcgctgggga atgaatcagg      1920
ccacggcgct aatcacgacg cgctgtatcg ctggatcaaa tctgtcgatc cttcccgccc      1980
ggtgcagtat gaaggcggcg gagccgacac cacggccacc gatattattt gcccgatgta      2040
cgcgcgcgtg gatgaagacc agcccttccc ggctgtgccg aaatggtcca tcaaaaaatg      2100
gctttcgcta cctggagaga cgcgcccgct gatcctttgc gaatacgccc acgcgatggg      2160
taacagtctt ggcggtttcg ctaaatactg gcaggcgttt cgtcagtatc cccgtttaca      2220
gggcggcttc gtctgggact gggtggatca gtcgctgatt aaatatgatg aaaacggcaa      2280
cccgtggtcg gcttacggcg gtgatttttgg cgatacgccg aacgatcgcc agttctgtat      2340
gaacggtctg gtcttttgccg accgcacgcc gcatccagcg ctgacggaag caaaacacca      2400
gcagcagttt ttccagttcc gtttatccgg gcaaaccatc gaagtgacca gcgaatacct      2460
gttccgtcat agcgataacg agctcctgca ctggatggtg gcgctggatg gtaagccgct      2520
ggcaagcggt gaagtgcctc tggatgtcgc tccacaaggt aaacagttga ttgaactgcc      2580
tgaactaccg cagccggaga gcgccgggca actctggctc acagtacgcg tagtgcaacc      2640
gaacgcgacc gcatggtcag aagcggca catcagcgcc tggcagcagt ggcgtctggc      2700
ggaaaacctc agtgtgacgc tccccgccgc gtcccacgcc atcccgcatc tgaccaccag      2760
cgaaatggat ttttgcatcg agctgggtaa taagcgttgg caatttaacc gccagtcagg      2820
ctttctttca cagatgtgga ttggcgataa aaaacaactg ctgacgccgc tgcgcgatca      2880
gttcacccgt gcaccgctgg ataacgacat tggcgtaagt gaagcgaccc gcattgaccc      2940
taacgcctgg gtcgaacgct ggaaggcggc gggccattac caggccgaag cagcgttgtt      3000
gcagtgcacg gcagatacac ttgctgatgc ggtgctgatt acgaccgctc acgcgtggca      3060
gcatcagggg aaaaccttat ttatcagccg gaaaacctac cggattgatg gtagtggtca      3120
aatggcgatt accgttgatg ttgaagtggc gagcgataca ccgcatccgg cgcggattgg      3180
cctgaactgc cagctggcgc aggtagcaga gcgggtaaac tggctcggat tagggccgca      3240
agaaaactat cccgaccgcc ttactgccgc ctgttttgac cgctgggatc tgccattgtc      3300
agacatgtat acccccgtacg tcttcccgag cgaaaacggt ctgcgctgcg ggacgcgcga      3360
```

```
attgaattat ggcccacacc agtggcgcgg cgacttccag ttcaacatca gccgctacag    3420
tcaacagcaa ctgatggaaa ccagccatcg ccatctgctg cacgcggaag aaggcacatg    3480
gctgaatatc gacggtttcc atatggggat tggtggcgac gactcctgga gcccgtcagt    3540
atcggcggaa ttccagctga gcgccggtcg ctaccattac cagttggtct ggtgtcgggg    3600
atccgtcgac taaggccaaa gagtctaatt tttgttcatc aatgggttat aacatatggg    3660
ttatattata agtttgtttt aagttttga gactgataag aatgtttcga tcgaatattc     3720
catagaacaa caatagtatt acctaattac caagtcttaa tttagcaaaa atgtaattgc    3780
ttatagaaaa aataaattat ttatttgaaa tttaaagtca acttgtcatt taatgtcttg    3840
tagacttttg aaagtcttac gatacaatta gtatctaata tacatgggtt cattctacat    3900
tctatattag tgatgatttc tttagctagt aatacatttt aattatattc ggctttgatg    3960
attttctgat ttttccgaa cggattttcg tagacccttt cgatctcata atggctcatt    4020
ttattgcgat ggacggtcag gagagctcca cttttgaatt tctgttcgca gacaccgcat    4080
ttgtagcaca tagccgggac atccggtttg gggagatttt ccagtctctg ttgcaattgg    4140
ttttcgggaa tgcgttgcag gcgcatacgc tctatatcct ccgaacggcg ctggttgacc    4200
ctagcattta cataaggatc agcagcaaaa tttgcctctg cttcattgcc cggaatcaca    4260
gcaatcagat gtccctttcg gttacgatgg atattcaggt gcgaaccgca cacaaagctc    4320
tcgccgcaca ctccacactg atatggtcgc tcgccctgtg gcgccgcata tggatcttaa    4380
ggtcgttgga ctgcacaaag ctcttgctgc acattttgca ggagtacggc ctttgacccg    4440
tgtgcaatcg catgtgtcgc gccagcttgt tctgcgaaat aaacttcttg gagcagatgc    4500
ggccgcccgg ggtgggcgaa gaactccagc atgagatccc cgcgctggag gatcatccag    4560
ccggcgtccc ggaaaacgat tccgaagccc aacctttcat agaaggcggc ggtggaatcg    4620
aaatctcgtg atggcaggtt gggcgtcgct tggtcggtca tttcgaaccc cagagtcccg    4680
ctcagaagaa ctcgtcaaga aggcgataga aggcgatgcg ctgcgaatcg ggagcggcga    4740
taccgtaaag cacgaggaag cggtcagccc attcgccgcc aagctcttca gcaatatcac    4800
gggtagccaa cgctatgtcc tgatagcggt ccgccacacc cagccggcca cagtcgatga    4860
atccagaaaa gcggccattt tccaccatga tattcggcaa gcaggcatcg ccatgggtca    4920
cgacgagatc ctcgccgtcg ggcatgcgcg ccttgagcct ggcgaacagt tcggctggcg    4980
cgagcccctg atgctcttcg tccagatcat cctgatcgac aagaccggct tccatccgag    5040
tacgtgctcg ctcgatgcga tgtttcgctt ggtggtcgaa tgggcaggta gccggatcaa    5100
gcgtatgcag ccgccgcatt gcatcagcca tgatggatac tttctcggca ggagcaaggt    5160
gagatgacag gagatcctgc cccggcactt cgcccaatag cagccagtcc cttcccgctt    5220
cagtgacaac gtcgagcaca gctgcgcaag gaacgcccgt cgtggccagc cacgatagcc    5280
gcgctgcctc gtcctgcagt tcattcaggg caccggacag gtcggtcttg acaaaaagaa    5340
ccgggcgccc ctgcgctgac agccggaaca cggcggcatc agagcagccg attgtctgtt    5400
gtgcccagtc atagccgaat agcctctcca cccaagcggc cggagaacct gcgtgcaatc    5460
catcttgttc aatcatgcga aacgatcctc atcctgtctc ttgatcagat cttgatcccc    5520
tgcgccatca gatccttggc ggcaagaaag ccatccagtt tactttgcag gcttcccaa    5580 ccttaccaga gggcgcccca gctggcaatt ccggttcgct tgctgtccat aaaaccgccc    5640
agtctagcta tcgccatgta agcccactgc aagctacctg cttctctttt gcgcttgcgt    5700
```

```
tttcccttgt ccagatagcc cagtagctga cattcatccg gggtcagcac cgtttctgcg    5760
gactggcttt ctacgtgttc cgcttccttt agcagccctt gcgccctgag tgcttgcggc    5820
agcgtgaagc taattcatgg ttataaattt ttgttaaatc agctcatttt ttaaccaata    5880
ggccgaaatc ggcaaaatcc cttataaatc aaaagaatag cccgagatag ggttgagtgt    5940
tgttccagtt tggaacaaga gtccactatt aaagaacgtg gactccaacg tcaaagggcg    6000
aaaaaccgtc tatcagggcg atggcccgat cagcttatgc ggtgtgaaat accgcacaga    6060
tgcgtaagga gaaaataccg catcaggcgc tcttccgctt cctcgctcac tgactcgctg    6120
cgctcggtcg ttcggctgcg gcgagcggta tcagctcact caaaggcggt aatacggtta    6180
tccacagaat caggggataa cgcaggaaag aacatgtgag caaaaggcca gcaaaaggcc    6240
aggaaccgta aaaaggccgc gttgctggcg ttttttccata ggctccgccc ccctgacgag    6300
catcacaaaa atcgacgctc aagtcagagg tggcgaaacc cgacaggact ataaagatac    6360
caggcgtttc ccctggaag ctccctcgtg cgctctcctg ttccgaccct gccgcttacc    6420
ggatacctgt ccgcctttct cccttcggga agcgtggcgc tttctcatag ctcacgctgt    6480
aggtatctca gttcggtgta ggtcgttcgc tccaagctgg gctgtgtgca cgaaccccc     6540 gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggg gttttttgt ttgcaagcag cagattacgc     6840
gcagaaaaaa aggatctcaa gaagatcctt tgatctttc ttactgaacg gtgatcccca     6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt accgcgggcc cgggatccac cggtcgccac    7260
catggtgagc aagggcgagg agctgttcac cggggtggtg cccatcctgg tcgagctgga    7320
cggcgacgta aacggccaca agttcagcgt gtccggcgag ggcgagggcg atgccaccta    7380
cggcaagctg accctgaagt tcatctgcac caccggcaag ctgcccgtgc cctggcccac    7440
cctcgtgacc accctgacct acggcgtgca gtgcttcagc cgctaccccg accacatgaa    7500
gcagcacgac ttcttcaagt ccgccatgcc cgaaggctac gtccaggagc gcaccatctt    7560
cttcaaggac gacggcaact acaagacccg cgccgaggtg aagttcgagg gcgacaccct    7620
ggtgaaccgc atcgagctga agggcatcga cttcaaggag gacggcaaca tcctggggca    7680
caagctggag tacaactaca acagccacaa cgtctatatc atggccgaca agcagaagaa    7740
cggcatcaag gtgaacttca agatccgcca caacatcgag gacggcagcg tgcagctcgc    7800
cgaccactac cagcagaaca cccccatcgg cgacggcccc gtgctgctgc ccgacaacca    7860
ctacctgagc acccagtccg ccctgagcaa agaccccaac gagaagcgcg atcacatggt    7920
cctgctggag ttcgtgaccg ccgccgggat cactctcggc atggacgagc tgtacaagta    7980
aagcggccgc gactctagat cataatcagc cataccacat ttgtagaggt tttacttgct    8040
ttaaaaaacc tcccacacct ccccctgaac ctgaaacata aaatgaatgc aattgttgtt    8100
```

```
gttaacttgt ttattgcagc ttataatggt tacaaataaa gcaatagcat cacaaatttc    8160
acaaataaag catttttttc actgcattct agttgtggtt tgtccaaact catcaatgta    8220
tcttaaagct tatcgatacg cgtacggcgc gcctagtgga tcccatgcgt caattttacg    8280
catgattatc tttaacgtac gtcacaatat gattatcttt ctagggttaa tctagctgcg    8340
tgttctgcag cgtgtcgagc atcttcatct gctccatcac gctgtaaaac acatttgcac    8400
cgcgagtctg cccgtcctcc acgggttcaa aaacgtgaat gaacgaggcg cgcccgccgg    8460
gtaactcacg gggtatccat gtccatttct gcggcatcca gccaggatac ccgtcctcgc    8520
tgacgtaata tcccagcgcc gcaccgctgt cattaatctg cacaccggca cggcagttcc    8580
ggctgtcgcc ggtattgttc gggttgctga tgcgcttcgg gctgaccatc cggaactgtg    8640
tccggaaaag ccgcgacgaa ctggtatccc aggtggcctg aacgaacagt tcaccgttaa    8700
aggcgtgcat ggccacacct tcccgaatca tcatggtaaa cgtgcgtttt cgctcaacgt    8760
caatgcagca gcagtcatcc tcggcaaact ctttccatgc cgcttcaacc tcgcgggaaa    8820
aggcacgggc ttcttcctcc ccgatgccca gatagcgcca gcttgggcga tgactgagcc    8880
ggaaaaaaga cccgacgata tgatcctgat gcagctagat taaccctaga aagatagtct    8940
gcgtaaaatt gacgcatggg atcccccggg ctgcaggaat tcgatatcaa gcttatcgat    9000
accgtcgaag ctt                                                       9013

<210> SEQ ID NO 51
<211> LENGTH: 4951
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 51
ctaaattgta agcgttaata ttttgttaaa attgcgctta aattttttgtt aaatcagctc      60 atttttttaac caataggccg aaatcggcaa atcccttat aaatcaaaag aatagaccga     120 gataggggttg agtgttgttc cagttttggaa caagagtcca ctattaaaga acgtggactc    180
caacgtcaaa gggcgaaaaa ccgtctatca gggcgatggc ccactacgtg aaccatcacc    240
ctaatcaagt ttttgggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccgccg ggtaactcac ggggtatcca tgtccatttc     660
tgcggcatcc agccaggata cccgtcctcg ctgacgtaat atcccagcgc cgcaccgctg    720
tcattaatct gcacaccggc acggcagttc cggctgtcgc cggtattgtt cgggttgctg    780
atgcgcttcg ggctgaccat ccggaactgt gtccggaaaa gccgcgacga actggtatcc    840
caggtggcct gaacgaacag ttcaccgtta aaggcgtgca tggccacacc ttcccgaatc    900
atcatggtaa acgtgcgttt tcgctcaacg tcaatgcagc agcagtcatc ctcggcaaac    960
tctttccatg ccgcttcaac ctcgcgggaa aaggcacggg cttcttcctc cccgatgccc   1020
agatagcgcc agcttgggcg atgactgagc cggaaaaaag acccgacgat atgatcctga   1080
```

```
tgcagctaga ttaaccctag aaagatagtc tgcgtaaaat tgacgcatga tctaattaac    1140
cctcactaaa gggaacaaaa gctggagctc caccgcggtg gcggccgctc tagaactagt    1200
gttcccacaa tggttaattc gagctcgccc ggggatctaa ttcaattaga gactaattca    1260
attagagcta attcaattag gatccaagct tatcgatttc gaaccctcga ccgccggagt    1320
ataaatagag gcgcttcgtc tacggagcga caattcaatt caaacaagca aagtgaacac    1380
gtcgctaagc gaaagctaag caaataaaca agcgcagctg aacaagctaa acaatcgggg    1440
taccgctaga gtcgacggta cgatccaccg gtcgccacca tggtgagcaa gggcgaggag    1500
ctgttcaccg gggtggtgcc catcctggtc gagctggacg gcgacgtaaa cggccacaag    1560
ttcagcgtgt ccggcgaggg cgagggcgat gccacctacg gcaagctgac cctgaagttc    1620
atctgcacca ccggcaagct gcccgtgccc tggcccaccc tcgtgaccac cttcggctac    1680
ggcctgcagt gcttcgcccg ctaccccgac cacatgaagc agcacgactt cttcaagtcc    1740
gccatgcccg aaggctacgt ccaggagcgc accatcttct tcaaggacga cggcaactac    1800
aagacccgcg ccgaggtgaa gttcgagggc gacaccctgg tgaaccgcat cgagctgaag    1860
ggcatcgact tcaaggagga cggcaacatc ctggggcaca agctggagta caactacaac    1920
agccacaacg tctatatcat ggccgacaag cagaagaacg gcatcaaggt gaacttcaag    1980
atccgccaca acatcgagga cggcagcgtg cagctcgccg accactacca gcagaacacc    2040
cccatcggcg acggccccgt gctgctgccc gacaaccact acctgagcta ccagtccgcc    2100
ctgagcaaag accccaacga gaagcgcgat cacatggtcc tgctggagtt cgtgaccgcc    2160
gccgggatca ctctcggcat ggacgagctg tacaagtaaa gcggccgcga ctctagatca    2220
taatcagcca taccacattt gtagaggttt tacttgcttt aaaaaacctc ccacacctcc    2280
ccctgaacct gaaacataaa atgaatgcaa ttgttgttgt taacttgttt attgcagctt    2340
ataatggtta caaataaagc aatagcatca caaatttcac aaataaagca tttttttcac    2400
tgcattctag ttgtggtttg tccaaactca tcaatgtatc ttaaagctta tcgatacgcg    2460
tacggcgcgc ctaggcacta gtggatcccc cgggctgcag gaattcgata tcaagcttat    2520
cgataccgtc gacctcgagg ggggcccggt acccaattcg ccctatagt gagtcgtatt    2580 aagatcacgc gtagatccat gcgtcaattt tacgcatgat tatctttaac gtacgtcaca    2640
atatgattat ctttctaggg ttaatctagc tgcgtgttct gcagcgtgtc gagcatcttc    2700
atctgctcca tcacgctgta aaacacattt gcaccgcgag tctgcccgtc ctccacgggt    2760
tcaaaaacgt gaatgaacga ggcgcgcttg gcgtaatcat ggtcatagct gtttcctgtg    2820
tgaaattgtt atccgctcac aattccacac aacatacgag ccggaagcat aaagtgtaaa    2880
gcctggggtg cctaatgagt gagctaactc acattaattg cgttgcgctc actgcccgct    2940
ttccagtcgg gaaacctgtc gtgccagctg cattaatgaa tcggccaacg cgcgggggaga   3000 ggcggtttgc gtattgggcg ctcttccgct tcctcgctca ctgactcgct gcgctcggtc    3060
gttcggctgc ggcgagcggt atcagctcac tcaaaggcgg taatacggtt atccacagaa    3120
tcaggggata acgcaggaaa gaacatgtga gcaaaaggcc agcaaaaggc caggaaccgt    3180
aaaaaggccg cgttgctggc gttttttccat aggctccgcc cccctgacga gcatcacaaa   3240
aatcgacgct caagtcagag gtggcgaaac ccgacaggac tataaagata ccaggcgttt    3300
ccccctggaa gctccctcgt gcgctctcct gttccgaccc tgccgcttac cggatacctg    3360
tccgcctttc tcccttcggg aagcgtggcg ctttctcata gctcacgctg taggtatctc    3420
```

```
agttcggtgt aggtcgttcg ctccaagctg ggctgtgtgc acgaaccccc cgttcagccc   3480
gaccgctgcg ccttatccgg taactatcgt cttgagtcca acccggtaag acacgactta   3540
tcgccactgg cagcagccac tggtaacagg attagcagag cgaggtatgt aggcggtgct   3600
acagagttct tgaagtggtg gcctaactac ggctacacta aaggacagt atttggtatc    3660 tgcgctctgc tgaagccagt taccttcgga aaaagagttg gtagctcttg atccggcaaa   3720
caaaccaccg ctggtagcgg tggttttttt gtttgcaagc agcagattac gcgcagaaaa   3780
aaaggatctc aagaagatcc tttgatcttt tctacggggt ctgacgctca gtggaacgaa   3840
aactcacgtt aagggatttt ggtcatgaga ttatcaaaaa ggatcttcac ctagatcctt   3900
ttaaattaaa aatgaagttt taaatcaatc taaagtatat atgagtaaac ttggtctgac   3960
agttaccaat gcttaatcag tgaggcacct atctcagcga tctgtctatt tcgttcatcc   4020
atagttgcct gactccccgt cgtgtagata actacgatac gggagggctt accatctggc   4080
cccagtgctg caatgatacc gcgagaccca cgctcaccgg ctccagattt atcagcaata   4140
aaccagccag ccggaagggc cgagcgcaga agtggtcctg caactttatc cgcctccatc   4200
cagtctatta attgttgccg ggaagctaga gtaagtagtt cgccagttaa tagtttgcgc   4260
aacgttgttg ccattgctac aggcatcgtg gtgtcacgct cgtcgtttgg tatggcttca   4320
ttcagctccg gttcccaacg atcaaggcga gttacatgat cccccatgtt gtgcaaaaaa   4380
gcggttagct ccttcggtcc tccgatcgtt gtcagaagta agttggccgc agtgttatca   4440
ctcatggtta tggcagcact gcataattct cttactgtca tgccatccgt aagatgcttt   4500
tctgtgactg gtgagtactc aaccaagtca ttctgagaat agtgtatgcg gcgaccgagt   4560
tgctcttgcc cggcgtcaat acgggataat accgcgccac atagcagaac tttaaaagtg   4620
ctcatcattg gaaaacgttc ttcggggcga aaactctcaa ggatcttacc gctgttgaga   4680
tccagttcga tgtaacccac tcgtgcaccc aactgatctt cagcatcttt tactttcacc   4740
agcgtttctg ggtgagcaaa aacaggaagg caaaatgccg caaaaaaggg aataagggcg   4800
acacggaaat gttgaatact catactcttc ctttttcaat attattgaag catttatcag   4860
ggttattgtc tcatgagcgg atacatattt gaatgtattt agaaaaataa acaaataggg   4920
gttccgcgca catttccccg aaaagtgcca c                                  4951
```

<210> SEQ ID NO 52
<211> LENGTH: 4952
<212> TYPE: DNA
<213> ORGANISM: Artificial Sequence
<220> FEATURE:
<223> OTHER INFORMATION: Description of Artificial Sequence: Synthetic
    nucleotide construct

<400> SEQUENCE: 52

```
ctaaattgta agcgttaata ttttgttaaa attcgcgtta aattttttgtt aaatcagctc     60 attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
```

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccgccg ggtaactcac ggggtatcca tgtccatttc     660
tgcggcatcc agccaggata cccgtcctcg ctgacgtaat atcccagcgc cgcaccgctg    720
tcattaatct gcacaccggc acggcagttc cggctgtcgc cggtattgtt cgggttgctg    780
atgcgcttcg ggctgaccat ccggaactgt gtccggaaaa gccgcgacga actggtatcc    840
caggtggcct gaacgaacag ttcaccgtta aaggcgtgca tggccacacc ttcccgaatc    900
atcatggtaa acgtgcgttt tcgctcaacg tcaatgcagc agcagtcatc ctcggcaaac    960
tctttccatg ccgcttcaac ctcgcgggaa aaggcacggg cttcttcctc cccgatgccc   1020
agatagcgcc agcttgggcg atgactgagc cggaaaaaag acccgacgat atgatcctga   1080
tgcagctaga ttaaccctag aaagatagtc tgcgtaaaat tgacgcatga tctaattaac   1140
cctcactaaa gggaacaaaa gctggagctc caccgcggtg cggccgctc tagaactagt    1200 gccgtacgcg tatcgataag ctttaagata cattgatgag tttggacaaa ccacaactag   1260
aatgcagtga aaaaaatgct ttatttgtga aatttgtgat gctattgctt tatttgtaac   1320
cattataagc tgcaataaac aagttaacaa caacaattgc attcatttta tgtttcaggt   1380
tcagggggag gtgtgggagg ttttttaaag caagtaaaac ctctacaaat gtggtatggc   1440
tgattatgat ctagagtcgc ggccgcttta cttgtacagc tcgtccatgc cgagagtgat   1500
cccggcggcg gtcacgaact ccagcaggac catgtgatcg cgcttctcgt tgggtctttt   1560
gctcagggcg gactgggtgc tcaggtagtg gttgtcgggc agcagcacgg ggccgtcgcc   1620 gatggggtg ttctgctggt agtggtcggc gagctgcacg ctgccgtcct cgatgttgtg    1680
gcggatcttg aagttcacct tgatgccgtt cttctgcttg tcggccatga tatagacgtt   1740
gtggctgttg tagttgtact ccagcttgtg ccccaggatg ttgccgtcct ccttgaagtc   1800
gatgcccttc agctcgatgc ggttcaccag ggtgtcgccc tcgaacttca cctcggcgcg   1860
ggtcttgtag ttgccgtcgt ccttgaagaa gatggtgcgc tcctggacgt agccttcggg   1920
catggcggac ttgaagaagt cgtgctgctt catgtggtcg gggtagcggc tgaagcactg   1980
cacgccgtag gtcagggtgg tcacgagggt gggccagggc acgggcagct gccggtggt    2040 gcagatgaac ttcagggtca gcttgccgta gtggcatcg ccctcgccct cgccggacac    2100
gctgaacttg tggccgttta cgtcgccgtc cagctcgacc aggatgggca ccaccccggt   2160
gaacagctcc tcgcccttgc tcaccatggt ggcgaccggt ggatcccggg cccgcggtac   2220
cgtcgactct agcggtaccc cgattgttta gcttgttcag ctgcgcttgt ttatttgctt   2280
agctttcgct tagcgacgtg ttcactttgc ttgtttgaat tgaattgtcg ctccgtagac   2340
gaagcgcctc tatttatact ccggcggtcg agggttcgaa atcgataagc ttggatccta   2400
attgaattag ctctaattga attagtctct aattgaatta gatccccggg cgagctcgaa   2460
ttaaccattg tgggaacact agtggatccc ccgggctgca ggaattcgat atcaagctta   2520
tcgataccgt cgacctcgag ggggggcccg gtacccaatt cgccctatag tgagtcgtat   2580
taagatcacg cgtagatcca tgcgtcaatt ttacgcatga ttatctttaa cgtacgtcac   2640
aatatgatta tctttctagg gttaatctag ctgcgtgttc tgcagcgtgt cgagcatctt   2700
catctgctcc atcacgctgt aaaacacatt tgcaccgcga gtctgccgt cctccacggg    2760 ttcaaaaacg tgaatgaacg aggcgcgctt ggcgtaatca tggtcatagc tgtttcctgt   2820
gtgaaattgt tatccgctca caattccaca caacatacga gccggaagca taaagtgtaa   2880
```

```
agcctggggt gcctaatgag tgagctaact cacattaatt gcgttgcgct cactgcccgc    2940
tttccagtcg ggaaacctgt cgtgccagct gcattaatga atcggccaac gcgcggggag    3000
aggcggtttg cgtattgggc gctcttccgc ttcctcgctc actgactcgc tgcgctcggt    3060
cgttcggctg cggcgagcgg tatcagctca ctcaaaggcg gtaatacggt tatccacaga    3120
atcaggggat aacgcaggaa agaacatgtg agcaaaaggc cagcaaaagg ccaggaaccg    3180
taaaaaggcc gcgttgctgg cgttttccca taggctccgc cccccctgacg agcatcacaa    3240
aaatcgacgc tcaagtcaga ggtggcgaaa cccgacagga ctataaagat accaggcgtt    3300
tccccctgga agctccctcg tgcgctctcc tgttccgacc ctgccgctta ccggatacct    3360
gtccgccttt ctcccttcgg gaagcgtggc gctttctcat agctcacgct gtaggtatct    3420
cagttcggtg taggtcgttc gctccaagct gggctgtgtg cacgaacccc ccgttcagcc    3480
cgaccgctgc gccttatccg gtaactatcg tcttgagtcc aacccggtaa gacacgactt    3540
atcgccactg gcagcagcca ctggtaacag gattagcaga gcgaggtatg taggcggtgc    3600
tacagagttc ttgaagtggt ggcctaacta cggctacact agaaggacag tatttggtat    3660
ctgcgctctg ctgaagccag ttaccttcgg aaaaagagtt ggtagctctt gatccggcaa    3720
acaaaccacc gctggtagcg gtggtttttt tgtttgcaag cagcagatta cgcgcagaaa    3780
aaaaggatct caagaagatc ctttgatctt ttctacgggg tctgacgctc agtggaacga    3840
aaactcacgt taagggattt tggtcatgag attatcaaaa aggatcttca cctagatcct    3900
tttaaattaa aaatgaagtt ttaaatcaat ctaaagtata tatgagtaaa cttggtctga    3960
cagttaccaa tgcttaatca gtgaggcacc tatctcagcg atctgtctat ttcgttcatc    4020
catagttgcc tgactccccg tcgtgtagat aactacgata cgggagggct taccatctgg    4080
ccccagtgct gcaatgatac cgcgagaccc acgctcaccg gctccagatt tatcagcaat    4140
aaaccagcca gccggaaggg ccgagcgcag aagtggtcct gcaactttat ccgcctccat    4200
ccagtctatt aattgttgcc gggaagctag agtaagtagt tcgccagtta atagtttgcg    4260
caacgttgtt gccattgcta caggcatcgt ggtgtcacgc tcgtcgtttg gtatggcttc    4320
attcagctcc ggttcccaac gatcaaggcg agttacatga tcccccatgt tgtgcaaaaa    4380
agcggttagc tccttcggtc ctccgatcgt tgtcagaagt aagttggccg cagtgttatc    4440
actcatggtt atggcagcac tgcataattc tcttactgtc atgccatccg taagatgctt    4500
ttctgtgact ggtgagtact caaccaagtc attctgagaa tagtgtatgc ggcgaccgag    4560
ttgctcttgc ccggcgtcaa tacgggataa taccgcgcca catagcagaa ctttaaaagt    4620
gctcatcatt ggaaaacgtt cttcgggcg aaaactctca aggatcttac cgctgttgag    4680
atccagttcg atgtaaccca ctcgtgcacc caactgatct tcagcatctt ttactttcac    4740
cagcgtttct gggtgagcaa aaacaggaag gcaaaatgcc gcaaaaaagg gaataagggc    4800
gacacggaaa tgttgaatac tcatactctt cctttttcaa tattattgaa gcatttatca    4860
gggttattgt ctcatgagcg gatacatatt tgaatgtatt tagaaaaata aacaaatagg    4920
ggttccgcgc acatttcccc gaaaagtgcc ac                                  4952
```

<210> SEQ ID NO 53
<211> LENGTH: 4941
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 53

```
ctaaattgta agcgttaata ttttgttaaa attcgcgtta aattttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcccgccg ggtaactcac ggggtatcca tgtccatttc   660
tgcggcatcc agccaggata cccgtcctcg ctgacgtaat atcccagcgc cgcaccgctg   720
tcattaatct gcacaccggc acggcagttc cggctgtcgc cggtattgtt cgggttgctg   780
atgcgcttcg ggctgaccat ccggaactgt gtccggaaaa gccgcgacga actggtatcc   840
caggtggcct gaacgaacag ttcaccgtta aaggcgtgca tggccacacc ttcccgaatc   900
atcatggtaa acgtgcgttt tcgctcaacg tcaatgcagc agcagtcatc ctcggcaaac   960
tctttccatg ccgcttcaac ctcgcgggaa aaggcacggg cttcttcctc cccgatgccc  1020
agatagcgcc agcttgggcg atgactgagc cggaaaaaag acccgacgat atgatcctga  1080
tgcagctaga ttaaccctag aaagatagtc tgcgtaaaat tgacgcatga tctaattaac  1140
cctcactaaa gggaacaaaa gctggagctc caccgcggtg gcgccgcctc tagaactagt  1200
gttcccacaa tggttaattc gagctcgccc ggggatctaa ttcaattaga gactaattca  1260
attagagcta attcaattag gatccaagct tatcgatttc gaaccctcga ccgccggagt  1320
ataaatagag gcgcttcgtc tacggagcga caattcaatt caaacaagca aagtgaacac  1380
gtcgctaagc gaaagctaag caaataaaca agcgcagctg aacaagctaa acaatcgggg  1440
taccgctaga gtcgacggta cgatccaccg gtcgccacca tggtgagcaa gggcgaggag  1500
ctgttcaccg gggtggtgcc catcctggtc gagctggacg gcgacgtaaa cggccacaag  1560
ttcagcgtgt ccggcgaggg cgagggcgat gccacctacg gcaagctgac cctgaagttc  1620
atctgcacca ccggcaagct gcccgtgccc tggcccaccc tcgtgaccac cctgacctgg  1680
ggcgtgcagt gcttcagccg ctaccccgac cacatgaagc agcacgactt cttcaagtcc  1740
gccatgcccg aaggctacgt ccaggagcgc accatcttct tcaaggacga cggcaactac  1800
aagacccgcg ccgaggtgaa gttcgagggc gacaccctgg tgaaccgcat cgagctgaag  1860
ggcatcgact tcaaggagga cggcaacatc ctggggcaca agctggagta caactacatc  1920
agccacaacg tctatatcac cgccgacaag cagaagaacg gcatcaaggc aacttcaag   1980
atccgccaca acatcgagga cggcagcgtg cagctcgccg accactacca gcagaacacc  2040
cccatcggcg acggccccgt gctgctgccc gacaaccact acctgagcac ccagtccgcc  2100
ctgagcaaag accccaacga gaagcgcgat cacatggtcc tgctggagtt cgtgaccgcc  2160
gccgggatca ctctcggcat ggacgagctg tacaagtaaa gcggccgcga ctctagatca  2220
taatcagcca taccacattt gtagaggttt tacttgcttt aaaaaacctc ccacacctcc  2280
```

-continued

```
ccctgaacct gaaacataaa atgaatgcaa ttgttgttgt taacttgttt attgcagctt    2340
ataatggtta caaataaagc aatagcatca caaatttcac aaataaagca ttttttttcac   2400
tgcattctag ttgtggtttg tccaaactca tcaatgtatc ttaaagctta tcgatacgcg    2460
tacggcacta gtggatcccc cgggctgcag gaattcgata tcaagcttat cgataccgtc    2520
gacctcgagg gggggcccgg tacccaattc gccctatagt gagtcgtatt aagatcacgc    2580
gtagatccat cgtcaattt tacgcatgat tatctttaac gtacgtcaca atatgattat    2640
cttttctaggg ttaatctagc tgcgtgttct gcagcgtgtc gagcatcttc atctgctcca   2700
tcacgctgta aaacacattt gcaccgcgag tctgcccgtc ctccacgggt tcaaaaacgt    2760
gaatgaacga ggcgcgcttg gcgtaatcat ggtcatagct gtttcctgtg tgaaattgtt    2820
atccgctcac aattccacac aacatacgag ccggaagcat aaagtgtaaa gcctggggtg    2880
cctaatgagt gagctaactc acattaattg cgttgcgctc actgcccgct ttccagtcgg    2940
gaaacctgtc gtgccagctg cattaatgaa tcggccaacg cgcggggaga ggcggtttgc    3000
gtattgggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt attggtatc tgcgctctgc    3660
tgaagccagt taccttcgga aaaagagttg gtagctcttg atccggcaaa caaaccaccg    3720
ctggtagcgg tggtttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaattaaa    3900
aatgaagttt taaatcaatc taaagtatat atgagtaaac ttggtctgac agttaccaat    3960
gcttaatcag tgaggcacct atctcagcga tctgtctatt tcgttcatcc atagttgcct    4020
gactccccgt cgtgtagata actacgatac gggagggctt accatctggc cccagtgctg    4080
caatgatacc gcgagaccca cgctcaccgg ctccagattt atcagcaata aaccagccag    4140
ccggaagggc cgagcgcaga agtggtcctg caactttatc cgcctccatc cagtctatta    4200
attgttgccg ggaagctaga gtaagtagtt cgccagttaa tagtttgcgc aacgttgttg    4260
ccattgctac aggcatcgtg gtgtcacgct cgtcgtttgg tatggcttca ttcagctccg    4320
gttcccaacg atcaaggcga gttacatgat cccccatgtt gtgcaaaaaa gcggttagct    4380
ccttcggtcc tccgatcgtt gtcagaagta agttggccgc agtgttatca ctcatggtta    4440
tggcagcact gcataattct cttactgtca tgccatccgt aagatgcttt tctgtgactg    4500
gtgagtactc aaccaagtca ttctgagaat agtgtatgcg gcgaccgagt tgctcttgcc    4560
cggcgtcaat acgggataat accgcgccac atagcagaac tttaaaagtg ctcatcattg    4620
gaaaacgttc ttcggggcga aaactctcaa ggatcttacc gctgttgaga tccagttcga    4680
```

```
tgtaacccac tcgtgcaccc aactgatctt cagcatcttt tactttcacc agcgtttctg      4740
ggtgagcaaa aacaggaagg caaaatgccg caaaaaggg aataagggcg acacggaaat       4800
gttgaatact catactcttc cttttcaat attattgaag catttatcag ggttattgtc       4860
tcatgagcgg atacatattt gaatgtattt agaaaaataa acaaataggg gttccgcgca      4920
catttccccg aaaagtgcca c                                                4941
```

<210> SEQ ID NO 54
<211> LENGTH: 4943
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 54

```
cacctgacgc gccctgtagc ggcgcattaa gcgcggcggg tgtggtggtt acgcgcagcg        60
tgaccgctac acttgccagc gccctagcgc ccgctccttt cgctttcttc ccttcctttc       120
tcgccacgtt cgccggcttt ccccgtcaag ctctaaatcg gggctccct ttagggttcc        180 gatttagtgc tttacggcac ctcgacccca aaaaacttga ttagggtgat ggttcacgta       240
gtgggccatc gccctgatag acggtttttc gccctttgac gttggagtcc acgttcttta      300
atagtggact cttgttccaa actggaacaa cactcaaccc tatctcggtc tattcttttg       360
atttataagg gattttgccg atttcggcct attggttaaa aaatgagctg atttaacaaa       420
aatttaacgc gaattttaac aaaatattaa cgcttacaat ttccattcgc cattcaggct       480
gcgcaactgt tgggaagggc gatcggtgcg ggcctcttcg ctattacgcc agctggcgaa       540
agggggatgt gctgcaaggc gattaagttg gtaacgcca gggttttccc agtcacgacg       600
ttgtaaaacg acggccagtg aattgtaata cgactcacta tagggcgaat tgggtaccgg       660
gccccccctc gaggtcgacg gtatcgataa gcttgatatc gaattcctgc agcccggggg      720
atcccatgcg tcaattttac gcagactatc tttctagggt taatctagct gcatcaggat       780
catatcgtcg ggtctttttt ccggctcagt catcgcccaa gctggcgcta tctgggcatc       840
ggggaggaag aagcccgtgc cttttcccgc gaggttgaag cggcatggaa agagtttgcc       900
gaggatgact gctgctgcat tgacgttgag cgaaaacgca cgtttaccat gatgattcgg       960
gaaggtgtgg ccatgcacgc ctttaacggt gaactgttcg ttcaggccac ctgggatacc      1020
agttcgtcgc ggcttttccg gacacagttc cggatggtca gcccgaagcg catcagcaac      1080
ccgaacaata ccggcgacag ccggaactgc cgtgccggtg tgcagattaa tgacagcggt      1140
gcggcgctgg gatattacgt cagcgaggac gggtatcctg gctggatgcc gcagaaatgg      1200
acatggatac cccgtgagtt acccggcggc tcgttcattc acgttttga acccgtggag      1260 gacgggcaga ctcgcggtgc aaatgtgttt tacagcgtga tggagcagat gaagatgctc      1320
gacacgctgc agaacacgca gctagattaa ccctagaaag ataatcatat tgtgacgtac      1380
gttaaagata atcatgcgta aaattgacgc atgggatcca ctagtgttcc cacaatggtt      1440
aattcgagct cgcccgggga tctaattcaa ttagagacta attcaattag agctaattca      1500
attaggatcc aagcttatcg atttcgaacc ctcgaccgcc ggagtataaa tagaggcgct      1560
tcgtctacgg agcgacaatt caattcaaac aagcaaagtg aacacgtcgc taagcgaaag      1620
ctaagcaaat aaacaagcgc agctgaacaa gctaaacaat cggggtaccg ctagagtcga      1680
cggtacgatc caccggtcgc caccatggtg agcaagggcg aggagctgtt caccggggtg      1740
```

```
gtgcccatcc tggtcgagct ggacggcgac gtaaacggcc acaagttcag cgtgtccggc   1800
gagggcgagg gcgatgccac ctacggcaag ctgaccctga agttcatctg caccaccggc   1860
aagctgcccg tgcccctggcc caccctcgtg accaccctga cctggggcgt gcagtgcttc   1920
agccgctacc ccgaccacat gaagcagcac gacttcttca gtccgccat gcccgaaggc   1980 tacgtccagg agcgcaccat cttcttcaag gacgacggca actacaagac ccgcgccgag   2040
gtgaagttcg agggcgacac cctggtgaac cgcatcgagc tgaagggcat cgacttcaag   2100
gaggacggca acatcctggg gcacaagctg gagtacaact acatcagcca caacgtctat   2160
atcaccgccg acaagcagaa gaacggcatc aaggccaact tcaagatccg ccacaacatc   2220
gaggacggca gcgtgcagct cgccgaccac taccagcaga caccccccat cggcgacggc   2280
cccgtgctgc tgcccgacaa ccactacctg agcacccagt ccgccctgag caaagacccc   2340
aacgagaagc gcgatcacat ggtcctgctg gagttcgtga ccgccgccgg gatcactctc   2400
ggcatggacg agctgtacaa gtaaagcggc cgcgactcta gatcataatc agccatacca   2460
catttgtaga ggttttactt gctttaaaaa acctcccaca cctccccctg aacctgaaac   2520
ataaaatgaa tgcaattgtt gttgttaact tgtttattgc agcttataat ggttacaaat   2580
aaagcaatag catcacaaat ttcacaaata aagcattttt ttcactgcat tctagttgtg   2640
gtttgtccaa actcatcaat gtatcttaaa gcttatcgat acgcgtacgg cgcgcctagg   2700
ccggccgata ctagttctag agcggccgcc accgcggtgg agctccagct tttgttccct   2760
ttagtgaggg ttaatttcga gcttggcgta atcatggtca tagctgtttc ctgtgtgaaa   2820
ttgttatccg ctcacaattc cacacaacat acgagccgga agcataaagt gtaaagcctg   2880
gggtgcctaa tgagtgagct aactcacatt aattgcgttg cgctcactgc ccgctttcca   2940
gtcgggaaac ctgtcgtgcc agctgcatta atgaatcggc caacgcgcgg ggagaggcgg   3000
tttgcgtatt gggcgctctt ccgcttcctc gctcactgac tcgctgcgct cggtcgttcg   3060
gctgcggcga gcggtatcag ctcactcaaa ggcggtaata cggttatcca cagaatcagg   3120
ggataacgca ggaaagaaca tgtgagcaaa aggccagcaa aaggccagga accgtaaaaa   3180
ggccgcgttg ctggcgtttt tccataggct ccgcccccct gacgagcatc acaaaaatcg   3240
acgctcaagt cagaggtggc gaaacccgac aggactataa agataccagg cgtttccccc   3300
tggaagctcc ctcgtgcgct ctcctgttcc gaccctgccg cttaccggat acctgtccgc   3360
ctttctccct tcgggaagcg tggcgctttc tcatagctca cgctgtaggt atctcagttc   3420
ggtgtaggtc gttcgctcca agctgggctg tgtgcacgaa ccccccgttc agcccgaccg   3480
ctgcgcctta tccggtaact atcgtcttga gtccaacccg gtaagacacg acttatcgcc   3540
actggcagca gccactggta acaggattag cagagcgagg tatgtaggcg gtgctacaga   3600
gttcttgaag tggtggccta actacggcta cactagaagg acagtatttg gtatctgcgc   3660
tctgctgaag ccagttacct tcggaaaaag agttggtagc tcttgatccg gcaaacaaac   3720
caccgctggt agcggtggtt ttttgtttg caagcagcag attacgcgca gaaaaaaagg   3780
atctcaagaa gatcctttga tcttttctac ggggtctgac gctcagtgga acgaaaactc   3840
acgttaaggg attttggtca tgagattatc aaaaaggatc ttcacctaga tccttttaaa   3900
ttaaaaatga agttttaaat caatctaaag tatatatgag taaacttggt ctgacagtta   3960
ccaatgctta atcagtgagg cacctatctc agcgatctgt ctatttcgtt catccatagt   4020
tgcctgactc cccgtcgtgt agataactac gatacgggag ggcttaccat ctggccccag   4080
```

```
tgctgcaatg ataccgcgag acccacgctc accggctcca gatttatcag caataaacca   4140
gccagccgga agggccgagc gcagaagtgg tcctgcaact ttatccgcct ccatccagtc   4200
tattaattgt tgccgggaag ctagagtaag tagttcgcca gttaatagtt tgcgcaacgt   4260
tgttgccatt gctacaggca tcgtggtgtc acgctcgtcg tttggtatgg cttcattcag   4320
ctccggttcc caacgatcaa ggcgagttac atgatccccc atgttgtgca aaaaagcggt   4380
tagctccttc ggtcctccga tcgttgtcag aagtaagttg gccgcagtgt tatcactcat   4440
ggttatggca gcactgcata attctcttac tgtcatgcca tccgtaagat gcttttctgt   4500
gactggtgag tactcaacca agtcattctg agaatagtgt atgcggcgac cgagttgctc   4560
ttgcccggcg tcaatacggg ataataccgc gccacatagc agaactttaa aagtgctcat   4620
cattggaaaa cgttcttcgg ggcgaaaact ctcaaggatc ttaccgctgt tgagatccag   4680
ttcgatgtaa cccactcgtg cacccaactg atcttcagca tctttactt tcaccagcgt   4740 ttctgggtga gcaaaaacag gaaggcaaaa tgccgcaaaa aagggaataa gggcgacacg   4800
gaaatgttga atactcatac tcttcctttt tcaatattat tgaagcattt atcagggtta   4860
ttgtctcatg agcggataca tatttgaatg tatttagaaa aataaacaaa taggggttcc   4920
gcgcacattt ccccgaaaag tgc                                            4943
```

<210> SEQ ID NO 55
<211> LENGTH: 4944
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 55

```
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240
gtgggccatc gccctgatag acggtttttc gccctttgac gttggagtcc acgttcttta    300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gaggtcgacg gtatcgataa gcttgatatc gaattcctgc agcccggggg    720
atcccatgcg tcaattttac gcagactatc tttctagggt taatctagct gcatcaggat    780
catatcgtcg gtctttttt ccggctcagt catcgcccaa gctggcgcta tctgggcatc    840
ggggaggaag aagcccgtgc cttttcccgc gaggttgaag cggcatggaa agagtttgcc    900
gaggatgact gctgctgcat tgacgttgag cgaaaacgca cgtttaccat gatgattcgg    960
gaaggtgtgg ccatgcacgc ctttaacggt gaactgttcg ttcaggccac ctgggatacc   1020
agttcgtcgc ggcttttccg gacacagttc cggatggtca gcccgaagcg catcagcaac   1080
ccgaacaata ccggcgacag ccggaactgc cgtgccggtg tgcagattaa tgacagcggt   1140
```

```
gcggcgctgg gatattacgt cagcgaggac gggtatcctg gctggatgcc gcagaaatgg     1200
acatggatac cccgtgagtt acccggcggc tcgttcattc acgttttga acccgtggag      1260 gacgggcaga ctcgcggtgc aaatgtgttt tacagcgtga tggagcagat gaagatgctc    1320
gacacgctgc agaacacgca gctagattaa ccctagaaag ataatcatat tgtgacgtac    1380
gttaaagata atcatgcgta aaattgacgc atgggatcca ctagtgttcc cacaatggtt    1440
aattcgagct cgcccgggga tctaattcaa ttagagacta attcaattag agctaattca   1500
attaggatcc aagcttatcg atttcgaacc ctcgaccgcc ggagtataaa tagaggcgct   1560
tcgtctacgg agcgacaatt caattcaaac aagcaaagtg aacacgtcgc taagcgaaag   1620
ctaagcaaat aaacaagcgc agctgaacaa gctaaacaat cggggtaccg ctagagtcga   1680
cggtaccgcg ggcccgggat ccaccggtcg ccaccatggt gagcaagggc gaggagctgt   1740
tcaccggggt ggtgcccatc ctggtcgagc tggacggcga cgtaaacggc cacaagttca   1800
gcgtgtccgg cgagggcgag ggcgatgcca cctacggcaa gctgaccctg aagttcatct   1860
gcaccaccgg caagctgccc gtgccctggc ccaccctcgt gaccaccctg acctacggcg   1920
tgcagtgctt cagccgctac cccgaccaca tgaagcagca cgacttcttc aagtccgcca   1980
tgcccgaagg ctacgtccag gagcgcacca tcttcttcaa ggacgacggc aactacaaga   2040
cccgcgccga ggtgaagttc gagggcgaca ccctggtgaa ccgcatcgag ctgaagggca   2100
tcgacttcaa ggaggacggc aacatcctgg ggcacaagct ggagtacaac tacaacagcc   2160
acaacgtcta tatcatggcc gacaagcaga agaacggcat caaggtgaac ttcaagatcc   2220
gccacaacat cgaggacggc agcgtgcagc tcgccgacca ctaccagcag aacacccccca  2280 tcggcgacgg ccccgtgctg ctgcccgaca ccactacct gagcacccag tccgccctga   2340
gcaaagaccc caacgagaag cgcgatcaca tggtcctgct ggagttcgtg accgccgccg   2400
ggatcactct cggcatggac gagctgtaca gtaaagcggg ccgcgactct agatcataat   2460
cagccatacc acatttgtag aggttttact tgctttaaaa aacctcccac acctccccct   2520
gaacctgaaa cataaaatga atgcaattgt tgttgttaac ttgtttattg cagcttataa   2580
tggttacaaa taaagcaata gcatcacaaa tttcacaaat aaagcatttt ttcactgca   2640 ttctagttgt ggtttgtcca aactcatcaa tgtatcttaa agcttatcga tacgcgtacg   2700
gcgcgcctag actagttcta gagcggccgc caccgcggtg gagctccagc ttttgttccc   2760
tttagtgagg gttaatttcg agcttggcgt aatcatggtc atagctgttt cctgtgtgaa   2820
attgttatcc gctcacaatt ccacacaaca tacgagccgg aagcataaag tgtaaagcct   2880
ggggtgccta atgagtgagc taactcacat taattgcgtt gcgctcactg cccgctttcc   2940
agtcgggaaa cctgtcgtgc cagctgcatt aatgaatcgg ccaacgcgcg gggagaggcg   3000
gtttgcgtat tgggcgctct tccgcttcct cgctcactga ctcgctgcgc tcggtcgttc   3060
ggctgcggcg agcggtatca gctcactcaa aggcggtaat acggttatcc acagaatcag   3120
gggataacgc aggaaagaac atgtgagcaa aaggccagca aaaggccagg aaccgtaaaa   3180
aggccgcgtt gctggcgttt ttccataggc tccgcccccc tgacgagcat cacaaaaatc   3240
gacgctcaag tcagaggtgg cgaaacccga caggactata agataccagg cgtttccccc   3300
ctggaagctc cctcgtgcgc tctcctgttc cgaccctgcc gcttaccgga tacctgtccg   3360
cctttctccc ttcgggaagc gtggcgcttt ctcatagctc acgctgtagg tatctcagtt   3420
cggtgtaggt cgttcgctcc aagctgggct gtgtgcacga accccccgtt cagcccgacc   3480
gctgcgcctt atccggtaac tatcgtcttg agtccaaccc ggtaagacac gacttatcgc   3540
```

```
cactggcagc agccactggt aacaggatta gcagagcgag gtatgtaggc ggtgctacag    3600
agttcttgaa gtggtggcct aactacggct acactagaag gacagtattt ggtatctgcg    3660
ctctgctgaa gccagttacc ttcggaaaaa gagttggtag ctcttgatcc ggcaaacaaa    3720
ccaccgctgg tagcgtggt ttttttgttt gcaagcagca gattacgcgc agaaaaaaag    3780
gatctcaaga agatccttg atcttttcta cggggtctga cgctcagtgg aacgaaaact    3840
cacgttaagg gattttggtc atgagattat caaaaaggat cttcacctag atccttttaa    3900
attaaaaatg aagttttaaa tcaatctaaa gtatatatga gtaaacttgg tctgacagtt    3960
accaatgctt aatcagtgag gcacctatct cagggatctg tctatttcgt tcatccatag    4020
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
gctccggttc ccaacgatca aggcgagtta catgatcccc catgttgtgc aaaaaagcgg    4380
ttagctcctt cggtcctccg atcgttgtca gaagtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg ggcgaaaac tctcaaggat cttaccgctg ttgagatcca    4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
ggaaatgttg aatactcata ctcttccttt ttcaatatta ttgaagcatt tatcagggtt    4860
attgtctcat gagcggatac atatttgaat gtatttagaa aaataaacaa ataggggttc    4920
cgcgcacatt tccccgaaaa gtgc                                          4944
```

<210> SEQ ID NO 56
<211> LENGTH: 4944
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 56

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctccct ttagggttcc      180 gatttagtgc tttacggcac ctcgacccca aaaaacttga ttagggtgat ggttcacgta     240
gtgggccatc gccctgatag acggttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
```

```
ttgtaaaacg acggccagtg aattgtaata cgactcacta tagggcgaat tgggtaccgg    660
gcccccccctc gaggtcgacg gtatcgataa gcttgatatc gaattcctgc agcccggggg   720
atcccatgcg tcaattttac gcagactatc tttctagggt taatctagct gcatcaggat    780
catatcgtcg ggtctttttt ccggctcagt catcgcccaa gctggcgcta tctgggcatc    840
ggggaggaag aagcccgtgc cttttcccgc gaggttgaag cggcatggaa agagtttgcc    900
gaggatgact gctgctgcat tgacgttgag cgaaaacgca cgtttaccat gatgattcgg    960
gaaggtgtgg ccatgcacgc ctttaacggt gaactgttcg ttcaggccac ctgggatacc   1020
agttcgtcgc ggcttttccg gacacagttc cggatggtca gcccgaagcg catcagcaac   1080
ccgaacaata ccggcgacag ccggaactgc cgtgccggtg tgcagattaa tgacagcggt   1140
gcggcgctgg gatattacgt cagcgaggac gggtatcctg gctggatgcc gcagaaatgg   1200
acatggatac cccgtgagtt acccggcggc tcgttcattc acgttttga acccgtggag    1260
gacgggcaga ctcgcggtgc aaatgtgttt tacagcgtga tggagcagat gaagatgctc   1320
gacacgctgc agaacacgca gctagattaa ccctagaaag ataatcatat tgtgacgtac   1380
gttaaagata atcatgcgta aaattgacgc atgggatcca ctagtgttcc cacaatggtt   1440
aattcgagct cgcccgggga tctaattcaa ttagagacta attcaattag agctaattca   1500
attaggatcc aagcttatcg atttcgaacc ctcgaccgcc ggagtataaa tagaggcgct   1560
tcgtctacgg agcgacaatt caattcaaac aagcaaagtg aacacgtcgc taagcgaaag   1620
ctaagcaaat aaacaagcgc agctgaacaa gctaaacaat cggggtaccg ctagagtcga   1680
cggtacgatc caccggtcgc caccatggtg agcaagggcg aggagctgtt caccggggtg   1740
gtgcccatcc tggtcgagct ggacggcgac gtaaacggcc acaagttcag cgtgtccggc   1800
gagggcgagg gcgatgccac ctacggcaag ctgaccctga agttcatctg caccaccggc   1860
aagctgcccg tgccctggcc cacccttcgtg accaccttcg gctacggcct gcagtgcttc   1920
gcccgctacc ccgaccacat gaagcagcac gacttcttca gtccgccat gcccgaaggc   1980
tacgtccagg agcgcaccat cttcttcaag gacgacggca actacaagac ccgcgccgag   2040
gtgaagttcg agggcgacac cctggtgaac cgcatcgagc tgaagggcat cgacttcaag   2100
gaggacggca acatcctggg gcacaagctg gagtacaact acaacagcca caacgtctat   2160
atcatggccg acaagcagaa gaacggcatc aaggtgaact tcaagatccg ccacaacatc   2220
gaggacggca gcgtgcagct cgccgaccac taccagcaga acacccccat cggcgacggc   2280
cccgtgctgc tgcccgacaa ccactacctg agctaccagt ccgccctgag caagacccc   2340
aacgagaagc gcgatcacat ggtcctgctg gagttcgtga ccgccgccgg gatcactctc   2400
ggcatggacg agctgtacaa gtaaagcggc cgcgactcta gatcataatc agccatacca   2460
catttgtaga ggttttactt gctttaaaaa acctcccaca cctccccctg aacctgaaac   2520
ataaaatgaa tgcaattgtt gttgttaact tgtttattgc agcttataat ggttacaaat   2580
aaagcaatag catcacaaat ttcacaaata aagcattttt ttcactgcat tctagttgtg   2640
gtttgtccaa actcatcaat gtatcttaaa gcttatcgat acgcgtacgg cgcgcctagg   2700
ccggccgatc actagttcta gagcggccgc caccgcggtg gagctccagc ttttgttccc   2760
tttagtgagg gttaatttcg agcttggcgt aatcatggtc atagctgttt cctgtgtgaa   2820
attgttatcc gctcacaatt ccacacaaca tacgagccgg aagcataaag tgtaaagcct   2880
ggggtgccta atgagtgagc taactcacat taattgcgtt gcgctcactg cccgctttcc   2940
```

```
agtcgggaaa cctgtcgtgc cagctgcatt aatgaatcgg ccaacgcgcg gggagaggcg      3000
gtttgcgtat tgggcgctct tccgcttcct cgctcactga ctcgctgcgc tcggtcgttc      3060
ggctgcggcg agcggtatca gctcactcaa aggcggtaat acggttatcc acagaatcag      3120
gggataacgc aggaaagaac atgtgagcaa aaggccagca aaaggccagg aaccgtaaaa      3180
aggccgcgtt gctggcgttt ttccataggc tccgcccccc tgacgagcat cacaaaaatc      3240
gacgctcaag tcagaggtgg cgaaacccga caggactata agataccagg cgtttcccc       3300 ctggaagctc cctcgtgcgc tctcctgttc cgaccctgcc gcttaccgga tacctgtccg      3360
cctttctccc ttcgggaagc gtggcgcttt ctcatagctc acgctgtagg tatctcagtt      3420
cggtgtaggt cgttcgctcc aagctgggct gtgtgcacga accccccgtt cagcccgacc      3480
gctgcgcctt atccggtaac tatcgtcttg agtccaaccc ggtaagacac gacttatcgc      3540
cactggcagc agccactggt aacaggatta gcagagcgag gtatgtaggc ggtgctacag      3600
agttcttgaa gtggtggcct aactacggct acactagaag gacagtattt ggtatctgcg      3660
ctctgctgaa gccagttacc ttcggaaaaa gagttggtag ctcttgatcc ggcaaacaaa      3720
ccaccgctgg tagcggtggt ttttttgttt gcaagcagca gattacgcgc agaaaaaaag      3780
gatctcaaga agatcctttg atcttttcta cggggtctga cgctcagtgg aacgaaaact      3840
cacgttaagg gattttggtc atgagattat caaaaaggat cttcacctag atccttttaa      3900
attaaaaatg aagttttaaa tcaatctaaa gtatatatga gtaaacttgg tctgacagtt      3960
accaatgctt aatcagtgag gcacctatct cagcgatctg tctatttcgt tcatccatag      4020
ttgcctgact ccccgtcgtg tagataacta cgatacggga gggcttacca tctggcccca      4080
gtgctgcaat gataccgcga gacccacgct caccggctcc agatttatca gcaataaacc      4140
agccagccgg aagggccgag cgcagaagtg gtcctgcaac tttatccgcc tccatccagt      4200
ctattaattg ttgccgggaa gctagagtaa gtagttcgcc agttaatagt ttgcgcaacg      4260
ttgttgccat tgctacaggc atcgtggtgt cacgctcgtc gtttggtatg gcttcattca      4320
gctccggttc ccaacgatca aggcgagtta catgatcccc catgttgtgc aaaaaagcgg      4380
ttagctcctt cggtcctccg atcgttgtca agtaagtt ggccgcagtg ttatcactca       4440
tggttatggc agcactgcat aattctctta ctgtcatgcc atccgtaaga tgcttttctg      4500
tgactggtga gtactcaacc aagtcattct gagaatagtg tatgcggcga ccgagttgct      4560
cttgcccggc gtcaatacgg gataataccg cgccacatag cagaacttta aaagtgctca      4620
tcattggaaa acgttcttcg gggcgaaaac tctcaaggat cttaccgctg ttgagatcca      4680
gttcgatgta acccactcgt gcacccaact gatcttcagc atcttttact ttcaccagcg      4740
tttctgggtg agcaaaaaca ggaaggcaaa atgccgcaaa aaagggaata agggcgacac      4800
ggaaatgttg aatactcata ctcttccttt ttcaatatta ttgaagcatt tatcagggtt      4860
attgtctcat gagcggatac atatttgaat gtatttagaa aaataaacaa ataggggttc      4920
cgcgcacatt tccccgaaaa gtgc                                             4944
```

<210> SEQ ID NO 57
<211> LENGTH: 7670
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 57

```
aacgcgcggg gagaggcggt ttgcgtattg ggcgctcttc cgcttcctcg ctcactgact      60
cgctgcgctc ggtcgttcgg ctgcggcgag cggtatcagc tcactcaaag gcggtaatac     120
ggttatccac agaatcaggg gataacgcag gaaagaacat gtgagcaaaa ggccagcaaa     180
aggccaggaa ccgtaaaaag gccgcgttgc tggcgttttt ccataggctc cgcccccctg     240
acgagcatca caaaaatcga cgctcaagtc agaggtggcg aaacccgaca ggactataaa     300
gataccaggc gtttccccct ggaagctccc tcgtgcgctc tcctgttccg accctgccgc     360
ttaccggata cctgtccgcc tttctccctt cgggaagcgt ggcgctttct caatgctcac     420
gctgtaggta tctcagttcg gtgtaggtcg ttcgctccaa gctgggctgt gtgcacgaac     480
ccccccgttca gcccgaccgc tgcgccttat ccggtaacta tcgtcttgag tccaacccgg    540
taagacacga cttatcgcca ctggcagcag ccactggtaa caggattagc agagcgaggt    600
atgtaggcgg tgctacagag ttcttgaagt ggtggcctaa ctacggctac actagaagga    660
cagtatttgg tatctgcgct ctgctgaagc cagttacctt cggaaaaaga gttggtagct    720
cttgatccgg caaacaaacc accgctggta gcggtggttt ttttgtttgc aagcagcaga    780
ttacgcgcag aaaaaaagga tctcaagaag atcctttgat cttttctacg gggtctgacg    840
ctcagtggaa cgaaaactca cgttaaggga ttttggtcat gagattatca aaaaggatct    900
tcacctagat ccttttaaat taaaaatgaa gttttaaatc aatctaaagt atatatgagt    960
aaacttggtc tgacagttac caatgcttaa tcagtgaggc acctatctca gcgatctgtc    1020
tatttcgttc atccatagtt gcctgactcc ccgtcgtgta gataactacg atacgggagg    1080
gcttaccatc tggccccagt gctgcaatga taccgcgaga cccacgctca ccggctccag    1140
atttatcagc aataaaccag ccagccggaa gggccgagcg cagaagtggt cctgcaactt    1200
tatccgcctc catccagtct attaattgtt gccgggaagc tagagtaagt agttcgccag    1260
ttaatagttt gcgcaacgtt gttgccattg ctacaggcat cgtggtgtca cgctcgtcgt    1320
ttggtatggc ttcattcagc tccggttccc aacgatcaag gcgagttaca tgatccccca    1380
tgttgtgcaa aaaagcggtt agctccttcg gtcctccgat cgttgtcaga agtaagttgg    1440
ccgcagtgtt atcactcatg gttatggcag cactgcataa ttctcttact gtcatgccat    1500
ccgtaagatg cttttctgtg actggtgagt actcaaccaa gtcattctga aatagtgta    1560
tgcggcgacc gagttgctct tgcccggcgt caatacggga taataccgcg ccacatagca    1620
gaactttaaa agtgctcatc attggaaaac gttcttcggg gcgaaaactc tcaaggatct    1680
taccgctgtt gagatccagt tcgatgtaac ccactcgtgc acccaactga tcttcagcat    1740
cttttacttt caccagcgtt tctgggtgag caaaaacagg aaggcaaaat gccgcaaaaa    1800
agggaataag ggcgacacgg aaatgttgaa tactcatact cttcctttt caatattatt     1860
gaagcattta tcagggttat tgtctcatga gcggatacat atttgaatgt atttagaaaa    1920
ataaacaaat aggggttccg cgcacatttc cccgaaaagt gccacctgac gtctaagaaa    1980
ccattattat catgacatta acctataaaa ataggcgtat cacggggccc tgaggtgaac    2040
caattgtcac acgtaatatt acgacaacta ccgtgcacag gctttgataa ctccttcacg    2100
tagtattcac cgagtggtac tccgttggtc tgtgttcctc ttcccaaata aggcattcca    2160
tttatcatat acttcgtacc actgtcacac atcatgagga ttttattcc atacttactt     2220
ggcttgtttg ggatatacat cctaaacgga caccgtcctc taaaaccaag taactgttca    2280
tctatggtca aatgagcccc tggagtgtaa ttttgtatgc actgatggat aaagagatcc    2340
catattttc taacaggagt aaatacatcg ttttctcgaa gtgtgggccg tatacttttg     2400
```

```
tcatccattc taagacatcg tatcaaaaaa tccaaaacga tccacagact cattacagag    2460
acgtacacat tgacaaagat cgatccaaag aggtcatctg tggacatgtg gttatctttt    2520
ctcactgctg tcattaccag aataccaaag aaagcataga tttcatcttc attcgtgtca    2580
cgaaatgtag cacctgtcat agattcccga cgtttcaatg atatctcagc atttgtccat    2640
tttacaattt gcgaaattat ctcatcagta aaaatagtt tgaagcataa aagtgggtca     2700
tatatattgc ggcacatacg cgtcggacct ctttgagatc tgacaatgtt cagtgcagag    2760
actcggctac cgctcgtgga ctttgaagtt aaattcagat ataaagacgc tgaaaatcat    2820
ttgattttcg ctctaacata ccaccctaaa gattataaat ttaatgaatt attaaaatac    2880
gtacaacaat tgtctgtaaa tcaacaacgc acagaatcta gcgcttaata aatgtactaa    2940
taacaatgta tcgtgttta atacgccgga ccagtgaaca gaggtgcgtc tggtgcaaac     3000
tcctttactt tgaacaccag ggaaacttca aggagaattt cctcctcttc agcagagtcg    3060
gtaccggtca cccgggatc cccctgccc ggttattatt atttttgaca ccagaccaac      3120
tggtaatggt agcgaccggc gctcagctgg aattccgccg atactgacgg gctccaggag    3180
tcgtcgccac caatcccat atggaaaccg tcgatattca gccatgtgcc ttcttccgcg     3240
tgcagcagat ggcgatggct ggtttccatc agttgctgtt gactgtagcg gctgatgttg    3300
aactggaagt cgccgcgcca ctggtgtggg ccataattca attcgcgcgt cccgcagcgc    3360
agaccgtttt cgctcgggaa gacgtacggg gtatacatgt ctgacaatgg cagatcccag    3420
cggtcaaaac aggcggcagt aaggcggtcg ggatagtttt cttgcggccc taatccgagc    3480
cagtttaccc gctctgctac ctgcgccagc tggcagttca ggccaatccg cgccggatgc    3540
ggtgtatcgc tcgccacttc aacatcaacg gtaatcgcca tttgaccact accatcaatc    3600
cggtaggttt tccggctgat aaataaggtt ttcccctgat gctgccacgc gtgagcggtc    3660
gtaatcagca ccgcatcagc aagtgtatct gccgtgcact gcaacaacgc tgcttcggcc    3720
tggtaatggc ccgccgcctt ccagcgttcg acccaggcgt tagggtcaat gcgggtcgct    3780
tcacttacgc caatgtcgtt atccagcggt gcacgggtga actgatcgcg cagcggcgtc    3840
agcagttgtt ttttatcgcc aatccacatc tgtgaaagaa agcctgactg gcggttaaat    3900
tgccaacgct tattcccag ctcgatgcaa aaatccattt cgctggtggt cagatgcggg     3960
atggcgtggg acgcggcggg gagcgtcaca ctgaggtttt ccgccagacg ccactgctgc    4020
caggcgctga tgtgcccggc ttctgaccat gcggtcgcgt tcggttgcac tacgcgtact    4080
gtgagccaga gttgcccggc gctctccggc tgcggtagtt caggcagttc aatcaactgt    4140
ttaccttgtg gagcgacatc cagaggcact tcaccgcttg ccagcggctt accatccagc    4200
gccaccatcc agtgcaggag ctcgttatcg ctatgacgga acaggtattc gctggtcact    4260
tcgatggttt gcccggataa acggaactgg aaaaactgct gctggtgttt gcttccgtc     4320 agcgctggat gcgcgtgcg gtcggcaaag accagaccgt tcatacagaa ctggcgatcg     4380
ttcggcgtat cgccaaaatc accgccgtaa gccgaccacg ggttgccgtt tcatcatat     4440 ttaatcagcg actgatccac ccagtccag acgaagccgc cctgtaaacg gggatactga     4500
cgaaacgcct gccagtattt agcgaaaccg ccaagactgt tacccatcgc gtgggcgtat    4560
tcgcaaagga tcagcgggcg cgtctctcca ggtagcgaaa gccatttttt gatggaccat    4620
ttcggcacag ccgggaaggg ctggtcttca tccacgcgcg cgtacatcgg gcaaataata    4680
tcggtggccg tggtgtcggc tccgccgcct tcatactgca ccgggcggga aggatcgaca    4740
```

```
gatttgatcc agcgatacag cgcgtcgtga ttagcgccgt ggcctgattc attccccagc    4800
gaccagatga tcacactcgg gtgattacga tcgcgctgca ccattcgcgt tacgcgttcg    4860
ctcatcgccg gtagccagcg cggatcatcg gtcagacgat tcattggcac catgccgtgg    4920
gtttcaatat tggcttcatc caccacatac aggccgtagc ggtcgcacag cgtgtaccac    4980
agcggatggt tcggataatg cgaacagcgc acggcgttaa agttgttctg cttcatcagc    5040
aggatatcct gcaccatcgt ctgctcatcc atgacctgac catgcagagg atgatgctcg    5100
tgacggttaa cgcctcgaat cagcaacggc ttgccgttca gcagcagcag accattttca    5160
atccgcacct cgcggaaacc gacatcgcag gcttctgctt caatcagcgt gccgtcggcg    5220
gtgtgcagtt caaccaccgc acgatagaga ttcgggattt cggcgctcca cagtttcggg    5280
ttttcgacgt tcagacgtag tgtgacgcga tcggcataac caccacgctc atcgataatt    5340
tcaccgccga aaggcgcggt gccgctggcg acctgcgttt caccctgcca taaagaaact    5400
gttacccgta ggtagtcacg caactcgccg cacatctgaa cttcagcctc cagtacagcg    5460
cggctgaaat catcattaaa gcgagtggca acatggaaat cgctgatttg tgtagtcggt    5520
ttatgcagca acgagacgtc acggaaaatg ccgctcatcc gccacatatc ctgatcttcc    5580
agataactgc cgtcactcca acgcagcacc atcaccgcga ggcggttttc tccggcgcgt    5640
aaaaatgcgc tcaggtcaaa ttcagacggc aaacgactgt cctggccgta accgacccag    5700
cgcccgttgc accacagatg aaacgccgag ttaacgccat caaaaataat tcgcgtctgg    5760
ccttcctgta gccagctttc atcaacatta aatgtgagcg agtaacaacc cgtcggattc    5820
tccgtgggaa caaacggcgg attgaccgta atgggatagg ttacgttggt gtagatgggc    5880
gcatcgtaac cgtgcatctg ccagtttgag gggacgacga cgggatccgt tttttattat    5940
caaaactgtt acgaaaacag taaaatactt atttattcgg accaacaatg tttattctta    6000
cctctaatag tcctctgtgg caaggtcaag attctgttag aagccaatga agaacctggt    6060
tgttcaataa catttttgttc gtctaatatt tcactacgct tgacgttggc tgacacttca    6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc attttattat atattagtca cgatatctat    6300
aacaagaaaa tatatatata ataagttatc acgtaagtag aacatgaaat aacaatatta    6360
attatcgtat gagttaaatc ttaaaagtca cgtaaaagat aatcatgcgt catttttgact    6420 cacgcggtcg ttatagttca aaatcagtga cacttaccgc attgacaagc acgcctcagc    6480
cgagctccaa gcggcgactg agatgtccta aattgcaaac agcgacggat tcgcgctatt    6540
tagaaagaga gagcaatatt tcaagaatgc atgcgtcaat tttacgcaga ctatctttct    6600
agggttaatc tagaggatcc tctagattaa ccctagaaag ataatcatat tgtgacgtac    6660
gttaaagata atcatgcgta aaattgacgc atgtgttttt atcggtctgt atatcgaggt    6720
ttatttatta atttgaatag atattaagtt ttattatatt tacacttaca tactaataat    6780
aaattcaaca aacaatttat ttatgtttat ttatttatta aaaaaaaaca aaaactcaaa    6840
atttcttcta agtaacaaaa ctttttaaac attctctctt ttacaaaaat aaacttattt    6900
tgtactttaa aaacagtcat gttgtattat aaaataagta attagcttaa cttatacata    6960
atagaaacaa attatactta ttagtcagtc cagaaacaac tttggcacat atcaatatta    7020
tgctctcgac aaataacttt tttgcatttt ttgcacgatg catttgcctt tcgccttatt    7080
ttagaggggc agtaagtaca gtaagtacgt ttttttcatta ctggctcttc agtactgtca    7140
```

-continued

```
tctgatgtac caggcacttc atttggcaaa atattagaga tattatcgcg caaatatctc   7200
ttcaaagtag gagcttctaa acggttacgc ataaacgatg acgtcaggct catgtaaagg   7260
tttctcataa attttttgcg actttgaacc ttttctccct tgctactgac attatggctg   7320
tatataataa aagaatttat gcaggcaatg tttatcattc cgtacaataa tgccataggc   7380
cacctattcg tcttcctact gcaggtcatc acagaacaca tttggtctag cgtgtccact   7440
ccgcctttag tttgattata atacataacc atttgcggtt taccggtact ttcgttgata   7500
gaagcatcct catcacaaga tgataataag tataccatct tagctggctt cggtttatat   7560
gagacgagag taaggggtcc gtcaaaacaa aacatcgatg ttcccactgg cctggagcga   7620
ctgtttttca gtacttccgg tatctcgcgt ttgtttgatc gcacggtacc               7670
```

<210> SEQ ID NO 58
<211> LENGTH: 286
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 58

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
```

```
                   260                 265                 270
Arg Gln Ile Ala Glu Ile Gly Ala Ser Leu Ile Lys His Trp
        275                 280                 285

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Phe Lys Val His Glu Arg
1               5

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Trp Ser Glu
1

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Gly Met Phe Phe Arg Arg
1               5

<210> SEQ ID NO 62
<211> LENGTH: 229
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 62

Gly Thr Val Arg Ser Asn Lys Arg Glu Ile Pro Glu Val Leu Lys Asn
1               5                   10                  15

Ser Arg Ser Arg Pro Val Gly Thr Ser Met Phe Cys Phe Asp Gly Pro
            20                  25                  30

Leu Thr Leu Val Ser Tyr Lys Pro Lys Pro Ala Lys Met Val Tyr Leu
        35                  40                  45

Leu Ser Ser Cys Asp Glu Asp Ala Ser Ile Asn Glu Ser Thr Gly Lys
    50                  55                  60

Pro Gln Met Val Met Tyr Tyr Asn Gln Thr Lys Gly Gly Val Asp Thr
65                  70                  75                  80

Leu Asp Gln Met Cys Ser Val Met Thr Cys Ser Arg Lys Thr Asn Arg
                85                  90                  95

Trp Pro Met Ala Leu Leu Tyr Gly Met Ile Asn Ile Ala Cys Ile Asn
            100                 105                 110
```

```
Ser Phe Ile Ile Tyr Ser His Asn Val Ser Ser Lys Gly Glu Lys Val
            115                 120                 125
Gln Ser Arg Lys Lys Phe Met Arg Asn Leu Tyr Met Ser Leu Thr Ser
    130                 135                 140
Ser Phe Met Arg Asn Arg Leu Glu Ala Pro Thr Leu Lys Arg Tyr Leu
145                 150                 155                 160
Arg Asp Asn Ile Ser Asn Ile Leu Pro Asn Glu Val Pro Gly Thr Ser
                165                 170                 175
Asp Asp Ser Thr Glu Glu Pro Val Met Lys Lys Arg Thr Tyr Cys Thr
            180                 185                 190
Tyr Cys Pro Ser Lys Ile Arg Arg Lys Ala Asn Ala Ser Cys Lys Lys
            195                 200                 205
Cys Lys Lys Val Ile Cys Arg Glu His Asn Ile Asp Met Cys Gln Ser
    210                 215                 220
Cys Phe Trp Thr Asp
225
```

```
<210> SEQ ID NO 63
<211> LENGTH: 9984
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 63
aacgcgcggg gagaggcggt ttgcgtattg ggcgctcttc cgcttcctcg ctcactgact      60
cgctgcgctc ggtcgttcgg ctgcggcgag cggtatcagc tcactcaaag gcggtaatac    120
ggttatccac agaatcaggg gataacgcag gaaagaacat gtgagcaaaa ggccagcaaa    180
aggccaggaa ccgtaaaaag gccgcgttgc tggcgttttt ccataggctc cgcccccctg    240
acgagcatca caaaaatcga cgctcaagtc agaggtggcg aaacccgaca ggactataaa    300
gataccaggc gtttccccct ggaagctccc tcgtgcgctc tcctgttccg accctgccgc    360
ttaccggata cctgtccgcc tttctccctt cgggaagcgt ggcgctttct caatgctcac    420
gctgtaggta tctcagttcg gtgtaggtcg ttcgctccaa gctgggctgt gtgcacgaac    480
ccccgttca gcccgaccgc tgcgccttat ccggtaacta tcgtcttgag tccaacccgg    540
taagacacga cttatcgcca ctggcagcag ccactggtaa caggattagc agagcgaggt    600
atgtaggcgg tgctacagag ttcttgaagt ggtggcctaa ctacggctac actagaagga    660
cagtatttgg tatctgcgct ctgctgaagc cagttacctt cggaaaaaga gttggtagct    720
cttgatccgg caaacaaacc accgctggta gcggtggttt ttttgtttgc aagcagcaga    780
ttacgcgcag aaaaaaagga tctcaagaag atcctttgat cttttctacg ggtctgacg    840
ctcagtggaa cgaaaactca cgttaaggga ttttggtcat gagattatca aaaaggatct    900
tcacctagat ccttttaaat taaaatgaa gttttaaatc aatctaaagt atatatgagt    960
aaacttggtc tgacagttac caatgcttaa tcagtgaggc acctatctca gcgatctgtc   1020
tatttcgttc atccatagtt gcctgactcc ccgtcgtgta gataactacg atacgggagg   1080
gcttaccatc tggccccagt gctgcaatga taccgcgaga cccacgctca ccggctccag   1140
atttatcagc aataaaccag ccagccggaa gggccgagcg cagaagtggt cctgcaactt   1200
tatccgcctc catccagtct attaattgtt gccgggaagc tagagtaagt agttcgccag   1260
ttaatagttt gcgcaacgtt gttgccattg ctacaggcat cgtggtgtca cgctcgtcgt   1320
```

```
ttggtatggc ttcattcagc tccggttccc aacgatcaag gcgagttaca tgatccccca    1380
tgttgtgcaa aaaagcggtt agctccttcg gtcctccgat cgttgtcaga agtaagttgg    1440
ccgcagtgtt atcactcatg gttatggcag cactgcataa ttctcttact gtcatgccat    1500
ccgtaagatg cttttctgtg actggtgagt actcaaccaa gtcattctga gaatagtgta    1560
tgcggcgacc gagttgctct tgcccggcgt caatacggga taataccgcg ccacatagca    1620
gaactttaaa agtgctcatc attggaaaac gttcttcggg gcgaaaactc tcaaggatct    1680
taccgctgtt gagatccagt tcgatgtaac ccactcgtgc acccaactga tcttcagcat    1740
cttttacttt caccagcgtt tctgggtgag caaaaacagg aaggcaaaat gccgcaaaaa    1800
agggaataag ggcgacacgg aaatgttgaa tactcatact cttcctttt caatattatt    1860 gaagcattta tcagggttat tgtctcatga gcggatacat atttgaatgt atttagaaaa    1920
ataaacaaat aggggttccg cgcacatttc cccgaaaagt gccacctgac gtctaagaaa    1980
ccattattat catgacatta acctataaaa ataggcgtat cacggggccc tgagtgaac    2040 caattgtcac acgtaatatt acgacaacta ccgtgcacag gctttgataa ctccttcacg    2100
tagtattcac cgagtggtac tccgttggtc tgtgttcctc ttcccaaata aggcattcca    2160
tttatcatat acttcgtacc actgtcacac atcatgagga tttttattcc atacttactt    2220
ggcttgtttg ggatatacat cctaaacgga caccgtcctc taaaaccaag taactgttca    2280
tctatggtca aatgagcccc tggagtgtaa ttttgtatgc actgatggat aaagagatcc    2340 catattttc taacaggagt aaatacatcg ttttctcgaa gtgtgggccg tatacttttg     2400
tcatccattc taagacatcg tatcaaaaaa tccaaaacga tccacagact cattacagag    2460
acgtacacat tgacaaagat cgatccaaag aggtcatctg tggacatgtg gttatctttt    2520
ctcactgctg tcattaccag aataccaaag aaagcataga tttcatcttc attcgtgtca    2580
cgaaatgtag cacctgtcat agattcccga cgtttcaatg atatctcagc atttgtccat    2640
tttacaattt gcgaaattat ctcatcagta aaaaatagtt tgaagcataa aagtgggtca    2700
tatatattgc ggcacatacg cgtcggacct ctttgagatc tgacaatgtt cagtgcagag    2760
actcggctac cgctcgtgga ctttgaagtt aaattcagat ataaagacgc tgaaaatcat    2820
ttgattttcg ctctaacata ccaccctaaa gattataaat ttaatgaatt attaaaatac    2880
gtacaacaat tgtctgtaaa tcaacaacgc acagaatcta gcgcttaata aatgtactaa    2940
taacaatgta tcgtgtttta atacgccgga ccagtgaaca gaggtgcgtc tggtgcaaac    3000
tcctttactt tgaacaccag ggaaacttca aggagaattt cctcctcttc agcagagtcg    3060
gtaccggtca cccggggatc cccctgccc ggttattatt attttttgaca ccagaccaac    3120 tggtaatggt agcgaccggc gctcagctgg aattccgccg atactgacgg gctccaggag    3180
tcgtcgccac caatccccat atggaaaccg tcgatattca gccatgtgcc ttcttccgcg    3240
tgcagcagat ggcgatggct ggtttccatc agttgctgtt gactgtagcg gctgatgttg    3300
aactggaagt cgccgcgcca ctggtgtggg ccataattca attcgcgcgt cccgcagcgc    3360
agaccgtttt cgctcgggaa gacgtacggg gtatacatgt ctgacaatgg cagatcccag    3420
cggtcaaaac aggcggcagt aaggcggtcg ggatagtttt cttgcggccc taatccgagc    3480
cagtttaccc gctctgctac ctgcgccagc tggcagttca ggccaatccg cgccggatgc    3540
ggtgtatcgc tcgccacttc aacatcaacg gtaatcgcca tttgaccact accatcaatc    3600
cggtaggttt tccggctgat aaataaggtt ttccctgat gctgccacgc gtgagcggtc    3660
gtaatcagca ccgcatcagc aagtgtatct gccgtgcact gcaacaacgc tgcttcggcc    3720
```

```
tggtaatggc ccgccgcctt ccagcgttcg acccaggcgt tagggtcaat gcgggtcgct   3780
tcacttacgc caatgtcgtt atccagcggt gcacgggtga actgatcgcg cagcggcgtc   3840
agcagttgtt ttttatcgcc aatccacatc tgtgaaagaa agcctgactg gcggttaaat   3900
tgccaacgct tattacccag ctcgatgcaa aaatccattt cgctggtggt cagatgcggg   3960
atggcgtggg acgcggcggg gagcgtcaca ctgaggtttt ccgccagacg ccactgctgc   4020
caggcgctga tgtgcccggc ttctgaccat gcggtcgcgt tcggttgcac tacgcgtact   4080
gtgagccaga gttgcccggc gctctccggc tgcggtagtt caggcagttc aatcaactgt   4140
ttaccttgtg gagcgacatc cagaggcact tcaccgcttg ccagcggctt accatccagc   4200
gccaccatcc agtgcaggag ctcgttatcg ctatgacgga acaggtattc gctggtcact   4260
tcgatggttt gcccggataa acggaactgg aaaaactgct gctggtgttt tgcttccgtc   4320
agcgctggat gcggcgtgcg gtcggcaaag accagaccgt tcatacagaa ctggcgatcg   4380
ttcggcgtat cgccaaaatc accgccgtaa gccgaccacg ggttgccgtt ttcatcatat   4440
ttaatcagcg actgatccac ccagtcccag acgaagccgc cctgtaaacg gggatactga   4500
cgaaacgcct gccagtattt agcgaaaccg ccaagactgt tacccatcgc gtgggcgtat   4560
tcgcaaagga tcagcgggcg cgtctctcca ggtagcgaaa gccattttt gatggaccat   4620 tcggcacag ccgggaaggg ctggtcttca tccacgcgcg cgtacatcgg gcaaataata   4680
tcggtggccg tggtgtcggc tccgccgcct tcatactgca ccgggcggga aggatcgaca   4740
gatttgatcc agcgatacag cgcgtcgtga ttagcgccgt ggcctgattc attccccagc   4800
gaccagatga tcacactcgg gtgattacga tcgcgctgca ccattcgcgt tacgcgttcg   4860
ctcatcgccg gtagccagcg cggatcatcg gtcagacgat tcattggcac catgccgtgg   4920
gtttcaatat tggcttcatc caccacatac aggccgtagc ggtcgcacag cgtgtaccac   4980
agcggatggt tcgataatg cgaacagcgc acggcgttaa agttgttctg cttcatcagc   5040
aggatatcct gcaccatcgt ctgctcatcc atgacctgac catgcagagg atgatgctcg   5100
tgacggttaa cgcctcgaat cagcaacggc ttgccgttca gcagcagcag accattttca   5160
atccgcacct cgcggaaacc gacatcgcag gcttctgctt caatcagcgt gccgtcggcg   5220
gtgtgcagtt caaccaccgc acgatagaga ttcgggattt cggcgctcca cagtttcggg   5280
ttttcgacgt tcagacgtag tgtgacgcga tcggcataac caccacgctc atcgataatt   5340
tcaccgccga aggcgcggt gccgctggcg acctgcgttt caccctgcca taaagaaact   5400
gttacccgta ggtagtcacg caactcgccg cacatctgaa cttcagcctc cagtacagcg   5460
cggctgaaat catcattaaa gcgagtggca acatggaaat cgctgatttg tgtagtcggt   5520
ttatgcagca acgagacgtc acggaaaatg ccgctcatcc gccacatatc ctgatcttcc   5580
agataactgc cgtcactcca acgcagcacc atcaccgcga ggcggttttc tccggcgcgt   5640
aaaaatgcgc tcaggtcaaa ttcagacggc aaacgactgt cctggccgta accgacccag   5700
cgcccgttgc accacagatg aaacgccgag ttaacgccat caaaaataat tcgcgtctgg   5760
ccttcctgta gccagctttc atcaacatta aatgtgagcg agtaacaacc cgtcggattc   5820
tccgtgggaa caaacggcgg attgaccgta atggataggt tacgttggt gtagatgggc   5880 gcatcgtaac cgtgcatctg ccagtttgag gggacgacga cgggatccgt tttttttatta   5940 caaaactgtt acgaaaacag taaaatactt atttattcgg accaacaatg tttattctta   6000
cctctaatag tcctctgtgg caaggtcaag attctgttag aagccaatga agaacctggt   6060
```

```
tgttcaataa catttttgttc gtctaatatt tcactacgct tgacgttggc tgacacttca    6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc atttttattat atattagtca cgatatctat    6300
aacaagaaaa tatatatata ataagttatc acgtaagtag aacatgaaat aacaatatta    6360
attatcgtat gagttaaatc ttaaaagtca cgtaaaagat aatcatgcgt cattttgact    6420
cacgcggtcg ttatagttca aaatcagtga cacttaccgc attgacaagc acgcctcagc    6480
cgagctccaa gcggcgactg agatgtccta aattgcaaac agcgacggat tcgcgctatt    6540
tagaaagaga gagcaatatt tcaagaatgc atgcgtcaat tttacgcaga ctatctttct    6600
agggttaatc tagcttttct aatttaacct ttgtcaggtt accaactact aaggttgtag    6660
gctcaagagg gtgtgtcctg tcgtaggtaa ataactgacc tgtcgagctt aatattctat    6720
attgttgttc tttctgcaaa aaagtgggga agtgagtaat gaaattattt ctaacattta    6780
tctgcatcat accttccgag catttattaa gcatttcgct ataagttctc gctggaagag    6840 gtagttttt cattgtactt taccttcatc tctgttcatt atcatcgctt ttaaaacggt    6900
tcgaccttct aatcctatct gaccattata atttttttaga atggtttcat aagaaagctc    6960
tgaatcaacg gactgcgata ataagtggtg gtatccagaa tttgtcactt caagtaaaaa    7020
cacctcacga gttaaaacac ctaagttctc accgaatgtc tcaatatccg gacggataat    7080
atttattgct tctcttgacc gtaggacttt ccacatgcag gatttttggaa cctcttgcag    7140 tactactggg gaatgagttg caattattgc tacaccattg cgtgcatcga gtaagtcgct    7200
taatgttcgt aaaaaagcag agagcaaagg tggatgcaga tgaacctctg gttcatcgaa    7260
taaaactaat gacttttcgc caacgacatc tactaatctt gtgatagtaa ataaaacaat    7320
tgcatgtcca gagctcattc gaagcagata tttctggata ttgtcataaa acaatttagt    7380
gaatttatca tcgtccactt gaatctgtgg ttcattacgt cttaactctt catatttaga    7440
aatgaggctg atgagttcca tatttgaaaa gttttcatca ctacttagtt ttttgatagc    7500
ttcaagccag agttgtcttt ttctatctac tctcatacaa ccaataaatg ctgaaatgaa    7560
ttctaagcgg agatcgccta gtgattttaa actattgctg gcagcattct tgagtccaat    7620
ataaaagtat tgtgtacctt ttgctgggtc aggttgttct ttaggaggag taaaaggatc    7680
aaatgcacta aacgaaactg aaacaagcga tcgaaaatat ccctttggga ttcttgactc    7740
gataagtcta ttattttcag agaaaaaata ttcattgttt tctgggttgg tgattgcacc    7800
aatcattcca ttcaaaattg ttgttttacc acacccattc cgcccgataa aagcatgaat    7860
gttcgtgctg ggcatagaat taaccgtcac ctcaaaaggt atagttaaat cactgaatcc    7920
gggagcactt tttctattaa atgaaaagtg gaaatctgac aattctggca aaccatttaa    7980
cacacgtgcg aactgtccat gaatttctga aagagttacc cctctaagta atgaggtgtt    8040
aaggacgctt tcatttttcaa tgtcggctaa tcgatttggc catactacta aatcctgaat    8100
agctttaaga aggttatgtt taaaaccatc gcttaatttg ctgagattaa catagtagtc    8160
aatgctttca cctaaggaaa aaacatttc agggagttga ctgaattttt tatctattaa    8220
tgaataagtg cttacttctt cttttttgacc tacaaaacca attttaacat ttccgatatc    8280 gcattttca ccatgctcat caaagacagt aagataaaac attgtaacaa aggaatagtc    8340
attccaacca tctgctcgta ggaatgcctt atttttttct actgcaggaa tatcccgcc    8400 tcttttcaata acactaaact ccaacatata gtaacccttaa attttattaa aataaccgca    8460
```

-continued

```
atttatttgg cggcaacaca ggatctctct tttaagttac tctctattac atacgttttc   8520
catctaaaaa ttagtagtat tgaacttaac ggggcatcgt attgtagttt tccatattta   8580
gctttctgct tccttttgga taacccactg ttattcatgt tgcatggtgc actgtttata   8640
ccaacgatat agtctattaa tgcatatata gtatcgccga acgattagct cttcaggctt   8700
ctgaagaagc gtttcaagta ctaataagcc gatagatagc cacggacttc gtagccattt   8760
ttcataagtg ttaacttccg ctcctcgctc ataacagaca ttcactacag ttatggcgga   8820
aaggtatgca tgctgggtgt ggggaagtcg tgaaagaaaa gaagtcagct gcgtcgtttg   8880
acatcactgc tatcttctta ctggttatgc aggtcgtagt gggtggcaca caaagctaga   8940
ttaaccctag aaagataatc atattgtgac gtacgttaaa gataatcatg cgtaaaattg   9000
acgcatgtgt tttatcggt ctgtatatcg aggtttattt attaatttga atagatatta    9060
agttttatta tatttacact tacatactaa taataaattc aacaaacaat ttatttatgt   9120
ttatttattt attaaaaaaa aacaaaaact caaaatttct tctaaagtaa caaaactttt   9180
aaacattctc tcttttacaa aaataaactt attttgtact ttaaaaacag tcatgttgta   9240
ttataaaata agtaattagc ttaacttata cataatagaa acaaattata cttattagtc   9300
agtccagaaa caactttggc acatatcaat attatgctct cgacaaataa cttttttgca   9360
ttttttgcac gatgcatttg cctttcgcct tattttagag gggcagtaag tacagtaagt   9420
acgttttttc attactggct cttcagtact gtcatctgat gtaccaggca cttcatttgg   9480
caaaatatta gagatattat cgcgcaaata tctcttcaaa gtaggagctt ctaaacggtt   9540
acgcataaac gatgacgtca ggctcatgta aaggtttctc ataaattttt tgcgactttg   9600
aaccttttct cccttgctac tgacattatg gctgtatata ataaaagaat ttatgcaggc   9660
aatgtttatc attccgtaca ataatgccat aggccaccta ttcgtcttcc tactgcaggt   9720
catcacagaa cacatttggt ctagcgtgtc cactccgcct ttagtttgat tataatacat   9780
aaccatttgc ggtttaccgg tactttcgtt gatagaagca tcctcatcac aagatgataa   9840
taagtatacc atcttagctg gcttcggttt atatgagacg agagtaaggg gtccgtcaaa   9900
acaaaacatc gatgttccca ctggcctgga gcgactgttt ttcagtactt ccggtatctc   9960
gcgtttgttt gatcgcacgg tacc                                          9984
```

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Met Leu Gly Arg Tyr Asp Ala Asp Lys Cys
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Val Tyr Ser Cys Ser Arg Lys Lys

<210> SEQ ID NO 66
<211> LENGTH: 229
<212> TYPE: PRT
<213> ORGANISM: Artificial Sequence
<220> FEATURE:
<223> OTHER INFORMATION: Description of Artificial Sequence: Synthetic protein

<400> SEQUENCE: 66

```
Gly Thr Val Arg Ser Asn Lys Arg Glu Ile Pro Glu Val Leu Lys Asn
1               5                   10                  15

Ser Arg Ser Arg Pro Val Gly Thr Ser Met Phe Cys Phe Asp Gly Pro
            20                  25                  30

Leu Thr Leu Val Ser Tyr Lys Pro Lys Pro Ala Lys Met Val Tyr Leu
        35                  40                  45

Leu Ser Ser Cys Asp Glu Asp Ala Ser Ile Asn Glu Ser Thr Gly Lys
    50                  55                  60

Pro Gln Met Val Met Tyr Tyr Asn Gln Thr Lys Gly Gly Val Asp Thr
65                  70                  75                  80

Leu Asp Gln Met Cys Ser Val Met Thr Cys Ser Arg Lys Thr Asn Arg
                85                  90                  95

Trp Pro Met Ala Leu Leu Tyr Gly Met Ile Asn Ile Ala Cys Ile Asn
            100                 105                 110

Ser Phe Ile Ile Tyr Ser His Asn Val Ser Ser Lys Gly Glu Lys Val
        115                 120                 125

Gln Ser Arg Lys Lys Phe Met Arg Asn Leu Tyr Met Ser Leu Thr Ser
    130                 135                 140

Ser Phe Met Arg Asn Arg Leu Glu Ala Pro Thr Leu Lys Arg Tyr Leu
145                 150                 155                 160

Arg Asp Asn Ile Ser Asn Ile Leu Pro Asn Glu Val Pro Gly Thr Ser
                165                 170                 175

Asp Asp Ser Thr Glu Glu Pro Val Met Lys Lys Arg Thr Tyr Cys Thr
            180                 185                 190

Tyr Cys Pro Ser Lys Ile Arg Arg Lys Ala Asn Ala Ser Cys Lys Lys
        195                 200                 205

Cys Lys Lys Val Ile Cys Arg Glu His Asn Ile Asp Met Cys Gln Ser
    210                 215                 220

Cys Phe Trp Thr Asp
225
```

<210> SEQ ID NO 67
<211> LENGTH: 7411
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 67

| | | | | | |
|---|---|---|---|---|---|
| ctaaattgta | agcgttaata | ttttgttaaa | attcgcgtta | aattttgtt | aaatcagctc | 60 |
| atttttaac | caataggccg | aaatcggcaa | atcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |

```
ccccgatt       agagcttgac  ggggaaagcc  ggcgaacgtg  gcgagaaagg  aagggaagaa   360
agcgaaagga     gcgggcgcta  gggcgctggc  aagtgtagcg  gtcacgctgc  gcgtaaccac   420
cacacccgcc     gcgcttaatg  cgccgctaca  gggcgcgtcc  cattcgccat  tcaggctgcg   480
caactgttgg     gaagggcgat  cggtgcgggc  ctcttcgcta  ttacgccagc  tggcgaaagg   540
gggatgtgct     gcaaggcgat  taagttgggt  aacgccaggg  ttttcccagt  cacgacgttg   600
taaaacgacg     gccagtgagc  gcgcgtaata  cgactcacta  tagggcgaat  gggtaccgg    660
gccccccctc     gaggtcgacg  gtatcgataa  gcttgatatc  gaattctaaa  aaaaatcatg   720
aatggcatca     actctgaatc  aaatctttgc  agatgcacct  acttctcatt  tccactgtca   780
catcattttt     ccagatctcg  ctgcctgtta  tgtggcccac  aaaccaagac  acgttttatg   840
gccattaaag     ctggctgatc  gtcgccaaac  accaaataca  tatcaatatg  tacattcgag   900
aaagaagcga     tcaagaagc   gtcttcgggc  gagtaggaga  atgcggagga  aaggagaac    960
gagctgatct     agtatctctc  cacaatccaa  tgccaactga  ccaactgcc   atattcggag  1020
caatttgaag     ccaatttcca  tcgcctggcg  atcgctccat  tcttggctat  atgttttca   1080
ccgttcccgg     ggccattttc  aaagactcgt  cggtaagata  agattgtgtc  actcgctgtc  1140
tctcttcatt     tgtcgaagaa  tgctgaggaa  tttcgcgatg  acgtcggcga  gtattttgaa  1200
gaatgagaat     aatttgtatt  tatacgaaaa  tcagttagtg  gaattttcta  caaaaacatg  1260
ttatctatag     ataattttgt  tgcaaaatat  gttgactatg  acaaagattg  tatgtatata  1320
cctttaatgt     attctcattt  tcttatgtat  ttataatggc  aatgatgata  ctgatgatat  1380
tttaagatga     tgccagacca  caggctgatt  tctgcgtctt  ttgccgaacg  cagtgcatgt  1440
gcggttgttg     ttttttggaa  tagtttcaat  tttcggactg  tccgctttga  tttcagtttc  1500
ttggcttatt     caaaaagcaa  agtaaagcca  aaaaagcgag  atggcaatac  caatgcggc   1560
aaaacggtag     tggaaggaaa  ggggtgcggg  gcagcggaag  gaagggtggg  gcggggcgtg  1620
gcggggtctg     tggctgggcg  cgacgtcacc  gacgttggag  ccactccttt  gaccatgtgt  1680
gcgtgtgtgt     attattcgtg  tctcgccact  cgccggttgt  tttttttcttt ttatctcgct  1740
ctctctagcg     ccatctcgta  cgcatgctca  acgcaccgca  tgttgccgtg  tcctttatgc  1800
gtcattttgg     ctcgaaatag  gcaattattt  aaacaaagat  tagtcaacga  aaacgctaaa  1860
ataaataagt     ctacaatatg  gttacttatt  gccatgtgtg  tgcagccaac  gatagcaaca  1920
aaagcaacaa     cacagtggct  ttccctcttt  cacttttgt   ttgcaagcgc  gtgcgagcaa  1980
gacggcacga     ccggcaaacg  caattacgct  gacaaagagc  agacgaagtt  ttggccgaaa  2040
aacatcaagg     cgcctgatac  gaatgcattt  gcaataacaa  ttgcgatatt  taatattgtt  2100
tatgaagctg     tttgacttca  aaacacacaa  aaaaaaaaat  aaaacaaatt  atttgaaaga  2160
gaattaggaa     tcggacagct  tatcgttacg  ggctaacagc  acaccgagac  gaaatagctt  2220
acctgacgtc     acagcctctg  gaagaactgc  cgccaagcag  acgatgcaga  ggacgacaca  2280
tagagtagcg     gagtaggcca  gcgtagtacg  catgtgcttg  tgtgtgaggc  gtctctctct  2340
tcgtctcctg     tttgcgcaaa  cgcatagact  gcactgagaa  aatcgattac  ctattttta   2400
tgaatgaata     tttgcactat  tactattcaa  aactattaag  atagcaatca  cattcaatag  2460
ccaaatacta     taccacctga  gcgatgcaac  gaaatgatca  atttgagcaa  aaatgctgca  2520
tatttaggac     ggcatcatta  tagaaatgct  tcttgctgtg  tacttttctc  tcgtctggca  2580
gctgtttcgc     cgttattgtt  aaaaccggct  taagttaggt  gtgttttcta  cgactagtga  2640
tgcccctact     agaagatgtg  tgttgcacaa  atgtccctga  ataaccaatt  tgaagtgcag  2700
```

-continued

```
atagcagtaa acgtaagcta atatgaatat tatttaactg taatgtttta atatcgctgg    2760
acattactaa taaacccact ataaacacat gtacatatgt atgttttggc atacaatgag    2820
tagttgggga aaaaatgtgt aaaagcaccg tgaccatcac agcataaaga taaccagctg    2880
aagtatcgaa tatgagtaac ccccaaattg aatcacatgc cgcaactgat aggacccatg    2940
gaagtacact cttcatggcg atatacaaga cacacacaag cacgaacacc cagttgcgga    3000
ggaaattctc cgtaaatgaa aacccaatcg gcgaacaatt catacccata tatggtaaaa    3060
gttttgaacg cgacttgaga gcggagagca ttgcggctga taaggtttta gcgctaagcg    3120
ggctttataa aacgggctgc gggaccagtt ttcatatcgg atcctatata ataaaatggg    3180
tagttcttta gacgatgagc atatcctctc tgctcttctg caaagcgatg acgagcttgt    3240
tggtgaggat tctgacagtg aaatatcaga tcacgtaagt gaagatgacg tccagagcga    3300
tacagaagaa gcgtttatag atgaggtaca tgaagtgcag ccaacgtcaa gcggtagtga    3360
aatattagac gaacaaaatg ttattgaaca accaggttct tcattggctt ctaacagaat    3420
cttgaccttg ccacagagga ctattagagg taagaataaa cattgttggt caacttcaaa    3480
gtccacgagg cgtagccgag tctctgcact gaacattgtc agatctcaaa gaggtccgac    3540
gcgtatgtgc cgcaatatat atgacccact tttatgcttc aaactatttt ttactgatga    3600
gataatttcg gaaattgtaa aatggacaaa tgctgagata tcattgaaac gtcgggaatc    3660
tatgacaggt gctacatttc gtgacacgaa tgaagatgaa atctatgctt tctttggtat    3720
tctggtaatg acagcagtga gaaaagataa ccacatgtcc acagatgacc tctttgatcg    3780
atctttgtca atggtgtacg tctctgtaat gagtcgtgat cgttttgatt ttttgatacg    3840
atgtcttaga atggatgaca aaagtatacg gcccacactt cgagaaaacg atgtatttac    3900
tcctgttaga aaaatatggg atctctttat ccatcagtgc atacaaaatt acactccagg    3960
ggctcatttg accatagatg aacagttact tggttttaga ggacggtgtc cgtttaggat    4020
gtatatccca aacaagccaa gtaagtatgg aataaaaatc ctcatgatgt gtgacagtgg    4080
tacgaagtat atgataaatg gaatgcctta tttgggaaga ggaacacaga ccaacggagt    4140
accactcggt gaatactacg tgaaggagtt atcaaagcct gtgcacggta gttgtcgtaa    4200
tattacgtgt gacaattggt tcacctcaat ccctttggca aaaaacttac tacaagaacc    4260
gtataagtta accattgtgg gaaccgtgcg atcaaacaaa cgcgagatac cggaagtact    4320
gaaaaacagt cgctccaggc cagtgggaac atcgatgttt tgttttgacg gacccttac     4380
tctcgtctca tataaaccga agccagctaa gatggtatac ttattatcat cttgtgatga    4440
ggatgcttct atcaacgaaa gtaccggtaa accgcaaatg gttatgtatt ataatcaaac    4500
taaaggcgga gtggacacgc tagaccaaat gtgttctgtg atgacctgca gtaggaagac    4560
gaataggtgg cctatggcat tattgtacgg aatgataaac attgcctgca taaattcttt    4620
tattatatac agccataatg tcagtagcaa gggagaaaag gttcaaagtc gcaaaaaatt    4680
tatgagaaac ctttacatga gcctgacgtc atcgtttatg cgtaagcgtt tagaagctcc    4740
tactttgaag agatatttgc gcgataatat ctctaatatt ttgccaaatg aagtgcctgg    4800
tacatcagat gacagtactg aagagccagt aatgaaaaaa cgtacttact gtacttactg    4860
cccctctaaa ataaggcgaa aggcaaatgc atcgtgcaaa aaatgcaaaa aagttatttg    4920
tcgagagcat aatattgata tgtgccaaag ttgtttctga ctgactaata agtataattt    4980
gtttctatta tgtataagtt aagctaatta cttattttat aatacaacat gactgttttt    5040
```

```
aaagtacaaa ataagtttat ttttgtaaaa gagagaatgt ttaaaagttt tgttacttta      5100
gaagaaattt tgagttttg tttttttta ataaataaat aaacataaat aaattgtttg       5160
ttgaatttgg atccactagt tctagagcgg ccgccaccgc ggtggagctc cagcttttgt      5220
tccctttagt gagggttaat tgcgcgcttg gcgtaatcat ggtcatagct gtttcctgtg      5280
tgaaattgtt atccgctcac aattccacac aacatacgag ccggaagcat aaagtgtaaa      5340
gcctggggtg cctaatgagt gagctaactc acattaattg cgttgcgctc actgcccgct      5400
ttccagtcgg gaaacctgtc gtgccagctg cattaatgaa tcggccaacg cgcggggaga      5460
ggcggtttgc gtattgggcg ctcttccgct tcctcgctca ctgactcgct gcgctcggtc      5520
gttcggctgc ggcgagcggt atcagctcac tcaaaggcgg taatacggtt atccacagaa      5580
tcaggggata acgcaggaaa gaacatgtga gcaaaaggcc agcaaaaggc caggaaccgt      5640
aaaaaggccg cgttgctggc gttttccat aggctccgcc cccctgacga gcatcacaaa       5700
aatcgacgct caagtcagag gtggcgaaac ccgacaggac tataaagata ccaggcgttt      5760 cccctggaa gctccctcgt gcgctctcct gttccgaccc tgccgcttac cggatacctg       5820 tccgccttc tcccttcggg aagcgtggcg ctttctcata gctcacgctg taggtatctc       5880
agttcggtgt aggtcgttcg ctccaagctg ggctgtgtgc acgaaccccc cgttcagccc      5940
gaccgctgcg ccttatccgg taactatcgt cttgagtcca acccggtaag acacgactta      6000
tcgccactgg cagcagccac tggtaacagg attagcagag cgaggtatgt aggcggtgct      6060
acagagttct tgaagtggtg cctaactac ggctacacta aaggacagt atttggtatc        6120 tgcgctctgc tgaagccagt taccttcgga aaaagagttg gtagctcttg atccggcaaa      6180
caaaccaccg ctggtagcgg tggtttttt gtttgcaagc agcagattac gcgcagaaaa       6240
aaaggatctc aagaagatcc tttgatcttt tctacgggt ctgacgctca gtggaacgaa       6300
aactcacgtt aagggatttt ggtcatgaga ttatcaaaa ggatcttcac ctagatcctt       6360
ttaaattaaa aatgaagttt taaatcaatc taaagtatat atgagtaaac ttggtctgac      6420
agttaccaat gcttaatcag tgaggcacct atctcagcga tctgtctatt tcgttcatcc      6480
atagttgcct gactccccgt cgtgtagata actacgatac gggagggctt accatctggc      6540
cccagtgctg caatgatacc gcgagaccca cgctcaccgg ctccagattt atcagcaata      6600
aaccagccag ccggaagggc cgagcgcaga agtggtcctg caactttatc cgcctccatc      6660
cagtctatta attgttgccg ggaagctaga gtaagtagtt cgccagttaa tagtttgcgc      6720
aacgttgttg ccattgctac aggcatcgtg gtgtcacgct cgtcgtttgg tatggcttca      6780
ttcagctccg gttcccaacg atcaaggcga gttacatgat cccccatgtt gtgcaaaaaa      6840
gcggttagct ccttcggtcc tccgatcgtt gtcagaagta agttggccgc agtgttatca      6900
ctcatggtta tggcagcact gcataattct cttactgtca tgccatccgt aagatgcttt      6960
tctgtgactg gtgagtactc aaccaagtca ttctgagaat agtgtatgcg gcgaccgagt      7020
tgctcttgcc cggcgtcaat acgggataat accgcgccac atagcagaac tttaaaagtg      7080
ctcatcattg gaaaacgttc ttcggggcga aaactctcaa ggatcttacc gctgttgaga      7140
tccagttcga tgtaacccac tcgtgcaccc aactgatctt cagcatcttt tactttcacc      7200
agcgtttctg ggtgagcaaa aacaggaagg caaaatgccg caaaaaaggg aataagggcg      7260
acacggaaat gttgaatact catactcttc ctttttcaat attattgaag catttatcag      7320
ggttattgtc tcatgagcgg atacatattt gaatgtattt agaaaaataa acaaataggg      7380
gttccgcgca catttccccg aaaagtgcca c                                    7411
```

<210> SEQ ID NO 68
<211> LENGTH: 10330
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 68

| | | | | | |
|---|---|---|---|---|---|
| aagcttgggc | tgcaggtcga | cggatccaaa | ttcaacaaac | aatttattta | tgtttattta | 60 |
| tttattaaaa | aaaacaaaa | actcaaaatt | tcttctaaag | taacaaaact | tttaaacatt | 120 |
| ctctcttta | caaaaataaa | cttattttgt | actttaaaaa | cagtcatgtt | gtattataaa | 180 |
| ataagtaatt | agcttaactt | atacataata | gaaacaaatt | atacttatta | gtcagtcaga | 240 |
| aacaactttg | gcacatatca | atattatgct | ctcgacaaat | aacttttttg | catttttgc | 300 |
| acgatgcatt | tgcctttcgc | cttattttag | aggggcagta | agtacagtaa | gtacgttttt | 360 |
| tcattactgg | ctcttcagta | ctgtcatctg | atgtaccagg | cacttcattt | ggcaaaatat | 420 |
| tagagatatt | atcgcgcaaa | tatctcttca | agtaggagc | ttctaaacgc | ttacgcataa | 480 |
| acgatgacgt | caggctcatg | taaaggtttc | tcataaattt | tttgcgactt | tgaacctttt | 540 |
| ctcccttgct | actgacatta | tggctgtata | aataaaaga | atttatgcag | gcaatgttta | 600 |
| tcattccgta | caataatgcc | ataggccacc | tattcgtctt | cctactgcag | gtcatcacag | 660 |
| aacacatttg | gtctagcgtg | tccactccgc | ctttagtttg | attataatac | ataaccattt | 720 |
| gcggttacc | ggtactttcg | ttgatagaag | catcctcatc | acaagatgat | aataagtata | 780 |
| ccatcttagc | tggcttcggt | ttatatgaga | cgagagtaag | gggtccgtca | aaacaaaaca | 840 |
| tcgatgttcc | cactggcctg | gagcgactgt | ttttcagtac | ttccggtatc | tcgcgtttgt | 900 |
| ttgatcgcac | ggttcccaca | atggttaact | tatacggttc | ttgtagtaag | tttttttgcca | 960 |
| aagggattga | ggtgaaccaa | ttgtcacacg | taatattacg | acaactaccg | tgcacaggct | 1020 |
| ttgataactc | cttcacgtag | tattcaccga | gtggtactcc | gttggtctgt | gttcctcttc | 1080 |
| ccaaataagg | cattccattt | atcatatact | tcgtaccact | gtcacacatc | atgaggattt | 1140 |
| ttattccata | cttacttggc | ttgtttggga | tatacatcct | aaacggacac | cgtcctctaa | 1200 |
| aaccaagtaa | ctgttcatct | atggtcaaat | gagcccctgg | agtgtaattt | tgtatgcact | 1260 |
| gatggataaa | gagatcccat | atttttctaa | caggagtaaa | tacatcgttt | tctcgaagtg | 1320 |
| tgggccgtat | acttttgtca | tccattctaa | gacatcgtat | caaaaaatca | aaacgatcac | 1380 |
| gactcattac | agagacgtac | accattgaca | agatcgatc | aaagaggtca | tctgtggaca | 1440 |
| tgtggttatc | ttttctcact | gctgtcatta | ccagaatacc | aaagaaagca | tagatttcat | 1500 |
| cttcattcgt | gtcacgaaat | gtagcacctg | tcatagattc | ccgacgtttc | aatgatatct | 1560 |
| cagcatttgt | ccatttaca | atttccgaaa | ttatctcatc | agtaaaaaat | agttgaagc | 1620 |
| ataaaagtgg | gtcatatata | ttgcggcaca | tacgcgtcgg | acctctttga | gatctgacaa | 1680 |
| tgttcagtgc | agagactcgg | ctacgcctcg | tggactttga | agttgaccaa | caatgtttat | 1740 |
| tcttacctct | aatagtcctc | tgtggcaagg | tcaagattct | gttagaagcc | aatgaagaac | 1800 |
| ctggttgttc | aataacattt | tgttcgtcta | atatttcact | accgcttgac | gttggctgca | 1860 |
| cttcatgtac | ctcatctata | aacgcttctt | ctgtatcgct | ctggacgtca | tcttcactta | 1920 |
| cgtgatctga | tatttcactg | tcagaatcct | caccaacaag | ctcgtcatcg | ctttgcagaa | 1980 |
| gagcagagag | gatatgctca | tcgtctaaag | aactacccat | tttattatat | aggatccccg | 2040 |

```
acaccagacc aactggtaat ggtagcgacc ggcgctcagc tggaattagg ccttctagac   2100
cgcggccgca gatctgttaa cgaattccca attccctatt cagagttctc ttcttgtatt   2160
caataattac ttcttggcag atttcagtag ttgcagttga tttacttggt tgctggttac   2220
ttttaattga ttcactttaa cttgcacttt actgcagatt gtttagcttg ttcagctgcg   2280
cttgtttatt tgcttagctt tcgcttagcg acgtgttcac ttgcttgttt gaattgaatt   2340
gtcgctccgt agacgaagcg ctctatttat actccggcgc tcttttcgcg aacattcgag   2400
gcgcgctctc tcgaaccaac gagagcagta tgccgtttac tgtgtgacag agtgagagag   2460
cattagtgca gagagggaga cccaaaaaga aagagagaa taacgaataa cggccagaga    2520
aatttctcga gttttcttct gccaaacaaa tgacctacca caataaccag tttgttttgg   2580
gattctaggg ggatcgggga tcaattctag tatgtatgta agttaataaa accctttttt   2640
ggagaatgta gatttaaaaa aacatatttt tttttattt tttactgcac tggatatcat    2700
tgaacttatc tgatcagttt taaatttact tcgatccaag ggtatttgaa gtaccaggtt   2760
ctttcgatta cctctcactc aaaatgacat tccactcaaa gtcagcgctg tttgcctcct   2820
tctctgtcca cagaaatatc gccgtctctt tcgccgctgc gtccgctatc tctttcgcca   2880
ccgtttgtag cgttacctag cgtcaatgtc cgccttcagt tgcactttgt cagcggtttc   2940
gtgacgaagc tccaagcggt ttacgccatc aattaaacac aaagtgctgt gccaaaactc   3000
ctctcgcttc ttattttgt ttgttttttg agtgattggg gtggtgattg gttttgggtg     3060
ggtaagcagg ggaaagtgtg aaaaatcccg gcaatgggcc aagaggatca ggagctatta   3120
attcgcggag gcagcaaaca cccatctgcc gagcatctga acaatgtgag tagtacatgt   3180
gcatacatct taagttcact tgatctatag gaactgcgat tgcaacatca aattgtctgc   3240
ggcgtgagaa ctgcgaccca caaaaatccc aaaccgcaat cgcacaaaca aatagtgaca   3300
cgaaacagat tattctggta gctgtgctcg ctatataaga caattttaa gatcatatca     3360 tgatcaagac atctaaaggc attcattttc gactacattc tttttttacaa aaaatataac   3420 aaccagatat tttaagctga tcctagatgc acaaaaaata aataaaagta taaacctact   3480
tcgtaggata cttcgttttg ttcggggtta gatgagcata acgcttgtag ttgatatttg   3540
agatccccta tcattgcagg gtgacagcgg agcggcttcg cagagctgca ttaaccaggg   3600
cttcgggcag gccaaaaact acggcacgct cctgccaccc agtccgccgg aggactccgg   3660
ttcagggagc ggccaactag ccgagaacct cacctatgcc tggcacaata tggacatctt   3720
tggggcggtc aatcagccgg gctccggatg gcggcagctg gtcaaccgga cacgcggact   3780
attctgcaac gagcgacaca taccggcgcc caggaaacat ttgctcaaga acggtgagtt   3840
tctattcgca gtcggctgat ctgtgtgaaa tcttaataaa gggtccaatt accaatttga   3900
aactcagttt gcggcgtggc ctatccgggc gaacttttgg ccgtgatggg cagttccggt   3960
gccggaaaga cgaccctgct gaatgccctt gcctttcgat cgccgcaggg catccaagta   4020
tcgccatccg ggatgcgact gctcaatggc caacctgtgg acgccaagga gatgcaggcc   4080
aggtgcgcct atgtccagca ggatgacctc tttatcggct ccctaacggc cagggaacac   4140 ctgatttttcc aggccatggt gcggatgcca cgacatctga cctatcggca gcgagtggcc   4200
cgcgtggatc aggtgatcca ggagctttcg ctcagcaaat gtcagcacac gatcatcggt   4260
gtgcccggca gggtgaaagg tctgtccggc ggagaaaggg agcgtctggc attcgcctcc   4320
gaggcactaa ccgatccgcc gcttctgatc tgcgatgagc ccacctccgg actggactca   4380
```

```
tttaccgccc acagcgtcgt ccaggtgctg aagaagctgt cgcagaaggg caagaccgtc    4440
atcctgacca ttcatcagcc gtcttccgag ctgtttgagc tctttgacaa gatccttctg    4500
atggccgagg gcagggtagc tttcttgggc actcccagcg aagccgtcga cttcttttcc    4560
tagtgagttc gatgtgttta ttaagggtat ctagcattac attacatctc aactcctatc    4620
cagcgtgggt gcccagtgtc ctaccaacta caatccggcg gacttttacg tacaggtgtt    4680
ggccgttgtg cccggacggg agatcgagtc ccgtgatcgg atcgccaaga tatgcgacaa    4740
ttttgctatt agcaaagtag cccgggatat ggagcagttg ttggccacca aaaatttgga    4800
gaagccactg gagcagccgg agaatgggta cacctacaag gccacctggt tcatgcagtt    4860
ccgggcggtc ctgtggcgat cctggctgtc ggtgctcaag gaaccactcc tcgtaaaagt    4920
gcgacttatt cagacaacgg tgagtggttc cagtggaaac aaatgatata acgcttacaa    4980
ttcttggaaa caaattcgct agattttagt tagaattgcc tgattccaca cccttcttag    5040
tttttttcaa tgagatgtat agtttatagt tttgcagaaa ataaataaat ttcatttaac    5100
tcgcgaacat gttgaagata tgaatattaa tgagatgcga gtaacatttt aatttgcaga    5160
tggttgccat cttgattggc ctcatctttt tgggccaaca actcacgcaa gtgggcgtga    5220
tgaatatcaa cggagccatc ttcctcttcc tgaccaacat gaccttcaa aacgtctttg    5280 ccacgataaa tgtaagtctt gtttagaata catttgcata ttaataattt actaactttc    5340
taatgaatcg attcgattta ggtgttcacc tcagagctgc cagttttat gagggaggcc    5400 cgaagtcgac tttatcgctg tgacacatac tttctgggca aaacgattgc cgaattaccg    5460 cttttttctca cagtgccact ggtcttcacg gcgattgcct atccgatgat cggactgcgg    5520
gccggagtgc tgcacttctt caactgcctg gcgctggtca ctctggtggc caatgtgtca    5580
acgtccttcg gatatctaat atcctgcgcc agctcctcga cctcgatggc gctgtctgtg    5640
ggtccgccgg ttatcatacc attcctgctc tttggcggct tcttcttgaa ctcgggctcg    5700
gtgccagtat acctcaaatg gttgtcgtac ctctcatggt tccgttacgc caacgagggt    5760
ctgctgatta accaatgggc ggacgtggag ccgggcgaaa ttagctgcac atcgtcgaac    5820
accacgtgcc ccagttcggg caaggtcatc ctggagacgc ttaacttctc cgccgccgat    5880
ctgccgctgg actacgtggg tctggccatt ctcatcgtga gcttccgggt gctcgcatat    5940
ctggctctaa gacttcgggc ccgacgcaag gagtagccga catatatccg aaataactgc    6000
ttgttttttt ttttaccatt attaccatcg tgtttactgt ttattgcccc ctcaaaaagc    6060
taatgtaatt atatttgtgc caataaaaac aagatatgac ctatagaata caagtatttc    6120
cccttcgaac atccccacaa gtagactttg gatttgtctt ctaaccaaaa gacttacaca    6180
cctgcatacc ttcatcaaa aactcgttta tcgctacata aaacaccggg atatattttt    6240
tatatacata cttttcaaat cgcgcgccct cttcataatt cacctccacc acaccacgtt    6300
tcgtagttgc tctttcgctg tctcccaccc gctctccgca acacattcac cttttgttcg    6360
acgaccttgg agcgactgtc gttagttccg cgcgattcgg ttcgctcaaa tggttccgag    6420
tggttcattt cgtctcaata gaaattagta ataaatattt gtatgtacaa tttatttgct    6480
ccaatatatt tgtatatatt tccctcacag ctatatttat tctaatttaa tattatgact    6540
ttttaaggta attttttgtg acctgttcgg agtgattagc gttacaattt gaactgaaag    6600
tgacatccag tgtttgttcc ttgtgtagat gcatctcaaa aaaatggtgg cataatagt    6660 gttgttata tatcaaaaa ataagaacta taataataag aatacattta atttagaaaa    6720
tgcttggatt tcactggaac tagaattaat tcggctgctg ctctaaacga cgcatttcgt    6780
```

```
actccaaagt acgaattttt tccctcaagc tcttattttc attaaacaat gaacaggacc   6840
taacgcacag tcacgttatt gtttacataa atgattttt ttactattca aacttactct    6900
gtttgtgtac tcccactggt atagccttct tttatctttt ctggttcagg ctctatcact   6960
ttactaggta cggcatctgc gttgagtcgc ctccttttaa atgtctgacc ttttgcaggt   7020
gcagccttcc actgcgaatc tttaaagtgg gtatcacaaa tttgggagtt ttcaccaagg   7080
ctgcacccaa ggctctgctc ccacaatttt ctcttaatag cacacttcgg cacgtgaatt   7140
aattttactc cagtcacagc ttgcagcaaa atttgcaata tttcattttt ttttattcca   7200
cgtaagggtt aatgttttca aaaaaaatt cgtccgcaca caacctttcc tctcaacaag    7260
caaacgtgca ctgaatttaa gtgtatactt cggtaagctt cggctatcga cgggaccacc   7320
ttatgttatt tcatcatggg ccagacccac gtagtccagc ggcagatcgg cggcggagaa   7380
gttaagcgtc tccaggatga ccttgcccga actggggcac gtggtgttcg acgatgtgca   7440
gctaatttcg cccggctcca cgtccgccca ttggttaatc agcagaccct cgttggcgta   7500
acggaaccat gagaggtacg acaaccattt gaggtatact ggcaccgagc ccgagttcaa   7560
gaagaaggcg ttttttccata ggctccgccc ccctgacgag catcacaaaa atcgacgctc   7620
aagtcagagg tggcgaaacc cgacaggact ataaagatac caggcgtttc ccctggaag    7680
ctccctcgtg cgctctcctg ttccgaccct gccgcttacc ggatacctgt ccgcctttct   7740
cccttcggga agcgtggcgc tttctcaatg ctcacgctgt aggtatctca gttcggtgta   7800
ggtcgttcgc tccaagctgg gctgtgtgca cgaaccccc gttcagcccg accgctgcgc    7860
cttatccggt aactatcgtc ttgagtccaa cccggtaaga cacgacttat cgccactggc   7920
agcagccact ggtaacagga ttagcagagc gaggtatgta ggcggtgcta cagagttctt   7980
gaagtggtgg cctaactacg gctacactag aaggacagta tttggtatct gcgctctgct   8040
gaagccagtt accttcggaa aaagagttgg tagctcttga tccggcaaac aaaccaccgc   8100
tggtagcggt ggtttttttg tttgcaagca gcagattacg cgcagaaaaa aaggatctca   8160
agaagatcct ttgatctttt ctacggggtc tgacgctcag tggaacgaaa actcacgtta   8220
agggattttg gtcatgagat tatcaaaaag gatcttcacc tagatccttt taaattaaaa   8280
atgaagtttt aaatcaatct aaagtatata tgagtaaact tggtctgaca gttaccaatg   8340
cttaatcagt gaggcaccta tctcagcgat ctgtctattt cgttcatcca tagttgcctg   8400
actccccgtc gtgtagataa ctacgatacg ggagggctta ccatctggcc ccagtgctgc   8460
aatgataccg cgagacccac gctcaccggc tccagattta tcagcaataa accagccagc   8520
cggaagggcc gagcgcagaa gtggtcctgc aactttatcc gcctccatcc agtctattaa   8580
ttgttgccgg gaagctgagt aagtagtcg ccagttaata gtttgcgcaa cgttgttgcc    8640
attgctacag gcatcgtggt gtcacgctcg tcgtttggta tggcttcatt cagctccggt   8700
tcccaacgat caaggcgagt tacatgatcc cccatgttgt gcaaaaaagc ggttagctcc   8760
ttcggtcctc cgatcgttgt cagaagtaag ttggccgcag tgttatcact catggttatg   8820
gcagcactgc ataattctct tactgtcatg ccatccgtaa gatgcttttc tgtgactggt   8880
gagtactcaa ccaagtcatt ctgagaatag tgtatgcggc gaccgagttg ctcttgcccg   8940
gcgtcaatac gggataatac cgcgccacat agcagaactt taaaagtgct catcattgga   9000
aaacgttctt cggggcgaaa actctcaagg atcttaccgc tgttgagatc cagttcgatg   9060
taacccactc gtgcacccaa ctgatcttca gcatctttta ctttcaccag cgtttctggg   9120
```

| | |
|---|---|
| tgagcaaaaa caggaaggca aaatgccgca aaaaagggaa taagggcgac acggaaatgt | 9180 |
| tgaatactca tactcttcct tttcaatat tattgaagca tttatcaggg ttattgtctc | 9240 |
| atgagcggat acatatttga atgtatttag aaaaataaac aaatagggt tccgcgcaca | 9300 |
| tttccccgaa aagtgccacc tgacgtctaa gaaaccatta ttatcatgac attaacctat | 9360 |
| aaaaataggc gtatcacgag gcccttttcgt ctcgcgcgtt tcggtgatga cggtgaaaac | 9420 |
| ctctgacaca tgcagctccc ggagacggtc acagcttgtc tgtaagcgga tgccgggagc | 9480 |
| agacaagccc gtcagggcgc gtcagcgggt gttggcgggt gtcggggctg gcttaactat | 9540 |
| gcggcatcag agcagattgt actgagagtg caccatatgc ggtgtgaaat accgcaccga | 9600 |
| atcgcgcgga actaacgaca gtcgctccaa ggtcgtcgaa caaaaggtga atgtgttgcg | 9660 |
| gagagcgggt gggagacagc gaaagagcaa ctacgaaacg tggtgtggtg gaggtgaatt | 9720 |
| atgaagaggg cgcgcgattt gaaaagtatg tatataaaaa atatatcccg gtgttttatg | 9780 |
| tagcgataaa cgagttttg atgtaaggta tgcaggtgtg taagtctttt ggttagaaga | 9840 |
| caaatccaaa gtctacttgt ggggatgttc gaagggaaa tacttgtatt ctataggtca | 9900 |
| tatcttgttt ttattggcac aaatataatt acattagctt tttgaggggg caataaacag | 9960 |
| taaacacgat ggtaataatg gtaaaaaaaa aaacaagcag ttatttcgga tatatgtcgg | 10020 |
| ctactccttg cgtcgggccc gaagtcttag agccagatat gcgagcaccc ggaagctcac | 10080 |
| gatgagaatg gccagaccat gatgaaataa cataaggtgg tcccgtcggc aagagacatc | 10140 |
| cacttaacgt atgcttgcaa taagtgcgag tgaaaggaat agtattctga gtgtcgtatt | 10200 |
| gagtctgagt gagacagcga tatgattgtt gattaaccct tagcatgtcc gtgggggttg | 10260 |
| aattaactca taatattaat tagacgaaat tatttttaaa gttttatttt taataatttg | 10320 |
| cgagtacgca | 10330 |

<210> SEQ ID NO 69
<211> LENGTH: 1785
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 69

| | |
|---|---|
| atgggtagtt ctttagacga tgagcatatc ctctctgctc ttctgcaaag cgatgacgag | 60 |
| cttgttggtg aggattctga cagtgaaata tcagatcacg taagtgaaga tgacgtccag | 120 |
| agcgatacag aagaagcgtt tatagatgag gtacatgaag tgcagccaac gtcaagcggt | 180 |
| agtgaaatat tagacgaaca aaatgttatt gaacaaccag gttcttcatt ggcttctaac | 240 |
| agaatcttga ccttgccaca gaggactatt agaggtaaga ataaacattg ttggtcaact | 300 |
| tcaaagtcca cgaggcgtag ccgagtctct gcactgaaca ttgtcagatc tcaaagaggt | 360 |
| ccgacgcgta tgtgccgcaa tatatatgac ccacttttat gcttcaaact attttttact | 420 |
| gatgagataa tttcggaaat tgtaaaatgg acaaatgctg agatatcatt gaaacgtcgg | 480 |
| gaatctatga caggtgctac atttcgtgac acgaatgaag atgaaatcta tgctttcttt | 540 |
| ggtattctgg taatgacagc agtgagaaaa gataaccaca tgtccacaga tgacctcttt | 600 |
| gatcgatctt tgtcaatggt gtacgtctct gtaatgagtc gtgatcgttt tgattttttg | 660 |
| atacgatgtc ttagaatgga tgacaaaagt atacggccca cacttcgaga aaacgatgta | 720 |
| tttactcctg ttagaaaaat atgggatctc tttatccatc agtgcataca aaattacact | 780 |

| | |
|---|---|
| ccagggctc atttgaccat agatgaacag ttacttggtt ttagaggacg gtgtccgttt | 840 |
| aggatgtata tcccaaacaa gccaagtaag tatggaataa aaatcctcat gatgtgtgac | 900 |
| agtggtacga agtatatgat aaatggaatg ccttatttgg gaagaggaac acagaccaac | 960 |
| ggagtaccac tcggtgaata ctacgtgaag gagttatcaa agcctgtgca cggtagttgt | 1020 |
| cgtaatatta cgtgtgacaa ttggttcacc tcaatccctt tggcaaaaaa cttactacaa | 1080 |
| gaaccgtata agttaaccat tgtgggaacc gtgcgatcaa acaaacgcga gataccggaa | 1140 |
| gtactgaaaa acagtcgctc caggccagtg gaacatcga tgttttgttt tgacggaccc | 1200 |
| cttactctcg tctcatataa accgaagcca gctaagatgg tatacttatt atcatcttgt | 1260 |
| gatgaggatg cttctatcaa cgaaagtacc ggtaaaccgc aaatggttat gtattataat | 1320 |
| caaactaaag gcggagtgga cacgctagac caaatgtgtt ctgtgatgac ctgcagtagg | 1380 |
| aagacgaata ggtggcctat ggcattattg tacggaatga taaacattgc ctgcataaat | 1440 |
| tcttttatta tatacagcca taatgtcagt agcaagggag aaaaggttca aagtcgcaaa | 1500 |
| aaatttatga gaaacctta catgagcctg acgtcatcgt ttatgcgtaa gcgtttagaa | 1560 |
| gctcctactt tgaagagata tttgcgcgat aatatctcta atattttgcc aaatgaagtg | 1620 |
| cctggtacat cagatgacag tactgaagag ccagtaatga aaaaacgtac ttactgtact | 1680 |
| tactgcccct ctaaaataag gcgaaaggca aatgcatcgt gcaaaaaatg caaaaaagtt | 1740 |
| atttgtcgag agcataatat tgatatgtgc caaagttgtt tctga | 1785 |

<210> SEQ ID NO 70
<211> LENGTH: 1785
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 70

| | |
|---|---|
| atgggtagca gcctggatga tgaacatatc ctgagcgcgc tgctgcagag cgacgacgaa | 60 |
| ctggttggtg aagatagcga cagcgaaatc agcgatcacg tgagcgaaga cgacgttcag | 120 |
| agcgataccg aagaagcgtt catcgacgaa gttcacgaag tgcagccgac cagcagcggt | 180 |
| agcgaaatcc tggatgaaca gaacgttatc gaacagccgg gtagcagcct ggcgagcaac | 240 |
| cgtatcctga ccctgccgca gcgcaccatc cgtggtaaaa acaaacactg ttggagcacc | 300 |
| agcaaaagca cccgccgtag ccgtgttagc gcgctgaaca ttgttcgtag ccagcgtggt | 360 |
| ccgacccgta tgtgccgcaa catctacgat ccgctgctgt gcttcaaact gttcttcacc | 420 |
| gatgaaatca tcagcgaaat cgtgaaatgg accaacgccg aaatcagcct gaaacgtcgc | 480 |
| gaaagcatga ccggcgcgac cttccgcgat accaacgaag atgaaatcta cgccttcttc | 540 |
| ggtatcctgg tgatgaccgc ggtgcgtaaa gataaccaca tgagcaccga tgatctgttt | 600 |
| gatcgtagcc tgagcatggt ttacgttagc gttatgagcc gtgaccgttt cgattttctg | 660 |
| atccgttgtc tgcgtatgga tgataaaagc atccgcccga ccctgcgcga aaacgatgtg | 720 |
| ttcacccccgg ttcgcaaaat ctgggatctg ttcatccacc agtgcatcca gaactacacc | 780 |
| ccgggcgcgc acctgaccat cgatgaacag ctgctggggtt ttcgtggtcg ctgtccgttt | 840 |
| cgtatgtaca tcccgaacaa accgagcaaa tacggtatca aaatcctgat gatgtgtgac | 900 |
| agcggtacca agtacatgat caacggtatg ccgtatctgg gtcgtggtac ccagaccaac | 960 |
| ggtgtgccgc tgggtgaata ctacgtgaaa gaactgagca aaccggtgca cggtagctgt | 1020 |

```
cgtaacatca cctgtgacaa ctggttcacc agcatcccgc tggcgaaaaa cctgctgcag      1080
gaaccgtata aactgaccat cgtgggtacc gttcgtagca acaaacgtga atcccggaa      1140 gtgctgaaaa acagccgtag ccgtccggtg ggcaccagca tgttctgttt cgatggtccg      1200
ctgaccctgg ttagctacaa accgaaaccg gcgaaaatgg tgtacctgct gagcagctgc      1260
gacgaagacg cgagcatcaa cgaaagcacc ggtaaaccgc agatggttat gtactacaac      1320
cagaccaaag gcggtgtgga cccctggat cagatgtgca gcgttatgac ctgcagccgc       1380
aaaaccaacc gctggccgat ggcgctgctg tacggtatga tcaacatcgc ctgcatcaac      1440
agctttatca tctacagcca taacgttagc agcaaaggtg aaaagttca gagccgcaaa      1500 aaatttatgc gtaacctgta catgagcctg accagcagct tcatgcgtaa acgtctggaa      1560
gccccgaccc tgaaacgtta tctgcgcgat aacatcagca acatcctgcc gaacgaagtg      1620
ccgggtacca gcgatgatag caccgaagaa ccggtgatga aaaaacgtac ctactgtacc      1680
tactgcccga gcaaaatccg ccgtaaagcg aacgcgagct gcaaaaaatg caaaaaagtt      1740
atctgtcgtg aacataacat cgatatgtgc cagagctgtt tctga                     1785

<210> SEQ ID NO 71
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ccctagaaag ataatcatat tgtgacgtac gttaaagata atcatgcgta aaattgacgc      60
atg                                                                   63

<210> SEQ ID NO 72
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccctagaaag ataatcatat tgtgacgtac gttaaagata atcatgagta aattgacgca      60
tg                                                                    62

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acttctagag tcctaaattg caaacagcga c                                    31

<210> SEQ ID NO 74
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
```
acttctagac acgtaagtag aacatgaaat aac                                33

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acttctagat cactgtcaga atcctcacca ac                                 32

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acttctagaa gaagccaatg aagaacctgg                                    30

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acttctagaa ataaataaat aaacataaat aaattg                             36

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acttctagag aaaggcaaat gcatcgtgc                                     29

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acttctagac gcaaaaaatt tatgagaaac c                                  31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acttctagag atgaggatgc ttctatcaac g         31

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acttctagac gcgagatacc ggaagtactg           30

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acttctagac tcgagagaga atgtttaaaa gttttgtt   38

<210> SEQ ID NO 83
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
acttctagac atgcgtcaat tttacgcaga ctatctttct agggttaatc tagctgcatc   60
agg                                        63

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgactagtg ttcccacaat ggttaattcg           30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acgactagtg ccgtacgcgt atcgataagc           30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggatcctata taataaaatg ggtagttctt        30

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggatccaaat tcaacaaaca atttatttat g        31

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggatcctcta gattaaccct agaaagata        29

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 89
taatacgact cactataggg nnnnnnnnnn ctat        34

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 90
taatacgact cactataggg nnnnnnnnnn agtgc        35

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 91
taatacgact cactataggg nnnnnnnnnn gaattc                                36

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 92
taatacgact cactataggg nnnnnnnnnn agtact                                36

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 93
taatacgact cactataggg nnnnnnnnnn aagctt                                36

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 94
taatacgact cactataggg nnnnnnnnnn ggatcc                                36

<210> SEQ ID NO 95
<211> LENGTH: 34
```

<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(30)
<223> OTHER INFORMATION: a, c, g, t, unknown or other
<220> FEATURE:
<221> NAME/KEY: misc_feature
<222> LOCATION: (21)..(30)
<223> OTHER INFORMATION: n is a, c, g, or t

<400> SEQUENCE: 95
taatacgact cactataggg nnnnnnnnnn ctag                                34

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
attttacgca gactatcttt cta                                           23

<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ttaatacgac tcactat                                                  17

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ggatccgcgg taagtgtcac tga                                           23

<210> SEQ ID NO 99
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ggatcctcga tatacagacc gataaaaaca catg                               34

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 100
actgggccca tactaataat aaattcaaca aac                                        33

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ttatttcatg ttctacttac gtg                                                  23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tgattatctt taacgtacgt cac                                                  23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gtcagtccag aaacaacttt ggc                                                  23

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ctagaaattt atttatgttt atttatttat ta                                        32

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acgcgtagat cttaatacga ctcactatag gg                                        32

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
```

```
acgcgtagat ctaattaacc ctcactaaag gg                                    32

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ccaaacttcg gcgatgtttt cttaa                                            25

<210> SEQ ID NO 108
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tagaattcat gtttccaatt ttttaa                                           26

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tcgggtggca cgttgtggat tttaa                                            25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaatacgtca ctccccttcc cttaa                                            25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
agctgcactc accggatgtc cttaa                                            25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
```
cccaaagtat agttaaatag cttaa                                          25

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtttatttat gattagagcc tttaa                                          25

<210> SEQ ID NO 114
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgttgttttt ttgtccccac gtttaa                                         26

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ctgcctctag ccgcctgctt tattaa                                         26

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ttaaattcgc atatgtgcaa atgtt                                          25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ttaagcatgt ccttaagcat aaaat                                          25

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ttaatgctag ctgcatgcag gatgc                                          25

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ttaaacaaaa aatgaaacat aagg                                           24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ttaaaggaat taataaaaat acaa                                           24

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ttaatctcct ccgcccttct tcaatt                                         26

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttaaacaaac acctttgaca aattt                                          25

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttaatattaa ttgaaaataa atgca                                          25

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
yyttttttaa rtaayag                                                   17

<210> SEQ ID NO 125
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: misc_feature
<222> LOCATION: (3)..(3)
<223> OTHER INFORMATION: n is a, c, g, or t

<400> SEQUENCE: 125
atnatttaaa t                                                              11

<210> SEQ ID NO 126
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Ser Leu Cys Thr Glu His Cys Gln Ile Ser Lys Arg Ser Asp Ala
1               5                   10                  15

Tyr Val Pro Gln Tyr Ile
            20

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Thr Phe Met Leu Gln Thr Ile Phe Tyr
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Asn Phe Ala Asn Cys Lys Met Asp Lys Cys
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Ile Ile Glu Thr Ser Gly Ile Tyr Asp Arg Cys Tyr Ile Ser
1               5                   10                  15

```
<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asn Leu Cys Phe Leu Trp Tyr Ser Gly Asn Asp Ser Ser Glu Lys Arg
1               5                   10                  15

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro His Val His Arg
1               5

<210> SEQ ID NO 132
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Leu Trp Ile Asp Leu Cys Gln Cys Val Arg Leu Cys Asn Glu Ser
1               5                   10                  15

Val Asp Arg Phe Gly Phe Phe Asp Thr Met Ser
            20                  25

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Lys Tyr Thr Ala His Thr Ser Arg Lys Arg Cys Ile Tyr Ser Cys
1               5                   10                  15

<210> SEQ ID NO 134
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys Asn Met Gly Ser Leu Tyr Pro Ser Val His Thr Lys Leu His Ser
1               5                   10                  15

Arg Gly Ser Phe Asp His Arg
            20

<210> SEQ ID NO 135
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Val Thr Trp Phe
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Thr Val Ser Val
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Val Tyr Pro Lys Gln Ala Lys
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Val Trp Asn Lys Asn Pro His Asp Val
1               5

<210> SEQ ID NO 139
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Trp Tyr Glu Val Tyr Asp Lys Trp Asn Ala Leu Phe Gly Lys Arg
1               5                   10                  15

Asn Thr Asp Gln Arg Ser Thr Thr Arg
            20                  25

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 140

Ile Leu Arg Glu Gly Val Ile Lys Ala Cys Ala Arg
1               5                   10

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Leu Val His Leu Arg Ala Pro
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Ala Tyr Phe Tyr Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Ser Ile Leu Leu Phe Ser
1               5

<210> SEQ ID NO 144
<211> LENGTH: 949
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 144

Gln Phe Cys Asn Lys Lys Thr Asp Pro Val Val Pro Ser Asn Trp
1               5                   10                  15

Gln Met His Gly Tyr Asp Ala Pro Ile Tyr Thr Asn Val Thr Tyr Pro
                20                  25                  30

Ile Thr Val Asn Pro Pro Phe Val Pro Thr Glu Asn Pro Thr Gly Cys
            35                  40                  45

Tyr Ser Leu Thr Phe Asn Val Asp Glu Ser Trp Leu Gln Glu Gly Gln
        50                  55                  60

Thr Arg Ile Ile Phe Asp Gly Val Asn Ser Ala Phe His Leu Trp Cys
65                  70                  75                  80

Asn Gly Arg Trp Val Gly Tyr Gly Gln Asp Ser Arg Leu Pro Ser Glu
                85                  90                  95

Phe Asp Leu Ser Ala Phe Leu Arg Ala Gly Glu Asn Arg Leu Ala Val
            100                 105                 110
```

```
Met Val Leu Arg Trp Ser Asp Gly Ser Tyr Leu Glu Asp Gln Asp Met
            115                 120                 125

Trp Arg Met Ser Gly Ile Phe Arg Asp Val Ser Leu Leu His Lys Pro
    130                 135                 140

Thr Thr Gln Ile Ser Asp Phe His Val Ala Thr Arg Phe Asn Asp Asp
145                 150                 155                 160

Phe Ser Arg Ala Val Leu Glu Ala Glu Val Gln Met Cys Gly Glu Leu
                165                 170                 175

Arg Asp Tyr Leu Arg Val Thr Val Ser Leu Trp Gln Gly Glu Thr Gln
            180                 185                 190

Val Ala Ser Gly Thr Ala Pro Phe Gly Gly Glu Ile Asp Glu Arg
    195                 200                 205

Gly Gly Tyr Ala Asp Arg Val Thr Leu Arg Leu Asn Val Glu Asn Pro
210                 215                 220

Lys Leu Trp Ser Ala Glu Ile Pro Asn Leu Tyr Arg Ala Val Val Glu
225                 230                 235                 240

Leu His Thr Ala Asp Gly Thr Leu Ile Glu Ala Glu Ala Cys Asp Val
                245                 250                 255

Gly Phe Arg Glu Val Arg Ile Glu Asn Gly Leu Leu Leu Leu Asn Gly
            260                 265                 270

Lys Pro Leu Leu Ile Arg Gly Val Asn Arg His Glu His His Pro Leu
    275                 280                 285

His Gly Gln Val Met Asp Glu Gln Thr Met Val Gln Asp Ile Leu Leu
            290                 295                 300

Met Lys Gln Asn Asn Phe Asn Ala Val Arg Cys Ser His Tyr Pro Asn
305                 310                 315                 320

His Pro Leu Trp Tyr Thr Leu Cys Asp Arg Tyr Gly Leu Tyr Val Val
                325                 330                 335

Asp Glu Ala Asn Ile Glu Thr His Gly Met Val Pro Met Asn Arg Leu
            340                 345                 350

Thr Asp Asp Pro Arg Trp Leu Pro Ala Met Ser Glu Arg Val Thr Arg
    355                 360                 365

Met Val Gln Arg Asp Arg Asn His Pro Ser Val Ile Ile Trp Ser Leu
    370                 375                 380

Gly Asn Glu Ser Gly His Gly Ala Asn His Asp Ala Leu Tyr Arg Trp
385                 390                 395                 400

Ile Lys Ser Val Asp Pro Ser Arg Pro Val Gln Tyr Glu Gly Gly Gly
                405                 410                 415

Ala Asp Thr Thr Ala Thr Asp Ile Ile Cys Pro Met Tyr Ala Arg Val
            420                 425                 430

Asp Glu Asp Gln Pro Phe Pro Ala Val Pro Lys Trp Ser Ile Lys Lys
    435                 440                 445

Trp Leu Ser Leu Pro Gly Glu Thr Arg Pro Leu Ile Leu Cys Glu Tyr
450                 455                 460

Ala His Ala Met Gly Asn Ser Leu Gly Gly Phe Ala Lys Tyr Trp Gln
465                 470                 475                 480

Ala Phe Arg Gln Tyr Pro Arg Leu Gln Gly Gly Phe Val Trp Asp Trp
                485                 490                 495

Val Asp Gln Ser Leu Ile Lys Tyr Asp Glu Asn Gly Asn Pro Trp Ser
            500                 505                 510

Ala Tyr Gly Gly Asp Phe Gly Asp Thr Pro Asn Asp Arg Gln Phe Cys
    515                 520                 525
```

-continued

Met Asn Gly Leu Val Phe Ala Asp Arg Thr Pro His Pro Ala Leu Thr
   530                 535                 540

Glu Ala Lys His Gln Gln Gln Phe Phe Gln Phe Arg Leu Ser Gly Gln
545                 550                 555                 560

Thr Ile Glu Val Thr Ser Glu Tyr Leu Phe Arg His Ser Asp Asn Glu
            565                 570                 575

Leu Leu His Trp Met Val Ala Leu Asp Gly Lys Pro Leu Ala Ser Gly
        580                 585                 590

Glu Val Pro Leu Asp Val Ala Pro Gln Gly Lys Gln Leu Ile Glu Leu
            595                 600                 605

Pro Glu Leu Pro Gln Pro Glu Ser Ala Gly Gln Leu Trp Leu Thr Val
610                 615                 620

Arg Val Val Gln Pro Asn Ala Thr Ala Trp Ser Glu Ala Gly His Ile
625                 630                 635                 640

Ser Ala Trp Gln Gln Trp Arg Leu Ala Glu Asn Leu Ser Val Thr Leu
                645                 650                 655

Pro Ala Ala Ser His Ala Ile Pro His Leu Thr Thr Ser Glu Met Asp
            660                 665                 670

Phe Cys Ile Glu Leu Gly Asn Lys Arg Trp Gln Phe Asn Arg Gln Ser
            675                 680                 685

Gly Phe Leu Ser Gln Met Trp Ile Gly Asp Lys Lys Gln Leu Leu Thr
        690                 695                 700

Pro Leu Arg Asp Gln Phe Thr Arg Ala Pro Leu Asp Asn Asp Ile Gly
705                 710                 715                 720

Val Ser Glu Ala Thr Arg Ile Asp Pro Asn Ala Trp Val Glu Arg Trp
                725                 730                 735

Lys Ala Ala Gly His Tyr Gln Ala Glu Ala Ala Leu Leu Gln Cys Thr
            740                 745                 750

Ala Asp Thr Leu Ala Asp Ala Val Leu Ile Thr Thr Ala His Ala Trp
        755                 760                 765

Gln His Gln Gly Lys Thr Leu Phe Ile Ser Arg Lys Thr Tyr Arg Ile
    770                 775                 780

Asp Gly Ser Gly Gln Met Ala Ile Thr Val Asp Val Glu Val Ala Ser
785                 790                 795                 800

Asp Thr Pro His Pro Ala Arg Ile Gly Leu Asn Cys Gln Leu Ala Gln
                805                 810                 815

Val Ala Glu Arg Val Asn Trp Leu Gly Leu Gly Pro Gln Glu Asn Tyr
            820                 825                 830

Pro Asp Arg Leu Thr Ala Ala Cys Phe Asp Arg Trp Asp Leu Pro Leu
        835                 840                 845

Ser Asp Met Tyr Thr Pro Tyr Val Phe Pro Ser Glu Asn Gly Leu Arg
850                 855                 860

Cys Gly Thr Arg Glu Leu Asn Tyr Gly Pro His Gln Trp Arg Gly Asp
865                 870                 875                 880

Phe Gln Phe Asn Ile Ser Arg Tyr Ser Gln Gln Leu Met Glu Thr
                885                 890                 895

Ser His Arg His Leu Leu His Ala Glu Glu Gly Thr Trp Leu Asn Ile
            900                 905                 910

Asp Gly Phe His Met Gly Ile Gly Gly Asp Asp Ser Trp Ser Pro Ser
        915                 920                 925

Val Ser Ala Glu Phe Gln Leu Ser Ala Gly Arg Tyr His Tyr Gln Leu
930                 935                 940

Val Trp Cys Gln Lys

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Tyr Pro Leu Cys Ser Ser Ala Arg Arg
1               5                   10

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Ala Cys Trp
1

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asn Ile Arg Ser Arg Lys
1               5

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Arg Pro Glu Arg Tyr Arg Arg Ser Val Tyr Arg
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Val Ser Gln Arg Gln Ala
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Asn Ile Arg Arg Thr Lys Cys Tyr
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Thr Arg Phe Phe Ile Gly Phe
1               5

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Asn Leu Asp Leu Ala Thr Glu Asp Tyr
1               5                   10

<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Thr Leu Leu Val
1

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Phe His Tyr Ser Leu Pro His Phe Phe Ala Glu Arg Thr Thr Ile
1               5                   10                  15

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Ile Lys Leu Asp Arg Ser Val Ile Tyr Leu Arg Gln Asp Thr Pro
1               5                   10                  15

Ser

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Tyr Asn Leu Ser Ser Trp
1               5

<210> SEQ ID NO 157
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Pro Asp Lys Gly
1

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ile Pro Thr Ser Arg Trp Leu Glu
1               5

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Phe Leu Cys Tyr Asn Val Leu Ser Tyr Cys Leu
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Met Arg Tyr Arg Lys Cys
1               5

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 161

Asn Trp Phe Cys Arg Ser Lys Arg Arg Ser Lys His Leu Phe Ile Asn
1               5                   10                  15
Arg

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Lys Ile Gln Ser Thr Pro
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asn Val Phe Phe Leu Arg
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Gln Gln Ile Lys Arg Trp Phe
1               5

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Tyr Ser Gly Phe Ser Ser Met Ala Lys Ser Ile Ser Arg His
1               5                   10                  15

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

His Leu Ile Thr
1

<210> SEQ ID NO 167
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Gly Asn Ser Phe Arg Asn Ser Trp Thr Val Arg Thr Cys Val Lys
1               5                   10                  15

Trp Phe Ala Arg Ile Val Arg Phe Pro Leu Phe Ile
            20                  25

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Lys Cys Ser Arg Ile Gln
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Asn Tyr Thr Phe
1               5

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Tyr Ala Gln His Glu His Ser Cys Phe Tyr Arg Ala Glu Trp Val
1               5                   10                  15

Trp

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Asn Asn Phe Glu Trp Asn Asp Trp Cys Asn His Gln Pro Arg Lys
1               5                   10                  15

Gln

<210> SEQ ID NO 172
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 172

Ile Phe Phe Leu
1

<210> SEQ ID NO 173
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Tyr Arg Val Lys Asn Pro Lys Gly Ile Phe Ser Ile Ala Cys Phe
1               5                   10                  15

Ser Phe Val

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Phe Tyr Ser Ser
1               5

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Pro Ser Lys Arg Tyr Thr Ile Leu Leu Tyr Trp Thr Gln Glu Cys Cys
1               5                   10                  15

Gln Gln

<210> SEQ ID NO 176
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Phe Lys Ile Thr Arg Arg Ser Pro Leu Arg Ile His Phe Ser Ile Tyr
1               5                   10                  15

Trp Leu Tyr Glu Ser Arg
            20

<210> SEQ ID NO 177
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 177

Lys Lys Thr Thr Leu Ala
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Tyr Gln Lys Thr Lys
1               5

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Lys Leu Phe Lys Tyr Gly Thr His Gln Pro His Phe
1               5                   10

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Val Lys Thr
1

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Thr Asp Ser Ser Gly Arg
1               5

<210> SEQ ID NO 182
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Tyr Pro Glu Ile Ser Ala Ser Glu Leu Trp Thr Cys Asn Cys
1               5                   10                  15

Phe Ile Tyr Tyr His Lys Ile Ser Arg Cys Arg Trp Arg Lys Val Ile
```

```
                    20                  25                  30

Ser Phe Ile Arg
        35

<210> SEQ ID NO 183
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Arg Gly Ser Ser Ala Ser Thr Phe Ala Leu Cys Phe Phe Thr Asn
1               5                   10                  15

Ile Lys Arg Leu Thr Arg Cys Thr Gln Trp Cys Ser Asn Asn Cys Asn
            20                  25                  30

Ser Phe Pro Ser Ser Thr Ala Arg Gly Ser Lys Ile Leu His Val Glu
        35                  40                  45

Ser Pro Thr Val Lys Arg Ser Asn Lys Tyr Tyr Pro Ser Gly Tyr
    50                  55                  60

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Leu Arg Cys Phe Asn Ser
1               5

<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Val Phe Thr
1

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Asp Lys Phe Trp Ile Pro Pro Leu Ile Ile Ala Val Arg
1               5                   10

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 187

Phe Arg Ala Phe Leu
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asn His Ser Lys Lys Leu
1               5

<210> SEQ ID NO 189
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Trp Ser Asp Arg Ile Arg Arg Ser Asn Arg Phe Lys Ser Asp Asp Asn
1               5                   10                  15

Glu Gln Arg

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Thr Met Lys Lys Leu Pro Leu Pro Ala Arg Thr Tyr Ser
1               5                   10
```